US012516128B2

(12) United States Patent
Wesche et al.

(10) Patent No.: US 12,516,128 B2
(45) Date of Patent: Jan. 6, 2026

(54) EpCAM BINDING PROTEINS AND METHODS OF USE

(71) Applicant: Harpoon Therapeutics, Inc., South San Francisco, CA (US)

(72) Inventors: Holger Wesche, San Francisco, CA (US); Richard J. Austin, San Francisco, CA (US); Shuoyen Jack Lin, San Bruno, CA (US); Bryan Lemon, Mountain View, CA (US); Kevin Wright, Redwood City, CA (US); Sony Rocha, San Francisco, CA (US); Kathryn Kwant, San Bruno, CA (US)

(73) Assignee: Harpoon Therapeutics, Inc., South San Francisco, CA (US)

( * ) Notice: Subject to any disclaimer, the term of this patent is extended or adjusted under 35 U.S.C. 154(b) by 890 days.

(21) Appl. No.: 17/611,054

(22) PCT Filed: May 14, 2020

(86) PCT No.: PCT/US2020/032985

§ 371 (c)(1),
(2) Date: Nov. 12, 2021

(87) PCT Pub. No.: WO2020/232303

PCT Pub. Date: Nov. 19, 2020

(65) Prior Publication Data

US 2022/0267462 A1 Aug. 25, 2022

Related U.S. Application Data

(60) Provisional application No. 62/847,778, filed on May 14, 2019.

(51) Int. Cl.

| | |
|---|---|
| ***C07K 16/30*** | (2006.01) |
| ***A61K 38/17*** | (2006.01) |
| ***A61K 39/00*** | (2006.01) |
| ***A61K 39/395*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/725*** | (2006.01) |
| ***C07K 16/18*** | (2006.01) |
| ***C07K 16/28*** | (2006.01) |

(52) U.S. Cl.

CPC .......... *C07K 16/30* (2013.01); *A61K 38/1774* (2013.01); *A61K 39/001166* (2018.08); *A61K 39/39558* (2013.01); *A61K 40/11* (2025.01); *A61K 40/31* (2025.01); *A61K 40/4254* (2025.01); *A61P 35/00* (2018.01); *C07K 14/7051* (2013.01); *C07K 16/18* (2013.01); *C07K 16/2809* (2013.01); *A61K 2039/505* (2013.01); *A61K 2239/31* (2023.05); *A61K 2239/38* (2023.05); *A61K 2239/59* (2023.05); *C07K 2317/24* (2013.01); *C07K 2317/31* (2013.01); *C07K 2317/35* (2013.01); *C07K 2317/565* (2013.01); *C07K 2317/569* (2013.01); *C07K 2317/622* (2013.01); *C07K 2317/734* (2013.01); *C07K 2317/76* (2013.01); *C07K 2317/92* (2013.01); *C07K 2319/02* (2013.01); *C07K 2319/03* (2013.01); *C07K 2319/33* (2013.01)

(58) Field of Classification Search

CPC ........ A61K 39/001166; C07K 2317/31; C07K 2317/569

See application file for complete search history.

(56) References Cited

U.S. PATENT DOCUMENTS

| | | | |
|---|---|---|---|
| 4,816,567 | A | 3/1989 | Cabilly et al. |
| 4,943,533 | A | 7/1990 | Mendelsohn et al. |
| 5,061,620 | A | 10/1991 | Tsukamoto et al. |
| 5,199,942 | A | 4/1993 | Gillis |
| 5,225,539 | A | 7/1993 | Winter |
| 5,350,674 | A | 9/1994 | Boenisch et al. |
| 5,399,346 | A | 3/1995 | Anderson et al. |
| 5,530,101 | A | 6/1996 | Queen et al. |
| 5,565,332 | A | 10/1996 | Hoogenboom et al. |
| 5,580,859 | A | 12/1996 | Felgner et al. |
| 5,585,089 | A | 12/1996 | Queen et al. |

(Continued)

FOREIGN PATENT DOCUMENTS

| | | | |
|---|---|---|---|
| CA | 3040823 | A1 | 4/2018 |
| CN | 1563092 | A | 1/2005 |

(Continued)

OTHER PUBLICATIONS

Baeuerle, PA et al., EpCAM (CD326) finding its role in cancer, British Journal of Cancer, 96, 417-423, 2007.
Agata et al. Expression of the PD-1 antigen on the surface of stimulated mouse T and B lymphocytes. Int. Immunol 8:765-75 (1996).
Al-Lazikani et al.: Standard conformations for the canonical structures of immunoglobulins. J. Mol Biology 273(4):927-948 (1997).
Almagro et al. Humanization of antibodies. Front Biosci 13:1619-1633 (2008).
Altschul et al. Basic local alignment search tool. J Mol Biol 215(3):403-410 (1990).

(Continued)

*Primary Examiner* — Julie Wu
*Assistant Examiner* — Bryan William Heck
(74) *Attorney, Agent, or Firm* — Benjamin D. Atkins; Andrew W. Custer

(57) ABSTRACT

Provided herein are EpCAM binding proteins, pharmaceutical compositions comprising such proteins or fragments thereof, as well as nucleic acids, recombinant expression vectors and host cells for making such EpCAM binding proteins. Also disclosed are methods of using the disclosed EpCAM binding proteins in the prevention, and/or treatment diseases, conditions and disorders.

25 Claims, 42 Drawing Sheets

Specification includes a Sequence Listing.

(56) References Cited

U.S. PATENT DOCUMENTS

| | | | |
|---|---|---|---|
| 5,585,362 | A | 12/1996 | Wilson et al. |
| 5,589,466 | A | 12/1996 | Felgner et al. |
| 5,759,808 | A | 6/1998 | Casterman et al. |
| 5,766,886 | A | 6/1998 | Studnicka et al. |
| 5,773,292 | A | 6/1998 | Bander |
| 5,800,988 | A | 9/1998 | Casterman et al. |
| 5,840,526 | A | 11/1998 | Casterman et al. |
| 5,844,093 | A | 12/1998 | Kettleborough et al. |
| 5,858,358 | A | 1/1999 | June et al. |
| 5,859,205 | A | 1/1999 | Adair et al. |
| 5,874,541 | A | 2/1999 | Casterman et al. |
| 5,883,223 | A | 3/1999 | Gray |
| 6,005,079 | A | 12/1999 | Casterman et al. |
| 6,015,695 | A | 1/2000 | Casterman et al. |
| 6,107,090 | A | 8/2000 | Bander |
| 6,120,766 | A | 9/2000 | Hale et al. |
| 6,136,311 | A | 10/2000 | Bander |
| 6,326,193 | B1 | 12/2001 | Liu et al. |
| 6,331,415 | B1 | 12/2001 | Cabilly et al. |
| 6,352,694 | B1 | 3/2002 | June et al. |
| 6,407,213 | B1 | 6/2002 | Carter et al. |
| 6,534,055 | B1 | 3/2003 | June et al. |
| 6,548,640 | B1 | 4/2003 | Winter |
| 6,670,453 | B2 | 12/2003 | Frenken et al. |
| 6,692,964 | B1 | 2/2004 | June et al. |
| 6,759,518 | B1 | 7/2004 | Kontermann et al. |
| 6,767,711 | B2 | 7/2004 | Bander |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,060,808 | B1 | 6/2006 | Goldstein et al. |
| 7,067,318 | B2 | 6/2006 | June et al. |
| 7,144,575 | B2 | 12/2006 | June et al. |
| 7,163,680 | B2 | 1/2007 | Bander |
| 7,172,869 | B2 | 2/2007 | June et al. |
| 7,175,843 | B2 | 2/2007 | June et al. |
| 7,232,566 | B2 | 6/2007 | June et al. |
| 7,247,301 | B2 | 7/2007 | Van De Winkel et al. |
| 7,262,276 | B2 | 8/2007 | Huang et al. |
| 7,595,378 | B2 | 9/2009 | Van De Winkel et al. |
| 7,666,414 | B2 | 2/2010 | Bander |
| 7,723,484 | B2 | 5/2010 | Beidler et al. |
| 7,807,162 | B2 | 10/2010 | Silence |
| 7,850,971 | B2 | 12/2010 | Maddon et al. |
| 7,939,072 | B2 | 5/2011 | Yarden et al. |
| 8,114,965 | B2 | 2/2012 | Maddon et al. |
| 8,188,223 | B2 | 5/2012 | Beirnaert et al. |
| 8,236,308 | B2 | 8/2012 | Kischel et al. |
| 8,470,330 | B2 | 6/2013 | Maddon et al. |
| 8,623,356 | B2 | 1/2014 | Christopherson et al. |
| 8,629,244 | B2 | 1/2014 | Kolkman et al. |
| 8,703,135 | B2 | 4/2014 | Beste et al. |
| 8,784,821 | B1 | 7/2014 | Kufer et al. |
| 8,846,042 | B2 | 9/2014 | Zhou |
| 8,907,071 | B2 | 12/2014 | Sullivan et al. |
| 8,937,164 | B2 | 1/2015 | Descamps et al. |
| 8,986,972 | B2 | 3/2015 | Stull et al. |
| 9,089,615 | B2 | 7/2015 | Stull et al. |
| 9,089,616 | B2 | 7/2015 | Stull et al. |
| 9,089,617 | B2 | 7/2015 | Stull et al. |
| 9,090,683 | B2 | 7/2015 | Stull et al. |
| 9,107,961 | B2 | 8/2015 | Stull et al. |
| 9,127,071 | B2 | 9/2015 | Yoshida et al. |
| 9,133,271 | B1 | 9/2015 | Stull et al. |
| 9,155,803 | B1 | 10/2015 | Stull et al. |
| 9,169,316 | B2 | 10/2015 | Baty et al. |
| 9,309,327 | B2 | 4/2016 | Humphreys et al. |
| 9,327,022 | B2 | 5/2016 | Zhang et al. |
| 9,334,318 | B1 | 5/2016 | Stull et al. |
| 9,340,621 | B2 | 5/2016 | Kufer et al. |
| 9,345,787 | B2 | 5/2016 | Hemminki et al. |
| 9,352,051 | B1 | 5/2016 | Stull et al. |
| 9,353,182 | B2 | 5/2016 | Stull et al. |
| 9,358,304 | B1 | 6/2016 | Stull et al. |
| 9,480,757 | B2 | 11/2016 | Stull et al. |
| 9,481,724 | B2 | 11/2016 | Ravetch et al. |
| 9,486,537 | B2 | 11/2016 | Stull et al. |
| 9,708,412 | B2 | 7/2017 | Baeuerle et al. |
| 9,764,042 | B1 | 9/2017 | Stull et al. |
| 9,770,518 | B1 | 9/2017 | Stull et al. |
| 9,775,916 | B1 | 10/2017 | Stull et al. |
| 9,855,343 | B2 | 1/2018 | Stull et al. |
| 9,861,708 | B2 | 1/2018 | Stull et al. |
| 9,867,887 | B1 | 1/2018 | Stull et al. |
| 9,878,053 | B2 | 1/2018 | Stull et al. |
| 9,920,115 | B2 | 3/2018 | Dubridge et al. |
| 9,931,420 | B2 | 4/2018 | Stull et al. |
| 9,931,421 | B2 | 4/2018 | Stull et al. |
| 9,937,268 | B2 | 4/2018 | Stull et al. |
| 10,066,016 | B2 | 9/2018 | Dubridge et al. |
| 10,100,106 | B2 | 10/2018 | Dubridge et al. |
| 10,137,204 | B2 | 11/2018 | Stull et al. |
| 10,428,120 | B2 | 10/2019 | Kontermann et al. |
| 10,543,271 | B2 | 1/2020 | Wesche et al. |
| 10,544,221 | B2 | 1/2020 | Dubridge et al. |
| 10,730,954 | B2 | 8/2020 | Wesche et al. |
| 10,815,311 | B2 | 10/2020 | Wesche et al. |
| 10,844,134 | B2 | 11/2020 | Baeuerle et al. |
| 10,849,973 | B2 | 12/2020 | Dubridge et al. |
| 10,927,180 | B2 | 2/2021 | Wesche et al. |
| 10,954,311 | B2 | 3/2021 | Baeuerle et al. |
| 11,111,311 | B2 | 9/2021 | Yoshida et al. |
| 11,136,403 | B2 | 10/2021 | Wesche et al. |
| 2004/0101519 | A1 | 5/2004 | June et al. |
| 2005/0042664 | A1 | 2/2005 | Wu et al. |
| 2005/0048617 | A1 | 3/2005 | Wu et al. |
| 2005/0100543 | A1 | 5/2005 | Hansen et al. |
| 2005/0175606 | A1 | 8/2005 | Huang et al. |
| 2006/0034810 | A1 | 2/2006 | Riley et al. |
| 2006/0046971 | A1 | 3/2006 | Stuhler et al. |
| 2006/0121005 | A1 | 6/2006 | Berenson et al. |
| 2006/0228364 | A1 | 10/2006 | Dennis et al. |
| 2006/0252096 | A1 | 11/2006 | Zha et al. |
| 2007/0014794 | A1 | 1/2007 | Carter et al. |
| 2007/0178082 | A1 | 8/2007 | Silence et al. |
| 2007/0269422 | A1 | 11/2007 | Beirnaert et al. |
| 2008/0069772 | A1 | 3/2008 | Stuhler et al. |
| 2008/0260757 | A1 | 10/2008 | Holt et al. |
| 2009/0028880 | A1 | 1/2009 | Beirnaert et al. |
| 2009/0117108 | A1 | 5/2009 | Wang et al. |
| 2009/0136485 | A1 | 5/2009 | Chu et al. |
| 2009/0252683 | A1 | 10/2009 | Kischel et al. |
| 2009/0259026 | A1 | 10/2009 | Tomlinson et al. |
| 2010/0122358 | A1 | 5/2010 | Bruggemann et al. |
| 2010/0150918 | A1 | 6/2010 | Kufer et al. |
| 2010/0166734 | A1 | 7/2010 | Dolk |
| 2010/0189651 | A1 | 7/2010 | Stagliano et al. |
| 2010/0189727 | A1 | 7/2010 | Rodeck et al. |
| 2010/0266531 | A1 | 10/2010 | Hsieh et al. |
| 2010/0291112 | A1 | 11/2010 | Kellner et al. |
| 2010/0311119 | A1 | 12/2010 | Hermans et al. |
| 2011/0129458 | A1 | 6/2011 | Dolk et al. |
| 2011/0165621 | A1 | 7/2011 | Dreier et al. |
| 2011/0262439 | A1 | 10/2011 | Kufer et al. |
| 2011/0275787 | A1 | 11/2011 | Kufer et al. |
| 2011/0313135 | A1 | 12/2011 | Vanhove et al. |
| 2012/0039899 | A1 | 2/2012 | Olsen et al. |
| 2012/0231024 | A1 | 9/2012 | Elsaesser-Beile et al. |
| 2012/0328619 | A1 | 12/2012 | Fey et al. |
| 2013/0017200 | A1 | 1/2013 | Scheer et al. |
| 2013/0136744 | A1 | 5/2013 | Bouche et al. |
| 2013/0266568 | A1 | 10/2013 | Brinkmann et al. |
| 2013/0267686 | A1 | 10/2013 | Brinkmann et al. |
| 2013/0273055 | A1 | 10/2013 | Borges et al. |
| 2013/0315906 | A1 | 11/2013 | Lowman et al. |
| 2013/0330335 | A1 | 12/2013 | Bremel et al. |
| 2014/0004121 | A1 | 1/2014 | Fanslow, III et al. |
| 2014/0023664 | A1 | 1/2014 | Lowman et al. |
| 2014/0045195 | A1 | 2/2014 | Daugherty et al. |
| 2014/0073767 | A1 | 3/2014 | Lee et al. |
| 2014/0088295 | A1 | 3/2014 | Smith et al. |

(56) References Cited

U.S. PATENT DOCUMENTS

| | | | |
|---|---|---|---|
| 2014/0205601 | A1 | 7/2014 | Beirnaert et al. |
| 2014/0242075 | A1 | 8/2014 | Parren et al. |
| 2014/0302037 | A1 | 10/2014 | Borges et al. |
| 2014/0322218 | A1 | 10/2014 | Xiao et al. |
| 2015/0037334 | A1 | 2/2015 | Kufer et al. |
| 2015/0056206 | A1 | 2/2015 | Zhou |
| 2015/0064169 | A1 | 3/2015 | Wang et al. |
| 2015/0079088 | A1 | 3/2015 | Lowman et al. |
| 2015/0079093 | A1 | 3/2015 | Stuhler |
| 2015/0093336 | A1 | 4/2015 | Van Ginderachter et al. |
| 2015/0174268 | A1 | 6/2015 | Li et al. |
| 2015/0175697 | A1 | 6/2015 | Bonvini et al. |
| 2015/0183875 | A1 | 7/2015 | Cobbold et al. |
| 2015/0232557 | A1 | 8/2015 | Tan et al. |
| 2015/0274836 | A1 | 10/2015 | Ho et al. |
| 2015/0274844 | A1 | 10/2015 | Blankenship et al. |
| 2015/0328332 | A1 | 11/2015 | Stull et al. |
| 2016/0017058 | A1 | 1/2016 | Kim et al. |
| 2016/0024174 | A1 | 1/2016 | Odunsi et al. |
| 2016/0032011 | A1 | 2/2016 | Zhang et al. |
| 2016/0032019 | A1 | 2/2016 | Xiao et al. |
| 2016/0039942 | A1 | 2/2016 | Cobbold et al. |
| 2016/0068605 | A1 | 3/2016 | Nemeth et al. |
| 2016/0115241 | A1 | 4/2016 | Yan et al. |
| 2016/0130331 | A1 | 5/2016 | Stull et al. |
| 2016/0215063 | A1 | 7/2016 | Bernett et al. |
| 2016/0251440 | A1 | 9/2016 | Roobrouck et al. |
| 2016/0257721 | A1 | 9/2016 | Lieber et al. |
| 2016/0319040 | A1 | 11/2016 | Dreier et al. |
| 2016/0340444 | A1 | 11/2016 | Baeuerle et al. |
| 2016/0355842 | A1 | 12/2016 | Parks et al. |
| 2017/0029502 | A1 | 2/2017 | Raum et al. |
| 2017/0037149 | A1 | 2/2017 | Raum et al. |
| 2017/0152316 | A1 | 6/2017 | Cobbold et al. |
| 2017/0204164 | A1 | 7/2017 | Himmler et al. |
| 2017/0275373 | A1 | 9/2017 | Kufer et al. |
| 2017/0334979 | A1 | 11/2017 | Dubridge et al. |
| 2017/0334997 | A1 | 11/2017 | Dubridge et al. |
| 2017/0349660 | A1 | 12/2017 | Saville et al. |
| 2017/0369563 | A1 | 12/2017 | Dubridge et al. |
| 2018/0016323 | A1 | 1/2018 | Brandenburg et al. |
| 2018/0134789 | A1 | 5/2018 | Baeuerle et al. |
| 2018/0148508 | A1 | 5/2018 | Wang et al. |
| 2018/0318417 | A1 | 11/2018 | Schuetz et al. |
| 2018/0326060 | A1 | 11/2018 | Wesche et al. |
| 2018/0346601 | A1 | 12/2018 | Dettling et al. |
| 2019/0031749 | A1 | 1/2019 | Dubridge et al. |
| 2019/0046656 | A1 | 2/2019 | Stull et al. |
| 2019/0092862 | A1 | 3/2019 | Cui et al. |
| 2019/0225702 | A1 | 7/2019 | Baeuerle et al. |
| 2019/0247510 | A1 | 8/2019 | Stull et al. |
| 2020/0115461 | A1 | 4/2020 | Evnin et al. |
| 2020/0148771 | A1 | 5/2020 | Paeuerle et al. |
| 2020/0231672 | A1 | 7/2020 | Dubridge et al. |
| 2020/0270362 | A1 | 8/2020 | Wesche et al. |
| 2020/0289646 | A1 | 9/2020 | Wesche et al. |
| 2021/0047439 | A1 | 2/2021 | Wesche et al. |
| 2021/0095047 | A1 | 4/2021 | Baeuerle et al. |
| 2021/0100902 | A1 | 4/2021 | Dubridge et al. |
| 2021/0171649 | A1 | 6/2021 | Wesche et al. |
| 2021/0179735 | A1 | 6/2021 | Baeuerle et al. |
| 2021/0269530 | A1 | 9/2021 | Lin et al. |
| 2021/0284728 | A1 | 9/2021 | Lin et al. |
| 2021/0292421 | A1 | 9/2021 | Lin et al. |
| 2021/0355219 | A1 | 11/2021 | Lin et al. |
| 2021/0380715 | A1 | 12/2021 | Yoshida et al. |
| 2024/0228656 | A1* | 7/2024 | Wesche .................. C07K 16/30 |

FOREIGN PATENT DOCUMENTS

| | | | |
|---|---|---|---|
| CN | 101646689 | A | 2/2010 |
| CN | 105968201 | A | 9/2016 |
| CN | 105968204 | A | 9/2016 |
| CN | 108484771 | A | 9/2018 |
| CN | 108530538 | A | 9/2018 |
| CN | 108586614 | A | 9/2018 |
| CN | 109593786 | A | 4/2019 |
| EP | 0239400 | A2 | 9/1987 |
| EP | 0519596 | A1 | 12/1992 |
| EP | 0592106 | A1 | 4/1994 |
| EP | 1378520 | A1 | 1/2004 |
| EP | 1736484 | A1 | 12/2006 |
| EP | 2336179 | A1 | 6/2011 |
| EP | 2817338 | A2 | 12/2014 |
| EP | 3093293 | A1 | 11/2016 |
| EP | 3093294 | A1 | 11/2016 |
| EP | 3095797 | A1 | 11/2016 |
| EP | 3337517 | A2 | 6/2018 |
| EP | 3556400 | A1 | 10/2019 |
| FR | 901228 | A | 7/1945 |
| JP | 2005501517 | A | 1/2005 |
| JP | 2016500655 | A | 1/2016 |
| JP | 2019052750 | A | 4/2019 |
| WO | WO-9109967 | A1 | 7/1991 |
| WO | WO-9307105 | A1 | 4/1993 |
| WO | WO-9404678 | A1 | 3/1994 |
| WO | WO-9937681 | A2 | 7/1999 |
| WO | WO-0043507 | A1 | 7/2000 |
| WO | WO-0130381 | A2 | 5/2001 |
| WO | WO-0190190 | A2 | 11/2001 |
| WO | WO-0196584 | A2 | 12/2001 |
| WO | WO-02085945 | A2 | 10/2002 |
| WO | WO-03025020 | A1 | 3/2003 |
| WO | WO-03035694 | A2 | 5/2003 |
| WO | WO-03064606 | A2 | 8/2003 |
| WO | WO-2004003019 | A2 | 1/2004 |
| WO | WO-2004041867 | A2 | 5/2004 |
| WO | WO-2004042404 | A1 | 5/2004 |
| WO | WO-2004049794 | A2 | 6/2004 |
| WO | WO-2005040220 | A1 | 5/2005 |
| WO | WO-2006020258 | A2 | 2/2006 |
| WO | WO-2006122787 | A1 | 11/2006 |
| WO | WO-2007024715 | A2 | 3/2007 |
| WO | WO-2007042261 | A2 | 4/2007 |
| WO | WO-2007062466 | A1 | 6/2007 |
| WO | WO-2007115230 | A2 | 10/2007 |
| WO | WO-2008028977 | A2 | 3/2008 |
| WO | WO-2009025846 | A2 | 2/2009 |
| WO | WO-2009030285 | A1 | 3/2009 |
| WO | WO-2009147248 | A2 | 12/2009 |
| WO | WO-2010003118 | A1 | 1/2010 |
| WO | WO-2010037836 | A2 | 4/2010 |
| WO | WO-2010037837 | A2 | 4/2010 |
| WO | WO-2010081173 | A2 | 7/2010 |
| WO | WO-2011039368 | A2 | 4/2011 |
| WO | WO-2011051327 | A2 | 5/2011 |
| WO | WO-2011079283 | A1 | 6/2011 |
| WO | WO-2011117423 | A1 | 9/2011 |
| WO | WO-2011161260 | A1 | 12/2011 |
| WO | WO-2012131053 | A1 | 10/2012 |
| WO | WO-2012138475 | A1 | 10/2012 |
| WO | WO-2012158818 | A2 | 11/2012 |
| WO | WO-2012175400 | A1 | 12/2012 |
| WO | WO-2013036130 | A1 | 3/2013 |
| WO | WO-2013045707 | A2 | 4/2013 |
| WO | WO-2013104804 | A2 | 7/2013 |
| WO | WO-2013110531 | A1 | 8/2013 |
| WO | WO-2013126712 | A1 | 8/2013 |
| WO | WO-2013128027 | A1 | 9/2013 |
| WO | WO-2013128194 | A1 | 9/2013 |
| WO | WO-2014033304 | A2 | 3/2014 |
| WO | WO-2014052064 | A1 | 4/2014 |
| WO | WO-2014132072 | A1 | 9/2014 |
| WO | WO-2014138306 | A1 | 9/2014 |
| WO | WO-2014140358 | A1 | 9/2014 |
| WO | WO-2014144689 | A1 | 9/2014 |
| WO | WO-2014151910 | A1 | 9/2014 |
| WO | WO-2015031693 | A1 | 3/2015 |
| WO | WO-2015103072 | A1 | 7/2015 |
| WO | WO-2015127407 | A1 | 8/2015 |
| WO | WO-2015146437 | A1 | 10/2015 |
| WO | WO-2015150447 | A1 | 10/2015 |
| WO | WO-2015184207 | A1 | 12/2015 |
| WO | WO-2016009029 | A1 | 1/2016 |

(56) References Cited

FOREIGN PATENT DOCUMENTS

| | | | |
|---|---|---|---|
| WO | WO-2016046778 | A2 | 3/2016 |
| WO | WO-2016055551 | A1 | 4/2016 |
| WO | WO-2016105450 | A2 | 6/2016 |
| WO | WO-2016125017 | A1 | 8/2016 |
| WO | WO-2016130819 | A2 | 8/2016 |
| WO | WO-2016138038 | A1 | 9/2016 |
| WO | WO-2016171999 | A2 | 10/2016 |
| WO | WO-2016179003 | A1 | 11/2016 |
| WO | WO-2016180982 | A1 | 11/2016 |
| WO | WO-2016182064 | A1 | 11/2016 |
| WO | WO-2016187101 | A2 | 11/2016 |
| WO | WO-2016187594 | A1 | 11/2016 |
| WO | WO-2016210447 | A1 | 12/2016 |
| WO | WO-2017021349 | A1 | 2/2017 |
| WO | WO-2017021356 | A1 | 2/2017 |
| WO | WO-2017025038 | A1 | 2/2017 |
| WO | WO-2017025698 | A1 | 2/2017 |
| WO | WO-2017027392 | A1 | 2/2017 |
| WO | WO-2017031104 | A1 | 2/2017 |
| WO | WO-2017041749 | A1 | 3/2017 |
| WO | WO-2017079528 | A1 | 5/2017 |
| WO | WO-2017136549 | A1 | 8/2017 |
| WO | WO-2017156178 | A1 | 9/2017 |
| WO | WO-2017157305 | A1 | 9/2017 |
| WO | WO-2017161206 | A1 | 9/2017 |
| WO | WO-2017162587 | A1 | 9/2017 |
| WO | WO-2017201442 | A1 | 11/2017 |
| WO | WO-2017201488 | A1 | 11/2017 |
| WO | WO-2017201493 | A1 | 11/2017 |
| WO | WO-2018017863 | A1 | 1/2018 |
| WO | WO-2018026953 | A1 | 2/2018 |
| WO | WO-2018067993 | A1 | 4/2018 |
| WO | WO-2018071777 | A1 | 4/2018 |
| WO | WO-2018098354 | A1 | 5/2018 |
| WO | WO-2018098356 | A1 | 5/2018 |
| WO | WO-2018136725 | A1 | 7/2018 |
| WO | WO-2018160671 | A1 | 9/2018 |
| WO | WO-2018160754 | A2 | 9/2018 |
| WO | WO-2018165619 | A1 | 9/2018 |
| WO | WO-2018204717 | A1 | 11/2018 |
| WO | WO-2018209298 | A1 | 11/2018 |
| WO | WO-2018209304 | A1 | 11/2018 |
| WO | WO-2018232020 | A1 | 12/2018 |
| WO | WO-2019075359 | A1 | 4/2019 |
| WO | WO-2019075378 | A1 | 4/2019 |
| WO | WO-2019222278 | A1 | 11/2019 |
| WO | WO-2019222282 | A1 | 11/2019 |
| WO | WO-2019222283 | A1 | 11/2019 |
| WO | WO-2019246004 | A1 | 12/2019 |
| WO | WO-2020053263 | A1 | 3/2020 |
| WO | WO-2020060593 | A1 | 3/2020 |
| WO | WO-2020061482 | A1 | 3/2020 |
| WO | WO-2020061526 | A1 | 3/2020 |
| WO | WO-2020069028 | A1 | 4/2020 |
| WO | WO-2020232303 | A1 | 11/2020 |
| WO | WO-2021097060 | A1 | 5/2021 |
| WO | WO-2021231434 | A1 | 11/2021 |
| WO | WO-2022098909 | A1 | 5/2022 |

OTHER PUBLICATIONS

Altschul et al. Gapped BLAST and PSI-BLAST: a new generation of protein database search programs. Nucleic Acids Res 25:3389-3402 (1997).

Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).

Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14, 2018-Apr. 18, 2018).

Baca et al. Antibody humanization using monovalent phage display. J Biol Chem 272(16):10678-10684 (1997).

Baeuerle et al. Bispecific T-cell engaging antibodies for cancer therapy. Cancer Res 69:4941-4944 (2009).

Balzar et al. Epidermal growth factor-like repeats mediate lateral and reciprocal interactions of Ep-CAM molecules in homophilic adhesions. Mol Cell Biol 21(7):2570-80 (2001).

Balzar et al. The biology of the 17-1A antigen (Ep-CAM). J. Mol. Med. 77:699-712 (1999).

Barrett et al. Treatment of advanced leukemia in mice with mRNA engineered T cells. Hum Gene Ther 22:1575-1586 (2011).

Batzer et al. Enhanced evolutionary PCR using oligonucleotides with inosine at the 3'-terminus. Nucleic Acids Res. 19(18):5081 (1991).

Baum et al. Antitumor activities of PSMAxCD3 diabodies by redirected T-cell lysis of prostate cancer cells. Immunotherapy 5(1):27-38 (2013).

Bedouelle et al. Diversity and junction residues as hotspots of binding energy in an antibody neutralizing the dengue virus. FEBS J 273(1):34-46 (2006).

Bendell et al. Abstract 5552: First-in-human phase I study of HPN424, a tri-specific half-life extended PSMA-targeting T-cell engager in patients with metastatic castration-resistant prostate cancer (mCRPC). J Clin Oncol 38(15):5552 (May 2020).

Bird et al. Single-chain antigen-binding proteins. Science 242(4877):423-426 (1988).

Blank et al. Interaction of PD-L1 on tumor cells with PD-1 on tumor-specific T cells as a mechanism of immune evasion: implications for tumor immunotherapy. Cancer Immunol Immunother 54:307-314 (2005).

Bortoletto et al. Optimizing anti-CD3 affinity for effective T cell targeting against tumor cells. Eur J Immunol 32:3102-3107 (2002).

Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).

Brauchle et al. Characterization of a Novel FLT3 BiTE Molecule for the Treatment of Acute Myeloid Leukemia. Mol Cancer Ther 19:1875-88 (2020).

Brown et al. Tolerance of single, but not multiple, amino acid replacements in antibody VH CDR 2: a means of minimizing B cell wastage from somatic hypermutation? J Immunol 156(9):3285-3291 (1996).

Caldas et al. Design and synthesis of germline-based hemi-humanized single-chain Fv against the CD18 surface antigen. Protein Eng 13(5):353-360 (2000).

Caldas et al. Humanization of the anti-CD18 antibody 6.7: an unexpected effect of a framework residue in binding to antigen. Mol Immunol. 39(15):941-952 (2003).

Carter et al. Humanization of an anti-p185HER2 antibody for human cancer therapy. PNAS USA 89(10):4285-4289 (1992).

Carter et al. PD-1: PD-L inhibitory pathway affects both CD4(+) and CD8(+) T cells and is overcome by IL-2. Eur J Immunol 32:634-643 (2002).

Casset et al. A peptide mimetic of an anti-CD4 monoclonal antibody by rational design. Biochemical and Biophysical Research Communication 307:198-205 (2003).

Chang et al. Loop-sequence features and stability determinants in antibody variable domains by high-throughput experiments. Structure 22(1):9-21 (2014).

Chang et al. Molecular cloning of mesothelin, a differentiation antigen present on mesothelium, mesotheliomas, and ovarian cancers. PNAS USA 93:136-140 (1996).

Chatalic et al. A Novel 111 In-labeled Anti-PSMA Nanobody for Targeted SPECT/CT Imaging of Prostate Cancer. J Nucl Med 56(7):1094-1099 and Supplemental Data (2015).

Chaubal et al. Ep-CAM—a marker for the detection of disseminated tumor cells in patients suffering from SCCHN. Anticancer Res 19:2237-2242 (1999).

Chen et al. Fusion protein linkers: Property, design and functionality. Advanced Drug Delivery Reviews 65:1357-1369 (2013).

Chen et al. Selection and analysis of an optimized anti-VEGF antibody: Crystal structure of an affinity-matured Fab in complex with antigen. J Mol Bio 293:865-881 (1999).

(56) References Cited

OTHER PUBLICATIONS

Chien et al. Significant structural and functional change of an antigen-binding site by a distant amino acid substitution: proposal of a structural mechanism. PNAS USA 86(14):5532-5536 (1989).
Cho et al. Targeting B Cell Maturation Antigen (BCMA) in Multiple Myeloma: Potential Uses of BCMA-Based Immunotherapy. Front Immunol 9:1821 (2018).
Choi et al. Engineering of Immunoglobulin Fc heterodimers using yeast surface-displayed combinatorial Fc library screening. PLOS One 10(12):e0145349 (2015).
Chothia et al. Canonical structures for the hypervariable regions of immunoglobulins. J Mol Biol 196(4):901-917 (1987).
Chothia, et al. Conformations of immunoglobulin hypervariable regions. Nature 342(6252):877-83 (1989).
Corso et al. Real-time detection of mesothelin in pancreatic cancer cell line supernatant using an acoustic wave immunosensor. Cancer Detect Prey 30:180-187 (2006).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients with mesothelioma and lung cancer. Clin. Cancer Res. 13:5076-5081 (2007).
Dao et al. Targeting the intracellular WT1 oncogene product with a therapeutic human antibody. Sci Transi Med 5(176):176ra33 (2013).
De Genst et al. Antibody repertoire development in camelids. Dev Comp Immunol 30(1-2):187-198 (2006).
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Dennis et al. Imaging Tumors with an Albumin-Binding Fab, a Novel Tumor-Targeting Agent. Cancer Res 67(1):254-61 (2007).
Document D28—Investigation of human CD3ε variants binding to monoclonal antibodies. Submitted by Pfizer to the European Patent Register on Apr. 30, 2014 in connection with their opposition to the EP2155783 patent. (3 pages) (2014).
Document D78—CD3ε N-terminal peptide bound to the CDRs of SP24. Submitted by Janssen Biotech to the European Patent Register on Mar. 18, 2016 in connection with their opposition to the EP2155783 patent (1 page) (2016).
Document D79—Interactions between CD3ε and SP34 CDR residues. CD38 residues are in ellipses, SP34 CDR residues are in boxes. Submitted by Janssen Biotech to the European Patent Register on Mar. 18, 2016 in connection with their opposition to the EP2155783 patent (1 page) (2016).
Document D83—Alignment of variable domains from the prior art and the patent. Submitted by Janssen Biotech to the European Patent Register on Mar. 18, 2016 in connection with their opposition to the EP2155783 patent (1 page) (2016).
Dong et al. B7-H1 pathway and its role in the evasion of tumor immunity. J Mol Med 81:281-287 (2003).
Elango et al. Optimized transfection of mRNA transcribed from a d(A/T)100 tail-containing vector. Biochim Biophys Res Commun 330:958-966 (2005).
Eyvazi et al. Antibody Based EpCAM Targeted Therapy of Cancer, Review and Update. Curr Cancer Drug Targets. 18(9):857-868 (2018).
Foote et al. Antibody Framework Residues Affecting the Conformation of the Hypervariable Loops. J. Mol. Biol. 224(2):487-99 (1992).
Frankel et al. Targeting T cells to tumor cells using bispecific antibodies. Curr Opin Chem Biol 17(3):385-392 (2013).
Freeman et al. Engagement of the PD-1 immunoinhibitory receptor by a novel B7 family member leads to negative regulation of lymphocyte activation. J Exp Med 192:1027-1034 (2000).
Garland et al. The use of Teflon cell culture bags to expand functionally active CD8+ cytotoxic T lymphocytes. J Immunol Meth 227(1-2):53-63 (1999).
Gastl et al. Ep-CAM overexpression in breast cancer as a predictor of survival. Lancet. 356:1981-1982 (2000).
Giusti et al. Somatic diversification of S107 from an antiphosphocholine to an anti-DNA autoantibody is due to a single base change in its heavy chain variable region. PNAS USA 84(9):2926-30 (1987).
Glaser et al. Novel antibody hinge regions for efficient production of CH2 domain-deleted antibodies. J. Biol. Chem. 280:41494-503 (2005).
Goettlinger et al. The epithelial cell surface antigen 17-1A, a target for antibody-mediated tumor therapy: its biochemical nature, tissue distribution and recognition by different monoclonal antibodies. Int J Cancer. 38:47-53 (1986).
Goldman et al. Enhancing Stability of Camelid and Shark Single Domain Antibodies: An Overview. Front. Immunol. 8:865 (2017).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Gross et al. Endowing T cells with antibody specificity using chimeric T cell receptors. FASEB J. 6(15):3370-3378 (1992).
Grupp et al. Chimeric antigen receptor-modified T cells for acute lymphoid leukemia. NEJM 368:1509-1518 (2013).
Gubbels et al. Mesothelin-MUC16 binding is a high affinity, N-glycan dependent interaction that facilitates peritoneal metastasis of ovarian tumors. Mol Cancer 5:50 (2006).
Gussow et al. Chapter 5: Humanization of Monoclonal Antibodies. Methods in Enzymology 203:99-121 (1991).
Haanen et al. Selective expansion of cross-reactive CD8(+) memory T cells by viral variants. J Exp Med 190(9):1319-1328 (1999).
Halaby et al. The immunoglobulin fold family: sequence analysis and 3D structure comparisons. Prot Eng 12(7):563-571 (1999).
Han et al. Masked Chimeric Antigen Receptor for Tumor-Specific Activation. Molecular Therapy 25(1):274-284 (2017).
Harding et al. The immunogenicity of humanized and fully human antibodies: residual immunogenicity resides in the CDR regions. MAbs 2(3):256-265 (2010).
Harmsen et al. Properties, production, and applications of camelid single-domain antibody fragments. Appl. Microbiol. Biotechnol. 77:13-22 (2007).
Hassan et al. Detection and quantitation of serum mesothelin, a tumor marker for patients with mesothelioma and ovarian cancer. Clin Cancer Res 12:447-453 (2006).
Hassan et al. Mesothelin: a new target for immunotherapy. Clin Cancer Res 10:3937-3942 (2004).
Hassan et al. Mesothelin targeted cancer immunotherapy. Eur J Cancer 44:46-53 (2008).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).
Hassan et al. Preclinical evaluation of MORAb-009, a chimeric antibody targeting tumor-associated mesothelin. Cancer Immun. 7:20 (2007).
Hellstrom et al. Mesothelin variant 1 is released from tumor cells as a diagnostic marker. Cancer Epidemiol Biomarkers Prey 15:1014-1020 (2006).
Hipp et al. A novel BCMA/CD3 bispecific T-cell engager for the treatment of multiple myeloma induces selective lysis in vitro and in vivo. Leukemia 31(8):1743-1751 (2017).
Ho et al. A novel high-affinity human monoclonal antibody to mesothelin. Int J Cancer 128:2020-2030 (2011).
Ho et al. Mesothelin expression in human lung cancer. Clin Cancer Res 13:1571-1575 (2007).
Ho et al. Mesothelin is shed from tumor cells. Cancer Epidemiol Biomarkers Prey 15:1751 (2006).
Holliger et al. "Diabodies": small bivalent and bispecific antibody fragments. PNAS USA 90(14):6444-6448 (1993).

(56) References Cited

OTHER PUBLICATIONS

Holm et al. Functional mapping and single chain construction of the anti-cytokeratin 8 monoclonal antibody TS1. Mol Immunol 44(6):1075-1084 (2007).
Holt et al. Anti-serum albumin domain antibodies for extending the half-lives of short-lived drugs. Protein Eng Des Sel 21(5):283-288 (2008).
Hopp et al. The effects of affinity and valency of an albumin-binding domain (ABD) on the half-life of a single-chain diabody-ABD fusion protein. Protein Eng. Des. Sel. 23(11):827-34 (2010).
Huck et al. Sequence of a human immunoglobulin gamma 3 heavy chain constant region gene: comparison with the other human C gamma genes. Nucl. Acids Res. 14:1779-89 (1986).
Huston et al. Protein engineering of antibody binding sites: recovery of specific activity in an anti-digoxin single-chain Fv analogue produced in *Escherichia coli*. PNAS USA 85(16):5879-5883 (1988).
Hutchinson et al. Mutagenesis at a specific position in a DNA sequence. J Biol Chem 253:6551-6560 (1978).
Izumoto et al. Phase II clinical trial of Wilms tumor 1 peptide vaccination for patients with recurrent glioblastoma multiforme. J Neurosurg 108:963-971 (2008).
Janssen letter—Submission under Rule 116 EPC. Submitted by Janssen Biotech to the European Patent Register on Mar. 18, 2016 in connection with their opposition to the EP2155783 patent (6 pages) (2016).
Jones et al. Replacing the complementarity-determining regions in a human antibody with those from a mouse. Nature 321:522-525 (1986).
Julian et al. Efficient affinity maturation of antibody variable domains requires co-selection of compensatory mutations to maintain thermodynamic stability. Sci Rep 7:45259 (2017).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Kabat et al. Sequences of proteins of immunological interest. NIH Publ. No. 91-3242 1:647-669 (1991).
Kalos et al. T cells with chimeric antigen receptors have potent antitumor effects and can establish memory in patients with advanced leukemia. Sci Transl Med 3(95):95ra73 (2011).
Kojima et al. Molecular cloning and expression of megakaryocyte potentiating factor cDNA. J Biol Chem 270:21984-21990 (1995).
Konishi et al. B7-H1 expression on non-small cell lung cancer cells and its relationship with tumor-infiltrating lymphocytes and their PD-1 expression. Clin Cancer Res 10:5094-5100 (2004).
Koprowski et al. Colorectal carcinoma antigens detected by hybridoma antibodies. Somatic Cell Genet. 5:957-971 (1979).
Škrlec et al. Non-immunoglobulin scaffolds: a focus on their targets. Trends in Biotechnol 33:408-418 (2015).
Krzywinska et al. CD45 Isoform Profile Identifies Natural Killer (NK) Subsets with Differential Activity. PLoS One 11(4):e0150434 (2016).
Laabi et al. The BCMA gene, preferentially expressed during B lymphoid maturation, is bidirectionally transcribed. Nucleic Acids Res 22(7):1147-1154 (1994).
Latchman et al. PD-L2 is a second ligand for PD-1 and inhibits T cell activation. Nat Immunol 2:261-268 (2001).
Le Gall et al. Immunosuppressive properties of anti-CD3 single-chain Fv and diabody. J Immunol Methods 285(1):111-127 (2004).
Leibl et al. Ovarian granulosa cell tumors frequently express EGFR (Her-1), Her-3, and Her-4: An immunohistochemical study. Gynecol Oncol 101(1):18-23 (2006).
Li et al. Development of novel tetravalent anti-CD20 antibodies with potent antitumor activity. Cancer Res 68:2400-2408 (2008).
Litvinov et al. Epithelial cell adhesion molecule (Ep-CAM) modulates cell-cell interactions mediated by classic cadherins. J Cell Biol. 139:1337-1348 (1997).
Litvinov et al. Expression of Ep-CAM in cervical squamous epithelia correlates with an increased proliferation and the disappearance of markers for terminal differentiation. Am. J. Pathol. 148:865-75 (1996).
Liu et al. A New Format of Single Chain Tri-specific Antibody with Diminished Molecular Size Efficiently Induces Ovarian Tumor Cell Killing. Biotechnology Letters 27(22):1821-1827 (2005).
Liu et al. MGD011, a CD19 x CD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).
Lowman et al. Monovalent phage display: A method for selecting variant proteins from random libraries. Methods 3:205-216 (1991).
Lu et al. In vitro and in vivo antitumor effect of a trivalent bispecific antibody targeting ErbB2 and CD16. Cancer Biol Ther. 7(11):1744-1750 (2008).
Lutterbuese et al. T cell-engaging BiTE antibodies specific for EGFR potently eliminate KRAS- and BRAF-mutated colorectal cancer cells. PNAS 107:12605-12610 (2007).
MacCallum et al.: Antibody-antigen interactions: contact analysis and binding site topography. J Mol Biol. 262(5):732-745 (1996).
Mariuzza et al. The structural basis of antigen-antibody recognition. Annu Rev Biophys Biophys Chem 16:139-159 (1987).
Mason et al. CD79a: a novel marker for B-cell neoplasms in routinely processed tissue samples. Blood 86(4):1453-1459 (1995).
Milone et al. Chimeric receptors containing CD137 signal transduction domains mediate enhanced survival of T cells and increased antileukemic efficacy in vivo. Mol Ther 17(8):1453-1464 (2009).
Mirsky et al. Antibody-Specific Model of Amino Acid Substitution for Immunological Inferences from Alignments of Antibody Sequences. Mol. Biol. Evol. 32(3):806-819 (2014).
Müller et al. Improved Pharmacokinetics of Recombinant Bispecific Antibody Molecules by Fusion to Human Serum Albumin. J. Biol. Chem. 282(17):12650-60 (2007).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Muller et al. Improving the pharmacokinetic properties of biologics by fusion to an anti-HSA shark VNAR domain. MAbs 4(6):673-685 (2012).
Mumtaz et al. Design of liposomes for circumventing the reticuloendothelial cells. Glycobiology 5:505-10 (1991).
Muul et al. Persistence and expression of the adenosine deaminase gene for 12 years and immune reaction to gene transfer components: long-term results of the first clinical gene therapy trial. Blood 101(7):2563-2569 (2003).
Muyldermans. Nanobodies: natural single-domain antibodies. Annu Rev Biochem 82:775-797 (2013).
Nacheva et al. Preventing nondesired RNA-primed RNA extension catalyzed by T7 RNA polymerase. Eur J Biochem 270:1458-1465 (2003).
Nazarian et al. Characterization of bispecific T-cell Engager (BiTE) antibodies with a high-capacity T-cell dependent cellular cytotoxicity (TDCC) assay. J Biomol Screen 20:519-527 (2015).
Needleman et al. A general method applicable to the search for similarities in the amino acid sequence of two proteins. J. Mol. Biol. 48:443-453 (1970).
Nelson et al. Antibody fragments Hope and Hype. mAbs 2(1):77-83 (2010).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Nunez-Prado et al. The coming of age of engineered multivalent antibodies. Drug Discovery Today 20(5):588-594 (2015).
Ohiro et al. A homogeneous and noncompetitive immunoassay based on the enhanced fluorescence resonance energy transfer by leucine zipper interaction. Anal Chem 74(22):5786-5792 (2002).

(56) References Cited

OTHER PUBLICATIONS

Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Ordonez. Application of mesothelin immunostaining in tumor diagnosis. Am J Surg Pathol 27:1418-1428 (2003).
Osta et al. EpCAM is overexpressed in breast cancer and is a potential target for breast cancer gene therapy. Cancer Res 64:5818-24 (2004).
Padlan. Anatomy of the Antibody Molecule. Mol Immunol 31(3):169-217 (1994).
Padlan, et al., A possible procedure for reducing the immunogenicity of antibody variable domains while preserving their ligand-binding properties. Mol Immunol 28(4-5):489-498 (1991).
Padlan et al. Structure of an antibody-antigen complex: Crystal structure of the HyHEL-10 Fab-lysozyme complex. PNAS USA 86:5938-5942 (1989).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX. J Immunol 183:749-758 (2009).
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
PCT/US2019/052270 International Search Report and Written Opinion dated Mar. 5, 2020.
PCT/US/2020/032985 International Search Report and Written Opinion dated Oct. 15, 2020.
PCT/US2020/060184 International Search Report and Written Opinion dated Mar. 4, 2021.
Pearson et al. Improved Tools for Biological Sequence Comparison. PNAS USA 85:2444-48 (1988).
Pedersen et al. Comparison of surface accessible residues in human and murine immunoglobulin Fv domains. Implication for humanization of murine antibodies. J Mol Biol 235(3):959-973 (1994).
Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Piyathilake et al. The expression of Ep-CAM (17-1A) in squamous cell cancers of the lung. Hum Pathol. 31:482-487 (2000).
Poczatek et al. Ep-Cam levels in prostatic adenocarcinoma and prostatic intraepithelial neoplasia. J Urol. 162:1462-1464 (1999).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Presta: Antibody Engineering. Curr Op Struct Biol 2:593-596 (1992).
Presta et al. Humanization of an antibody directed against IgE. J Immunol 151:2623-2632 (1993).
Quak et al. Production of a monoclonal antibody (K 931) to a squamous cell carcinoma associated antigen identified as the 17-1A antigen. Hybridoma 9:377-387 (1990).
Ramadoss et al. An Anti-B Cell Maturation Antigen Bispecific Antibody for Multiple Myeloma. J. Ann. Chem. Soc. 137(16):5288-91 (2015).
Riechmann et al. Reshaping human antibodies for therapy. Nature, 332.6162:323-7 (1988).
Riechmann et al. Single domain antibodies: comparison of camel VH and camelised human VH domains. J Immunol Methods 231(1-2):25-38 (1999).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg et al. Use of tumor-infiltrating lymphocytes and interleukin-2 in the immunotherapy of patients with metastatic melanoma. A preliminary report. NEJM 319:1676 (1988).
Rosok et al. A Combinatorial Library Strategy for the Rapid Humanization of Anticarcinoma BR96 Fab. J Biol Chem 271:22611-22618 (1996).
Rossolini et al. Use of deoxyinosine-containing primers vs degenerate primers for polymerase chain reaction based on ambiguous sequence information. Mol Cell Probes 8(2):91-98 (1994).
Rozan et al. Single-domain antibody-based and linker-free bispecific antibodies targeting FcγRIII induce potent antitumor activity without recruiting regulatory T cells. Mol Cancer Ther 12(8):1481-1491 (2013).
Rudikoff et al. Single amino acid substitution altering antigen-binding Specificity. PNAS USA 79:1979-1983 (1982).
Rump et al. Binding of ovarian cancer antigen CA125/MUC16 to mesothelin mediates cell adhesion. J Biol Chem 279:9190-9198 (2004).
Running Deer et al. High-level expression of proteins in mammalian cells using transcription regulatory sequences from the Chinese hamster EF-1alpha gene. Biotechnol Prog. 20:880-889 (2004).
Sadelain et al. Targeting tumours with genetically enhanced T lymphocytes. Nat Rev Cancer 3(1):35-45 (2003).
Sadelain et al. The basic principles of chimeric antigen receptor design. Cancer Discov. 3(4):388-98 (2013).
Saerens et al. Identification of a universal VHH framework to graft non-canonical antigen-binding loops of camel single-domain antibodies. J. Mol. Biol. 352(3):597-607 (2005).
Sandhu. A rapid procedure for the humanization of monoclonal antibodies. Gene 150(2):409-410 (1994).
Sandler et al. Nondermatologic adverse events associated with anti-EGFR therapy. Oncology (Williston Park) 20(5 Suppl 2):35-40 (2006).
Sastry et al. Targeting hepatitis B virus-infected cells with a T-cell receptor-like antibody. J Virol 85(5):1935-1942 (2011).
Schenborn et al. A novel transcription property of SP6 and T7 RNA polymerases: dependence on template structure. Nuc Acids Res 13:6223-6236 (1985).
Scheraga. Predicting three-dimensional structures of oligopeptides. Rev Computational Chem 3:73-142 (1992).
Schmidt et al. Cloning and Characterization of Canine Prostate-Specific Membrane Antigen. The Prostate 73:642-650 (2013).
Schmittgen et al. Expression of prostate specific membrane antigen and three alternatively spliced variants of PSMA in prostate cancer patients. Int J Cancer 107:323-329 (2003).
Sergeeva et al. An anti-PR1/HLA-A2 T-cell receptor-like antibody mediates complement-dependent cytotoxicity against acute myeloid leukemia progenitor cells. Blood 117(16):4262-4272 (2011).
Sheng et al. Novel Transgenic Mouse Model for Studying Human Serum Albumin as a Biomarker of Carcinogenic Exposure. Chem. Res. Toxicol. 29(5):797-809 (2016).
Simon et al. Epithelial glycoprotein is a member of a family of epithelial cell surface antigens homologous to nidogen, a matrix adhesion protein. PNAS USA 87:2755-2759 (1990).
Sims et al. A humanized CD18 antibody can block function without cell destruction. J Immunol. 151:2296-2308 (1993).
Smirnova et al. Identification of new splice variants of the genes BAFF and BCMA. Mol. Immunol. 45 (4):1179-83 (2008).
Smith et al. Comparison of Biosequences. Advances in Applied Mathematics. 2:482-489 (1981).
Song et al. CD27 costimulation augments the survival and antitumor activity of redirected human T cells in vivo. Blood 119(3):696-706 (2012).

(56) References Cited

OTHER PUBLICATIONS

Spiess et al. Alternative molecular formats and therapeutic applications for bispecific antibodies. Mol. Immunol. 67(2 Pt A):95-106 (2015).
Stehle et al. Albumin-based drug carriers: comparison between serum albumins of different species on pharmacokinetics and tumor uptake of the conjugate. Anticancer Drugs. 10(8):785-90 (1999).
Stepinski et al. Synthesis and properties of mRNAs containing the novel 'anti-reverse' cap analogs 7-methyl(3'0-methyl)GpppG and 7-methyl(e'-deoxy)GpppG. RNA 7:1486-1495 (2001).
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.
Stirewalt et al. The role of FLT3 in haematopoietic malignancies. Nat Rev Cancer 3:650-665 (2003).
Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
STROP. Veracity of microbial transglutaminase. Bioconjugate Chem. 25(5):855-862 (2014).
Studnicka et al. Human-engineered monoclonal antibodies retain full specific binding activity by preserving non-CDR complementarity-modulating residues. Pro Eng 7(6):805-814 (1994).
Su et al. PSMA specific single chain antibody-mediated targeted knockdown of Notch1 inhibits human prostate cancer cell proliferation and tumor growth. Cancer Lett. 338 (2): 282-291 (2013).
Tan et al. Influence of the hinge region on complement activation, C1q binding, and segmental flexibility in chimeric human immunoglobulins. PNAS USA 87:162-166 (1990).
Tan et al. "Superhumanized" antibodies: reduction of immunogenic potential by complementarity-determining region grafting with human germline sequences: application to an anti-CD28. J Immunol 169:1119-1125 (2002).
Tang et al. A human single-domain antibody elicits potent antitumor activity by targeting an epitope in mesothelin close to the cancer cell surface. Mol. Cancer Thera 12(4):416-426 (2013).
Tassev et al. Retargeting NK92 cells using an HLA-A2-restricted, EBNA3C-specific chimeric antigen receptor. Cancer Gene Ther 19(2):84-100 (2012).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Thomas. Cetuximab: adverse event profile and recommendations for toxicity management. Clin J Oncol Nurs. 9(3):332-8 (2005).
Thomas et al. Mesothelin-specific CD8(+) T cell responses provide evidence of in vivo cross-priming by antigen-presenting cells in vaccinated pancreatic cancer patients. J Exp Med 200:297-306 (2004).
Tijink et al. Improved tumor targeting of anti-epidermal growth factor receptor nanobodies through albumin binding: taking advantage of modular Nanobody technology. Mol. Cancer Ther. 7(8):2288-97 (2008).
Tiller et al. Facile Affinity Maturation of Antibody Variable Domains Using Natural Diversity Mutagenesis. Front. Immunol. 8:986 (2017).
Trebak et al. Oligomeric state of the colon carcinoma-associated glycoprotein GA733-2 (Ep-CAM/EGP40) and its role in GA733-mediated homotypic cell-cell adhesion. J Biol Chem. 276:2299-2309 (2001).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Ui-Tei et al. Sensitive assay of RNA interference in *Drosophila* and Chinese hamster cultured cells using firefly luciferase gene as target. FEBS Letters 479: 79-82 (2000).
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol biol 310:591-601 (2001).
Van Der Linden et al. Induction of immune responses and molecular cloning of the heavy chain antibody repertoire of Lama glama. J Immunol Methods 240:185-195 (2000).
Vaughan et al. Human antibodies by design. Nature Biotech 16:535-539 (1998).
Verhoeyen et al. Reshaping human antibodies: Grafting an antilysozyme activity. Science 239:1534-1536 (1988).
Verma et al. TCR mimic monoclonal antibody targets a specific peptide/HLA class I complex and significantly impedes tumor growth in vivo using breast cancer models. J Immunol 184(4):2156-2165 (2010).
Vincke et al. General strategy to humanize a camelid single-domain antibody and identification of a universal humanized nanobody scaffold. J. Biol. Chem. 284(5):3273-3284 (2009).
Wang et al. A New Recombinant Single Chain Trispecific Antibody Recruits T Lymphocytes to Kill CEA (Carcinoma Embryonic Antigen) Positive Tumor Cells In Vitro Efficiently. Journal of Biochemistry 135(4):555-565 (2004).
Willemsen et al. A phage display selected fab fragment with MHC class I-restricted specificity for MAGE-A1 allows for retargeting of primary human T lymphocytes. Gene Ther 8(21):1601-1608 (2001).
Winkler et al. Changing the antigen binding specificity by single point mutations of an anti-p24 (HIV-1) antibody. J Immunol. 165(8):4505-4514 (2000).
Wu et al. Humanization of a murine monoclonal antibody by simultaneous optimization of framework and CDR residues. J.Mol. Biol. 294:151-162 (1999).
Yan et al. Engineering upper hinge improves stability and effector function of a human IgG1. J. Biol. Chem. 287:5891 (2012).
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
Yoshinaga et al. Ig L-chain shuffling for affinity maturation of phage library-derived human anti-human MCP-1 antibody blocking its chemotactic activity. J Biochem 143(5):593-601 (2008).
Yu et al. Rationalization and design of the complementarity determining region sequences in an antibody-antigen recognition interface. PLoS One 7(3):e33340 (2012).
Zabetakis et al. Contributions of the complementarity determining regions to the thermal stability of a single-domain antibody. PLoS One 8(10):e77678 (2013).
Zare et al. Production of nanobodies against prostate-specific membrane antigen (PSMA) recognizing LnCaP cells. Int. J. Biol. Markers 29(2):e169-e179 (2014).
Zhang et al. New High Affinity Monoclonal Antibodies Recognize Non-Overlapping Epitopes on Mesothelin for Monitoring and Treating Mesothelioma. Sci Rep 5:9928 (2015).
Zhu et al. Combody: one-domain antibody multimer with improved avidity. Immunology and Cell Biology 88(6):667-675 (2010).
Jiang et al. Protritac: A protease cleavable T cell Engager Platform. Scientific Reports 6(Suppl 1):115 Available at https://calidibio.com/wp-content/uploads/2019/10/609-Abstract-_SITC-2018.pdf (2018).
Kim et al. Strategies and 1-17 Advancement in Antibody-Drug Conjugate Optimization for Targeted Cancer Therapeutics. Biomol Ther (Seoul) 23(6):493-509 (2015).
Lucchi et al. The Masking Game: Design of Activatable Antibodies and Mimetics for Selective Thera-peutics Cell Control. ACS Cent Sci 7(5):724-738 (2021).
PCT/US2016/033644 International Search Report and Written Opinion dated Sep. 6, 2016.
PCT/US2017/033665 International Search Report and Written Opinion dated Oct. 18, 2017.
PCT/US2017/056530 International Search Report and Written Opinion dated Jan. 23, 2018.
PCT/US2017/063121 International Search Report and Written Opinion dated Mar. 26, 2018.

(56) References Cited

OTHER PUBLICATIONS

PCT/US2017/063126 International Search Report and Written Opinion dated Apr. 5, 2018.
PCT/US2018/014396 International Search Report and Written Opinion dated Jun. 14, 2018.
PCT/US2018/020185 International Search Report and Written Opinion dated Jun. 15, 2018.
PCT/US2018/020307 International Search Report and Written Opinion dated Aug. 24, 2018.
PCT/US2018/030983 International Search Report and Written Opinion dated Sep. 25, 2018.
PCT/US2018/032418 International Search Report and Written Opinion dated Sep. 24, 2018.
PCT/US2018/032427 International Search Report and Written Opinion dated Sep. 13, 2018.
PCT/US2018/055659 International Search Report and Written Opinion dated Feb. 21, 2019.
PCT/US2018/055682 International Search Report and Written Opinion dated Mar. 1, 2019.
PCT/US2019/032224 International Search Report and Written Opinion dated Aug. 28, 2019.
PCT/US2019/052206 International Search Report and Written Opinion dated Feb. 14, 2020.
PCT/US2019/053017 International Search Report and Written Opinion dated Jan. 31, 2020.
Trail et al. Antibody drug 1-17 conjugates for treatment of breast cancer: Novel targets and diverse approaches in ADC design. Pharmacol Ther 181:126-142 (2018).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Apr. 25, 2019.
U.S. Appl. No. 15/600,264 Office Action dated Apr. 26, 2018.
U.S. Appl. No. 15/600,264 Office Action dated Nov. 27, 2018.
U.S. Appl. No. 15/600,264 Office Action dated Oct. 3, 2017.
U.S. Appl. No. 15/600,582 Office Action dated Nov. 16, 2017.
U.S. Appl. No. 15/630,259 Office Action dated Dec. 30, 2019.
U.S. Appl. No. 15/630,259 Office Action dated Sep. 30, 2020.
U.S. Appl. No. 15/704,620 Office Action dated Oct. 26, 2017.
U.S. Appl. No. 15/821,498 Office Action dated Apr. 21, 2020.
U.S. Appl. No. 15/821,498 Office Action dated May 3, 2019.
U.S. Appl. No. 15/821,498 Office Action dated Oct. 26, 2018.
U.S. Appl. No. 15/821,530 Office Action dated Apr. 22, 2020.
U.S. Appl. No. 15/821,530 Office Action dated Apr. 3, 2019.
U.S. Appl. No. 15/821,530 Office Action dated Sep. 25, 2018.
U.S. Appl. No. 15/977,968 Office Action dated Feb. 21, 2019.
U.S. Appl. No. 15/977,988 Office Action dated Aug. 20, 2019.
U.S. Appl. No. 15/977,988 Office Action dated Mar. 26, 2019.
U.S. Appl. No. 15/977,988 Pre-Interview First Office Action dated Jan. 25, 2019.
U.S. Appl. No. 16/159,545 Office Action dated Aug. 6, 2019.
U.S. Appl. No. 16/159,545 Office Action dated Dec. 2, 2019.
U.S. Appl. No. 16/159,554 Office Action dated Jun. 7, 2019.
U.S. Appl. No. 16/159,554 Office Action dated Mar. 16, 2021.
U.S. Appl. No. 16/159,554 Office Action dated Oct. 1, 2019.
U.S. Appl. No. 16/159,554 Office Action dated Oct. 5, 2020.
U.S. Appl. No. 16/583,070 Office Action dated Mar. 3, 2020.
Austin et al. TriTACs, a Novel Class of T-Cell-Engaging Protein Constructs Designed for the Treatment of Solid Tumors. Mol Cancer Ther 20(1):109-120 (2021).
Dickopf et al. Format and geometries matter: Structure-based design defines the functionality of bispecific antibodies. Comput Struct Biotechnol J 18:1221-1227 (2020).
Gorshkova et al. Single domain antibodies and bioengineering drugs on their basis: new opportunities for diagnostics and therapy. Medical Immunology (Russia) 18(6):505-520 (2016) (English Abstract).
Lin et al. ProTriTAC: A Protease-Activatable T Cell Engager Platform that Links Half-Life Extension to Functional Masking Society for Immunotherapy of Cancer (SITC) Annual Meeting. Nov. 2018, Available at https://www.harpoontx.com/file.cfm/43/docs/SITC_2018_ProTriTAC_Poster.pdf.
Lv et al. Mesothelin as a biomarker for targeted therapy. Biomark Res 7:18 (2019).
PCT/US2022/019302 International Search Report and Written Opinion dated Jun. 27, 2022.
PCT/US2022/022871 International Search Report and Written Opinion dated Aug. 3, 2022.
Roda-Navarro et al. Understanding the Spatial Topology of Artificial Immunological Synapses Assembled in T Cell-Redirecting Strategies: A Major Issue in Cancer Immunotherapy. Front Cell Dev Biol 7:370 (2020).
U.S. Appl. No. 16/339,263 Office Action dated May 3, 2022.
U.S. Appl. No. 16/773,843 Office Action dated Aug. 11, 2022.

* cited by examiner

EpCAM ProTriTAC (NCLV)

FIG. 30

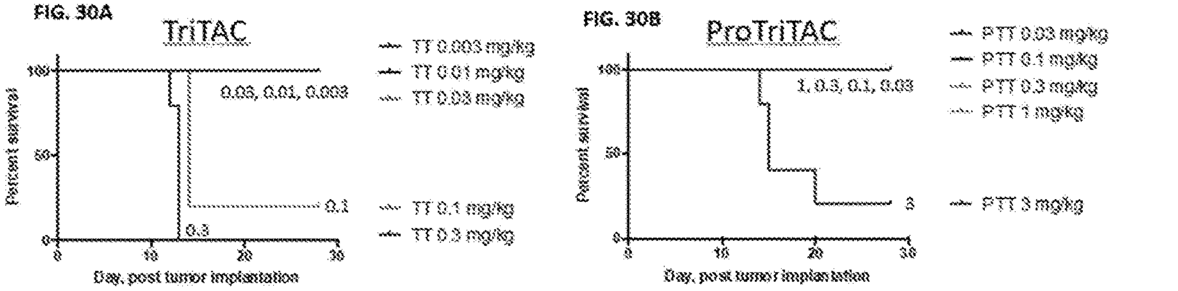

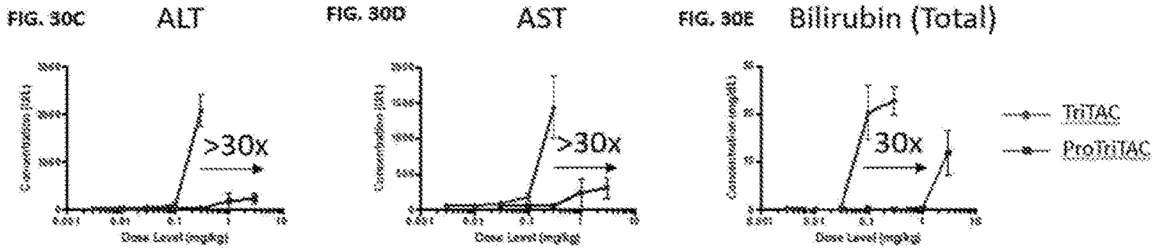

FIG. 31

Mouse Liver Histopathology Scoring

| | GFP TriTAC | TriTAC | | | | | ProTriTAC | | | | |
|---|---|---|---|---|---|---|---|---|---|---|---|
| mg/kg | 0.3 | 0.003 | 0.01 | 0.03 | 0.1 | 0.3 | 0.03 | 0.1 | 0.3 | 1 | 3 |
| Group | F | C | E | A | K | H | D | B | G | I | J |
| Article type | CA | Tri | Tri | Tri | Tri | Tri | Pro | Pro | Pro | Pro | Pro |
| Dose (mg/kg) | 0 | 0.003 | 0.01 | 0.03 | 0.1 | 0.3 | 0.03 | 0.1 | 0.3 | 1.0 | 3.0 |
| No. Animals In Group | 10 | 10 | 10 | 10 | 5 | 5 | 10 | 10 | 5 | 5 | 4 |
| Liver | | | | | | | | | | | |
| Coagulation necrosis (hepatocellular) | (0)* | (0) | (0) | (0) | (5) | (5) | (0) | (0) | (0) | (0) | (4) |
| Minimal | - | - | - | - | 1 | - | - | - | - | - | 1 |
| Mild | - | - | - | - | 2 | 1 | - | - | - | - | 2 |
| Moderate | - | - | - | - | 2 | 3 | - | - | - | - | - |
| Marked | - | - | - | - | - | 1 | - | - | - | - | 1 |
| Portal fibrosis | (1) | (1) | (1) | (1) | (5) | (5) | (2) | (2) | (0) | (0) | (4) |
| Minimal | 1 | 1 | 1 | 1 | 1 | - | 2 | 2 | - | - | - |
| Mild | - | - | - | - | 3 | 1 | - | - | - | - | 2 |
| Moderate | - | - | - | - | 1 | 4 | - | - | - | - | 2 |
| Bile ductule dilation | (0) | (0) | (0) | (0) | (5) | (5) | (0) | (0) | (0) | (0) | (4) |
| Minimal | - | - | - | - | - | - | - | - | - | - | - |
| Mild | - | - | - | - | 3 | 1 | - | - | - | - | 1 |
| Moderate | - | - | - | - | 1 | 1 | - | - | - | - | 2 |
| Marked | - | - | - | - | 1 | - | - | - | - | - | - |
| Severe | - | - | - | - | - | 3 | - | - | - | - | 1 |

* Numbers in parentheses represent the number of animals with the finding.
Tri = TriTAC, Pro = ProTriTAC, CA = Control antibody (anti-GFP TriTAC)

0.1 mg/kg TriTAC = 3 mg/kg ProTriTAC

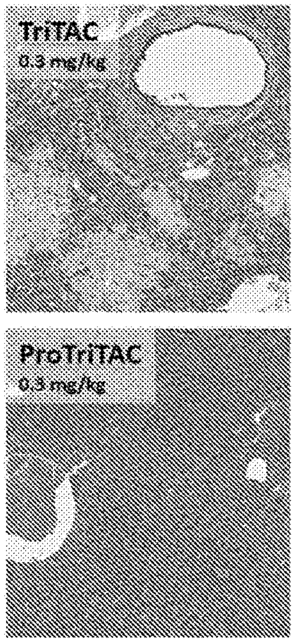

EpCAM BINDING PROTEINS AND METHODS OF USE

CROSS-REFERENCE

This application is the U.S. National Stage Application of PCT Application No. PCT/US2020/032985 filed on May 14, 2020, and claims the benefit of U.S. Provisional Application No. 62/847,778 filed on May 14, 2019, PCT Application No. PCT/US2019/032307 filed on May 14, 2019, PCT Application No. PCT/US2019/032224 filed on May 14, 2019, PCT Application No. PCT/US2019/US032302 filed on May 14, 2019, and PCT Application No. PCT/US2019/032306 filed on May 14, 2019, each incorporated by reference herein in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

Studies have shown that epithelial cell adhesion/activating molecule (EpCAM/CD326) is expressed on essentially all human adenocarcinoma, on certain squamous cell carcinoma, on retinoblastoma, and on hepatocellular carcinoma. See, e.g., Baeuerle P A, Gires O. EpCAM (CD326) finding its role in cancer. EpCAM is part of the signature of cancer-propagating cells in numerous solid tumors and of normal progenitor and stem cells. See Id. EpCAM has been causally implicated in proliferation, migration, and signal transduction in cancers, e.g., in breast cancer. See, e.g., Osta W A, Chen Y, Mikhitarian K, et al. EpCAM is overexpressed in breast cancer and is a potential target for breast cancer gene therapy. Cancer Res 2004; 64:5818-24.

Edrecolomab, an anti-EpCAM antibody showed limited efficacy in the phase III studies. See Eyvazi S, Farajnia S, Dastmalchi S, Kanipour F, Zarredar H, Bandehpour M. Antibody Based EpCAM Targeted Therapy of Cancer, Review and Update. Curr Cancer Drug Targets. 2018; 18(9): 857-868. Other anti-EpCAM antibodies used in various clinical studies include Adecatumumab (a wholly human monoclonal antibody), Catumaxomab (a chimeric antibody), Oportuzumab Monatox (an scFv antibody conjugated to *Pseudomonas* exotoxin A (ETA), Citatuzumab Bogatox (Fab fragment with bouganin toxin), immono-conjugate antibody Tucotuzumab (monoclonal antibody with IL2). See Id.

There is a need for a greater choice of treatment options which allows physicians to select the therapeutic with the best side effect profile for an individual patient. The present disclosure provides novel polypeptides and protein therapeutics useful in methods of treatment, particularly for treatment of conditions associated with abnormal expression of EpCAM.

SUMMARY OF THE INVENTION

One embodiment provides an EpCAM binding domain comprising a complementarity determining region 1 (CDR1), a CDR2, and a CDR3, wherein the CDR1 comprises a sequence selected from the group consisting of SEQ ID Nos. 39-76, or a sequence comprising one or more substitutions in a sequence selected from the group consisting of SEQ ID Nos. 39-76; the CDR2 comprising a sequence selected from the group consisting of SEQ ID Nos. 77-114 or a sequence comprising one or more substitutions in a sequence selected from the group consisting of SEQ ID Nos. 77-114; and the CDR3 comprising a sequence selected from the group consisting of SEQ ID Nos. 115-152 or a sequence comprising one or more substitutions in a sequence selected from the group consisting of SEQ ID Nos. 115-152. In some embodiments, the CDR1 comprises a sequence selected from the group consisting of SEQ ID Nos. 39-76; the CDR2 comprising a sequence selected from the group consisting of SEQ ID Nos. 77-114; and the CDR3 comprising a sequence selected from the group consisting of SEQ ID Nos. 115-152. In some embodiments, the EpCAM binding domain comprises an amino acid sequence that is at least about 75% identical to a sequence selected from the group consisting of SEQ ID Nos. 1-38, 207-209, and 496-497.

In some embodiments, the EpCAM binding domain is part of a multispecific protein. In some embodiments, the multispecific protein further comprises a CD3 binding domain. In some embodiments, the multispecific protein comprises an active drug format. In some embodiments, the multispecific protein further comprises a bulk serum protein binding domain. In some embodiments, the bulk serum protein comprises a serum albumin protein. In some embodiments, the serum albumin protein comprises a human serum albumin protein. In some embodiments, the bulk serum protein binding domain comprises a sequence that is at least 75% identical the sequence as set forth in SEQ ID No. 378. In some embodiments, the CD3 binding domain comprises a sequence that is at least 75% identical the sequence as set forth in SEQ ID No. 379. In some embodiments, the multispecific protein comprises a sequence that is at least about 75% identical to the sequence as set forth in SEQ ID No. 492. In some embodiments, the bulk serum protein binding domain is a binding moiety comprising a linker and a masking moiety, wherein the masking moiety is capable of masking the binding of the EpCAM binding domain or the CD3 binding domain, to their respective targets. In some embodiments, the multispecific protein comprises a non-cleavable prodrug format. In some embodiments, the masking moiety comprises a sequence selected from the group consisting of: SEQ ID Nos. 380-424, or a sequence comprising one or more substitutions in a sequence selected from the group consisting of: SEQ ID Nos. 380-424. In some embodiments, the linker comprises a sequence selected from the group consisting of: SEQ ID Nos. 425-471, 503-507, and 581, or a sequence comprising one or more substitutions in a sequence selected from the group consisting of: SEQ ID Nos. 425-471, 503-507, and 581. In some embodiments, the bulk serum protein binding domain comprises a sequence that is at least 75% identical the sequence selected from the group consisting of SEQ ID Nos. 472-473 and 482-483. In some embodiments, the CD3 binding domain comprises a sequence that is at least 75% identical to the sequence as set forth in SEQ ID No. 474.

In some embodiments, the multispecific protein comprises a sequence that is at least 75% identical to a sequence selected from the group consisting of SEQ ID Nos. 495, 498-502, 569-570, 572, 573, 575, 576, 577, and 578. In some embodiments, the multispecific protein comprises a sequence that is at least 75% identical to a sequence selected from the group consisting of SEQ ID Nos. 495 and 502. In some embodiments, the multispecific protein comprises a sequence that is at least 75% identical to a sequence selected from the group consisting of SEQ ID Nos. 498-501, 569-570, 572, 573, 575, 576, 577, and 578. In some embodiments, the active drug comprises a sequence that is at least 75% identical to a sequence selected from the group consisting of SEQ ID Nos. 153-179, 180-206, 210-212, 494, 571, and 574.

In some embodiments, the EpCAM binding domain is part of a chimeric antigen receptor (a CAR) or a conditionally activatable chimeric antigen receptor (a ProCAR), wherein the CAR further comprises at least one of a transmembrane domain, a costimulatory domain, and an intracellular signaling domain. In some embodiments, the EpCAM binding domain is part of the ProCAR and the ProCAR further comprises (a) a binding moiety comprising a non-CDR loop and a cleavable linker; (b) a transmembrane domain; and (c) an intracellular signaling domain; wherein the binding moiety is capable of masking the binding of the EpCAM binding domain to its target. In some embodiments, the binding moiety further comprises one or more complementarity determining regions (CDRs). In some embodiments, the CDR loop provides a binding site specific for a bulk serum protein. In some embodiments, the bulk serum protein comprises at least one of: a serum albumin, a transferrin, an IgG1, an IgG2, an IgG4, an IgG3, an IgA monomer, a Factor XIII, a fibrinogen, a pentameric IgM. In some embodiments, the bulk serum protein comprises the serum albumin. In some embodiments, the serum albumin is a human serum albumin. In some embodiments, the ProCAR further comprising a costimulatory domain, wherein the costimulatory domain is a functional signaling domain of a protein selected from the group consisting of OX40, CD2, CD27, CD28, CDS, ICAM-1, LFA-1 (CD11a/CD18), ICOS (CD278), and 4-1BB (CD137), and amino acid sequences thereof having at least one but not more than 20 modifications thereto. In some embodiments, the at least one but not more than 20 modifications thereto comprises a modification of an amino acid that mediates cell signaling or a modification of an amino acid that is phosphorylated in response to a ligand binding to the encoded T-cell receptor fusion protein. In some embodiments, the transmembrane domain comprises a transmembrane domain of a protein selected from the group consisting of a TCR alpha chain, a TCR beta chain, a TCR zeta chain, a CD3 epsilon TCR subunit, a CD3 gamma TCR subunit, a CD3 delta TCR subunit, CD45, CD4, CD5, CD8, CD9, CD16, CD22, CD33, CD28, CD37, CD64, CD80, CD86, CD134, CD137, CD154, functional fragments thereof, and amino acid sequences thereof having at least one but not more than 20 modifications thereto. In some embodiments, the intracellular signaling domain is derived from CD3 epsilon CD3 gamma, CD3 delta, CD3 alpha, CD3 beta, or a combination thereof. In some embodiments, the EpCAM binding domain is part of the ProCAR, and wherein the ProCAR comprises a sequence that is at least about 75% identical to a sequence selected from the group consisting of SEQ ID Nos. 485-491.

One embodiment provides a method for the treatment or amelioration of a proliferative disease, or a tumorous disease, comprising the administration of an EpCAM binding domain according to this disclosure, or a pharmaceutical composition comprising the same, to a subject in need thereof. In some embodiments, the subject is human.

One embodiment provides a conditionally active chimeric antigen receptor (ProCAR) that comprises a single polypeptide chain, comprising (a) a binding moiety comprising a non-CDR loop and a cleavable linker; (b) an EpCAM binding domain, wherein the EpCAM binding domain comprises a complementarity determining region 1 (CDR1), a CDR2, and a CDR3, wherein the CDR1 comprises a sequence selected from the group consisting of SEQ ID Nos. 39-76, or a sequence comprising one or more substitutions in a sequence selected from the group consisting of SEQ ID Nos. 39-76; the CDR2 comprising a sequence selected from the group consisting of SEQ ID Nos. 77-114 or a sequence comprising one or more substitutions in a sequence selected from the group consisting of SEQ ID Nos. 77-114; and the CDR3 comprising a sequence selected from the group consisting of SEQ ID Nos. 115-152 or a sequence comprising one or more substitutions in a sequence selected from the group consisting of SEQ ID Nos. 115-152; (c) a transmembrane domain; and (d) an intracellular signaling domain; wherein the binding moiety is capable of masking the binding of the EpCAM binding domain to its target. In some embodiments, the EpCAM binding domain comprises a sequence that is at least about 75% identical to a sequence selected from the group consisting of SEQ ID Nos. 1-38, 207-209, and 496-497.

One embodiment provides a conditionally active EpCAM binding protein comprising a binding moiety (M) which comprises a non-CDR loop, a cleavable linker (L), a first target antigen binding domain (T1), and a second target antigen binding domain (T2), wherein at least one of the first target antigen binding domain (T1) and the second target antigen binding domain (T2) comprises an EpCAM binding domain, wherein the EpCAM binding domain comprises a complementarity determining region 1 (CDR1), a CDR2, and a CDR3, wherein the CDR1 comprises a sequence selected from the group consisting of SEQ ID Nos. 39-76, or a sequence comprising one or more substitutions in a sequence selected from the group consisting of SEQ ID Nos. 39-76; the CDR2 comprising a sequence selected from the group consisting of SEQ ID Nos. 77-114 or a sequence comprising one or more substitutions in a sequence selected from the group consisting of SEQ ID Nos. 77-114; and the CDR3 comprising a sequence selected from the group consisting of SEQ ID Nos. 115-152 or a sequence comprising one or more substitutions in a sequence selected from the group consisting of SEQ ID Nos. 115-152, wherein the non-CDR loop is capable of binding to the EpCAM binding domain or the second target antigen binding domain, and wherein the binding moiety is capable of masking the binding of the EpCAM binding domain or the second target antigen binding domain to its target. In some embodiments, the binding moiety comprises a masking moiety and wherein the masking moiety comprises a sequence selected from the group consisting of SEQ ID Nos. 380-424, or a sequence comprising one or more substitutions relative to a sequence selected from the group consisting of SEQ ID Nos. 380-424. In some embodiments, the linker comprises a sequence selected from the group consisting of: SEQ ID Nos. 425-471, 503-506, and 581, or a sequence comprising one or more substitutions relative to a sequence selected from the group consisting of: SEQ ID Nos. 425-471, 503-506, and 581. In some embodiments, the binding moiety comprises a sequence that is at least 75% identical the sequence selected from the group consisting of SEQ ID Nos. 472-473 and 482-483. In some embodiments, the second target antigen binding domain (T2) comprises a CD3 binding domain. In some embodiments, the CD3 binding domain comprises a sequence that is at least 75% identical to the sequence as set forth in SEQ ID No. 474.

One embodiment provides a method for the treatment or amelioration of a proliferative disease, or a tumorous disease, comprising the administration of a conditionally active chimeric antigen receptor according to this disclosure, or a pharmaceutical composition comprising the same, to a subject in need thereof. In some embodiments, the subject is human. One embodiment provides a method for the treatment or amelioration of a proliferative disease, or a tumorous disease, comprising the administration of a conditionally active EpCAM binding protein according to this disclosure, or a pharmaceutical composition comprising the same, to a subject in need thereof. In some embodiments, the subject is human.

In some embodiments, the binding domain is a humanized antibody or an antigen binding fragment thereof. In some embodiments, the binding domain is a single domain antibody, a VHH domain, a scFv, a VH domain, a VL domain, a Fab, a Fab', a non-Ig domain, a ligand, a knottin, or a small molecule entity. In some embodiments, the binding domain comprises the single domain antibody. In some embodiments, the binding domain binds to EpCAM with a binding affinity (Kd) of about 0.001 nM to about 500 nM. In some embodiments, the binding domain binds to human EpCAM, mouse EpCAM, cynomolgus EpCAM, or a combination thereof. One embodiment provides a multispecific protein comprising an EpCAM binding domain, wherein the EpCAM binding domain is according to this disclosure. In some embodiments, the multispecific protein comprises the EpCAM binding domain according to this disclosure (anti-EpCAM domain), and a CD3 binding domain (anti-CD3 domain). In some embodiments, the anti-EpCAM domain and the anti-CD3 domain are in an anti-EpCAM:anti-CD3 orientation. In some embodiments, the anti-EpCAM domain and the anti-CD3 domain are in an anti-CD3:anti-EpCAM orientation. In some embodiments, the CD3 binding domain (anti-CD3 domain), and an albumin binding domain (anti-ALB domain). In some embodiments, the anti-CD3 domain comprises an amino acid as set forth in SEQ ID No. 379 or SEQ ID No. 474. In some embodiments, the anti-ALB domain comprises an amino acid sequence as set forth in SEQ ID No. 375, SEQ ID No. 472, SEQ ID No. 473, SEQ ID No. 482, or SEQ ID No. 483. In some embodiments, the anti-EpCAM domain, the anti-CD3 domain, and the anti-ALB domain are in an anti-CD3:anti-ALB:anti-EpCAM orientation. In some embodiments, the anti-EpCAM domain, the anti-CD3 domain, and the anti-ALB domain are in an anti-EpCAM:anti-ALB:anti-CD3 orientation. In some embodiments, the anti-EpCAM domain, the anti-CD3 domain, and the anti-ALB domain are in an anti-ALB:anti-EpCAM:anti-CD3 orientation. In some embodiments, the anti-EpCAM domain, the anti-CD3 domain, and the anti-ALB domain are in an anti-CD3:anti-EpCAM:anti-ALB orientation. In some embodiments, the anti-EpCAM domain, the anti-CD3 domain, and the anti-ALB domain are in an anti-ALB:anti-CD3:anti-EpCAM orientation. In some embodiments, the anti-EpCAM domain, the anti-CD3 domain, and the anti-ALB domain are in an anti-EpCAM:anti-CD3:anti-ALB orientation.

One embodiment provides a multivalent protein comprising a sequence as set forth in any one of SEQ ID Nos. 495, 498-502, 569-570, 572, 573, 575, 576, 577, and 578. One embodiment provides an active drug comprising a sequence as set forth in any one of SEQ ID Nos. 494, 571, and 574. One embodiment provides a multivalent protein comprising a sequence as set forth in any one of SEQ ID Nos. 485-491.

One embodiment provides a pharmaceutical composition comprising (i) (a) an EpCAM binding domain according to this disclosure; (i) (b) a conditionally active chimeric antigen receptor according to this disclosure; (i) (c) a conditionally active EpCAM binding protein according to this disclosure; (i) (d) a multispecific protein according to this disclosure; (i) (e) a multivalent protein according to this disclosure; or (i) (f) an active drug according to this disclosure, and (ii) a pharmaceutically acceptable carrier.

One embodiment provides a process for the production of an EpCAM binding domain according to this disclosure, said process comprising culturing a host transformed or transfected with a vector comprising a nucleic acid sequence encoding the EpCAM binding domain according to this disclosure, under conditions allowing the expression of the EpCAM binding domain and recovering and purifying the produced protein from the culture.

One embodiment provides a process for the production of a multispecific protein according to this disclosure, said process comprising culturing a host transformed or transfected with a vector comprising one or more nucleic acid sequences encoding the domains of the multispecific EpCAM binding protein according to this disclosure under conditions allowing the expression of the multispecific protein and recovering and purifying the produced protein from the culture.

One embodiment provides a method for the treatment or amelioration of a proliferative disease, or a tumorous disease, comprising the administration of an EpCAM binding domain according to this disclosure, or a pharmaceutical composition comprising the same, to a subject in need thereof. One embodiment provides a method for the treatment or amelioration of a proliferative disease, or a tumorous disease, comprising the administration of the multispecific protein according to this disclosure, a multivalent protein according to this disclosure, an active drug according to this disclosure, or a pharmaceutical composition according to this disclosure, to a subject in need thereof. In some embodiments, the subject is human. In some embodiments, the method further comprises administration of an agent in combination with an EpCAM binding domain according to this disclosure, a multispecific protein according to this disclosure, a multivalent protein according to this disclosure, an active drug according to this disclosure, or a pharmaceutical composition according to this disclosure. In some embodiments, the EpCAM binding domain selectively binds to tumor cells expressing EpCAM. In some embodiments, the tumorous disease comprises a solid tumor disease. In some embodiments, the solid tumor disease is metastatic. In some embodiments, the tumorous disease comprises at least one of: a colorectal cancer, a prostate cancer, a neuroendocrine cancer, a thyroid cancer, a non-small cell lung cancer, a small cell lung cancer, a gastric cancer, an ovarian cancer, an endometrial cancer, a pancreatic cancer, a biliary track cancer, a gall bladder cancer, an esophageal cancer, a breast cancer, an adenocarcinoma. In some embodiments, the method further comprises administration of an agent in combination with conditionally active chimeric antigen receptor according to this disclosure, a conditionally active EpCAM binding protein according to this disclosure, or a pharmaceutical composition comprising the same. In some embodiments, the EpCAM binding domain selectively binds to tumor cells expressing EpCAM. In some embodiments, the tumorous disease comprises a solid tumor disease. In some embodiments, the solid tumor disease is metastatic. In some embodiments, the tumorous disease is at least one of: a colorectal cancer, a prostate cancer, a neuroendocrine cancer, a thyroid cancer, a non-small cell lung cancer, a small cell lung cancer, a gastric cancer, an ovarian cancer, an endometrial cancer, a pancreatic cancer, a biliary track cancer, a gall bladder cancer, an esophageal cancer, a breast cancer, an adenocarcinoma.

One embodiment provides a process for the production of a conditionally active chimeric antigen receptor according to this disclosure, said process comprising culturing a host transformed or transfected with a vector comprising a nucleic acid sequence encoding the conditionally active chimeric antigen receptor according to this disclosure, under conditions allowing the expression of the conditionally active chimeric antigen receptor and recovering and purifying the produced protein from the culture. One embodiment provides a process for the production of a conditionally active EpCAM binding protein according to this disclosure, said process comprising culturing a host transformed or transfected with a vector comprising one or more nucleic acid sequences encoding the domains of the conditionally active EpCAM binding protein according to this disclosure, under conditions allowing the expression of the conditionally active EpCAM binding protein and recovering and purifying the produced protein from the culture. One embodiment provides a process for the production of a multivalent protein according this disclosure, said process comprising culturing a host transformed or transfected with a vector comprising one or more nucleic acid sequences encoding the domains of the multivalent protein according to this disclosure, under conditions allowing the expression of the multivalent protein and recovering and purifying the produced protein from the culture. One embodiment provides a process for the production of an active drug according to this disclosure, said process comprising culturing a host transformed or transfected with a vector comprising one or more nucleic acid sequences encoding the domains of the active drug according to this disclosure, under conditions allowing the expression of the active drug and recovering and purifying the produced drug from the culture.

One embodiment provides a cell comprising a CAR according to this disclosure. One embodiment provides a cell comprising a ProCAR according to this disclosure. In some embodiments, the cell is a T cell or an NK cell. One embodiment provides a method comprising transfecting a cell according to this disclosure, with a vector or an RNA comprising a nucleotide sequence encoding the CAR or the ProCAR.

One embodiment provides a conditionally active chimeric antigen receptor that has a greater therapeutic index compared to a chimeric antigen receptor (CAR) that does not comprise the (a) binding moiety but is otherwise identical to the conditionally active chimeric antigen receptor. In some embodiments, the conditionally active chimeric antigen receptor has a therapeutic index that is at least about 5-fold to about 100-fold greater than that of a chimeric antigen receptor (CAR) that does not comprise the (a) binding moiety but is otherwise identical to the conditionally active chimeric antigen receptor. In some embodiments, the protein comprises a sequence that is at least about 75% identical to a sequence selected from the group consisting of SEQ ID Nos. 498-501, 569-570, 572, 573, 575, 576, 577, and 578. In some embodiments, the protein comprises a sequence that is at least about 75% identical to the sequence of SEQ ID No. 576. In some embodiments, the protein comprises a sequence as set forth in SEQ ID No. 576. In some embodiments, the conditionally active EpCAM binding protein has a greater therapeutic index compared to an EpCAM binding protein that does not comprise the binding moiety (M) or the cleavable linker (L) but is otherwise identical to the conditionally active EpCAM binding protein. In some embodiments, the conditionally active EpCAM binding protein has a therapeutic index that is at least about 5-fold to about 100-fold greater than that of an EpCAM binding protein that does not comprise the binding moiety (M) or the cleavable linker (L) but is otherwise identical to the conditionally active EpCAM binding protein.

One embodiment provides a pharmaceutical composition comprising: (i) (a) a conditionally active chimeric antigen receptor according to this disclosure; or (i) (b) a conditionally active EpCAM binding protein according to this disclosure, and (ii) a pharmaceutically acceptable carrier.

One embodiment provides a method of for the treatment or amelioration of a proliferative disease, or a tumorous disease, comprising the administration of the conditionally active chimeric antigen receptor according to this disclosure, or a pharmaceutical composition comprising the same, to a subject in need thereof.

One embodiment provides a method of for the treatment or amelioration of a proliferative disease, or a tumorous disease, comprising the administration of the conditionally active EpCAM binding protein according to this disclosure, or a pharmaceutical composition comprising the same, to a subject in need thereof. In some embodiments, the subject is human. In some embodiments, the tumorous disease comprises at least one of: a colorectal cancer, a prostate cancer, a neuroendocrine cancer, a thyroid cancer, a non-small cell lung cancer, a small cell lung cancer, a gastric cancer, an ovarian cancer, an endometrial cancer, a pancreatic cancer, a biliary track cancer, a gall bladder cancer, an esophageal cancer, a breast cancer, an adenocarcinoma.

One embodiment provides a method of increasing a therapeutic index of an EpCAM binding domain, the method comprising conjugating the EpCAM binding domain to a binding moiety comprising a cleavable linker and a non-CDR loop, wherein the non-CDR loop comprises a binding site specific for the EpCAM binding domain, wherein the EpCAM binding domain is masked from binding its target by the binding moiety, wherein the EpCAM binding domain is able to bind its target upon cleavage of the cleavable linker.

In some embodiments, the EpCAM binding domain comprises a complementarity determining region 1 (CDR1), a CDR2, and a CDR3, wherein the CDR1 comprises a sequence selected from the group consisting of SEQ ID Nos. 39-76, or a sequence comprising one or more substitutions in a sequence selected from the group consisting of SEQ ID Nos. 39-76; the CDR2 comprising a sequence selected from the group consisting of SEQ ID Nos. 77-114 or a sequence comprising one or more substitutions in a sequence selected from the group consisting of SEQ ID Nos. 77-114; and the CDR3 comprising a sequence selected from the group consisting of SEQ ID Nos. 115-152 or a sequence comprising one or more substitutions in a sequence selected from the group consisting of SEQ ID Nos. 115-152. In some embodiments, the EpCAM binding domain conjugated to the binding moiety is part of a conditionally active multispecific protein, wherein the multispecific protein further comprises a CD3 binding domain. In some embodiments, the binding moiety comprises a sequence that is at least about 75% identical to a sequence selected from the group consisting of SEQ ID Nos. 472-473 and 482-483. In some embodiments, the CD3 binding domain comprises a sequence that is at least about 75% identical to a sequence selected from the group consisting of SEQ ID No. 379 and 474. In some embodiments, the cleavable linker comprises a sequence selected from the group consisting of: SEQ ID Nos. 425-471, 503-506, and 581, or a sequence comprising one or more substitutions in a sequence selected from the group consisting of: SEQ ID Nos. 425-471, 503-506, and 581.

In some embodiments, the EpCAM binding domain comprises a sequence that is at least 75% identical to a sequence selected from the group consisting of SEQ ID Nos. 1-38, 207-209, and 496-497. In some embodiments, the conditionally active multispecific protein comprises a sequence that is at least 75% identical to a sequence selected from the group consisting of SEQ ID Nos. 498-501, 569-570, 572, 573, 575, 576, 577, and 578. In some embodiments, the conditionally active multispecific protein comprises a sequence that is at least 75% identical to SEQ ID No. 576. In some embodiments, the conditionally active multispecific protein comprises a sequence as set forth in SEQ ID No. 576. In some embodiments, the EpCAM binding domain conjugated to the binding moiety is part of a conditionally active chimeric antigen receptor, wherein the conditionally active chimeric antigen receptor further comprises at least one of: a transmembrane domain, an intracellular signaling domain, and a costimulatory domain. In some embodiments, the EpCAM binding domain comprises a complementarity determining region 1 (CDR1), a CDR2, and a CDR3, wherein the CDR1 comprises a sequence selected from the group consisting of SEQ ID Nos. 39-76, or a sequence comprising one or more substitutions in a sequence selected from the group consisting of SEQ ID Nos. 39-76; the CDR2 comprising a sequence selected from the group consisting of SEQ ID Nos. 77-114 or a sequence comprising one or more substitutions in a sequence selected from the group consisting of SEQ ID Nos. 77-114; and the CDR3 comprising a sequence selected from the group consisting of SEQ ID Nos. 115-152 or a sequence comprising one or more substitutions in a sequence selected from the group consisting of SEQ ID Nos. 115-152. In some embodiments, the binding moiety comprises a sequence that is at least about 75% identical to a sequence selected from the group consisting of SEQ ID Nos. 472-473 and 482-483. In some embodiments, the EpCAM binding domain comprises a sequence that is at least 75% identical to a sequence selected from the group consisting of SEQ ID Nos. 1-38, 207-209, and 496-497. In some embodiments, the conditionally active chimeric antigen receptor comprises a sequence that is at least about 75% identical to a sequence selected from the group consisting of SEQ ID Nos. 485-491.

One embodiment provides a method of increasing a therapeutic index of an EpCAM binding protein comprising a first target antigen binding domain and a second target antigen binding domain, wherein at least one of the first and the second target antigen binding domain comprises an EpCAM binding domain, the method comprising conjugating the first or the second target antigen binding domain to a binding moiety comprising a cleavable linker and a non-CDR loop,

- wherein the non-CDR loop comprises a binding site specific for the first or the second target antigen binding domain,
- wherein at least one of the first or the second target antigen binding domain is masked from binding its target by the binding moiety, and
- wherein the first or the second target antigen binding domain that is masked, is able to bind its target upon cleavage of the cleavable linker.

In some embodiments, the EpCAM binding domain comprises a complementarity determining region 1 (CDR1), a CDR2, and a CDR3, wherein the CDR1 comprises a sequence selected from the group consisting of SEQ ID Nos. 39-76, or a sequence comprising one or more substitutions in a sequence selected from the group consisting of SEQ ID Nos. 39-76; the CDR2 comprising a sequence selected from the group consisting of SEQ ID Nos. 77-114 or a sequence comprising one or more substitutions in a sequence selected from the group consisting of SEQ ID Nos. 77-114; and the CDR3 comprising a sequence selected from the group consisting of SEQ ID Nos. 115-152 or a sequence comprising one or more substitutions in a sequence selected from the group consisting of SEQ ID Nos. 115-152. In some embodiments, the non-CDR loop comprises a binding site specific for the EpCAM binding domain. In some embodiments, at least one of the first or the second target antigen binding domain comprises a CD3 binding domain. In some embodiments, the non-CDR loop comprises a binding site specific for the CD3 binding domain. In some embodiments, the CD3 binding domain comprises a sequence that is at least about 75% identical to SEQ ID No. 474. In some embodiments, the binding moiety comprises a sequence that is at least about 75% identical to a sequence selected from the group consisting of SEQ ID Nos. 472-473 and 482-483. In some embodiments, the EpCAM binding domain comprises a sequence that is at least 75% identical to a sequence selected from the group consisting of SEQ ID Nos. 1-38, 207-209, and 496-497. In some embodiments, the cleavable linker comprises a sequence selected from the group consisting of: SEQ ID Nos. 425-471, 503-506, and 581, or a sequence comprising one or more substitutions in a sequence selected from the group consisting of: SEQ ID Nos. 425-471, 503-506, and 581. In some embodiments, the conditionally active multispecific protein comprises a sequence that is at least 75% identical to a sequence selected from the group consisting of SEQ ID Nos. 498-501, 569-570, 572, 573, 575, 576, 577, and 578. In some embodiments, the conditionally active multispecific protein comprises a sequence that is at least 75% identical to SEQ ID No. 576. In some embodiments, the conditionally active multispecific protein comprises a as set forth in SEQ ID No. 576.

One embodiment provides a method of increasing a therapeutic index of an EpCAM binding protein comprising an EpCAM binding domain and a CD3 binding domain, the method comprising conjugating CD3 binding domain to a binding moiety comprising a cleavable linker and a non-CDR loop, wherein the non-CDR loop comprises a binding site specific for CD3 binding domain. In some embodiments, the EpCAM binding domain comprises a complementarity determining region 1 (CDR1), a CDR2, and a CDR3, wherein the CDR1 comprises a sequence selected from the group consisting of SEQ ID Nos. 39-76, or a sequence comprising one or more substitutions in a sequence selected from the group consisting of SEQ ID Nos. 39-76; the CDR2 comprising a sequence selected from the group consisting of SEQ ID Nos. 77-114 or a sequence comprising one or more substitutions in a sequence selected from the group consisting of SEQ ID Nos. 77-114; and the CDR3 comprising a sequence selected from the group consisting of SEQ ID Nos. 115-152 or a sequence comprising one or more substitutions in a sequence selected from the group consisting of SEQ ID Nos. 115-152. In some embodiments, the CD3 binding domain comprises a sequence that is at least about 75% identical to SEQ ID No. 474. In some embodiments, the binding moiety comprises a sequence that is at least about 75% identical to a sequence selected from the group consisting of SEQ ID Nos. 472-473 and 482-483. In some embodiments, the EpCAM binding domain comprises a sequence that is at least 75% identical to a sequence selected from the group consisting of SEQ ID Nos. 1-38, 207-209, and 496-497. In some embodiments, the cleavable linker comprises a sequence selected from the group consisting of:

SEQ ID Nos. 425-471, 503-506, and 581, or a sequence comprising one or more substitutions in a sequence selected from the group consisting of: SEQ ID Nos. 425-471, 503-506, and 581. In some embodiments, the conditionally active multispecific protein comprises a sequence that is at least 75% identical to a sequence selected from the group consisting of SEQ ID Nos. 498-501, 569-570, 572, 573, 575, 576, 577, and 578. In some embodiments, the conditionally active multispecific protein comprises a sequence that is at least 75% identical to SEQ ID No. 576. In some embodiments, the conditionally active multispecific protein comprises a as set forth in SEQ ID No. 576.

One embodiment provides an EpCAM targeting conditionally active multispecific protein, comprising: an EpCAM binding domain, a CD3 binding domain, an albumin binding domain, wherein the albumin binding domain comprises a non-CDR loops that comprises a binding site specific for the CD3 binding domain and a cleavable linker, wherein the EpCAM binding domain comprises a complementarity determining region 1 (CDR1), a CDR2, and a CDR3, wherein the CDR1 comprises a sequence selected from the group consisting of SEQ ID Nos. 39-76, or a sequence comprising one or more substitutions in a sequence selected from the group consisting of SEQ ID Nos. 39-76; the CDR2 comprising a sequence selected from the group consisting of SEQ ID Nos. 77-114 or a sequence comprising one or more substitutions in a sequence selected from the group consisting of SEQ ID Nos. 77-114; and the CDR3 comprising a sequence selected from the group consisting of SEQ ID Nos. 115-152 or a sequence comprising one or more substitutions in a sequence selected from the group consisting of SEQ ID Nos. 115-152. In some embodiments, the albumin binding domain comprises a sequence that is at least about 75% identical to a sequence selected from the group consisting of SEQ ID Nos. 472-473 and 482-483. In some embodiments, the EpCAM binding domain comprises a sequence that is at least 75% identical to a sequence selected from the group consisting of SEQ ID Nos. 1-38, 207-209, and 496-497. In some embodiments, the cleavable linker comprises a sequence selected from the group consisting of: SEQ ID Nos. 425-471, 503-506, and 581, or a sequence comprising one or more substitutions in a sequence selected from the group consisting of: SEQ ID Nos. 425-471, 503-506, and 581. In some embodiments, the conditionally active multispecific protein comprises a sequence that is at least 75% identical to a sequence selected from the group consisting of SEQ ID Nos. 498-501, 569-570, 572, 573, 575, 576, 577, and 578. In some embodiments, the conditionally active multispecific protein comprises a sequence that is at least 75% identical to SEQ ID No. 576. In some embodiments, the conditionally active multispecific protein comprises a as set forth in SEQ ID No. 576.

One embodiment provides a pharmaceutical composition comprising an EpCAM targeting conditionally active multispecific protein of this disclosure. In some embodiments, the pharmaceutical composition further comprises a pharmaceutically acceptable carrier. One embodiment provides a process for the production of EpCAM targeting conditionally active multispecific protein of this disclosure, said process comprising culturing a host transformed or transfected with a vector comprising one or more nucleic acid sequences encoding the domains of the EpCAM targeting conditionally active multispecific protein this disclosure, under conditions allowing the expression of the EpCAM targeting conditionally active multispecific protein and recovering and purifying the produced protein from the culture.

One embodiment provides a method for the treatment or amelioration of a proliferative disease, or a tumorous disease, comprising the administration of an of EpCAM targeting conditionally active multispecific protein of this disclosure, or a pharmaceutical composition comprising the same, to a subject in need thereof. In some embodiments, the tumorous disease comprises a solid tumor disease. In some embodiments, the solid tumor disease is metastatic. In some embodiments, the tumorous disease comprises at least one of: a colorectal cancer, a prostate cancer, a neuroendocrine cancer, a thyroid cancer, a non-small cell lung cancer, a small cell lung cancer, a gastric cancer, an ovarian cancer, an endometrial cancer, a pancreatic cancer, a biliary track cancer, a gall bladder cancer, an esophageal cancer, a breast cancer, an adenocarcinoma.

One embodiment provides an EpCAM binding domain comprising a sequence that is at least about 75% identical to a sequence selected from the group consisting of SEQ ID Nos. 1-38. In some embodiments, the EpCAM binding domain comprises a CDR1, a CDR2, and a CDR3. In some embodiments, the CDR1 comprises a sequence selected from the group consisting of SEQ ID Nos. 39-76, or one or more amino acid substitutions relative to a sequence selected from the group consisting of SEQ ID Nos. 39-76. In some embodiments, the CDR2 comprises a sequence selected from the group consisting of SEQ ID Nos. 77-114, or one or more amino acid substitutions relative to a sequence selected from the group consisting of SEQ ID Nos. 77-114. In some embodiments, the CDR3 comprises a sequence selected from the group consisting of SEQ ID Nos. 115-152, or one or more substitutions relative to a sequence selected from SEQ ID Nos. 115-152. In some embodiments, the EpCAM binding domain comprises a sequence that is at least about 75% identical to a sequence selected from the group consisting of SEQ ID Nos. 1-38. In some embodiments, the EpCAM binding domain comprises a sequence selected from the group consisting of SEQ ID Nos. 1-38. In some embodiments, the EpCAM binding domain is a humanized antibody or an antigen binding fragment thereof. In some embodiments, the EpCAM binding domain is a single domain antibody, a VHH domain, a scFv, a VH domain, a VL domain, a Fab, a Fab', a non-Ig domain, a ligand, a knottin, or a small molecule entity. In some embodiments, the EpCAM binding domain comprises the single domain antibody. In some embodiments, the binding domain binds to EpCAM with a binding affinity (Kd) of about 0.001 nM to about 500 nM. In some embodiments, the EpCAM binding domain binds to human EpCAM, mouse EpCAM, cynomolgus EpCAM, or a combination thereof.

One embodiment provides a multispecific protein comprising an EpCAM binding domain, wherein the EpCAM binding domain is according to this disclosure. In some embodiments, the multispecific protein comprises the EpCAM binding domain according to this disclosure (anti-EpCAM domain), and a CD3 binding domain (anti-CD3 domain). In some embodiments, the anti-EpCAM domain and the anti-CD3 domain are in an anti-EpCAM:anti-CD3 orientation. In some embodiments, the anti-EpCAM domain and the anti-CD3 domain are in an anti-CD3:anti-EpCAM orientation. In some embodiments, the multispecific protein comprises an EpCAM binding domain according to this disclosure (anti-EpCAM domain), the CD3 binding domain (anti-CD3 domain), and an albumin binding domain (anti-ALB domain). In some embodiments, the anti-CD3 domain comprises an amino acid as set forth in SEQ ID No. 379 or SEQ ID No. 474. In some embodiments, the anti-ALB domain comprises an amino acid sequence as set forth in SEQ ID No. 375, SEQ ID No. 472, SEQ ID No. 473, SEQ ID No. 482, or SEQ ID No. 483. In some embodiments, the anti-EpCAM domain, the anti-CD3 domain, and the anti-ALB domain are in an anti-CD3:anti-ALB:anti-EpCAM orientation. In some embodiments, the anti-EpCAM domain, the anti-CD3 domain, and the anti-ALB domain are in an anti-EpCAM:anti-ALB:anti-CD3 orientation. In some embodiments, the anti-EpCAM domain, the anti-CD3 domain, and the anti-ALB domain are in an anti-ALB:anti-EpCAM:anti-CD3 orientation. In some embodiments, the anti-EpCAM domain, the anti-CD3 domain, and the anti-ALB domain are in an anti-ALB:anti-EpCAM:anti-CD3 orientation. In some embodiments, the anti-EpCAM domain, the anti-CD3 domain, and the anti-ALB domain are in an anti-CD3:anti-EpCAM:anti-ALB orientation. In some embodiments, the anti-EpCAM domain, the anti-CD3 domain, and the anti-ALB domain are in an anti-ALB:anti-CD3:anti-EpCAM orientation. In some embodiments, the anti-EpCAM domain, the anti-CD3 domain, and the anti-ALB domain are in an anti-EpCAM:anti-CD3:anti-ALB orientation.

One embodiment provides a multivalent protein comprising a sequence as set forth in any one of SEQ ID Nos. 485-491. One embodiment provides a pharmaceutical composition comprising (i) (a) an EpCAM binding domain according to this disclosure, (i) (b) a multispecific protein according to this disclosure, or (i) (c) a multivalent protein according to this disclosure; and (ii) a pharmaceutically acceptable carrier.

One embodiment a process for the production of an EpCAM binding domain according to this disclosure, said process comprising culturing a host transformed or transfected with a vector comprising a nucleic acid sequence encoding the EpCAM binding domain according to this disclosure under conditions allowing the expression of the EpCAM binding domain and recovering and purifying the produced protein from the culture. One embodiment provides a process for the production of a multispecific protein according to any this disclosure, said process comprising culturing a host transformed or transfected with a vector comprising one or more nucleic acid sequences encoding the domains of the multispecific EpCAM binding protein according to this disclosure under conditions allowing the expression of the multispecific protein and recovering and purifying the produced protein from the culture.

One embodiment provides a method for the treatment or amelioration of a proliferative disease, or a tumorous disease, comprising the administration of an EpCAM binding domain according to this disclosure, or a pharmaceutical composition according to this disclosure, to a subject in need thereof.

One embodiment provides a method for the treatment or amelioration of a proliferative disease, or a tumorous disease, comprising the administration of the multispecific protein according to this disclosure, a multivalent protein according to this disclosure, or a pharmaceutical composition according to this disclosure, to a subject in need thereof. In some embodiments, the subject is human. In some embodiments, the method further comprises administration of an agent in combination with an EpCAM binding domain according to this disclosure, a multispecific protein according to this disclosure, a multivalent protein according this disclosure, or a pharmaceutical composition according to this disclosure. In some embodiments, the EpCAM binding domain selectively binds to tumor cells expressing EpCAM. In some embodiments, the tumorous disease comprises a solid tumor disease. In some embodiments, the solid tumor disease is metastatic.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 22A shows the results for CAPAN2 cells; FIG. 22B shows the results for DMS53 cells, FIG. 22C shows the results for HepG2 cells; FIG. 22D shows the results for KMRC3 cells; FIG. 22E shows the results for MDAPCA2b cells; FIG. 22F shows the results for OVCAR8 cells; FIG. 22G shows the results for PECAPJ41 cells; FIG. 22H shows the results for SKBR3 cells.

FIG. 24A illustrates IFN-gamma levels; FIG. 24B illustrates IL-2 levels; FIG. 24C illustrates IL-6 levels, and FIG. 24D illustrates IL-10 levels.

FIG. 29A shows results for control TriTAC; FIG. 29B shows the results for EpCAM TriTAC at 0.003 mg/kg; FIG. 29C shows the results for EpCAM TriTAC at 0.01 mg/kg; FIG. 29D shows the results for EpCAM TriTAC at 0.03 mg/kg; FIG. 29E shows the results for EpCAM TriTAC at 0.1 mg/kg; FIG. 29F shows the results for EpCAM TriTAC at 0.1 mg/kg; FIG. 29G shows the results for EpCAM ProTriTAC at 0.03 mg/kg; FIG. 29H shows the results for EpCAM ProTriTAC at 0.1 mg/kg; FIG. 29I shows the results for EpCAM ProTriTAC at 0.3 mg/kg; FIG. 29J shows the results for EpCAM ProTriTAC at 1 mg/kg; and FIG. 29K shows the results for EpCAM ProTriTAC at 3 mg/kg.

FIGS. 30A-30E show percent survival (FIGS. 30A-30B), alanine transaminase (ALT) (FIG. 30C), aspartate transaminase (AST) (FIG. 30D), and total bilirubin (FIG. 30E) levels following administering a ProTriTAC or TriTAC versions containing EpCAM binding domain.

FIG. 31 shows the results and summary for a histopathological study using a control GFP TriTAC, an EpCAM TriTAC, or an EpCAM ProTriTAC.

DETAILED DESCRIPTION OF THE INVENTION

Figure 32:
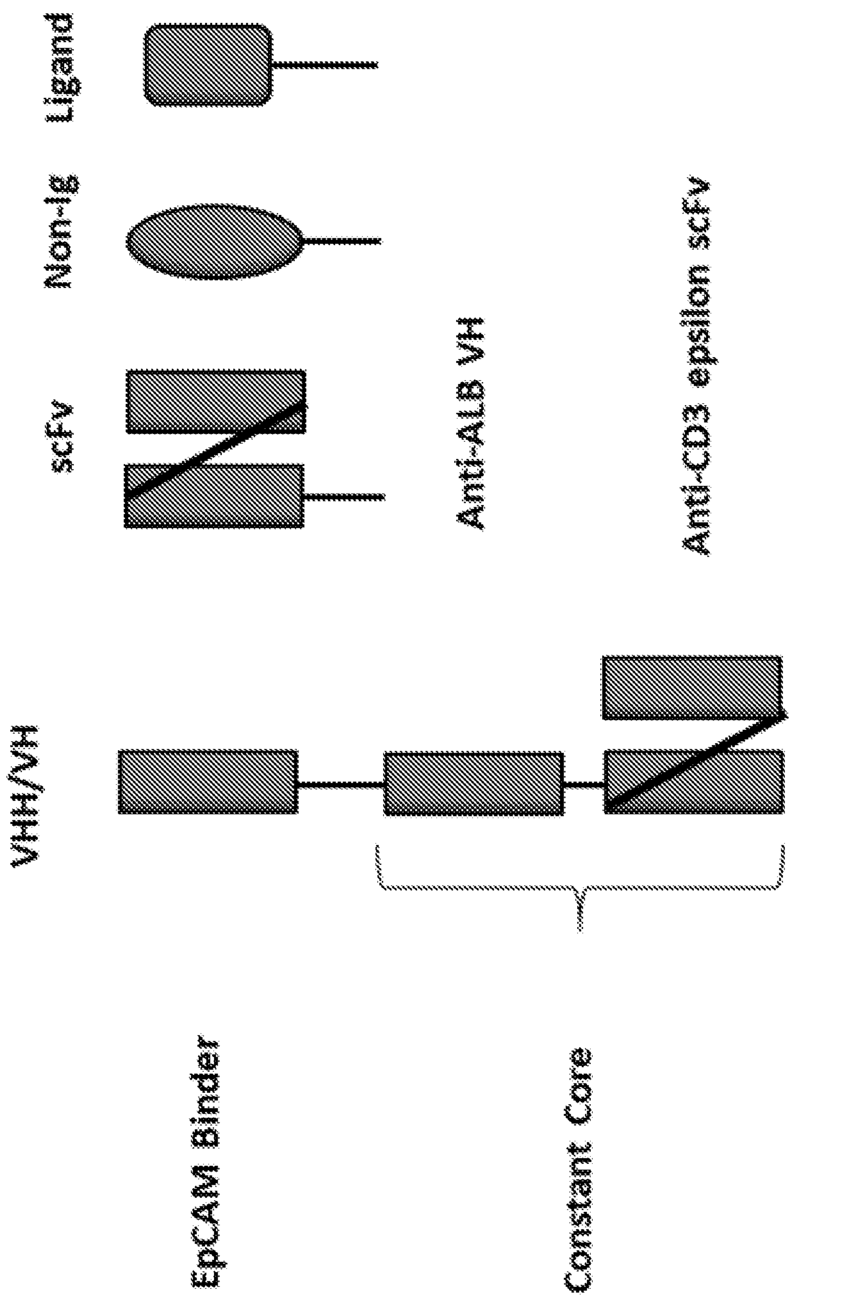
FIG. 32 provides a schematic representation of an EpCAM targeting trispecific protein.

Described herein are trispecific proteins that target EpCAM, pharmaceutical compositions thereof, as well as nucleic acids, recombinant expression vectors and host cells for making such proteins thereof. Also provided are methods of using the disclosed EpCAM targeting trispecific proteins in the prevention, and/or treatment of diseases, conditions and disorders. The EpCAM targeting trispecific proteins are capable of specifically binding to EpCAM as well as CD3 and have a half-life extension domain, such as a domain binding to human albumin (ALB). FIG. 32 depicts one non-limiting example of a trispecific EpCAM-binding protein.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

An "antibody" typically refers to a Y-shaped tetrameric protein comprising two heavy (H) and two light (L) polypeptide chains held together by covalent disulfide bonds and non-covalent interactions. Human light chains comprise a variable domain (VL) and a constant domain (CL) wherein the constant domain may be readily classified as kappa or lambda based on amino acid sequence and gene loci. Each heavy chain comprises one variable domain (VH) and a constant region, which in the case of IgG, IgA, and IgD, comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (generally from about 10 to about 60 amino acids in IgG). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues. There are two types of native disulfide bridges or bonds in immunoglobulin molecules: interchain and intrachain disulfide bonds. The location and number of interchain disulfide bonds vary according to the immunoglobulin class and species. Interchain disulfide bonds are located on the surface of the immunoglobulin, are accessible to solvent and are usually relatively easily reduced. In the human IgG1 isotype there are four interchain disulfide bonds, one from each heavy chain to the light chain and two between the heavy chains. The interchain disulfide bonds are not required for chain association. As is well known the cysteine rich IgG1 hinge region of the heavy chain has generally been held to consist of three parts: an upper hinge, a core hinge, and a lower hinge. Those skilled in the art will appreciate that that the IgG1 hinge region contain the cysteines in the heavy chain that comprise the interchain disulfide bonds (two heavy/heavy, two heavy/light), which provide structural flexibility that facilitates Fab movements. The interchain disulfide bond between the light and heavy chain of IgG1 are formed between C214 of the kappa or lambda light chain and C220 in the upper hinge region of the heavy chain. The interchain disulfide bonds between the heavy chains are at positions C226 and C229 (all numbered per the EU index according to Kabat, et al., infra.)

As used herein the term "antibody" includes polyclonal antibodies, multiclonal antibodies, monoclonal antibodies, chimeric antibodies, deimmunized, humanized and primatized antibodies, CDR grafted antibodies, human antibodies, recombinantly produced antibodies, intrabodies, multispecific antibodies, bispecific antibodies, monovalent antibodies (e.g., a monovalent IgG), multivalent antibodies, anti-idiotypic antibodies, synthetic antibodies, including muteins and variants thereof, immunospecific antibody fragments such as: hcIgG, a V-NAR, Fv, Fd, Fab, F(ab')2, F(ab'), Fab2, Fab3 fragments, single-chain fragments (e.g., di-scFv, scFv, scFvFc, scFv-zipper, scFab), disulfide-linked Fvs (sdFv), a Fd fragment consisting of the VH and CH1 domains, linear antibodies, single domain antibodies such as nanobodies or single variable domain antibodies comprising merely one variable domain such as sdAb (VH, VL, or VHH domains), "r IgG" ("half antibody"), diabodies, single chain diabodies, tandem diabodies (Tandab's), tandem di-scFv, tandem tri-scFv, "minibodies" are in some instances exemplified by a structure which is as follows: (VH-VL-CH3)2, (scFv-CH3) 2, ((scFv)2-CH3+CH3), ((scFv)2-CH3) or (scFv-CH3-scFv) 2, multibodies such as triabodies or tetrabodies, and derivatives thereof including Fc fusions and other modifications, and any other immunoreactive molecule so long as it comprises a domain having a binding site for preferential association or binding with an EpCAM-protein. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). Heavy-chain constant domains that correspond to the different classes of antibodies are typically denoted by the corresponding lower case Greek letter alpha, delta, epsilon, gamma, and mu, respectively. Light chains of the antibodies from any vertebrate species can be assigned to one of two clearly distinct types, called kappa (kappa) and lambda (lambda), based on the amino acid sequences of their constant domains. In some embodiments, the EpCAM binding proteins comprise a heavy chain only antibody, such as a VH or a VHH domain. In some cases, the EpCAM binding proteins comprise a heavy chain only antibody that is an engineered human VH domain. In some examples, the engineered human VH domain is produced by panning of phage display libraries. In some embodiments, the EpCAM binding proteins comprise a VHH. The term "VHH," as used herein, refers to single chain antibody binding domain devoid of light chain. In some cases, a VHH is derived from an antibody of the type that can be found in Camelidae or cartilaginous fish which are naturally devoid of light chains or to a synthetic and non-immunized VHH which can be constructed accordingly. Each heavy chain comprises a variable region encoded by V-, D- and J exons. A VHH, in some cases, is a natural VHH, such as a Camelid-derived VHH, or a recombinant protein comprising a heavy chain variable domain. In some embodiments, the VHH is derived from a species selected from the group consisting of camels, llamas, vicunas, guanacos, and cartilaginous fish (such as, but not limited to, sharks). In another embodiment, the VHH is derived from an alpaca (such as, but not limited to, a Huacaya Alpaca or a Suri alpaca).

As used herein, "Variable region" or "variable domain" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the Bsheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. The assignment of amino acids to each domain, framework region and CDR is, in some embodiments, in accordance with one of the numbering schemes provided by Kabat et al. (1991) Sequences of Proteins of Immunological Interest (5th Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) Handbook of Therapeutic Antibodies, 3rd Ed., Wily-VCH Verlag GmbH and Co or AbM (Oxford Molecular/MSI Pharmacopia) unless otherwise noted. In some embodiments of this disclosure, the EpCAM binding proteins comprise heavy chain only antibodies, such as VH or VHH domains, and comprise three CDRs. Such heavy chain only antibodies, in some embodiments, bind EpCAM as a monomer with no dependency on dimerisation with a VL (light chain variable) region for optimal binding affinity.

"Variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. It is not intended that CDRs of the present disclosure necessarily correspond to the Kabat numbering convention.

The term "Framework" or "FR" residues (or regions) refer to variable domain residues other than the CDR or hypervariable region residues as herein defined. A "human consensus framework" is a framework which represents the most commonly occurring amino acid residue in a selection of human immunoglobulin VL or VH framework sequences.

The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer softwares such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

As used herein, "elimination half-time" is used in its ordinary sense, as is described in Goodman and Gillman's The Pharmaceutical Basis of Therapeutics 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, $t^{1}/_{2}$ the time required for 50% completion of the process. The units of these two constants are time−1 and time, respectively. A first-order rate constant and the half-time of the reaction are simply related ($k \times t_{1/2}=0.693$) and may be interchanged accordingly. Since first-order elimination kinetics dictates that a constant fraction of drug is lost per unit time, a plot of the log of drug concentration versus time is linear at all times following the initial distribution phase (i.e., after drug absorption and distribution are complete). The half-time for drug elimination can be accurately determined from such a graph.

As used herein, the term "binding affinity" refers to the affinity of the proteins described in the disclosure to their binding targets, and is expressed numerically using "Kd" values. If two or more proteins are indicated to have comparable binding affinities towards their binding targets, then the Kd values for binding of the respective proteins towards their binding targets, are within ±2-fold of each other. If two or more proteins are indicated to have comparable binding affinities towards single binding target, then the Kd values for binding of the respective proteins towards said single binding target, are within ±2-fold of each other. If a protein is indicated to bind two or more targets with comparable binding affinities, then the Kd values for binding of said protein to the two or more targets are within #2-fold of each other. In general, a higher Kd value corresponds to a weaker binding. In some embodiments, the "Kd" is measured by a radiolabeled antigen binding assay (RIA) or surface plasmon resonance assays using a BIAcore™-2000 or a BIAcore™-3000 (BIAcore, Inc., Piscataway, N.J.). In certain embodiments, an "on-rate" or "rate of association" or "association rate" or "kon" and an "off-rate" or "rate of dissociation" or "dissociation rate" or "koff" are also determined with the surface plasmon resonance technique using a BIAcore™-2000 or a BIAcore™-3000 (BIAcore, Inc., Piscataway, N.J.). In additional embodiments, the "Kd", "kon", and "koff" are measured using the OCTET® Systems (Pall Life Sciences). In an exemplary method for measuring binding affinity using the OCTET® Systems, the ligand, e.g., biotinylated human or cynomolgus EpCAM, is immobilized on the OCTET® streptavidin capillary sensor tip surface which streptavidin tips are then activated according to manufacturer's instructions using about 20-50 μg/ml human or cynomolgus EpCAM protein. A solution of PBS/Casein is also introduced as a blocking agent. For association kinetic measurements, EpCAM binding protein variants are introduced at a concentration ranging from about 10 ng/ml to about 100 μg/mL, about 50 ng/ml to about 5 μg/mL, or about 2 ng/ml to about 20 g/mL. In some embodiments, the EpCAM binding single domain proteins are used at a concentration ranging from about 2 ng/mL to about 20 μg/mL. Complete dissociation is observed in case of the negative control, assay buffer without the binding proteins. The kinetic parameters of the binding reactions are then determined using an appropriate tool, e.g., ForteBio software.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

A "TriTAC," an "EpCAM targeting TriTAC," or an "EpCAM targeting trispecific protein," as used herein refers to a trispecific binding protein that is not conditionally activated, and comprises a binding moiety that is specific for a bulk serum protein, a first target antigen binding domain, and a second target antigen binding domain, wherein at least one of the first target antigen binding domain and the second target antigen binding domain comprises an EpCAM binding protein as described herein, and at least one of the first target antigen binding domain and the second target antigen binding domain comprises a domain that binds a CD3, such as a human CD3.

A "ProTriTAC," or an "EpCAM targeting protrispecific protein," as used herein refers to a trispecific binding protein that is conditionally activated, and comprises (i) a cleavable linker (e.g., comprising a sequence as set forth in SEQ ID Nos. 425-471 and SEQ ID Nos. 503-506)), (ii) a binding moiety that is specific for a bulk serum protein and also comprises a masking moiety (e.g., comprising a sequence as set forth in SEQ ID Nos. 380-424) which prohibits the binding of a first target antigen binding domain or a second target antigen binding domain to its target, wherein at least one of the first target antigen binding domain and the second target antigen binding domain comprises an EpCAM binding protein as described herein. The ProTriTAC proteins of this disclosure are, in some cases, activated from a masked state to an active state by cleavage of the cleavable linker, for example, in a protease rich environment, such as in a tumor microenvironment, to form an active drug. An active drug, as provided herein, in some instances, comprises an EpCAM binding domain of the disclosure and a CD3 binding domain of the disclosure. An example of an active drug is provided in SEQ ID Nos. 153-179, 180-206, 210-212, 494, 571, and 574, or a sequence that is at least about 75% to 100% identical to a sequence selected from the group consisting of SEQ ID Nos. 153-179, 180-206, 210-212, 494, 571, and 574 such as about 75%, about 80%, about 85%, about 90%, about 91%, about 92%, about 93%, about 94%, about 95%, about 96%, about 97%, about 98%, about 99%, or 100% identical to a sequence selected from the group consisting of SEQ ID Nos. 153-179, 180-206, 210-212, 494, 571, and 574.

A "non-cleavable prodrug," as used herein refers to a ProTriTAC as described above where the cleavable linker is replaced by a non-cleavable linker (e.g., a linker as in SEQ ID No. 507). An example of an active drug is provided in SEQ ID Nos. 495 and 502, or a sequence that is at least about 75% to 100% identical to a sequence selected from the group consisting of SEQ ID Nos. 495 and 502, such as about 75%, about 80%, about 85%, about 90%, about 91%, about 92%, about 93%, about 94%, about 95%, about 96%, about 97%, about 98%, about 99%, or 100% identical to a sequence selected from the group consisting of SEQ ID Nos. 495 and 502.

In a non-beta-sandwich scaffold (e.g., a DARPin, an affimer, an affibody), the "non-CDR loops" refer to an area that is (1) amenable for sequence randomization to allow engineered specificities to a second antigen, and (2) distal to the primary specificity determining region(s) typically used on the scaffold to allow simultaneous engagement of the scaffold to both antigens without steric interference. For this purpose, the primary specificity determining region(s) can be defined using the framework established in the Skrlec 2015 publication (Trends in Biotechnol, 33:408-418). An excerpt of the framework is listed below:

| Scaffold | Primary specificity determining region(s) |
|---|---|
| Affibody | 13 residues in two helices |
| Affimer | 12-36 residues |
| Anticalin | Four loops (up to 24 aa) |
| Avimer | 11 residues |
| Centyrin | 13 residues |
| DARPin | 7 residues in each n-repeat, or 8 residues in each n-repeat |
| Fynomer | 6 residues in the RT- and n-Src-loop |
| Kunitz domain | 1-2 loops |

"Chimeric antigen receptor" or "CAR" or "CARs", as used herein, refers to engineered receptors which provide antigen specificity to cells (for example T cells). CARs comprise multiple domains, for example, at least one target antigen binding domain, a transmembrane domain, one or more co-stimulatory domains, and an intracellular signaling domain. Each domain may be connected by a linker. A "ProCAR," as used herein, refers to a conditionally activatable CAR, comprising an EpCAM binding domain of this disclosure.

EpCAM Binding Proteins

Described herein are proteins that bind EpCAM, pharmaceutical compositions thereof, as well as nucleic acids, recombinant expression vectors and host cells for making such proteins thereof. Also provided are methods of using the disclosed EpCAM binding proteins in the prevention, and/or treatment of diseases, conditions and disorders. In some embodiments, the EpCAM binding proteins are part of multispecific (e.g., trispecific) proteins that comprise an EpCAM binding domain as described herein.

The epithelial cell adhesion molecule (EpCAM) is a membrane glycoprotein that is expressed in most normal human epithelia and overexpressed in most carcinomas. This molecule is responsible for cell-to-cell adhesion and additionally participates in signaling, cell migration, proliferation and differentiation. Therefore, EpCAM has been the target of immunotherapy in clinical trials of several solid tumors. It has been found to play an important role in the detection and isolation of circulating tumor cells (CTCs). EpCAM has been shown in various studies to be beneficial in diagnosis and therapy of various carcinomas. Furthermore, in many cases, tumor cells were observed to express EpCAM to a much higher degree than their parental epithelium or less aggressive forms of said cancers. For example, EpCAM expression was shown to be significantly higher on neoplastic tissue and in adenocarcinoma than on normal prostate epithelium ($n=76$; $p<0.0001$), suggesting that increased EpCAM expression represents an early event in the development of prostate cancer. See Poczatek, J Urol., 1999, 162, 1462-1644. In addition, in the majority of both squamous and adenocarcinomas of the cervix a strong EpCAM expression has been shown to correlate with an increased proliferation and the disappearance of markers for terminal differentiation. See Litvinov, Am. J. Pathol. 1996, 148, 865-75. One example is breast cancer where overexpression of EpCAM on tumor cells is a predictor of survival. See Gastl, Lancet. 2000, 356, 1981-1982. Furthermore, EpCAM has been described as a marker for the detection of disseminated tumor cells in patients suffering from squamous cell carcinoma of the head, neck and lung. See Chaubal, Anticancer Res 1999, 19, 2237-2242, Piyathilake, Hum Pathol. 2000, 31, 482-487. Normal squamous epithelium, as found in epidermis, oral cavity, epiglottis, pharynx, larynx and esophagus did not significantly express EpCAM. See Quak, Hybridoma, 1990, 9, 377-387.

EpCAM is contemplated to serve to adhere epithelial cells in an oriented and highly ordered fashion. See Litvinov, J Cell Biol. 1997, 139, 1337-1348. Upon malignant transformation of epithelial cells the rapidly growing tumor cells are believed to abandon the high cellular order of epithelia. Consequently, the surface distribution of EpCAM is contemplated to become less restricted and the molecule better exposed on tumor cells. Due to their epithelial cell origin, tumor cells from most carcinomas are expected to express EpCAM on their surface.

EpCAM, is a 40-kDa membrane-integrated glycoprotein of 314 amino acids with specific expression in certain epithelia and on many human carcinomas. See, e.g., in Balzar, J. Mol. Med. 1999, 77, 699-712). EpCAM was discovered and subsequently cloned through its recognition by the murine monoclonal antibody 17-1A/edrecolomab. See Goettlinger, Int J Cancer. 1986; 38, 47-53 and Simon, Proc. Natl. Acad. Sci. USA. 1990; 87, 2755-2759. Monoclonal antibody 17-1A was generated by immunization of mice with human colon carcinoma cells. See Koprowski, Somatic Cell Genet. 1979, 5, 957-971. The EGF-like repeats of EpCAM were shown to mediate lateral and reciprocal interactions in homophilic cell adhesion. See, e.g., Balzar, Mol. Cell. Biol. 2001, 21, 2570-2580) and, for that reason, is predominantly located between epithelial cells (Litvinov, J Cell Biol. 1997, 139, 1337-1348, Balzar, J Mol Med. 1999, 77, 699-712 and Trebak, J Biol Chem. 2001, 276, 2299-2309).

EpCAM is also known by the following alternate names: Epithelial Cell Adhesion Molecule, Tumor-Associated Calcium Signal Transducer, Major Gastrointestinal Tumor-Associated Protein GA733-2, Adenocarcinoma-Associated Antigen, Cell Surface Glycoprotein Trop-1, Epithelial Glycoprotein 314, TACSTD1, EGP314, MIC18, TROP1, M4S1, KSA, Membrane Component Chromosome 4 Surface marker (35 kD glycoprotein), Antigen identified by monoclonal antibody AUA-1, human epithelial glycoprotein-2, epithelial cell surface antigen, epithelial glycoprotein, KS ¼Antigen, CD326 Antigen, GA722-2, HEGP314, HNPCC8, Ep-CAM, DIAR5, EGP-2, EGP40, KS ¼, MK-1, MIS2, ESA, and EGP. Exemplary protein sequences for EpCAM is provided in UniProtkB ID Nos. P16422 and B5MCA4. In some embodiments, the EpCAM binding proteins of this disclosure binds to an EpCAM sequence provided in UniProtkB ID Nos. P16422 (SEQ ID No. 478) or B5MCA4 (SEQ ID No. 475).

In some embodiments, the EpCAM binding domain binds to an extracellular domain of the mature EpCAM protein. The human extracellular domain sequence is provided in SEQ ID No. 479; the cynomolgus extracellular domain sequence is provided in SEQ ID No. 480; and the mouse extracellular domain sequence is provided in SEQ ID No. 481.

In some embodiments, the EpCAM binding domain binds to a protein comprising a truncated sequence compared to SEQ ID No. 475. In some embodiments, the EPCAM binding domain binds to a protein comprising the sequence of SEQ ID No. 475. In some embodiments, the EpCAM binding domain binds to a protein comprising a truncated sequence compared to SEQ ID No. 476. In some embodiments, the EpCAM binding domain binds to a protein comprising the sequence of SEQ ID No. 476. In some embodiments, the EpCAM binding domain binds to a protein comprising a truncated sequence compared to SEQ ID No. 477. In some embodiments, the EpCAM binding domain binds to a protein comprising a truncated sequence compared to SEQ ID No. 477. In some embodiments, the EpCAM binding domain binds to a protein comprising a truncated sequence compared to SEQ ID No. 478. In some embodiments, the EpCAM binding domain binds to a protein comprising a truncated sequence compared to SEQ ID No. 478. In some embodiments, the EpCAM binding domain binds to a protein comprising a truncated sequence compared to SEQ ID No. 479. In some embodiments, the EpCAM binding domain binds to a protein comprising a truncated sequence compared to SEQ ID No. 479. In some embodiments, the EpCAM binding domain binds to a protein comprising a truncated sequence compared to SEQ ID No. 480. In some embodiments, the EpCAM binding domain binds to a protein comprising a truncated sequence compared to SEQ ID No. 480. In some embodiments, the EpCAM binding domain binds to a protein comprising a truncated sequence compared to SEQ ID No. 481. In some embodiments, the EpCAM binding domain binds to a protein comprising a truncated sequence compared to SEQ ID No. 481.

In some embodiments, the EpCAM binding domains disclosed herein recognize full-length EpCAM. In certain instances, the EpCAM binding domains disclosed herein recognize an epitope within EpCAM, such as, in some cases the EpCAM binding proteins interact with one or more amino acids found within a domain of human EpCAM. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within a domain of EpCAM. Alternatively, the epitope may consist of a plurality of non-contiguous amino acids (or amino acid sequences) located within a domain of EpCAM.

In some embodiments, the EpCAM binding proteins of this disclosure binds to the full length EpCAM protein or to a fragment thereof, such as epitope containing fragments within the full length EpCAM protein, as described above. In some cases, the epitope containing fragment comprises antigenic or immunogenic fragments and derivatives thereof of the EpCAM protein. Epitope containing fragments, including antigenic or immunogenic fragments, are, in some embodiments, 12 amino acids or more, e.g., 20 amino acids or more, 50 or 100 amino acids or more. The EpCAM fragments, in some embodiments, comprises 95% or more of the length of the full protein, 90% or more, 75% or 50% or 25% or 10% or more of the length of the full protein. In some embodiments, the epitope-containing fragments of EpCAM including antigenic or immunogenic fragments are capable of eliciting a relevant immune response in a patient. Derivatives of EpCAM include, in some embodiments, variants on the sequence in which one or more (e.g., 1-20 such as 15 amino acids, or up to 20% such as up to 10% or 5% or 1% by number of amino acids based on the total length of the protein) deletions, insertions or substitutions have been made to the EpCAM sequence provided in SEQ ID Nos. 475-481.

In some embodiments, substitutions comprise conservative substitutions. Derivatives and variants of, in some examples, have essentially the same biological function as the protein from which they are derived. For instance, derivatives and variants of EpCAM are, in some cases, comparably antigenic or immunogenic to the protein from which they are derived, have either the ligand-binding activity, or the active receptor-complex forming ability, or preferably both, of the protein from which they are derived, and have the same tissue distribution as EpCAM.

In some embodiments, the EpCAM binding protein specifically binds EpCAM with equivalent or better affinity as that of a reference EpCAM binding protein, and the EpCAM binding protein in such embodiments comprises an affinity matured EpCAM binding molecule, and is derived from the EpCAM binding parental molecule, comprising one or more amino acid mutations (e.g., a stabilizing mutation, a destabilizing mutation) with respect to the EpCAM binding parental molecule. In some embodiments, the affinity matured EpCAM binding molecule has superior stability with respect to selected destabilizing agents, as that of a reference EpCAM binding parental molecule. In some embodiments, the affinity matured EpCAM binding molecule is identified in a process comprising panning of one or more pre-candidate EpCAM binding molecules derived from one or more EpCAM binding parental molecule, expressed in a phage display library, against an EpCAM protein, such as a human EpCAM protein. The pre-candidate EpCAM binding molecule comprises, in some embodiments, amino acid substitutions in the variable regions, CDRs, or framework residues, relative to a parental molecule.

As used herein, "Phage display" refers to a technique by which variant polypeptides are displayed as fusion proteins to at least a portion of a coat protein on the surface of phage, e.g., filamentous phage, particles. A utility of phage display lies in the fact that large libraries of randomized protein variants can be rapidly and efficiently selected for those sequences that bind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. See e.g., Wells and Lowman, Curr. Opin. Struct. Biol, 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that selection is on the basis of intrinsic ligand affinity, and phagemid vectors are used, which simplify DNA manipulations. See e.g., Lowman and Wells, Methods: A companion to Methods in Enzymology, 3:205-0216 (1991).

In some embodiments, the panning comprises using varying binding times and concentrations to identify EpCAM binding molecules with increased or decreased on-rates, from pre-candidate EpCAM binding molecules. In some embodiments, the panning comprises using varying wash times to identify EpCAM binding molecules with increased or decreased off-rates, from pre-candidate EpCAM molecules. In some embodiments, the panning comprises using both varying binding times and varying wash times. In some embodiments, one or more stabilizing mutations are combined to increase the stability of the affinity matured EpCAM binding molecule, for example, by shuffling to create a second-stage combinatorial library from such mutants and conducting a second round of panning followed by a binding selection.

In some embodiments, the affinity matured EpCAM binding molecule comprises an equivalent or better affinity to a EpCAM protein (such as human EpCAM protein) as that of a EpCAM binding parental molecule, but that has reduced cross reactivity, or in some embodiments, increased cross reactivity, with selected substances, such as ligands, proteins, antigens, or the like, other than the EpCAM epitope for which the EpCAM binding parental molecule is specific, or is designed to be specific for. In regard to the latter, an affinity matured EpCAM binding molecule, in some embodiments, is more successfully tested in animal models if the affinity matured EpCAM binding molecule is reacted with both human EpCAM and the corresponding target of the animal model, e.g. mouse EpCAM or cynomolgus EpCAM. In some embodiments, the parental EpCAM binding molecule binds to human EpCAM with an affinity of about 500 nM or less, 400 nM or less, 300 nM or less, 200 nM or less, 100 nM or less, 50 nM or less, 10 nM or less, and to cynomolgus EpCAM with an affinity of about 500 nM or less, 400 nM or less, 300 nM or less, 200 nM or less, 100 nM or less, 50 nM or less, 15 nM or less, or 10 nM or less. In some embodiments, the affinity matured EpCAM binding molecule, identified after one round of panning, binds to human EpCAM with an affinity of about 5 nM or less, such as 1 nM or less, and to cynomolgus EpCAM with an affinity of about 7.5 nM or less, such as 1 nM or less. In some embodiments, the affinity matured EpCAM binding molecule, identified after two rounds of panning, binds to human EpCAM with an affinity of about 2.5 nM or less, and to cynomolgus EpCAM with an affinity of about 3.5 nM or less.

In some embodiments, the EpCAM binding protein comprises an antigen-specific binding domain polypeptide that specifically bind to targets, such as targets on diseased cells, or targets on other cells that support the diseased state, such as targets on stromal cells that support tumor growth or targets on immune cells that support disease-mediated immunosuppression. In some examples, the antigen-specific binding domain includes antibodies, single chain antibodies, Fabs, Fv, T-cell receptor binding domains, ligand binding domains, receptor binding domains, domain antibodies, single domain antibodies, minibodies, nanobodies, peptibodies, or various other antibody mimics (such as affimers, affitins, alphabodies, atrimers, CTLA4-based molecules, adnectins, anticalins, Kunitz domain-based proteins, avimers, knottins, fynomers, darpins, affibodies, affilins, monobodies and armadillo repeat protein-based proteins).

In some embodiments, the EpCAM binding domain is an anti-EpCAM antibody or an antigen binding fragment thereof, or an antibody variant of the EpCAM binding domain or an antigen binding fragment thereof. As used herein, the term "antibody variant" refers to variants and derivatives of an antibody or an antigen binding fragment as described herein. In certain embodiments, amino acid sequence variants of the anti-EpCAM antibodies or antigen binding fragments thereof, as described herein, are contemplated. For example, in certain embodiments amino acid sequence variants of anti-EpCAM antibodies or antigen binding fragments thereof, as described herein, are contemplated to improve the binding affinity and/or other biological properties of the same. Exemplary method for preparing amino acid variants include, but are not limited to, introducing appropriate modifications into the nucleotide sequence encoding the antibody or antigen binding fragment thereof, or by peptide synthesis. Such modifications include, for example, deletions from, and/or insertions into and/or substitutions of residues within the amino acid sequences of the antibody or antigen binding fragments thereof.

Any combination of deletion, insertion, and substitution can be made to arrive at the final construct, provided that the final construct possesses the desired characteristics, e.g., antigen-binding. In certain embodiments, variants having one or more amino acid substitutions are provided. Sites of interest for substitution mutagenesis include the CDRs and framework regions. Examples of such substitutions are described below. Amino acid substitutions may be introduced into an antibody or antigen binding fragments thereof of interest and the products screened for a desired activity, e.g., retained/improved antigen binding, decreased immunogenicity, altered Antibody dependent cellular cytotoxicity (ADCC), or improved T-cell mediated cytotoxicity (TDCC). Both conservative and non-conservative amino acid substitutions are contemplated for preparing the antibody variants.

In another example of a substitution to create a variant anti-EpCAM antibody or antigen binding fragments thereof, one or more hypervariable region residues of a parent antibody are substituted. In general, variants are then selected based on improvements in desired properties compared to a parent antibody or antigen binding fragments thereof, for example, increased affinity, reduced affinity, reduced immunogenicity, increased pH dependence of binding.

In some embodiments, the EpCAM binding domain is a single domain antibody (sdAb) such as a heavy chain variable domain (VH), a variable domain (VHH) of a llama derived sdAb, a peptide, a ligand or a small molecule entity specific for EpCAM. In some embodiments, the EpCAM binding domain described herein is any domain that binds to EpCAM including but not limited to domains from a monoclonal antibody, a polyclonal antibody, a recombinant antibody, a human antibody, a humanized antibody. In certain embodiments, the EpCAM binding domain is a single-domain antibody. In other embodiments, the EpCAM binding domain is a peptide. In further embodiments, the EpCAM binding domain is a small molecule.

Generally, it should be noted that the term single domain antibody as used herein in its broadest sense is not limited to a specific biological source or to a specific method of preparation. Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. For example, in some embodiments, the single domain antibodies of the disclosure are obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a species of mammal, such as from a human being, or by expression of a nucleic acid encoding such a camelized VH domain; (5) by "camelization" of a "domain antibody" or "Dab," or by expression of a nucleic acid encoding such a camelized VH domain; (6) by using synthetic or semi-synthetic techniques for preparing proteins, polypeptides or other amino acid sequences; (7) by preparing a nucleic acid encoding a single domain antibody using techniques for nucleic acid synthesis known in the field, followed by expression of the nucleic acid thus obtained; and/or (8) by any combination of one or more of the foregoing.

In one embodiment, a single domain antibody corresponds to the VHH domains of naturally occurring heavy chain antibodies directed against EpCAM. As further described herein, such VHH sequences can generally be generated or obtained by suitably immunizing a species of Llama with EpCAM, (i.e., so as to raise an immune response and/or heavy chain antibodies directed against EpCAM), by obtaining a suitable biological sample from said Llama (such as a blood sample, serum sample or sample of B-cells), and by generating VHH sequences directed against EpCAM, starting from said sample, using any suitable technique known in the field.

In another embodiment, such naturally occurring VHH domains against EpCAM, are obtained from naïve libraries of Camelid VHH sequences, for example by screening such a library using EpCAM, or at least one part, fragment, antigenic determinant or epitope thereof using one or more screening techniques known in the field. Such libraries and techniques are for example described in WO 99/37681, WO 01/90190, WO 03/025020 and WO 03/035694. Alternatively, improved synthetic or semi-synthetic libraries derived from naïve VHH libraries are used, such as VHH libraries obtained from naïve VHH libraries by techniques such as random mutagenesis and/or CDR shuffling, as for example described in WO 00/43507.

In a further embodiment, yet another technique for obtaining VHH sequences directed against EpCAM, involves suitably immunizing a transgenic mammal that is capable of expressing heavy chain antibodies (i.e., so as to raise an immune response and/or heavy chain antibodies directed against EpCAM), obtaining a suitable biological sample from said transgenic mammal (such as a blood sample, serum sample or sample of B-cells), and then generating VHH sequences directed against EpCAM, starting from said sample, using any suitable technique known in the field. For example, for this purpose, the heavy chain antibody-expressing rats or mice and the further methods and techniques described in WO 02/085945 and in WO 04/049794 can be used.

In some embodiments, an anti-EpCAM single domain antibody of this disclosure comprises a single domain antibody with an amino acid sequence that corresponds to the amino acid sequence of a non-human antibody and/or a naturally occurring VHH domain, e.g., a llama anti-EpCAM antibody, but that has been "humanized," i.e., by replacing one or more amino acid residues in the amino acid sequence of said non-human anti-EpCAM and/or the naturally occurring VHH sequence (and in particular in the framework sequences) by one or more of the amino acid residues that occur at the corresponding position(s) in a VH domain from a conventional 4-chain antibody from a human being (e.g., as indicated above). This can be performed in a manner known in the field, which will be clear to the skilled person, for example on the basis of the further description herein. Again, it should be noted that such humanized anti-EpCAM single domain antibodies of the disclosure are obtained in any suitable manner known per se (i.e., as indicated under points (1)-(8) above) and thus are not strictly limited to polypeptides that have been obtained using a polypeptide that comprises a naturally occurring VHH domain as a starting material. In some additional embodiments, a single domain anti-EpCAM antibody, as described herein, comprises a single domain antibody with an amino acid sequence that corresponds to the amino acid sequence of a naturally occurring VH domain, but that has been "camelized" i.e., by replacing one or more amino acid residues in the amino acid sequence of a naturally occurring VH domain from a conventional 4-chain antibody by one or more of the amino acid residues that occur at the corresponding position(s) in a VHH domain of a heavy chain antibody. Such "camelizing" substitutions are preferably inserted at amino acid positions that form and/or are present at the VH-VL interface, and/or at the so-called Camelidae hallmark residues. See, e.g., WO 94/04678 and Davies and Riechmann (1994 and 1996)). Preferably, the VH sequence that is used as a starting material or starting point for generating or designing the camelized single domain is preferably a VH sequence from a mammal, more preferably the VH sequence of a human being, such as a VH3 sequence. However, it should be noted that such camelized anti-EpCAM single domain antibodies of the disclosure, in certain embodiments, are obtained in any suitable manner known in the field (i.e., as indicated under points (1)-(8) above) and thus are not strictly limited to polypeptides that have been obtained using a polypeptide that comprises a non-human anti-EpCAM antibody and/or the naturally occurring VH domain as a starting material. For example, as further described herein, both "humanization" and "camelization" is performed by providing a nucleotide sequence that encodes a naturally occurring VHH domain or VH domain, respectively, and then changing, one or more codons in said nucleotide sequence in such a way that the new nucleotide sequence encodes a "humanized" or "camelized" single domain antibody, respectively. This nucleic acid can then be expressed, so as to provide a desired anti-EpCAM single domain antibody of the disclosure. Alternatively, in other embodiments, based on the amino acid sequence of a naturally occurring VHH domain or VH domain, respectively, the amino acid sequence of the desired humanized or camelized anti-EpCAM single domain antibody of the disclosure, respectively, are designed and then synthesized de novo using known techniques for peptide synthesis. In some embodiments, based on the amino acid sequence or nucleotide sequence of a naturally occurring VHH domain or VH domain, respectively, a nucleotide sequence encoding the desired humanized or camelized anti-EpCAM single domain antibody of the disclosure, respectively, is designed and then synthesized de novo using known techniques for nucleic acid synthesis, after which the nucleic acid thus obtained is expressed in using known expression techniques, so as to provide the desired anti-EpCAM single domain antibody of the disclosure.

Other suitable methods and techniques for obtaining the anti-EpCAM single domain antibody of the disclosure and/or nucleic acids encoding the same, starting from naturally occurring VH sequences or VHH sequences for example comprises combining one or more parts of one or more naturally occurring VH sequences (such as one or more framework (FR) sequences and/or complementarity determining region (CDR) sequences), one or more parts of one or more naturally occurring VHH sequences (such as one or more FR sequences or CDR sequences), and/or one or more synthetic or semi-synthetic sequences, in a suitable manner, so as to provide an anti-EpCAM single domain antibody of the disclosure or a nucleotide sequence or nucleic acid encoding the same.

In some embodiments, the EpCAM binding domain is an anti-EpCAM specific antibody comprising a heavy chain variable complementarity determining region CDR1, a heavy chain variable CDR2, a heavy chain variable CDR3, a light chain variable CDR1, a light chain variable CDR2, and a light chain variable CDR3. In some embodiments, the EpCAM binding domain comprises any domain that binds to EpCAM including but not limited to domains from a monoclonal antibody, a polyclonal antibody, a recombinant antibody, a human antibody, a humanized antibody, or antigen binding fragments such as single domain antibodies (sdAb), Fab, Fab', F(ab)2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. In some embodiments, the EpCAM binding domain is a single domain antibody. In some embodiments, the anti-EpCAM single domain antibody comprises heavy chain variable complementarity determining regions (CDR), CDR1, CDR2, and CDR3.

In some embodiments, the EpCAM binding domain is a polypeptide comprising an amino acid sequence that is comprised of four framework regions/sequences (f1-f4) interrupted by three complementarity determining regions/sequences, as represented by the formula: f1-r1-f2-r2-f3-r3-f4, wherein r1, r2, and r3 are complementarity determining regions CDR1, CDR2, and CDR3, respectively, and f1, f2, f3, and f4 are framework residues. The framework residues of the EpCAM binding protein of the present disclosure comprise, for example, 75, 76, 77, 78, 79, 80, 81, 82, 83, 84, 85, 86, 87, 88, 89, 90, 91, 92, 93, or 94 amino acid residues, and the complementarity determining regions comprise, for example, 24, 25, 26, 27, 28, 29, 30, 31, 32, 33, 34, 35, or 36 amino acid residues. In some embodiments, the EpCAM binding domain comprises an amino acid sequence selected from SEQ ID NOs: 1-38, 207-209, and 496-497.

In some embodiments, the binding proteins described herein comprise a polypeptide having a sequence selected from SEQ ID Nos. 1-38, subsequences thereof, and variants thereof. In some embodiments, the EpCAM binding protein comprises at least 70%-95% or more homology to a sequence selected from SEQ ID Nos. 1-38, subsequences thereof, and variants thereof. In some embodiments, the EpCAM binding protein comprises at least 60%, 61%, 62%, 63%, 63%, 65%, 66%, 67%, 68%, 69%, 70%, 75%, 80%, 85%, 90%, 95%, 96%, 97%, 98%, 99%, or more homology to a sequence selected from SEQ ID Nos. 1-38, 207-209, and 496-497, subsequences thereof, and variants thereof. In some embodiments, the EpCAM binding protein comprises at least 70%-95% or more identity to a sequence selected from SEQ ID Nos. 1-38, 207-209, and 496-497, subsequences thereof, and variants thereof. In some embodiments, the EpCAM binding protein comprises at least 60%, 61%, 62%, 63%, 63%, 65%, 66%, 67%, 68%, 69%, 70%, 75%, 80%, 85%, 90%, 95%, 96%, 97%, 98%, 99% or more identity to a sequence selected from SEQ ID Nos. 1-38, 207-209, and 496-497, subsequences thereof, and variants thereof.

In some embodiments, the CDR1 comprises the amino acid sequence as set forth in any one of SEQ ID Nos. 39-76 or a sequence comprising one or more substitutions compared to a sequence selected from the group consisting of SEQ ID Nos. 39-76. In some embodiments, the CDR2 comprises a sequence as set forth in any one of SEQ ID Nos. 77-114 or a sequence comprising one or more substitutions compared to a sequence selected from the group consisting of SEQ ID Nos. 77-114. In some embodiments, the CDR3 comprises a sequence as set forth in any one of SEQ ID Nos. 115-152 a sequence comprising one or more substitutions compared to a sequence selected from the group consisting of SEQ ID Nos. 115-152.

In various embodiments, the EpCAM binding domain of the present disclosure is at least about 60%, about 61%, at least about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID Nos. 1-38, 207-209, and 496-497.

In various embodiments, a complementarity determining region of the EpCAM binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID Nos. 39-76.

In various embodiments, a complementarity determining region of the EpCAM binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID Nos. 77-114.

In various embodiments, a complementarity determining region of the EpCAM binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID Nos. 115-152.

In some embodiments, the EpCAM binding domain is cross-reactive with human cynomolgus and mouse EpCAM. In some embodiments, the EpCAM binding domain is specific for human EpCAM. In certain embodiments, the EpCAM binding domains disclosed herein bind to human EpCAM with a human Kd (hKd). In certain embodiments, the EpCAM binding domains disclosed herein bind to cynomolgus EpCAM with a cyno Kd (cKd). In certain embodiments, the EpCAM binding domains disclosed herein bind to cynomolgus EpCAM with a mouse Kd (mKd). In certain embodiments, the EpCAM binding domains disclosed herein bind to both cynomolgus EpCAM and a human EpCAM, with a cyno Kd (cKd) and a human Kd (hKd), respectively. In certain embodiments, the EpCAM binding domains disclosed herein bind to cynomolgus EpCAM, mouse EpCAM, and a human EpCAM, with a cyno Kd (cKd), mouse Kd (mKd), and a human Kd (hKd), respectively. In some embodiments, the EpCAM binding protein binds to human, mouse and cynomolgus EpCAM with comparable binding affinities (i.e., hKd, mKd and cKd values do not differ by more than +10%). In some embodiments, the hKd, mKd and the cKd range from about 0.001 nM to about 500 nM. In some embodiments, the hKd, mKd and the cKd range from about 0.001 nM to about 450 nM. In some embodiments, the hKd, mKd and the cKd range from about 0.001 nM to about 400 nM. In some embodiments, the hKd, mKd and the cKd range from about 0.001 nM to about 350 nM. In some embodiments, the hKd, mKd and the cKd range from about 0.001 nM to about 300 nM. In some embodiments, the hKd, mKd and the cKd range from about 0.001 nM to about 250 nM. In some embodiments, the hKd, mKd and the cKd range from about 0.001 nM to about 200 nM. In some embodiments, the hKd, mKd and the cKd range from about 0.001 nM to about 150 nM. In some embodiments, the hKd, mKd and the cKd range from about 0.001 nM to about 100 nM. In some embodiments, the hKd, mKd and the cKd range from about 0.1 nM to about 90 nM. In some embodiments, the hKd, mKd and the cKd range from about 0.2 nM to about 80 nM. In some embodiments, the hKd, mKd and the cKd range from about 0.3 nM to about 70 nM. In some embodiments, the hKd, mKd and the cKd range from about 0.4 nM to about 50 nM. In some embodiments, the hKd, mKd and the cKd range from about 0.5 nM to about 30 nM. In some embodiments, the hKd, mKd and the cKd range from about 0.6 nM to about 10 nM. In some embodiments, the hKd, mKd and the cKd range from about 0.7 nM to about 8 nM. In some embodiments, the hKd, mKd and the cKd range from about 0.8 nM to about 6 nM. In some embodiments, the hKd, mKd and the cKd range from about 0.9 nM to about 4 nM. In some embodiments, the hKd, mKd and the cKd range from about 1 nM to about 2 nM.

In some embodiments, any of the foregoing EpCAM binding domains (e.g., anti-EpCAM single domain antibodies of SEQ ID Nos. 1-38) are affinity peptide tagged for ease of purification. In some embodiments, the affinity peptide tag is six consecutive histidine residues, also referred to as 6×-his (SEQ ID No. 377).

In certain embodiments, the EpCAM binding domains of the present disclosure preferentially bind membrane bound EpCAM over soluble EpCAM Membrane bound EpCAM refers to the presence of EpCAM in or on the cell membrane surface of a cell that expresses EpCAM. Soluble EpCAM refers to EpCAM that is no longer on in or on the cell membrane surface of a cell that expresses or expressed EpCAM. In certain instances, the soluble EpCAM is present in the blood and/or lymphatic circulation in a subject. In one embodiment, the EpCAM binding domains bind membrane-bound EpCAM at least 5 fold, 10 fold, 15 fold, 20 fold, 25 fold, 30 fold, 40 fold, 50 fold, 100 fold, 500 fold, or 1000 fold greater than soluble EpCAM. In one embodiment, the EpCAM binding proteins of the present disclosure preferentially bind membrane-bound EpCAM 30 fold greater than soluble EpCAM. Determining the preferential binding of an antigen binding protein to membrane bound EpCAM over soluble EpCAM can be readily determined using binding assays.

It is contemplated that in some embodiments the EpCAM binding protein is fairly small and no more than 25 kDa, no more than 20 kDa, no more than 15 kDa, or no more than 10 kDa in some embodiments. In certain instances, the EpCAM binding protein is 5 kDa or less if it is a peptide or small molecule entity.

In other embodiments, the EpCAM binding proteins described herein comprise small molecule entity (SME) binders for EpCAM. SME binders are small molecules averaging about 500 to 2000 Da in size and are attached to the EpCAM binding proteins by known methods, such as sortase ligation or conjugation. In these instances, the EpCAM binding protein comprises a domain comprising a sortase recognition sequence, e.g., LPETG (SEQ ID No. 376). To attach a SME binder to EpCAM binding protein comprising a sortase recognition sequence, the protein is incubated with a sortase and a SME binder whereby the sortase attaches the SME binder to the recognition sequence. In yet other embodiments, the EpCAM binding proteins described herein comprise a knottin peptide for binding EpCAM. Knottins are disulfide-stabilized peptides with a cysteine knot scaffold and have average sizes about 3.5 kDa. Knottins have been contemplated for binding to certain tumor molecules such as EpCAM. In further embodiments, the EPCAM binding proteins described herein comprise a natural EpCAM ligand.

In some embodiments, the EpCAM binding protein comprises more than one domain and are of a single-polypeptide design with flexible linkage of the domains. This allows for facile production and manufacturing of the EpCAM binding proteins as they can be encoded by single cDNA molecule to be easily incorporated into a vector. Further, in some embodiments where the EpCAM binding proteins described herein are a monomeric single polypeptide chain, there are no chain pairing issues or a requirement for dimerization. It is contemplated that, in such embodiments, the EpCAM binding proteins described herein have a reduced tendency to aggregate.

In the EpCAM binding proteins comprising more than one domain, the domains are linked by one or more internal linker. In certain embodiments, the internal linkers are "short," i.e., consist of 0, 1, 2, 3, 4, 5, 6, 7, 8, 9, 10, 11 or 12 amino acid residues. Thus, in certain instances, the internal linkers consist of about 12 or less amino acid residues. In the case of 0 amino acid residues, the internal linker is a peptide bond. In certain embodiments, the internal linkers are "long," i.e., consist of 15, 20 or 25 amino acid residues. In some embodiments, the internal linkers consist of about 3 to about 15, for example 8, 9 or 10 contiguous amino acid residues. Regarding the amino acid composition of the internal linkers, peptides are selected with properties that confer flexibility to the EpCAM binding proteins, do not interfere with the binding domains as well as resist cleavage from proteases. For example, glycine and serine residues generally provide protease resistance. Examples of internal linkers suitable for linking the domains in the EpCAM binding proteins include but are not limited to $(GS)_n$ (SEQ ID No. 365), $(GGS)_n$ (SEQ ID No. 366), $(GGGS)_n$ (SEQ ID No. 367), $(GGSG)_n$ (SEQ ID No. 368), $(GGSGG)_n$ (SEQ ID No. 369), $(GGGGS)_n$ (SEQ ID No. 370), $(GGGGG)_n$ (SEQ ID No. 371), or $(GGG)_n$ (SEQ ID No. 372), wherein n is 1, 2, 3, 4, 5, 6, 7, 8, 9, or 10. In one embodiment, the linker is (GGGGGGGGSGGGGSGGGGS) (SEQ ID No. 373), (GGGGSGGGGSGGGGS) (SEQ ID No. 374), or (GGGGSGGGS) (SEQ ID No. 375).

In some cases, where the EpCAM binding protein comprises more than one domain, the domains within the EpCAM binding proteins are conjugated using an enzymatic site-specific conjugation method which involves the use of a mammalian or bacterial transglutaminase enzyme. Microbial transglutaminases (mTGs) are versatile tools in modern research and biotechnology. The availability of large quantities of relatively pure enzymes, ease of use, and lack of regulation by calcium and guanosine-5'-triphosphate (GTP) has propelled mTG to be the main cross-linking enzyme used in both the food industry and biotechnology. Currently, mTGs are used in many applications to attach proteins and peptides to small molecules, polymers, surfaces, DNA, as well as to other proteins. See, e.g., Pavel Strp, Veracity of microbial transglutaminase, Bioconjugate Chem. 25, 5, 855-862.

In some examples are provided EpCAM binding proteins comprising more than one domain, wherein one of the domains comprises an acceptor glutamine in a constant region, which can then be conjugated to another domain via a lysine-based linker (e.g., any primary amine chain which is a substrate for TGase, e.g. comprising an alkylamine, oxoamine) wherein the conjugation occurs exclusively on one or more acceptor glutamine residues present in the targeting moiety outside of the antigen combining site (e.g., outside a variable region, in a constant region). Conjugation thus does not occur on a glutamine, e.g. an at least partly surface exposed glutamine, within the variable region. The EpCAM binding protein, in some examples, is formed by reacting one of the domains with a lysine-based linker in the presence of a TGase.

In some embodiments, where one or more domains within the EpCAM binding proteins are directly joined, a hybrid vector is made where the DNA encoding the directly joined domains are themselves directly ligated to each other. In some embodiments, where linkers are used, a hybrid vector is made where the DNA encoding one domain is ligated to the DNA encoding one end of a linker moiety and the DNA encoding another domain is ligated to the other end of the linker moiety.

In some embodiments, the EpCAM binding protein is a single chain variable fragments (scFv), single-domain antibody such as a heavy chain variable domain (VH), a light chain variable domain (VL) and a variable domain (VHH) of camelid derived single domain antibody. In other embodiments, the EpCAM binding protein is a non-Ig binding domain, i.e., an antibody mimetic, such as anticalins, affilins, affibody molecules, affimers, affitins, alphabodies, avimers, DARPins, fynomers, kunitz domain peptides, and monobodies. In further embodiments, the EpCAM binding protein is a ligand or peptide that binds to or associates with EpCAM. In yet further embodiments, the EpCAM binding protein is a knottin. In yet further embodiments, the binding domain to EpCAM is a small molecular entity.

In certain embodiments, the EpCAM binding proteins according to the present disclosure may be incorporated into EpCAM targeting trispecific proteins. In some embodiments, the trispecific proteins comprise a CD3 binding domain, a half-life extension domain, and an EpCAM binding domain according to this disclosure. In some embodiments, the EpCAM binding trispecific protein comprises a trispecific antibody.

Multispecific EpCAM Targeting Proteins, Such as EpCAM Targeting Trispecific Proteins (Also Referred to Herein as EpCAM Targeting TriTAC Proteins or Molecules)

In one aspect is described herein a multispecific or a multivalent protein comprising an EpCAM binding protein according to the present disclosure. In some embodiments, the multispecific protein further comprises a domain which specifically binds to CD3. In some embodiments, the multispecific protein further comprises a domain which specifically binds to human CD3. In some embodiments, the multispecific protein further comprises a domain which specifically binds to CD3-gamma. In some embodiments, the multispecific protein further comprises a domain which specifically binds to CD3-delta. In some embodiments, the multispecific protein further comprises a domain which specifically binds to CD3-epsilon.

In additional embodiments, the multispecific protein further comprises a domain which specifically binds to the T cell receptor (TCR). In some embodiments, the multispecific protein further comprises a domain which specifically binds the alpha chain of the TCR. In some embodiments, the multispecific protein further comprises a domain which specifically binds the β chain of the TCR.

In certain embodiments, the CD3 binding domain of the multispecific protein exhibits not only potent CD3 binding affinities with human CD3, but also shows excellent cross-reactivity with the respective cynomolgus monkey CD3 proteins. In some instances, the CD3 binding domain of the multispecific proteins are cross-reactive with CD3 from cynomolgus monkey. In certain instances, human:cynomolgous KD (hKd:cKd) ratios for CD3 binding are between 20:1 and 1:2.

In some embodiments, the CD3 binding domain of the multispecific protein is any domain that binds to CD3 including but not limited to domains from a monoclonal antibody, a polyclonal antibody, a recombinant antibody, a human antibody, a humanized antibody, or antigen binding fragments of the CD3 binding antibodies, such as single domain antibodies (sdAb), Fab, F(ab')2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. In some instances, it is beneficial for the CD3 binding domain to be derived from the same species in which the multispecific protein comprising a single domain serum albumin binding protein described herein will ultimately be used in. For example, for use in humans, it may be beneficial for the CD3 binding domain of the multispecific protein comprising an EpCAM binding protein described herein to comprise human or humanized residues from the antigen binding domain of an antibody or antibody fragment. Exemplary amino acid sequence for the CD3 binding domain of a multispecific (e.g., trispecific) EpCAM targeting TriTAC protein of this disclosure is provided as SEQ ID No. 379, or a sequence that is at least about 75% to 100% identical to SEQ ID No. 379, such as at least about 75%, about 80%, about 85%, about 90%, about 91%, about 92%, about 93%, about 94%, about 95%, about 96%, about 97%, about 98%, about 99%, or 100% identical to SEQ ID NO. 379.

In some embodiments, the serum albumin binding domain (also referred to herein as the half-life extension domain) of a multispecific protein comprising an EpCAM binding protein as described herein can be any domain that binds to serum albumin including but not limited to domains from a monoclonal antibody, a polyclonal antibody, a recombinant antibody, a human antibody, a humanized antibody. In some embodiments, the serum albumin binding domain is a single chain variable fragments (scFv), single-domain antibody such as a heavy chain variable domain (VH), a light chain variable domain (VL) and a variable domain (VHH) of camelid derived sdAb, or antigen binding fragments of the HSA binding antibodies, such as Fab, F(ab')2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain, peptide, ligand or small molecule entity specific for serum albumin. In certain embodiments, the HSA binding domain is a single-domain antibody. In other embodiments, the serum albumin binding domain is a peptide. In further embodiments, the serum albumin binding domain is a small molecule. It is contemplated that the serum albumin binding domain of the multispecific binding protein comprising a single chain variable fragment CD3 binding protein is fairly small and no more than 25 kD, no more than 20 kD, no more than 15 kD, or no more than 10 kD in some embodiments. In certain instances, the serum albumin binding is 5 kD or less if it is a peptide or small molecule entity. Exemplary amino acid sequence for a serum albumin binding domain of a multispecific (e.g., trispecific) EpCAM targeting TriTAC protein of this disclosure is provided as SEQ ID No. 378, or a sequence that is at least about 75% to 100% identical to SEQ ID No. 378, such as at least about 75%, about 80%, about 85%, about 90%, about 91%, about 92%, about 93%, about 94%, about 95%, about 96%, about 97%, about 98%, about 99%, or 100% identical to SEQ ID NO. 378.

The half-life extension domain of a multispecific binding protein, as described herein, comprising a single chain variable fragment CD3 binding protein provides for altered pharmacodynamics and pharmacokinetics of the single chain variable fragment CD3 binding protein itself. As above, the half-life extension domain extends the elimination half-time. The half-life extension domain also alters pharmacodynamic properties including alteration of tissue distribution, penetration, and diffusion of the single chain variable fragment CD3 binding protein. In some embodiments, the half-life extension domain provides for improved tissue (including tumor) targeting, tissue distribution, tissue penetration, diffusion within the tissue, and enhanced efficacy as compared with a protein without a half-life extension domain. In one embodiment, therapeutic methods effectively and efficiently utilize a reduced amount of the multispecific binding protein comprising a single chain variable fragment CD3 binding protein, resulting in reduced side effects, such as reduced off-target, such as non-tumor cell cytotoxicity.

Further, the binding affinity of the half-life extension domain, in some embodiments, is selected so as to target a specific elimination half-time in a particular multispecific binding protein comprising an EpCAM binding protein as described herein. Thus, in some embodiments, the half-life extension domain has a high binding affinity. In other embodiments, the half-life extension domain has a medium binding affinity. In yet other embodiments, the half-life extension domain has a low or marginal binding affinity. Exemplary binding affinities include $K_d$ of 10 nM or less (high), between 10 nM and 100 nM (medium), and greater than 100 nM (low). As above, binding affinities to serum albumin are determined by known methods such as Surface Plasmon Resonance (SPR).

An EpCAM targeting multispecific protein of this disclosure, in certain embodiments, comprises (A) a first domain which binds to a CD3; (B) a second domain which is an half-life extension domain; and (C) a third domain which is an EpCAM binding protein as described herein. In certain embodiments, the first domain comprises an scFv that specifically binds the CD3. The CD3, for instance, is a human CD3 protein. In certain embodiments, the second domain comprises an sdAb that specifically binds a bulk serum protein. In some instances, the bulk serum protein is albumin, such as, a serum albumin, such as, a human serum albumin.

The domains (A), (B), and (C), are, in some embodiments, linked via linkers L1 and L2, in any one of the following orientations: $H_2N$-(A)-L1-(C)-L2-(B)—COOH, $H_2N$—(B)-L1-(A)-L2-(C)—COOH, $H_2N$—(C)-L1-(B)-L2-(A)-COOH, $H_2N$—(C)-L1-(A)-L2-(B)—COOH, $H_2N$-(A)-L1-(B)—(C)-L2-COOH, or $H_2N$—(B)—(C)-(A)-COOH.

An EpCAM targeting multispecific protein of this disclosure, in some embodiments, comprises an amino acid sequence that is at least about 70% to about 100% identical to a sequence selected from the group consisting of SEQ ID Nos. 153-206 and 210-212. In some embodiments, an EpCAM targeting multispecific protein of this disclosure comprises an amino acid sequence that is at least about 70%, at least about 75%, at least about 76%, at least about 77%, about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, to about 100% identical to a sequence selected from the group consisting of SEQ ID Nos. 153-206 and 210-212.

Conditionally Active Multispecific EpCAM Targeting Proteins, Such as Conditionally Active EpCAM Targeting Trispecific Proteins (Also Referred to Herein as EpCAM Targeting ProTriTAC or Protrispecific Proteins or Molecules)

One embodiment of this disclosure provides a conditionally active multispecific protein comprising an EpCAM binding domain as disclosed herein (for example, in some embodiment this disclosure provides an EpCAM targeting protrispecific/ProTriTAC protein comprising an EpCAM binding domain of this disclosure).

In some embodiments, the conditionally active multispecific protein further comprises a domain which specifically binds to a CD3 and a binding moiety which specifically binds to a bulk serum protein, such as a human serum albumin. In some embodiments, the binding moiety is capable of masking the interaction of the EpCAM binding domain or the CD3 binding domain, to their targets. In some embodiments, a binding moiety of this disclosure comprises a masking moiety and a cleavable linker, such as a protease cleavable linker. Exemplary sequences for masking moiety within a binding moiety are provided in SEQ ID Nos. 380-424, or a sequence comprising one or more substitutions relative to a sequence selected from the group consisting of SEQ ID Nos. 380-424. In some embodiments, the binding moiety comprises a modified non-CDR loop sequence and a cleavable linker. In some embodiments, the cleavable linker comprises a sequence selected from the group consisting of SEQ ID Nos. 425-471, 503-506, 508-550, and 581, or a sequence that comprises one or substitutions relative to a sequence selected from the group consisting of SEQ ID Nos. 425-425-471, 503-506, 508-550, and 581. In some embodiments, the masking moiety comprises a modified non-CDR loop sequence and a non-cleavable linker. In some embodiments the non-cleavable linker comprises a sequence as set forth in SEQ ID No. 507, or a sequence comprising one or more substitutions relative to SEQ ID No. 507. In some embodiments, a binding moiety comprises a sequence that is at least about 75%, about 80%, about 85%, about 90%, about 91%, about 92%, about 93%, about 94%, about 95%, about 96%, about 97%, about 98%, about 99%, or about 100% identical to a sequence selected from the group consisting of SEQ ID Nos. 472-473, and 482-483. In some embodiments, a CD3 binding domain of an EpCAM ProTriTAC of this disclosure comprises a sequence that is at least about 75%, about 80%, about 85%, about 90%, about 91%, about 92%, about 93%, about 94%, about 95%, about 96%, about 97%, about 98%, about 99%, or about 100% identical to SEQ ID No. 474.

In some embodiments, an EpCAM targeting ProTriTAC of this disclosure, comprises, from N-terminal to C-terminal, comprise a binding moiety that is an anti-ALB domain comprising a non-CDR loop with a binding site for a CD3 binding domain (e.g., a CD3 binding domain having the sequence of SEQ ID No. 474, or at least about 75% identity to the same), a cleavable linker, the CD3 binding domain, and on the C-terminal end the anti-EpCAM binding domain. The EpCAM binding domain of the ProTriTAC, in some embodiments, is at least about 60%, about 61%, at least about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID Nos. 1-38, 207-209, and 496-497

In some embodiments, an EpCAM targeting ProTriTAC of this disclosure comprises an amino acid sequence that is at least about at least about 75%, about 80%, about 85%, about 90%, about 91%, about 92%, about 93%, about 94%, about 95%, about 96%, about 97%, about 98%, about 99%, or about 100% identical to a sequence selected from the group consisting of: SEQ ID Nos. 495, 498, 499, 500, 502, 569, 570, 572, 573, 575, 576, 577, and 578. In some embodiments, an EpCAM targeting ProTriTAC of this discloses comprises an amino acid sequence as set forth in SEQ ID No. 576, a pharmaceutical composition comprising the same, and method of using the same for treating a disease, such as a tumorous disease as described herein.

In some embodiments, an EpCAM targeting ProTriTAC of this disclosure, in a non-cleavable prodrug format, comprises an amino acid sequence that is at least about at least about 75%, about 80%, about 85%, about 90%, about 91%, about 92%, about 93%, about 94%, about 95%, about 96%, about 97%, about 98%, about 99%, or about 100% identical to a sequence selected from the group consisting of: SEQ ID Nos. 495 and 502.

An exemplary sequence for an active EpCAM targeting drug (CT), as described herein, is a sequence that is at least about 75%, about 80%, about 85%, about 90%, about 91%, about 92%, about 93%, about 94%, about 95%, about 96%, about 97%, about 98%, about 99%, or about 100% identical to SEQ ID No. 153-179, 180-206, 210-212, 494, 571, and 574.

The binding moiety is capable of synergistically expanding a therapeutic window of a conditionally active EpCAM targeting protrispecific protein, by both steric masking and specific masking. In some embodiments, the binding moiety combines both steric masking (for example, via binding to a bulk serum albumin) and specific masking (for example, via non-CDR loops binding to the CDRs of an anti-EpCAM domain or an anti-CD3 scFv domain). In some cases, modifying the non-CDR loops within the binding moiety does not affect albumin binding. The protease cleavable linker, in some cases, enables activation of an EpCAM targeting protrispecific protein in a single proteolytic event, thereby allowing more efficient conversion of the protrispecific molecule in tumor microenvironment. Further, tumor-associated proteolytic activation, in some cases, reveals active T cell engager with minimal off-tumor activity after activation. The present disclosure, in some embodiments, provides a half-life extended T cell engager format (ProTriTAC) comprising an EpCAM binding moiety as described herein, which in some cases represents a new and improved approach to engineer conditionally active T cell engagers.

The half-life of the EpCAM binding domain in a conditionally active protrispecific format is, in some embodiments, extended in systemic circulation by using the binding moiety as described above which acts as a safety switch that keeps the multispecific protein in the pro format in an inert state until it reaches the tumor microenvironment where it is conditionally activated by cleavage of the linker and is able to bind its target antigen(s). The safety switch, in certain instances, provides several advantages: some examples including (i) expanding the therapeutic window of the conditionally active EpCAM targeting protein; (ii) reducing target-mediated drug disposition by maintaining the conditionally active EpCAM targeting protein in systemic circulation; (iii) reducing the concentration of undesirable activated protein in systemic circulation, thereby minimizing the spread of chemistry, manufacturing, and controls related impurities, e.g., pre-activated drug product, endogenous viruses, host-cell proteins, DNA, leachables, anti-foam, antibiotics, toxins, solvents, heavy metals; (iv) reducing the concentration of undesirable activated proteins in systemic circulation, thereby minimizing the spread of product related impurities, aggregates, breakdown products, product variants due to: oxidation, deamidation, denaturation, loss of C-term Lys in MAbs; (v) preventing aberrant activation in circulation; (vi) reducing the toxicities associated with the leakage of activated species from diseased tissue or other pathophysiological conditions, e.g., tumors, autoimmune diseases, inflammations, viral infections, tissue remodeling events (such as myocardial infarction, skin wound healing), or external injury (such as X-ray, CT scan, UV exposure); and (vii) reducing non-specific binding of the conditionally active EpCAM targeting protein. Furthermore, post-activation, or in other words post breaking of the safety switch, the conditionally active EpCAM targeting protein is separated from the safety switch which provided extended half-life, and thus is cleared from circulation. For instance, if the drug is inadvertently activated outside of a tumor environment or if it leaks out of a tumor environment after activation, it is likely to be cleared rapidly and is less likely to cause damage to normal tissues, thus reducing toxicity.

In some embodiments, a conditionally active multispecific EpCAM binding protein as described herein has an improved therapeutic index as compared to that of an EpCAM binding protein that is not conditionally active, but is rather constitutively active. For instance, an EpCAM ProTriTAC, in some embodiments, has an increased therapeutic index than an EpCAM TriTAC. The increase in therapeutic index, in some embodiments, is from at least about 2-fold to about 1000-fold, such as about 4-fold to about 800-fold, about 6-fold to about 800-fold, about 6-fold to about 600-fold, about 10-fold to about 400-fold, about 20-fold to about 200-fold, about 30-fold to about 150-fold, about 50-fold to about 100-fold. The increase in therapeutic index, in some embodiments, is attributed to the conjugation of the EpCAM binding domain to a binding moiety as described above, with the non-CDR loop and the cleavable linker.

A "therapeutic index" (TI) (also referred to as "therapeutic window") is, in some embodiments, a comparison of the minimum amount of a therapeutic agent (e.g., an EpCAM TriTAC, an EpCAM ProTriTAC, an EpCAM CAR, an EpCAM ProCAR) that causes the therapeutic effect (e.g., improved survival of a patient with an EpCAM expressing cancer, treated with a therapeutic agent as mentioned above) to minimum tolerated dose. An example of therapeutic index expansion of a ProTriTAC is shown in Table 14. In some instances, the therapeutic index improvement is manifested in terms of an improved $EC_{50}$ of an EpCAM TriTAC compared to an EpCAM ProTriTAC, in T cell mediated killing of cancer cells.

In some embodiments, the conditionally active EpCAM targeting protein format gives the EpCAM binding domain a significantly longer serum half-life and reduces the likelihood of its undesirable activation in circulation, thereby producing a "biobetter" version.

A binding moiety as described herein comprises at least one non-CDR loop. In some embodiments, a non-CDR loop provides a binding site for binding of the binding moiety to an EpCAM binding domain of this disclosure. In some cases, the binding moiety masks binding of the EpCAM binding domain to its target antigen, e.g., via steric occlusion, via specific intermolecular interactions, or a combination of both.

In some embodiments, a binding moiety as described herein further comprises complementarity determining regions (CDRs), for instance, specific for binding a bulk serum protein (e.g., a human serum albumin). In some instances, a binding moiety of this disclosure is a domain derived from an immunoglobulin molecule (Ig molecule). The Ig may be of any class or subclass (IgG1, IgG2, IgG3, IgG4, IgA, IgE, IgM etc). A polypeptide chain of an Ig molecule folds into a series of parallel beta strands linked by loops. In the variable region, three of the loops constitute the "complementarity determining regions" (CDRs) which determine the antigen binding specificity of the molecule. An IgG molecule comprises at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs) with are hypervariable in sequence and/or involved in antigen recognition and/or usually form structurally defined loops, interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

Figure 26:
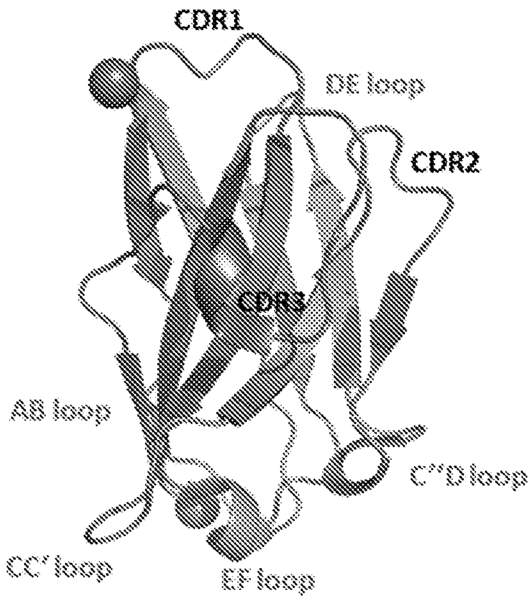
FIG. 26 illustrates a variable domain of an immunoglobulin molecule, comprising complementarity determining regions (CDR1, CDR2, and CDR3), and non-CDR loops connecting the beta strand (AB, CC', C" D, EF, and DE).

In some embodiments, a binding moiety of this disclosure is a heavy chain only antibody. As shown in FIGS. 26, the variable domain of a heavy chain only antibody has several beta strands that are arranged in two sheets. The variable domain of a heavy chain only antibody contains three hypervariable loops, or complementarity-determining regions (CDRs) and framework regions FR1, FR2, FR3, and FR4. The three CDRs of the variable domain (CDR1, CDR2, CDR3) cluster at one end of the beta barrel. The CDRs are the loops that connect beta strands B-C, C'-C", and F-G of the immunoglobulin fold, whereas the bottom loops that connect beta strands AB, CC', C"-D and E-F of the immunoglobulin fold, and the top loop that connects the D-E strands of the immunoglobulin fold are the non-CDR loops.

In some embodiments of this disclosure at least some or all of the amino acid sequences of FR1, FR2, FR3, and FR4 are part of the "non-CDR loop" of the binding moieties described herein, such as a binding moiety that is a heavy chain only antibody. In some embodiments of this disclosure, at least some amino acid residues of a constant domain, CH1, CH2, or CH3, are part of the "non-CDR loop" of the binding moieties described herein. Non-CDR loops comprise, in some embodiments, one or more of AB, CD, EF, and DE loops of a C1-set domain of an Ig or an Ig-like molecule; AB, CC', EF, FG, BC, and EC' loops of a C2-set domain of an Ig or an Ig-like molecule; DE, BD, GF, A (A1A2) B, and EF loops of I (Intermediate)-set domain of an Ig or Ig-like molecule.

Within the variable domain, the CDRs are believed to be responsible for antigen recognition and binding, while the FR residues are considered a scaffold for the CDRs. However, in certain cases, some of the FR residues play an important role in antigen recognition and binding. Framework region residues that affect Ag binding are divided into two categories. The first are FR residues that contact the antigen, thus are part of the binding-site, and some of these residues are close in sequence to the CDRs. Other residues are those that are far from the CDRs in sequence, but are in close proximity to it in the 3-D structure of the molecule, e.g., a loop in heavy chain.

In some embodiments, the non-CDR loop is modified to generate an antigen binding site specific for a bulk serum protein, such as albumin. In some embodiments, the non-CDR loop is modified to generate an antigen binding site specific for an EpCAM binding domain as described herein. In some embodiments, the non-CDR loop is modified to generate an antigen binding site specific for a CD3 binding domain as described herein.

It is contemplated that various techniques can be used for modifying the non-CDR loop, e.g., site-directed mutagenesis, random mutagenesis, insertion of at least one amino acid that is foreign to the non-CDR loop amino acid sequence, amino acid substitution. An antigen peptide is inserted into a non-CDR loop, in some examples. In some examples, an antigenic peptide is substituted for the non-CDR loop. The modification, to generate an antigen binding site, is in some cases in only one non-CDR loop. In other instances, more than one non-CDR loop are modified. For instance, the modification is in any one of the non-CDR loops shown in FIG. 26, i.e., AB, CC', C" D, EF, and D-E. In some cases, the modification is in the DE loop. In other cases the modifications are in all four of AB, CC', C"D, E-F loops.

In certain examples, the binding moieties described herein are bound to the EpCAM binding domain via their AB, CC', C" D, or EF loop and are bound to a bulk-serum protein, such as albumin, via their B-C, C'-C", or F-G loop. In certain examples, the binding moiety is bound to the EpCAM binding domain via its AB, CC', C" D, and EF loop and is bound to a bulk-serum protein, such as albumin, via its BC, C'C", and FG loop. In certain examples, the binding moiety is bound to the EpCAM binding domain via one or more of AB, CC', C" D, and E-F loop and is bound to a bulk-serum protein, such as albumin, via one or more of BC, C'C", and FG loop. In certain examples, the binding moiety is bound to a bulk serum protein, such as albumin, via its AB, CC', C" D, or EF loop and is bound to the EpCAM binding domain via its BC, C'C", or FG loop. In certain examples, the binding moiety is bound to a bulk serum protein, such as albumin, via its AB, CC', C" D, and EF loop and is bound to the EpCAM binding domain via its BC, C'C", and FG loop. In certain examples, the binding moiety of the first embodiment is bound to a bulk serum protein, such as albumin, via one or more of AB, CC', C" D, and E-F loop and is bound to the EpCAM binding protein, via one or more of BC, C'C", and FG loop. In certain examples, the binding moieties described herein are bound to a CD3 binding domain via their AB, CC', C" D, or EF loop and are bound to a bulk-serum protein, such as albumin, via their B-C, C'-C", or F-G loop. In certain examples, the binding moieties described herein are bound to a bulk serum protein, such as albumin, via their AB, CC', C" D, or EF loop and are bound to a CD3 binding domain, via their B-C, C'-C", or F-G loop. In certain examples, the binding moieties described herein are bound to a CD3 binding domain via their AB, CC', C" D, or EF loop and are bound to an EpCAM binding domain, via their B-C, C'-C", or F-G loop. In certain examples, the binding moieties described herein are bound to an EpCAM binding domain via their AB, CC', C" D, or EF loop and are bound to a CD3 binding domain, via their B-C, C'-C", or F-G loop.

The bulk serum protein comprises, for example, albumin, fibrinogen, or a globulin. In some embodiments, the binding moieties are engineered scaffolds. Engineered scaffolds comprise, for example, sdAb, a scFv, a Fab, a VHH, a fibronectin type III domain, immunoglobulin-like scaffold (as suggested in Halaby et al., 1999. Prot Eng 12(7): 563-571), DARPin, cystine knot peptide, lipocalin, three-helix bundle scaffold, protein G-related albumin-binding module, or a DNA or RNA aptamer scaffold.

In some cases, the binding moieties comprise a binding site for the bulk serum protein. In some embodiments, the CDRs within the binding moieties provide a binding site for the bulk serum protein. The bulk serum protein is, in some examples, a globulin, albumin, transferrin, IgG1, IgG2, IgG4, IgG3, IgA monomer, Factor XIII, Fibrinogen, IgE, or pentameric IgM. In some embodiments, the binding moieties comprise a binding site for an immunoglobulin light chain. In some embodiments, the CDRs provide a binding site for the immunoglobulin light chain. The immunoglobulin light chain is, in some examples, an Igk free light chain or an IgA free light chain.

In additional embodiments, the binding moieties are any kinds of polypeptides. For example, in certain instances the binding moieties are natural peptides, synthetic peptides, or fibronectin scaffolds, or engineered bulk serum proteins. In some examples, the binding moieties comprise any type of binding domain, including but not limited to, domains from a monoclonal antibody, a polyclonal antibody, a recombinant antibody, a human antibody, a humanized antibody. In some embodiments, the binding moiety is a single chain variable fragment (scFv), a soluble TCR fragment, a single-domain antibody such as a heavy chain variable domain (VH), a light chain variable domain (VL) and a variable domain (VHH) of camelid derived nanobody. In other embodiments, the binding moieties are non-Ig binding domains, i.e., antibody mimetic, such as anticalins, affilins, affibody molecules, affimers, affitins, alphabodies, avimers, DARPins, fynomers, kunitz domain peptides, and monobodies.

It is contemplated herein that the binding moiety described herein comprises at least one cleavable linker. In one aspect, the cleavable linker comprises a polypeptide having a sequence recognized and cleaved in a sequence-specific manner. The binding moiety described herein, in some cases, comprises a protease cleavable linker recognized and cleaved in a sequence-specific manner. In some embodiments, the protease cleavable linker is recognized in a sequence-specific manner by a matrix metalloprotease (MMP), for example a MMP9. In some cases, the protease cleavable linker recognized by a MMP9 comprises a polypeptide having an amino acid sequence PR(S/T)(L/I)(S/T). In some cases, the protease cleavable linker recognized by a MMP9 comprises a polypeptide having an amino acid sequence LEATA. In some cases, the protease cleavable linker is recognized in a sequence-specific manner by a MMP11.

Proteases are proteins that cleave proteins, in some cases, in a sequence-specific manner. Proteases include but are not limited to serine proteases, cysteine proteases, aspartate proteases, threonine proteases, glutamic acid proteases, metalloproteases, asparagine peptide lyases, serum proteases, cathepsins, Cathepsin B, Cathepsin C, Cathepsin D, Cathepsin E, Cathepsin K, Cathepsin L, kallikreins, hK1, hK10, hK15, plasmin, collagenase, Type IV collagenase, stromelysin, Factor Xa, chymotrypsin-like protease, trypsin-like protease, elastase-like protease, subtilisin-like protease, actinidain, bromelain, calpain, caspases, caspase-3, Mir1-CP, papain, HIV-1 protease, HSV protease, CMV protease, chymosin, renin, pepsin, matriptase, legumain, plasmepsin, nepenthesin, metalloexopeptidases, metalloendopeptidases, matrix metalloproteases (MMP), MMP1, MMP2, MMP3, MMP8, MMP9, MMP13, MMP11, MMP14, urokinase plasminogen activator (uPA), enterokinase, prostate-specific antigen (PSA, hK3), interleukin-1β converting enzyme, thrombin, FAP (FAP-α), dipeptidyl peptidase, and dipeptidyl peptidase IV (DPPIV/CD26).

TABLE 1

Exemplary proteases and protease recognition sequences

| Protease | Cleavage Domain Sequence | SEQ ID NO: |
|---|---|---|
| MMP7 | KRALGLPG | 508 |
| MMP7 | $(DE)_8$RPLALWRS$(DR)_8$ | 509 |
| MMP9 | PR(S/T)(L/I)(S/T) | 510 |
| MMP9 | LEATA | 511 |
| MMP11 | GGAANLVRGG | 512 |
| MMP14 | SGRIGFLRTA | 513 |
| MMP | PLGLAG | 514 |
| MMP | PLGLAX | 515 |
| MMP | PLGC(me)AG | 516 |
| MMP | ESPAYYTA | 517 |
| MMP | RLQLKL | 518 |
| MMP | RLQLKAC | 519 |
| MMP2, MMP9, MMP14 | EP(Cit)G(Hof)YL | 520 |
| Urokinase plasminogen activator (uPA) | SGRSA | 521 |
| Urokinase plasminogen activator (uPA) | DAFK | 523 |
| Urokinase plasminogen activator (uPA) | GGGRR | 524 |
| Lysosomal Enzyme | GFLG | 525 |
| Lysosomal Enzyme | ALAL | 526 |
| Lysosomal Enzyme | FK | 527 |
| Cathepsin B | NLL | 528 |
| Cathepsin D | PIC(Et)FF | 529 |
| Cathepsin K | GGPRGLPG | 530 |
| Prostate Specific Antigen | HSSKLQ | 531 |
| Prostate Specific Antigen | HSSKLQL | 532 |

TABLE 1-continued

Exemplary proteases and protease recognition sequences

| Protease | Cleavage Domain Sequence | SEQ ID NO: |
|---|---|---|
| Prostate Specific Antigen | HSSKLQEDA | 533 |
| Herpes Simplex Virus Protease | LVLASSSFGY | 534 |
| HIV Protease | GVSQNYPIVG | 535 |
| CMV Protease | GVVQASCRLA | 536 |
| Thrombin | F(Pip)RS | 537 |
| Thrombin | DPRSFL | 538 |
| Thrombin | PPRSFL | 539 |
| Caspase-3 | DEVD | 540 |
| Caspase-3 | DEVDP | 541 |
| Caspase-3 | KGSGDVEG | 542 |
| Interleukin 1β converting enzyme | GWEHDG | 543 |
| Enterokinase | EDDDDKA | 544 |
| FAP | KQEQNPGST | 545 |
| Kallikrein 2 | GKAFRR | 546 |
| Plasmin | DAFK | 547 |
| Plasmin | DVLK | 548 |
| Plasmin | DAFK | 549 |
| TOP | ALLLALL | 550 |

Proteases are known to be secreted by some diseased cells and tissues, for example tumor or cancer cells, creating a microenvironment that is rich in proteases or a protease-rich microenvironment. In some case, the blood of a subject is rich in proteases. In some cases, cells surrounding the tumor secrete proteases into the tumor microenvironment. Cells surrounding the tumor secreting proteases include but are not limited to the tumor stromal cells, myofibroblasts, blood cells, mast cells, B cells, NK cells, regulatory T cells, macrophages, cytotoxic T lymphocytes, dendritic cells, mesenchymal stem cells, polymorphonuclear cells, and other cells. In some cases, proteases are present in the blood of a subject, for example proteases that target amino acid sequences found in microbial peptides. This feature allows for targeted therapeutics such as antigen binding proteins to have additional specificity because T cells will not be bound by the antigen binding protein except in the protease rich microenvironment of the targeted cells or tissue.

Other non-limiting examples of linkers that may be utilized in constructs described herein are provided in the Sequence Listing below.

Integration into Chimeric Antigen Receptors (CAR)

The EpCAM binding proteins of the present disclosure can, in certain examples, be incorporated into a chimeric antigen receptor (CAR), or to a ProCAR. An engineered immune effector cell, e.g., a T cell or NK cell, can be used to express a CAR that includes an EpCAM binding protein containing, for example, an anti-EpCAM single domain antibody as described herein. In one embodiment, the CAR including the EpCAM binding protein as described herein is connected to a transmembrane domain via a hinge region, and further a costimulatory domain, e.g., a functional signaling domain obtained from OX40, CD27, CD28, CD5, ICAM-1, LFA-1 (CD11a/CD18), ICOS (CD278), or 4-1BB. In some embodiments, the CAR further comprises a sequence encoding an intracellular signaling domain, such as 4-1BB and/or CD3 zeta. Exemplary sequences for a ProCAR comprising an EpCAM binding domain is provided in SEQ ID Nos. 485-491, or sequences that are at least about 75% to 100% identical to a sequence selected from SEQ ID Nos. 485-491, such as about 75%, about 80%, about 85%, about 90%, about 91%, about 92%, about 93%, about 94%, about 95%, about 96%, about 97%, about 98%, about 99%, or 100%.

The conditionally active receptors described herein comprise at least one binding moiety comprising a non-CDR loop. In one aspect, the binding moiety masks binding of the EpCAM binding domain, until activation. The cleavable linker, for example, comprises a protease cleavage site or a pH dependent cleavage site. The cleavable linker, in certain instances, is cleaved only in a tumor microenvironment. Thus, the binding moiety, connected to the cleavable linker, and further bound to the EpCAM binding domain, in some examples, maintains the EpCAM binding domain in an inert state in circulation until the cleavable linker is cleaved off in a tumor microenvironment. In some embodiments, the binding moiety binds to the EpCAM binding domain. In some embodiments, a non-CDR loop provides a binding site for binding of the moiety to the EpCAM binding domain. In some embodiments, the binding moiety masks binding of the EpCAM binding domain to its target antigen, e.g. via steric occlusion, via specific intramolecular interactions, such as interactions within the different domains of the polypeptide comprising the binding moiety. In some embodiments, the binding moiety further comprises complimentary determining regions (CDRs).

In some instances, the binding moiety of a CAR or a proCAR as described herein is a domain derived from an immunoglobulin molecule (Ig molecule), as described above in the section corresponding to conditionally active multispecific EpCAM targeting proteins of this disclosure.

Figure 27:
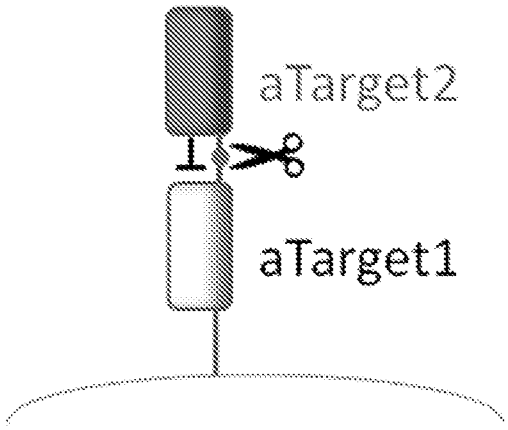
FIG. 27 illustrates an exemplary arrangement of a target antigen binding domain (aTarget 1), cleavable linker, and a binding moiety (aTarget 2) of the present disclosure.

FIG. 27 shows a schematic representation of a portion of an example cleavable conditionally active receptor of the present disclosure. The conditionally active receptor comprises an EpCAM binding domain (aTarget1), a cleavable linker, and a binding moiety (aTarget2). The EpCAM binding domain has specificity for a first target (EpCAM), while the binding moiety has specificity for a second target. The binding moiety also has a modified non-CDR loop, which inhibits binding of the EpCAM binding domain to its target. Once cleaved at the cleavable linker, the binding moiety can be released, enabling binding of the EpCAM binding domain.

Figure 28:
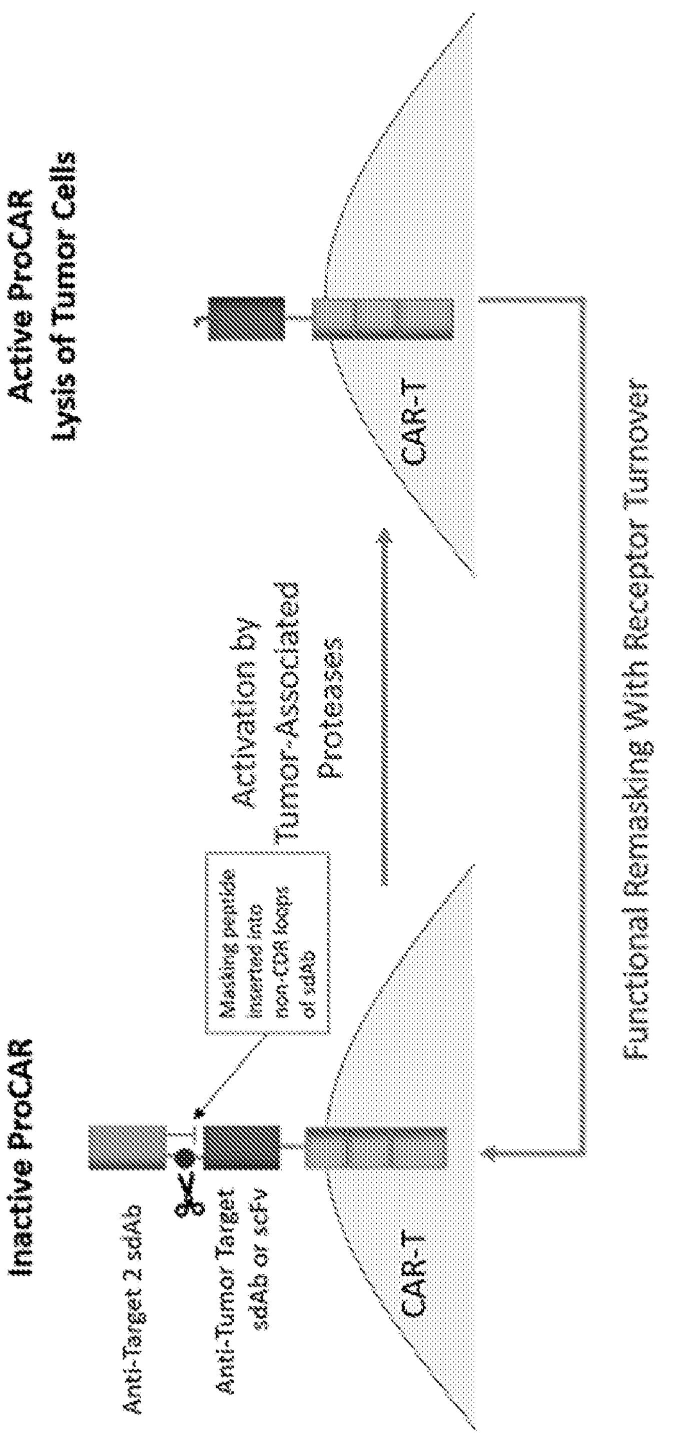
FIG. 28 illustrates an example of a conditionally active receptor as described herein.
Figure 29A:
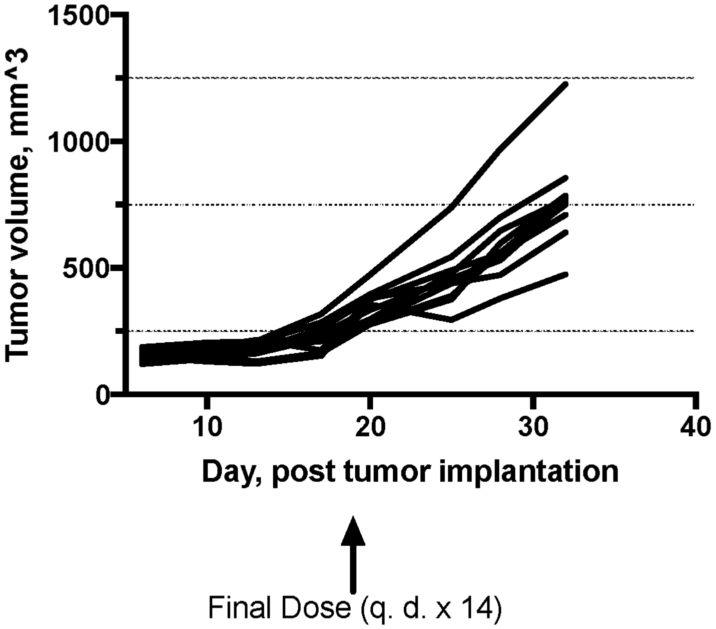
FIGS. 29A-29K show efficacy of Control TriTAC, EpCAM ProTriTAC and EpCAM TriTAC proteins in an established LoVo (colon cancer) tumor model.
Figure 29B:
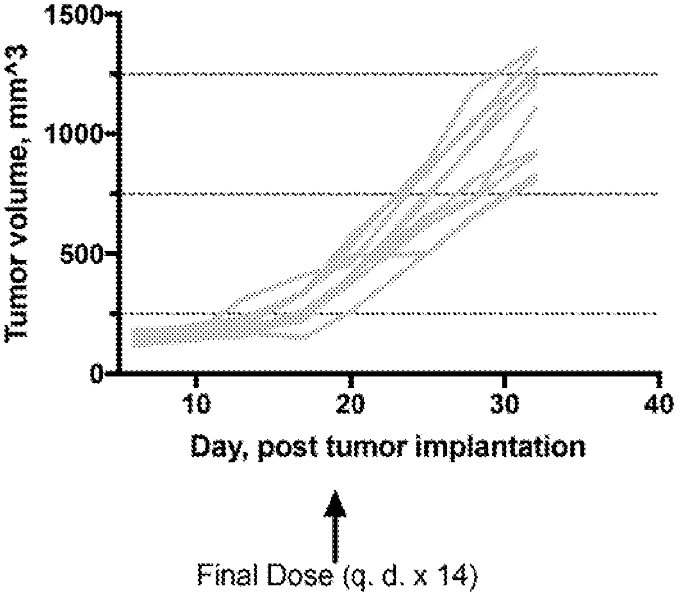
Figure 29C:
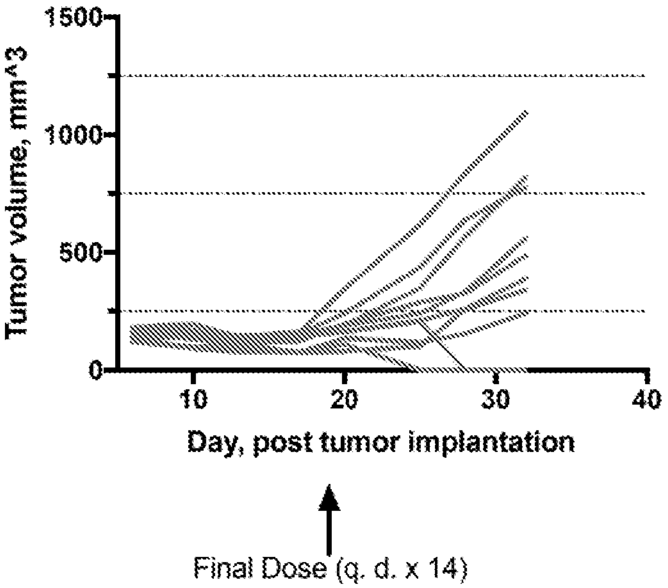
Figure 29D:
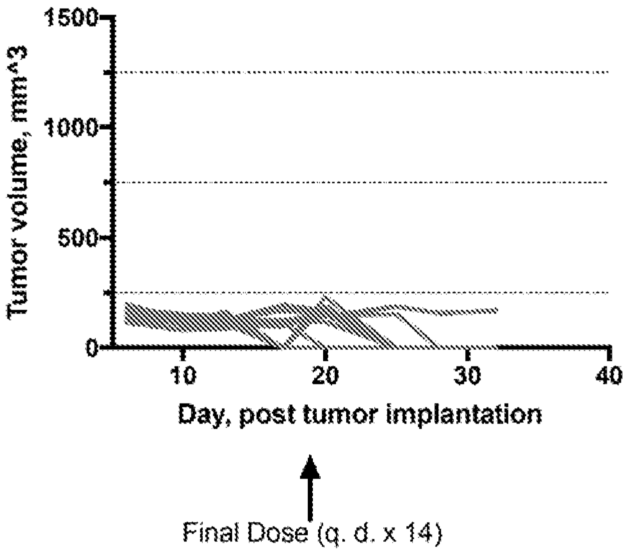
Figure 29E:
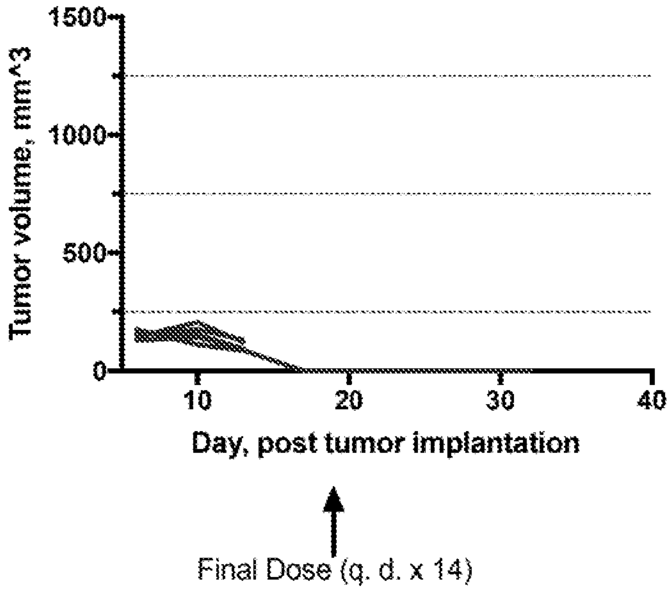
Figure 29F:
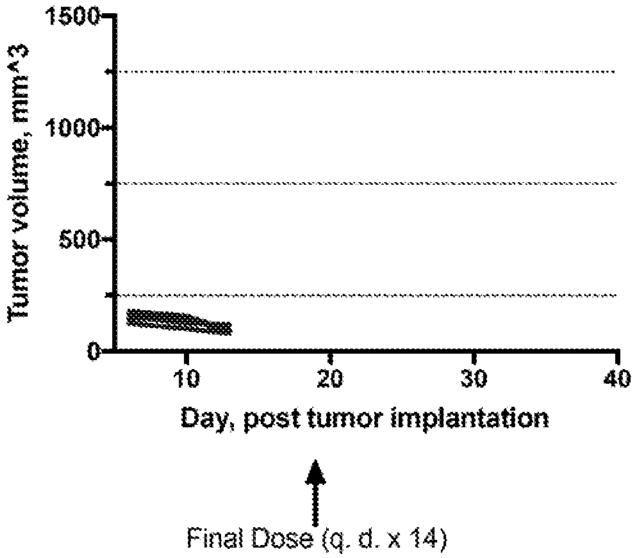
Figure 29G:
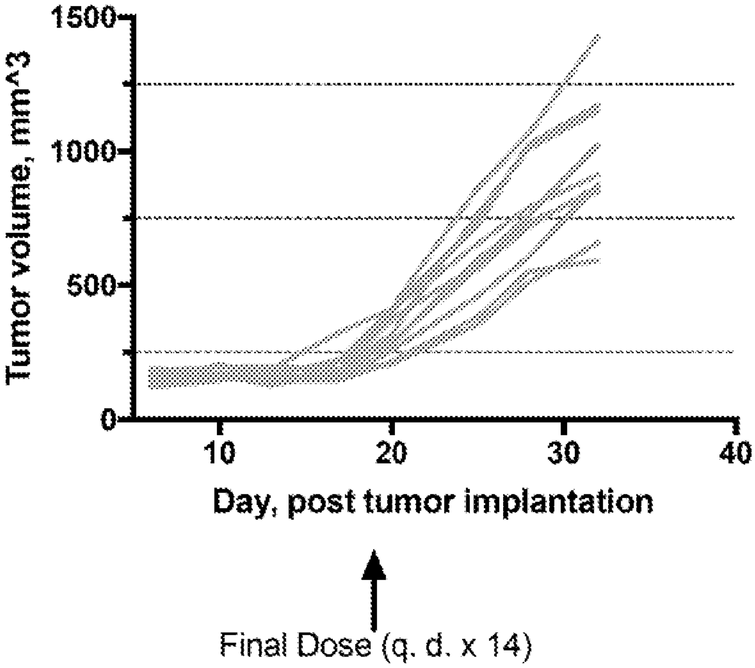
Figure 29H:
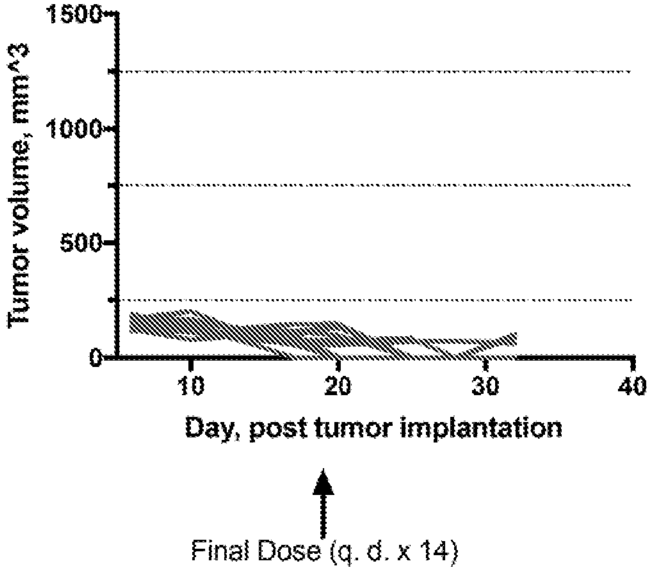
Figure 29I:
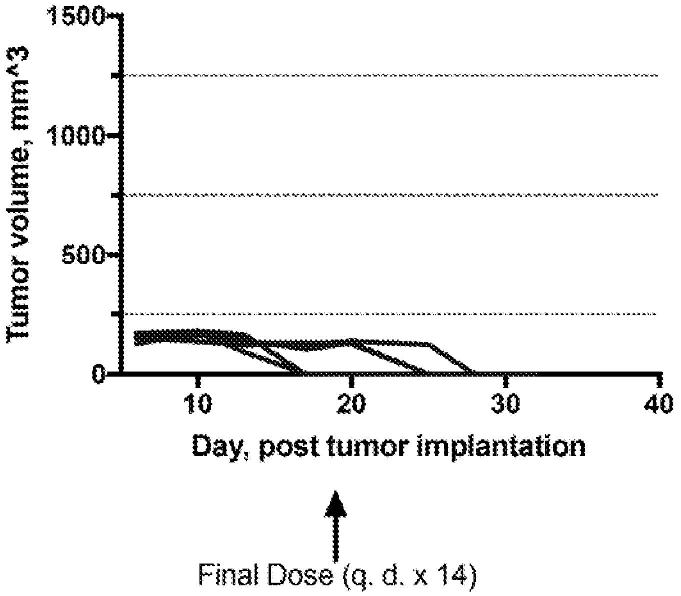
Figure 29J:
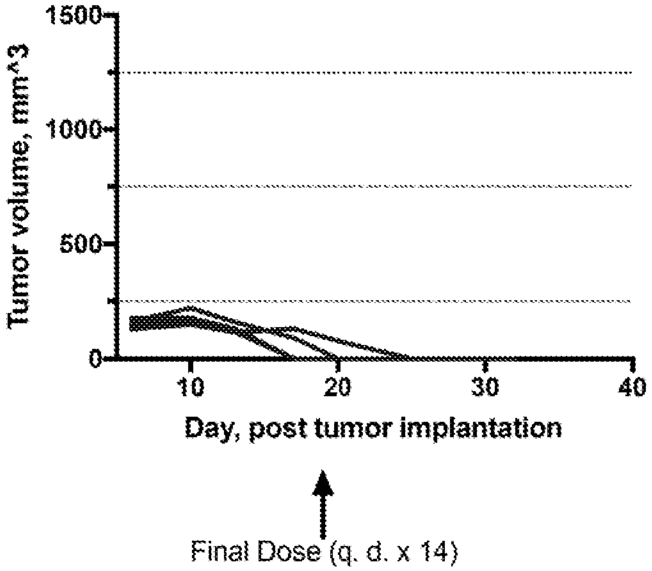
Figure 29K:
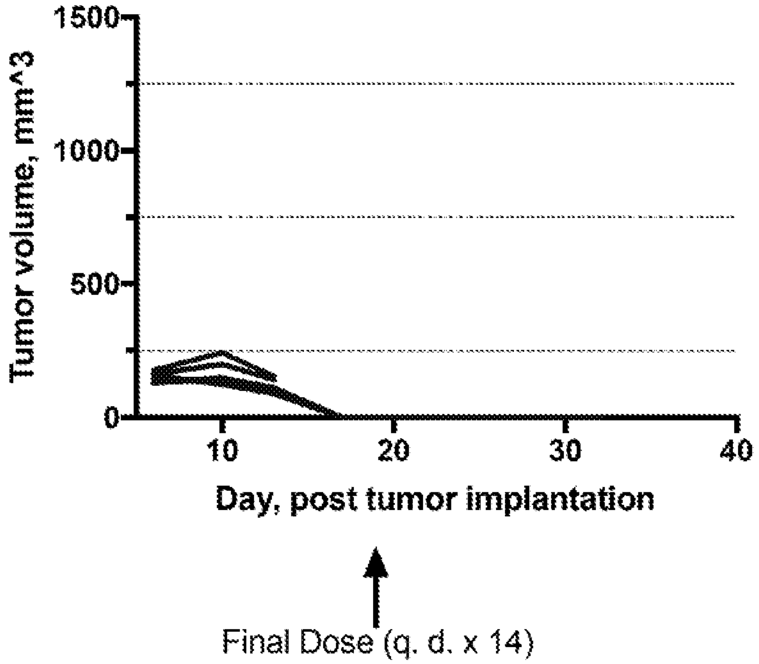

FIG. 28 shows a schematic representation of the activation of an example conditionally active receptor of the present disclosure. Inactive receptor (Inactive ProCAR) comprises an EpCAM binding domain (Anti-Tumor Target sdAb or scFv) connected to a binding moiety (Anti-Target 2 sdAb) via a linker comprising a protease cleavage site. The binding moiety comprises a masking peptide/moiety, inserted into one or more non-CDR loops, such that the binding moiety binds to and inhibits the EpCAM antigen binding domain. In some embodiments, the binding moiety has specificity for a given target, as described further elsewhere herein. The receptor also comprises a transmembrane domain and an intracellular signaling domain. The receptor is provided in a T-cell (CAR-T). Upon exposure to a tumor environment, the protease cleavage site is cleaved by tumor-associated proteases, thereby activating the receptor, generating the active receptor which does not comprise the binding moiety. The receptor now comprises an active antigen-binding domain. As the receptor is internalized by the cell, new receptors are generated which comprise the binding moiety and are inactive.

The cleavable linker of the binding moiety, in some embodiments, comprises a protease cleavable site similar to what is described above with respect to the conditionally active multispecific proteins comprising an EpCAM binding domain of this disclosure. For instance, the cleavable linker in some embodiments comprises a sequence selected from Table 1 or from other linker sequences provided in the sequence table.

Transmembrane Domain

The conditionally active chimeric antigen receptors, T-cell receptor fusion proteins, and T-cell receptors of the present disclosure include a transmembrane domain for insertion into a eukaryotic cell membrane. In some embodiments, the transmembrane domain is interposed between the EpCAM binding domain and the intracellular domain. In some embodiments, the transmembrane domain is interposed between the EpCAM binding domain and the costimulatory domain.

Any transmembrane (TM) domain that provides for insertion of a polypeptide into the cell membrane of a eukaryotic (e.g., mammalian) cell is suitable for use. As one non-limiting example, the TM sequence IYIWAPLAGTCGVLLLSLVITLYC (SEQ ID NO: 551) can be used. Additional non-limiting examples of suitable TM sequences include: a) CD8 beta derived:

```
a) CD8 beta derived:
                                   (SEQ ID NO: 552)
GLLVAGVLVLLVSLGVAIHLCC;

b) CD4 derived:
                                   (SEQ ID NO: 553)
ALIVLGGVAGLLLFIGLGIFFCVRC;

c) CD3 zeta derived:
                                   (SEQ ID NO: 554)
LCYLLDGILFIYGVILTALFLRV;

d) CD28 derived:
                                   (SEQ ID NO: 555)
WVLVVVGGVLACYSLLVTVAFIIFWV;

e) CD134 (OX40) derived:
                                   (SEQ ID NO: 556)
AAILGLGLVLGLLGPLAILLALYLL;
and

f) CD7 derived:
                                   (SEQ ID NO: 557)
ALPAALAVISFLLGLGLGVACVLA.
```

Hinge Region

In some cases, the conditionally active chimeric antigen receptors, T-cell receptor fusion proteins, and T-cell receptors of the present disclosure comprise a hinge region (also referred to herein as a "spacer"), where the hinge region is interposed between the EpCAM binding domain and the transmembrane domain. In some cases, the hinge region is an immunoglobulin heavy chain hinge region. In some cases, the hinge region is a hinge region polypeptide derived from a receptor (e.g., a CD8-derived hinge region).

The hinge region can have a length of from about 4 amino acids to about 50 amino acids (aa), e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

Suitable spacers can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

Exemplary spacers include glycine polymers $(G)_n$, glycine-serine polymers (including, for example, $(GS)_n$, $(GSGGS)_n$ and $(GGGS)_n$, where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, Rev. Computational Chem. 11173-142 (1992)). Exemplary spacers comprise amino acid sequences including, but not limited to, GGSG, GGSGG, GSGSG, GSGGG, GGGSG, GSSSG, and the like.

Immunoglobulin hinge region amino acid sequences are known in the art; see, e.g., Tan et al. (1990) *Proc. Natl. Acad. Sci. USA* 87: 162; and Huck et al. (1986) *Nucl. Acids Res.* 14: 1779. As non-limiting examples, an immunoglobulin hinge region can include one of the following amino acid sequences: DKTHT; CPPC; CPEPKSCDTPPPCPR (SEQ ID NO: 558); see, e.g., Glaser et al. (2005) *J. Biol. Chem.* 280:41494); ELKTPLGDTTHT (SEQ ID NO: 559); KSCDKTHTCP (SEQ ID NO: 560); KCCVDCP (SEQ ID NO: 561); KYGPPCP (SEQ ID NO: 562); EPKSCDKTHTCPPCP (SEQ ID NO: 563); human IgG1 hinge); ERKCCVECPPCP (SEQ ID NO: 564); human IgG2 hinge); ELKTPLGDTTHTCPRCP (SEQ ID NO: 565); human IgG3 hinge); SPNMVPHAHHAQ (SEQ ID NO: 566); human IgG4 hinge); and the like.

In some embodiments, the hinge region comprises an amino acid sequence of a human IgG1, IgG2, IgG3, or IgG4, hinge region. The hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO: 567); see, e.g., Yan et al. (2012) *J. Biol. Chem.* 287:5891.

In some embodiments, the hinge region comprises an amino acid sequence derived from human CD8; e.g., the hinge region comprises the amino acid sequence: TTTPAPRPPTPAPTIASQPLSLRPEACRPAAGGAVHTRGLDFACD (SEQ ID NO: 568), or a variant thereof.

Conditionally Active Chimeric Antigen Receptors

In one embodiment, the disclosure provides a conditionally active chimeric antigen receptor (CAR). A CAR generally comprises multiple domains, including a target antigen binding domain, a transmembrane domain, and an intracellular signaling domain. The conditionally active CAR of the present disclosure comprises multiple domains, including a binding moiety, a target antigen binding domain which binds EpCAM, a transmembrane domain, and an intracellular signaling domain. In some embodiments, the intracellular signaling domain is a signaling domain of a protein including, but not limited to, ZAP70, CD3 zeta, and 4-1BB.

In some embodiments, the conditionally active chimeric antigen receptor further comprises a costimulatory domain. In some embodiments, the costimulatory domain is a functional signaling domain of a protein including, but not limited to, OX40, CD2, CD27, CD28, CDS, ICAM-1, LFA-1 (CD11a/CD18), ICOS (CD278), and 4-1BB (CD137), and amino acid sequences thereof having at least one, two, or three modifications but not more than 20, 10, or 5 modifications thereto.

In some embodiments, the transmembrane domain comprises a transmembrane domain of a protein including, but not limited to, a TCR alpha chain, a TCR beta chain, a TCR zeta chain, a CD3 epsilon TCR subunit, a CD3 gamma TCR subunit, a CD3 delta TCR subunit, CD45, CD4, CD5, CD8, CD9, CD16, CD22, CD33, CD28, CD37, CD64, CD80, CD86, CD134, CD137, CD154, functional fragments thereof, and amino acid sequences thereof having at least one but not more than 20 modifications thereto.

In one aspect, the disclosure provides a cell (e.g., T-cell) engineered to express a CAR. In one aspect a cell is transformed with the CAR and the CAR is expressed on the cell surface. In some embodiments, the cell (e.g., T-cell) is transduced with a viral vector encoding a CAR. In some embodiments, the viral vector is a retroviral vector. In some embodiments, the viral vector is a lentiviral vector. In some such embodiments, the cell may stably express the CAR. In another embodiment, the cell (e.g., T cell) is transfected with a nucleic acid, e.g., mRNA, cDNA, DNA, encoding a CAR. In some such embodiments, the cell may transiently express the CAR.

Conditionally Active T-Cell Receptor Fusion Proteins

In one embodiment, the disclosure provides a conditionally active T-cell receptor fusion protein. As used herein, a "T-cell receptor (TCR) fusion protein" or "TFP" includes a recombinant polypeptide derived from the various polypeptides comprising the TCR that is generally capable of i) binding to a surface antigen on target cells and ii) interacting with other polypeptide components of the intact TCR complex, typically when co-located in or on the surface of a T-cell.

The conditionally active TFP comprises a binding moiety, an EpCAM binding domain, and a T-cell receptor subunit. In some embodiments, the T-cell receptor subunit further comprises at least a portion of a T-cell receptor extracellular domain, a transmembrane domain, and a T-cell receptor intracellular domain. In some embodiments, the transmembrane domain comprises a transmembrane domain of a protein including, but not limited to, a TCR alpha chain, a TCR beta chain, a TCR zeta chain, a CD3 epsilon TCR subunit, a CD3 gamma TCR subunit, a CD3 delta TCR subunit, CD45, CD4, CD5, CD8, CD9, CD16, CD22, CD33, CD28, CD37, CD64, CD80, CD86, CD134, CD137, CD154, functional fragments thereof, or amino acid sequences thereof having at least one, two, or three modifications but not more than 20, 10, or 5 modifications thereto.

In some embodiments, the T-cell receptor intracellular domain comprises a stimulatory domain. The stimulatory domain may be from T-cell receptor subunit, including but not limited to the beta subunit, alpha subunit, delta subunit, gamma subunit, epsilon subunit, or a combination thereof. In some embodiments, the stimulatory domain comprises an immunoreceptor tyrosine-based activation motif (ITAM) or portion thereof including, but not limited to, CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b 1 chain, Fc gamma receptor 262 chain, Fc gamma receptor 3a chain, Fc gamma receptor 3b chain, Fc beta receptor 1 chain, TYROBP (DAP12), CDS, CD16a, CD16b, CD22, CD23, CD32, CD64, CD79a, CD79b, CD89, CD278, CD66d, functional fragments thereof, and amino acid sequences thereof having at least one, two, or three modifications but not more than 20, 10, or 5 modifications thereto.

In some embodiments, the conditionally active TFP further comprises a costimulatory domain. In some embodiments, the costimulatory domain is a functional signaling domain of a protein including, but not limited to, OX40, CD2, CD27, CD28, CDS, ICAM-1, LFA-1 (CD11a/CD18), ICOS (CD278), and 4-1BB (CD137), and amino acid sequences thereof having at least one, two, or three modifications but not more than 20, 10, or 5 modifications thereto.

In some embodiments, the EpCAM binding domain is connected to the T-cell receptor extracellular domain by a linker sequence. In some instances, the encoded linker sequence comprises $(G_4S)_n$, wherein n=1 to 4. In some instances, the encoded linker sequence comprises a long linker (LL) sequence. In some instances, the encoded long linker sequence comprises $(G4S)_n$, wherein n=2 to 4. In some instances, the encoded linker sequence comprises a short linker (SL) sequence. In some instances, the encoded short linker sequence comprises $(G_4S)_n$, wherein n=1 to 3.

In one aspect, the disclosure provides a cell (e.g., T-cell) engineered to express a conditionally active T-cell receptor fusion protein (TFP). In one aspect a cell is transformed with the conditionally active TFP and the conditionally active TFP is expressed on the cell surface. In some embodiments, the cell (e.g., T-cell) is transduced with a viral vector encoding a conditionally active TFP. In some embodiments, the viral vector is a retroviral vector. In some embodiments, the viral vector is a lentiviral vector. In some such embodiments, the cell may stably express the conditionally active TFP. In another embodiment, the cell (e.g., T cell) is transfected with a nucleic acid, e.g., mRNA, cDNA, DNA, encoding a conditionally active TFP. In some such embodiments, the cell may transiently express the conditionally active TFP.

Conditionally Active T-Cell Receptors

In one embodiment, the disclosure provides a conditionally active T-cell receptor. A T-cell receptor generally comprises multiple subunits, including alpha, beta, delta, gamma, epsilon, and zeta subunits. The conditionally active T-cell receptor of the present disclosure comprises a binding moiety. In some embodiments, the binding moiety is attached to a T-cell receptor subunit including, but not limited to, the alpha subunit, beta subunit, or a combination thereof.

In some embodiments, the binding moiety is capable of masking the binding of the T-cell receptor to its target. In some embodiments, the binding moiety binds to T-cell receptor. In some embodiments, a non-CDR loop provides a binding site for binding of the moiety to the T-cell receptor. In some embodiments, the non-CDR loop provides a binding site specific for T-cell receptor alpha, T-cell receptor beta, or a combination thereof. In some embodiments, the binding moiety masks binding of the T-cell receptor to its target, e.g. via steric occlusion, via specific intermolecular interactions.

In one aspect, the disclosure provides a cell (e.g., T-cell) engineered to express a conditionally active T-cell receptor (TCR). In one aspect a cell is transformed with the conditionally active TCR and the conditionally active TCR is expressed on the cell surface. In some embodiments, the cell (e.g., T-cell) is transduced with a viral vector encoding a conditionally active TCR. In some embodiments, the viral vector is a retroviral vector. In some embodiments, the viral vector is a lentiviral vector. In some such embodiments, the cell may stably express the conditionally active TCR. In another embodiment, the cell (e.g., T cell) is transfected with a nucleic acid, e.g., mRNA, cDNA, DNA, encoding a conditionally active TCR. In some such embodiments, the cell may transiently express the conditionally active TCR.

Cells

In one embodiment, the present disclosure provides a cell comprising the chimeric antigen receptor or the conditionally active chimeric antigen receptor, conditionally active T-cell receptor fusion protein, or conditionally active T-cell receptor of the present disclosure. The cell may be a mammalian cell.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RATI cells, mouse L cells (ATCC No. CCLI.3), human embryonic kidney (HEK) cells (ATCC No. CRL1573), HLHepG2 cells, HuT-78, Jurkat, HL-60, NK cell lines (e.g., NKL, NK92, and YTS), and the like.

In some instances, the cell is not an immortalized cell line, but is instead a cell (e.g., a primary cell) obtained from an individual. For example, in some cases, the cell is an immune cell obtained from an individual. As an example, the cell is a T lymphocyte obtained from an individual. As another example, the cell is a cytotoxic cell obtained from an individual. As another example, the cell is a stem cell or progenitor cell obtained from an individual.

In recent studies, CAR constructs have been used to direct natural killer (NK) cell activity, reviewed by Hermanson & Kaufman (2015, Front Immunol 6:195) and Carlsten & Childs (2015, Front Immunol 6:266). Similar to T cells, NK cells can be transfected with CAR expression constructs and used to induce an immune response. Because NK cells do not require HLA matching, they can be used as allogeneic effector cells (Harmanson & Kaufman, 2015). Also, peripheral blood NK cells (PB-NK), of use for therapy, may be isolated from donors by a simple blood draw. The CAR constructs of use may contain similar elements to those used to make CAR-T cells.

As such, in some embodiments, the present disclosure provides a cell comprising an NK cell comprising the chimeric antigen receptor, the conditionally active chimeric antigen receptor, conditionally active T-cell receptor fusion protein, or conditionally active T-cell receptor of the present disclosure.

As discussed above in the context of a conditionally active EpCAM binding protein (e.g., an EpCAM ProTriTAC), in some embodiments, a conditionally active chimeric antigen receptor as described herein has an improved therapeutic index as compared to that of a chimeric antigen receptor comprising the same EpCAM binding domain as the conditionally active variant but is constitutively active instead of being conditionally active. For instance, an EpCAM ProCAR, in some embodiments, has an increased therapeutic index than an EpCAM CAR. The increased, in some embodiments, is from at least about 2-fold to about 1000-fold, such as about 4-fold to about 800-fold, about 6-fold to about 800-fold, about 6-fold to about 600-fold, about 10-fold to about 400-fold, about 20-fold to about 200-fold, about 30-fold to about 150-fold, about 50-fold to about 100-fold. The increase in therapeutic index, in some embodiments, is attributed to the conjugation of the EpCAM binding domain to a binding moiety as described above, with the non-CDR loop and the cleavable linker.

Methods of Generating a Cell Comprising a Conditionally Active Receptor

The present disclosure provides a method of generating a cell comprising a conditionally active chimeric antigen receptor, T-cell receptor fusion protein, or T-cell receptor. The method generally involves genetically modifying a mammalian cell with an expression vector, or an RNA (e.g., in vitro transcribed RNA), comprising nucleotide sequences encoding a conditionally active chimeric antigen receptor, T-cell receptor fusion protein, or T-cell receptor of the present disclosure. The genetic modification can be carried out in vivo, in vitro, or ex vivo. The cell can be, for example, an immune cell (e.g., a T lymphocyte or NK cell), a stem cell, or a progenitor cell.

In some cases, the genetic modification is carried out ex vivo. For example, a T lymphocyte, a stem cell, or an NK cell is obtained from an individual; and the cell obtained from the individual is genetically modified to express a conditionally active chimeric antigen receptor, T-cell receptor fusion protein, or T-cell receptor of the present disclosure.

Sources of T-Cells

In some embodiments, a source of T-cells is obtained from a subject. The term "subject," as used throughout this disclosure, is intended to include living organisms in which an immune response can be elicited (e.g., mammals). Examples of subjects include humans, dogs, cats, mice, rats, and transgenic species thereof. T-cells can be obtained from a number of sources, including, but not limited to, allogenic T cells (e.g., allogeneic donor-derived CAR T cells), natural killer cells (e.g., donor derived natural killer cells), peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T-cell lines available in the art, may be used. In certain embodiments of the present disclosure, T-cells can be obtained from a unit of blood collected from a subject using any number of techniques known to the skilled artisan, such as FICOLL™ separation. In one embodiment, cells from the circulating blood of an individual are obtained by apheresis. The apheresis product typically contains lymphocytes, including T-cells, monocytes, granulocytes, B cells, other nucleated white blood cells, red blood cells, and platelets. In one embodiment, the cells collected by apheresis are washed to remove the plasma fraction and to place the cells in an appropriate buffer or media for subsequent processing steps. In one embodiment of the disclosure, the cells are washed with phosphate buffered saline (PBS). In an alternative embodiment, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one embodiment, T-cells are isolated from peripheral blood lymphocytes by lysing the red blood cells and depleting the monocytes, for example, by centrifugation through a PERCOLL™ gradient or by counterflow centrifugal elutriation. A specific subpopulation of T-cells, such as CD3+, CD28+, CD4+, CD8+, CD45RA+, and CD45RO+ T-cells, can be further isolated by positive or negative selection techniques. For example, in one embodiment, T-cells are isolated by incubation with anti-CD3/anti-CD28 (e.g., 3×28)-conjugated beads, such as DYNABEADS® M-450 CD3/CD28 T, for a time period sufficient for positive selection of the desired T-cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. Longer incubation times may be used to isolate T-cells in any situation where there are few T-cells as compared to other cell types, such in isolating tumor infiltrating lymphocytes (TIL) from tumor tissue or from immunocompromised individuals. Further, use of longer incubation times can increase the efficiency of capture of CD8+ T-cells. Thus, by simply shortening or lengthening the time T-cells are allowed to bind to the CD3/CD28 beads and/or by increasing or decreasing the ratio of beads to T-cells (as described further herein), subpopulations of T-cells can be preferentially selected for or against at culture initiation or at other time points during the process. Additionally, by increasing or decreasing the ratio of anti-CD3 and/or anti-CD28 antibodies on the beads or other surface, subpopulations of T-cells can be preferentially selected for or against at culture initiation or at other desired time points. Multiple rounds of selection can also be used in the context of this disclosure. In certain embodiments, it may be desirable to perform the selection procedure and use the "unselected" cells in the activation and expansion process. "Unselected" cells can also be subjected to further rounds of selection.

Enrichment of a T-cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T-cells which typically express CD4+, CD25+, CD62Lhi, GITR+, and FoxP3+. Alternatively, in certain embodiments, T regulatory cells are depleted by anti-CD25 conjugated beads or other similar method of selection.

In one embodiment, a T-cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No. WO 2013/126712.

For isolation of a desired population of cells by positive or negative selection, the concentration of cells and surface (e.g., particles such as beads) can be varied. In certain embodiments, it may be desirable to significantly decrease the volume in which beads and cells are mixed together (e.g., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet one embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T-cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T-cells that normally have weaker CD28 expression.

In another embodiment, it may be desirable to use lower concentrations of cells. By significantly diluting the mixture of T-cells and surface (e.g., particles such as beads), interactions between the particles and cells is minimized. This selects for cells that express high amounts of desired antigens to be bound to the particles. For example, CD4+ T-cells express higher levels of CD28 and are more efficiently captured than CD8+ T-cells in dilute concentrations. In one embodiment, the concentration of cells used is 5×10e6/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T-cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present disclosure.

Also contemplated in the context of the disclosure is the collection of blood samples or apheresis product from a subject at a time period prior to when the expanded cells as described herein might be needed. As such, the source of the cells to be expanded can be collected at any time point necessary, and desired cells, such as T-cells, isolated and frozen for later use in T-cell therapy for any number of diseases or conditions that would benefit from T-cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T-cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further embodiment of the present disclosure, T-cells are obtained from a patient directly following treatment that leaves the subject with functional T-cells. In this regard, it has been observed that following certain cancer treatments, in particular treatments with drugs that damage the immune system, shortly after treatment during the period when patients would normally be recovering from the treatment, the quality of T-cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T-cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T-cells, B cells, dendritic cells, and other cells of the immune system.

Activation and Expansion of T-Cells

T-cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T-cells of the disclosure may be expanded by contact with a surface having attached thereto an agent that stimulates a CD3/TCR complex associated signal and a ligand that stimulates a costimulatory molecule on the surface of the T-cells. In particular, T-cell populations may be stimulated as described herein, such as by contact with an anti-CD3 antibody, or antigen binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of T-cells can be contacted with an anti-CD3 antibody and an anti-CD28 antibody, under conditions appropriate for stimulating proliferation of the T-cells. To stimulate proliferation of either CD4+ T-cells or CD8+ T-cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol. Meth.* 227(1-2):53-63, 1999).

In certain embodiments, the primary stimulatory signal and the costimulatory signal for the T-cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the costimulatory signal is bound to a cell surface and the agent providing the primary activation signal is in solution or coupled to a surface. In certain embodiments, both agents can be in solution. In one embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T-cells in the present disclosure.

In one embodiment, the two agents are immobilized on beads, either on the same bead, i.e., "cis," or to separate beads, i.e., "trans." By way of example, the agent providing the primary activation signal is an anti-CD3 antibody or an antigen binding fragment thereof and the agent providing the costimulatory signal is an anti-CD28 antibody or antigen binding fragment thereof; and both agents are co-immobilized to the same bead in equivalent molecular amounts. In one embodiment, a 1:1 ratio of each antibody bound to the beads for CD4+ T-cell expansion and T-cell growth is used. In certain embodiments of the present disclosure, a ratio of anti CD3:CD28 antibodies bound to the beads is used such that an increase in T-cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one embodiment of the present disclosure, more anti-CD28 antibody is bound to the particles than anti-CD3 antibody, i.e., the ratio of CD3:CD28 is less than one. In certain embodiments of the disclosure, the ratio of anti CD28 antibody to anti CD3 antibody bound to the beads is greater than 2:1. In one particular embodiment, a 1:100 CD3:CD28 ratio of antibody bound to beads is used. In one embodiment, a 1:75 CD3:CD28 ratio of antibody bound to beads is used. In a further embodiment, a 1:50 CD3:CD28 ratio of antibody bound to beads is used. In one embodiment, a 1:30 CD3:CD28 ratio of antibody bound to beads is used. In one embodiment, a 1:10 CD3:CD28 ratio of antibody bound to beads is used. In one embodiment, a 1:3 CD3:CD28 ratio of antibody bound to the beads is used. In yet one embodiment, a 3:1 CD3:CD28 ratio of antibody bound to the beads is/used.

Ratios of particles to cells from 1:500 to 500:1 and any integer values in between may be used to stimulate T-cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T-cells. The ratio of anti-CD3- and anti-CD28-coupled particles to T-cells that result in T-cell stimulation can vary as noted above, however certain values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T-cell. In one embodiment, a ratio of particles to cells of 1:1 or less is used. In one particular embodiment, a particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In one embodiment, particles are added on a daily or every other day basis to a final ratio of 1:1 on the first day, and 1:5 on the third and fifth days of stimulation. In one embodiment, the ratio of particles to cells is 2:1 on the first day of stimulation and adjusted to 1:10 on the third and fifth days of stimulation. In one embodiment, particles are added on a daily or every other day basis to a final ratio of 1:1 on the first day, and 1:10 on the third and fifth days of stimulation. One of skill in the art will appreciate that a variety of other ratios may be suitable for use in the present disclosure. In particular, ratios will vary depending on particle size and on cell size and type.

In further embodiments of the present disclosure, the cells, such as T-cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T-cells. In one embodiment the cells (for example, 104 to 109 T-cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In one embodiment, greater than 100 million cells/ml is used. In a further embodiment, a concentration of cells of 10, 15, 20, 25, 30, 35, 40, 45, or 50 million cells/ml is used. In yet one embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T-cells. Such populations of cells may have therapeutic value and would be desirable to obtain in certain embodiments. For example, using high concentration of cells allows more efficient selection of CD8+ T-cells that normally have weaker CD28 expression.

In one embodiment of the present disclosure, the mixture may be cultured for several hours (about 3 hours) to about 14 days or any hourly integer value in between. In one embodiment, the mixture may be cultured for 21 days. In one embodiment of the disclosure the beads and the T-cells are cultured together for about eight days. In one embodiment, the beads and T-cells are cultured together for 2-3 days. Several cycles of stimulation may also be desired such that culture time of T-cells can be 60 days or more. Conditions appropriate for T-cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T-cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T-cells that have been exposed to varied stimulation times may exhibit different characteristics. For example, typical blood or apheresed peripheral blood mononuclear cell products have a helper T-cell population (TH, CD4+) that is greater than the cytotoxic or suppressor T-cell population (TC, CD8+). Ex vivo expansion of T-cells by stimulating CD3 and CD28 receptors produces a population of T-cells that prior to about days 8-9 consists predominately of TH cells, while after about days 8-9, the population of T-cells comprises an increasingly greater population of TC cells.

EpCAM Binding Protein Modifications

The EpCAM binding proteins described herein, including EpCAM binding domains (e.g., an EpCAM binding sdAb of this disclosure) and EpCAM targeting multispecific proteins (e.g., an EpCAM targeting trispecific or protrispecific protein as described herein) encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in the EpCAM binding proteins described herein, including the peptide backbone, the amino acid side-chains, and the amino or carboxyl termini. Certain common peptide modifications that are useful for modification of the EpCAM binding proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

In some embodiments, derivatives of the EpCAM binding proteins as described herein comprise immunoreactive modulator derivatives and antigen binding molecules comprising one or more modifications.

In some embodiments, the EpCAM binding proteins of the disclosure are monovalent or multivalent bivalent, trivalent, etc.). As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen).

In some embodiments, the EpCAM binding proteins as set forth above are fused to an Fc region from any species, including but not limited to, human immunoglobulin, such as human IgG1, a human IgG2, a human IgG3, human IgG4, to generate Fc-fusion EpCAM binding proteins. In some embodiments, the Fc-fusion EpCAM binding proteins of this disclosure have extended half-life compared to an otherwise identical EpCAM binding protein. In some embodiments, the Fc-fusion EpCAM binding proteins of this disclosure contain inter alia one or more additional amino acid residue substitutions, mutations and/or modifications, e.g., in the Fc region. which result in a binding protein with preferred characteristics including, but not limited to: altered pharmacokinetics, extended serum half-life.

In some embodiments, such Fc-fused EpCAM binding proteins provide extended half-lives in a mammal, such as in a human, of greater than 5 days, greater than 10 days, greater than 15 days, greater than 20 days, greater than 25 days, greater than 30 days, greater than 35 days, greater than 40 days, greater than 45 days, greater than 2 months, greater than 3 months, greater than 4 months, or greater than 5 months. The increased half-life, in some cases, results in a higher serum titer which thus reduces the frequency of the administration of the EpCAM binding proteins and/or reduces the concentration of the antibodies to be administered. Binding to human FcRn in vivo and serum half-life of human FcRn high affinity binding polypeptides is assayed, in some examples, in transgenic mice or transfected human cell lines expressing human FcRn, or in primates to which the polypeptides with a variant Fc region are administered.

The EpCAM binding proteins, in some cases, are differentially modified during or after production, e.g., by glycosylation, acetylation, phosphorylation, amidation, derivatization by known protecting/blocking groups, proteolytic cleavage, linkage to an antibody molecule or other cellular ligand, etc. Any of numerous chemical modifications are carried out by techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Various post-translational modifications of the EpCAM binding proteins also encompassed by the disclosure include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. Moreover, the EpCAM binding proteins are, in some cases, modified with a detectable label, such as an enzymatic, fluorescent, radioisotopic or affinity label to allow for detection and isolation of the modulator.

Polynucleotides Encoding EpCAM Binding Proteins

Also provided, in some embodiments, are polynucleotide molecules encoding EpCAM binding proteins described herein. In some embodiments, the polynucleotide molecules are provided as a DNA construct. In other embodiments, the polynucleotide molecules are provided as a messenger RNA transcript.

The polynucleotide molecules are constructed by known methods such as by combining the genes encoding a single domain EpCAM binding protein or gene encoding various domains of EpCAM binding proteins comprising more than one domain. In some embodiments, the gene encoding the domains are either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotide in the respective host cell.

In some embodiments, the polynucleotide coding for an EpCAM binding protein as described herein is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described EpCAM binding protein. Examples of expression vectors for expression in *E. coli* are pSKK (Le Gall et al., J Immunol Methods. (2004) 285(1): 111-27) or pcDNA5 (Invitrogen) for expression in mammalian cells. Thus, the EpCAM binding proteins as described herein, in some embodiments, are produced by introducing a vector encoding the protein as described above into a host cell and culturing said host cell under conditions whereby the protein domains are expressed, may be isolated and, optionally, further purified.

Pharmaceutical Compositions

Also provided, in some embodiments, are pharmaceutical compositions comprising an anti-EpCAM binding protein described herein, a vector comprising the polynucleotide encoding the polypeptide of the EpCAM binding proteins or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents. A further embodiment provides one or more of the above described EpCAM binding proteins packaged in lyophilized form, or packaged in an aqueous medium.

In some embodiments of the pharmaceutical compositions, the EpCAM binding proteins described herein are encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the EpCAM binding protein is attached to liposomes. In some instances, the EpCAM binding proteins are conjugated to the surface of liposomes. In some instances, the EpCAM binding proteins are encapsulated within the shell of a liposome. In some instances, the liposome is a cationic liposome.

The EpCAM binding proteins described herein are contemplated for use as a medicament. Administration is effected by different ways, e.g. by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

In some embodiments, the EpCAM binding proteins of this disclosure are administered at a dosage of up to 10 mg/kg at a frequency of once a week. In some cases, the dosage ranges from about 1 ng/kg to about 10 mg/kg, for example about 1 ng/kg to about 70 ng/kg. In some embodiments, the dose is from about 1 ng/kg to about 10 ng/kg, about 5 ng/kg to about 15 ng/kg, about 12 ng/kg to about 20 ng/kg, about 18 ng/kg to about 30 ng/kg, about 25 ng/kg to about 50 ng/kg, about 35 ng/kg to about 60 ng/kg, about 45 ng/kg to about 70 ng/kg, about 65 ng/kg to about 85 ng/kg, about 80 ng/kg to about 1 μg/kg, about 0.5 ug/kg to about 5 μg/kg, about 2 μg/kg to about 10 μg/kg, about 7 μg/kg to about 15 μg/kg, about 12 μg/kg to about 25 μg/kg, about 20 μg/kg to about 50 μg/kg, about 35 μg/kg to about 70 μg/kg, about 45 μg/kg to about 80 μg/kg, about 65 μg/kg to about 90 μg/kg, about 85 μg/kg to about 0.1 mg/kg, about 0.095 mg/kg to about 10 mg/kg. In some cases, the dosage is about 0.1 mg/kg to about 0.2 mg/kg; about 0.25 mg/kg to about 0.5 mg/kg, about 0.45 mg/kg to about 1 mg/kg, about 0.75 mg/kg to about 3 mg/kg, about 2.5 mg/kg to about 4 mg/kg, about 3.5 mg/kg to about 5 mg/kg, about 4.5 mg/kg to about 6 mg/kg, about 5.5 mg/kg to about 7 mg/kg, about 6.5 mg/kg to about 8 mg/kg, about 7.5 mg/kg to about 9 mg/kg, or about 8.5 mg/kg to about 10 mg/kg. The frequency of administration, in some embodiments, is about less than daily, every other day, less than once a day, twice a week, weekly, once in 7 days, once in two weeks, once in three weeks, once in four weeks, or once a month. In some cases, the frequency of administration is weekly. In some cases, the frequency of administration is weekly and the dosage is up to 10 mg/kg. In some cases, duration of administration is from about 1 day to about 4 weeks or longer.

Methods of Treatments and Tumor Growth Reduction Properties

Also provided in certain embodiments are methods of treating a condition associated with malignant cells expressing EpCAM in a subject comprising administering to a subject in need thereof an effective amount of an EpCAM binding domains or multispecific proteins (including conditionally active multispecific proteins) comprising an EpCAM binding domain of this disclosure, or a CAR or a ProCAR comprising an EpCAM binding protein as described herein, or a pharmaceutical composition comprising the same. In some embodiments, the condition is a cancer.

In another aspect, the disclosure provides a method of inhibiting tumor growth or progression in a subject who has malignant cells expressing EpCAM, comprising administering to the subject in need thereof an effective amount of an EpCAM binding domains or multispecific proteins comprising an EpCAM binding domain of this disclosure, or a CAR comprising an EpCAM binding protein as described herein, or a pharmaceutical composition comprising the same. In another aspect, the disclosure provides a method of inhibiting metastasis of malignant cells expressing EpCAM in a subject, comprising administering to the subject in need thereof an effective amount of an EpCAM binding domains or multispecific proteins comprising an EpCAM binding domain of this disclosure, or a pharmaceutical composition comprising the same. In another aspect, the disclosure provides a method of inducing tumor regression in a subject who has malignant cells expressing EpCAM, comprising administering to the subject in need thereof an effective amount of an EpCAM binding domains or multispecific proteins comprising an EpCAM binding domain of this disclosure, or a pharmaceutical composition comprising the same. In some embodiments, the methods as described herein further comprise administering an effective amount of a second therapeutic agent. In some embodiments, the second therapeutic agent is a biotherapeutic agent, for example, an antibody. In some embodiments, the second therapeutic agent is a cytokine, TNFa (Tumor Necrosis Factor alpha), a PAP (phosphatidic acid phosphatase) inhibitor, an oncolytic virus, a kinase inhibitor, an IDO (Indoleamine-pyrrole 2,3-dioxygenase) inhibitor, a glutaminase GLS1 inhibitor, a CAR (Chimeric Antigen Receptor)-T cell or T cell therapy, a TLR (Toll-Like Receptor) Agonist (e.g., TLR3, TLR4, TLR5, TLR7, TLR9), or a tumor vaccine.

In certain embodiments, the EpCAM binding proteins of the disclosure reduce the growth of tumor cells in vivo when administered to a subject who has tumor cells that express EpCAM. Measurement of the reduction of the growth of tumor cells can be determined by multiple different methodologies well known in the art. Nonlimiting examples include direct measurement of tumor dimension, measurement of excised tumor mass and comparison to control subjects, measurement via imaging techniques (e.g., CT or MRI) that may or may not use isotopes or luminescent molecules (e.g., luciferase) for enhanced analysis, and the like. In specific embodiments, administration of the EpCAM binding proteins of the disclosure results in a reduction of in vivo growth of tumor cells as compared to a control antigen binding agent by at least about 10%, 20%, 30%, 40%, 50%, 60%, 70%, 80%, 90% or 100%, with an about 100% reduction in tumor growth indicating a complete response and disappearance of the tumor. In further embodiments, administration of the EpCAM binding proteins of the disclosure results in a reduction of in vivo growth of tumor cells as compared to a control antigen binding agent by about 50-100%, about 75-100% or about 90-100%. In further embodiments, administration of the EpCAM binding proteins of the disclosure results in a reduction of in vivo growth of tumor cells as compared to a control antigen binding agent by about 50-60%, about 60-70%, about 70-80%, about 80-90%, or about 90-100%.

In some embodiments, the EpCAM binding proteins of the present disclosure are administered to treat a neoplastic condition. Neoplastic conditions, in some embodiments, are benign or malignant; solid tumors or other blood neoplasia; and, in some embodiments, are selected from the group including, but not limited to: adrenal gland tumors, AIDS-associated cancers, alveolar soft part sarcoma, astrocytic tumors, autonomic ganglia tumors, bladder cancer (squamous cell carcinoma and transitional cell carcinoma), blastocoelic disorders, bone cancer (adamantinoma, aneurismal bone cysts, osteochondroma, osteosarcoma), brain and spinal cord cancers, metastatic brain tumors, breast cancer including triple negative breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, epithelial disorders, Ewing's tumors, extraskeletal myxoid chondrosarcoma, fibrogenesis imperfecta ossium, fibrous dysplasia of the bone, gallbladder and bile duct cancers, gastric cancer, gastrointestinal, gestational trophoblastic disease, germ cell tumors, glandular disorders, head and neck cancers, hypothalamic, intestinal cancer, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), macrophagal disorders, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterior unveal melanoma, rare hematologic disorders, renal metastatic cancer, rhabdoid tumor, rhabdomyosarcoma, sarcomas, skin cancer, soft-tissue sarcomas, squamous cell cancer, stomach cancer, stromal disorders, synovial sarcoma, testicular cancer, thymic carcinoma, thymoma, thyroid metastatic cancer, and uterine cancers (carcinoma of the cervix, endometrial carcinoma, and leiomyoma).

In certain embodiments the EpCAM binding proteins of the present disclosure are used as a front line therapy and administered to subjects who have not previously been treated for the cancerous condition. In other embodiments the EpCAM binding proteins of the present disclosure are used to treat subjects that have previously been treated (with an EpCAM binding protein of this disclosure or with other anti-cancer agent) and have relapsed or determined to be refractory to the previous treatment. In some embodiments the EpCAM binding proteins of the present disclosure are used to treat subjects that have recurrent tumors.

In some embodiments, an EpCAM binding protein as described herein, including a multispecific protein, a CAR or a ProCAR as described herein, is administered to treat a cancer with widespread EpCAM expression and prevalence, including, but not limited to, colorectal, prostate, neuroendocrine, thyroid, lung (both non-small cell lung and small cell lung cancers), gastric, ovarian, endometrial, pancreatic, biliary tract and gallbladder cancer, esophageal, breast, and all adenocarcinoma.

In some aspects, the EpCAM binding proteins of the present disclosure are administered to treat a proliferative disorder comprising a solid tumor including, but not limited to, adrenal, liver, kidney, bladder, breast, gastric, ovarian, cervical, uterine, esophageal, colorectal, prostate, pancreatic, lung (both small cell and non-small cell), thyroid, carcinomas, sarcomas, glioblastomas and various head and neck tumors.

In some embodiments, the EpCAM binding proteins of the present disclosure are administered to a subject suffering from melanoma. In some embodiments, the EpCAM binding proteins of the present disclosure are used to diagnose, monitor, treat or prevent melanoma. The term "melanoma," as used herein, includes all types of melanoma including, but not limited to, primary melanoma, malignant melanoma, cutaneous melanoma, extracutaneous melanoma, superficial spreading melanoma, polypoid melanoma, melanocarcinomas, melanoepitheliomas, melanosarcomas, melanoma in situ, nodular malignant melanoma, lentigo maligna melanoma, lentiginous melanoma, lentiginous malignant melanoma, mucosal lentiginous melanoma, mucosal melanoma, acral lentiginous melanoma, soft tissue melanoma, ocular melanoma, invasive melanoma, familial atypical mole and melanoma (FAM-M) syndrome, desmoplastic malignant melanoma or uveal melanoma.

In some embodiments, possible indications for administration of the EpCAM binding proteins of this disclosure or pharmaceutical compositions comprising the same are tumorous diseases especially epithelial cancers/carcinomas such as breast cancer, colon cancer, prostate cancer, head and neck cancer, skin cancer, cancers of the genito-urinary tract, e.g., ovarian cancer, endometrial cancer, cervix cancer and kidney cancer, lung cancer, gastric cancer, cancer of the small intestine, liver cancer, pancreas cancer, gall bladder cancer, cancers of the bile duct, esophagus cancer, cancer of the salivatory glands and cancer of the thyroid gland. In some embodiments, the administration of the EpCAM binding proteins of this disclosure or pharmaceutical compositions comprising the same is indicated for minimal residual disease, such as early solid tumor, advanced solid tumor or metastatic solid tumor, which is characterized by the local and non-local reoccurrence of the tumor caused by the survival of single cells.

In selected aspects an EpCAM binding proteins of the disclosure is incorporated into a chimeric antigen receptors (CAR) and the EpCAM CAR is administered in a CAR based therapy effective at treating a cancer, such as: epithelial cancers/carcinomas such as breast cancer, colon cancer, prostate cancer, head and neck cancer, skin cancer, cancers of the genito-urinary tract, e.g., ovarian cancer, endometrial cancer, cervix cancer and kidney cancer, lung cancer, gastric cancer, cancer of the small intestine, liver cancer, pancreas cancer, gall bladder cancer, cancers of the bile duct, esophagus cancer, cancer of the salivatory glands and cancer of the thyroid gland, small cell lung cancer, non-small cell lung cancer (e.g., squamous cell non-small cell lung cancer or squamous cell small cell lung cancer) and large cell neuroendocrine carcinoma (LCNEC).

A chimeric antigen receptor is generally an artificially constructed hybrid protein or polypeptide containing or comprising an antigen binding domain of an antibody linked to a signaling domain (e.g., T-cell signaling or T-cell activation domains). In some embodiments, CARs comprising the EpCAM binding protein of the present disclosure have the ability to redirect the specificity and reactivity of sensitized lymphocytes (e.g., T-cells) toward EpCAM positive target cells in a non-MHC-restricted manner by exploiting the antigen-binding properties of antibodies or antigen binding fragments thereof. The non-MHC-restricted antigen recognition gives T-cells expressing EpCAM CARs the ability to recognize tumorigenic EpCAM independent of antigen processing, thus bypassing a major mechanism of tumor escape. Moreover, when expressed in T-cells, CARs advantageously do not dimerize with endogenous T cell receptor (TCR) alpha and beta chains.

In some embodiments the disclosed EpCAM binding proteins are administered to refractory patients (i.e., those whose disease recurs during or shortly after completing a course of initial therapy); sensitive patients (i.e., those whose relapse is longer than 2-3 months after primary therapy); or patients exhibiting resistance to a platinum based agent (e.g., carboplatin, cisplatin, oxaliplatin) and/or a taxane (e.g., docetaxel, paclitaxel, larotaxel or cabazitaxel). In another embodiment the disclosed EpCAM CAR treatments are effective at treating ovarian cancer, including ovarian-serous carcinoma and ovarian-papillary serous carcinoma.

In another embodiment the EpCAM binding proteins of the disclosure, the EpCAM CAR, or the EpCAM sensitized lymphocytes, or any combination thereof are used in maintenance therapy to reduce or eliminate the chance of tumor recurrence following the initial presentation of the disease. In some cases, the disorder has been treated and the initial tumor mass eliminated, reduced or otherwise ameliorated so the patient is asymptomatic or in remission. At such time the subject is administered pharmaceutically effective amounts of the disclosed the EpCAM binding proteins of the disclosure, the EpCAM CAR, or the EpCAM sensitized lymphocytes, or any combination thereof one or more times regardless of if there is little or no indication of disease using standard diagnostic procedures. In some embodiments, the EpCAM binding proteins of the disclosure, the EpCAM CAR, or the EpCAM sensitized lymphocytes, or any combination thereof is administered on a regular schedule over a period of time, such as weekly, every two weeks, monthly, every six weeks, every two months, every three months every six months or annually, for example, to reduce the potential of disease recurrence. Moreover such treatments are in some embodiments continued for a period of weeks, months, years or even indefinitely depending on the patient response and clinical and diagnostic parameters.

In yet another embodiment, the EpCAM binding proteins of the disclosure, the EpCAM CAR, or the EpCAM sensitized lymphocytes, or any combination thereof are used to prophylactically or as an adjuvant therapy to prevent or reduce the possibility of tumor metastasis following a debulking procedure. As used in the present disclosure a "debulking procedure," is means any procedure, technique or method that eliminates, reduces, treats or ameliorates a tumor or tumor proliferation. Exemplary debulking procedures include, but are not limited to, surgery, radiation treatments (i.e., beam radiation), chemotherapy, immunotherapy or ablation. In some embodiments, at appropriate times, the EpCAM binding proteins of the disclosure, the EpCAM CAR, or the EpCAM sensitized lymphocytes, or any combination thereof are administered as suggested by clinical, diagnostic or theranostic procedures to reduce tumor metastasis. In some embodiments, the dosing regimen is accompanied by appropriate diagnostic or monitoring techniques that allow it to be modified.

Yet other embodiments of the disclosure comprise administering the EpCAM binding protein of the disclosure, the EpCAM CAR, or the EpCAM sensitized lymphocytes, or any combination thereof to subjects that are asymptomatic but at risk of developing a proliferative disorder. That is, in some embodiments, the EpCAM binding protein of the disclosure, the EpCAM CAR, or the EpCAM sensitized lymphocytes, or any combination thereof are used in preventative sense and given to patients that have been examined or tested and have one or more noted risk factors (e.g., genomic indications, family history, in vivo or in vitro test results, etc.) but have not developed neoplasia. In such cases those skilled in the art would be able to determine an effective dosing regimen through empirical observation or through accepted clinical practices.

In some embodiments of the methods described herein, the EpCAM binding proteins, or compositions as described herein are administered in combination with an agent for treatment of the particular disease, disorder or condition. Agents include but are not limited to, therapies involving antibodies, small molecules (e.g., chemotherapeutics), hormones (steroidal, peptide, and the like), radiotherapies (γ-rays, X-rays, and/or the directed delivery of radioisotopes, microwaves, UV radiation and the like), gene therapies (e.g., antisense, retroviral therapy and the like) and other immunotherapies. In some embodiments, an EpCAM binding protein as described herein is administered in combination with anti-diarrheal agents, anti-emetic agents, analgesics, opioids and/or non-steroidal anti-inflammatory agents. In some embodiments, an EpCAM binding protein as described herein is administered in combination with anti-cancer agents. Nonlimiting examples of anti-cancer agents that can be used in the various embodiments of the disclosure, including pharmaceutical compositions and dosage forms and kits of the disclosure, include: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1 interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinzolidine sulfate; vinzolidine sulfate; vorozole; zeniplatin; zinostatin; zorubicin hydrochloride. Other examples of anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-COA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In some embodiments, the EpCAM binding protein of the present disclosure is used in combination with gemcitabine. In some embodiments, the EpCAM binding protein as described herein is administered before, during, or after surgery.

Methods of Detection of EpCAM Expression and Diagnosis of EpCAM Associated Cancer According to another embodiment of the disclosure, kits for detecting expression of EpCAM in vitro or in vivo are provided. The kits include the foregoing EpCAM binding protein (e.g., an EpCAM binding protein containing a labeled anti-EpCAM single domain antibody or antigen binding fragments thereof), and one or more compounds for detecting the label. In some embodiments, the label is selected from the group consisting of a fluorescent label, an enzyme label, a radioactive label, a nuclear magnetic resonance active label, a luminescent label, and a chromophore label.

In some cases, EpCAM expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

In one embodiment, provided is a method of determining if a subject has cancer by contacting a sample from the subject with an anti-EpCAM single domain antibody as disclosed herein; and detecting binding of the single domain antibody to the sample. An increase in binding of the antibody to the sample as compared to binding of the antibody to a control sample identifies the subject as having cancer.

In another embodiment, provided is a method of confirming a diagnosis of cancer in a subject by contacting a sample from a subject diagnosed with cancer with an anti-EpCAM single domain antibody as disclosed herein; and detecting binding of the antibody to the sample. An increase in binding of the antibody to the sample as compared to binding of the antibody to a control sample confirms the diagnosis of cancer in the subject.

In some examples of the disclosed methods, the EpCAM single domain antibody is directly labeled. In some examples, the methods further include contacting a second antibody that specifically binds the anti-EpCAM single domain antibody with the sample; and detecting the binding of the second antibody. An increase in binding of the second antibody to the sample as compared to binding of the second antibody to a control sample detects cancer in the subject or confirms the diagnosis of cancer in the subject. In some cases, the cancer is a neuroendocrine cancer, prostate cancer, lung cancer, stomach cancer, squamous cell carcinoma, pancreatic cancer, cholangiocarcinoma, triple negative breast cancer or ovarian cancer (such as epithelial ovarian carcinoma), or any other type of cancer that expresses EpCAM. In some examples, the control sample is a sample from a subject without cancer. In particular examples, the sample is a blood or tissue sample.

In some cases, the antibody that binds (for example specifically binds) EpCAM is directly labeled with a detectable label. In another embodiment, the antibody that binds (for example, specifically binds) EpCAM (the first antibody) is unlabeled and a second antibody or other molecule that can bind the antibody that specifically binds EpCAM is labeled. A second antibody is chosen such that it is able to specifically bind the specific species and class of the first antibody. For example, if the first antibody is a llama IgG, then the secondary antibody may be an anti-llama-IgG. Other molecules that can bind to antibodies include, without limitation, Protein A and Protein G, both of which are available commercially. Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferon, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include 125I, 131I, 35S or 3H.

In an alternative embodiment, EpCAM can be assayed in a biological sample by a competition immunoassay utilizing EpCAM standards labeled with a detectable substance and an unlabeled antibody that specifically binds EpCAM. In this assay, the biological sample, the labeled EpCAM standards and the antibody that specifically bind EpCAM are combined and the amount of labeled EpCAM standard bound to the unlabeled antibody is determined. The amount of EpCAM in the biological sample is inversely proportional to the amount of labeled EpCAM standard bound to the antibody that specifically binds EpCAM.

The immunoassays and method disclosed herein can be used for a number of purposes. In one embodiment, the antibody that specifically binds EpCAM may be used to detect the production of EpCAM in cells in cell culture. In another embodiment, the antibody can be used to detect the amount of EpCAM in a biological sample, such as a tissue sample, or a blood or serum sample. In some examples, the EpCAM is cell-surface EpCAM. In other examples, the EpCAM is soluble EpCAM (e.g., EpCAM in a cell culture supernatant or soluble EpCAM in a body fluid sample, such as a blood or serum sample).

In one embodiment, a kit is provided for detecting EpCAM in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble EpCAM protein or fragment. Kits for detecting a polypeptide will typically comprise a single domain antibody, according to the present disclosure, that specifically binds EpCAM. In some embodiments, an antibody fragment, such as an scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds EpCAM. The instructional materials may be written, in an electronic form (such as a computer diskette or compact disk), may be visual (such as video files), or provided through an electronic network, for example, over the internet, World Wide Web, an intranet, or other network. The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting EpCAM in a biological sample generally includes the steps of contacting the biological sample with an antibody which specifically reacts, under immunologically reactive conditions, to an EpCAM polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells. See U.S. Pat. No. 5,061,620). Any of the single domain antibodies that bind EPCAM, as disclosed herein, can be used in these assays. Thus, the antibodies can be used in a conventional immunoassay, including, without limitation, an ELISA, an RIA, FACS, tissue immunohistochemistry, Western blot or immunoprecipitation.

EXAMPLES

Example 1: Screening of Phage Display Library for Identification of EpCAM Binding Domains Llamas were immunized with purified EpCAM protein expressed in Expi293 cells. A phage display library for expression of heavy variable antibody domains was constructed from circulating B cells. See van der Linden, de Geus, Stok, Bos, van Wassenaar, Verrips, and Frenken. 2000. J Immunol Methods 240:185-195. Phage clones were screened for binding to EpCAM by expressing anti-EpCAM proteins in *E coli*, preparing periplasmic extracts, and proteins were screened for human and cynomolgus EpCAM binding activity using a colorimetric ELISA. Thirty-eight unique heavy chain only sequences were identified (SEQ ID Nos. 1 to 38) that produced a signal in the ELISA screening relative to the control with human and/or cynomolgus EpCAM proteins (as shown in Table 2). The CDR1, CDR2, and CDR3 sequences for these heavy variable domains are, respectively, SEQ ID Nos. 39 to 76, SEQ ID Nos. 77 to 114, and SEQ ID Nos. 115 to 152.

TABLE 2

Binding of Llama anti-Human EpCAM heavy chain only single domain antibodies to Human and Cynomolgus EpCAM, as demonstrated by signal in an ELISA Assay (absorbance readings in a colorimetric ELISA assay), relative to control heavy chain only single domain antibodies

| Sequence name | ELISA Human EpCAM | ELISA Cynomolgus EpCAM | ELISA Control | Human EpCAM/ Control | Cynomolgus EpCAM/ Control |
|---|---|---|---|---|---|
| EPL90 | 1.6 | 1.7 | 0.2 | 10 | 10 |
| EPL118 | 3.4 | 2.9 | 0.7 | 5 | 4 |
| EPL138 | 3.1 | 2.7 | 0.9 | 3 | 3 |

TABLE 2-continued

Binding of Llama anti-Human EpCAM heavy chain only single domain antibodies to Human and Cynomolgus EpCAM, as demonstrated by signal in an ELISA Assay (absorbance readings in a colorimetric ELISA assay), relative to control heavy chain only single domain antibodies

| Sequence name | ELISA Human EpCAM | ELISA Cynomolgus EpCAM | ELISA Control | Human EpCAM/ Control | Cynomolgus EpCAM/ Control |
|---|---|---|---|---|---|
| EPL145 | 0.6 | 0.4 | 0.2 | 3 | 2 |
| EPL164 | 0.6 | 2.8 | 0.1 | 7 | 34 |
| EPL31 | 0.6 | 0.5 | 0.1 | 7 | 6 |
| EPL55 | 0.4 | 0.6 | 0.1 | 5 | 7 |
| EPL57 | 1.7 | 3.4 | 0.1 | 14 | 27 |
| EPL136 | 0.9 | 1.3 | 0.1 | 9 | 13 |
| EPL15 | 0.7 | 3.2 | 0.1 | 8 | 35 |
| EPL34 | 0.9 | 3.1 | 0.1 | 10 | 36 |
| EPL86 | 0.8 | 3.0 | 0.1 | 8 | 31 |
| EPL153 | 3.1 | 2.2 | 0.1 | 31 | 21 |
| EPL20 | 2.9 | 2.2 | 0.5 | 6 | 4 |
| EPL70 | 3.2 | 2.2 | 0.1 | 24 | 16 |
| EPL125 | 3.5 | 3.5 | 0.5 | 8 | 8 |
| EPL13 | 2.9 | 4.0 | 0.2 | 17 | 23 |
| EPL129 | 2.0 | 3.1 | 0.1 | 20 | 29 |
| EPL159 | 0.4 | 0.2 | 0.1 | 3 | 2 |
| EPL120 | 3.2 | 2.3 | 0.6 | 5 | 4 |
| EPL126 | 3.4 | 2.8 | 0.7 | 5 | 4 |
| EPL60 | 1.1 | 3.5 | 0.1 | 10 | 33 |
| EPL156 | 3.6 | 4.0 | 0.2 | 16 | 17 |
| EPL2 | 2.2 | 3.6 | 0.1 | 15 | 24 |
| EPL43 | 1.8 | 3.8 | 0.1 | 13 | 27 |
| EPL10 | 2.7 | 2.0 | 0.2 | 12 | 9 |
| EPL49 | 1.1 | 0.6 | 0.1 | 8 | 4 |
| EPL58 | 1.1 | 0.5 | 0.1 | 8 | 4 |
| EPL74 | 1.4 | 0.7 | 0.1 | 10 | 5 |
| EPL78 | 3.1 | 2.0 | 0.2 | 17 | 11 |
| EPL82 | 0.9 | 1.1 | 0.2 | 4 | 5 |
| EPL83 | 2.0 | 1.1 | 0.6 | 3 | 2 |
| EPL97 | 2.5 | 1.7 | 0.3 | 8 | 5 |
| EPL109 | 0.4 | 0.1 | 0.1 | 5 | 2 |
| EPL117 | 0.9 | 0.6 | 0.2 | 4 | 3 |
| EPL127 | 0.4 | 0.9 | 0.1 | 5 | 11 |
| EPL152 | 3.4 | 2.8 | 0.8 | 4 | 4 |
| EPL189 | 1.3 | 0.9 | 0.1 | 12 | 8 |

Example 2: Incorporation of EpCAM Binding Heavy Chain Only Single Domain Antibodies into Fusion Proteins and T Cell Dependent Cellular Cytotoxicity Assays Selected anti-EpCAM heavy chain only single domain antibodies from Example 1 were cloned into DNA constructs for expression of recombinant proteins. These expression constructs all encoded a signal peptide. One set of anti-EpCAM constructs (SEQ ID Nos. 153 to 179) was designed to express a fusion protein with a humanized anti-CD3 scFv domain on the N-terminus of the mature secreted fusion protein followed by a llama anti-EpCAM domain, with the two domains linked by the sequence GGGGSGGGS, and with a HHHHHH on the C-terminus. One second of anti-EpCAM constructs (SEQ ID Nos. 180 to 206) was designed to express a fusion protein with a llama anti-EpCAM domain on the N-terminus of the mature secreted fusion protein followed a humanized anti-CD3-scFv domain, with the two domains linked by the sequence GGGGSGGGS, and with a HHHHHH on the C-terminus.

These anti-EpCAM/anti-CD3 (from N-terminus to C-terminus) or anti-CD3/anti-EpCAM (from N terminus to C terminus) fusion protein constructs were transfected into Expi293 cells. The amount of anti-EpCAM/anti-CD3 fusion protein in the conditioned media from the transfected Expi293 cells was quantitated using by using an Octet instrument with streptavidin and loaded with biotinylated CD3-Fc fusion protein using an anti-CD3 fusion protein of similar molecular weight to the anti-EPCAM/ant-CD3 proteins as a standard.

The conditioned media were tested in a T-cell dependent cellular cytotoxicity assay. See Nazarian A A, Archibeque I L, Nguyen Y H, Wang P, Sinclair A M, Powers D A. 2015. J Biomol Screen. 20:519-27. In this assay, luciferase labelled NCI-H508 cells, which express EpCAM, were combined with purified human T cells and a titration of the anti-EpCAM/anti-CD3 fusion protein or the anti-CD3/anti-EpCAM. It was hypothesized that if the fusion protein directs T cells to kill the NCI-H508 cells, the signal in a luciferase assay performed at 48 hours after starting the experiment should decrease. FIGS. 1-4 provide the TDCC data in graphical format.

$EC_{50}$ values from the TDCC assays are listed in Table 3 (lists $EC_{50}$ data for SEQ ID Nos. 153-179) and Table 4 (lists $EC_{50}$ data for SEQ ID Nos. 180-206). The most potent molecule (EPL13) had an $EC_{50}$ value of about 1.6 pM. Some of the anti-EpCAM binding proteins were only active when present in an anti-CD3/anti-EpCAM configuration. One anti-EPCAM sequence, EPL34, was only active in the anti-EpCAM/anti-CD3 configuration. A negative control for the TDCC assays was anti-GFP/anti-CD3 protein, and this protein did not direct the T cells to kill the NCI-H508 cells (data not shown).

TABLE 3

$EC_{50}$ Values for Redirected T Cell Killing of NCI-H508 Cells by Anti-CD3/Anti-EPCAM Proteins Containing Llama Anti-Ep CAM Sequences (n/a = insufficient activity to calculate an $EC_{50}$ using the protein concentrations tested)

| Anti-EpCAM Sequence | NCI-H508 Cell Killing $EC_{50}$ (M) |
|---|---|
| EPL10 | n/a |
| EPL109 | 2.2E−09 |
| EPL117 | n/a |
| EPL120 | 5.8e-010 |
| EPL125 | 1.3E−09 |
| EPL127 | n/a |
| EPL13 | 1.6E−12 |
| EPL136 | 6.1E−12 |
| EPL138 | 7.9E−12 |
| EPL145 | n/a |
| EPL152 | n/a |
| EPL153 | 1.4E−10 |
| EPL156 | n/a |
| EPL164 | 3.6E−10 |
| EPL189 | n/a |
| EPL2 | n/a |
| EPL20 | n/a |
| EPL34 | n/a |
| EPL49 | n/a |
| EPL58 | n/a |
| EPL74 | 2.6E−09 |
| EPL78 | n/a |
| EPL82 | n/a |
| EPL83 | 3.1E−10 |
| EPL86 | 4.7E−10 |
| EPL90 | 9.2E−12 |
| EPL97 | n/a |

TABLE 4

EC$_{50}$ Values for Redirected T Cell Killing of NCI-H508 Cells by Anti-EpCAM/Anti-CD3 Proteins Containing Llama Anti-EpCAM Sequences (n/a = insufficient activity to calculate an EC$_{50}$ using the protein concentrations tested)

| Anti-EpCAM Sequence | NCI-H508 Cell Killing EC50 (M) |
|---|---|
| EPL10 | n/a |
| EPL109 | n/a |
| EPL117 | n/a |

TABLE 4-continued

EC$_{50}$ Values for Redirected T Cell Killing of NCI-H508 Cells by Anti-EpCAM/Anti-CD3 Proteins Containing Llama Anti-EpCAM Sequences (n/a = insufficient activity to calculate an EC$_{50}$ using the protein concentrations tested)

| Anti-EpCAM Sequence | NCI-H508 Cell Killing EC50 (M) |
|---|---|
| EPL120 | n/a |
| EPL125 | n/a |
| EPL127 | n/a |
| EPL13 | 1.6E−11 |
| EPL136 | 1.3E−10 |
| EPL138 | n/a |
| EPL145 | n/a |
| EPL152 | n/a |
| EPL153 | not expressed |
| EPL156 | n/a |
| EPL164 | n/a |
| EPL189 | n/a |
| EPL2 | n/a |
| EPL20 | n/a |
| EPL34 | 3.7E−10 |
| EPL49 | n/a |
| EPL58 | n/a |
| EPL74 | n/a |
| EPL78 | n/a |
| EPL82 | n/a |
| EPL83 | 2.1E−11 |
| EPL86 | 2.7E−10 |
| EPL90 | n/a |
| EPL97 | n/a |

Using conditioned media with known concentrations of anti-EpCAM/anti-CD3 or anti-CD3/anti-EpCAM fusion proteins, the binding affinities of the fusion proteins for human and cynomolgus monkey EpCAM proteins were measured. An Octet instrument with streptavidin tips were loaded with biotinylated human or cynomolgus EpCAM protein, and $K_D$ values were calculated by measuring the on rate and off rate of binding of the anti-EPCAM/anti-CD3 fusion or anti-CD3/anti-EpCAM fusion proteins to the biotinylated EpCAM proteins. The $K_D$ measurements were made using a single 50 nM concentration of the anti-EPCAM/anti-CD3 or anti-CD3/anti-EpCAM fusion proteins, which allowed for rank ordering potency. The measured relative affinities are listed in Table 5 All of the fusion proteins bound to cynomolgus EpCAM, with $K_D$ values ranging from 1.6 to 56 nM. Most, but not all of the fusion proteins were measured binding to human EpCAM with $K_D$ values ranging from 0.8 to 74 nM.

TABLE 5

Binding Affinities to Human and Cyno EpCAM of Anti-EPCAM/Anti-CD3 or Anti-CD3/Anti-EpCAM Fusion Proteins Containing Llama Anti-EpCAM Sequences

| Humanized | Anti-CD3/Anti-EpCAM | | Anti-EpCAM/Anti-CD3 | |
|---|---|---|---|---|
| anti-EpCAM Binder | hu KD (nM) | cy KD (nM) | hu KD (nM) | cy KD (nM) |
| EPL13 | 29 | 13 | 14 | 7.6 |
| EPL136 | 74 | 56 | 32 | 31 |
| EPL138 | 2.2 | 2.2 | 0.8 | 1.3 |
| EPL153 | n/q | 3.5 | No expression | |
| EPL164 | 3.1 | 3.6 | 2.1 | 2.9 |
| EPL34 | n/q | 14 | n/q | 6.4 |
| EPL83 | 1.1 | 3 | 1.6 | 3 |
| EPL86 | n/q | 8.3 | n/q | 7 |
| EPL90 | 1.9 | 1.6 | 0.8 | 1.2 |

Example 3: Humanization of EpCAM Binding Heavy Chain Only Single Domain Antibodies and T Cell Dependent Cellular Cytotoxicity Assays Three of the llama anti-EpCAM antibodies sequences identified in Example 1 were humanized by grafting their CDR sequences onto human germline sequences, while retaining some llama framework sequences to ensure the antibodies did not lose activity (SEQ ID Nos. 207 to 209).

These sequences were cloned into expression constructs for expression of anti-EpCAM/anti-CD3 fusion proteins (SEQ ID Nos. 210 to 212) in Expi293 cells, as described in Example 2.

The amount of anti-EpCAM/anti-CD3 fusion proteins present in the conditioned medium was quantitated as described in Example 2. The affinities of these humanized proteins for human, cynomolgus, and mouse EpCAM were measured as described in Example 2. The relative $K_D$ values calculated from these measurements are listed in Table 6. All three sequences bound to human and cynomolgus EpCAM, with relative $K_D$ values ranging from about 0.3 to about 18 nM. Two of the sequences also bound to mouse EpCAM, with $K_D$ values ranging from about 1.4 to about 1.8 nM.

TABLE 6

Binding Affinities to Human, Cynomolgus, and Mouse EpCAM of Anti-EpCAM/Anti-CD3 Fusion Proteins Containing Llama Anti-EpCAM Sequences (n/q = not quantifiable under the experimental conditions used)

| Humanized Anti-EpCAM Sequence | Human EpCAM (nM) | Cynomolgus EpCAM (nM) | Mouse EpCAM (nM) |
|---|---|---|---|
| H13 | 17 | 18 | n/q |
| H90 | 0.3 | 1.3 | 1.4 |
| H138 | 0.3 | 1.8 | 1.8 |

Figure 1:
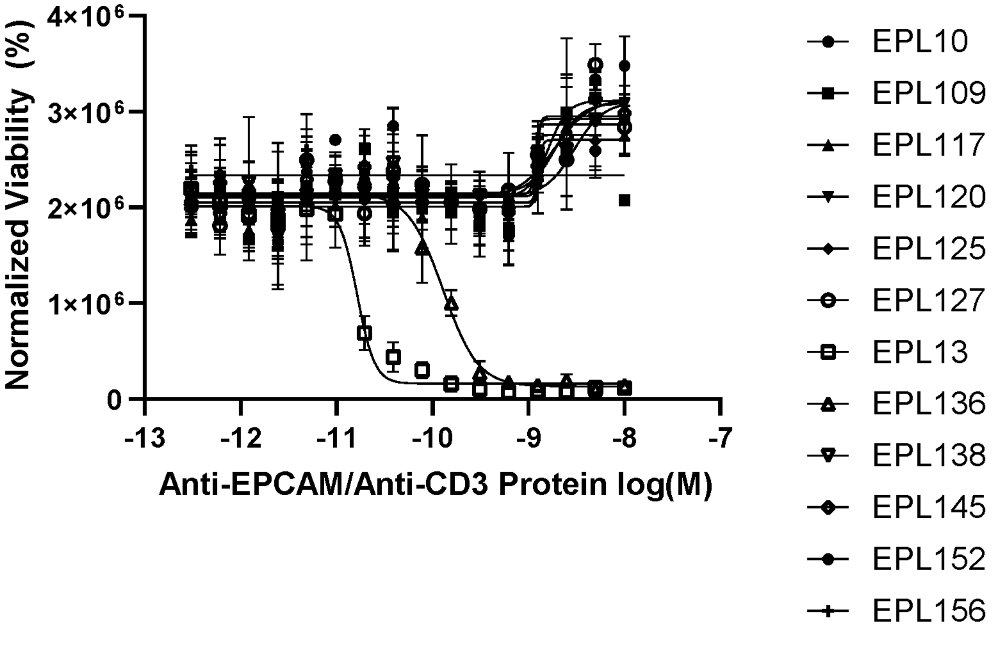
FIG. 1 provides results from a representative T cell dependency cellular cytotoxicity assay with NCI-H508 cells using exemplary fusion proteins of this disclosure containing an anti-EpCAM domain as described herein and an anti-CD3 domain.
Figure 2:
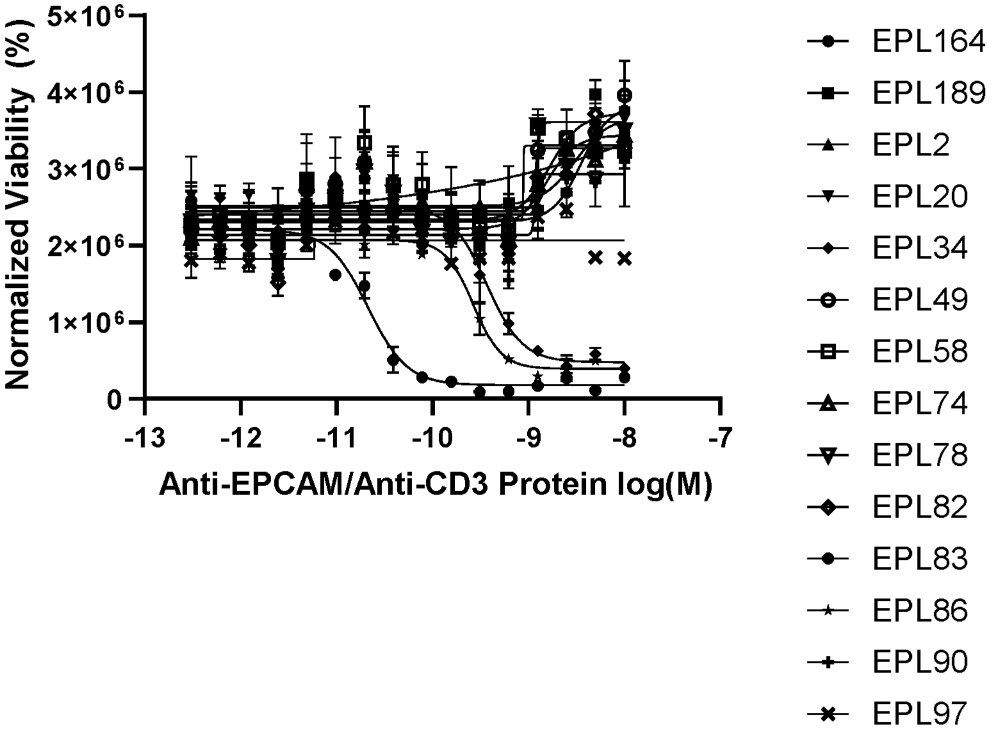
FIG. 2 provides results from a representative T cell dependency cellular cytotoxicity assay using exemplary fusion proteins of this disclosure containing an anti-EpCAM domain as described herein and an anti-CD3 domain.
Figure 3:
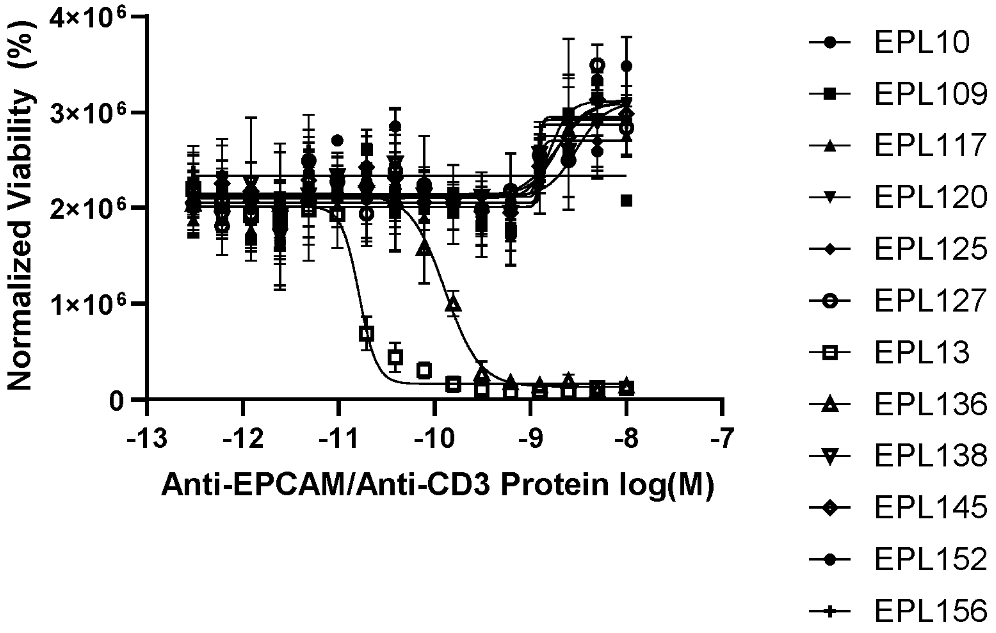
FIG. 3 provides results from a representative T cell dependency cellular cytotoxicity assay using exemplary fusion proteins of this disclosure containing an anti-EpCAM domain as described herein and an anti-CD3 domain.
Figure 4:
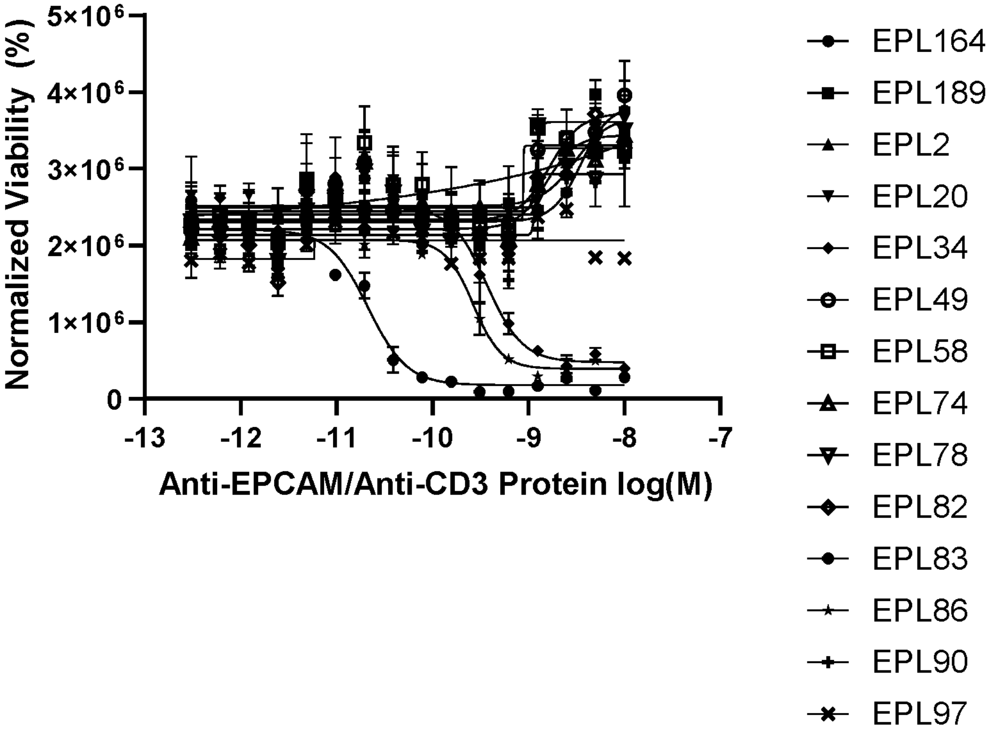
FIG. 4 provides results from a representative T cell dependency cellular cytotoxicity assay using exemplary fusion proteins of this disclosure containing an anti-EpCAM domain as described herein and an anti-CD3 domain.
Figure 5:
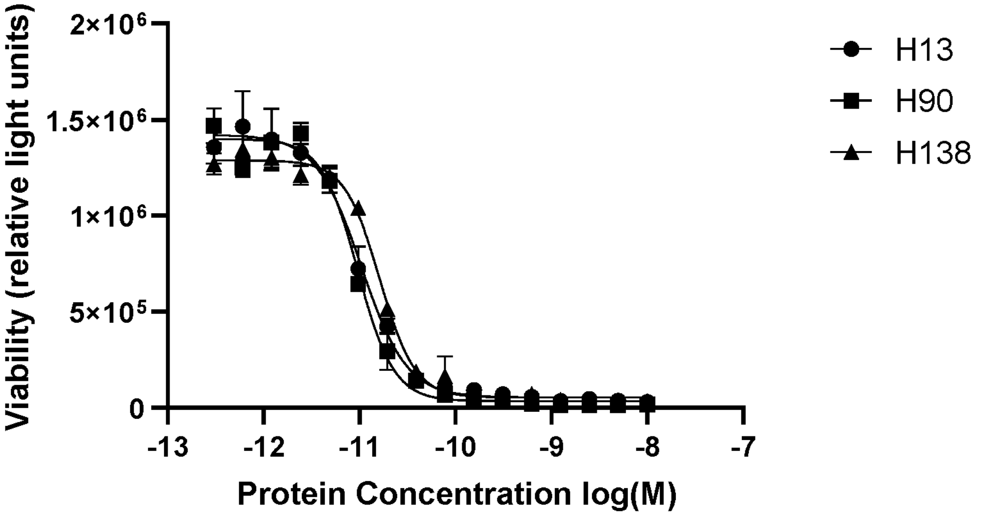
FIG. 5 provides results from a representative T cell dependency cellular cytotoxicity assay using exemplary fusion proteins of this disclosure containing a humanized anti-EpCAM domain as described herein and an anti-CD3 domain.

T cell killing potential of the anti-EpCAM/anti-CD3 fusion proteins present in the conditioned medium was assessed as described in Example 2. Results are provided in Table 7 and in FIG. 5.

TABLE 7

$EC_{50}$ Values for Redirected T Cell Killing of NCI-H508 Cells by Purified Anti-CD3/Anti-EpCAM Proteins Containing Humanized Anti-Ep CAM Sequences

| Humanized anti-EpCAM Binder Sequence | $EC_{50}$ (pm) |
|---|---|
| H13 | 10 |
| H90 | 10 |
| H138 | 16 |

Example 4: Xenograft Tumor Model

An EpCAM targeting fusion protein of this disclosure (e.g., a fusion protein which is a trispecific protein comprising an anti-EpCAM heavy chain only single domain antibody, an anti-CD3 scFv, and an anti-Albumin domain) is evaluated in a xenograft model. In order to determine efficacy of the exemplary EpCAM targeting fusion protein in vivo, multiple xenograft tumor models are used. Examples of common tumor cell lines for use in xenograft tumor studies include A549 (non-small cell lung carcinoma) cells, DU-145 (prostate) cells, MCF-7 (breast) cells, Colo 205 (colon) cells, 3T3/]GF-IR (mouse fibroblast) cells, NCI H441 cells, HEP G2 (hepatoma) cells, MDA MB 231 (breast) cells, HT-29 (colon) cells, MDA-MB-435s (breast) cells, U266 cells, SH-SYSY cells, Sk-Mel-2 cells, NCI-H929, RPM18226, and A431 cells. Immune-deficient NOD/SCID mice are sub-lethally irradiated (2 Gy) and subcutaneously inoculated with $1\times10^6$ tumor cells (e.g., NCI H441 cells) into their right dorsal flank. When tumors reach 100 to 200 $mm^3$, animals are allocated into 3 treatment groups. Groups 2 and 3 are intraperitoneally injected with $1.5\times10^7$ activated human T-cells. Three days later, animals from Group 3 are subsequently treated with the exemplary EpCAM targeting trispecific antigen-binding protein of. Groups 1 and 2 are only treated with vehicle. Body weight and tumor volume are determined for 30 days, beginning at least 5 days post treatment with the exemplary EpCAM targeting trispecific protein.

It is expected that animals treated with the exemplary EpCAM targeting trispecific protein have a statistically significant delay in tumor growth in comparison to the respective vehicle-treated control group.

Example 5: Proof-of-Concept Clinical Trial Protocol for Administration of the EpCAM Targeting Trispecific Antigen-Binding Protein of Example 4 to Ovarian Cancer Patients This is a Phase I/II clinical trial for studying an exemplary EpCAM targeting trispecific antigen-binding protein of this disclosure as a treatment for an epithelial ovarian cancer.

Study Outcomes:

Primary: Maximum tolerated dose of the exemplary EpCAM targeting trispecific protein.

Secondary: To determine whether in vitro response of the exemplary EpCAM targeting trispecific protein is associated with clinical response Phase I The maximum tolerated dose (MTD) will be determined in the phase I section of the trial.

1.1 The maximum tolerated dose (MTD) will be determined in the phase I section of the trial.

1.2 Patients who fulfill eligibility criteria will be entered into the trial to EpCAM targeting trispecific proteins of the previous examples.

1.3 The goal is to identify the highest dose of EpCAM targeting trispecific proteins of the previous examples that can be administered safely without severe or unmanageable side effects in participants. The dose given will depend on the number of participants who have been enrolled in the study prior and how well the dose was tolerated. Not all participants will receive the same dose.

Phase II 2.1 A subsequent phase II section will be treated at the MTD with a goal of determining if therapy with therapy of the exemplary EpCAM targeting trispecific protein results in at least a 20% response rate.

Primary Outcome for the Phase II—To determine if therapy of EpCAM targeting trispecific protein results in at least 20% of patients achieving a clinical response (blast response, minor response, partial response, or complete response)

Eligibility:

Histologically or cytologically confirmed epithelial ovarian cancer. May have Recurrent epithelial ovarian carcinoma or disease progression following failure of first-line, platinum-based chemotherapy with no more than one prior platinum based regimen therapy Adequate laboratory values of bone marrow function, renal function, liver function, and echocardiogram tests Phase III 3.1A subsequent phase III section will carried out with the exemplary EpCAM targeting trispecific protein, wherein secondary endpoints such as response rate (RR), patient recorded outcomes (PRO), progression-free survival (PFS), duration of progression free survival, time to progression (TIP), overall survival, health-related quality of life assessment, number of participants with overall survival, duration of response, time to response, number of participants with response, and time to tumor growth etc. will be assessed.

Example 6: Construction and Testing of Exemplary Multivalent Target Binding Proteins Constructs FIG. 6: The following ProCAR constructs were made, using EpCAM binder sequences provided herein. An exemplary construct including an anti-human EpCAM sdAb, a FLAG epitope, a CD8 hinge/transmembrane domain, a 4-1BB intracellular domain, and a CD3 zeta intracellular domain (SEQ ID NO: 485). An exemplary construct including an anti-human serum albumin sdAb, an anti-human EpCAM sdAb, a FLAG epitope, a CD8 hinge/transmembrane domain, a 4-1BB intracellular domain, and a CD3 zeta intracellular domain (SEQ ID NO: 486). An exemplary construct including an anti-human serum albumin sdAb, an anti-human EpCAM sdAb, a FLAG epitope, a CD8 hinge/transmembrane domain, a 4-1BB intracellular domain, and a CD3 zeta intracellular domain (SEQ ID NO: 487). An exemplary construct including an anti-human serum albumin sdAb, an anti-human EpCAM sdAb, a FLAG epitope, a CD8 hinge/transmembrane domain, a 4-1BB intracellular domain, and a CD3 zeta intracellular domain (SEQ ID NO:

488). An exemplary construct including an anti-human serum albumin sdAb, a protease cleavage site 3, an anti-human EpCAM sdAb, a FLAG epitope, a CD8 hinge/transmembrane domain, a 4-1BB intracellular domain, and a CD3 zeta intracellular domain (SEQ ID NO: 489). An exemplary construct including an anti-human serum albumin sdAb, a protease cleavage site 3, an anti-human EpCAM sdAb, a FLAG epitope, a CD8 hinge/transmembrane domain, a 4-1BB intracellular domain, and a CD3 zeta intracellular domain (SEQ ID NO: 490). An exemplary construct including an anti-GFP sdAb, a FLAG epitope, a CD8 hinge/transmembrane domain, a 4-1BB intracellular domain, and a CD3 zeta intracellular domain (SEQ ID NO: 491).

EpCAM Mask 1 Blocks ProCAR EpCAM-Binding Activity 300,000 primary human T cells isolated from healthy donors were infected with 1 mL lentiviral supernatant made from the indicated constructs from FIG. 6 to generate anti-EpCAM CAR-T cells, which were subsequently stained with anti-FLAG antibodies and EpCAM-Fc along with the indicated secondary antibodies. The data was analyzed by flow cytometry. FIG. 7 provides histograms of EpCAM-Fc/Alexa Fluor 647 staining of CAR-T cells that have been grouped into low (FIG. 7A), medium (FIG. 7B), or high (FIG. 7C) CAR expression based on anti-FLAG staining.

This data demonstrates the efficacy of EpCAM mask 1 blocking ProCAR EpCAM-binding activity.

EpCAM Mask 2 Blocks ProCAR EpCAM-Binding Activity 300,000 primary human T cells isolated from healthy donors were infected with 1 mL lentiviral supernatant made from the indicated constructs from FIG. 21 to generate anti-EpCAM CAR-T cells, which were subsequently stained with anti-FLAG antibodies and EpCAM-Fc along with the indicated secondary antibodies. The data was analyzed by flow cytometry.

Figure 6:
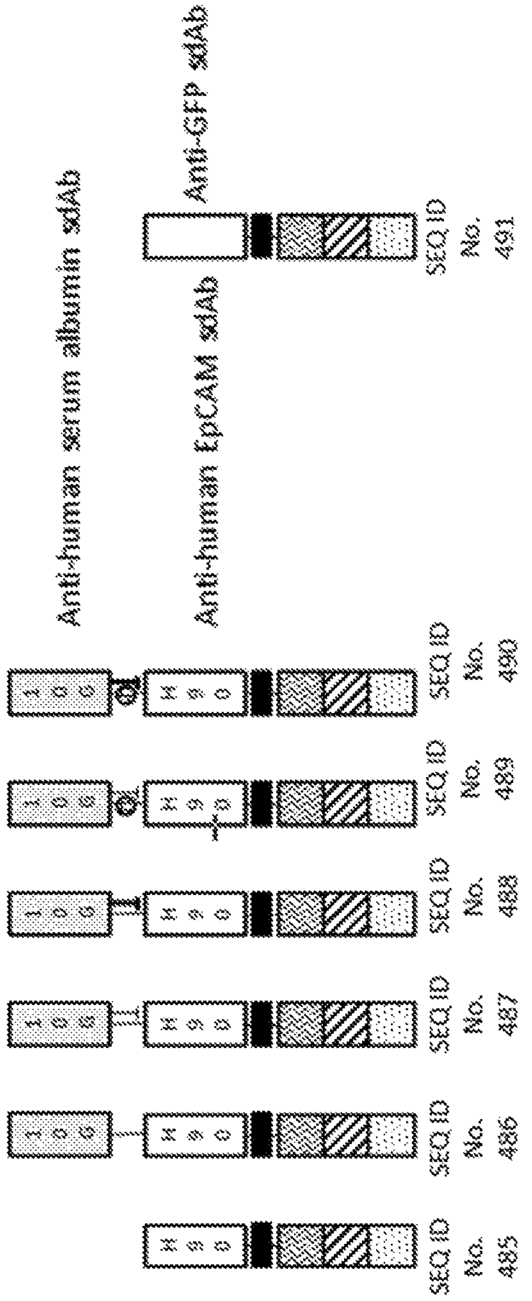
FIG. 6 illustrate exemplary ProCAR constructs. One exemplary construct includes an anti-human EpCAM sdAb, a FLAG epitope, a CD8 hinge/transmembrane domain, a 4-1BB intracellular domain, and a CD3 zeta intracellular domain (SEQ ID NO: 485). One exemplary construct includes an anti-human serum albumin sdAb, an anti-human EpCAM sdAb, a FLAG epitope, a CD8 hinge/transmembrane domain, a 4-1BB intracellular domain, and a CD3 zeta intracellular domain (SEQ ID NO: 486). One exemplary construct includes an anti-human serum albumin sdAb, an anti-human EpCAM sdAb, a FLAG epitope, a CD8 hinge/transmembrane domain, a 4-1BB intracellular domain, and a CD3 zeta intracellular domain (SEQ ID NO: 487). One exemplary construct includes an anti-human serum albumin sdAb, an anti-human EpCAM sdAb, a FLAG epitope, a CD8 hinge/transmembrane domain, a 4-1BB intracellular domain, and a CD3 zeta intracellular domain (SEQ ID NO: 488). One exemplary construct includes an anti-human serum albumin sdAb, a protease cleavage site 3, an anti-human EpCAM sdAb, a FLAG epitope, a CD8 hinge/transmembrane domain, a 4-1BB intracellular domain, and a CD3 zeta intracellular domain (SEQ ID NO: 489). One exemplary construct includes an anti-human serum albumin sdAb, a protease cleavage site 3, an anti-human EpCAM sdAb, a FLAG epitope, a CD8 hinge/transmembrane domain, a 4-1BB intracellular domain, and a CD3 zeta intracellular domain (SEQ ID NO: 490). One exemplary construct includes an anti-GFP sdAb, a FLAG epitope, a CD8 hinge/transmembrane domain, a 4-1BB intracellular domain, and a CD3 zeta intracellular domain (SEQ ID NO: 491).
Figure 7:
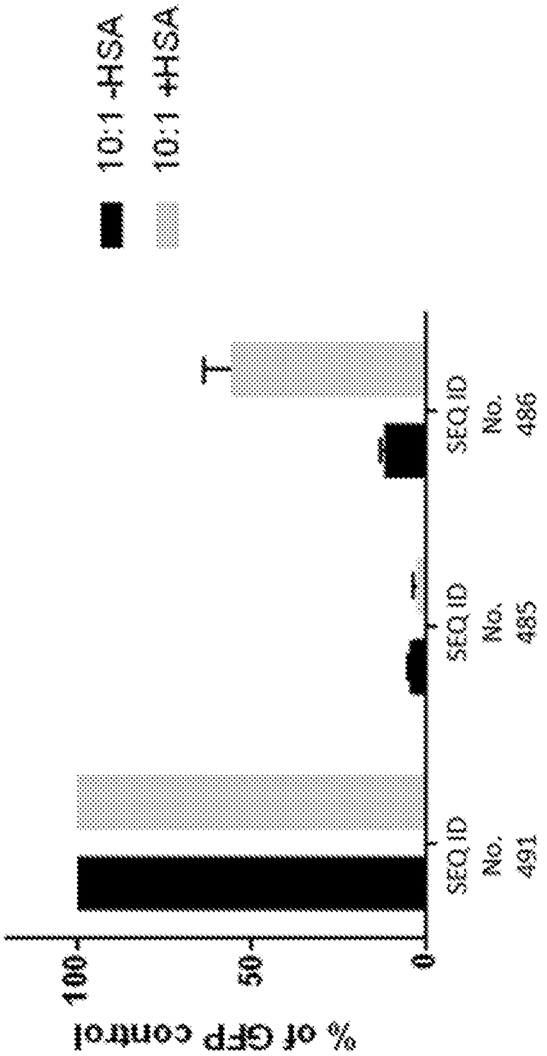
FIG. 7 demonstrates steric blocking of the anti-EpCAM sdAb H90 by HSA of the indicated constructs at ratios 10:1, 5:1, 2.5:1, and 1.25:1 CAR-T:Target cells.
Figure 8:
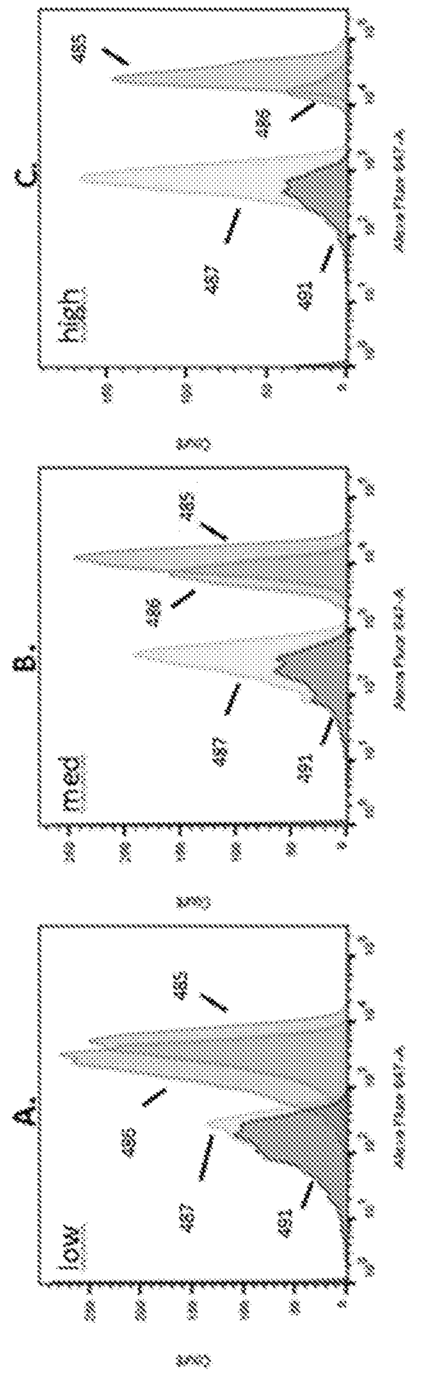
FIGS. 8A-8C provide histograms of EpCAM-Fc/Alexa Fluor 647 staining of CAR-T cells from FIG. 6 that have been grouped into low (FIG. 8A), medium (FIG. 8B), or high (FIG. 8C) CAR expression based on anti-FLAG staining that demonstrate the efficacy of EpCAM mask 1 in blocking ProCAR EpCAM-binding activity. The numbers refer to sequence identifiers (e.g., 491=SEQ ID No. 491).

FIG. 8 provides histograms of EpCAM-Fc/Alexa Fluor 647 staining of CAR-T cells from FIG. 6 that have been grouped into low (FIG. 8A), medium (FIG. 8B), or high (FIG. 8C) CAR expression based on anti-FLAG staining that demonstrate the efficacy of EpCAM mask 2 in blocking ProCAR EpCAM-binding activity.

Masking of Anti-EpCAM sdAb H90

300,000 primary human T cells isolated from healthy donors were infected with 1 mL lentiviral supernatant made from the indicated constructs from FIG. 6 to generate anti-EpCAM CAR-T cells, which were subsequently co-cultured with various ratios (CAR-T:Target cells) with EpCAM-expressing cancer cells that stably express luciferase. Luciferase activity was read 72 hours later as a proxy for cancer cell viability and normalized to the anti-GFP control CAR-T cells, C1081.

Figure 9:
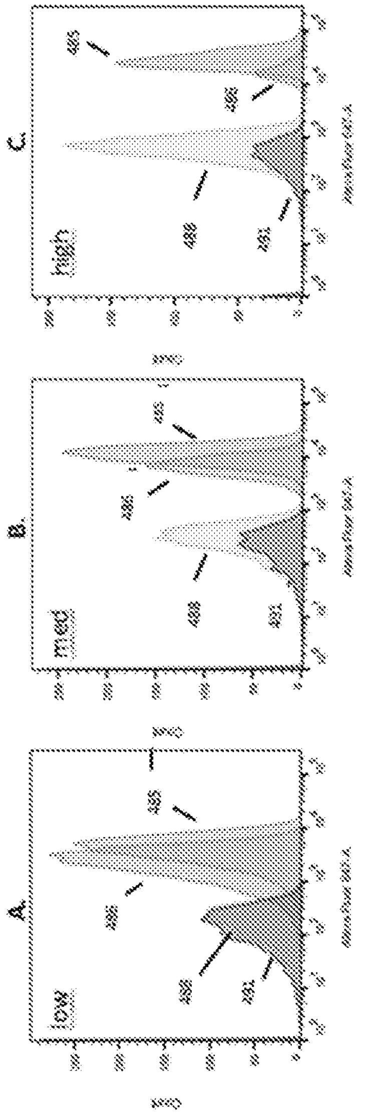
FIGS. 9A-9C provide histograms of EpCAM-Fc/Alexa Fluor 647 staining of CAR-T cells from FIG. 6 that have been grouped into low (FIG. 9A), medium (FIG. 9B), or high (FIG. 9C) CAR expression based on anti-FLAG staining that demonstrate the efficacy of EpCAM mask 2 in blocking ProCAR EpCAM-binding activity. The numbers refer to sequence identifiers (e.g., 488=SEQ ID No. 488).

The data provided in FIG. 9 demonstrates masking of the anti-EpCAM sdAb H90. SEQ ID No. 485 is the "naked" CAR, i.e., no anti-ALB domain. Addition of the anti-ALB domain (SEQ ID No. 486) has a small impact on cell killing activity. Addition of a mask to the CC' loop of the anti-ALB domain has a large impact on cell killing activity due to specific blocking of EpCAM binding.

Steric Blocking by HSA of Anti-EpCAM sdAb H90

300,000 primary human T cells isolated from healthy donors were infected with 1 mL lentiviral supernatant made from the indicated constructs from FIG. 6 to generate anti-EpCAM CAR-T cells, which were subsequently co-cultured with various ratios (CAR-T:Target cells) with EpCAM-expressing cancer cells that stably express luciferase in the presence or absence of human serum albumin (HSA). Luciferase activity was read 72 hours later as a proxy for cancer cell viability and normalized to the anti-GFP control CAR-T cells, C1081.

Figure 10:
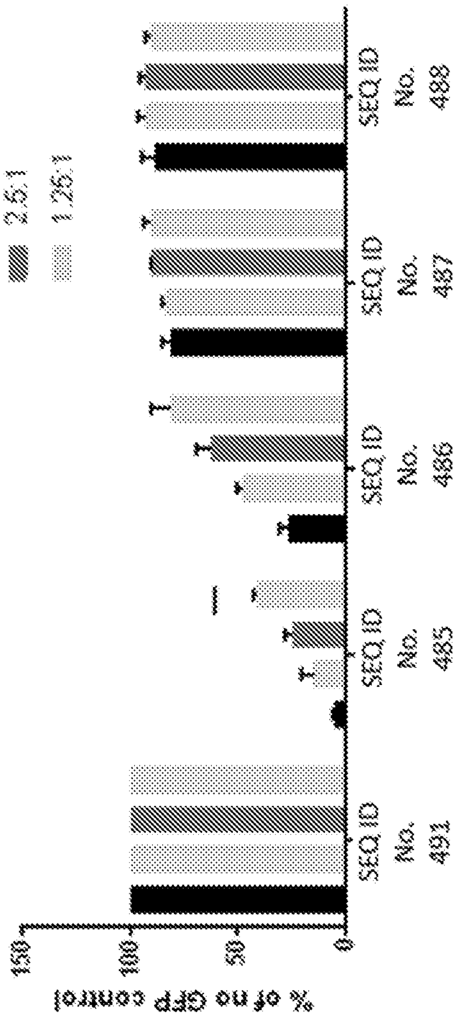
FIG. 10 demonstrates masking of the anti-EpCAM sdAb H90 of constructs of FIG. 6 at ratios 10:1, 5:1, 2.5:1, and 1.25:1 CAR-T:Target cells.

The data provided in FIG. 10 demonstrate steric blocking by HSA of the anti-EpCAM sdAb H90.

Example 7: EpCAM ProCAR Protease Site-Dependent Cell Killing

Chimeric antigen receptor-expressing T-cells (CAR T-cells) were generated by infecting isolated CD4/CD8 positive T cells from a healthy donor with lentivirus expressing the indicated constructs. FIG. 6 shows a diagram with the constructs used. Cells were incubated with Fc-tagged EpCAM extracellular domain (ECD). Cells were washed to remove unbound Fc-tagged EpCAM ECD. Cells were incubated with a secondary antibody conjugated to DyLight 650 that recognizes human Fc. Binding of the secondary antibody to cells was measured by flow cytometry.

Figure 11:
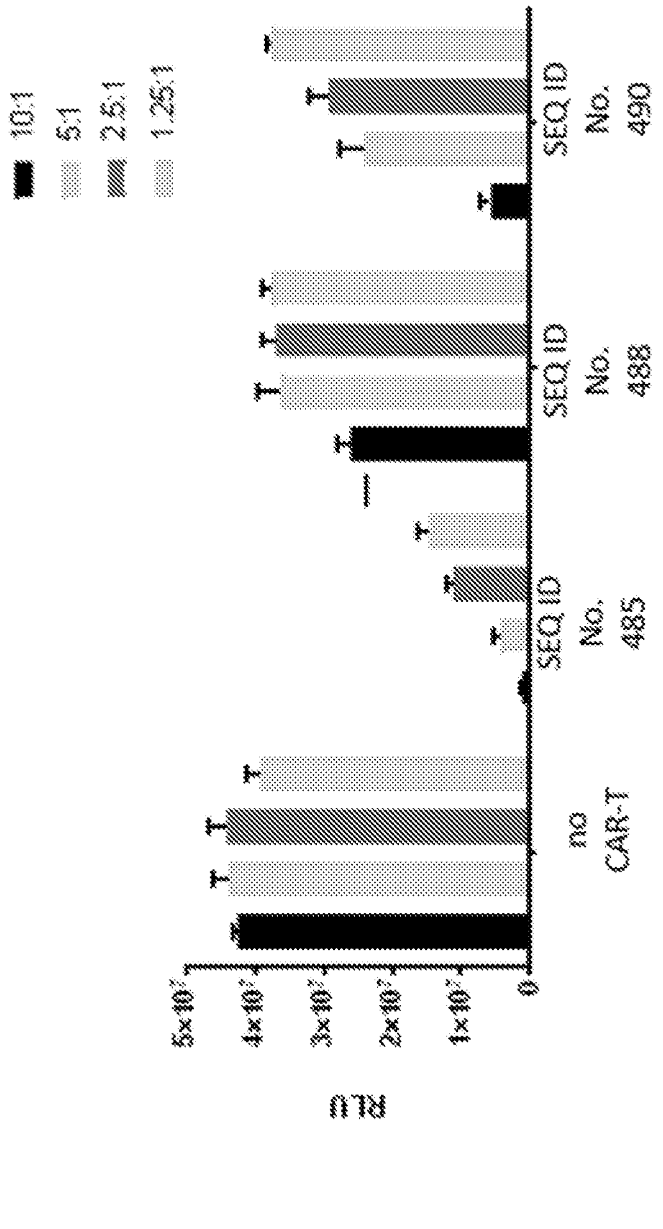
FIG. 11 demonstrates protease site-dependent activation of EpCAM ProCAR mask 2 cell killing activity.

FIG. 11 demonstrates protease site-dependent activation of EpCAM ProCAR mask 2 cell killing activity.

Example 8: Protease Activation of EpCAM Mask 1 ProCAR Antigen Binding Activity 300,000 primary human T cells isolated from healthy donors were infected with 1 mL lentiviral supernatant made from the indicated constructs from FIG. 6 to generate anti-EpCAM CAR-T cells, which were subsequently washed in PBS, and then treated for 1 hr. at room temp with either PBS or PBS containing 400 nM recombinant uPA protease and then stained with anti-FLAG antibodies and EpCAM-Fc along with the anti-mouse BV421 and anti-human Fc Alexa Fluor 647 secondary antibodies and analyzed by flow cytometry.

Figure 12:
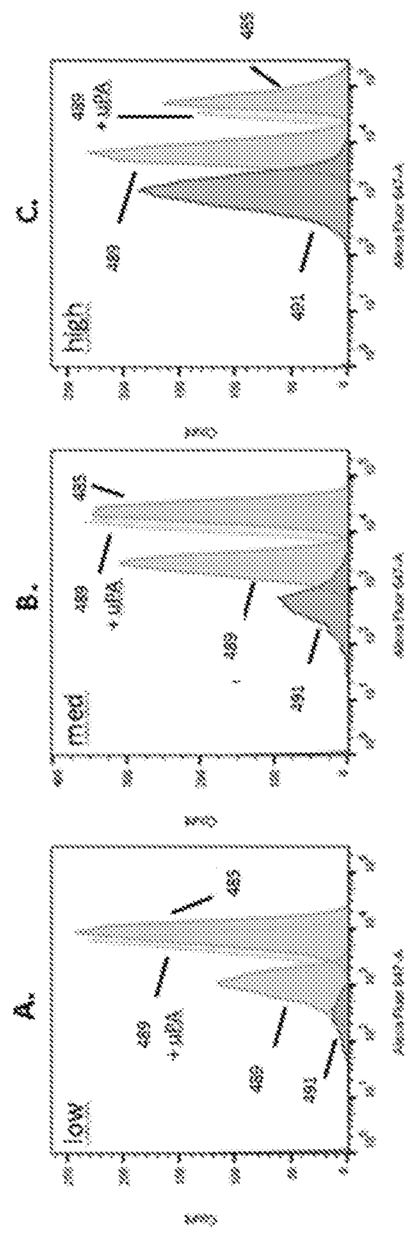
FIGS. 12A-12C illustrate protease activation of EpCAM Mask 1 ProCAR antigen binding activity at low (FIG. 12A), medium (FIG. 12B), or high (FIG. 12C) CAR expression based on anti-FLAG staining. The numbers refer to sequence identifiers (e.g., 489=SEQ ID No. 489).

Histograms of EpCAM-Fc staining of CAR-T cells that have been grouped into low (FIG. 12A), medium (FIG. 12B), or high (FIG. 12C) CAR expression based on anti-FLAG staining. These results demonstrate protease activation of EpCAM Mask 1 ProCAR antigen binding activity.

Example 9: Protease Activation of EpCAM Mask 2 ProCAR Antigen Binding Activity 300,000 primary human T cells isolated from healthy donors were infected with 1 mL lentiviral supernatant made from the indicated constructs from FIG. 6 to generate anti-EpCAM CAR-T cells, which were subsequently washed in PBS, and then treated for 1 hr. at room temp with either PBS or PBS containing 400 nM recombinant uPA protease and then stained with anti-FLAG antibodies and EpCAM-Fc along with the anti-mouse BV421 and anti-human Fc Alexa Fluor 647 secondary antibodies and analyzed by flow cytometry.

Figure 13:
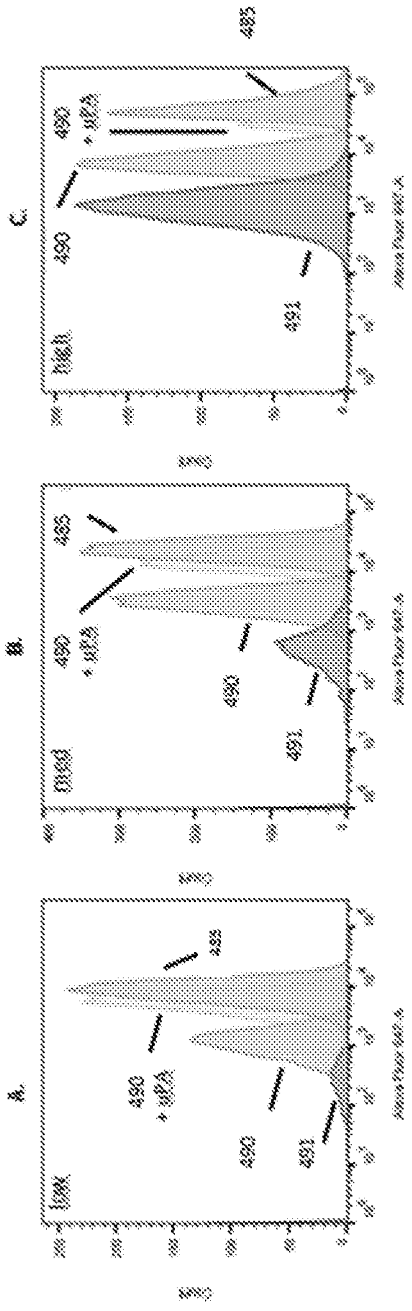
FIGS. 13A-13C illustrate protease activation of EpCAM Mask 2 ProCAR antigen binding activity at low (FIG. 13A), medium (FIG. 13B), or high (FIG. 13C) CAR expression based on anti-FLAG. The numbers refer to sequence identifiers (e.g., 485=SEQ ID No. 485).

Histograms of EpCAM-Fc staining of CAR-T cells that have been grouped into low (FIG. 13A), medium (FIG. 13B), or high (FIG. 13C) CAR expression based on anti-FLAG staining. These results demonstrate protease activation of EpCAM Mask 2 ProCAR antigen binding activity.

Figure 14A:
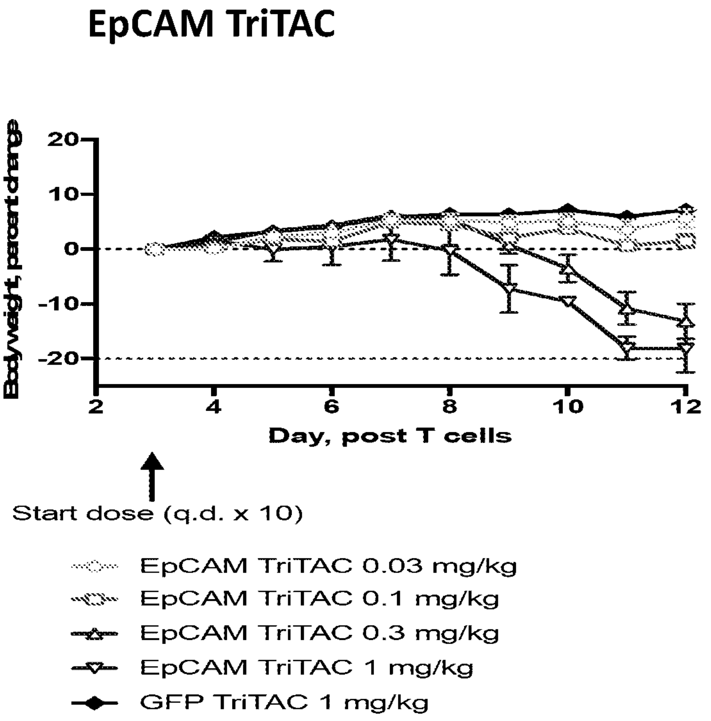
FIGS. 14A-14C show body weight percent change in mice, following administering exemplary EpCAM ProTriTAC molecules (EpCAM ProTriTAC containing linker L040 in FIG. 14B; EpCAM ProTriTAC containing a non-cleavable linker in FIG. 14C) and EpCAM TriTAC molecules (FIG. 14A) of this disclosure.
Figure 14B:
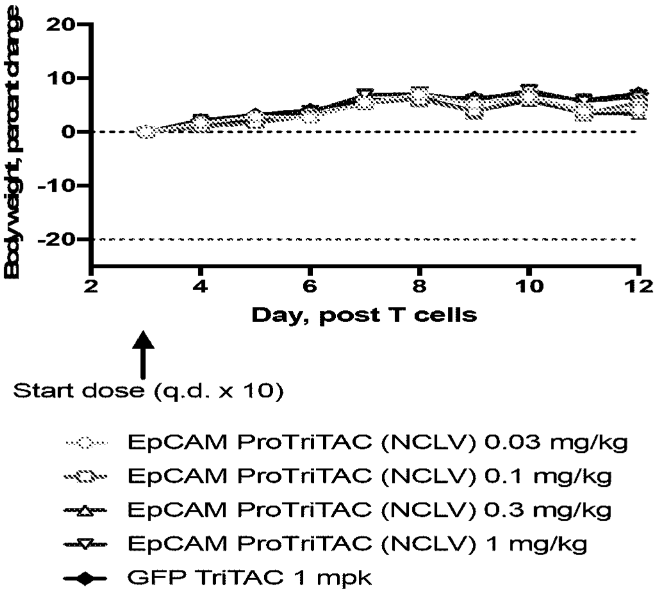
Figure 14C:
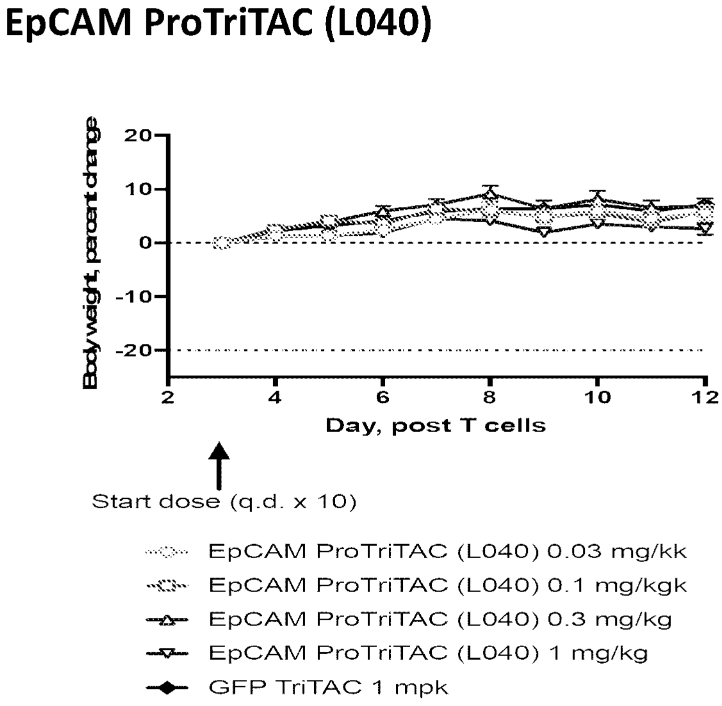

Example 10: Demonstration of Improved Tolerability in Mouse, Conferred by an Exemplary EpCAM Targeting ProTriTAC Molecule In this study, the tolerability of an exemplary EpCAM targeting ProTriTAC molecule was assessed. Seven weeks old NSG female tumor free mice were intraperitoneally injected with $2\times10^7$ expanded human T cells at the commencement of the study, i.e., at day 0. On day 2, treatment was started by dividing the mice into various groups and administering to them varying concentrations of the exemplary EpCAM targeting ProTriTAC molecule containing the linker sequence L040 (SEQ ID NO: 494), an EpCAM targeting TriTAC molecule (SEQ ID NO: 492), an EpCAM targeting ProTriTAC molecule containing a non-cleavable linker (EpCAM ProTriTAC (NCLV) (SEQ ID NO: 495), and a GFP TriTAC molecule as a control (SEQ ID NO: 493). The molecules were administered once daily for 10 days, at the following dosages: 0.03 mg/kg, 0.1 mg/kg, 0.3 mg/kg, and 1 mg/kg. Starting from day 2, body weight of the animals were recorded daily. As shown in FIGS. 14A-14C, the EpCAM targeting ProTriTAC molecule containing a non-cleavable linker (ProTriTAC (NCLV)) and a GFP TriTAC (used as a negative control) were very well tolerated in mice even at the highest dose of 1 mg/kg. The EpCAM targeted ProTriTAC molecule containing the linker sequence of L040 was well tolerated at the dosage of 1 mg/kg, whereas the EpCAM targeted TriTAC was well tolerated 0.1 mg/kg. It was thus observed that the EpCAM targeting ProTriTAC containing the L040 linker sequence conferred at least about 10 times improved tolerability, in mouse, compared to the EpCAM targeting TriTAC.)

Figure 15A:
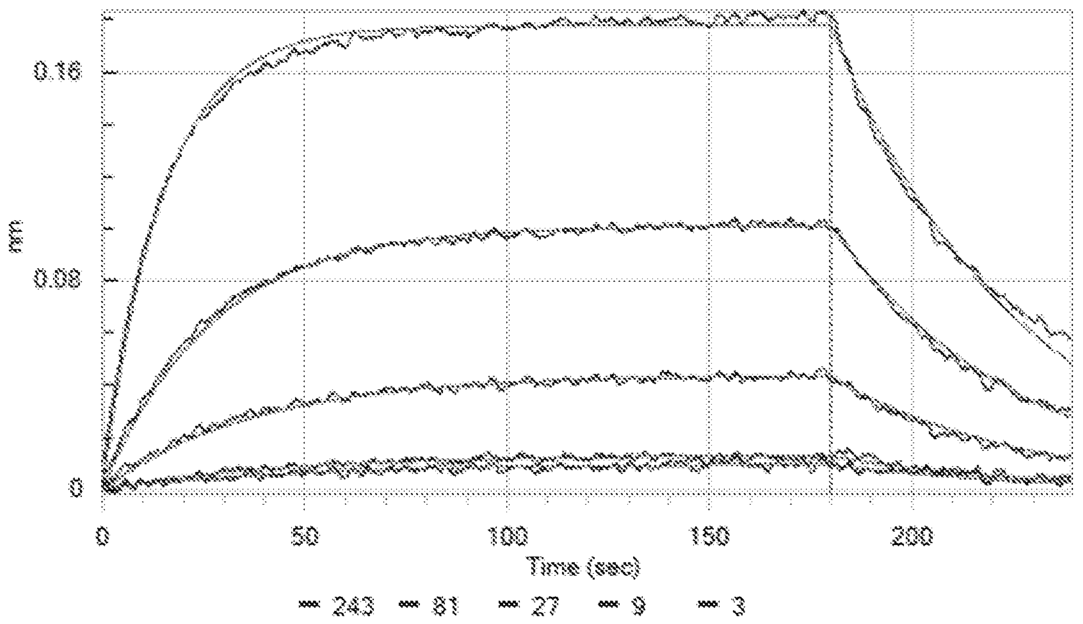
FIG. 15A-15C show binding kinetics for various EpCAM binding domains; H13 (FIG. 15A), H90 (FIG. 15B), and H90.2 (FIG. 15C).
Figure 15B:
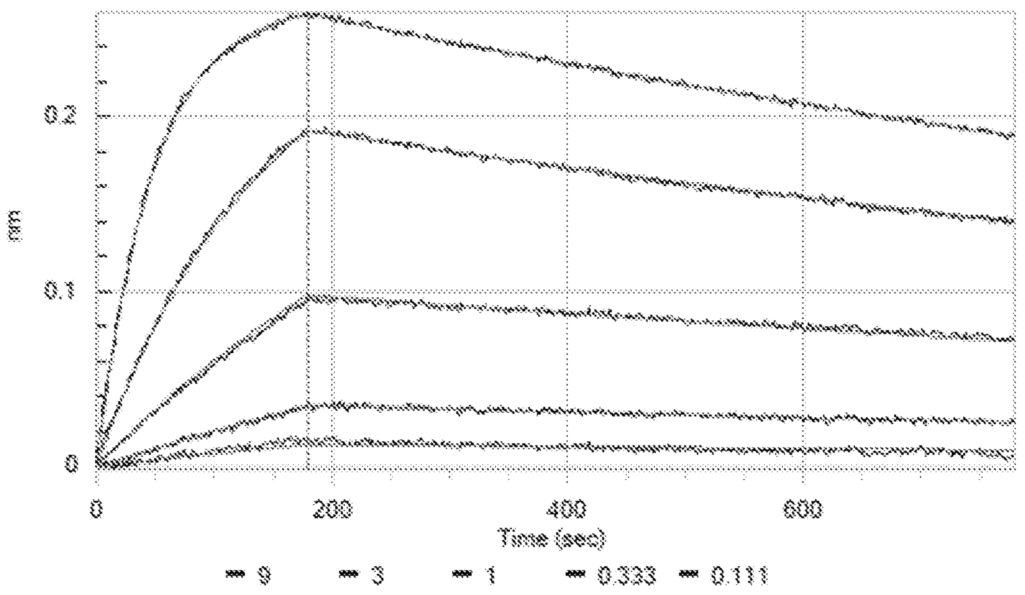
Figure 15C:
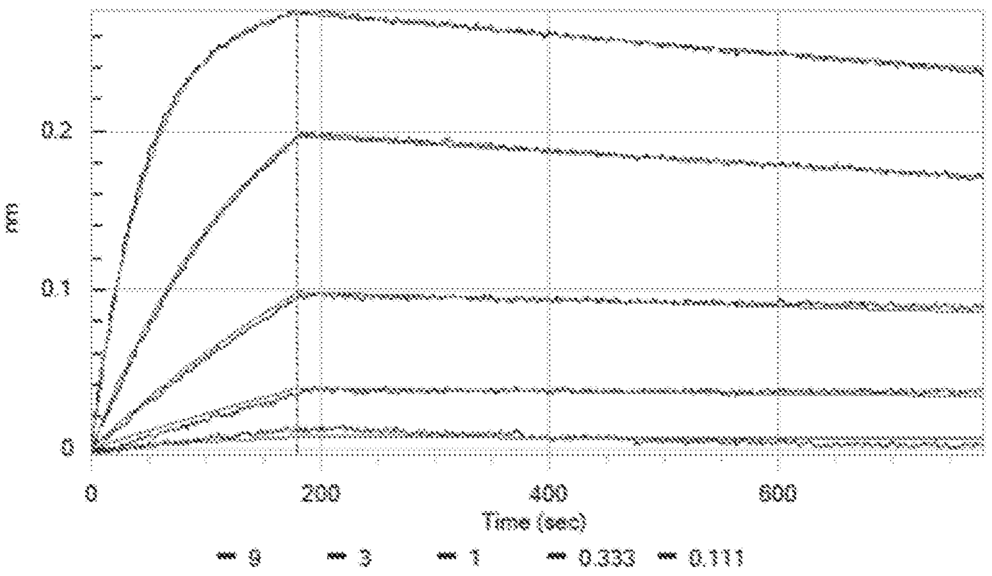

Example 11: Affinity of EpCAM Targeting ProTriTAC Proteins Toward Human, Cynomolgus, or Mouse EpCAM The affinities of various exemplary EpCAM targeting ProTriTAC proteins, toward human, cynomolgus, or mouse EpCAM were measured in a binding assay, which also looked at the binding kinetics for the interaction between the tested ProTriTAC proteins and human EpCAM. The binding kinetics are shown in FIGS. 15A, 15B, and 15C.

The affinity summary for the EpCAM targeting ProTriTAC proteins, containing exemplary EpCAM binding domains H13 (SEQ ID No. 207), H90 (SEQ ID No. 209), or H90.2 (SEQ ID No. 497), is provided in Table 8.

TABLE 8

Affinity summary for EpCAM targeting ProTriTAC proteins

| | H13 (SEQ ID No. 576) (nM) | (H90) (SEQ ID No. 577) (nM) | H90.2 (SEQ ID No. 578) (nM) |
|---|---|---|---|
| huEpCAM:Fc (SEQ ID No. 579) | 115 | 0.23 | 0.10 |
| cyEpCAM:Fc (SEQ ID No. 580) | 137 | 0.42 | 0.21 |
| muEpCAM (biotinylated version of mouse EpCAM antigen) | No binding | 0.26 | 0.15 |

Example 12: T Cell Engaging Capability and Specificity of Exemplary EpCAM Targeting Proteins in TriTAC Format, a Non-Cleavable Prodrug Format, or Active Drug Format Three exemplary humanized EpCAM targeting ProTriTAC proteins containing an exemplary EpCAM binding domain as described herein, H13 (SEQ ID NO. 207), H138.2 (SEQ ID No. 496), or H90.2 (SEQ ID No. 497), were tested in a T cell dependent cellular cytotoxicity (TDCC) assay (see Nazarian A A, Archibeque I L, Nguyen Y H, Wang P, Sinclair A M, Powers DA. 2015. J Biomol Screen. 20:519-27), using EpCAM expressing colon cancer cells HCT116. The H90.2 and H138.2 EpCAM binding domain sequences were largely similar to the EpCAM binding domain sequences H90 and H138, respectively, however, the first amino acid of framework 4 was modified (see SEQ ID No. 582). In particular, the EpCAM binding domain sequences H90 and H138 contained an Asn deamidation (NG) sites, which were altered to was altered to WG to remove the Asn deamidation, and an improvement in terms of protein stability (which in turn is likely to be advantageous for improving the manufacturability of the drug) was contemplated.

Figure 16A:
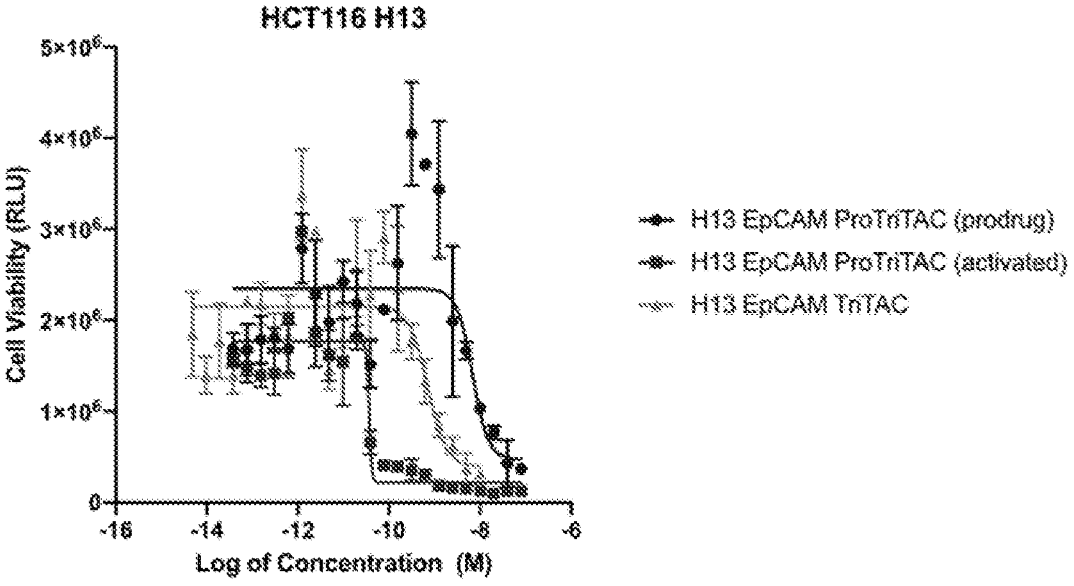
FIGS. 16A-16C show results of T cell dependent cytotoxicity assay (TDCC assay), on HCT116 cells, using ProTriTAC, TriTAC proteins, or active drugs (CT) containing EpCAM binding domains H13 (FIG. 16A), H90.2 (FIG. 16B), and H138.2 (FIG. 16C).

The results are shown in FIGS. 16A (H13), 16B (H90.2), and 16C (H138.2). The tested EpCAM binding proteins contained an EpCAM binding domain (H13, H90.2, or H138.2), an albumin binding domain (anti-ALB), and a CD3 binding domain (anti-CD3), wherein the anti-ALB domain further included a non-cleavable linker (NCLV) (the non-cleavable prodrug format), or a cleavable linker plus a masking domain (ACT). The activated EpCAM binding proteins (CT) (the active drug format) contained an EpCAM binding domain (H13, H90.2, or H138.2) and a CD3 binding domain (anti-CD3).

Figure 17A:
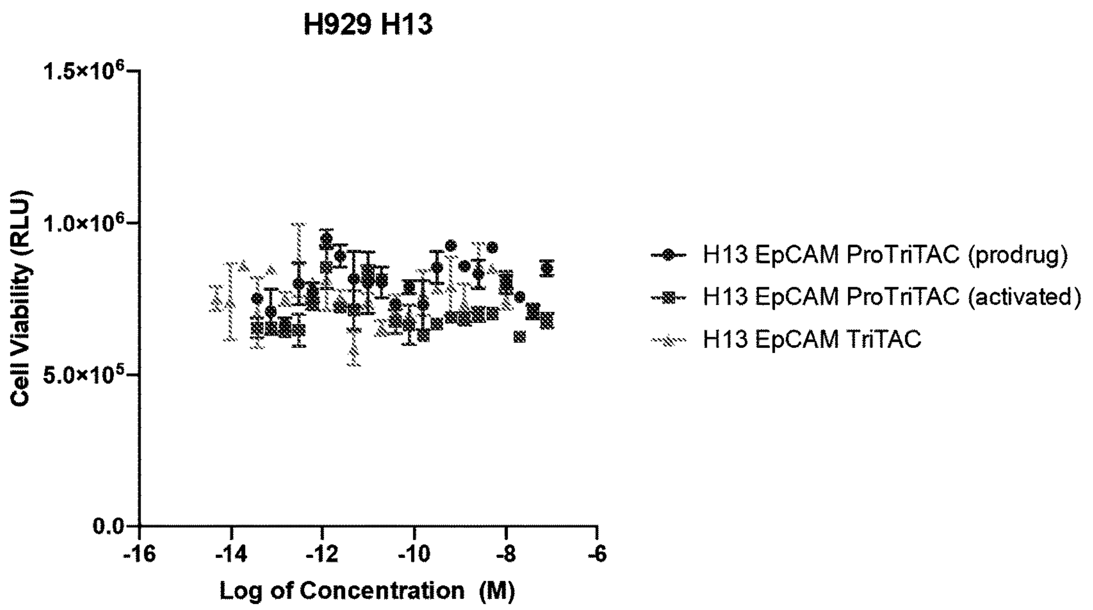
FIGS. 17A-17C show results of T cell dependent cytotoxicity assay (TDCC assay), on NCI-H929 cells, using ProTriTAC, TriTAC proteins, or active drugs (CT) containing EpCAM binding domains H13 (FIG. 17A), H90.2 (FIG. 17B), and H138.2 (FIG. 17C).
Figure 17B:
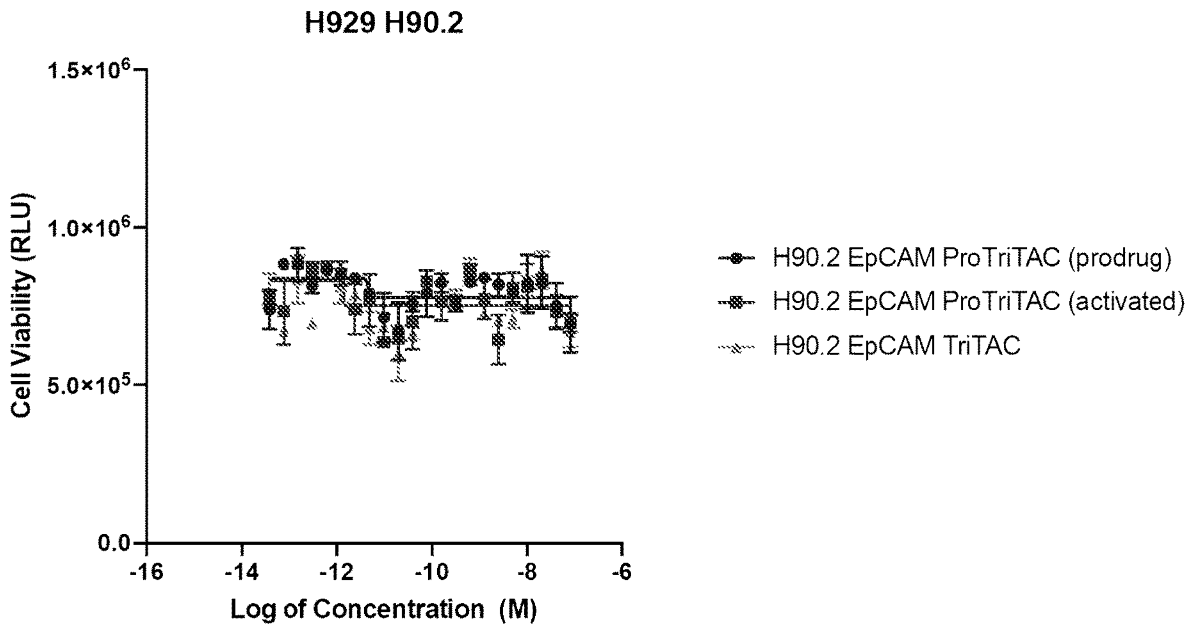
Figure 17C:
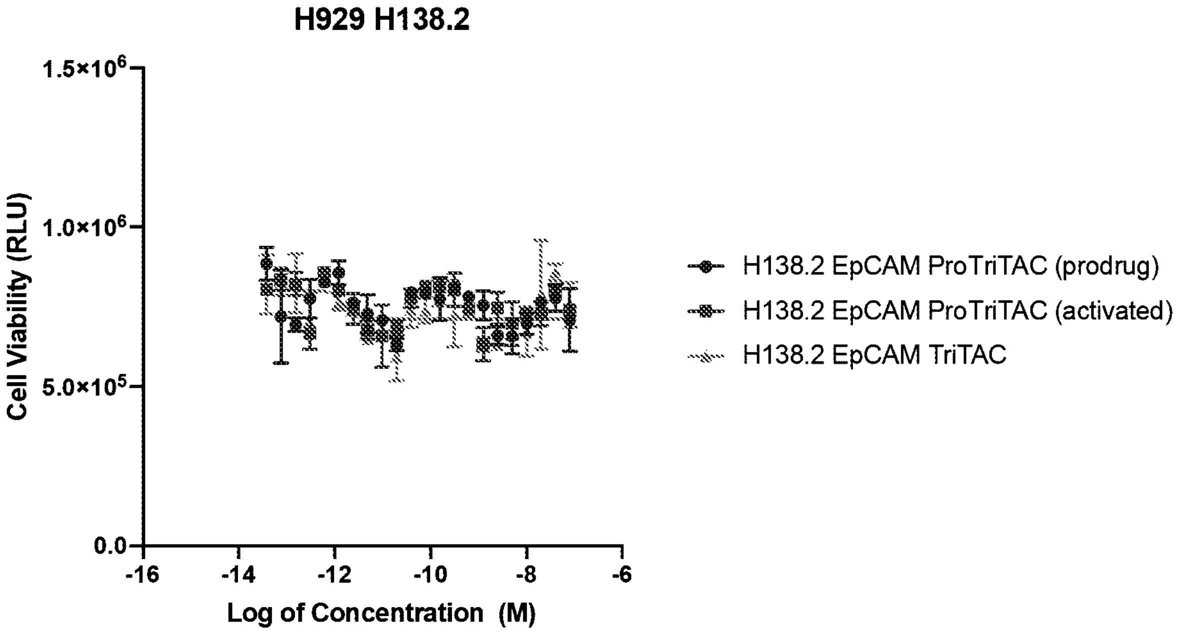

In this assay, luciferase labelled HCT116 cells were combined with purified human T cells and exposed to a titration of the exemplary EpCAM binding proteins as described above (NCLV, CT, ACT). It was hypothesized that if an EpCAM binding protein directed T cells to kill the EpCAM expressing HCT116 cells, then the viability of those cells, as determined by running a luciferase assay at 48 hours after starting the experiment, should decrease. A similar assay was also carried out using EpCAM-negative NCI-H929 myeloma cells, and, as shown in FIGS. 17A, 17B, and 17C, none of the proteins tested were able to engage T cells in killing the NCI-H929 cells.

Figure 16B:
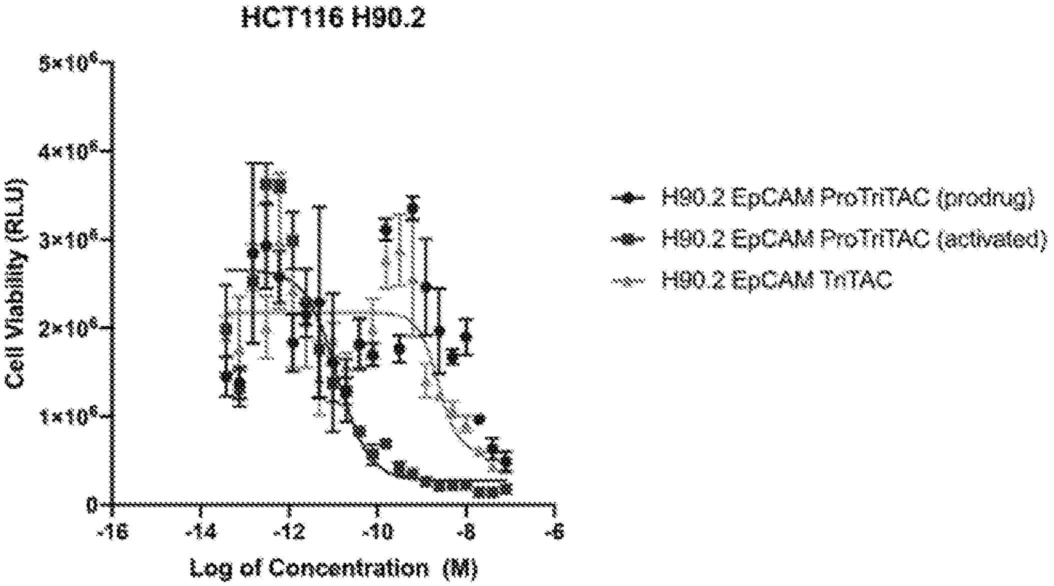
Figure 16C:
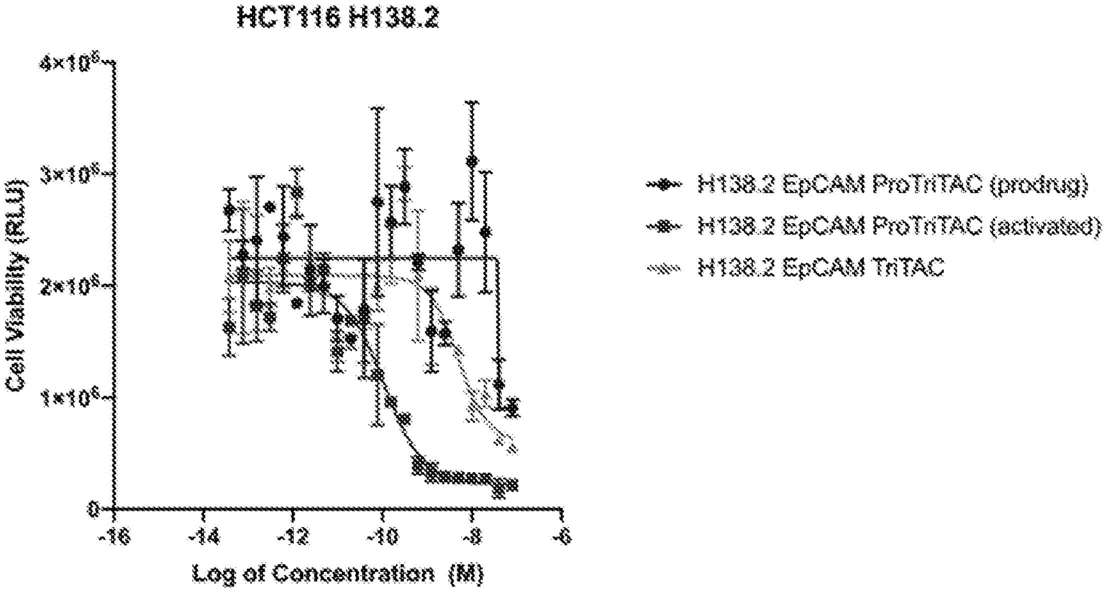

FIGS. 16A, 16B, and 16C illustrate representative TDCC data from the assay using HCT116 cells. $EC_{50}$ values from the TDCC assay are listed in Table 9. As seen in the plots and indicated by the $EC_{50}$ values, binding proteins containing any of the three EpCAM binding domains (H13, H90.2, or H138.2) functioned as T cell engagers in EpCAM expressing HCT116 colon cancer cells. Further, for the binding proteins with cleavable linker and masking domain (ACT), the $EC_{50}$ values were about 7 to 10 fold (H13 and H138.2) lower compared to that of the binding proteins with non-cleavable linker (NCLV) (the non-cleavable prodrug format); whereas for the active drug (CT), the $EC_{50}$ values were up to about 350 fold (H138.2) lower than that of the NCLV. The $EC_{50}$ of the active drug containing the H13 EpCAM binding domain was about 37 pM; H90.2 binding domain was about 11 pM; and H138.2 binding domain was about 107 pM.

TABLE 9

$EC_{50}$ values for TDCC assays using EpCAM ProTriTAC proteins, on HCT116 cells

| | $EC_{50}$(M) | Fold Shift to NCLV |
|---|---|---|
| EpCAM H13 ProTriTAC (NCLV) (SEQ ID No. 569) | 6.87E-09 | |
| EpCAM H13 ProTriTAC (CT) (SEQ ID No. 210) | 3.67E-11 | 187 |

TABLE 9-continued $EC_{50}$ values for TDCC assays using EpCAM ProTriTAC proteins, on HCT116 cells

| | $EC_{50}$(M) | Fold Shift to NCLV |
|---|---|---|
| EpCAM H13 ProTriTAC (ACT) (SEQ ID No. 570) | 7.07E-10 | 10 |
| EpCAM H90.2 ProTriTAC (NCLV) (SEQ ID No. 502) | | |
| EpCAM H90.2 ProTriTAC (CT) (SEQ ID No. 571) | 1.07E-11 | |
| EpCAM H90.2 ProTriTAC (ACT) (SEQ ID No. 572) | 2.67E-09 | |
| EpCAM H138.2 ProTriTAC (NCLV) (SEQ ID No. 573) | 3.73E-08 | |
| EpCAM H138.2 ProTriTAC (CT) (SEQ ID No. 574) | 1.07E-10 | 349 |
| EpCAM H138.2 ProTriTAC (ACT) (SEQ ID No. 575) | 5.01E-09 | 7 |

Figure 18A:
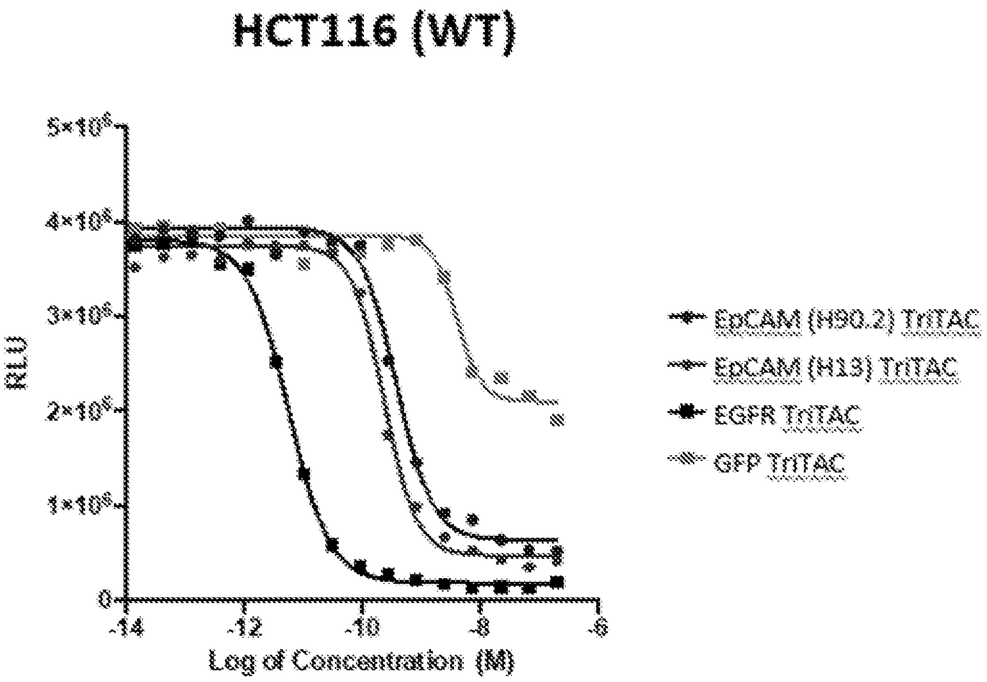
FIGS. 18A-18B show results of T cell dependent cytotoxicity assay (TDCC assay), on HCT116 cells (FIG. 18A) and HCT116 (EpCAM-knock out; KO) (FIG. 18B), using TriTAC, containing EpCAM binding domains H13 and H90.2.
Figure 18B:
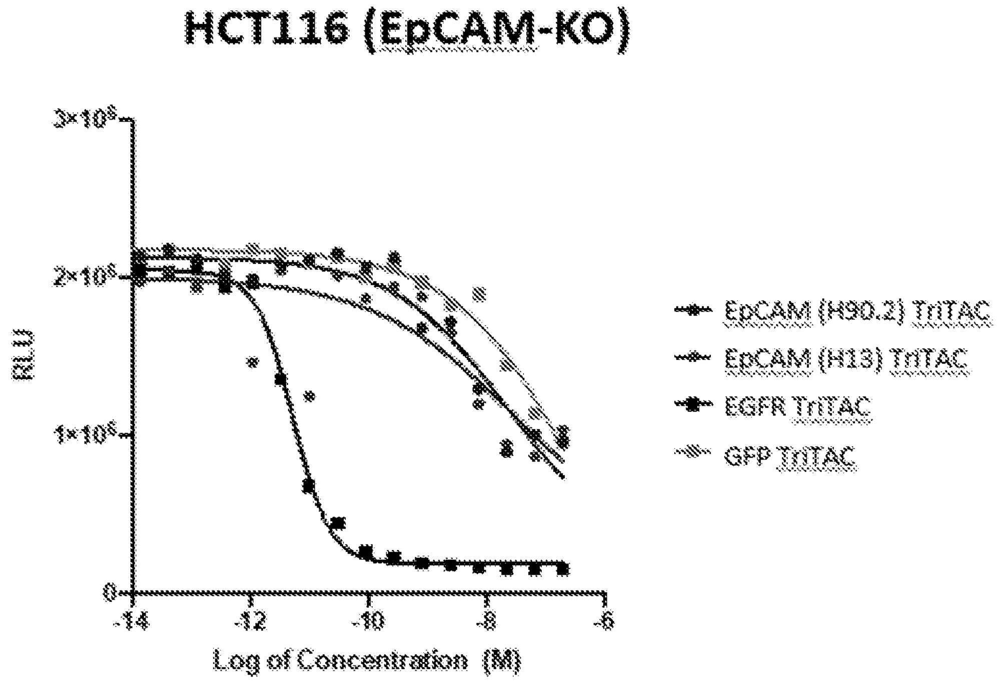

To further assess the EpCAM specific cell killing potential of the test EpCAM binding proteins, a TDCC assay as describe above, was carried out with HCT116 colon cancer cells that express EpCAM (wild-type) or HCT116 (EpCAM-KO) cells that do not express EpCAM. The EpCAM TriTAC proteins containing EpCAM binding domains H13 or H90.2 were tested in this assay, and controls proteins were a GFP TriTAC protein and an EGFR TriTAC protein. Results for this assay is shown in FIGS. 18A and 18B, and the $EC_{50}$ values are listed in Table 10.

Figure 19:
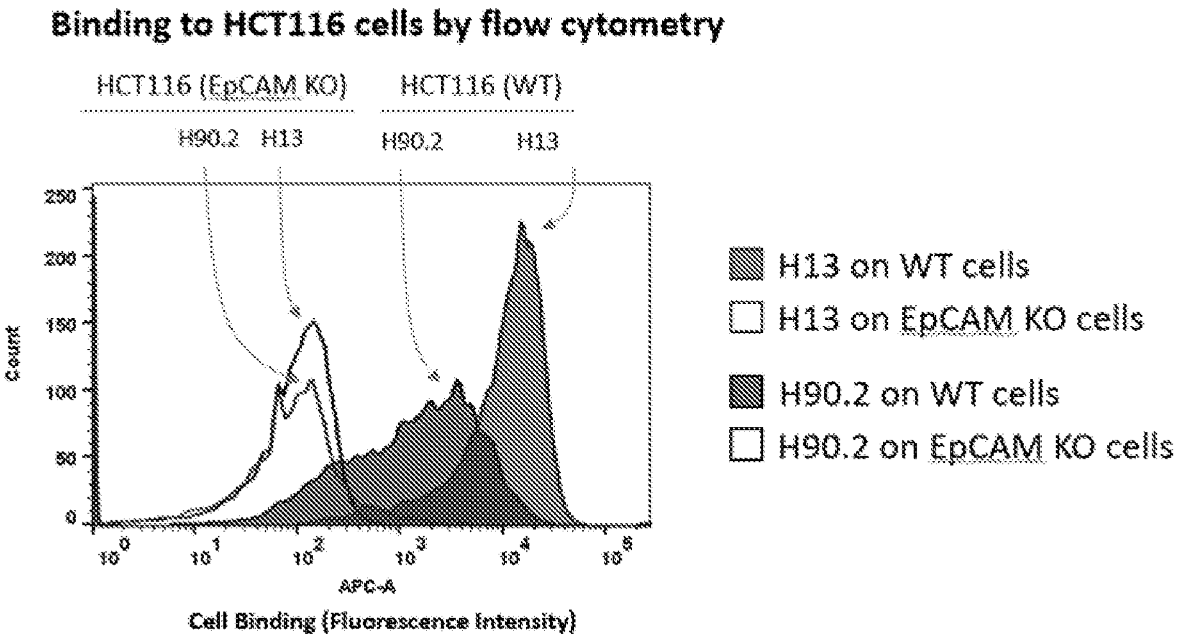
FIG. 19 shows results of a flow cytometry assay for measuring binding of HCT116 cells wild-type (WT) and HCT116 (EpCAM-knock out; KO) cells and EpCAM binding domains H13 and H90.2.

The EpCAM binding proteins exhibited differential killing of cells, based on expression of EpCAM. Specificity of binding was also confirmed by flow cytometry, as shown in FIG. 19. For the flow cytometry assay the cells were stained with 300 nM H13 or H90.2 in the CT format (active drug) and detected with 11D3-AF650 antibody.

TABLE 10

$EC_{50}$ values for TDCC assays using EpCAM TriTAC proteins, on HCT116 cells and HCT116 (EpCAM-KO) cells

| | HCT116 $EC_{50}$ (M) | HCT116 (EpCAM-KO) $EC_{50}$ (M) |
|---|---|---|
| EpCAM (H90.2) TriTAC | 3.8E−10 | 3.3E−09 |
| EpCAM (H13) TriTAC | 2.3E−10 | 3.5E−06 |
| EGFR TriTAC | 5.6E−12 | 5.3E−12 |
| GFP TriTAC | 4.0E−09 | 5.8E−07 |

Figure 20:
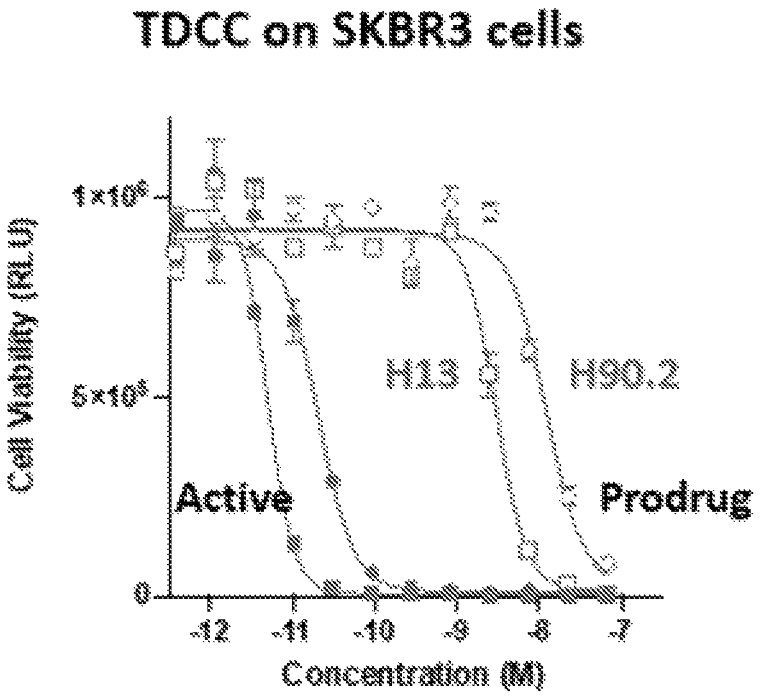
FIG. 20 shows results of a TDCC assay on SKBR3 cells, using a non-cleavable prodrug or active drug (CT) versions containing EpCAM binding domains H13 or H90.2

In further TDCC assays, using various other cell lines, the cell killing potential of two EpCAM binding proteins in CT format (the active drug, containing either the H13 or H90.2 EpCAM binding domain and an anti-CD3 domain) or the non-cleavable prodrug format (containing either H13 or H90.2 and anti-CD3 and anti-HSA with non-cleavable linker, NCLV), were compared. Results are provided in Table 11 and the plot of FIG. 20 is for the TDCC assay using SKBR3 (human breast cancer cells).

Figure 21A:
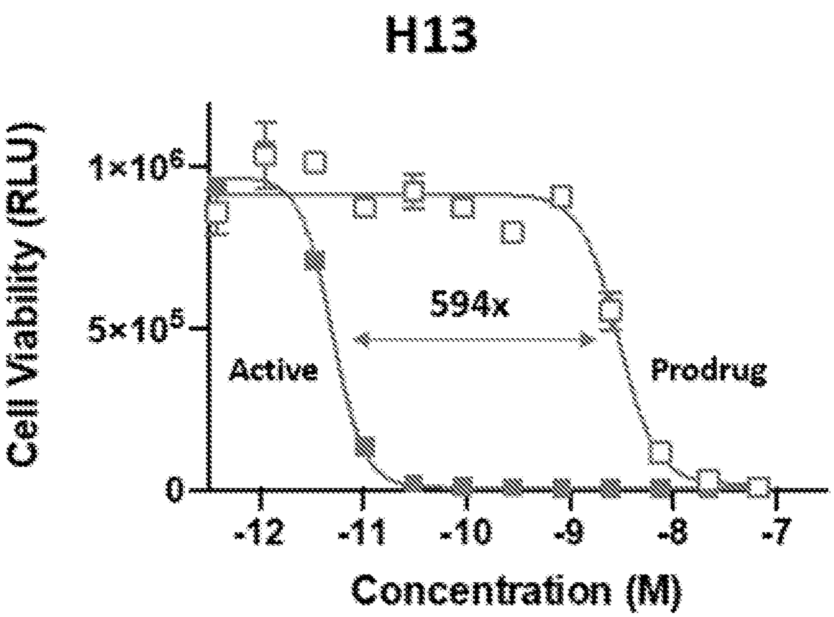
FIGS. 21A-21B illustrates representative plots demonstrating the masking effect achieved by the non-cleavable prodrug versions containing EpCAM binding domains H13 (FIG. 21A) or H90.2 (FIG. 21B), compared to active drugs containing the same.
Figure 21B:
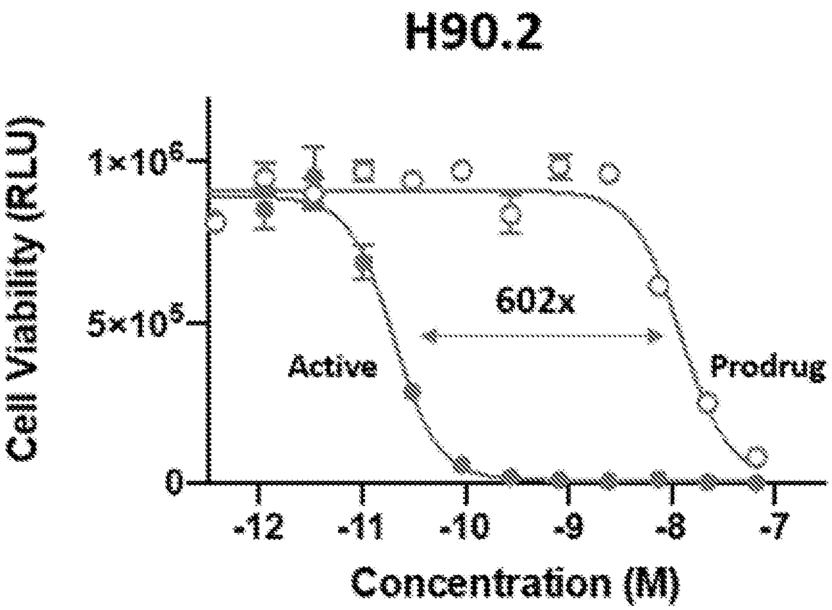
Figure 22A:
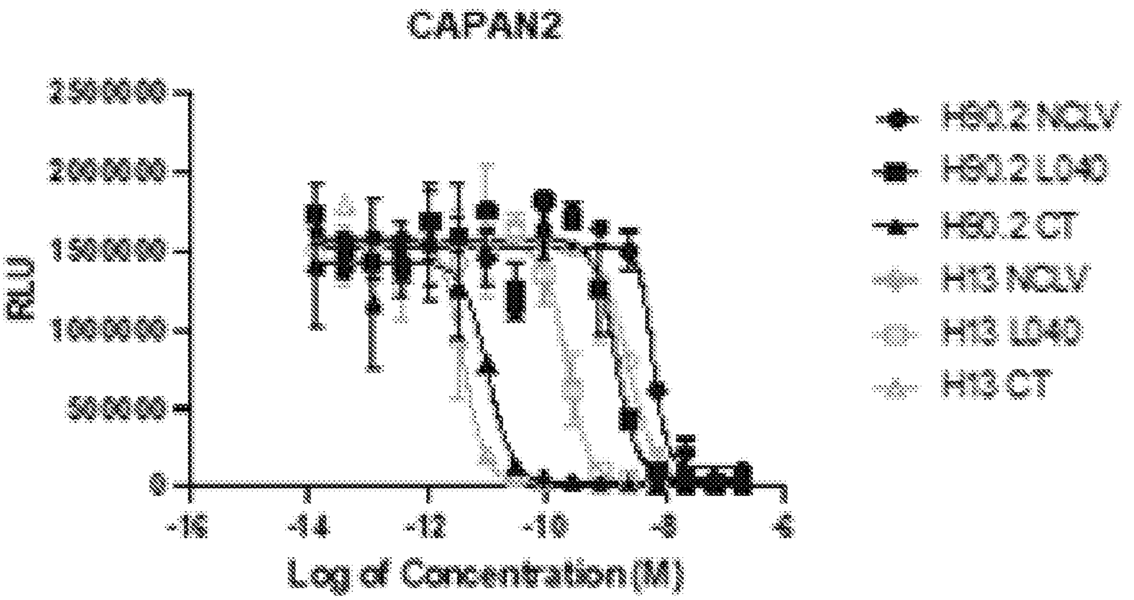
FIGS. 22A-22H show results of a TDCC assay on various cell lines, using a non-cleavable prodrug (NCLV), ProTriTAC (L040), or active drug (CT) versions containing EpCAM binding domains H13 or H90.2.
Figure 22B:
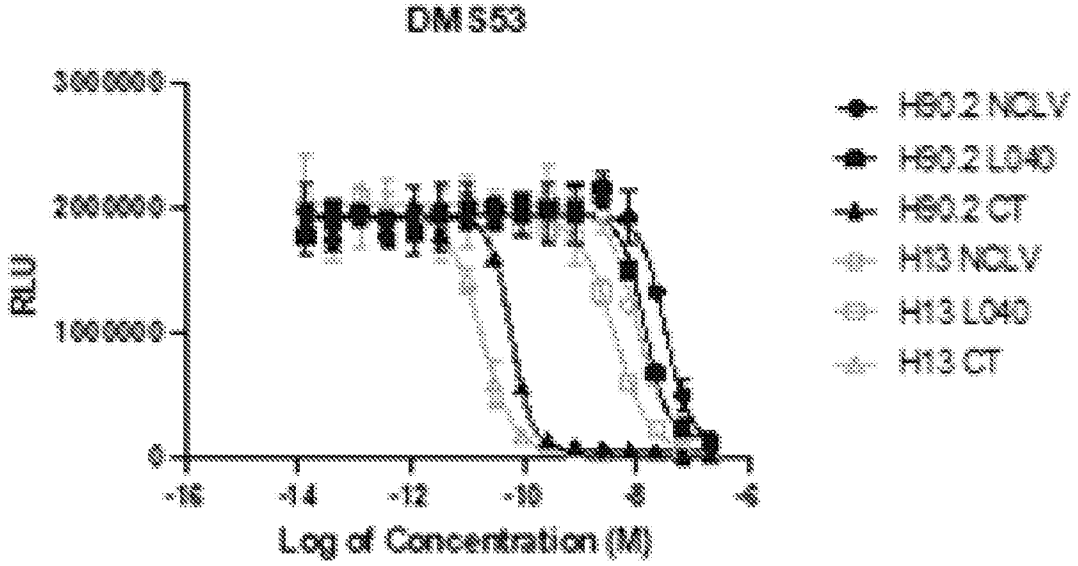
Figure 22C:
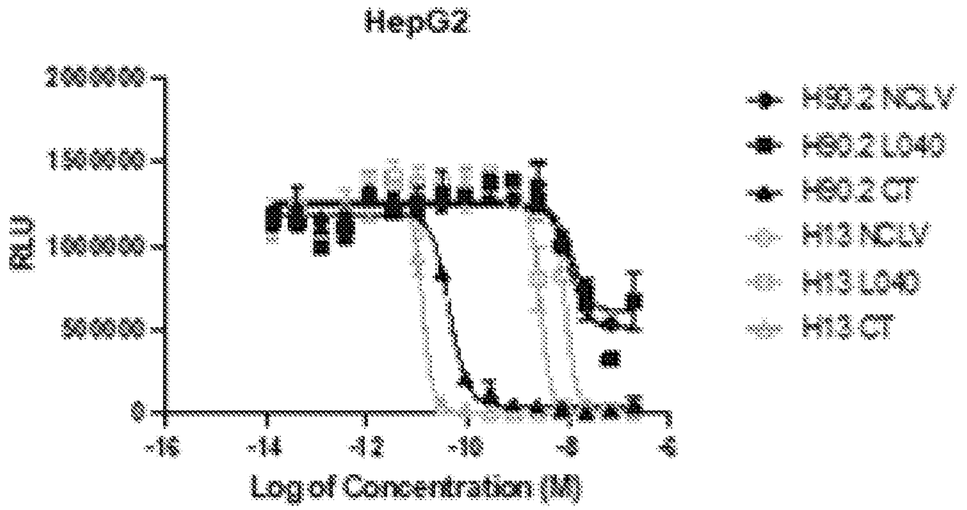
Figure 22D:
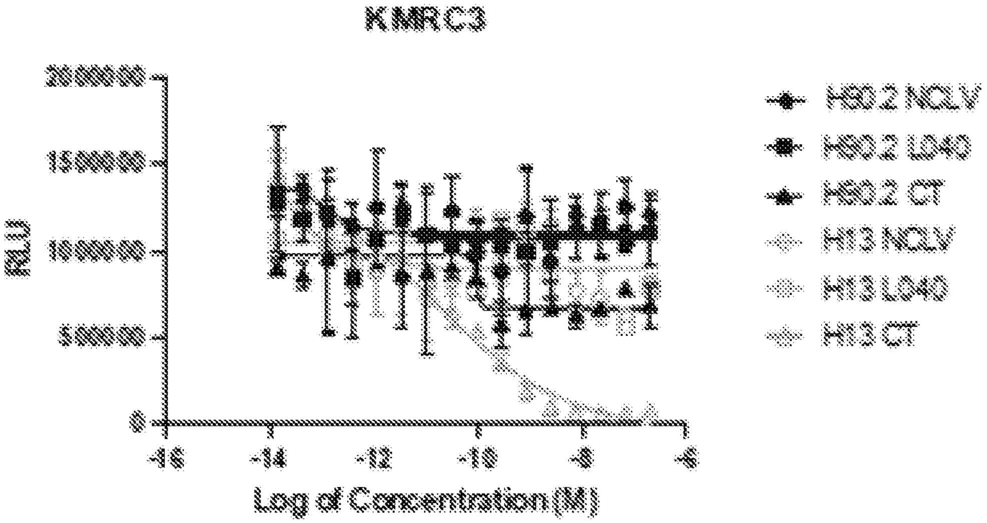
Figure 22E:
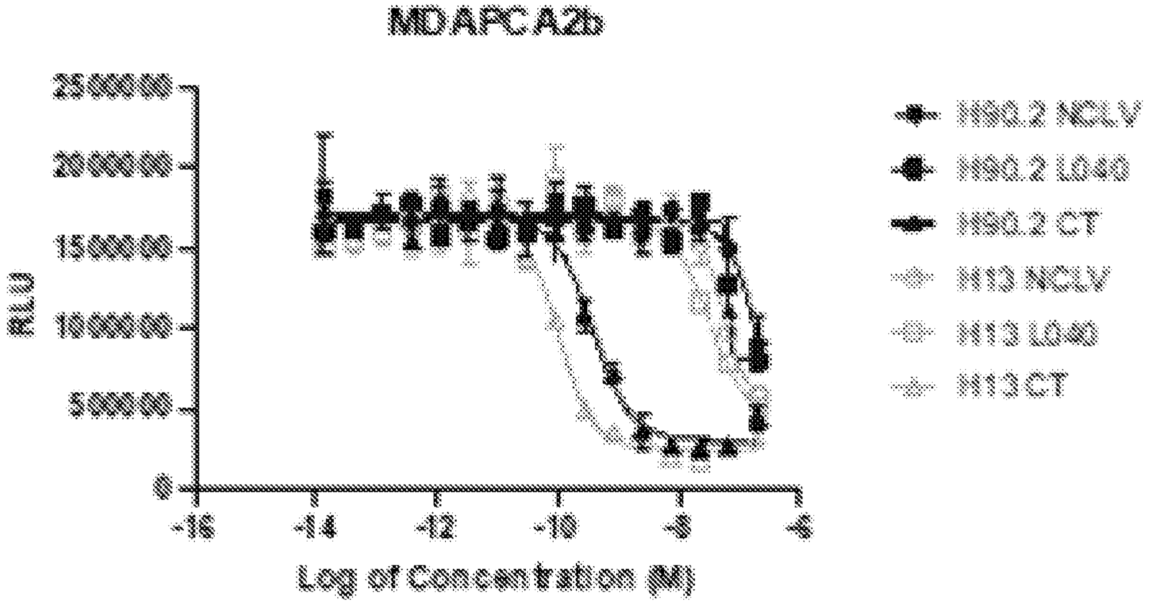
Figure 22F:
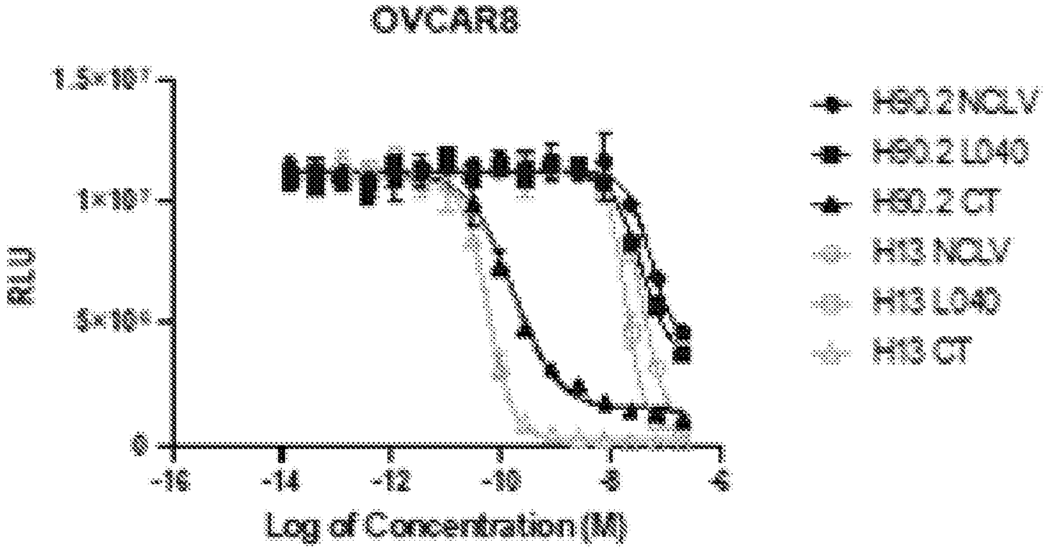
Figure 22G:
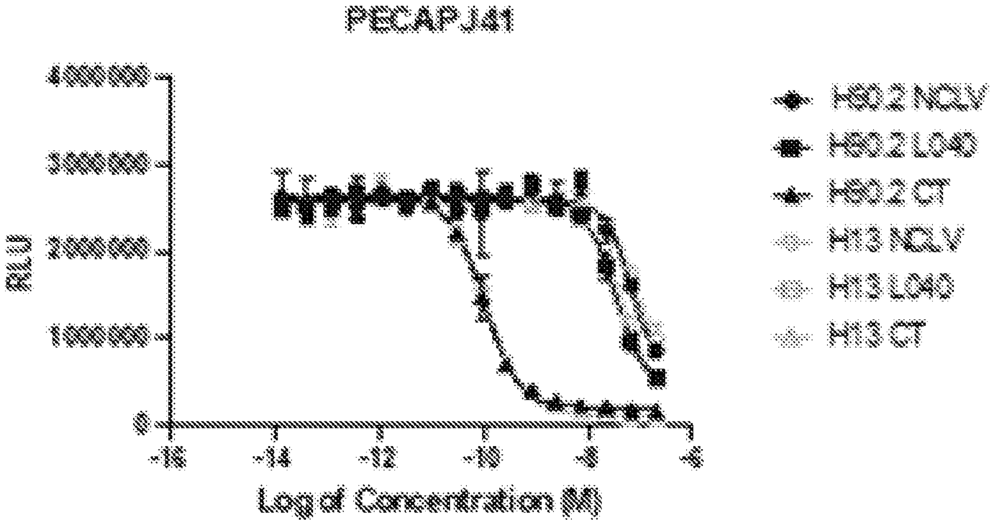
Figure 22H:
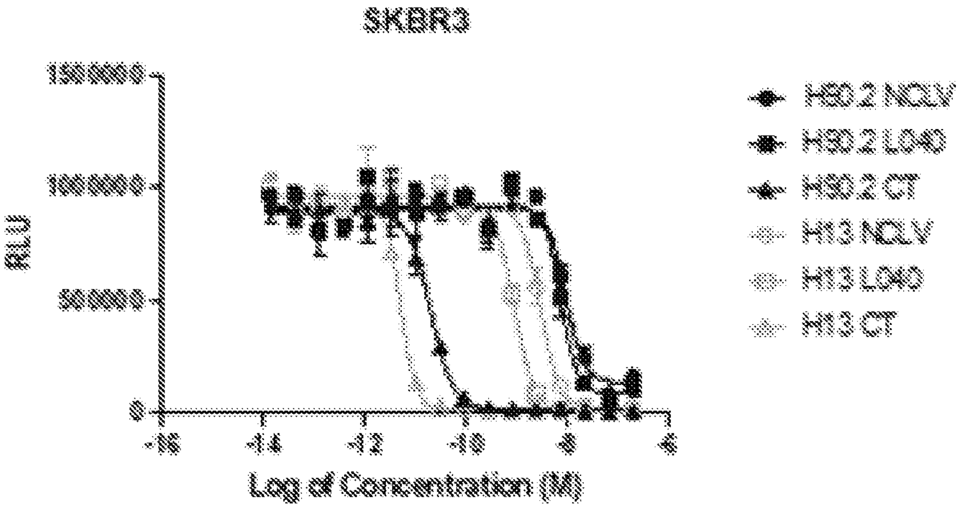

It was observed that the active drug containing the EpCAM binding domain H13 was about 3× more potent than the active drug containing the EpCAM binding domain H90.2 in TDCC assays in vitro. The proteins, when compared between their active drug and non-cleavable prodrug formats (CT vs. NCLV), exhibited similar 400-600× masking, in TDCC assays with multiple EpCAM-expressing cells. Representative plots demonstrating the masking effect achieved by the non-cleavable prodrug format, is shown in FIGS. 21A and 21B.

TABLE 11

$EC_{50}$ values for TDCC assays using active EpCAM targeting active drugs (CT format), tested in various cell lines

| | | Active Drug Potency (pM) | | H90.2/H13 |
|---|---|---|---|---|
| TDCC $EC_{50}$ (pM) | | H13 | H90.2 | Ratio |
| CAPAN2 | Pancreas | 4 | 11 | 2.6 |
| SKBR3 | Breast | 5 | 20 | 4.0 |
| TT | Esophagus | 8 | 13 | 1.7 |
| HEPG2 | Liver | 13 | 44 | 3.3 |
| HCT116 | Colon | 14 | 19 | 1.4 |
| SW780 | Bladder | 16 | 56 | 3.6 |
| DMS53 | Lung | 18 | 60 | 3.4 |
| OVCAR8 | Ovary | 57 | 160 | 2.8 |
| HELA | Cervix | 62 | 280 | 4.4 |
| MDAPCA2b | Prostate | 98 | 380 | 3.8 |
| PECAPJ41 | Head & Neck | 120 | 100 | 0.8 |
| Average | | 34 | 90 | 2.9x |

Additional TDCC assays were carried out with cell lines (including CAPAN2, DMS53, HepG2, KMRC3, MDAPCA2b, and SKBR3) for a comparison of H13 containing EpCAM binding protein NCLV (non-cleavable prodrug); ProTriTAC (with cleavable linker L040), and active drug CT. The $EC_{50}$ values are provided in Table 12 and representative plots are shown in FIGS. 22A, 22B, 22C, 22D, 22E, 22F, 22G, and 22H.

TABLE 12

$EC_{50}$ values for TDCC assays using active EpCAM targeting active drugs (CT format), tested in various cell lines

| Cell Line | EpCAM binding domain | Format | $EC_{50}$ (M) |
|---|---|---|---|
| CAPAN2 (Pancreas) | H90.2 | NCLV | 6.31E−09 |
| | | L040 | 1.53E−09 |
| | | CT | 1.06E−11 |
| | H13 | NCLV | 2.49E−09 |
| | | L040 | 2.23E−10 |
| | | CT | 4.06E−12 |
| DMS53 (Lung) | H90.2 | NCLV | 3.26E−08 |
| | | L040 | 1.42E−08 |
| | | CT | 6.04E−11 |
| | H13 | NCLV | 1.01E−08 |
| | | L040 | 4.11E−09 |
| | | CT | 1.76E−11 |
| HepG2 (Liver) | H90.2 | NCLV | 1.18E−08 |
| | | L040 | 1.08E−08 |
| | | CT | 4.37E−11 |
| | H13 | NCLV | 8.63E−09 |
| | | L040 | 2.79E−09 |
| | | CT | 1.32E−11 |
| OVCAR8 (Ovary) | H90.2 | NCLV | 5.14E−08 |
| | | L040 | 3.53E−08 |
| | | CT | 1.61E−10 |

TABLE 12-continued

EC50 values for TDCC assays using active EpCAM targeting active drugs (CT format), tested in various cell lines

| Cell Line | EpCAM binding domain | Format | $EC_{50}$ (M) |
|---|---|---|---|
| | H13 | NCLV | 3.49E−08 |
| | | L040 | 1.83E−08 |
| | | CT | 5.66E−11 |
| PECAPJ41 (Head & Neck) | H90.2 | NCLV | 6.48E−08 |
| | | L040 | 3.17E−08 |
| | | CT | 1.01E−10 |
| | H13 | NCLV | 7.57E−08 |
| | | L040 | 4.53E−08 |
| | | CT | 1.24E−10 |
| SKBR3 (Breast) | H90.2 | NCLV | 9.53E−09 |
| | | L040 | 7.52E−09 |
| | | CT | 2.02E−11 |
| | H13 | NCLV | 2.95E−09 |
| | | L040 | 8.76E−10 |
| | | CT | 4.98E−12 |
| KMRC3 | H90.2 | NCLV | |
| | | L040 | |
| | | CT | |
| | H13 | NCLV | |
| | | L040 | |
| | | CT | 1.60E−11 |
| MDAPCA2b | H90.2 | NCLV | |
| | | L040 | 6.74E−08 |
| | | CT | 3.77E−10 |
| | H13 | NCLV | 5.34E−08 |
| | | L040 | 3.07E−08 |
| | | CT | 9.81E−11 |

Example 13: Anti-Tumor Efficacy and Tolerability of EpCAM Targeting ProTriTAC Compared to EpCAM Targeting TriTAC The in vivo efficacy of EpCAM ProTriTAC containing EpCAM binding domain H13 was assessed in an established HT29 colorectal tumor model and compared to that of an EpCAM TriTAC containing the EpCAM binding domain H13.

Figure 23A:
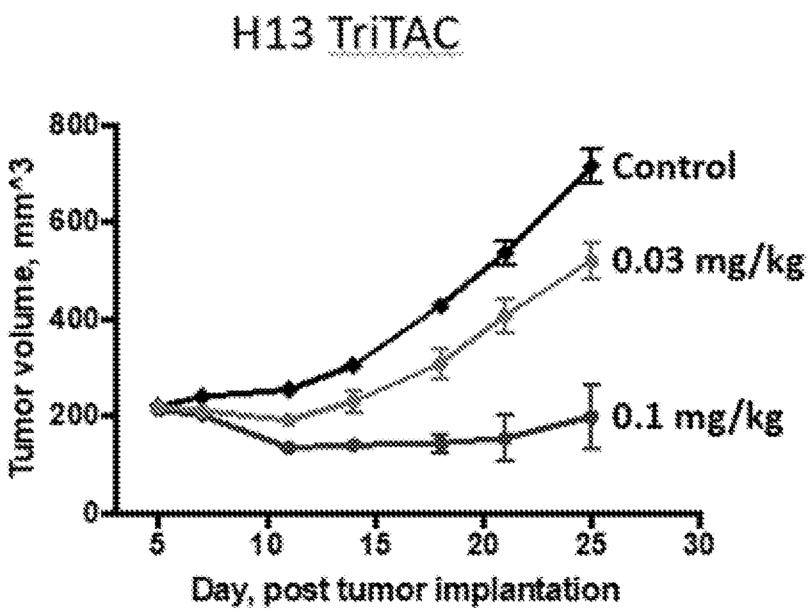
FIGS. 23A-23B show efficacy of ProTriTAC (FIG. 23B) and TriTAC (FIG. 23A) versions containing EpCAM binding domain H13, in a mouse tumor model.
Figure 23B:
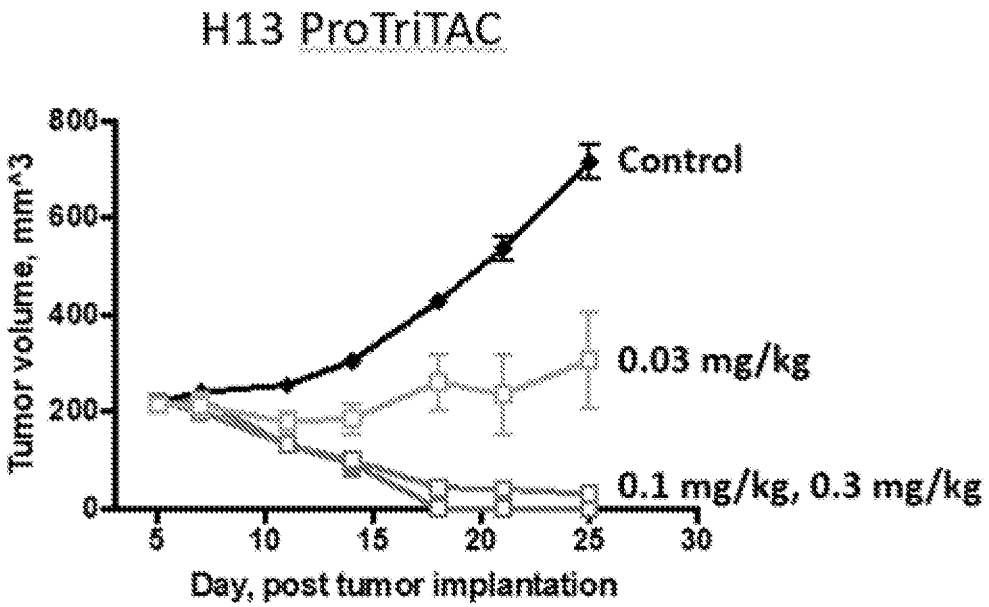
Figures 24A, 24B, 24C, 24D:
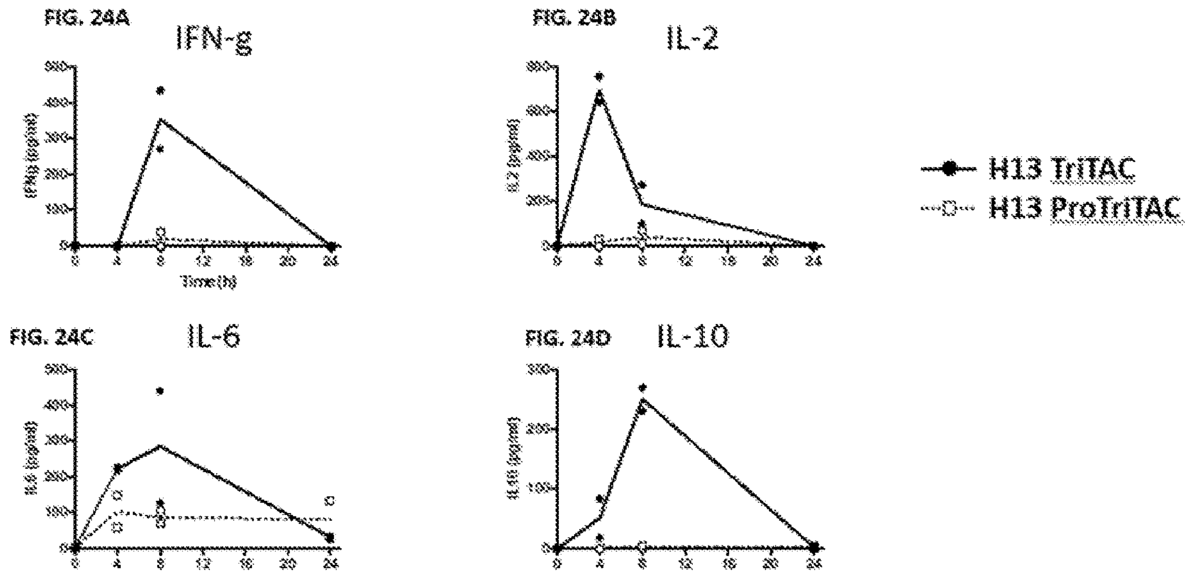
FIGS. 24A-24D show cytokine profiles following administration of ProTriTAC and TriTAC versions containing EpCAM binding domain H13, in cynomolgus monkeys.

On day 5, following tumor implantation, mice were injected with either the test EpCAM H13 ProTriTAC at 0.3 mg/kg or 0.1 mg/kg; the test EpCAM H13 TriTAC at 0.3 mg/kg; or a control TriTAC at comparable doses, and tumor volumes were measured for a period of about 20 days. As shown in FIGS. 23A and 23B, The EpCAM H13 ProTriTAC was more efficacious than the EpCAM H13 TriTAC in the mouse tumor model.

In another study, cynomolgus monkeys were injected with comparable doses (30 μg/kg) of the EpCAM H13 ProTriTAC or the EpCAM H13 TriTAC and the cytokine levels (IFN-gamma; IL-2; IL-6; and IL-10). Results are shown in FIGS. 24A, 24B, 24C, and 24D, which indicates that the EpCAM H13 ProTriTAC exhibited markedly reduced cytokine production compared to the EpCAM H13 TriTAC, in a single-dose cyno study at 30 μg/kg.

Figures 25A, 25B:
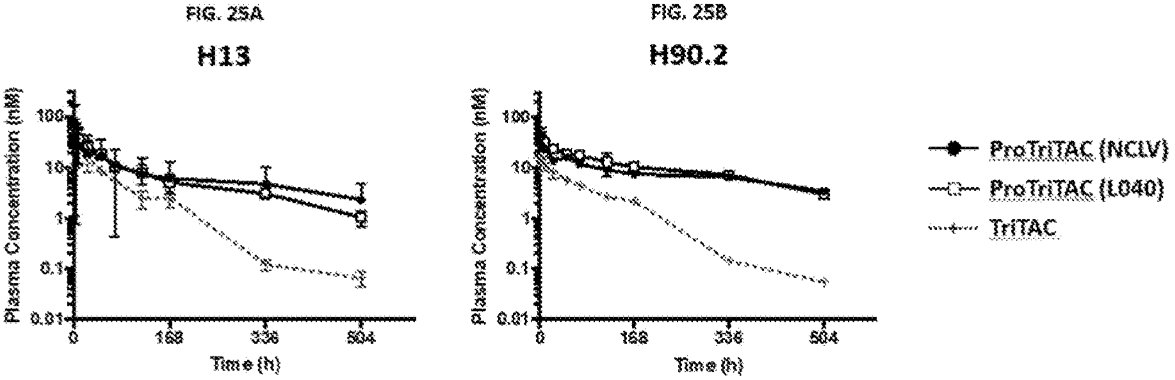
FIGS. 25A-25B show plasma concentrations following administration of ProTriTAC and TriTAC versions containing EpCAM binding domain H13 (FIG. 25A) or H90.2 (FIG. 25B), in cynomolgus monkeys.

Example 14: Pharmacokinetic Properties of Exemplary EpCAM Binding Proteins, in Cynomolgus Monkeys Binding proteins containing the EpCAM binding domain H13 or H90.2 (in TriTAC format; ProTriTAC NCLV format; and ProTriTAC with cleavable linker L040 format) were administered to cynomolgus monkeys and the pharmacokinetic properties of the same were assessed. FIGS. 25A and 25B show the plasma concentration of the tested proteins, over time, in the cynomolgus monkeys. In addition, Table 13 summarizes the pharmacokinetic parameters.

TABLE 13

PK parameters for EpCAM binding trispecific proteins, in cynomolgus monkeys

| | | Cmax (nM) | $AUC_{0\text{-}inf}$ (hour* nM) | Half-Life (day) |
|---|---|---|---|---|
| H13 | ProTriTAC (NCLV) | 77 | 4586 | 9.7 |
| | ProTriTAC (L040) | 47 | 3643 | 5.8 |
| | TriTAC | 38 | 1588 | 2.5 |
| H90.2 | ProTriTAC (NCLV) | 44 | 5603 | 10.5 |
| | ProTriTAC (L040) | 47 | 6387 | 7.7 |
| | TriTAC | 25 | 1126 | 2.6 |

Example 15: Assessing Therapeutic Index (Efficacy and Toxicity) of EpCAM Targeting ProTriTAC/TriTAC Proteins In this study, various doses of an EpCAM targeting TriTAC protein or an EpCAM targeting ProTriTAC protein, containing EpCAM binding domain H90, or a control TriTAC protein, were injected to mice bearing LoVo tumor model (colon cancer model). Results are shown in FIGS. 29A-29K. The safety and tolerability of the ProTriTAC and TriTAC versions were also tested and the results are shown in FIGS. 30A-30E. The percent survival is shown in FIGS. 30A-30B and the clinical chemistry parameters (ALT, AST, and total bilirubin) are shown in FIGS. 30C, 30D, and 30E. The overall results demonstrate that the ProTriTAC format is about 30× better tolerated than the TriTAC format in the same LoVo tumor-bearing mice. This observation was further corroborated through histopathological studies, and the summary is provided in FIG. 31 and Table 14.

Thus, this study demonstrated a therapeutic index expansion of about 10×, for the ProTriTAC format, based on the efficacy and safety of the drug in the same animal.

TABLE 14

Comparative therapeutic index of TriTAC and ProTriTAC formats

| | Minimum Efficacious Dose | Maximum Tolerated Dose | Therapeutic Index (TI) |
|---|---|---|---|
| EpCAM TriTAC | 0.03 mg/kg | 0.03 mg/kg | 1 |
| EpCAM ProTriTAC | 0.1 mg/kg | 1 mg/kg | 10 |
| ProTriTAC Advantage | 0.3x | 30x | 10x |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Sequences

-continued

| SEQ ID NO: | Anti-EpCAM sequence name | Amino Acid Sequence |
|---|---|---|
| 1 | EPL90 | QVQLQESGGGLVQAGGSLRLSCAAS GFIFRAASMAWYRQSPGNERELVAS ISSGAFTNYADSVKARFTISRDNAK NTVYLQMNSLKPEDTAVYFCGATFL RSDGHHTINGQGTQVTVSS |
| 2 | EPL118 | QVQLQESGGGLVQAGGSLRLSCAAS GFIFRAASMGWFRQSPGNERELVAT VSSGDFTNYADSVKGRFTISRDNAK NTVYLQMNSLKPEDTAVYFCGATFV RSDGHHTIYGQGTQVTVSS |
| 3 | EPL138 | QVQLQESGGGLVQAGGSLRLSCAAS GFIFRAASMDWYRQFPGNERESIAT ISSGGFTNYADSVKGRFTISRDNAK NTVYLQMNSLKPEDTAVYFCGATFL RSDGHHTINGQGTQVTVSS |
| 4 | EPL145 | QVQLQESGGGLVQAGGSLRLSCAAS GFIFRAASMGWFRQSPGNERELVAT VSSGGFTNYADSVKGRFTISRDNAK NTVYLQMNSLKPEDTAVYFCGATFV RSDGHHTIYGQGTQVTVSS |
| 5 | EPL164 | QVQLQESGGGLVQAGGSLRLSCAAS GFIFRAASMDWYRQSPGTQPELVAT ISSTGFTNYANSVKGRFTISRDNAK NTVYLQMNSLKPEDTAVYFCGATFL RSDGQHSIYGQGTQVTVSS |
| 6 | EPL31 | QVQLQESGGGLVHTGGSLRLSCAAS GDTFLRYAMGWFRQAPGKEREFVAA ITWNGGNTDYAGSLKGRFTISRDNT KNTVYLQMNSLKPEDTAVYYCAADL TFGLASSHYQYDYWGQGTQVTVSS |
| 7 | EPL55 | QVQLQESGGGLVQAGGSLRLSCAAS GDTFLRYAMGWFRQAPGKEREFVAA ITWNGGNTDYAGSLKGRFTISRDNT KNTVYLQMNSLKPEDTAVYYCAADL TFGLASSHYQYDYWGQGTQVTVSS |
| 8 | EPL57 | QVQLQESGGGLVHTGGSLRLSCAFS GDTFLRYAMGWFRQAPGKEREFVAA ITWNGGNTDYADSLKGRFTISRDNT KNTVYLQMNSLRPEDTAVYYCAADL TFGLASSHYQYDYWGQGTQVTVSS |
| 9 | EPL136 | QVQLQESGGGLVQPGGSLRLSCAAS GDTFLRYAMGWFRQAPGKEREFVAA ITWNGGNTDYAGSLKGRFTISRDNT KNTVYLQMNSLKPEDTAVYYCAADL TFGLASSHYQYDYWGQGTQVTVSS |
| 10 | EPL15 | QVQLQESGGGSVLAGGSLRLSCAAS GFTFSSYYMSWVRQAPGKGLEWVSG IHYTGDWTNYADSVKGRFTISRDNA KNELYLEMNNLKPEDTAVYYCARGS DKGQGTQVTVSS |
| 11 | EPL34 | QVQLQESGGGSVQAGGSLRLSCAAS GFTFSSYYMSWVRQAPGKGLEWVSG IHYTGDWTNYADSVKGRFTISRDNA KNELYLEMNNLKPEDTAVYYCARGS DKGQGTQVTVSS |
| 12 | EPL86 | QVQLQESGGGLVQPGGSLRLSCAAS GFTFSDWAMSWVRQAPGKGLEWVSG IHYGDHTTHYADFVKGRFTISRDDA KNTLYLQMNSLKPEDTAVYYCARGS TKGQGTQVTVSS |
| 13 | EPL153 | QVQLQESGGGLVQPGGSLRLSCAAS GFTFSDWAMSWVRQAPGKGLEWVSS IHYGDHTTHYADFVKGRFTISRDDA KNTLYLQMNSLKPEDTAVYYCEKGT TRGQGTQVTVSS |
| 14 | EPL20 | QVQLQESGGGLVQAGGSLKLSCAAS GNVERAATMAWYRQAPEKQREMVAT IASGGTTNYADFVKGRFTISRDNAK NTVYLQMNTLKPEDTAVYYCNAGYL TSLGPKNYWGQGTQVTVSS |
| 15 | EPL70 | QVQLQESGGGLVQPGGSLRLSCAAS GNVERAATMAWYRQAPEKXREMVAT IASGGTTNYADFVKGRFTISRDNAK NTVYLQMNTLKPEDTAVYYCNAGYL TSLGPKNYWGQGTQVTVSS |
| 16 | EPL125 | QVQLQESGGGLVQAGGSLRLSCAAS GNVERAATMAWYRQVPEKQREMVAT IASGGTTNYADFVKGRFTISRDNAK NTVYLQMNTLKPEDTAVYYCNALYL TSLGPKSYWGQGTQVTVSS |
| 17 | EPL13 | QVQLQESGGGLVQPGGSLRLSCAAS GFAFGNHWMYWYRQAPGRGRELVAS ISSGGSTNYVDSVKGRFTISRDNAR NTVYLQMYSLKPEDTAVYYCGTSDN WGQGTQVTVSS |
| 18 | EPL129 | QVQLQESGGGLVQAGGSLRLSCAAS GFAFGNHWMYWYRQAPGRGRELVAS ISSGGSTNYVDSVKGRFTISRDNAR NTVYLQMYSLRPEDTAVYYCGTSDN WGQGTQVTVSS |
| 19 | EPL159 | QVQLQESGGGLVQAGGSLRLSCAAS GFAFGNHWMYWYRQAPGRGRELVAS ISSGGSTNYVDSVKGRFTISRDNAR NTVYLQMYSLKPEDTAVYYCGTSDN WGQGTQVTVSS |
| 20 | EPL120 | QVQLQESGGGLVQAGGSLRLSCAAS GFIFRAASISWYRQSPGNERELVAT INSGGFTNYADSVLGRFTISRDNAK NTGYLQMNSLKPEDTAVYFCAATFL RSDGQPPIWGQGTQVTVSS |
| 21 | EPL126 | QVQLQESGGGLVQAGGSLRLSCAAS GFIFRAASMGWYRQSPGNERELVAT INSGGFTNYADSVKGRFTISRDNAK NTGYLQMNSLKPEDTAVYFCAATFL RSDGQPPIWGQGTQVTVSS |
| 22 | EPL60 | QVQLQESGGGLVQAGGSLRLSCAAS EYILSMYRMAWYRQAPGKVRELVAD MSSGGTTNYADFVKGRFTISRDNDR NTVYLQMNRLQPEDTAAYYCNVAGR TGPPSYDAFNNWGQGTQVTVSS |
| 23 | EPL156 | QVQLQESGGGLVQPGASLRVSCAAS EYILSMYRMAWYRQAPGKVRELVAD MSSGGTTNYADFVKGRFTISRDNDR NTVYLQMNRLQPEDTAAYYCNVAGR TGPPSYDAFNNWGQGTQVTVSS |
| 24 | EPL2 | QVQLQESGGGLVQPGGSLRLSCAAS ESISSFIAVGWYRQAPGKERELVAG INRSGFTYYTDSVKGRFSISRDNAK NTVLLQMTSLKPEDTAVYYCNAGGL YFSNAYTQGDYWGQGTQVTVSS |
| 25 | EPL43 | QVQLQESGGGLVQTGGSLRLSCAAS ESISSFIAVGWYRQAPGKERELVAG INRSGFTYYTDSVKGRFSISRDNAK NTVLLQMTSLKPEDTAVYYCNAGGL YFSNAYTQGDYWGQGTQVTVSS |
| 26 | EPL10 | QVQLQESGGGLVQAGGSLRLSCAAS GSVERANVMGWYRQAPGKQHELVAR IDPGGTTTYADPVKGRFTISRDNAK |

-continued

| | | |
|---|---|---|
| | | KTVYLQMNSLKPDDTAVYYCNAIILLSGGPKDYWGQGTQVTVSS |
| 27 | EPL49 | QVQLQESGGGLVQAGGSLRLSCAPSGRTSSIFGMGWFRQAPGKEREFVASINWSGGSTSYADSVKGRFTISRDNAKNEMYLQMNSLKFEDTAVYVCAAAVLTNKPSWNFWGQGTQVTVSS |
| 28 | EPL58 | QVQLQESGGGLVQAGGSLRLSCAASGPIFSDTIRTMGWYRQAAGKQRELVATIASFPSRTNYVDSVKGRFTISRDIAKNTVYLQMDSLKPEDTAVYYCNVDLASIPTKTYWGQGTQVTVSS |
| 29 | EPL74 | QVQLQESGGGLVQAGGSLRLSCAASGSIFGINAMGWYRQAPGKQRESVAFITIGGNTNYLDSVKGRFTISRDNAKNTVYLQMNGLKPEDTAVYYCNTNPPLILTAGGLYWGQGTQVTVSS |
| 30 | EPL78 | QVQLQESGGGLVQPGGSLRLSCATSANRFNINVMGWYRQAPGQQRELVATINIGGSTDYADSVKGRFTISRDNAKNTVYLQLSDLKPEDTAVYYCNVKLRVSGPTGPNVYWGQGTQVTVSS |
| 31 | EPL82 | QVQLQESGGGLVQAGGSLKLSCTASGTILSTMAWYRQAPGKQRELVATISRGGTTNYSDSVKGRFAISRDSTKNTVYLQMNSLKPEDTAVYYCNTPLTDYGMGYNWGQGTQVTVSS |
| 32 | EPL83 | QVQLQESGGGLVQAGGSLRLSCAVSGSIFSLNTLAWYRQAPGRQRDLIARITGGGTTVYADSVKGRFTISRDNAKNTVYLQMNSLKPEDTAVYYCNLMVRHPSGSTYEYWGQGTQVTVSS |
| 33 | EPL97 | QVQLQESGGGLVQAGGSLRLSCAASGIIFRGTTMGWFRQAPGKQRESVASISPLGTTSYSGSVEGRFTVSRDNAKNTLFLQMNSLKSEDTAVYYCNAIQVTNVGPRVYWGQGTQVTVSS |
| 34 | EPL109 | QVQLQESGGGLVQPGGSLRLSCASSGFTLDDYTIGWFRQAPGKEREGVSCISRRDDSTYYADSVKGRFTISRDNAKNTVDLQMISLRPEDTAVYYCAATPRSYTLRCLGKFDFQGQGTQVTVSS |
| 35 | EPL117 | QVQLQESGGGLVQAGGSLRLSCAASGNIVRMTNMAWYRQAPGKQREFVATISAGGSTTYVDSVKDRFTISRDNTKNTVYLQMNYLKPEDTAVYYCATGSILTNRGAIPGSWGHGTQVTVSS |
| 36 | EPL127 | QVQLQESGGGLVQAGGSLRLSCAAPGFAFNDHAILWFRQAPGKEREGVSEICRDGTTYYTDSVKGRFTISSDNAKNTVYLQMNSVKTDDTAVYYCAVDRRRYYCSGNRAFSSDYYYWGQGTQVTVSS |
| 37 | EPL152 | QVQLQESGGGLVQAGGSLRLSCVHSGSIFRASTMAWYRQAPGKQRELVAQIMSGGGTNYAGSVKGRFTISRDNANNTVYLQMNSLKPEDTAVYYCNAAQITSWGPKVYWGQGTQVTVSS |
| 38 | EPL189 | QVQLQESGGGLVQPGGSLRLSCAASGRINSINTMGWYRQAPGNQRELVAEITRGGTTNYADSVQGRYAISRDNAKNLVYLQMNSLKPEDTDVYYCNAQTFPTFSRPTGLDYWGQGTQVTVSS |

-continued

| SEQ ID NO: | Anti-EpCAM sequence CDR1 | Amino Acid Sequence |
|---|---|---|
| 39 | EPL90 | GFIFRAASMA |
| 40 | EPL118 | GFIFRAASMG |
| 41 | EPL138 | GFIFRAASMD |
| 42 | EPL145 | GFIFRAASMG |
| 43 | EPL164 | GFIFRAASMD |
| 44 | EPL31 | GDTFLRYAMG |
| 45 | EPL55 | GDTFLRYAMG |
| 46 | EPL57 | GDTFLRYAMG |
| 47 | EPL136 | GDTFLRYAMG |
| 48 | EPL15 | GFTFSSYYMS |
| 49 | EPL34 | GFTFSSYYMS |
| 50 | EPL86 | GFTFSDWAMS |
| 51 | EPL153 | GFTFSDWAMS |
| 52 | EPL20 | GNVFRAATMA |
| 53 | EPL70 | GNVFRAATMA |
| 54 | EPL125 | GNVFRAATMA |
| 55 | EPL13 | GFAFGNHWMY |
| 56 | EPL129 | GFAFGNHWMY |
| 57 | EPL159 | GFAFGNHWMY |
| 58 | EPL120 | GFIFRAASIS |
| 59 | EPL126 | GFIFRAASMG |
| 60 | EPL60 | EYILSMYRMA |
| 61 | EPL156 | EYILSMYRMA |
| 62 | EPL2 | ESISSFIAVG |
| 63 | EPL43 | ESISSFIAVG |
| 64 | EPL10 | GSVFRANVMG |
| 65 | EPL49 | GRTSSIFGMG |
| 66 | EPL58 | GPIFSDTIRTMG |
| 67 | EPL74 | GSIFGINAMG |
| 68 | EPL78 | ANRFNINVMG |
| 69 | EPL82 | GTILSTMA |
| 70 | EPL83 | GSIFSLNTLA |
| 71 | EPL97 | GIIFRGITMG |
| 72 | EPL109 | GFTLDDYTIG |
| 73 | EPL117 | GNIVRMTNMA |
| 74 | EPL127 | GFAFNDHAIL |
| 75 | EPL152 | GSIFRASTMA |
| 76 | EPL189 | GRINSINTMG |

-continued

| SEQ ID NO: | Anti-EpCAM sequence CDR2 | Amino Acid Sequence |
|---|---|---|
| 77 | EPL90 | SISSGAFTNYADSVKA |
| 78 | EPL118 | TVSSGDFTNYADSVKG |
| 79 | EPL138 | TISSGGFTNYADSVKG |
| 80 | EPL145 | TVSSGGFTNYADSVKG |
| 81 | EPL164 | TISSTGFTNYANSVKG |
| 82 | EPL31 | AITWNGGNTDYAGSLKG |
| 83 | EPL55 | AITWNGGNTDYAGSLKG |
| 84 | EPL57 | AITWNGGNTDYADSLKG |
| 85 | EPL136 | AITWNGGNTDYAGSLKG |
| 86 | EPL15 | GIHYTGDWTNYADSVKG |
| 87 | EPL34 | GIHYTGDWTNYADSVKG |
| 88 | EPL86 | GIHYGDHTTHYADFVKG |
| 89 | EPL153 | SIHYGDHTTHYADFVKG |
| 90 | EPL20 | TIASGGTTNYADFVKG |
| 91 | EPL70 | TIASGGTTNYADFVKG |
| 92 | EPL125 | TIASGGTTNYADFVKG |
| 93 | EPL13 | SISSGGSTNYVDSVKG |
| 94 | EPL129 | SISSGGSTNYVDSVKG |
| 95 | EPL159 | SISSGGSTNYVDSVKG |
| 96 | EPL120 | TINSGGFTNYADSVLG |
| 97 | EPL126 | TINSGGFTNYADSVKG |
| 98 | EPL60 | DMSSGGTTNYADFVKG |
| 99 | EPL156 | DMSSGGTTNYADFVKG |
| 100 | EPL2 | GINRSGFTYYTDSVKG |
| 101 | EPL43 | GINRSGFTYYTDSVKG |
| 102 | EPL10 | RIDPGGTTTYADPVKG |
| 103 | EPL49 | SINWSGGSTSYADSVKG |
| 104 | EPL58 | TIASFPSRTNYVDSVKG |
| 105 | EPL74 | FITIGGNTNYLDSVKG |
| 106 | EPL78 | TINIGGSTDYADSVKG |
| 107 | EPL82 | TISRGGTTNYSDSVKG |
| 108 | EPL83 | RITGGGTTVYADSVKG |
| 109 | EPL97 | SISPLGTTSYSGSVEG |
| 110 | EPL109 | CISRRDDSTYYADSVKG |
| 111 | EPL117 | TISAGGSTTYVDSVKD |
| 112 | EPL127 | EICRDGTTYYTDSVKG |
| 113 | EPL152 | QIMSGGGTNYAGSVKG |
| 114 | EPL189 | EITRGGTTNYADSVQG |

-continued

| SEQ ID NO: | Anti-EpCAM sequence CDR3 | Amino Acid Sequence |
|---|---|---|
| 115 | EPL90 | TFLRSDGHHTI |
| 116 | EPL118 | TFVRSDGHHTI |
| 117 | EPL138 | TFLRSDGHHTI |
| 118 | EPL145 | TFVRSDGHHTI |
| 119 | EPL164 | TFLRSDGQHSI |
| 120 | EPL31 | DLTFGLASSHYQYDY |
| 121 | EPL55 | DLTFGLASSHYQYDY |
| 122 | EPL57 | DLTFGLASSHYQYDY |
| 123 | EPL136 | DLTFGLASSHYQYDY |
| 124 | EPL15 | GSD |
| 125 | EPL34 | GSD |
| 126 | EPL86 | GST |
| 127 | EPL153 | GTT |
| 128 | EPL20 | GYLTSLGPKNY |
| 129 | EPL70 | GYLTSLGPKNY |
| 130 | EPL125 | LYLTSLGPKSY |
| 131 | EPL13 | SDN |
| 132 | EPL129 | SDN |
| 133 | EPL159 | SDN |
| 134 | EPL120 | TFLRSDGQPPI |
| 135 | EPL126 | TFLRSDGQPPI |
| 136 | EPL60 | AGRTGPPSYDAFNN |
| 137 | EPL156 | AGRTGPPSYDAFNN |
| 138 | EPL2 | GGLYFSNAYTQGDY |
| 139 | EPL43 | GGLYFSNAYTQGDY |
| 140 | EPL10 | IILLSGGPKDY |
| 141 | EPL49 | AVLTNKPSWNF |
| 142 | EPL58 | DLASIPTKTY |
| 143 | EPL74 | NPPLILTAGGLY |
| 144 | EPL78 | KLRVSGPTGPNVY |
| 145 | EPL82 | PLTDYGMGYN |
| 146 | EPL83 | MVRHPSGSTYEY |
| 147 | EPL97 | IQVTNVGPRVY |
| 148 | EPL109 | TPRSYTLRCLGKFDF |
| 149 | EPL117 | GSILTNRGAIPGS |
| 150 | EPL127 | DRRRYYCSGNRAFSSDYYY |
| 151 | EPL152 | AQITSWGPKVY |
| 152 | EPL189 | QTFPTFSRPTGLDY |

-continued

| SEQ ID NO: | Anti-CD3/Anti-EpCAM sequence name | Amino Acid Sequence |
|---|---|---|
| 153 | EPL10 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAASGSVFRANVMG<br>WYRQAPGKQHELVARIDPGGTTTYA<br>DPVKGRFTISRDNAKKTVYLQMNSL<br>KPDDTAVYYCNAIILLSGGPKDYWG<br>QGTQVTVSSHHHHHH* |
| 154 | EPL109 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQPGGSLRLSCASSGETLDDYTIG<br>WFRQAPGKEREGVSCISRRDDSTYY<br>ADSVKGRFTISRDNAKNTVDLQMIS<br>LRPEDTAVYYCAATPRSYTLRCLGK<br>EDEQGQGTQVTVSSHHHHHH* |
| 155 | EPL117 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAASGNIVRMTNMA<br>WYRQAPGKQREFVATISAGGSTTYV<br>DSVKDRFTISRDNTKNTVYLQMNYL<br>KPEDTAVYYCATGSILTNRGAIPGS<br>WGHGTQVTVSSHHHHHH* |
| 156 | EPL120 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAASGETFRAASIS<br>WYRQSPGNERELVATINSGGETNYA<br>DSVLGRETISRDNAKNTGYLQMNSL<br>KPEDTAVYFCAATFLRSDGQPPIWG<br>QGTQVTVSSHHHHHH* |
| 157 | EPL125 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAASGNVFRAATMA<br>WYRQVPEKQREMVATIASGGTTNYA<br>DEVKGRETISRDNAKNTVYLQMNTL<br>KPEDTAVYYCNALYLTSLGPKSYWG<br>QGTQVTVSSHHHHHH* |
| 158 | EPL127 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAAPGFAENDHAIL<br>WFRQAPGKEREGVSEICRDGTTYYT<br>DSVKGRFTISSDNAKNTVYLQMNSV<br>KTDDTAVYYCAVDRRRYYCSGNRAF<br>SSDYYYWGQGTQVTVSSHHHHHH* |
| 159 | EPL13 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQPGGSLRLSCAASGFAFGNHWMY<br>WYRQAPGRGRELVASISSGGSTNYV<br>DSVKGRFTISRDNARNTVYLQMYSL<br>KPEDTAVYYCGTSDNWGQGTQVTVS<br>SHHHHHH* |
| 160 | EPL136 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQPGGSLRLSCAASGDTFLRYAMG<br>WERQAPGKEREEVAAITWNGGNTDY<br>AGSLKGRFTISRDNTKNTVYLQMNS<br>LKPEDTAVYYCAADLTFGLASSHYQ<br>YDYWGQGTQVTVSSHHHHHH* |
| 161 | EPL138 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAASGFIFRAASMD<br>WYRQFPGNERESIATISSGGFTNYA |

-continued

| | | |
|---|---|---|
| | | DSVKGRFTISRDNAKNTVYLQMNSL<br>KPEDTAVYFCGATFLRSDGHHTING<br>QGTQVTVSSHHHHHH* |
| 162 | EPL145 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAASGFIFRAASMG<br>WFRQSPGNERELVATVSSGGFTNYA<br>DSVKGRFTISRDNAKNTVYLQMNSL<br>KPEDTAVYFCGATFVRSDGHHTIYG<br>QGTQVTVSSHHHHHH* |
| 163 | EPL152 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCVHSGSIFRASTMA<br>WYRQAPGKQRELVAQIMSGGGTNYA<br>GSVKGRFTISRDNANNTVYLQMNSL<br>KPEDTAVYYCNAAQITSWGPKVYWG<br>QGTQVTVSSHHHHHH* |
| 164 | EPL153 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQPGGSLRLSCAASGFTFSDWAMS<br>WVRQAPGKGLEWVSSIHYGDHTTHY<br>ADEVKGRETISRDDAKNTLYLQMNS<br>LKPEDTAVYYCEKGTTRGQGTQVTV<br>SSHHHHHH* |
| 165 | EPL156 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQPGASLRVSCAASEYILSMYRMA<br>WYRQAPGKVRELVADMSSGGTTNYA<br>DEVKGRETISRDNDRNTVYLQMNRL<br>QPEDTAAYYCNVAGRTGPPSYDAFN<br>NWGQGTQVTVSSHHHHHH* |
| 166 | EPL164 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAASGETFRAASMD<br>WYRQSPGTQPELVATISSTGETNYA<br>NSVKGRETISRDNAKNTVYLQMNSL<br>KPEDTAVYFCGATFLRSDGQHSIYG<br>QGTQVTVSSHHHHHH* |
| 167 | EPL189 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQPGGSLRLSCAASGRINSINTMG<br>WYRQAPGNQRELVAEITRGGTTNYA<br>DSVQGRYAISRDNAKNLVYLQMNSL<br>KPEDTDVYYCNAQTFPTFSRPTGLD<br>YWGQGTQVTVSSHHHHHH* |
| 168 | EPL2 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQPGGSLRLSCAASESISSFIAVG<br>WYRQAPGKERELVAGINRSGFTYYT<br>DSVKGRFSISRDNAKNTVLLQMTSL<br>KPEDTAVYYCNAGGLYFSNAYTQGD<br>YWGQGTQVTVSSHHHHHH* |
| 169 | EPL20 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLKLSCAASGNVFRAATMA<br>WYRQAPEKQREMVATIASGGTTNYA<br>DEVKGRETISRDNAKNTVYLQMNTL<br>KPEDTAVYYCNAGYLTSLGPKNYWG<br>QGTQVTVSSHHHHHH* |
| 170 | EP L34 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>SVQAGGSLRLSCAASGFTFSSYYMS<br>WVRQAPGKGLEWVSGIHYTGDWTNY<br>ADSVKGRFTISRDNAKNELYLEMNN<br>LKPEDTAVYYCARGSDKGQGTQVTV<br>SSHHHHHH* |

-continued

| | | |
|---|---|---|
| 171 | EPL49 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAPSGRTSSIFGMG<br>WERQAPGKEREFVASINWSGGSTSY<br>ADSVKGRFTISRDNAKNEMYLQMNS<br>LKFEDTAVYYCAAAVLTNKPSWNFW<br>GQGTQVTVSSHHHHHH* |
| 172 | EP L58 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAASGPIFSDTIRT<br>MGWYRQAAGKQRELVATIASFPSRT<br>NYVDSVKGRFTISRDIAKNTVYLQM<br>DSLKPEDTAVYYCNVDLASIPTKTY<br>WGQGTQVTVSSHHHHHH* |
| 173 | EPL74 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAASGSIFGINAMG<br>WYRQAPGKQRESVAFITIGGNTNYL<br>DSVKGRFTISRDNAKNTVYLQMNGL<br>KPEDTAVYYCNTNPPLILTAGGLYW<br>GQGTQVTVSSHHHHHH* |
| 174 | EPL78 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQPGGSLRLSCATSANRFNINVMG<br>WYRQAPGQQRELVATINIGGSTDYA<br>DSVKGRFTISRDNAKNTVYLQLSDL<br>KPEDTAVYYCNVKLRVSGPTGPNVY<br>WGQGTQVTVSSHHHHHH* |
| 175 | EPL82 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGETFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLKLSCTASGTILSTMAWY<br>RQAPGKQRELVATISRGGTTNYSDS<br>VKGRFAISRDSTKNTVYLQMNSLKP<br>EDTAVYYCNTPLTDYGMGYNWGQGT<br>QVTVSSHHHHHH* |
| 176 | EPL83 | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGFTFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAVSGSIFSLNTLA<br>WYRQAPGRQRDLIARITGGGTTVYA<br>DSVKGRFTISRDNAKNTVYLQMNSL<br>KPEDTAVYYCNLMVRHPSGSTYEYW<br>GQGTQVTVSSHHHHHH* |
| 177 | EPL86 | VVGGGGTQTVVTQEPSLTVSPGGTV<br>TLTCASSTGAVTSGNYPNWVQQKPG<br>QAPRGLIGGTKELVPGTPARFSGSL<br>LGGKAALTLSGVQPEDEAEYYCTLW<br>YSNRWVEGGGTKLTVLGGGGSGGGG<br>SGGGGSEVQLVESGGGLVQPGGSLK<br>LSCAASGFTFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQPGGSLRLSCAASGFTFSDWAMS<br>WVRQAPGKGLEWVSGIHYGDHTTHY<br>ADFVKGRFTISRDDAKNTLYLQMNS<br>LKPEDTAVYYCARGSTKGQGTQVTV<br>SSHHHHHH* |
| 178 | EPL90 | VVGGGGTQTVVTQEPSLTVSPGGTV<br>TLTCASSTGAVTSGNYPNWVQQKPG<br>QAPRGLIGGTKELVPGTPARFSGSL<br>LGGKAALTLSGVQPEDEAEYYCTLW<br>YSNRWVEGGGTKLTVLGGGGSGGGG<br>SGGGGSEVQLVESGGGLVQPGGSLK<br>LSCAASGFTFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAASGFIFRAASMA<br>WYRQSPGNERELVASISSGAFTNYA<br>DSVKARFTISRDNAKNTVYLQMNSL<br>KPEDTAVYFCGATFLRSDGHHTING<br>QGTQVTVSSHHHHHH* |
| 179 | EPL97 | VVGGGGTQTVVTQEPSLTVSPGGTV<br>TLTCASSTGAVTSGNYPNWVQQKPG<br>QAPRGLIGGTKELVPGTPARFSGSL<br>LGGKAALTLSGVQPEDEAEYYCTLW<br>YSNRWVEGGGTKLTVLGGGGSGGGG<br>SGGGGSEVQLVESGGGLVQPGGSLK<br>LSCAASGFTFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSQVQLQESGGG<br>LVQAGGSLRLSCAASGIIFRGTTMG<br>WFRQAPGKQRESVASISPLGTTSYS<br>GSVEGRFTVSRDNAKNTLFLQMNSL<br>KSEDTAVYYCNAIQVTNVGPRVYWG<br>QGTQVTVSSHHHHHH* |

-continued

| SEQ ID NO: | Anti-EpCAM/ Anti-CD3 sequence name | Amino Acid Sequence |
|---|---|---|
| 180 | EPL10 | GGGSQVQLQESGGGLVQAGGSLRLSCAASGSVERANVMGWYRQAPGKQHELVARIDPGGTTTYADPVKGRFTISRDNAKKTVYLQMNSLKPDDTAVYYCNAIILLSGGPKDYWGQGTQVTVSSGGGGSGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKELVPGTPARFSGSLLGGKAALTLSGVQPEDEAEYYCTLWYSNRWVFGGGTKLTVLHHHHHH* |
| 181 | EPL109 | GGGSQVQLQESGGGLVQPGGSLRLSCASSGFTLDDYTIGWFRQAPGKEREGVSCISRRDDSTYYADSVKGRFTISRDNAKNTVDLQMISLRPEDTAVYYCAATPRSYTLRCLGKFDFQGQGTQVTVSSGGGGSGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANEGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 182 | EPL117 | GGGSQVQLQESGGGLVQAGGSLRLSCAASGNIVRMTNMAWYRQAPGKQREFVATISAGGSTTYVDSVKDRFTISRDNTKNTVYLQMNYLKPEDTAVYYCATGSILTNRGAIPGSWGHGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANEGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 183 | EPL120 | GGGSQVQLQESGGGLVQAGGSLRLSCAASGFIFRAASISWYRQSPGNERELVATINSGGFTNYADSVLGRFTISRDNAKNTGYLQMNSLKPEDTAVYFCAATFLRSDGQPPIWGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 184 | EPL125 | GGGSQVQLQESGGGLVQAGGSLRLSCAASGNVFRAATMAWYRQVPEKQREMVATIASGGTTNYADFVKGRFTISRDNAKNTVYLQMNTLKPEDTAVYYCNALYLTSLGPKSYWGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 185 | EPL127 | GGGSQVQLQESGGGLVQAGGSLRLSCAAPGFAENDHAILWFRQAPGKEREGVSEICRDGTTYYTDSVKGRFTISSDNAKNTVYLQMNSVKTDDTAVYYCAVDRRRYYCSGNRAFSSDYYYWGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 186 | EPL13 | GGGSQVQLQESGGGLVQPGGSLRLSCAASGFAFGNHWMYWYRQAPGRGRELVASISSGGSTNYVDSVKGRFTISRDNARNTVYLQMYSLKPEDTAVYYCGTSDNWGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 187 | EPL136 | GGGSQVQLQESGGGLVQPGGSLRLSCAASGDTFLRYAMGWERQAPGKEREFVAAITWNGGNTDYAGSLKGRFTISRDNTKNTVYLQMNSLKPEDTAVYYCAADLTFGLASSHYQYDYWGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 188 | EPL138 | GGGSQVQLQESGGGLVQAGGSLRLSCAASGFIFRAASMDWYRQFPGNERESIATISSGGFTNYADSVKGRFTISRDNAKNTVYLQMNSLKPEDTAVYFCGATFLRSDGHHTINGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |

-continued

| | | |
|---|---|---|
| 189 | EPL145 | GGGSQVQLQESGGGLVQAGGSLRLSCAASGFIFRAASMGWFRQSPGNERELVATVSSGGFTNYADSVKGRFTISRDNAKNTVYLQMNSLKPEDTAVYFCGATFVRSDGHHTIYGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 190 | EPL152 | GGGSQVQLQESGGGLVQAGGSLRLSCVHSGSIERASTMAWYRQAPGKQRELVAQIMSGGGTNYAGSVKGRFTISRDNANNTVYLQMNSLKPEDTAVYYCNAAQITSWGPKVYWGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 191 | EPL153 | GGGSQVQLQESGGGLVQPGGSLRLSCAASGETFSDWAMSWVRQAPGKGLEWVSSIHYGDHTTHYADFVKGRFTISRDDAKNTLYLQMNSLKPEDTAVYYCEKGTTRGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 192 | EPL156 | GGGSQVQLQESGGGLVQPGASLRVSCAASEYILSMYRMAWYRQAPGKVRELVADMSSGGTTNYADFVKGRFTISRDNDRNTVYLQMNRLQPEDTAAYYCNVAGRTGPPSYDAFNNWGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 193 | EPL164 | GGGSQVQLQESGGGLVQAGGSLRLSCAASGFIFRAASMDWYRQSPGTQPELVATISSTGFTNYANSVKGRFTISRDNAKNTVYLQMNSLKPEDTAVYFCGATFLRSDGQHSIYGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 194 | EPL189 | GGGSQVQLQESGGGLVQPGGSLRLSCAASGRINSINTMGWYRQAPGNQRELVAEITRGGTTNYADSVQGRYAISRDNAKNLVYLQMNSLKPEDTDVYYCNAQTFPTFSRPTGLDYWGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 195 | EPL2 | GGGSQVQLQESGGGLVQPGGSLRLSCAASESISSFIAVGWYRQAPGKERELVAGINRSGFTYYTDSVKGRFSISRDNAKNTVLLQMTSLKPEDTAVYYCNAGGLYFSNAYTQGDYWGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 196 | EPL20 | GGGSQVQLQESGGGLVQAGGSLKLSCAASGNVFRAATMAWYRQAPEKQREMVATIASGGTTNYADFVKGRFTISRDNAKNTVYLQMNTLKPEDTAVYYCNAGYLTSLGPKNYWGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 197 | EPL34 | GGGSQVQLQESGGGSVQAGGSLRLSCAASGETFSSYYMSWVRQAPGKGLEWVSGIHYTGDWTNYADSVKGRFTISRDNAKNELYLEMNNLKPEDTAVYYCARGSDKGQGTQVTVSSGGGGSGGGSEVQLVESGGGLVQPGGSLKLSCAASGETFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARESGSLLGGKAALTLSGVQPEDEAEYYCTLWYSNRWVFGGGTKLTVLHHHHHH* |
| 198 | EPL49 | GGGSQVQLQESGGGLVQAGGSLRLSCAPSGRTSSIFGMGWERQAPGKEREFVASINWSGGSTSYADSVKGRFTISRDNAKNEMYLQMNSLKFEDTAVYVCAAAVLTNKPSWNFWGQGTQVTVSSG |

-continued

| SEQ ID NO: | Name | Amino Acid Sequence |
|---|---|---|
| | | GGGSGGGSEVQLVESGGGLVQPGGS<br>LKLSCAASGETFNKYAINWVRQAPG<br>KGLEWVARIRSKYNNYATYYADQVK<br>DRFTISRDDSKNTAYLQMNNLKTED<br>TAVYYCVRHANFGNSYISYWAYWGQ<br>GTLVTVSSGGGGSGGGGSGGGGSQT<br>VVTQEPSLTVSPGGTVTLTCASSTG<br>AVTSGNYPNWVQQKPGQAPRGLIGG<br>TKFLVPGTPARESGSLLGGKAALTL<br>SGVQPEDEAEYYCTLWYSNRWVFGG<br>GTKLTVLHHHHHH* |
| 199 | EPL58 | GGGSQVQLQESGGGLVQAGGSLRLS<br>CAASGPIFSDTIRTMGWYRQAAGKQ<br>RELVATIASFPSRTNYVDSVKGRFT<br>ISRDIAKNTVYLQMDSLKPEDTAVY<br>YCNVDLASIPTKTYWGQGTQVTVSS<br>GGGGSGGGSEVQLVESGGGLVQPGG<br>SLKLSCAASGETFNKYAINWVRQAP<br>GKGLEWVARIRSKYNNYATYYADQV<br>KDRFTISRDDSKNTAYLQMNNLKTE<br>DTAVYYCVRHANEGNSYISYWAYWG<br>QGTLVTVSSGGGGSGGGGSGGGGSQ<br>TVVTQEPSLTVSPGGTVTLTCASST<br>GAVTSGNYPNWVQQKPGQAPRGLIG<br>GTKFLVPGTPARESGSLLGGKAALT<br>LSGVQPEDEAEYYCTLWYSNRWVFG<br>GGTKLTVLHHHHHH* |
| 200 | EPL74 | GGGSQVQLQESGGGLVQAGGSLRLS<br>CAASGSIEGINAMGWYRQAPGKQRE<br>SVAFTTIGGNTNYLDSVKGRFTISR<br>DNAKNTVYLQMNGLKPEDTAVYYCN<br>TNPPLILTAGGLYWGQGTQVTVSSG<br>GGGSGGGSEVQLVESGGGLVQPGGS<br>LKLSCAASGETFNKYAINWVRQAPG<br>KGLEWVARIRSKYNNYATYYADQVK<br>DRFTISRDDSKNTAYLQMNNLKTED<br>TAVYYCVRHANFGNSYISYWAYWGQ<br>GTLVTVSSGGGGSGGGGSGGGGSQT<br>VVTQEPSLTVSPGGTVTLTCASSTG<br>AVTSGNYPNWVQQKPGQAPRGLIGG<br>TKFLVPGTPARESGSLLGGKAALTL<br>SGVQPEDEAEYYCTLWYSNRWVFGG<br>GTKLTVLHHHHHH* |
| 201 | EPL78 | GGGSQVQLQESGGGLVQPGGSLRLS<br>CATSANRFNINVMGWYRQAPGQQRE<br>LVATINIGGSTDYADSVKGRFTISR<br>DNAKNTVYLQLSDLKPEDTAVYYCN<br>VKLRVSGPTGPNVYWGQGTQVTVSS<br>GGGGSGGGSEVQLVESGGGLVQPGG<br>SLKLSCAASGETFNKYAINWVRQAP<br>GKGLEWVARIRSKYNNYATYYADQV<br>KDRFTISRDDSKNTAYLQMNNLKTE<br>DTAVYYCVRHANEGNSYISYWAYWG<br>QGTLVTVSSGGGGSGGGGSGGGGSQ<br>TVVTQEPSLTVSPGGTVTLTCASST<br>GAVTSGNYPNWVQQKPGQAPRGLIG<br>GTKFLVPGTPARESGSLLGGKAALT<br>LSGVQPEDEAEYYCTLWYSNRWVFG<br>GGTKLTVLHHHHHH* |
| 202 | EPL82 | GGGSQVQLQESGGGLVQAGGSLKLS<br>CTASGTILSTMAWYRQAPGKQRELV<br>ATISRGGTTNYSDSVKGRFAISRDS<br>TKNTVYLQMNSLKPEDTAVYYCNTP<br>LTDYGMGYNWGQGTQVTVSSGGGGS<br>GGGSEVQLVESGGGLVQPGGSLKLS<br>CAASGETFNKYAINWVRQAPGKGLE<br>WVARIRSKYNNYATYYADQVKDRFT<br>ISRDDSKNTAYLQMNNLKTEDTAVY<br>YCVRHANFGNSYISYWAYWGQGTLV<br>TVSSGGGGSGGGGSGGGGSQTVVTQ<br>EPSLTVSPGGTVTLTCASSTGAVTS<br>GNYPNWVQQKPGQAPRGLIGGTKFL<br>VPGTPARESGSLLGGKAALTLSGVQ<br>PEDEAEYYCTLWYSNRWVFGGGTKL<br>TVLHHHHHH* |
| 203 | EPL83 | GGGSQVQLQESGGGLVQAGGSLRLS<br>CAVSGSIFSLNTLAWYRQAPGRQRD<br>LIARITGGGTTVYADSVKGRFTISR<br>DNAKNTVYLQMNSLKPEDTAVYYCN<br>LMVRHPSGSTYEYWGQGTQVTVSSG<br>GGGSGGGSEVQLVESGGGLVQPGGS<br>LKLSCAASGETFNKYAINWVRQAPG<br>KGLEWVARIRSKYNNYATYYADQVK<br>DRFTISRDDSKNTAYLQMNNLKTED<br>TAVYYCVRHANFGNSYISYWAYWGQ<br>GTLVTVSSGGGGSGGGGSGGGGSQT<br>VVTQEPSLTVSPGGTVTLTCASSTG<br>AVTSGNYPNWVQQKPGQAPRGLIGG<br>TKFLVPGTPARESGSLLGGKAALTL<br>SGVQPEDEAEYYCTLWYSNRWVFGG<br>GTKLTVLHHHHHH* |
| 204 | EPL86 | GGGSQVQLQESGGGLVQPGGSLRLS<br>CAASGETFSDWAMSWVRQAPGKGLE<br>WVSGIHYGDHTTHYADFVKGRFTIS<br>RDDAKNTLYLQMNSLKPEDTAVYYC<br>ARGSTKGQGTQVTVSSGGGGSGGGS<br>EVQLVESGGGLVQPGGSLKLSCAAS<br>GETFNKYAINWVRQAPGKGLEWVAR<br>IRSKYNNYATYYADQVKDRFTISRD<br>DSKNTAYLQMNNLKTEDTAVYYCVR<br>HANFGNSYISYWAYWGQGTLVTVSS<br>GGGGSGGGGSGGGGSQTVVTQEPSL<br>TVSPGGTVTLTCASSTGAVTSGNYP<br>NWVQQKPGQAPRGLIGGTKFLVPGT<br>PARESGSLLGGKAALTLSGVQPEDE<br>AEYYCTLWYSNRWVFGGGTKLTVLH<br>HHHHH* |
| 205 | EPL90 | GGGSQVQLQESGGGLVQAGGSLRLS<br>CAASGFIFRAASMAWYRQSPGNERE<br>LVASISSGAFTNYADSVKARFTISR<br>DNAKNTVYLQMNSLKPEDTAVYFCG<br>ATFLRSDGHHTINGQGTQVTVSSGG<br>GGSGGGSEVQLVESGGGLVQPGGSL<br>KLSCAASGFTFNKYAINWVRQAPGK<br>GLEWVARIRSKYNNYATYYADQVKD<br>RFTISRDDSKNTAYLQMNNLKTEDT<br>AVYYCVRHANFGNSYISYWAYWGQG<br>TLVTVSSGGGGSGGGGSGGGGSQTV<br>VTQEPSLTVSPGGTVTLTCASSTGA<br>VTSGNYPNWVQQKPGQAPRGLIGGT<br>KFLVPGTPARFSGSLLGGKAALTLS<br>GVQPEDEAEYYCTLWYSNRWVFGGG<br>TKLTVLHHHHHH* |
| 206 | EPL97 | GGGSQVQLQESGGGLVQAGGSLRLS<br>CAASGIIFRGTTMGWFRQAPGKQRE<br>SVASISPLGTTSYSGSVEGRFTVSR<br>DNAKNTLFLQMNSLKSEDTAVYYCN<br>AIQVTNVGPRVYWGQGTQVTVSSGG<br>GGSGGGSEVQLVESGGGLVQPGGSL<br>KLSCAASGFTFNKYAINWVRQAPGK<br>GLEWVARIRSKYNNYATYYADQVKD<br>RFTISRDDSKNTAYLQMNNLKTEDT<br>AVYYCVRHANFGNSYISYWAYWGQG<br>TLVTVSSGGGGSGGGGSGGGGSQTV<br>VTQEPSLTVSPGGTVTLTCASSTGA<br>VTSGNYPNWVQQKPGQAPRGLIGGT<br>KFLVPGTPARFSGSLLGGKAALTLS<br>GVQPEDEAEYYCTLWYSNRWVFGGG<br>TKLTVLHHHHHH* |

| SEQ ID NO: | Humanized Anti-EpCAM sequence name | Amino Acid Sequence |
|---|---|---|
| 207 | H13 | EVQLVESGGGLVQPGGSLTLSCAAS<br>GFAFGNHWMYWYRQAPGRGRELVAS<br>ISSGGSTNYVDSVKGRFTISRDNAK<br>NTLYLQMNSLRAEDTAVYYCGTSDN<br>WGQGTLVTVSS |

-continued

| | | |
|---|---|---|
| 208 | H138 | EVQLLESGGGLVQPGGSLTLSCAASGFIFRAASMDWYRQFPGNERESIATISSGGFTNYADSVKGRFTISRDNSKNTLYLQMNSLRAEDTAVYYCGATFLRSDGHHTINGQGTLVTVSS |
| 209 | H90 | EVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSS |

| SEQ ID NO: | Humanized Anti-CD3/Anti-EpCAM sequence name | Amino Acid Sequence |
|---|---|---|
| 210 | H13 | VVGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLVESGGGLVQPGGSLTLSCAASGFAFGNHWMYWYRQAPGRGRELVASISSGGSTNYVDSVKGRFTISRDNAKNTLYLQMNSLRAEDTAVYYCGTSDNWGQGTLVTVSSHHHHHH* |
| 211 | H138 | VVGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMDWYRQFPGNERESIATISSGGFTNYADSVKGRFTISRDNSKNTLYLQMNSLRAEDTAVYYCGATFLRSDGHHTINGQGTLVTVSSHHHHHH* |
| 212 | H90 | VVGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSSHHHHHH* |

| Anti-EpCAM sequence name | SEQ ID No. | Framework 1 sequence |
|---|---|---|
| 213 | EPL90 | QVQLQESGGGLVQAGGSLRLSCAAS |
| 214 | EPL118 | QVQLQESGGGLVQAGGSLRLSCAAS |
| 215 | EPL138 | QVQLQESGGGLVQAGGSLRLSCAAS |
| 216 | EPL145 | QVQLQESGGGLVQAGGSLRLSCAAS |
| 217 | EPL164 | QVQLQESGGGLVQAGGSLRLSCAAS |
| 218 | EPL31 | QVQLQESGGGLVHTGGSLRLSCAAS |
| 219 | EPL55 | QVQLQESGGGLVQAGGSLRLSCAAS |
| 220 | EPL57 | QVQLQESGGGLVHTGGSLRLSCAFS |
| 221 | EPL136 | QVQLQESGGGLVQPGGSLRLSCAAS |
| 222 | EPL15 | QVQLQESGGGSVLAGGSLRLSCAAS |
| 223 | EPL34 | QVQLQESGGGSVQAGGSLRLSCAAS |
| 224 | EPL86 | QVQLQESGGGLVQPGGSLRLSCAAS |
| 225 | EPL153 | QVQLQESGGGLVQPGGSLRLSCAAS |
| 226 | EPL20 | QVQLQESGGGLVQAGGSLKLSCAAS |
| 227 | EPL70 | QVQLQESGGGLVQPGGSLRLSCAAS |
| 228 | EPL125 | QVQLQESGGGLVQAGGSLRLSCAAS |
| 229 | EPL13 | QVQLQESGGGLVQPGGSLRLSCAAS |
| 230 | EPL129 | QVQLQESGGGLVQAGGSLRLSCAAS |
| 231 | EPL159 | QVQLQESGGGLVQAGGSLRLSCAAS |
| 232 | EPL120 | QVQLQESGGGLVQAGGSLRLSCAAS |
| 233 | EPL126 | QVQLQESGGGLVQAGGSLRLSCAAS |
| 234 | EPL60 | QVQLQESGGGLVQAGGSLRLSCAAS |
| 235 | EPL156 | QVQLQESGGGLVQPGASLRVSCAAS |
| 236 | EPL2 | QVQLQESGGGLVQPGGSLRLSCAAS |
| 237 | EPL43 | QVQLQESGGGLVQTGGSLRLSCAAS |
| 238 | EPL10 | QVQLQESGGGLVQAGGSLRLSCAAS |
| 239 | EPL49 | QVQLQESGGGLVQAGGSLRLSCAPS |
| 240 | EPL58 | QVQLQESGGGLVQAGGSLRLSCAAS |
| 241 | EPL74 | QVQLQESGGGLVQAGGSLRLSCAAS |
| 242 | EPL78 | QVQLQESGGGLVQPGGSLRLSCATS |
| 243 | EPL82 | QVQLQESGGGLVQAGGSLKLSCTAS |
| 244 | EPL83 | QVQLQESGGGLVQAGGSLRLSCAVS |
| 245 | EPL97 | QVQLQESGGGLVQAGGSLRLSCAAS |
| 246 | EPL109 | QVQLQESGGGLVQPGGSLRLSCASS |
| 247 | EPL117 | QVQLQESGGGLVQAGGSLRLSCAAS |
| 248 | EPL127 | QVQLQESGGGLVQAGGSLRLSCAAP |
| 249 | EPL152 | QVQLQESGGGLVQAGGSLRLSCVHS |
| 250 | EPL189 | QVQLQESGGGLVQPGGSLRLSCAAS |

-continued

| Anti-EpCAM sequence name | SEQ ID No. | Framework 2 sequence |
|---|---|---|
| EPL90 | 251 | WYRQSPGNERELVA |
| EPL118 | 252 | WFRQSPGNERELVA |
| EPL138 | 253 | WYRQFPGNERESIA |
| EPL145 | 254 | WFRQSPGNERELVA |
| EPL164 | 255 | WYRQSPGTQPELVA |
| EPL31 | 256 | WFRQAPGKEREFVA |
| EPL55 | 257 | WFRQAPGKEREFVA |
| EPL57 | 258 | WFRQAPGKEREFVA |
| EPL136 | 259 | WFRQAPGKEREFVA |
| EPL15 | 260 | WVRQAPGKGLEWVS |
| EPL34 | 261 | WVRQAPGKGLEWVS |
| EPL86 | 262 | WVRQAPGKGLEWVS |
| EPL153 | 263 | WVRQAPGKGLEWVS |
| EPL20 | 264 | WYRQAPEKQREMVA |
| EPL70 | 265 | WYRQAPEKXREMVA |
| EPL125 | 266 | WYRQVPEKQREMVA |
| EPL13 | 267 | WYRQAPGRGRELVA |
| EPL129 | 268 | WYRQAPGRGRELVA |
| EPL159 | 269 | WYRQAPGRGRELVA |
| EPL120 | 270 | WYRQSPGNERELVA |
| EPL126 | 271 | WYRQSPGNERELVA |
| EPL60 | 272 | WYRQAPGKVRELVA |
| EPL156 | 273 | WYRQAPGKVRELVA |
| EPL2 | 274 | WYRQAPGKERELVA |
| EPL43 | 275 | WYRQAPGKERELVA |
| EPL10 | 276 | WYRQAPGKQHELVA |
| EPL49 | 277 | WFRQAPGKEREFVA |
| EPL58 | 278 | WYRQAAGKQRELVA |
| EPL74 | 279 | WYRQAPGKQRESVA |
| EPL78 | 280 | WYRQAPGQQRELVA |
| EPL82 | 281 | WYRQAPGKQRELVA |
| EPL83 | 282 | WYRQAPGRQRDLIA |
| EPL97 | 283 | WFRQAPGKQRESVA |
| EPL109 | 284 | WFRQAPGKEREGVS |
| EPL117 | 285 | WYRQAPGKQREFVA |
| EPL127 | 286 | WFRQAPGKEREGVS |
| EPL152 | 287 | WYRQAPGKQRELVA |
| EPL189 | 288 | WYRQAPGNQRELVA |

| Anti-EpCAM sequence name | SEQ ID No. | Framework 3 sequence |
|---|---|---|
| EPL90 | 289 | RFTISRDNAKNTVYLQMNS LKPEDTAVYFCGA |
| EPL118 | 290 | RFTISRDNAKNTVYLQMNS LKPEDTAVYFCGA |
| EPL138 | 291 | RFTISRDNAKNTVYLQMNS LKPEDTAVYFCGA |
| EPL145 | 292 | RFTISRDNAKNTVYLQMNS LKPEDTAVYFCGA |
| EPL164 | 293 | RFTISRDNAKNTVYLQMNS LKPEDTAVYFCGA |
| EPL31 | 294 | RFTISRDNTKNTVYLQMNS LKPEDTAVYYCAA |
| EPL55 | 295 | RFTISRDNTKNTVYLQMNS LKPEDTAVYYCAA |
| EPL57 | 296 | RFTISRDNTKNTVYLQMNS LRPEDTAVYYCAA |
| EPL136 | 297 | RFTISRDNTKNTVYLQMNS LKPEDTAVYYCAA |
| EPL15 | 298 | RFTISRDNAKNELYLEMNN LKPEDTAVYYCAR |
| EPL34 | 299 | RFTISRDNAKNELYLEMNN LKPEDTAVYYCAR |
| EPL86 | 300 | RFTISRDDAKNTLYLQMNS LKPEDTAVYYCAR |
| EPL153 | 301 | RFTISRDDAKNTLYLQMNS LKPEDTAVYYCEK |
| EPL20 | 302 | RFTISRDNAKNTVYLQMNT LKPEDTAVYYCNA |
| EPL70 | 303 | RFTISRDNAKNTVYLQMNT LKPEDTAVYYCNA |
| EPL125 | 304 | RFTISRDNAKNTVYLQMNT LKPEDTAVYYCNA |
| EPL13 | 305 | RFTISRDNARNTVYLQMYS LKPEDTAVYYCGT |
| EPL129 | 306 | RFTISRDNARNTVYLQMYS LRPEDTAVYYCGT |
| EPL159 | 307 | RFTISRDNARNTVYLQMYS LKPEDTAVYYCGT |
| EPL120 | 308 | RFTISRDNAKNTGYLQMNS LKPEDTAVYFCAA |
| EPL126 | 309 | RFTISRDNAKNTGYLQMNS LKPEDTAVYFCAA |
| EPL60 | 310 | RFTISRDNDRNTVYLQMNR LQPEDTAAYYCNV |
| EPL156 | 311 | RFTISRDNDRNTVYLQMNR LQPEDTAAYYCNV |
| EPL2 | 312 | RFSISRDNAKNTVLLQMTS LKPEDTAVYYCNA |

-continued

| | | |
|---|---|---|
| EPL43 | 313 | RFSISRDNAKNTVLLQMTS LKPEDTAVYYCNA |
| EPL10 | 314 | RFTISRDNAKKTVYLQMNS LKPDDTAVYYCNA |
| EPL49 | 315 | RFTISRDNAKNEMYLQMNS LKFEDTAVYVCAA |
| EPL58 | 316 | RFTISRDIAKNTVYLQMDS LKPEDTAVYYCNV |
| EPL74 | 317 | RFTISRDNAKNTVYLQMNG LKPEDTAVYYCNT |
| EPL78 | 318 | RFTISRDNAKNTVYLQLSD LKPEDTAVYYCNV |
| EPL82 | 319 | RFAISRDSTKNTVYLQMNS LKPEDTAVYYCNT |
| EPL83 | 320 | RFTISRDNAKNTVYLQMNS LKPEDTAVYYCNL |
| EPL97 | 321 | RFTVSRDNAKNTLFLQMNS LKSEDTAVYYCNA |
| EPL109 | 322 | RFTISRDNAKNTVDLQMIS LRPEDTAVYYCAA |
| EPL117 | 323 | RFTISRDNTKNTVYLQMNY LKPEDTAVYYCAT |
| EPL127 | 324 | RFTISSDNAKNTVYLQMNS VKTDDTAVYYCAV |
| EPL152 | 325 | RFTISRDNANNTVYLQMNS LKPEDTAVYYCNA |
| EPL189 | 326 | RYAISRDNAKNLVYLQMNS LKPEDTDVYYCNA |

| Anti-EpCAM sequence name | SEQ ID No. | Framework 4 sequence |
|---|---|---|
| EPL90 | 327 | NGQGTQVTVSS |
| EPL118 | 328 | YGQGTQVTVSS |
| EPL138 | 329 | NGQGTQVTVSS |
| EPL145 | 330 | YGQGTQVTVSS |
| EPL164 | 331 | YGQGTQVTVSS |
| EPL31 | 332 | WGQGTQVTVSS |
| EPL55 | 333 | WGQGTQVTVSS |
| EPL57 | 334 | WGQGTQVTVSS |
| EPL136 | 335 | WGQGTQVTVSS |
| EPL15 | 336 | KGQGTQVTVSS |
| EPL34 | 337 | KGQGTQVTVSS |
| EPL86 | 338 | KGQGTQVTVSS |
| EPL153 | 339 | RGQGTQVTVSS |
| EPL20 | 340 | WGQGTQVTVSS |
| EPL70 | 341 | WGQGTQVTVSS |
| EPL125 | 342 | WGQGTQVTVSS |

-continued

| | | |
|---|---|---|
| EPL13 | 343 | WGQGTQVTVSS |
| EPL129 | 344 | WGQGTQVTVSS |
| EPL159 | 345 | WGQGTQVTVSS |
| EPL120 | 346 | WGQGTQVTVSS |
| EPL126 | 347 | WGQGTQVTVSS |
| EPL60 | 348 | WGQGTQVTVSS |
| EPL156 | 349 | WGQGTQVTVSS |
| EPL2 | 350 | WGQGTQVTVSS |
| EPL43 | 351 | WGQGTQVTVSS |
| EPL10 | 352 | WGQGTQVTVSS |
| EPL49 | 353 | WGQGTQVTVSS |
| EPL58 | 354 | WGQGTQVTVSS |
| EPL74 | 355 | WGQGTQVTVSS |
| EPL78 | 356 | WGQGTQVTVSS |
| EPL82 | 357 | WGQGTQVTVSS |
| EPL83 | 358 | WGQGTQVTVSS |
| EPL97 | 359 | WGQGTQVTVSS |
| EPL109 | 360 | QGQGTQVTVSS |
| EPL117 | 361 | WGHGTQVTVSS |
| EPL127 | 362 | WGQGTQVTVSS |
| EPL152 | 363 | WGQGTQVTVSS |
| EPL189 | 364 | WGQGTQVTVSS |

| SEQ ID NO: | Description | Amino Acid Sequence |
|---|---|---|
| 365 | Linker | (GS)n |
| 366 | Linker | (GGS)n |
| 367 | Linker | (GGGS)n |
| 368 | Linker | (GGSG)n |
| 369 | Linker | (GGSGG)n |
| 370 | Linker | (GGGGS)n |
| 371 | Linker | (GGGGG)n |
| 372 | Linker | (GGG)n |
| 373 | Linker | GGGGSGGGGSGGGGSGGGGS |
| 374 | Linker | GGGGSGGGGSGGGGS |
| 375 | Linker | GGGGSGGGS |
| 376 | Sortase | LPETG |
| 377 | Histidine tag | HHHHHH |
| 378 | Anti-HSA sdAb clone 10G | EVQLVESGGGLVQPGNSLRLSCAA SGFTFSKFGMSWVRQAPGKGLEWV SSISGSGRDTLYADSVKGRFTISR DNAKTTLYLQMNSLRPEDTAVYYC TIGGSLSVSSQGTLVTVSS |

-continued

| | | |
|---|---|---|
| 379 | Anti-CD3, clone 2B2 | EVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVL |
| 380 | Exemplary masking sequence | GGGGGLDGNEEPGG |
| 381 | Exemplary masking sequence | APGKG |
| 382 | Exemplary masking sequence | GGQDGNEEMGGG |
| 383 | Exemplary masking sequence | GGQDGNEEGG |
| 384 | Exemplary masking sequence | GGGGQDGNEEMGGGGG |
| 385 | Exemplary masking sequence | APFGSEM |
| 386 | Exemplary masking sequence | AWNGPYE |
| 387 | Exemplary masking sequence | AQDNGDTKTG |
| 388 | Exemplary masking sequence | AEAKETQG |
| 389 | Exemplary masking sequence | ATRREQVEG |
| 390 | Exemplary masking sequence | AQAPSQP |
| 391 | Exemplary masking sequence | ATRSRTRNDG |
| 392 | Exemplary masking sequence | ADVDAPDGLG |
| 393 | Exemplary masking sequence | AADISDPGG |
| 394 | Exemplary masking sequence | ALSVDPSG |
| 395 | Exemplary masking sequence | ARLSVDPG |

-continued

| | | |
|---|---|---|
| 396 | Exemplary masking sequence | AVEAADRG |
| 397 | Exemplary masking sequence | GGPDGNEEMGGG |
| 398 | Exemplary masking sequence | GGFDGNEEMGGG |
| 399 | Exemplary masking sequence | GGGDGNEEMGGG |
| 400 | Exemplary masking sequence | GGEMDGEGQNGG |
| 401 | Exemplary masking sequence | GGGGGPDGNEEPGG |
| 402 | Exemplary masking sequence | GGGGSLDGNEEPGG |
| 403 | Exemplary masking sequence | GGGGALDGNEEPGG |
| 404 | Exemplary masking sequence | GGGGGLDGNEEPGG |
| 405 | Exemplary masking sequence | GGGALDGNEEPGG |
| 406 | Exemplary masking sequence | GGGGGPDGNEEPGGG |
| 407 | Exemplary masking sequence | GGSGALDGNEEPGG |
| 408 | Exemplary masking sequence | GGSGSLDGNEEPGG |
| 409 | Exemplary masking sequence | GGSGGPDGNEEPGG |
| 410 | Exemplary masking sequence | GGVRDGPDGNEEPGG |
| 411 | Exemplary masking sequence | GGSGGPDGNEEPGGGG |
| 412 | Exemplary masking sequence | GGGRGPDGNEEPGG |
| 413 | Exemplary masking sequence | GGSGGLDGNEEPGG |
| 414 | Exemplary masking sequence | GGGVGPDGNEEPGG |
| 415 | Exemplary masking sequence | GGGEGPDGNEEPGG |

-continued

| | | |
|---|---|---|
| 416 | Exemplary masking sequence | GGGVALDGNEEPGG |
| 417 | Exemplary masking sequence | GGGRALDGNEEPGG |
| 418 | Exemplary masking sequence | GGYAGLDGNEEPGG |
| 419 | Exemplary masking sequence | GGAGGPDGNEEPGG |
| 420 | Exemplary masking sequence | GGRGGPDGNEEPGG |
| 421 | Exemplary masking sequence | GGGGPDGNEEPGGGG |
| 422 | Exemplary masking sequence | GGGEALDGNEEPGG |
| 423 | Exemplary masking sequence | GGDASLDGNEEPGG |
| 424 | Exemplary masking sequence | GGRDAPDGNEEGG |
| 425 | Exemplary cleavable linker sequence | KRALGLPG |
| 426 | Exemplary cleavable linker sequence | $(DE)_8$RPLALWRS$(DR)_8$ |
| 427 | Exemplary cleavable linker sequence | PR(S/T)(L/I)(S/T) |
| 428 | Exemplary cleavable linker sequence | LEATA |
| 429 | Exemplary cleavable linker sequence | GGAANLVRGG |
| 430 | Exemplary cleavable linker sequence | SGRIGFLRTA |
| 431 | Exemplary cleavable linker sequence | PLGLAG |
| 432 | Exemplary cleavable linker sequence | PLGLAX |

-continued

| | | |
|---|---|---|
| 433 | Exemplary cleavable linker sequence | PLGC(me)AG |
| 434 | Exemplary cleavable linker sequence | ESPAYYTA |
| 435 | Exemplary cleavable linker sequence | RLQLKL |
| 436 | Exemplary cleavable linker sequence | RLQLKAC |
| 437 | Exemplary cleavable linker sequence | EP(Cit)G(Hof)YL |
| 438 | Exemplary cleavable linker sequence | SGRSA |
| 439 | Exemplary cleavable linker sequence | DAFK |
| 440 | Exemplary cleavable linker sequence | GGGRR |
| 441 | Exemplary cleavable linker sequence | GFLG |
| 442 | Exemplary cleavable linker sequence | ALAL |
| 443 | Exemplary cleavable linker sequence | FK |
| 444 | Exemplary cleavable linker sequence | NLL |
| 445 | Exemplary cleavable linker sequence | PIC(Et)FF |
| 446 | Exemplary cleavable linker sequence | GGPRGLPG |
| 447 | Exemplary cleavable linker sequence | HSSKLQ |
| 448 | Exemplary cleavable linker sequence | HSSKLQL |

| | | |
|---|---|---|
| 449 | Exemplary cleavable linker sequence | HSSKLQEDA |
| 450 | Exemplary cleavable linker sequence | LVLASSSFGY |
| 451 | Exemplary cleavable linker sequence | GVSQNYPIVG |
| 452 | Exemplary cleavable linker sequence | GVVQASCRLA |
| 453 | Exemplary cleavable linker sequence | F(Pip)RS |
| 454 | Exemplary cleavable linker sequence | DPRSFL |
| 455 | Exemplary cleavable linker sequence | PPRSFL |
| 456 | Exemplary cleavable linker sequence | DEVD |
| 457 | Exemplary cleavable linker sequence | DEVDP |
| 458 | Exemplary cleavable linker sequence | KGSGDVEG |
| 459 | Exemplary cleavable linker sequence | GWEHDG |
| 460 | Exemplary cleavable linker sequence | EDDDDKA |
| 461 | Exemplary cleavable linker sequence | KQEQNPGST |
| 462 | Exemplary cleavable linker sequence | GKAFRR |
| 463 | Exemplary cleavable linker sequence | DAFK |
| 464 | Exemplary cleavable linker sequence | DVLK |
| 465 | Exemplary cleavable linker sequence | DAFK |
| 466 | Exemplary cleavable linker sequence | ALLLALL |
| 467 | Exemplary cleavable linker sequence | KPLGLQARVV |
| 468 | Exemplary cleavable linker sequence | PQASTGRSGG |
| 469 | Exemplary cleavable linker sequence | PQGSTGRAAG |
| 470 | Exemplary cleavable linker sequence | PPASSGRAGG |
| 471 | Exemplary cleavable linker sequence | PIPVQGRAH |
| 472 | Exemplary anti-albumin (HSA) sequence with masking moiety (identified in bold and italics) | EVQLVESGGGLVQPGNSLRLSCAASGFTFSKFGMSWVRQ***GGGGGLDGNEEPGG***LEWVSSISGSGRDTLYADSVKGRFTISRDNAKTTLYLQMNSLRPEDTAVYYCTIGGSLSVSSQGTLVTVSS |
| 473 | Exemplary anti-albumin (HSA) sequence with masking moiety (identified in bold and italics) and cleavable linker (identified in bold and underline) | EVQLVESGGGLVQPGNSLRLSCAASGFTFSKFGMSWVRQ***GGGGGLDGNEEPGG***LEWVSSISGSGRDTLYADSVKGRFTISRDNAKTTLYLQMNSLRPEDTAVYYCTIGGSLSVSSQGTLVTVSSGGGG**KPLGLQARVV**GGGGT |
| 474 | Exemplary anti-CD3 scFv of a proTriTAC molecule containing an anti-EpCAM | QTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDD |

-continued

| | | |
|---|---|---|
| | binding domain of this disclosure | SKNTAYLQMNNLKTEDTAVYYCVRHANFGNSYISYWAYWGQGTLVTVSS |
| 475 | Human EpCAM | >tr\|B5MCA4\|B5MCA4_HUMAN Epithelial cell adhesion molecule OS = *Homo sapiens* OX = 9606 GN = EPCAM PE = 1 SV = 1 METKHLGRGGAGRAGPHLWRGPRPNCSAGAGGGEPTHSPNSRAVTHQRAPAARECVCENYKLAVNCFVNNNRQCQCTSVGAQNTVICSKLAAKCLVMKAEMNGSKLGRRAKPEGALQNNDGLYDPDCDESGLFKAKQCNGTSMCWCVNTAGVRRTDKDTEITCSERVRTYWIIIELKHKAREKPYDSKSLRTALQKEITTRYQLDPKFITSILYENNVITIDLVQNSSQKTQNDVDIADVAYYFEKDVKGESLFHSKKMDLTVNGEQLDLDPGQTLIYYVDEKAPEFSMQGLKAGVIAVIWWIAWAGIWLVISRKKRMAKYEKAEIKEMGEMHRELNA |
| 476 | Cynomolgus EpCAM | OS = *Macaca fascicularis* OX = 9541 GN = EPCAM PE = 4 SV = 1 CVCENYKLAVNCFLNDNGQCQCTSIGAQNTVLCSKLAAKCLVMKAEMNGSKLGRRAKPEGALQNNDGLYDPDCDESGLFKAKQCNGTSTCWCVNTAGVRRTDKDTEITCSERVRTYWIIIELKHKAREKPYDVQSLRTALEEAIKTRYQLDPKFITNILYEDNVITIDLVQNSSQKTQNDVDIADVAYYFEKDVKGESLFHSKKMDLRVNGEQLDLDPGQTLIYYVDEKAPEFSMQGLKAGVIAVIWWIAIVAGIWLVISRKKRMAKYEKAEIKEMGEIHRELNA |
| 477 | Mouse EpCAM | >sp\|Q99JW5\|EPCAM_MOUSE Epithelial cell adhesion molecule OS = *Mus musculus* OX = 10090 GN = Epcam PE = 1 SV = 1 MAGPQALAFGLLLAVVTATLAAAQRDCVCDNYKLATSCSLNEYGECQCTSYGTQNTVICSKLASKCLAMKAEMTHSKSGRRIKPEGAIQNNDGLYDPDCDEQGLFKAKQCNGTATCWCVNTAGVRRTDKDTEITCSERVRTYWIIIELKHKERESPYDHQSLQTALQEAFTSRYKLNQKFIKNIMYENNVITIDLMQNSSQKTQDDVDIADVAYYFEKDVKGESLFHSSKSMDLRVNGEPLDLDPGQTLIYYVDEKAPEFSMQGLTAGIIAVIVVVSLAVIAGIWLVISTRKKSAKYEKAEIKEMGEIHRELNA |
| 478 | Human EpCAM | >sp\|P16422\|EPCAM_HUMAN Epithelial cell adhesion molecule OS = *Homo sapiens* OX = 9606 GN = EPCAM PE = 1 SV = 2 MAPPQVLAFGLLLAAATATFAAAQEECVCENYKLAVNCFVNNNRQCQCTSVGAQNTVICSKLAAKCLVMKAEMNGSKLGRRAKPEGALQNNDGLYDPDCDESGLFKAKQCNGTSMCWCVNTAGVRRTDKDTEITCSERVRTYWIIIELKHKAREKPYDSKSLRTALQKEITTRYQLDPKFITSILYENNVITIDLVQNSSQKTQNDVDIADVAYYFEKDVKGESLFHSKKMDLTVNGEQLDLDPGQTLIYYVDEKAPEFSMQGLKAGVIAVIVVVIAWAGIWLVISRKKRMAKYEKAEIKEMGEMHRELNA |
| 479 | Human EpCAM extracellular domain sequence | QEECVCENYKLAVNCFVNNNRQCQCTSVGAQNTVICSKLAAKCLVMKAEMNGSKLGRRAKPEGALQNNDGLYDPDCDESGLFKAKQCNGTSMCWCVNTAGVRRTDKDTEITCSERVRTYWIIIELKHKAREKPYDSKSLRTALQKEITTRYQLDPKFITSILYENNVITIDLVQNSSQKTQNDVDIADVAYYFEKDVKGESLFHSKKMDLTVNGEQLDLDPGQTLIYYVDEKAPEFSMQGLK |
| 480 | Cynomolgus EpCAM extracellular domain sequence | QKECVCENYKLAVNCFLNDNGQCQCTSIGAQNTVLCSKLAAKCLVMKAEMNGSKLGRRAKPEGALQNNDGLYDPDCDESGLFKAKQCNGTSTCWCVNTAGVRRTDKDTEITCSERVRTYVJIIELKHKAREKPYDVQSLRTALEEAIKTRYQLDPKFITNILYEDNVITIDLVQNSSQKTQNDVDIADVAYYFEKDVKGESLFHSKKMDLRVNGEQLDLDPGQTLIYYVDEKAPEFSMQGLK |
| 481 | Mouse EpCAM extracellular domain sequence | QRDCVCDNYKLATSCSLNEYGECQCTSYGTQNTVICSKLASKCLAMKAEMTHSKSGRRIKPEGAIQNNDGLYDPDCDEQGLFKAKQCNGTATCWCVNTAGVRRTDKDTEITCSERVRTYWIIIELKHKERESPYDHQSLQTALQEAFTSRYKLNQKFIKNIMYENNVITIDLMQNSSQKTQDDVDIADVAYYFEKDVKGESLFHSSKSMDLRVNGEPLDLDPGQTLIYYVDEKAPEFSMQGLT |
| 482 | 10G sdAb H90 Mask 1 | EVQLVESGGGLVQPGNSLRLSCAASGFTFSKFGMSWVRQRQSTFMAMDMPILEWVSSISGSGRDTLYADSVKGRFTISRDNAKTTLYLQMNSLRPEDTAVYYCTIGGSLSVSSQGTLVTVSS |
| 483 | 10G sdAb H90 Mask 2 | EVQLVESGGGLVQPGNSLRLSCAASGFTFSKFGMSWVRQQAYWWGNSRDLEWVSSISGSGRDTLYADSVKGRFTISRDNAKTTLYLQMNSLRPEDTAVYYCTIGGSLSVSSQGTLVTVSS |
| 484 | H90 sdAb | EVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSS |
| 485 | Exemplary construct | MALPVTALLLPLALLLHAARPEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSSTSDYKDDDDKTTTPAPRPPTPAPTIASQPLSLRPEACRPAAGGAVHTRGLDFACDIYIWAPLAGTCGVLLLSLVITLYKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 486 | Exemplary construct | MALPVTALLLPLALLLHAARPEVQLVESGGGLVQPGNSLRLSCAASGFTFSKFGMSWVRQAPGKGLEWVSSISGSGRDTLYADSVKGRFTISRDNAKTTLYLQMNSLRPEDTAVYYCTIGGSLSVSSQGTLVTVSSGSGGSGGGGSGGGGSGEVQLLESGGGLVQPGGSLTLSCAASGFIFRAASMAWYRQSPGNERELVASISSGAFTNYADSVKARFTISRD |

-continued

| | | |
|---|---|---|
| | | NSKNTLYLQMNSLRAEDTAVYYCGATFLRSDGHHTINGQGTLVTVSSTSDYKDDDDKTTTPAPRPPTPAPTIASQPLSLRPEACRPAAGGAVHTRGLDFACDIYIWAPLAGTCGVLLLSLVITLYKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 487 | Exemplary construct | MALPVTALLLPLALLLHAARPEVQLVESGGGLVQPGNSLRLSCAASGFTFSKFGMSWVRQRQSTFMAMDMPILEWVSSISGSGRDTLYADSVKGRFTISRDNAKTTLYLQMNSLRPEDTAVYYCTIGGSLSVSSQGTLVTVSSGSGGSGGGGSGGGGGSGEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSSTSDYKDDDDKTTTPAPRPPTPAPTIASQPLSLRPEACRPAAGGAVHTRGLDFACDIYIWAPLAGTCGVLLLSLVITLYKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 488 | Exemplary construct | MALPVTALLLPLALLLHAARPEVQLVESGGGLVQPGNSLRLSCAASGFTFSKFGMSWVRQQAYWWGNSRDLEWVSSISGSGRDTLYADSVKGRFTISRDNAKTTLYLQMNSLRPEDTAVYYCTIGGSLSVSSQGTLVTVSSGSGGSGGGGSGGGGGSGEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSSTSDYKDDDDKTTTPAPRPPTPAPTIASQPLSLRPEACRPAAGGAVHTRGLDFACDIYIWAPLAGTCGVLLLSLVITLYKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 489 | Exemplary construct | MALPVTALLLPLALLLHAARPEVQLVESGGGLVQPGNSLRLSCAASGFTFSKFGMSWVRQRQSTFMAMDMPILEWVSSISGSGRDTLYADSVKGRFTISRDNAKTTLYLQMNSLRPEDTAVYYCTIGGSLSVSSQGTLVTVSSGGGGPQGSTGRAAGGGGGTEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSSTSDYKDDDDKTTTPAPRPPTPAPTIASQPLSLRPEACRPAAGGAVHTRGLDFACDIYIWAPLAGTCGVLLLSLVITLYKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 490 | Exemplary construct | MALPVTALLLPLALLLHAARPEVQLVESGGGLVQPGNSLRLSCAASGFTFSKFGMSWVRQQAYWWGNSRDLEWVSSISGSGRDTLYADSVKGRFTISRDNAKTTLYLQMNSLRPEDTAVYYCTIGGSLSVSSQGTLVTVSSGGGGPQGSTGRAAGGGGGTEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSSTSDYKDDDDKTTTPAPRPPTPAPTIASQPLSLRPEACRPAAGGAVHTRGLDFACDIYIWAPLAGTCGVLLLSLVTTLYKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 491 | Exemplary construct | MALPVTALLLPLALLLHAARPQVQLVESGGALVQPGGSLRLSCAASGFPVNRYSMRWYRQAPGKEREWVAGMSSAGDRSSYEDSVKGRFTISRDDARNTVYLQMNSLKPEDTAVYYCNVNVGFEYWGQGTQVTVSSTSDYKDDDDKTTTPAPRPPTPAPTIASQPLSLRPEACRPAAGGAVHTRGLDFACDIYIWAPLAGTCGVLLLSLVITLYKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 492 | EpCAM TriTAC | EVQLVESGGGLVQPGNSLRLSCAASGFTFSKFGMSWVRQAPGKGLEWVSSISGSGRDTLYADSVKGRFTISRDNAKTTLYLQMNSLRPEDTAVYYCTIGGSLSVSSQGTLVTVSSGGGGSGGGSQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSSHHHHHH |
| 493 | GFP TriTAC | QVQLVESGGALVQPGGSLRLSCAASGFPVNRYSMRWYRQAPGKEREWVAGMSSAGDRSSYEDSVKGRFTISRDDARNTVYLQMNSLKPEDTAVYYCNVNVGFEYWGQGTQVTVSSGGGGSGGGSEVQLVESGGGLVQPGNSLRLSCAASGFTFSKFGMSWVRQAPGKGLEWVSSISGSGRDTLYADSVKGRFTISRDNAKTTLYLQMNSLRPEDTAVYYCTIGGSLSVSSQGTLVTVSSGGGGSGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGGSGGGGSQTVVTQEPSLTVSPGGTVTLTCASSTGAVTSGNYPNWVQQKPGQAPRGLIGGTKFLVPGTPARFSGSLLGGKAALTLSGVQPEDEAE |

| SEQ ID NO: | Anti-EpCAM sequence name | Amino Acid Sequence |
|---|---|---|
| | | YYCTLWYSNRWVFGGGTKLTVLHHHHHH |
| 494 | EpCAM ProTriTAC L040 (CT) | QTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSSHHHHHH |
| 495 | EpCAM ProTriTAC non-cleavable | EVQLVESGGGLVQPGNSLRLSCAASGFTFSKFGMSWVRQGGGGGLDGNEEPGGLEWVSSISGSGRDTLYADSVKGRFTISRDNAKTTLYLQMNSLRPEDTAVYYCTIGGSLSVSSQGTLVTVSSGGGGSGGGGSGGVVGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSSHHHHHH |

| SEQ ID NO: | Anti-EpCAM sequence name | Amino Acid Sequence |
|---|---|---|
| 496 | H138.2 | EVQLLESGGGLVQPGGSLTLSCAASGFIFRAASMDWYRQFPGNERESIATISSGGFTNYADSVKGRFTISRDNSKNTLYLQMNSLRAEDTAVYYCGATFLRSDGHHTIWGQGTLVTVSS |
| 497 | H90.2 | EVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTIWGQGTLVTVSS |

| SEQ ID NO: | EpCAM ProTriTAC sequence (Anti-Alb: Anti-CD3:Anti-EpCAM) | Amino Acid Sequence |
|---|---|---|
| 498 | Exemplary EpCAM ProTriTAC (L040)(H90.2) | EVQLVESGGGLVQPGNSLRLSCAASGFTFSKFGMSWVRQGGGGGLDGNEEPGGLEWVSSISGSGRDTLYADSVKGRFTISRDNAKTTLYLQMNSLRPEDTAVYYCTIGGSLSVSSQGTLVTVSSGGGPQASTGRSGGGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTIWGQGTLVTVSSHHHHHH |
| 499 | Exemplary EpCAM ProTriTAC (L041)(H90.2) | EVQLVESGGGLVQPGNSLRLSCAASGFTFSKFGMSWVRQGGGGGLDGNEEPGGLEWVSSISGSGRDTLYADSVKGRFTISRDNAKTTLYLQMNSLRPEDTAVYYCTIGGSLSVSSQGTLVTVSSGGGPQGSTGRAAGGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTIWGQGTLVTVSSHHHHHH |
| 500 | Exemplary EpCAM ProTriTAC (L043)(H90.2) | EVQLVESGGGLVQPGNSLRLSCAASGFTFSKFGMSWVRQGGGGGLDGNEEPGGLEWVSSISGSGRDTLYADSVKGRFTISRDNAKTTLYLQMNSLRPEDTAVYYCTIGGSLSVSSQGTLVTVSSGGGPQGSTARSAGGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTIWGQGTLVTVSSHHHHHH* |
| 501 | Exemplary EpCAM ProTriTAC (L001)(H90.2) | EVQLVESGGGLVQPGNSLRLSCAASGFTFSKFGMSWVRQGGGGGLDGNEEPGGLEWVSSISGSGRDTLYADSVKGRFTISRDNAKTTLYLQMNSLRPEDTAVYYCTIGGSLSVSSQGTLVTVSSGGGKPLGLQARVVGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTINGQGTLVTVSSHHHHHH |

-continued

| | | |
|---|---|---|
| 502 | Exemplary EpCAM non-cleavable prodrug (NCLV) (H90.2) | EVQLVESGGGLVQPGNSLRLSCAASGFTFSKFGMSWVRQGGGGGLDGNEEPGGLEWVSSISGSGRDTLYADSVKGRFTISRDNAKTTLYLQMNSLRPEDTAVYYCTIGGSLSVSSQGTLVTVSSGGGGSGGGGSGGVVGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTIWGQGTLVTVSSHHHHHH |

| SEQ ID NO: | Linker | Amino Acid Sequence |
|---|---|---|
| 503 | Exemplary linker sequence (L040) | GGGGPQASTGRSGGGGGG |
| 504 | Exemplary linker sequence (L041) | GGGGPQGSTGRAAGGGGG |
| 505 | Exemplary linker sequence (L043) | GGGGPQGSTARSAGGGGG |
| 506 | Exemplary linker sequence (L001) | GGGGKPLGLQARWGGGG |
| 507 | Exemplary linker sequence (NCLV) | GGGGSGGGGSGGWGGGG |

| SEQ ID NO: | EpCAM Binding Protein sequence | Amino Acid Sequence |
|---|---|---|
| 569 | H13 non-cleavable prodrug (NCLV) | EVQLVESGGGLVQPGNSLRLSCAASGFTFSKFGMSWVRQGGGGGLDGNEEPGGLEWVSSISGSGRDTLYADSVKGRFTISRDNAKTTLYLQMNSLRPEDTAVYYCTIGGSLSVSSQGTLVTVSSGGGGSGGGGSGGVVGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLVESGGGLVQPGGSLTLSCAASGFAFGNHWMYWYRQAPGRGRELVASISSGGSTNYVDSVKGRFTISRDNAKNTLYLQMNSLRAEDTAVYYCGTSDNWGQGTLVTVSSHHHHHH* |

-continued

| | | |
|---|---|---|
| 570 | EpCAM-H13 TriTAC (ACT) | EVQLVESGGGLVQPGNSLRLSCAASGFTFSKFGMSWVRQAPGKGLEWVSSISGSGRDTLYADSVKGRFTISRDNAKTTLYLQMNSLRPEDTAVYYCTIGGSLSVSSQGTLVTVSSGGGGSGGGSQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLVESGGGLVQPGGSLTLSCAASGFAFGNHWMYWYRQAPGRGRELVASISSGGSTNYVDSVKGRFTISRDNAKNTLYLQMNSLRAEDTAVYYCGTSDNWGQGTLVTVSSHHHHHH* |
| 571 | EpCAM-H90.2 (CT) | VVGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTIWGQGTLVTVSSHHHHHH* |
| 572 | EpCAM TriTAC-H90.2 (ACT) | EVQLVESGGGLVQPGNSLRLSCAASGFTFSKFGMSWVRQAPGKGLEWVSSISGSGRDTLYADSVKGRFTISRDNAKTTLYLQMNSLRPEDTAVYYCTIGGSLSVSSQGTLVTVSSGGGGSGGGSQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMAWYRQSPGNERELVASISSGAFTNYADSVKARFTISRDNSKNTLYLQMNSLRAEDTAVYYCGATFLRSDGHHTIWGQGTLVTVSSHHHHHH* |
| 573 | EpCAM-H138.2 ProTriTAC (NCLV) | EVQLVESGGGLVQPGNSLRLSCAASGFTFSKFGMSWVRQGGGGGLDGNEEPGGLEWVSSISGSGRDTLYADSVKGRFTISRDNAKTTLYLQMNSLRPEDTAVYYCTIGGSLSVSSQGTLVTVSSGGGGSGGGGSGGVVGGGGTQTVVTQEPSLTVSPGGTVTLTCASSTGAVTSGNYPNWVQQKPGQAPRGLIGGTKFLVPGTPARFSGSLLGGKAALTLSGVQPEDEAEYYCTLWYSNRWVFGGGTKLTVLGGGGSGGGGSGGGGSEVQLVESGGGLVQPGGSLKLSCAASGFTFNKYAINWVRQAPGKGLEWVARIRSKYNNYATYYADQVKDRFTISRDDSKNTAYLQMNNLKTEDTAVYYCVRHANFGNSYISYWAYWGQGTLVTVSSGGGGSGGGSEVQLLESGGGLVQPGGSLTLSCAASGFIFRAASMDWYRQFPGNERESIATISSGGFTNYADS |

-continued

| | | |
|---|---|---|
| | | VKGRFTISRDNSKNTLYLQMNSLRA<br>EDTAVYYCGATFLRSDGHHTIWGQG<br>TLVTVSSHHHHHH* |
| 574 | EpCAM<br>ProTriTAC-<br>H138.2<br>(CT) | VVGGGGTQTVVTQEPSLTVSPGGTV<br>TLTCASSTGAVTSGNYPNWVQQKPG<br>QAPRGLIGGTKFLVPGTPARFSGSL<br>LGGKAALTLSGVQPEDEAEYYCTLW<br>YSNRWVFGGGTKLTVLGGGGSGGGG<br>SGGGGSEVQLVESGGGLVQPGGSLK<br>LSCAASGFTFNKYAINWVRQAPGKG<br>LEWVARIRSKYNNYATYYADQVKDR<br>FTISRDDSKNTAYLQMNNLKTEDTA<br>VYYCVRHANFGNSYISYWAYWGQGT<br>LVTVSSGGGGSGGGSEVQLLESGGG<br>LVQPGGSLTLSCAASGFIFRAASMD<br>WYRQFPGNERESIATISSGGFTNYA<br>DSVKGRFTISRDNSKNTLYLQMNSL<br>RAEDTAVYYCGATFLRSDGHHTIWG<br>QGTLVTVSSHHHHHH* |
| 575 | EpCAM<br>H138.2<br>TriTAC<br>DG/WG | EVQLVESGGGLVQPGNSLRLSCAAS<br>GFTFSKFGMSWVRQAPGKGLEWVSS<br>ISGSGRDTLYADSVKGRFTISRDNA<br>KTTLYLQMNSLRPEDTAVYYCTIGG<br>SLSVSSQGTLVTVSSGGGGSGGGSQ<br>TVVTQEPSLTVSPGGTVTLTCASST<br>GAVTSGNYPNWVQQKPGQAPRGLIG<br>GTKFLVPGTPARFSGSLLGGKAALT<br>LSGVQPEDEAEYYCTLWYSNRWVFG<br>GGTKLTVLGGGGSGGGGSGGGGSEV<br>QLVESGGGLVQPGGSLKLSCAASGF<br>TFNKYAINWVRQAPGKGLEWVARIR<br>SKYNNYATYYADQVKDRFTISRDDS<br>KNTAYLQMNNLKTEDTAVYYCVRHA<br>NFGNSYISYWAYWGQGTLVTVSSGG<br>GGSGGGSEVQLLESGGGLVQPGGSL<br>TLSCAASGFIFRAASMDWYRQFPGN<br>ERESIATISSGGFTNYADSVKGRFT<br>ISRDNSKNTLYLQMNSLRAEDTAVY<br>YCGATFLRSDGHHTIWGQGTLVTVS<br>SHHHHHH* |
| 576 | EpCAM HI3<br>Mask27 L040 | EVQLVESGGGLVQPGNSLRLSCAAS<br>GFTFSKFGMSWVRQGGGGGLDGNEE<br>PGGLEWVSSISGSGRDTLYADSVKG<br>RFTISRDNAKTTLYLQMNSLRPEDT<br>AVYYCTIGGSLSVSSQGTLVTVSSG<br>GGGPQASTGRSGGGGGGSQTVVTQE<br>PSLTVSPGGTVTLTCASSTGAVTSG<br>NYPNWVQQKPGQAPRGLIGGTKFLV<br>PGTPARFSGSLLGGKAALTLSGVQP<br>EDEAEYYCTLWYSNRWVFGGGTKLT<br>VLGGGGSGGGGSGGGGSEVQLVESG<br>GGLVQPGGSLKLSCAASGFTFNKYA<br>INWVRQAPGKGLEWVARIRSKYNNY<br>ATYYADQVKDRFTISRDDSKNTAYL<br>QMNNLKTEDTAVYYCVRHANFGNSY<br>ISYWAYWGQGTLVTVSSGGGGSGGG<br>SEVQLVESGGGLVQPGGSLTLSCAA<br>SGFAFGNHWMYWYRQAPGRGRELVA<br>SISSGGSTNYVDSVKGRFTISRDNA<br>KNTLYLQMNSLRAEDTAVYYCGTSD<br>NWGQGTLVTVSSHHHHHH* |
| 577 | EpCAM H90<br>Mask27 L040 | EVQLVESGGGLVQPGNSLRLSCAAS<br>GFTFSKFGMSWVRQGGGGGLDGNEE<br>PGGLEWVSSISGSGRDTLYADSVKG<br>RFTISRDNAKTTLYLQMNSLRPEDT<br>AVYYCTIGGSLSVSSQGTLVTVSSG<br>GGGPQASTGRSGGGGGGTQTVVTQE<br>PSLTVSPGGTVTLTCASSTGAVTSG<br>NYPNWVQQKPGQAPRGLIGGTKFLV<br>PGTPARFSGSLLGGKAALTLSGVQP<br>EDEAEYYCTLWYSNRWVFGGGTKLT<br>VLGGGGSGGGGSGGGGSEVQLVESG<br>GGLVQPGGSLKLSCAASGFTFNKYA<br>INWVRQAPGKGLEWVARIRSKYNNY<br>ATYYADQVKDRFTISRDDSKNTAYL |

-continued

| | | |
|---|---|---|
| | | QMNNLKTEDTAVYYCVRHANFGNSY<br>ISYWAYWGQGTLVTVSSGGGGSGGG<br>SEVQLLESGGGLVQPGGSLTLSCAA<br>SGFIFRAASMAWYRQSPGNERELVA<br>SISSGAFTNYADSVKARFTISRDNS<br>KNTLYLQMNSLRAEDTAVYYCGATF<br>LRSDGHHTINGQGTLVTVSSHHHHH<br>H* |
| 578 | EpCAM H90.2<br>Mask27 L040 | EVQLVESGGGLVQPGNSLRLSCAAS<br>GFTFSKFGMSWVRQGGGGGLDGNEE<br>PGGLEWVSSISGSGRDTLYADSVKG<br>RFTISRDNAKTTLYLQMNSLRPEDT<br>AVYYCTIGGSLSVSSQGTLVTVSSG<br>GGGPQASTGRSGGGGGGSQTVVTQE<br>PSLTVSPGGTVTLTCASSTGAVTSG<br>NYPNWVQQKPGQAPRGLIGGTKFLV<br>PGTPARFSGSLLGGKAALTLSGVQP<br>EDEAEYYCTLWYSNRWVFGGGTKLT<br>VLGGGGSGGGGSGGGGSEVQLVESG<br>GGLVQPGGSLKLSCAASGFTFNKYA<br>INWVRQAPGKGLEWVARIRSKYNNY<br>ATYYADQVKDRFTISRDDSKNTAYL<br>QMNNLKTEDTAVYYCVRHANFGNSY<br>ISYWAYWGQGTLVTVSSGGGGSGGG<br>SEVQLLESGGGLVQPGGSLTLSCAA<br>SGFIFRAASMAWYRQSPGNERELVA<br>SISSGAFTNYADSVKARFTISRDNS<br>KNTLYLQMNSLRAEDTAVYYCGATF<br>LRSDGHHTIWGQGTLVTVSSHHHHH<br>H* |

| SEQ ID NO: | | Amino Acid Sequence |
|---|---|---|
| 579 | 1.7 Bn<br>huEpCAM<br>aa22-265<br>FLAG huIgG1<br>Fc (biotin-<br>huEpCAM-rc) | QEECVCENYKLAVNCFVNNNRQCQC<br>TSVGAQNTVICSKLAAKCLVMKAEM<br>NGSKLGRRAKPEGALQNNDGLYDPD<br>CDESGLFKAKQCNGTSMCWCVNTAG<br>VRRTDKDTEITCSERVRTYWIIIEL<br>KHKAREKPYDSKSLRTALQKEITTR<br>YQLDPKFITSILYENNVITIDLVQN<br>SSQKTQNDVDIADVAYYFEKDVKGE<br>SLFHSKKMDLTVNGEQLDLDPGQTL<br>IYYVDEKAPEFSMQGLKDYKDDDDK<br>GGGGSDKTHTCPPCPAPELLGGPSV<br>FLFPPKPKDTLMISRTPEVTCVVVD<br>VSHEDPEVKFNWYVDGVEVHNAKTK<br>PREEQYNSTYRVVSVLTVLHQDWLN<br>GKEYKCKVSNKALPAPIEKTISKAK<br>GQPREPQVYTLPPSREEMTKNQVSL<br>TCLVKGFYPSDIAVEWESNGQPENN<br>YKTTPPVLDSDGSFFLYSKLTVDKS<br>RWQQGNVFSCSVMHEALHNHYTQKS<br>LSLSPGK* |
| 580 | 1.9-Bn<br>cyEpCAM<br>aa24-265<br>FLAG huIgG1<br>Fc(biotin-<br>cyEpCAM-Fc) | QKECVCENYKLAVNCFLNDNGQCQC<br>TSIGAQNTVLCSKLAAKCLVMKAEM<br>NGSKLGRRAKPEGALQNNDGLYDPD<br>CDESGLFKAKQCNGTSTCWCVNTAG<br>VRRTDKDTEITCSERVRTYWIIIEL<br>KHKAREKPYDVQSLRTALEEAIKTR<br>YQLDPKFITNILYEDNVITIDLVQN<br>SSQKTQNDVDIADVAYYFEKDVKGE<br>SLFHSKKMDLRVNGEQLDLDPGQTL<br>IYYVDEKAPEFSMQGLKDYKDDDDK<br>GGGGSDKTHTCPPCPAPELLGGPSV<br>FLFPPKPKDTLMISRTPEVTCVVVD<br>VSHEDPEVKFNWYVDGVEVHNAKTK<br>PREEQYNSTYRVVSVLTVLHQDWLN |

GKEYKCKVSNKALPAPIEKTISKAK
GQPREPQVYTLPPSREEMTKNQVSL
TCLVKGFYPSDIAVEWESNGQPENN
YKTTPPVLDSDGSFFLYSKLTVDKS
RWQQGNVFSCSVMHEALHNHYTQKS
LSLSPGK*

| | | |
|---|---|---|
| 581 | Linker | GGGGT |
| 582 | Framework 4 for H90.2 and H138.2 | WGQGTLVTVSS |

What is claimed is:

1. A multispecific protein comprising (a) an EpCAM binding domain, (b) a CD3ε binding domain, and (c) a bulk serum protein binding domain that binds to a human serum albumin protein, wherein the multispecific protein comprises an amino acid sequence of any one of SEQ ID NOS: 495, 498-502, 569-570, 572, 573, 575, 576, 577, and 578.

2. The multispecific protein of claim 1, wherein the bulk serum protein binding domain is a binding moiety comprising a linker and a masking moiety, and wherein the masking moiety is capable of masking the binding of the EpCAM binding domain or the CD38 binding domain, to their respective targets.

3. The multispecific protein of claim 1, wherein the multispecific protein comprises the amino acid sequence of SEQ ID NO: 495.

4. The multispecific protein of claim 1, wherein the multispecific protein comprises the amino acid sequence of SEQ ID NO: 498.

5. The multispecific protein of claim 1, wherein the multispecific protein comprises the amino acid sequence of SEQ ID NO: 499.

6. The multispecific protein of claim 1, wherein the multispecific protein comprises the amino acid sequence of SEQ ID NO: 500.

7. The multispecific protein of claim 1, wherein the multispecific protein comprises the amino acid sequence of SEQ ID NO: 501.

8. The multispecific protein of claim 1, wherein the multispecific protein comprises the amino acid sequence of SEQ ID NO: 502.

9. The multispecific protein of claim 1, wherein the multispecific protein comprises the amino acid sequence of SEQ ID NO: 569.

10. The multispecific protein of claim 1, wherein the multispecific protein comprises the amino acid sequence of SEQ ID NO: 570.

11. The multispecific protein of claim 1, wherein the multispecific protein comprises the amino acid sequence of SEQ ID NO: 572.

12. The multispecific protein of claim 1, wherein the multispecific protein comprises the amino acid sequence of SEQ ID NO: 573.

13. The multispecific protein of claim 1, wherein the multispecific protein comprises the amino acid sequence of SEQ ID NO: 575.

14. The multispecific protein of claim 1, wherein the multispecific protein comprises the amino acid sequence of SEQ ID NO: 576.

15. The multispecific protein of claim 1, wherein the multispecific protein comprises the amino acid sequence of SEQ ID NO: 577.

16. The multispecific protein of claim 1, wherein the multispecific protein comprises the amino acid sequence of SEQ ID NO: 578.

17. A pharmaceutical composition comprising (i) the multispecific protein according to claim 1, and (ii) a pharmaceutically acceptable carrier.

18. A polynucleotide encoding the multispecific protein of claim 1.

19. A vector comprising the polynucleotide of claim 18.

20. A pharmaceutical composition comprising (i) the vector according to claim 19, and (ii) a pharmaceutically acceptable carrier.

21. A method for the treatment or amelioration of a proliferative disease, or a tumorous disease, comprising administering a multispecific protein to a subject in need thereof wherein the multispecific protein comprises (a) an EpCAM binding domain, (b) a CD3ε binding domain, and (c) a bulk serum protein binding domain that binds to a human serum albumin protein, and wherein the multispecific protein comprises an amino acid sequence of any one of SEQ ID NOS: 498-501, 570, 572, and 575-578.

22. The method of claim 21, wherein the tumorous disease comprises a solid tumor disease.

23. The method of claim 22, wherein the solid tumor disease is metastatic.

24. The method of claim 21, wherein the tumorous disease comprises a colorectal cancer, a prostate cancer, a neuroendocrine cancer, a thyroid cancer, a non-small cell lung cancer, a small cell lung cancer, a gastric cancer, an ovarian cancer, an endometrial cancer, a pancreatic cancer, a biliary tract cancer, a gall bladder cancer, an esophageal cancer, a breast cancer, or an adenocarcinoma.

25. The method of claim 21, wherein the subject is human.

* * * * *

SEQUENCE LISTING

<160> NUMBER OF SEQ ID NOS: 595

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ile Phe Arg Ala Ala
20 25 30

Ser Met Ala Trp Tyr Arg Gln Ser Pro Gly Asn Glu Arg Glu Leu Val
35 40 45

Ala Ser Ile Ser Ser Gly Ala Phe Thr Asn Tyr Ala Asp Ser Val Lys
50 55 60

Ala Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Phe Cys Gly
85 90 95

Ala Thr Phe Leu Arg Ser Asp Gly His His Thr Ile Asn Gly Gln Gly
100 105 110

Thr Gln Val Thr Val Ser Ser
115

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ile Phe Arg Ala Ala
20 25 30

Ser Met Gly Trp Phe Arg Gln Ser Pro Gly Asn Glu Arg Glu Leu Val
35 40 45

Ala Thr Val Ser Ser Gly Asp Phe Thr Asn Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Phe Cys Gly
85 90 95

```
Ala Thr Phe Val Arg Ser Asp Gly His His Thr Ile Tyr Gly Gln Gly
            100                 105                 110

Thr Gln Val Thr Val Ser Ser
        115


<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ile Phe Arg Ala Ala
            20                  25                  30

Ser Met Asp Trp Tyr Arg Gln Phe Pro Gly Asn Glu Arg Glu Ser Ile
        35                  40                  45

Ala Thr Ile Ser Ser Gly Gly Phe Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Phe Cys Gly
                85                  90                  95

Ala Thr Phe Leu Arg Ser Asp Gly His His Thr Ile Asn Gly Gln Gly
            100                 105                 110

Thr Gln Val Thr Val Ser Ser
        115


<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ile Phe Arg Ala Ala
            20                  25                  30

Ser Met Gly Trp Phe Arg Gln Ser Pro Gly Asn Glu Arg Glu Leu Val
        35                  40                  45

Ala Thr Val Ser Ser Gly Gly Phe Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Phe Cys Gly
                85                  90                  95

Ala Thr Phe Val Arg Ser Asp Gly His His Thr Ile Tyr Gly Gln Gly
            100                 105                 110

Thr Gln Val Thr Val Ser Ser
        115


<210> SEQ ID NO 5
```

<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ile Phe Arg Ala Ala
            20                  25                  30

Ser Met Asp Trp Tyr Arg Gln Ser Pro Gly Thr Gln Pro Glu Leu Val
        35                  40                  45

Ala Thr Ile Ser Ser Thr Gly Phe Thr Asn Tyr Ala Asn Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Phe Cys Gly
                85                  90                  95

Ala Thr Phe Leu Arg Ser Asp Gly Gln His Ser Ile Tyr Gly Gln Gly
            100                 105                 110

Thr Gln Val Thr Val Ser Ser
        115

<210> SEQ ID NO 6
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Glu Ser Gly Gly Gly Leu Val His Thr Gly Gly
1               5                   10                  15

Ser Leu Arg Leu Ser Cys Ala Ala Ser Gly Asp Thr Phe Leu Arg Tyr
            20                  25                  30

Ala Met Gly Trp Phe Arg Gln Ala Pro Gly Lys Glu Arg Glu Phe Val
        35                  40                  45

Ala Ala Ile Thr Trp Asn Gly Gly Asn Thr Asp Tyr Ala Gly Ser Leu
    50                  55                  60

Lys Gly Arg Phe Thr Ile Ser Arg Asp Asn Thr Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Phe Gly Leu Ala Ser Ser His Tyr Gln Tyr Asp
            100                 105                 110

Tyr Trp Gly Gln Gly Thr Gln Val Thr Val Ser Ser
        115                 120

<210> SEQ ID NO 7
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Glu Ser Gly Gly Gly Leu Val Gln Ala Gly Gly
1 5 10 15

Ser Leu Arg Leu Ser Cys Ala Ala Ser Gly Asp Thr Phe Leu Arg Tyr
20 25 30

Ala Met Gly Trp Phe Arg Gln Ala Pro Gly Lys Glu Arg Glu Phe Val
35 40 45

Ala Ala Ile Thr Trp Asn Gly Gly Asn Thr Asp Tyr Ala Gly Ser Leu
50 55 60

Lys Gly Arg Phe Thr Ile Ser Arg Asp Asn Thr Lys Asn Thr Val Tyr
65 70 75 80

Leu Gln Met Asn Ser Leu Lys Pro Glu Asp Thr Ala Val Tyr Tyr Cys
85 90 95

Ala Ala Asp Leu Thr Phe Gly Leu Ala Ser Ser His Tyr Gln Tyr Asp
100 105 110

Tyr Trp Gly Gln Gly Thr Gln Val Thr Val Ser Ser
115 120

<210> SEQ ID NO 8
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Gln Val Gln Leu Gln Glu Ser Gly Gly Gly Leu Val His Thr Gly Gly
1 5 10 15

Ser Leu Arg Leu Ser Cys Ala Phe Ser Gly Asp Thr Phe Leu Arg Tyr
20 25 30

Ala Met Gly Trp Phe Arg Gln Ala Pro Gly Lys Glu Arg Glu Phe Val
35 40 45

Ala Ala Ile Thr Trp Asn Gly Gly Asn Thr Asp Tyr Ala Asp Ser Leu
50 55 60

Lys Gly Arg Phe Thr Ile Ser Arg Asp Asn Thr Lys Asn Thr Val Tyr
65 70 75 80

Leu Gln Met Asn Ser Leu Arg Pro Glu Asp Thr Ala Val Tyr Tyr Cys
85 90 95

Ala Ala Asp Leu Thr Phe Gly Leu Ala Ser Ser His Tyr Gln Tyr Asp
100 105 110

Tyr Trp Gly Gln Gly Thr Gln Val Thr Val Ser Ser
115 120

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Gln Val Gln Leu Gln Glu Ser Gly Gly Gly Leu Val Gln Pro Gly Gly
1 5 10 15

Ser Leu Arg Leu Ser Cys Ala Ala Ser Gly Asp Thr Phe Leu Arg Tyr
20 25 30

```
Ala Met Gly Trp Phe Arg Gln Ala Pro Gly Lys Glu Arg Glu Phe Val
        35                  40                  45

Ala Ala Ile Thr Trp Asn Gly Gly Asn Thr Asp Tyr Ala Gly Ser Leu
    50                  55                  60

Lys Gly Arg Phe Thr Ile Ser Arg Asp Asn Thr Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Phe Gly Leu Ala Ser Ser His Tyr Gln Tyr Asp
            100                 105                 110

Tyr Trp Gly Gln Gly Thr Gln Val Thr Val Ser Ser
        115                 120


<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Gly Gly Ser Val Leu Ala Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile His Tyr Thr Gly Asp Trp Thr Asn Tyr Ala Asp Ser Val
    50                  55                  60

Lys Gly Arg Phe Thr Ile Ser Arg Asp Asn Ala Lys Asn Glu Leu Tyr
65                  70                  75                  80

Leu Glu Met Asn Asn Leu Lys Pro Glu Asp Thr Ala Val Tyr Tyr Cys
                85                  90                  95

Ala Arg Gly Ser Asp Lys Gly Gln Gly Thr Gln Val Thr Val Ser Ser
            100                 105                 110


<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile His Tyr Thr Gly Asp Trp Thr Asn Tyr Ala Asp Ser Val
    50                  55                  60

Lys Gly Arg Phe Thr Ile Ser Arg Asp Asn Ala Lys Asn Glu Leu Tyr
65                  70                  75                  80

Leu Glu Met Asn Asn Leu Lys Pro Glu Asp Thr Ala Val Tyr Tyr Cys
                85                  90                  95
```

```
Ala Arg Gly Ser Asp Lys Gly Gln Gly Thr Gln Val Thr Val Ser Ser
            100                 105                 110


<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asp Trp
            20                  25                  30

Ala Met Ser Trp Val Arg Gln Ala Pro Gly Lys Gly Leu Glu Trp Val
        35                  40                  45

Ser Gly Ile His Tyr Gly Asp His Thr Thr His Tyr Ala Asp Phe Val
    50                  55                  60

Lys Gly Arg Phe Thr Ile Ser Arg Asp Asp Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Arg Gly Ser Thr Lys Gly Gln Gly Thr Gln Val Thr Val Ser Ser
            100                 105                 110


<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asp Trp
            20                  25                  30

Ala Met Ser Trp Val Arg Gln Ala Pro Gly Lys Gly Leu Glu Trp Val
        35                  40                  45

Ser Ser Ile His Tyr Gly Asp His Thr Thr His Tyr Ala Asp Phe Val
    50                  55                  60

Lys Gly Arg Phe Thr Ile Ser Arg Asp Asp Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Glu Lys Gly Thr Thr Arg Gly Gln Gly Thr Gln Val Thr Val Ser Ser
            100                 105                 110


<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 14

Gln Val Gln Leu Gln Glu Ser Gly Gly Gly Leu Val Gln Ala Gly Gly
1 5 10 15

Ser Leu Lys Leu Ser Cys Ala Ala Ser Gly Asn Val Phe Arg Ala Ala
20 25 30

Thr Met Ala Trp Tyr Arg Gln Ala Pro Glu Lys Gln Arg Glu Met Val
35 40 45

Ala Thr Ile Ala Ser Gly Gly Thr Thr Asn Tyr Ala Asp Phe Val Lys
50 55 60

Gly Arg Phe Thr Ile Ser Arg Asp Asn Ala Lys Asn Thr Val Tyr Leu
65 70 75 80

Gln Met Asn Thr Leu Lys Pro Glu Asp Thr Ala Val Tyr Tyr Cys Asn
85 90 95

Ala Gly Tyr Leu Thr Ser Leu Gly Pro Lys Asn Tyr Trp Gly Gln Gly
100 105 110

Thr Gln Val Thr Val Ser Ser
115

<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (44)..(44)
<223> OTHER INFORMATION: Any amino acid

<400> SEQUENCE: 15

Gln Val Gln Leu Gln Glu Ser Gly Gly Gly Leu Val Gln Pro Gly Gly
1 5 10 15

Ser Leu Arg Leu Ser Cys Ala Ala Ser Gly Asn Val Phe Arg Ala Ala
20 25 30

Thr Met Ala Trp Tyr Arg Gln Ala Pro Glu Lys Xaa Arg Glu Met Val
35 40 45

Ala Thr Ile Ala Ser Gly Gly Thr Thr Asn Tyr Ala Asp Phe Val Lys
50 55 60

Gly Arg Phe Thr Ile Ser Arg Asp Asn Ala Lys Asn Thr Val Tyr Leu
65 70 75 80

Gln Met Asn Thr Leu Lys Pro Glu Asp Thr Ala Val Tyr Tyr Cys Asn
85 90 95

Ala Gly Tyr Leu Thr Ser Leu Gly Pro Lys Asn Tyr Trp Gly Gln Gly
100 105 110

Thr Gln Val Thr Val Ser Ser
115

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Gln Val Gln Leu Gln Glu Ser Gly Gly Gly Leu Val Gln Ala Gly Gly
1 5 10 15

```
Ser Leu Arg Leu Ser Cys Ala Ala Ser Gly Asn Val Phe Arg Ala Ala
            20                  25                  30

Thr Met Ala Trp Tyr Arg Gln Val Pro Glu Lys Gln Arg Glu Met Val
        35                  40                  45

Ala Thr Ile Ala Ser Gly Gly Thr Thr Asn Tyr Ala Asp Phe Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Lys Pro Glu Asp Thr Ala Val Tyr Tyr Cys Asn
                85                  90                  95

Ala Leu Tyr Leu Thr Ser Leu Gly Pro Lys Ser Tyr Trp Gly Gln Gly
            100                 105                 110

Thr Gln Val Thr Val Ser Ser
        115


<210> SEQ ID NO 17
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ala Phe Gly Asn His
            20                  25                  30

Trp Met Tyr Trp Tyr Arg Gln Ala Pro Gly Arg Gly Arg Glu Leu Val
        35                  40                  45

Ala Ser Ile Ser Ser Gly Gly Ser Thr Asn Tyr Val Asp Ser Val Lys
    50                  55                  60

Gly Arg Phe Thr Ile Ser Arg Asp Asn Ala Arg Asn Thr Val Tyr Leu
65                  70                  75                  80

Gln Met Tyr Ser Leu Lys Pro Glu Asp Thr Ala Val Tyr Tyr Cys Gly
                85                  90                  95

Thr Ser Asp Asn Trp Gly Gln Gly Thr Gln Val Thr Val Ser Ser
            100                 105                 110


<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ala Phe Gly Asn His
            20                  25                  30

Trp Met Tyr Trp Tyr Arg Gln Ala Pro Gly Arg Gly Arg Glu Leu Val
        35                  40                  45

Ala Ser Ile Ser Ser Gly Gly Ser Thr Asn Tyr Val Asp Ser Val Lys
    50                  55                  60

Gly Arg Phe Thr Ile Ser Arg Asp Asn Ala Arg Asn Thr Val Tyr Leu
65                  70                  75                  80
```

```
Gln Met Tyr Ser Leu Arg Pro Glu Asp Thr Ala Val Tyr Tyr Cys Gly
                85                  90                  95

Thr Ser Asp Asn Trp Gly Gln Gly Thr Gln Val Thr Val Ser Ser
            100                 105                 110


<210> SEQ ID NO 19
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ala Phe Gly Asn His
            20                  25                  30

Trp Met Tyr Trp Tyr Arg Gln Ala Pro Gly Arg Gly Arg Glu Leu Val
        35                  40                  45

Ala Ser Ile Ser Ser Gly Gly Ser Thr Asn Tyr Val Asp Ser Val Lys
    50                  55                  60

Gly Arg Phe Thr Ile Ser Arg Asp Asn Ala Arg Asn Thr Val Tyr Leu
65                  70                  75                  80

Gln Met Tyr Ser Leu Lys Pro Glu Asp Thr Ala Val Tyr Tyr Cys Gly
                85                  90                  95

Thr Ser Asp Asn Trp Gly Gln Gly Thr Gln Val Thr Val Ser Ser
            100                 105                 110


<210> SEQ ID NO 20
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ile Phe Arg Ala Ala
            20                  25                  30

Ser Ile Ser Trp Tyr Arg Gln Ser Pro Gly Asn Glu Arg Glu Leu Val
        35                  40                  45

Ala Thr Ile Asn Ser Gly Gly Phe Thr Asn Tyr Ala Asp Ser Val Leu
    50                  55                  60

Gly Arg Phe Thr Ile Ser Arg Asp Asn Ala Lys Asn Thr Gly Tyr Leu
65                  70                  75                  80

Gln Met Asn Ser Leu Lys Pro Glu Asp Thr Ala Val Tyr Phe Cys Ala
                85                  90                  95

Ala Thr Phe Leu Arg Ser Asp Gly Gln Pro Pro Ile Trp Gly Gln Gly
            100                 105                 110

Thr Gln Val Thr Val Ser Ser
        115


<210> SEQ ID NO 21
<211> LENGTH: 119
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 21

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ile Phe Arg Ala Ala
            20                  25                  30

Ser Met Gly Trp Tyr Arg Gln Ser Pro Gly Asn Glu Arg Glu Leu Val
        35                  40                  45

Ala Thr Ile Asn Ser Gly Gly Phe Thr Asn Tyr Ala Asp Ser Val Lys
    50                  55                  60

Gly Arg Phe Thr Ile Ser Arg Asp Asn Ala Lys Asn Thr Gly Tyr Leu
65                  70                  75                  80

Gln Met Asn Ser Leu Lys Pro Glu Asp Thr Ala Val Tyr Phe Cys Ala
                85                  90                  95

Ala Thr Phe Leu Arg Ser Asp Gly Gln Pro Pro Ile Trp Gly Gln Gly
            100                 105                 110

Thr Gln Val Thr Val Ser Ser
        115


<210> SEQ ID NO 22
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Glu Ser Gly Gly Gly Leu Val Gln Ala Gly Gly
1               5                   10                  15

Ser Leu Arg Leu Ser Cys Ala Ala Ser Glu Tyr Ile Leu Ser Met Tyr
            20                  25                  30

Arg Met Ala Trp Tyr Arg Gln Ala Pro Gly Lys Val Arg Glu Leu Val
        35                  40                  45

Ala Asp Met Ser Ser Gly Gly Thr Thr Asn Tyr Ala Asp Phe Val Lys
    50                  55                  60

Gly Arg Phe Thr Ile Ser Arg Asp Asn Asp Arg Asn Thr Val Tyr Leu
65                  70                  75                  80

Gln Met Asn Arg Leu Gln Pro Glu Asp Thr Ala Ala Tyr Tyr Cys Asn
                85                  90                  95

Val Ala Gly Arg Thr Gly Pro Pro Ser Tyr Asp Ala Phe Asn Asn Trp
            100                 105                 110

Gly Gln Gly Thr Gln Val Thr Val Ser Ser
        115                 120


<210> SEQ ID NO 23
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Glu Ser Gly Gly Gly Leu Val Gln Pro Gly Ala
1               5                   10                  15
```

```
Ser Leu Arg Val Ser Cys Ala Ala Ser Glu Tyr Ile Leu Ser Met Tyr
            20                  25                  30

Arg Met Ala Trp Tyr Arg Gln Ala Pro Gly Lys Val Arg Glu Leu Val
        35                  40                  45

Ala Asp Met Ser Ser Gly Gly Thr Thr Asn Tyr Ala Asp Phe Val Lys
    50                  55                  60

Gly Arg Phe Thr Ile Ser Arg Asp Asn Asp Arg Asn Thr Val Tyr Leu
65                  70                  75                  80

Gln Met Asn Arg Leu Gln Pro Glu Asp Thr Ala Ala Tyr Tyr Cys Asn
                85                  90                  95

Val Ala Gly Arg Thr Gly Pro Pro Ser Tyr Asp Ala Phe Asn Asn Trp
            100                 105                 110

Gly Gln Gly Thr Gln Val Thr Val Ser Ser
        115                 120


<210> SEQ ID NO 24
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Glu Ser Gly Gly Gly Leu Val Gln Pro Gly Gly
1               5                   10                  15

Ser Leu Arg Leu Ser Cys Ala Ala Ser Glu Ser Ile Ser Ser Phe Ile
            20                  25                  30

Ala Val Gly Trp Tyr Arg Gln Ala Pro Gly Lys Glu Arg Glu Leu Val
        35                  40                  45

Ala Gly Ile Asn Arg Ser Gly Phe Thr Tyr Tyr Thr Asp Ser Val Lys
    50                  55                  60

Gly Arg Phe Ser Ile Ser Arg Asp Asn Ala Lys Asn Thr Val Leu Leu
65                  70                  75                  80

Gln Met Thr Ser Leu Lys Pro Glu Asp Thr Ala Val Tyr Tyr Cys Asn
                85                  90                  95

Ala Gly Gly Leu Tyr Phe Ser Asn Ala Tyr Thr Gln Gly Asp Tyr Trp
            100                 105                 110

Gly Gln Gly Thr Gln Val Thr Val Ser Ser
        115                 120


<210> SEQ ID NO 25
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Glu Ser Gly Gly Gly Leu Val Gln Thr Gly Gly
1               5                   10                  15

Ser Leu Arg Leu Ser Cys Ala Ala Ser Glu Ser Ile Ser Ser Phe Ile
            20                  25                  30

Ala Val Gly Trp Tyr Arg Gln Ala Pro Gly Lys Glu Arg Glu Leu Val
        35                  40                  45

Ala Gly Ile Asn Arg Ser Gly Phe Thr Tyr Tyr Thr Asp Ser Val Lys
    50                  55                  60
```

Gly Arg Phe Ser Ile Ser Arg Asp Asn Ala Lys Asn Thr Val Leu Leu
65 70 75 80

Gln Met Thr Ser Leu Lys Pro Glu Asp Thr Ala Val Tyr Tyr Cys Asn
85 90 95

Ala Gly Gly Leu Tyr Phe Ser Asn Ala Tyr Thr Gln Gly Asp Tyr Trp
100 105 110

Gly Gln Gly Thr Gln Val Thr Val Ser Ser
115 120

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Gln Val Gln Leu Gln Glu Ser Gly Gly Gly Leu Val Gln Ala Gly Gly
1 5 10 15

Ser Leu Arg Leu Ser Cys Ala Ala Ser Gly Ser Val Phe Arg Ala Asn
20 25 30

Val Met Gly Trp Tyr Arg Gln Ala Pro Gly Lys Gln His Glu Leu Val
35 40 45

Ala Arg Ile Asp Pro Gly Gly Thr Thr Thr Tyr Ala Asp Pro Val Lys
50 55 60

Gly Arg Phe Thr Ile Ser Arg Asp Asn Ala Lys Lys Thr Val Tyr Leu
65 70 75 80

Gln Met Asn Ser Leu Lys Pro Asp Asp Thr Ala Val Tyr Tyr Cys Asn
85 90 95

Ala Ile Ile Leu Leu Ser Gly Gly Pro Lys Asp Tyr Trp Gly Gln Gly
100 105 110

Thr Gln Val Thr Val Ser Ser
115

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

Gln Val Gln Leu Gln Glu Ser Gly Gly Gly Leu Val Gln Ala Gly Gly
1 5 10 15

Ser Leu Arg Leu Ser Cys Ala Pro Ser Gly Arg Thr Ser Ser Ile Phe
20 25 30

Gly Met Gly Trp Phe Arg Gln Ala Pro Gly Lys Glu Arg Glu Phe Val
35 40 45

Ala Ser Ile Asn Trp Ser Gly Gly Ser Thr Ser Tyr Ala Asp Ser Val
50 55 60

Lys Gly Arg Phe Thr Ile Ser Arg Asp Asn Ala Lys Asn Glu Met Tyr
65 70 75 80

Leu Gln Met Asn Ser Leu Lys Phe Glu Asp Thr Ala Val Tyr Val Cys
85 90 95

Ala Ala Ala Val Leu Thr Asn Lys Pro Ser Trp Asn Phe Trp Gly Gln
100 105 110

```
Gly Thr Gln Val Thr Val Ser Ser
        115                 120


<210> SEQ ID NO 28
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Gln Glu Ser Gly Gly Gly Leu Val Gln Ala Gly Gly
1               5                   10                  15

Ser Leu Arg Leu Ser Cys Ala Ala Ser Gly Pro Ile Phe Ser Asp Thr
            20                  25                  30

Ile Arg Thr Met Gly Trp Tyr Arg Gln Ala Ala Gly Lys Gln Arg Glu
        35                  40                  45

Leu Val Ala Thr Ile Ala Ser Phe Pro Ser Arg Thr Asn Tyr Val Asp
    50                  55                  60

Ser Val Lys Gly Arg Phe Thr Ile Ser Arg Asp Ile Ala Lys Asn Thr
65                  70                  75                  80

Val Tyr Leu Gln Met Asp Ser Leu Lys Pro Glu Asp Thr Ala Val Tyr
                85                  90                  95

Tyr Cys Asn Val Asp Leu Ala Ser Ile Pro Thr Lys Thr Tyr Trp Gly
            100                 105                 110

Gln Gly Thr Gln Val Thr Val Ser Ser
        115                 120


<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Gly Ile Asn
            20                  25                  30

Ala Met Gly Trp Tyr Arg Gln Ala Pro Gly Lys Gln Arg Glu Ser Val
        35                  40                  45

Ala Phe Ile Thr Ile Gly Gly Asn Thr Asn Tyr Leu Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Gly Leu Lys Pro Glu Asp Thr Ala Val Tyr Tyr Cys Asn
                85                  90                  95

Thr Asn Pro Pro Leu Ile Leu Thr Ala Gly Gly Leu Tyr Trp Gly Gln
            100                 105                 110

Gly Thr Gln Val Thr Val Ser Ser
        115                 120


<210> SEQ ID NO 30
<211> LENGTH: 121
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 30

Gln Val Gln Leu Gln Glu Ser Gly Gly Gly Leu Val Gln Pro Gly Gly
1 5 10 15

Ser Leu Arg Leu Ser Cys Ala Thr Ser Ala Asn Arg Phe Asn Ile Asn
20 25 30

Val Met Gly Trp Tyr Arg Gln Ala Pro Gly Gln Gln Arg Glu Leu Val
35 40 45

Ala Thr Ile Asn Ile Gly Gly Ser Thr Asp Tyr Ala Asp Ser Val Lys
50 55 60

Gly Arg Phe Thr Ile Ser Arg Asp Asn Ala Lys Asn Thr Val Tyr Leu
65 70 75 80

Gln Leu Ser Asp Leu Lys Pro Glu Asp Thr Ala Val Tyr Tyr Cys Asn
85 90 95

Val Lys Leu Arg Val Ser Gly Pro Thr Gly Pro Asn Val Tyr Trp Gly
100 105 110

Gln Gly Thr Gln Val Thr Val Ser Ser
115 120

<210> SEQ ID NO 31
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

Gln Val Gln Leu Gln Glu Ser Gly Gly Gly Leu Val Gln Ala Gly Gly
1 5 10 15

Ser Leu Lys Leu Ser Cys Thr Ala Ser Gly Thr Ile Leu Ser Thr Met
20 25 30

Ala Trp Tyr Arg Gln Ala Pro Gly Lys Gln Arg Glu Leu Val Ala Thr
35 40 45

Ile Ser Arg Gly Gly Thr Thr Asn Tyr Ser Asp Ser Val Lys Gly Arg
50 55 60

Phe Ala Ile Ser Arg Asp Ser Thr Lys Asn Thr Val Tyr Leu Gln Met
65 70 75 80

Asn Ser Leu Lys Pro Glu Asp Thr Ala Val Tyr Tyr Cys Asn Thr Pro
85 90 95

Leu Thr Asp Tyr Gly Met Gly Tyr Asn Trp Gly Gln Gly Thr Gln Val
100 105 110

Thr Val Ser Ser
115

<210> SEQ ID NO 32
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 32

Gln Val Gln Leu Gln Glu Ser Gly Gly Gly Leu Val Gln Ala Gly Gly
1 5 10 15

```
Ser Leu Arg Leu Ser Cys Ala Val Ser Gly Ser Ile Phe Ser Leu Asn
            20                  25                  30

Thr Leu Ala Trp Tyr Arg Gln Ala Pro Gly Arg Gln Arg Asp Leu Ile
        35                  40                  45

Ala Arg Ile Thr Gly Gly Gly Thr Thr Val Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Met Val Arg His Pro Ser Gly Ser Thr Tyr Glu Tyr Trp Gly Gln
            100                 105                 110

Gly Thr Gln Val Thr Val Ser Ser
        115                 120


<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Ile Phe Arg Gly Thr
            20                  25                  30

Thr Met Gly Trp Phe Arg Gln Ala Pro Gly Lys Gln Arg Glu Ser Val
        35                  40                  45

Ala Ser Ile Ser Pro Leu Gly Thr Thr Ser Tyr Ser Gly Ser Val Glu
    50                  55                  60

Gly Arg Phe Thr Val Ser Arg Asp Asn Ala Lys Asn Thr Leu Phe Leu
65                  70                  75                  80

Gln Met Asn Ser Leu Lys Ser Glu Asp Thr Ala Val Tyr Tyr Cys Asn
                85                  90                  95

Ala Ile Gln Val Thr Asn Val Gly Pro Arg Val Tyr Trp Gly Gln Gly
            100                 105                 110

Thr Gln Val Thr Val Ser Ser
        115


<210> SEQ ID NO 34
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Gln Glu Ser Gly Gly Gly Leu Val Gln Pro Gly Gly
1               5                   10                  15

Ser Leu Arg Leu Ser Cys Ala Ser Ser Gly Phe Thr Leu Asp Asp Tyr
            20                  25                  30

Thr Ile Gly Trp Phe Arg Gln Ala Pro Gly Lys Glu Arg Glu Gly Val
        35                  40                  45

Ser Cys Ile Ser Arg Arg Asp Asp Ser Thr Tyr Tyr Ala Asp Ser Val
    50                  55                  60
```

```
Lys Gly Arg Phe Thr Ile Ser Arg Asp Asn Ala Lys Asn Thr Val Asp
65                  70                  75                  80

Leu Gln Met Ile Ser Leu Arg Pro Glu Asp Thr Ala Val Tyr Tyr Cys
                85                  90                  95

Ala Ala Thr Pro Arg Ser Tyr Thr Leu Arg Cys Leu Gly Lys Phe Asp
            100                 105                 110

Phe Gln Gly Gln Gly Thr Gln Val Thr Val Ser Ser
        115                 120


<210> SEQ ID NO 35
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Val Arg Met Thr
            20                  25                  30

Asn Met Ala Trp Tyr Arg Gln Ala Pro Gly Lys Gln Arg Glu Phe Val
        35                  40                  45

Ala Thr Ile Ser Ala Gly Gly Ser Thr Thr Tyr Val Asp Ser Val Lys
    50                  55                  60

Asp Arg Phe Thr Ile Ser Arg Asp Asn Thr Lys Asn Thr Val Tyr Leu
65                  70                  75                  80

Gln Met Asn Tyr Leu Lys Pro Glu Asp Thr Ala Val Tyr Tyr Cys Ala
                85                  90                  95

Thr Gly Ser Ile Leu Thr Asn Arg Gly Ala Ile Pro Gly Ser Trp Gly
            100                 105                 110

His Gly Thr Gln Val Thr Val Ser Ser
        115                 120


<210> SEQ ID NO 36
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Glu Ser Gly Gly Gly Leu Val Gln Ala Gly Gly
1               5                   10                  15

Ser Leu Arg Leu Ser Cys Ala Ala Pro Gly Phe Ala Phe Asn Asp His
            20                  25                  30

Ala Ile Leu Trp Phe Arg Gln Ala Pro Gly Lys Glu Arg Glu Gly Val
        35                  40                  45

Ser Glu Ile Cys Arg Asp Gly Thr Thr Tyr Tyr Thr Asp Ser Val Lys
    50                  55                  60

Gly Arg Phe Thr Ile Ser Ser Asp Asn Ala Lys Asn Thr Val Tyr Leu
65                  70                  75                  80

Gln Met Asn Ser Val Lys Thr Asp Asp Thr Ala Val Tyr Tyr Cys Ala
                85                  90                  95

Val Asp Arg Arg Arg Tyr Tyr Cys Ser Gly Asn Arg Ala Phe Ser Ser
            100                 105                 110
```

```
Asp Tyr Tyr Tyr Trp Gly Gln Gly Thr Gln Val Thr Val Ser Ser
        115                 120                 125


<210> SEQ ID NO 37
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Glu Ser Gly Gly Gly Leu Val Gln Ala Gly Gly
1               5                   10                  15

Ser Leu Arg Leu Ser Cys Val His Ser Gly Ser Ile Phe Arg Ala Ser
            20                  25                  30

Thr Met Ala Trp Tyr Arg Gln Ala Pro Gly Lys Gln Arg Glu Leu Val
        35                  40                  45

Ala Gln Ile Met Ser Gly Gly Gly Thr Asn Tyr Ala Gly Ser Val Lys
    50                  55                  60

Gly Arg Phe Thr Ile Ser Arg Asp Asn Ala Asn Asn Thr Val Tyr Leu
65                  70                  75                  80

Gln Met Asn Ser Leu Lys Pro Glu Asp Thr Ala Val Tyr Tyr Cys Asn
                85                  90                  95

Ala Ala Gln Ile Thr Ser Trp Gly Pro Lys Val Tyr Trp Gly Gln Gly
            100                 105                 110

Thr Gln Val Thr Val Ser Ser
        115


<210> SEQ ID NO 38
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Ile Asn Ser Ile Asn
            20                  25                  30

Thr Met Gly Trp Tyr Arg Gln Ala Pro Gly Asn Gln Arg Glu Leu Val
        35                  40                  45

Ala Glu Ile Thr Arg Gly Gly Thr Thr Asn Tyr Ala Asp Ser Val Gln
    50                  55                  60

Gly Arg Tyr Ala Ile Ser Arg Asp Asn Ala Lys Asn Leu Val Tyr Leu
65                  70                  75                  80

Gln Met Asn Ser Leu Lys Pro Glu Asp Thr Asp Val Tyr Tyr Cys Asn
                85                  90                  95

Ala Gln Thr Phe Pro Thr Phe Ser Arg Pro Thr Gly Leu Asp Tyr Trp
            100                 105                 110

Gly Gln Gly Thr Gln Val Thr Val Ser Ser
        115                 120


<210> SEQ ID NO 39
<211> LENGTH: 10
<212> TYPE: PRT
<213> ORGANISM: Artificial Sequence
```

<220> FEATURE:
<223> OTHER INFORMATION: Description of Artificial Sequence: Synthetic
peptide

<400> SEQUENCE: 39

Gly Phe Ile Phe Arg Ala Ala Ser Met Ala
1 5 10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Gly Phe Ile Phe Arg Ala Ala Ser Met Gly
1 5 10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Gly Phe Ile Phe Arg Ala Ala Ser Met Asp
1 5 10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Gly Phe Ile Phe Arg Ala Ala Ser Met Gly
1 5 10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Gly Phe Ile Phe Arg Ala Ala Ser Met Asp
1 5 10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Gly Asp Thr Phe Leu Arg Tyr Ala Met Gly
1 5 10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Asp Thr Phe Leu Arg Tyr Ala Met Gly
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Asp Thr Phe Leu Arg Tyr Ala Met Gly
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Asp Thr Phe Leu Arg Tyr Ala Met Gly
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Phe Thr Phe Ser Ser Tyr Tyr Met Ser
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Thr Phe Ser Ser Tyr Tyr Met Ser
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Phe Thr Phe Ser Asp Trp Ala Met Ser
1 5 10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Gly Phe Thr Phe Ser Asp Trp Ala Met Ser
1 5 10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Gly Asn Val Phe Arg Ala Ala Thr Met Ala
1 5 10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Gly Asn Val Phe Arg Ala Ala Thr Met Ala
1 5 10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Gly Asn Val Phe Arg Ala Ala Thr Met Ala
1 5 10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Gly Phe Ala Phe Gly Asn His Trp Met Tyr
1 5 10

<210> SEQ ID NO 56
<211> LENGTH: 10
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 56

Gly Phe Ala Phe Gly Asn His Trp Met Tyr
1 5 10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Gly Phe Ala Phe Gly Asn His Trp Met Tyr
1 5 10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Gly Phe Ile Phe Arg Ala Ala Ser Ile Ser
1 5 10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Gly Phe Ile Phe Arg Ala Ala Ser Met Gly
1 5 10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Glu Tyr Ile Leu Ser Met Tyr Arg Met Ala
1 5 10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Glu Tyr Ile Leu Ser Met Tyr Arg Met Ala
1 5 10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Glu Ser Ile Ser Ser Phe Ile Ala Val Gly
1               5                   10
```

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Glu Ser Ile Ser Ser Phe Ile Ala Val Gly
1               5                   10
```

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Gly Ser Val Phe Arg Ala Asn Val Met Gly
1               5                   10
```

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Gly Arg Thr Ser Ser Ile Phe Gly Met Gly
1               5                   10
```

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Gly Pro Ile Phe Ser Asp Thr Ile Arg Thr Met Gly
1               5                   10
```

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ser Ile Phe Gly Ile Asn Ala Met Gly
1 5 10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Ala Asn Arg Phe Asn Ile Asn Val Met Gly
1 5 10

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Gly Thr Ile Leu Ser Thr Met Ala
1 5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Gly Ser Ile Phe Ser Leu Asn Thr Leu Ala
1 5 10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Gly Ile Ile Phe Arg Gly Thr Thr Met Gly
1 5 10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Gly Phe Thr Leu Asp Asp Tyr Thr Ile Gly
1 5 10

<210> SEQ ID NO 73
<211> LENGTH: 10

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Gly Asn Ile Val Arg Met Thr Asn Met Ala
1 5 10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Gly Phe Ala Phe Asn Asp His Ala Ile Leu
1 5 10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Gly Ser Ile Phe Arg Ala Ser Thr Met Ala
1 5 10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Gly Arg Ile Asn Ser Ile Asn Thr Met Gly
1 5 10

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Ser Ile Ser Ser Gly Ala Phe Thr Asn Tyr Ala Asp Ser Val Lys Ala
1 5 10 15

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Thr Val Ser Ser Gly Asp Phe Thr Asn Tyr Ala Asp Ser Val Lys Gly
1 5 10 15

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Thr Ile Ser Ser Gly Gly Phe Thr Asn Tyr Ala Asp Ser Val Lys Gly
1 5 10 15

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Thr Val Ser Ser Gly Gly Phe Thr Asn Tyr Ala Asp Ser Val Lys Gly
1 5 10 15

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Thr Ile Ser Ser Thr Gly Phe Thr Asn Tyr Ala Asn Ser Val Lys Gly
1 5 10 15

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Ala Ile Thr Trp Asn Gly Gly Asn Thr Asp Tyr Ala Gly Ser Leu Lys
1 5 10 15

Gly

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Ala Ile Thr Trp Asn Gly Gly Asn Thr Asp Tyr Ala Gly Ser Leu Lys
1 5 10 15

Gly

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Ala Ile Thr Trp Asn Gly Gly Asn Thr Asp Tyr Ala Asp Ser Leu Lys
1 5 10 15

Gly

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Ala Ile Thr Trp Asn Gly Gly Asn Thr Asp Tyr Ala Gly Ser Leu Lys
1 5 10 15

Gly

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Gly Ile His Tyr Thr Gly Asp Trp Thr Asn Tyr Ala Asp Ser Val Lys
1 5 10 15

Gly

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Gly Ile His Tyr Thr Gly Asp Trp Thr Asn Tyr Ala Asp Ser Val Lys
1 5 10 15

Gly

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Gly Ile His Tyr Gly Asp His Thr Thr His Tyr Ala Asp Phe Val Lys
1 5 10 15

Gly

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Ser Ile His Tyr Gly Asp His Thr Thr His Tyr Ala Asp Phe Val Lys
1 5 10 15

Gly

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Thr Ile Ala Ser Gly Gly Thr Thr Asn Tyr Ala Asp Phe Val Lys Gly
1 5 10 15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Thr Ile Ala Ser Gly Gly Thr Thr Asn Tyr Ala Asp Phe Val Lys Gly
1 5 10 15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Thr Ile Ala Ser Gly Gly Thr Thr Asn Tyr Ala Asp Phe Val Lys Gly
1 5 10 15

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Ser Ile Ser Ser Gly Gly Ser Thr Asn Tyr Val Asp Ser Val Lys Gly
1 5 10 15

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Ser Ile Ser Ser Gly Gly Ser Thr Asn Tyr Val Asp Ser Val Lys Gly
1 5 10 15

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Ser Ile Ser Ser Gly Gly Ser Thr Asn Tyr Val Asp Ser Val Lys Gly
1 5 10 15

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Thr Ile Asn Ser Gly Gly Phe Thr Asn Tyr Ala Asp Ser Val Leu Gly
1 5 10 15

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Thr Ile Asn Ser Gly Gly Phe Thr Asn Tyr Ala Asp Ser Val Lys Gly
1 5 10 15

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Asp Met Ser Ser Gly Gly Thr Thr Asn Tyr Ala Asp Phe Val Lys Gly
1 5 10 15

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Asp Met Ser Ser Gly Gly Thr Thr Asn Tyr Ala Asp Phe Val Lys Gly
1 5 10 15

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Gly Ile Asn Arg Ser Gly Phe Thr Tyr Tyr Thr Asp Ser Val Lys Gly
1 5 10 15

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Gly Ile Asn Arg Ser Gly Phe Thr Tyr Tyr Thr Asp Ser Val Lys Gly
1 5 10 15

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Arg Ile Asp Pro Gly Gly Thr Thr Thr Tyr Ala Asp Pro Val Lys Gly
1 5 10 15

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Ser Ile Asn Trp Ser Gly Gly Ser Thr Ser Tyr Ala Asp Ser Val Lys
1 5 10 15

Gly

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Thr Ile Ala Ser Phe Pro Ser Arg Thr Asn Tyr Val Asp Ser Val Lys
1 5 10 15

Gly

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Phe Ile Thr Ile Gly Gly Asn Thr Asn Tyr Leu Asp Ser Val Lys Gly
1 5 10 15

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Thr Ile Asn Ile Gly Gly Ser Thr Asp Tyr Ala Asp Ser Val Lys Gly
1 5 10 15

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Thr Ile Ser Arg Gly Gly Thr Thr Asn Tyr Ser Asp Ser Val Lys Gly
1 5 10 15

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Arg Ile Thr Gly Gly Gly Thr Thr Val Tyr Ala Asp Ser Val Lys Gly
1 5 10 15

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Ser Ile Ser Pro Leu Gly Thr Thr Ser Tyr Ser Gly Ser Val Glu Gly
1 5 10 15

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Cys Ile Ser Arg Arg Asp Asp Ser Thr Tyr Tyr Ala Asp Ser Val Lys
1 5 10 15

Gly

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Thr Ile Ser Ala Gly Gly Ser Thr Thr Tyr Val Asp Ser Val Lys Asp
1 5 10 15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Glu Ile Cys Arg Asp Gly Thr Thr Tyr Tyr Thr Asp Ser Val Lys Gly
1 5 10 15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Gln Ile Met Ser Gly Gly Gly Thr Asn Tyr Ala Gly Ser Val Lys Gly
1 5 10 15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Glu Ile Thr Arg Gly Gly Thr Thr Asn Tyr Ala Asp Ser Val Gln Gly
1 5 10 15

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Thr Phe Leu Arg Ser Asp Gly His His Thr Ile
1 5 10

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Thr Phe Val Arg Ser Asp Gly His His Thr Ile
1 5 10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Thr Phe Leu Arg Ser Asp Gly His His Thr Ile
1 5 10

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Thr Phe Val Arg Ser Asp Gly His His Thr Ile
1 5 10

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Thr Phe Leu Arg Ser Asp Gly Gln His Ser Ile
1 5 10

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

Asp Leu Thr Phe Gly Leu Ala Ser Ser His Tyr Gln Tyr Asp Tyr
1 5 10 15

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

Asp Leu Thr Phe Gly Leu Ala Ser Ser His Tyr Gln Tyr Asp Tyr
1 5 10 15

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Asp Leu Thr Phe Gly Leu Ala Ser Ser His Tyr Gln Tyr Asp Tyr
1 5 10 15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Asp Leu Thr Phe Gly Leu Ala Ser Ser His Tyr Gln Tyr Asp Tyr
1 5 10 15

<210> SEQ ID NO 124
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Gly Ser Asp
1

<210> SEQ ID NO 125
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Gly Ser Asp
1

<210> SEQ ID NO 126
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Gly Ser Thr
1

<210> SEQ ID NO 127
<211> LENGTH: 3

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Gly Thr Thr
1

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Gly Tyr Leu Thr Ser Leu Gly Pro Lys Asn Tyr
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Gly Tyr Leu Thr Ser Leu Gly Pro Lys Asn Tyr
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Leu Tyr Leu Thr Ser Leu Gly Pro Lys Ser Tyr
1               5                   10

<210> SEQ ID NO 131
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 131

Ser Asp Asn
1

<210> SEQ ID NO 132
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Ser Asp Asn
1

<210> SEQ ID NO 133
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Ser Asp Asn
1

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Thr Phe Leu Arg Ser Asp Gly Gln Pro Pro Ile
1 5 10

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Thr Phe Leu Arg Ser Asp Gly Gln Pro Pro Ile
1 5 10

<210> SEQ ID NO 136
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Ala Gly Arg Thr Gly Pro Pro Ser Tyr Asp Ala Phe Asn Asn
1 5 10

<210> SEQ ID NO 137
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

Ala Gly Arg Thr Gly Pro Pro Ser Tyr Asp Ala Phe Asn Asn
1 5 10

<210> SEQ ID NO 138
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Gly Gly Leu Tyr Phe Ser Asn Ala Tyr Thr Gln Gly Asp Tyr
1 5 10

<210> SEQ ID NO 139
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Gly Gly Leu Tyr Phe Ser Asn Ala Tyr Thr Gln Gly Asp Tyr
1 5 10

<210> SEQ ID NO 140
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 140

Ile Ile Leu Leu Ser Gly Gly Pro Lys Asp Tyr
1 5 10

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Ala Val Leu Thr Asn Lys Pro Ser Trp Asn Phe
1 5 10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 142

Asp Leu Ala Ser Ile Pro Thr Lys Thr Tyr
1 5 10

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

Asn Pro Pro Leu Ile Leu Thr Ala Gly Gly Leu Tyr
1               5                   10

<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Lys Leu Arg Val Ser Gly Pro Thr Gly Pro Asn Val Tyr
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Pro Leu Thr Asp Tyr Gly Met Gly Tyr Asn
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Met Val Arg His Pro Ser Gly Ser Thr Tyr Glu Tyr
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ile Gln Val Thr Asn Val Gly Pro Arg Val Tyr
1               5                   10

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Thr Pro Arg Ser Tyr Thr Leu Arg Cys Leu Gly Lys Phe Asp Phe
1               5                   10                  15

<210> SEQ ID NO 149
<211> LENGTH: 13

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Gly Ser Ile Leu Thr Asn Arg Gly Ala Ile Pro Gly Ser
1 5 10

<210> SEQ ID NO 150
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Asp Arg Arg Arg Tyr Tyr Cys Ser Gly Asn Arg Ala Phe Ser Ser Asp
1 5 10 15

Tyr Tyr Tyr

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Ala Gln Ile Thr Ser Trp Gly Pro Lys Val Tyr
1 5 10

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Gln Thr Phe Pro Thr Phe Ser Arg Pro Thr Gly Leu Asp Tyr
1 5 10

<210> SEQ ID NO 153
<211> LENGTH: 390
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 153

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

```
Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Gln Val Gln Leu Gln Glu Ser
            260                 265                 270

Gly Gly Gly Leu Val Gln Ala Gly Gly Ser Leu Arg Leu Ser Cys Ala
        275                 280                 285

Ala Ser Gly Ser Val Phe Arg Ala Asn Val Met Gly Trp Tyr Arg Gln
    290                 295                 300

Ala Pro Gly Lys Gln His Glu Leu Val Ala Arg Ile Asp Pro Gly Gly
305                 310                 315                 320

Thr Thr Thr Tyr Ala Asp Pro Val Lys Gly Arg Phe Thr Ile Ser Arg
                325                 330                 335

Asp Asn Ala Lys Lys Thr Val Tyr Leu Gln Met Asn Ser Leu Lys Pro
            340                 345                 350

Asp Asp Thr Ala Val Tyr Tyr Cys Asn Ala Ile Ile Leu Leu Ser Gly
        355                 360                 365

Gly Pro Lys Asp Tyr Trp Gly Gln Gly Thr Gln Val Thr Val Ser Ser
    370                 375                 380

His His His His His His
385                 390
```

<210> SEQ ID NO 154
<211> LENGTH: 395
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 154

```
Val Val Gly Gly Gly Gly Thr Gln Thr Val Val Thr Gln Glu Pro Ser
1               5                   10                  15
```

```
Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Gln Val Gln Leu Gln Glu Ser
            260                 265                 270

Gly Gly Gly Leu Val Gln Pro Gly Gly Ser Leu Arg Leu Ser Cys Ala
        275                 280                 285

Ser Ser Gly Phe Thr Leu Asp Asp Tyr Thr Ile Gly Trp Phe Arg Gln
    290                 295                 300

Ala Pro Gly Lys Glu Arg Glu Gly Val Ser Cys Ile Ser Arg Arg Asp
305                 310                 315                 320

Asp Ser Thr Tyr Tyr Ala Asp Ser Val Lys Gly Arg Phe Thr Ile Ser
                325                 330                 335

Arg Asp Asn Ala Lys Asn Thr Val Asp Leu Gln Met Ile Ser Leu Arg
            340                 345                 350

Pro Glu Asp Thr Ala Val Tyr Tyr Cys Ala Ala Thr Pro Arg Ser Tyr
        355                 360                 365

Thr Leu Arg Cys Leu Gly Lys Phe Asp Phe Gln Gly Gln Gly Thr Gln
    370                 375                 380

Val Thr Val Ser Ser His His His His His His
385                 390                 395
```

<210> SEQ ID NO 155
<211> LENGTH: 392
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 155

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Ala Gly Gly Ser Leu Arg Leu Ser Cys Ala
275 280 285

Ala Ser Gly Asn Ile Val Arg Met Thr Asn Met Ala Trp Tyr Arg Gln
290 295 300

Ala Pro Gly Lys Gln Arg Glu Phe Val Ala Thr Ile Ser Ala Gly Gly
305 310 315 320

Ser Thr Thr Tyr Val Asp Ser Val Lys Asp Arg Phe Thr Ile Ser Arg
325 330 335

Asp Asn Thr Lys Asn Thr Val Tyr Leu Gln Met Asn Tyr Leu Lys Pro
340 345 350

Glu Asp Thr Ala Val Tyr Tyr Cys Ala Thr Gly Ser Ile Leu Thr Asn
355 360 365

Arg Gly Ala Ile Pro Gly Ser Trp Gly His Gly Thr Gln Val Thr Val
370 375 380

Ser Ser His His His His His His
385 390

<210> SEQ ID NO 156
<211> LENGTH: 390
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 156

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Ala Gly Gly Ser Leu Arg Leu Ser Cys Ala
275 280 285

Ala Ser Gly Phe Ile Phe Arg Ala Ala Ser Ile Ser Trp Tyr Arg Gln
290 295 300

Ser Pro Gly Asn Glu Arg Glu Leu Val Ala Thr Ile Asn Ser Gly Gly
305 310 315 320

Phe Thr Asn Tyr Ala Asp Ser Val Leu Gly Arg Phe Thr Ile Ser Arg
325 330 335

Asp Asn Ala Lys Asn Thr Gly Tyr Leu Gln Met Asn Ser Leu Lys Pro
340 345 350

Glu Asp Thr Ala Val Tyr Phe Cys Ala Ala Thr Phe Leu Arg Ser Asp
355 360 365

Gly Gln Pro Pro Ile Trp Gly Gln Gly Thr Gln Val Thr Val Ser Ser
370 375 380

His His His His His His
385 390

<210> SEQ ID NO 157
<211> LENGTH: 390
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Ala Gly Gly Ser Leu Arg Leu Ser Cys Ala
275 280 285

Ala Ser Gly Asn Val Phe Arg Ala Ala Thr Met Ala Trp Tyr Arg Gln
290 295 300

Val Pro Glu Lys Gln Arg Glu Met Val Ala Thr Ile Ala Ser Gly Gly
305 310 315 320

Thr Thr Asn Tyr Ala Asp Phe Val Lys Gly Arg Phe Thr Ile Ser Arg
325 330 335

Asp Asn Ala Lys Asn Thr Val Tyr Leu Gln Met Asn Thr Leu Lys Pro
340 345 350

Glu Asp Thr Ala Val Tyr Tyr Cys Asn Ala Leu Tyr Leu Thr Ser Leu
355 360 365

Gly Pro Lys Ser Tyr Trp Gly Gln Gly Thr Gln Val Thr Val Ser Ser
370 375 380

His His His His His His
385 390

<210> SEQ ID NO 158
<211> LENGTH: 398
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Ala Gly Gly Ser Leu Arg Leu Ser Cys Ala
275 280 285

Ala Pro Gly Phe Ala Phe Asn Asp His Ala Ile Leu Trp Phe Arg Gln
290 295 300

Ala Pro Gly Lys Glu Arg Glu Gly Val Ser Glu Ile Cys Arg Asp Gly
305 310 315 320

Thr Thr Tyr Tyr Thr Asp Ser Val Lys Gly Arg Phe Thr Ile Ser Ser
325 330 335

Asp Asn Ala Lys Asn Thr Val Tyr Leu Gln Met Asn Ser Val Lys Thr
340 345 350

Asp Asp Thr Ala Val Tyr Tyr Cys Ala Val Asp Arg Arg Arg Tyr Tyr
355 360 365

Cys Ser Gly Asn Arg Ala Phe Ser Ser Asp Tyr Tyr Tyr Trp Gly Gln
370 375 380

Gly Thr Gln Val Thr Val Ser Ser His His His His His His
385 390 395

<210> SEQ ID NO 159
<211> LENGTH: 382
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 159

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Pro Gly Gly Ser Leu Arg Leu Ser Cys Ala
275 280 285

Ala Ser Gly Phe Ala Phe Gly Asn His Trp Met Tyr Trp Tyr Arg Gln
290 295 300

Ala Pro Gly Arg Gly Arg Glu Leu Val Ala Ser Ile Ser Ser Gly Gly
305 310 315 320

Ser Thr Asn Tyr Val Asp Ser Val Lys Gly Arg Phe Thr Ile Ser Arg
325 330 335

Asp Asn Ala Arg Asn Thr Val Tyr Leu Gln Met Tyr Ser Leu Lys Pro
340 345 350

Glu Asp Thr Ala Val Tyr Tyr Cys Gly Thr Ser Asp Asn Trp Gly Gln
355 360 365

Gly Thr Gln Val Thr Val Ser Ser His His His His His His
370 375 380

<210> SEQ ID NO 160
<211> LENGTH: 395
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 160

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Pro Gly Gly Ser Leu Arg Leu Ser Cys Ala
275 280 285

Ala Ser Gly Asp Thr Phe Leu Arg Tyr Ala Met Gly Trp Phe Arg Gln
290 295 300

Ala Pro Gly Lys Glu Arg Glu Phe Val Ala Ala Ile Thr Trp Asn Gly
305 310 315 320

Gly Asn Thr Asp Tyr Ala Gly Ser Leu Lys Gly Arg Phe Thr Ile Ser
325 330 335

Arg Asp Asn Thr Lys Asn Thr Val Tyr Leu Gln Met Asn Ser Leu Lys
340 345 350

Pro Glu Asp Thr Ala Val Tyr Tyr Cys Ala Ala Asp Leu Thr Phe Gly
355 360 365

Leu Ala Ser Ser His Tyr Gln Tyr Asp Tyr Trp Gly Gln Gly Thr Gln
370 375 380

Val Thr Val Ser Ser His His His His His His
385 390 395

<210> SEQ ID NO 161
<211> LENGTH: 390
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 161

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Gln Val Gln Leu Gln Glu Ser
            260                 265                 270

Gly Gly Gly Leu Val Gln Ala Gly Gly Ser Leu Arg Leu Ser Cys Ala
        275                 280                 285

Ala Ser Gly Phe Ile Phe Arg Ala Ala Ser Met Asp Trp Tyr Arg Gln
    290                 295                 300

Phe Pro Gly Asn Glu Arg Glu Ser Ile Ala Thr Ile Ser Ser Gly Gly
305                 310                 315                 320

Phe Thr Asn Tyr Ala Asp Ser Val Lys Gly Arg Phe Thr Ile Ser Arg
                325                 330                 335

Asp Asn Ala Lys Asn Thr Val Tyr Leu Gln Met Asn Ser Leu Lys Pro
            340                 345                 350

Glu Asp Thr Ala Val Tyr Phe Cys Gly Ala Thr Phe Leu Arg Ser Asp
        355                 360                 365

Gly His His Thr Ile Asn Gly Gln Gly Thr Gln Val Thr Val Ser Ser
    370                 375                 380

His His His His His His
385                 390

<210> SEQ ID NO 162
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

```
Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Gln Val Gln Leu Gln Glu Ser
            260                 265                 270

Gly Gly Gly Leu Val Gln Ala Gly Gly Ser Leu Arg Leu Ser Cys Ala
        275                 280                 285

Ala Ser Gly Phe Ile Phe Arg Ala Ala Ser Met Gly Trp Phe Arg Gln
    290                 295                 300

Ser Pro Gly Asn Glu Arg Glu Leu Val Ala Thr Val Ser Ser Gly Gly
305                 310                 315                 320

Phe Thr Asn Tyr Ala Asp Ser Val Lys Gly Arg Phe Thr Ile Ser Arg
                325                 330                 335

Asp Asn Ala Lys Asn Thr Val Tyr Leu Gln Met Asn Ser Leu Lys Pro
            340                 345                 350

Glu Asp Thr Ala Val Tyr Phe Cys Gly Ala Thr Phe Val Arg Ser Asp
        355                 360                 365

Gly His His Thr Ile Tyr Gly Gln Gly Thr Gln Val Thr Val Ser Ser
    370                 375                 380

His His His His His His
385                 390
```

<210> SEQ ID NO 163
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30
```

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Ala Gly Gly Ser Leu Arg Leu Ser Cys Val
275 280 285

His Ser Gly Ser Ile Phe Arg Ala Ser Thr Met Ala Trp Tyr Arg Gln
290 295 300

Ala Pro Gly Lys Gln Arg Glu Leu Val Ala Gln Ile Met Ser Gly Gly
305 310 315 320

Gly Thr Asn Tyr Ala Gly Ser Val Lys Gly Arg Phe Thr Ile Ser Arg
325 330 335

Asp Asn Ala Asn Asn Thr Val Tyr Leu Gln Met Asn Ser Leu Lys Pro
340 345 350

Glu Asp Thr Ala Val Tyr Tyr Cys Asn Ala Ala Gln Ile Thr Ser Trp
355 360 365

Gly Pro Lys Val Tyr Trp Gly Gln Gly Thr Gln Val Thr Val Ser Ser
370 375 380

His His His His His His
385 390

<210> SEQ ID NO 164
<211> LENGTH: 383
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 164

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Pro Gly Gly Ser Leu Arg Leu Ser Cys Ala
275 280 285

Ala Ser Gly Phe Thr Phe Ser Asp Trp Ala Met Ser Trp Val Arg Gln
290 295 300

Ala Pro Gly Lys Gly Leu Glu Trp Val Ser Ser Ile His Tyr Gly Asp
305 310 315 320

His Thr Thr His Tyr Ala Asp Phe Val Lys Gly Arg Phe Thr Ile Ser
325 330 335

Arg Asp Asp Ala Lys Asn Thr Leu Tyr Leu Gln Met Asn Ser Leu Lys
340 345 350

Pro Glu Asp Thr Ala Val Tyr Tyr Cys Glu Lys Gly Thr Thr Arg Gly
355 360 365

Gln Gly Thr Gln Val Thr Val Ser Ser His His His His His His
370 375 380

<210> SEQ ID NO 165
<211> LENGTH: 393
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 165

```
Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Gln Val Gln Leu Gln Glu Ser
            260                 265                 270

Gly Gly Gly Leu Val Gln Pro Gly Ala Ser Leu Arg Val Ser Cys Ala
        275                 280                 285

Ala Ser Glu Tyr Ile Leu Ser Met Tyr Arg Met Ala Trp Tyr Arg Gln
    290                 295                 300

Ala Pro Gly Lys Val Arg Glu Leu Val Ala Asp Met Ser Ser Gly Gly
305                 310                 315                 320

Thr Thr Asn Tyr Ala Asp Phe Val Lys Gly Arg Phe Thr Ile Ser Arg
                325                 330                 335

Asp Asn Asp Arg Asn Thr Val Tyr Leu Gln Met Asn Arg Leu Gln Pro
            340                 345                 350

Glu Asp Thr Ala Ala Tyr Tyr Cys Asn Val Ala Gly Arg Thr Gly Pro
        355                 360                 365

Pro Ser Tyr Asp Ala Phe Asn Asn Trp Gly Gln Gly Thr Gln Val Thr
    370                 375                 380
```

Val Ser Ser His His His His His His
385 390

<210> SEQ ID NO 166
<211> LENGTH: 390
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 166

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Ala Gly Gly Ser Leu Arg Leu Ser Cys Ala
275 280 285

Ala Ser Gly Phe Ile Phe Arg Ala Ala Ser Met Asp Trp Tyr Arg Gln
290 295 300

Ser Pro Gly Thr Gln Pro Glu Leu Val Ala Thr Ile Ser Ser Thr Gly
305 310 315 320

Phe Thr Asn Tyr Ala Asn Ser Val Lys Gly Arg Phe Thr Ile Ser Arg
325 330 335

Asp Asn Ala Lys Asn Thr Val Tyr Leu Gln Met Asn Ser Leu Lys Pro
340 345 350

```
Glu Asp Thr Ala Val Tyr Phe Cys Gly Ala Thr Phe Leu Arg Ser Asp
        355                 360                 365

Gly Gln His Ser Ile Tyr Gly Gln Gly Thr Gln Val Thr Val Ser Ser
    370                 375                 380

His His His His His His
385                 390


<210> SEQ ID NO 167
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Gln Val Gln Leu Gln Glu Ser
            260                 265                 270

Gly Gly Gly Leu Val Gln Pro Gly Gly Ser Leu Arg Leu Ser Cys Ala
        275                 280                 285

Ala Ser Gly Arg Ile Asn Ser Ile Asn Thr Met Gly Trp Tyr Arg Gln
    290                 295                 300

Ala Pro Gly Asn Gln Arg Glu Leu Val Ala Glu Ile Thr Arg Gly Gly
305                 310                 315                 320
```

```
Thr Thr Asn Tyr Ala Asp Ser Val Gln Gly Arg Tyr Ala Ile Ser Arg
                325                 330                 335

Asp Asn Ala Lys Asn Leu Val Tyr Leu Gln Met Asn Ser Leu Lys Pro
            340                 345                 350

Glu Asp Thr Asp Val Tyr Tyr Cys Asn Ala Gln Thr Phe Pro Thr Phe
        355                 360                 365

Ser Arg Pro Thr Gly Leu Asp Tyr Trp Gly Gln Gly Thr Gln Val Thr
    370                 375                 380

Val Ser Ser His His His His His His
385                 390


<210> SEQ ID NO 168
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Gln Val Gln Leu Gln Glu Ser
            260                 265                 270
```

```
Gly Gly Gly Leu Val Gln Pro Gly Gly Ser Leu Arg Leu Ser Cys Ala
        275                 280                 285

Ala Ser Glu Ser Ile Ser Ser Phe Ile Ala Val Gly Trp Tyr Arg Gln
    290                 295                 300

Ala Pro Gly Lys Glu Arg Glu Leu Val Ala Gly Ile Asn Arg Ser Gly
305                 310                 315                 320

Phe Thr Tyr Tyr Thr Asp Ser Val Lys Gly Arg Phe Ser Ile Ser Arg
                325                 330                 335

Asp Asn Ala Lys Asn Thr Val Leu Leu Gln Met Thr Ser Leu Lys Pro
            340                 345                 350

Glu Asp Thr Ala Val Tyr Tyr Cys Asn Ala Gly Gly Leu Tyr Phe Ser
        355                 360                 365

Asn Ala Tyr Thr Gln Gly Asp Tyr Trp Gly Gln Gly Thr Gln Val Thr
    370                 375                 380

Val Ser Ser His His His His His His
385                 390
```

<210> SEQ ID NO 169
<211> LENGTH: 390
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 169

```
Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220
```

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Ala Gly Gly Ser Leu Lys Leu Ser Cys Ala
275 280 285

Ala Ser Gly Asn Val Phe Arg Ala Ala Thr Met Ala Trp Tyr Arg Gln
290 295 300

Ala Pro Glu Lys Gln Arg Glu Met Val Ala Thr Ile Ala Ser Gly Gly
305 310 315 320

Thr Thr Asn Tyr Ala Asp Phe Val Lys Gly Arg Phe Thr Ile Ser Arg
325 330 335

Asp Asn Ala Lys Asn Thr Val Tyr Leu Gln Met Asn Thr Leu Lys Pro
340 345 350

Glu Asp Thr Ala Val Tyr Tyr Cys Asn Ala Gly Tyr Leu Thr Ser Leu
355 360 365

Gly Pro Lys Asn Tyr Trp Gly Gln Gly Thr Gln Val Thr Val Ser Ser
370 375 380

His His His His His His
385 390

<210> SEQ ID NO 170
<211> LENGTH: 383
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 170

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

```
Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Gln Val Gln Leu Gln Glu Ser
            260                 265                 270

Gly Gly Gly Ser Val Gln Ala Gly Gly Ser Leu Arg Leu Ser Cys Ala
        275                 280                 285

Ala Ser Gly Phe Thr Phe Ser Ser Tyr Tyr Met Ser Trp Val Arg Gln
    290                 295                 300

Ala Pro Gly Lys Gly Leu Glu Trp Val Ser Gly Ile His Tyr Thr Gly
305                 310                 315                 320

Asp Trp Thr Asn Tyr Ala Asp Ser Val Lys Gly Arg Phe Thr Ile Ser
                325                 330                 335

Arg Asp Asn Ala Lys Asn Glu Leu Tyr Leu Glu Met Asn Asn Leu Lys
            340                 345                 350

Pro Glu Asp Thr Ala Val Tyr Tyr Cys Ala Arg Gly Ser Asp Lys Gly
        355                 360                 365

Gln Gly Thr Gln Val Thr Val Ser Ser His His His His His His
    370                 375                 380
```

<210> SEQ ID NO 171
<211> LENGTH: 391
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 171

```
Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Ser Gly Gly
        115                 120                 125

Gly Gly Ser Glu Val Gln Leu Val Glu Ser Gly Gly Gly Leu Val Gln
    130                 135                 140
```

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Ala Gly Gly Ser Leu Arg Leu Ser Cys Ala
275 280 285

Pro Ser Gly Arg Thr Ser Ser Ile Phe Gly Met Gly Trp Phe Arg Gln
290 295 300

Ala Pro Gly Lys Glu Arg Glu Phe Val Ala Ser Ile Asn Trp Ser Gly
305 310 315 320

Gly Ser Thr Ser Tyr Ala Asp Ser Val Lys Gly Arg Phe Thr Ile Ser
325 330 335

Arg Asp Asn Ala Lys Asn Glu Met Tyr Leu Gln Met Asn Ser Leu Lys
340 345 350

Phe Glu Asp Thr Ala Val Tyr Val Cys Ala Ala Ala Val Leu Thr Asn
355 360 365

Lys Pro Ser Trp Asn Phe Trp Gly Gln Gly Thr Gln Val Thr Val Ser
370 375 380

Ser His His His His His His
385 390

<210> SEQ ID NO 172
<211> LENGTH: 392
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 172

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Ala Gly Gly Ser Leu Arg Leu Ser Cys Ala
275 280 285

Ala Ser Gly Pro Ile Phe Ser Asp Thr Ile Arg Thr Met Gly Trp Tyr
290 295 300

Arg Gln Ala Ala Gly Lys Gln Arg Glu Leu Val Ala Thr Ile Ala Ser
305 310 315 320

Phe Pro Ser Arg Thr Asn Tyr Val Asp Ser Val Lys Gly Arg Phe Thr
325 330 335

Ile Ser Arg Asp Ile Ala Lys Asn Thr Val Tyr Leu Gln Met Asp Ser
340 345 350

Leu Lys Pro Glu Asp Thr Ala Val Tyr Tyr Cys Asn Val Asp Leu Ala
355 360 365

Ser Ile Pro Thr Lys Thr Tyr Trp Gly Gln Gly Thr Gln Val Thr Val
370 375 380

Ser Ser His His His His His His
385 390

<210> SEQ ID NO 173
<211> LENGTH: 391
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 173

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

```
Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Gln Val Gln Leu Gln Glu Ser
            260                 265                 270

Gly Gly Gly Leu Val Gln Ala Gly Gly Ser Leu Arg Leu Ser Cys Ala
        275                 280                 285

Ala Ser Gly Ser Ile Phe Gly Ile Asn Ala Met Gly Trp Tyr Arg Gln
    290                 295                 300

Ala Pro Gly Lys Gln Arg Glu Ser Val Ala Phe Ile Thr Ile Gly Gly
305                 310                 315                 320

Asn Thr Asn Tyr Leu Asp Ser Val Lys Gly Arg Phe Thr Ile Ser Arg
                325                 330                 335

Asp Asn Ala Lys Asn Thr Val Tyr Leu Gln Met Asn Gly Leu Lys Pro
            340                 345                 350

Glu Asp Thr Ala Val Tyr Tyr Cys Asn Thr Asn Pro Pro Leu Ile Leu
        355                 360                 365

Thr Ala Gly Gly Leu Tyr Trp Gly Gln Gly Thr Gln Val Thr Val Ser
    370                 375                 380

Ser His His His His His His
385                 390
```

<210> SEQ ID NO 174
<211> LENGTH: 392
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 174

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Pro Gly Gly Ser Leu Arg Leu Ser Cys Ala
275 280 285

Thr Ser Ala Asn Arg Phe Asn Ile Asn Val Met Gly Trp Tyr Arg Gln
290 295 300

Ala Pro Gly Gln Gln Arg Glu Leu Val Ala Thr Ile Asn Ile Gly Gly
305 310 315 320

Ser Thr Asp Tyr Ala Asp Ser Val Lys Gly Arg Phe Thr Ile Ser Arg
325 330 335

Asp Asn Ala Lys Asn Thr Val Tyr Leu Gln Leu Ser Asp Leu Lys Pro
340 345 350

Glu Asp Thr Ala Val Tyr Tyr Cys Asn Val Lys Leu Arg Val Ser Gly
355 360 365

Pro Thr Gly Pro Asn Val Tyr Trp Gly Gln Gly Thr Gln Val Thr Val
370 375 380

Ser Ser His His His His His His
385 390

```
<210> SEQ ID NO 175
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Gln Val Gln Leu Gln Glu Ser
            260                 265                 270

Gly Gly Gly Leu Val Gln Ala Gly Gly Ser Leu Lys Leu Ser Cys Thr
        275                 280                 285

Ala Ser Gly Thr Ile Leu Ser Thr Met Ala Trp Tyr Arg Gln Ala Pro
    290                 295                 300

Gly Lys Gln Arg Glu Leu Val Ala Thr Ile Ser Arg Gly Gly Thr Thr
305                 310                 315                 320

Asn Tyr Ser Asp Ser Val Lys Gly Arg Phe Ala Ile Ser Arg Asp Ser
                325                 330                 335

Thr Lys Asn Thr Val Tyr Leu Gln Met Asn Ser Leu Lys Pro Glu Asp
            340                 345                 350

Thr Ala Val Tyr Tyr Cys Asn Thr Pro Leu Thr Asp Tyr Gly Met Gly
        355                 360                 365
```

Tyr Asn Trp Gly Gln Gly Thr Gln Val Thr Val Ser Ser His His His
    370                 375                 380

His His His
385

<210> SEQ ID NO 176
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Gln Val Gln Leu Gln Glu Ser
            260                 265                 270

Gly Gly Gly Leu Val Gln Ala Gly Gly Ser Leu Arg Leu Ser Cys Ala
        275                 280                 285

Val Ser Gly Ser Ile Phe Ser Leu Asn Thr Leu Ala Trp Tyr Arg Gln
    290                 295                 300

Ala Pro Gly Arg Gln Arg Asp Leu Ile Ala Arg Ile Thr Gly Gly Gly
305                 310                 315                 320

Thr Thr Val Tyr Ala Asp Ser Val Lys Gly Arg Phe Thr Ile Ser Arg
                325                 330                 335

Asp Asn Ala Lys Asn Thr Val Tyr Leu Gln Met Asn Ser Leu Lys Pro
340 345 350

Glu Asp Thr Ala Val Tyr Tyr Cys Asn Leu Met Val Arg His Pro Ser
355 360 365

Gly Ser Thr Tyr Glu Tyr Trp Gly Gln Gly Thr Gln Val Thr Val Ser
370 375 380

Ser His His His His His His
385 390

<210> SEQ ID NO 177
<211> LENGTH: 383
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 177

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Pro Gly Gly Ser Leu Arg Leu Ser Cys Ala
275 280 285

```
Ala Ser Gly Phe Thr Phe Ser Asp Trp Ala Met Ser Trp Val Arg Gln
    290                 295                 300

Ala Pro Gly Lys Gly Leu Glu Trp Val Ser Gly Ile His Tyr Gly Asp
305                 310                 315                 320

His Thr Thr His Tyr Ala Asp Phe Val Lys Gly Arg Phe Thr Ile Ser
                325                 330                 335

Arg Asp Asp Ala Lys Asn Thr Leu Tyr Leu Gln Met Asn Ser Leu Lys
            340                 345                 350

Pro Glu Asp Thr Ala Val Tyr Tyr Cys Ala Arg Gly Ser Thr Lys Gly
        355                 360                 365

Gln Gly Thr Gln Val Thr Val Ser Ser His His His His His His
    370                 375                 380


<210> SEQ ID NO 178
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255
```

```
Gly Gly Gly Gly Ser Gly Gly Gly Ser Gln Val Gln Leu Gln Glu Ser
            260                 265                 270

Gly Gly Gly Leu Val Gln Ala Gly Gly Ser Leu Arg Leu Ser Cys Ala
        275                 280                 285

Ala Ser Gly Phe Ile Phe Arg Ala Ala Ser Met Ala Trp Tyr Arg Gln
    290                 295                 300

Ser Pro Gly Asn Glu Arg Glu Leu Val Ala Ser Ile Ser Ser Gly Ala
305                 310                 315                 320

Phe Thr Asn Tyr Ala Asp Ser Val Lys Ala Arg Phe Thr Ile Ser Arg
                325                 330                 335

Asp Asn Ala Lys Asn Thr Val Tyr Leu Gln Met Asn Ser Leu Lys Pro
            340                 345                 350

Glu Asp Thr Ala Val Tyr Phe Cys Gly Ala Thr Phe Leu Arg Ser Asp
        355                 360                 365

Gly His His Thr Ile Asn Gly Gln Gly Thr Gln Val Thr Val Ser Ser
    370                 375                 380

His His His His His His
385                 390
```

<210> SEQ ID NO 179
<211> LENGTH: 390
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

```
Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220
```

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Gln Val Gln Leu Gln Glu Ser
260 265 270

Gly Gly Gly Leu Val Gln Ala Gly Gly Ser Leu Arg Leu Ser Cys Ala
275 280 285

Ala Ser Gly Ile Ile Phe Arg Gly Thr Thr Met Gly Trp Phe Arg Gln
290 295 300

Ala Pro Gly Lys Gln Arg Glu Ser Val Ala Ser Ile Ser Pro Leu Gly
305 310 315 320

Thr Thr Ser Tyr Ser Gly Ser Val Glu Gly Arg Phe Thr Val Ser Arg
325 330 335

Asp Asn Ala Lys Asn Thr Leu Phe Leu Gln Met Asn Ser Leu Lys Ser
340 345 350

Glu Asp Thr Ala Val Tyr Tyr Cys Asn Ala Ile Gln Val Thr Asn Val
355 360 365

Gly Pro Arg Val Tyr Trp Gly Gln Gly Thr Gln Val Thr Val Ser Ser
370 375 380

His His His His His His
385 390

<210> SEQ ID NO 180
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

Gly Gly Gly Ser Gln Val Gln Leu Gln Glu Ser Gly Gly Gly Leu Val
1 5 10 15

Gln Ala Gly Gly Ser Leu Arg Leu Ser Cys Ala Ala Ser Gly Ser Val
20 25 30

Phe Arg Ala Asn Val Met Gly Trp Tyr Arg Gln Ala Pro Gly Lys Gln
35 40 45

His Glu Leu Val Ala Arg Ile Asp Pro Gly Gly Thr Thr Thr Tyr Ala
50 55 60

Asp Pro Val Lys Gly Arg Phe Thr Ile Ser Arg Asp Asn Ala Lys Lys
65 70 75 80

Thr Val Tyr Leu Gln Met Asn Ser Leu Lys Pro Asp Asp Thr Ala Val
85 90 95

Tyr Tyr Cys Asn Ala Ile Ile Leu Leu Ser Gly Gly Pro Lys Asp Tyr
100 105 110

Trp Gly Gln Gly Thr Gln Val Thr Val Ser Ser Gly Gly Gly Gly Ser
115 120 125

Gly Gly Gly Ser Glu Val Gln Leu Val Glu Ser Gly Gly Gly Leu Val
130 135 140

Gln Pro Gly Gly Ser Leu Lys Leu Ser Cys Ala Ala Ser Gly Phe Thr
145 150 155 160

Phe Asn Lys Tyr Ala Ile Asn Trp Val Arg Gln Ala Pro Gly Lys Gly
165 170 175

Leu Glu Trp Val Ala Arg Ile Arg Ser Lys Tyr Asn Asn Tyr Ala Thr
180 185 190

Tyr Tyr Ala Asp Gln Val Lys Asp Arg Phe Thr Ile Ser Arg Asp Asp
195 200 205

Ser Lys Asn Thr Ala Tyr Leu Gln Met Asn Asn Leu Lys Thr Glu Asp
210 215 220

Thr Ala Val Tyr Tyr Cys Val Arg His Ala Asn Phe Gly Asn Ser Tyr
225 230 235 240

Ile Ser Tyr Trp Ala Tyr Trp Gly Gln Gly Thr Leu Val Thr Val Ser
245 250 255

Ser Gly Gly Gly Gly Ser Gly Gly Gly Gly Ser Gly Gly Gly Gly Ser
260 265 270

Gln Thr Val Val Thr Gln Glu Pro Ser Leu Thr Val Ser Pro Gly Gly
275 280 285

Thr Val Thr Leu Thr Cys Ala Ser Ser Thr Gly Ala Val Thr Ser Gly
290 295 300

Asn Tyr Pro Asn Trp Val Gln Gln Lys Pro Gly Gln Ala Pro Arg Gly
305 310 315 320

Leu Ile Gly Gly Thr Lys Phe Leu Val Pro Gly Thr Pro Ala Arg Phe
325 330 335

Ser Gly Ser Leu Leu Gly Gly Lys Ala Ala Leu Thr Leu Ser Gly Val
340 345 350

Gln Pro Glu Asp Glu Ala Glu Tyr Tyr Cys Thr Leu Trp Tyr Ser Asn
355 360 365

Arg Trp Val Phe Gly Gly Gly Thr Lys Leu Thr Val Leu His His His
370 375 380

His His His
385

<210> SEQ ID NO 181
<211> LENGTH: 392
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 181

Gly Gly Gly Ser Gln Val Gln Leu Gln Glu Ser Gly Gly Gly Leu Val
1 5 10 15

Gln Pro Gly Gly Ser Leu Arg Leu Ser Cys Ala Ser Ser Gly Phe Thr
20 25 30

Leu Asp Asp Tyr Thr Ile Gly Trp Phe Arg Gln Ala Pro Gly Lys Glu
35 40 45

Arg Glu Gly Val Ser Cys Ile Ser Arg Arg Asp Asp Ser Thr Tyr Tyr
50 55 60

Ala Asp Ser Val Lys Gly Arg Phe Thr Ile Ser Arg Asp Asn Ala Lys
65 70 75 80

Asn Thr Val Asp Leu Gln Met Ile Ser Leu Arg Pro Glu Asp Thr Ala
85 90 95

Val Tyr Tyr Cys Ala Ala Thr Pro Arg Ser Tyr Thr Leu Arg Cys Leu
100 105 110

Gly Lys Phe Asp Phe Gln Gly Gln Gly Thr Gln Val Thr Val Ser Ser
115 120 125

Gly Gly Gly Gly Ser Gly Gly Gly Ser Glu Val Gln Leu Val Glu Ser
130 135 140

Gly Gly Gly Leu Val Gln Pro Gly Gly Ser Leu Lys Leu Ser Cys Ala
145 150 155 160

Ala Ser Gly Phe Thr Phe Asn Lys Tyr Ala Ile Asn Trp Val Arg Gln
165 170 175

Ala Pro Gly Lys Gly Leu Glu Trp Val Ala Arg Ile Arg Ser Lys Tyr
180 185 190

Asn Asn Tyr Ala Thr Tyr Tyr Ala Asp Gln Val Lys Asp Arg Phe Thr
195 200 205

Ile Ser Arg Asp Asp Ser Lys Asn Thr Ala Tyr Leu Gln Met Asn Asn
210 215 220

Leu Lys Thr Glu Asp Thr Ala Val Tyr Tyr Cys Val Arg His Ala Asn
225 230 235 240

Phe Gly Asn Ser Tyr Ile Ser Tyr Trp Ala Tyr Trp Gly Gln Gly Thr
245 250 255

Leu Val Thr Val Ser Ser Gly Gly Gly Gly Ser Gly Gly Gly Gly Ser
260 265 270

Gly Gly Gly Gly Ser Gln Thr Val Val Thr Gln Glu Pro Ser Leu Thr
275 280 285

Val Ser Pro Gly Gly Thr Val Thr Leu Thr Cys Ala Ser Ser Thr Gly
290 295 300

Ala Val Thr Ser Gly Asn Tyr Pro Asn Trp Val Gln Gln Lys Pro Gly
305 310 315 320

Gln Ala Pro Arg Gly Leu Ile Gly Gly Thr Lys Phe Leu Val Pro Gly
325 330 335

Thr Pro Ala Arg Phe Ser Gly Ser Leu Leu Gly Gly Lys Ala Ala Leu
340 345 350

Thr Leu Ser Gly Val Gln Pro Glu Asp Glu Ala Glu Tyr Tyr Cys Thr
355 360 365

Leu Trp Tyr Ser Asn Arg Trp Val Phe Gly Gly Gly Thr Lys Leu Thr
370 375 380

Val Leu His His His His His His
385 390

<210> SEQ ID NO 182
<211> LENGTH: 389
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

Gly Gly Gly Ser Gln Val Gln Leu Gln Glu Ser Gly Gly Gly Leu Val
1 5 10 15

Gln Ala Gly Gly Ser Leu Arg Leu Ser Cys Ala Ala Ser Gly Asn Ile
20 25 30

Val Arg Met Thr Asn Met Ala Trp Tyr Arg Gln Ala Pro Gly Lys Gln
35 40 45

Arg Glu Phe Val Ala Thr Ile Ser Ala Gly Gly Ser Thr Thr Tyr Val
50 55 60

Asp Ser Val Lys Asp Arg Phe Thr Ile Ser Arg Asp Asn Thr Lys Asn
65 70 75 80

Thr Val Tyr Leu Gln Met Asn Tyr Leu Lys Pro Glu Asp Thr Ala Val
85 90 95

Tyr Tyr Cys Ala Thr Gly Ser Ile Leu Thr Asn Arg Gly Ala Ile Pro
100 105 110

Gly Ser Trp Gly His Gly Thr Gln Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Gly Ser Leu Lys Leu Ser Cys Ala Ala Ser Gly
145 150 155 160

Phe Thr Phe Asn Lys Tyr Ala Ile Asn Trp Val Arg Gln Ala Pro Gly
165 170 175

Lys Gly Leu Glu Trp Val Ala Arg Ile Arg Ser Lys Tyr Asn Asn Tyr
180 185 190

Ala Thr Tyr Tyr Ala Asp Gln Val Lys Asp Arg Phe Thr Ile Ser Arg
195 200 205

Asp Asp Ser Lys Asn Thr Ala Tyr Leu Gln Met Asn Asn Leu Lys Thr
210 215 220

Glu Asp Thr Ala Val Tyr Tyr Cys Val Arg His Ala Asn Phe Gly Asn
225 230 235 240

Ser Tyr Ile Ser Tyr Trp Ala Tyr Trp Gly Gln Gly Thr Leu Val Thr
245 250 255

Val Ser Ser Gly Gly Gly Gly Ser Gly Gly Gly Gly Ser Gly Gly Gly
260 265 270

Gly Ser Gln Thr Val Val Thr Gln Glu Pro Ser Leu Thr Val Ser Pro
275 280 285

Gly Gly Thr Val Thr Leu Thr Cys Ala Ser Ser Thr Gly Ala Val Thr
290 295 300

Ser Gly Asn Tyr Pro Asn Trp Val Gln Gln Lys Pro Gly Gln Ala Pro
305 310 315 320

Arg Gly Leu Ile Gly Gly Thr Lys Phe Leu Val Pro Gly Thr Pro Ala
325 330 335

Arg Phe Ser Gly Ser Leu Leu Gly Gly Lys Ala Ala Leu Thr Leu Ser
340 345 350

Gly Val Gln Pro Glu Asp Glu Ala Glu Tyr Tyr Cys Thr Leu Trp Tyr
355 360 365

Ser Asn Arg Trp Val Phe Gly Gly Gly Thr Lys Leu Thr Val Leu His
370 375 380

His His His His His
385

<210> SEQ ID NO 183
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 183

Gly Gly Gly Ser Gln Val Gln Leu Gln Glu Ser Gly Gly Gly Leu Val
1 5 10 15

Gln Ala Gly Gly Ser Leu Arg Leu Ser Cys Ala Ala Ser Gly Phe Ile
20 25 30

Phe Arg Ala Ala Ser Ile Ser Trp Tyr Arg Gln Ser Pro Gly Asn Glu
35 40 45

Arg Glu Leu Val Ala Thr Ile Asn Ser Gly Gly Phe Thr Asn Tyr Ala
50 55 60

Asp Ser Val Leu Gly Arg Phe Thr Ile Ser Arg Asp Asn Ala Lys Asn
65 70 75 80

Thr Gly Tyr Leu Gln Met Asn Ser Leu Lys Pro Glu Asp Thr Ala Val
85 90 95

Tyr Phe Cys Ala Ala Thr Phe Leu Arg Ser Asp Gly Gln Pro Pro Ile
100 105 110

Trp Gly Gln Gly Thr Gln Val Thr Val Ser Ser Gly Gly Gly Gly Ser
115 120 125

Gly Gly Gly Ser Glu Val Gln Leu Val Glu Ser Gly Gly Gly Leu Val
130 135 140

Gln Pro Gly Gly Ser Leu Lys Leu Ser Cys Ala Ala Ser Gly Phe Thr
145 150 155 160

Phe Asn Lys Tyr Ala Ile Asn Trp Val Arg Gln Ala Pro Gly Lys Gly
165 170 175

Leu Glu Trp Val Ala Arg Ile Arg Ser Lys Tyr Asn Asn Tyr Ala Thr
180 185 190

Tyr Tyr Ala Asp Gln Val Lys Asp Arg Phe Thr Ile Ser Arg Asp Asp
195 200 205

Ser Lys Asn Thr Ala Tyr Leu Gln Met Asn Asn Leu Lys Thr Glu Asp
210 215 220

Thr Ala Val Tyr Tyr Cys Val Arg His Ala Asn Phe Gly Asn Ser Tyr
225 230 235 240

Ile Ser Tyr Trp Ala Tyr Trp Gly Gln Gly Thr Leu Val Thr Val Ser
245 250 255

Ser Gly Gly Gly Gly Ser Gly Gly Gly Gly Ser Gly Gly Gly Gly Ser
260 265 270

Gln Thr Val Val Thr Gln Glu Pro Ser Leu Thr Val Ser Pro Gly Gly
275 280 285

Thr Val Thr Leu Thr Cys Ala Ser Ser Thr Gly Ala Val Thr Ser Gly
290 295 300

Asn Tyr Pro Asn Trp Val Gln Gln Lys Pro Gly Gln Ala Pro Arg Gly
305 310 315 320

Leu Ile Gly Gly Thr Lys Phe Leu Val Pro Gly Thr Pro Ala Arg Phe
325 330 335

Ser Gly Ser Leu Leu Gly Gly Lys Ala Ala Leu Thr Leu Ser Gly Val
340 345 350

Gln Pro Glu Asp Glu Ala Glu Tyr Tyr Cys Thr Leu Trp Tyr Ser Asn
355 360 365

Arg Trp Val Phe Gly Gly Gly Thr Lys Leu Thr Val Leu His His His
370 375 380

His His His
385

<210> SEQ ID NO 184
<211> LENGTH: 387
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 184

Gly Gly Gly Ser Gln Val Gln Leu Gln Glu Ser Gly Gly Gly Leu Val
1 5 10 15

Gln Ala Gly Gly Ser Leu Arg Leu Ser Cys Ala Ala Ser Gly Asn Val
20 25 30

Phe Arg Ala Ala Thr Met Ala Trp Tyr Arg Gln Val Pro Glu Lys Gln
35 40 45

Arg Glu Met Val Ala Thr Ile Ala Ser Gly Gly Thr Thr Asn Tyr Ala
50 55 60

Asp Phe Val Lys Gly Arg Phe Thr Ile Ser Arg Asp Asn Ala Lys Asn
65 70 75 80

Thr Val Tyr Leu Gln Met Asn Thr Leu Lys Pro Glu Asp Thr Ala Val
85 90 95

Tyr Tyr Cys Asn Ala Leu Tyr Leu Thr Ser Leu Gly Pro Lys Ser Tyr
100 105 110

Trp Gly Gln Gly Thr Gln Val Thr Val Ser Ser Gly Gly Gly Gly Ser
115 120 125

Gly Gly Gly Ser Glu Val Gln Leu Val Glu Ser Gly Gly Gly Leu Val
130 135 140

Gln Pro Gly Gly Ser Leu Lys Leu Ser Cys Ala Ala Ser Gly Phe Thr
145 150 155 160

Phe Asn Lys Tyr Ala Ile Asn Trp Val Arg Gln Ala Pro Gly Lys Gly
165 170 175

Leu Glu Trp Val Ala Arg Ile Arg Ser Lys Tyr Asn Asn Tyr Ala Thr
180 185 190

Tyr Tyr Ala Asp Gln Val Lys Asp Arg Phe Thr Ile Ser Arg Asp Asp
195 200 205

Ser Lys Asn Thr Ala Tyr Leu Gln Met Asn Asn Leu Lys Thr Glu Asp
210 215 220

Thr Ala Val Tyr Tyr Cys Val Arg His Ala Asn Phe Gly Asn Ser Tyr
225 230 235 240

Ile Ser Tyr Trp Ala Tyr Trp Gly Gln Gly Thr Leu Val Thr Val Ser
245 250 255

Ser Gly Gly Gly Gly Ser Gly Gly Gly Gly Ser Gly Gly Gly Gly Ser
260 265 270

Gln Thr Val Val Thr Gln Glu Pro Ser Leu Thr Val Ser Pro Gly Gly
275 280 285

Thr Val Thr Leu Thr Cys Ala Ser Ser Thr Gly Ala Val Thr Ser Gly
290 295 300

Asn Tyr Pro Asn Trp Val Gln Gln Lys Pro Gly Gln Ala Pro Arg Gly
305 310 315 320

Leu Ile Gly Gly Thr Lys Phe Leu Val Pro Gly Thr Pro Ala Arg Phe
325 330 335

Ser Gly Ser Leu Leu Gly Gly Lys Ala Ala Leu Thr Leu Ser Gly Val
340 345 350

Gln Pro Glu Asp Glu Ala Glu Tyr Tyr Cys Thr Leu Trp Tyr Ser Asn
355 360 365

Arg Trp Val Phe Gly Gly Gly Thr Lys Leu Thr Val Leu His His His
370 375 380

His His His
385

<210> SEQ ID NO 185
<211> LENGTH: 395
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 185

```
Gly Gly Gly Ser Gln Val Gln Leu Gln Glu Ser Gly Gly Gly Leu Val
1               5                   10                  15

Gln Ala Gly Gly Ser Leu Arg Leu Ser Cys Ala Ala Pro Gly Phe Ala
            20                  25                  30

Phe Asn Asp His Ala Ile Leu Trp Phe Arg Gln Ala Pro Gly Lys Glu
        35                  40                  45

Arg Glu Gly Val Ser Glu Ile Cys Arg Asp Gly Thr Thr Tyr Tyr Thr
    50                  55                  60

Asp Ser Val Lys Gly Arg Phe Thr Ile Ser Ser Asp Asn Ala Lys Asn
65                  70                  75                  80

Thr Val Tyr Leu Gln Met Asn Ser Val Lys Thr Asp Asp Thr Ala Val
                85                  90                  95

Tyr Tyr Cys Ala Val Asp Arg Arg Arg Tyr Tyr Cys Ser Gly Asn Arg
            100                 105                 110

Ala Phe Ser Ser Asp Tyr Tyr Tyr Trp Gly Gln Gly Thr Gln Val Thr
        115                 120                 125

Val Ser Ser Gly Gly Gly Gly Ser Gly Gly Gly Ser Glu Val Gln Leu
    130                 135                 140

Val Glu Ser Gly Gly Gly Leu Val Gln Pro Gly Gly Ser Leu Lys Leu
145                 150                 155                 160

Ser Cys Ala Ala Ser Gly Phe Thr Phe Asn Lys Tyr Ala Ile Asn Trp
                165                 170                 175

Val Arg Gln Ala Pro Gly Lys Gly Leu Glu Trp Val Ala Arg Ile Arg
            180                 185                 190

Ser Lys Tyr Asn Asn Tyr Ala Thr Tyr Tyr Ala Asp Gln Val Lys Asp
        195                 200                 205

Arg Phe Thr Ile Ser Arg Asp Asp Ser Lys Asn Thr Ala Tyr Leu Gln
    210                 215                 220

Met Asn Asn Leu Lys Thr Glu Asp Thr Ala Val Tyr Tyr Cys Val Arg
225                 230                 235                 240

His Ala Asn Phe Gly Asn Ser Tyr Ile Ser Tyr Trp Ala Tyr Trp Gly
                245                 250                 255

Gln Gly Thr Leu Val Thr Val Ser Ser Gly Gly Gly Gly Ser Gly Gly
            260                 265                 270

Gly Gly Ser Gly Gly Gly Gly Ser Gln Thr Val Val Thr Gln Glu Pro
        275                 280                 285

Ser Leu Thr Val Ser Pro Gly Gly Thr Val Thr Leu Thr Cys Ala Ser
    290                 295                 300

Ser Thr Gly Ala Val Thr Ser Gly Asn Tyr Pro Asn Trp Val Gln Gln
305                 310                 315                 320

Lys Pro Gly Gln Ala Pro Arg Gly Leu Ile Gly Gly Thr Lys Phe Leu
                325                 330                 335

Val Pro Gly Thr Pro Ala Arg Phe Ser Gly Ser Leu Leu Gly Gly Lys
            340                 345                 350

Ala Ala Leu Thr Leu Ser Gly Val Gln Pro Glu Asp Glu Ala Glu Tyr
        355                 360                 365

Tyr Cys Thr Leu Trp Tyr Ser Asn Arg Trp Val Phe Gly Gly Gly Thr
    370                 375                 380

Lys Leu Thr Val Leu His His His His His His
385                 390                 395
```

```
<210> SEQ ID NO 186
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gly Gly Gly Ser Gln Val Gln Leu Gln Glu Ser Gly Gly Gly Leu Val
1               5                   10                  15

Gln Pro Gly Gly Ser Leu Arg Leu Ser Cys Ala Ala Ser Gly Phe Ala
            20                  25                  30

Phe Gly Asn His Trp Met Tyr Trp Tyr Arg Gln Ala Pro Gly Arg Gly
        35                  40                  45

Arg Glu Leu Val Ala Ser Ile Ser Ser Gly Gly Ser Thr Asn Tyr Val
    50                  55                  60

Asp Ser Val Lys Gly Arg Phe Thr Ile Ser Arg Asp Asn Ala Arg Asn
65                  70                  75                  80

Thr Val Tyr Leu Gln Met Tyr Ser Leu Lys Pro Glu Asp Thr Ala Val
                85                  90                  95

Tyr Tyr Cys Gly Thr Ser Asp Asn Trp Gly Gln Gly Thr Gln Val Thr
            100                 105                 110

Val Ser Ser Gly Gly Gly Gly Ser Gly Gly Gly Ser Glu Val Gln Leu
        115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Asn Lys Tyr Ala Ile Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Gln Val Lys Asp
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Ala Asn Phe Gly Asn Ser Tyr Ile Ser Tyr Trp Ala Tyr Trp Gly
225                 230                 235                 240

Gln Gly Thr Leu Val Thr Val Ser Ser Gly Gly Gly Gly Ser Gly Gly
                245                 250                 255

Gly Gly Ser Gly Gly Gly Gly Ser Gln Thr Val Val Thr Gln Glu Pro
            260                 265                 270

Ser Leu Thr Val Ser Pro Gly Gly Thr Val Thr Leu Thr Cys Ala Ser
        275                 280                 285

Ser Thr Gly Ala Val Thr Ser Gly Asn Tyr Pro Asn Trp Val Gln Gln
    290                 295                 300

Lys Pro Gly Gln Ala Pro Arg Gly Leu Ile Gly Gly Thr Lys Phe Leu
305                 310                 315                 320

Val Pro Gly Thr Pro Ala Arg Phe Ser Gly Ser Leu Leu Gly Gly Lys
                325                 330                 335

Ala Ala Leu Thr Leu Ser Gly Val Gln Pro Glu Asp Glu Ala Glu Tyr
            340                 345                 350

Tyr Cys Thr Leu Trp Tyr Ser Asn Arg Trp Val Phe Gly Gly Gly Thr
        355                 360                 365
```

Lys Leu Thr Val Leu His His His His His His
370 375

<210> SEQ ID NO 187
<211> LENGTH: 392
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

Gly Gly Gly Ser Gln Val Gln Leu Gln Glu Ser Gly Gly Gly Leu Val
1 5 10 15

Gln Pro Gly Gly Ser Leu Arg Leu Ser Cys Ala Ala Ser Gly Asp Thr
20 25 30

Phe Leu Arg Tyr Ala Met Gly Trp Phe Arg Gln Ala Pro Gly Lys Glu
35 40 45

Arg Glu Phe Val Ala Ala Ile Thr Trp Asn Gly Gly Asn Thr Asp Tyr
50 55 60

Ala Gly Ser Leu Lys Gly Arg Phe Thr Ile Ser Arg Asp Asn Thr Lys
65 70 75 80

Asn Thr Val Tyr Leu Gln Met Asn Ser Leu Lys Pro Glu Asp Thr Ala
85 90 95

Val Tyr Tyr Cys Ala Ala Asp Leu Thr Phe Gly Leu Ala Ser Ser His
100 105 110

Tyr Gln Tyr Asp Tyr Trp Gly Gln Gly Thr Gln Val Thr Val Ser Ser
115 120 125

Gly Gly Gly Gly Ser Gly Gly Gly Ser Glu Val Gln Leu Val Glu Ser
130 135 140

Gly Gly Gly Leu Val Gln Pro Gly Gly Ser Leu Lys Leu Ser Cys Ala
145 150 155 160

Ala Ser Gly Phe Thr Phe Asn Lys Tyr Ala Ile Asn Trp Val Arg Gln
165 170 175

Ala Pro Gly Lys Gly Leu Glu Trp Val Ala Arg Ile Arg Ser Lys Tyr
180 185 190

Asn Asn Tyr Ala Thr Tyr Tyr Ala Asp Gln Val Lys Asp Arg Phe Thr
195 200 205

Ile Ser Arg Asp Asp Ser Lys Asn Thr Ala Tyr Leu Gln Met Asn Asn
210 215 220

Leu Lys Thr Glu Asp Thr Ala Val Tyr Tyr Cys Val Arg His Ala Asn
225 230 235 240

Phe Gly Asn Ser Tyr Ile Ser Tyr Trp Ala Tyr Trp Gly Gln Gly Thr
245 250 255

Leu Val Thr Val Ser Ser Gly Gly Gly Gly Ser Gly Gly Gly Gly Ser
260 265 270

Gly Gly Gly Gly Ser Gln Thr Val Val Thr Gln Glu Pro Ser Leu Thr
275 280 285

Val Ser Pro Gly Gly Thr Val Thr Leu Thr Cys Ala Ser Ser Thr Gly
290 295 300

Ala Val Thr Ser Gly Asn Tyr Pro Asn Trp Val Gln Gln Lys Pro Gly
305 310 315 320

Gln Ala Pro Arg Gly Leu Ile Gly Gly Thr Lys Phe Leu Val Pro Gly
325 330 335

Thr Pro Ala Arg Phe Ser Gly Ser Leu Leu Gly Gly Lys Ala Ala Leu
340 345 350

```
Thr Leu Ser Gly Val Gln Pro Glu Asp Glu Ala Glu Tyr Tyr Cys Thr
        355                 360                 365

Leu Trp Tyr Ser Asn Arg Trp Val Phe Gly Gly Gly Thr Lys Leu Thr
    370                 375                 380

Val Leu His His His His His His
385                 390


<210> SEQ ID NO 188
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Gly Gly Gly Ser Gln Val Gln Leu Gln Glu Ser Gly Gly Gly Leu Val
1               5                   10                  15

Gln Ala Gly Gly Ser Leu Arg Leu Ser Cys Ala Ala Ser Gly Phe Ile
            20                  25                  30

Phe Arg Ala Ala Ser Met Asp Trp Tyr Arg Gln Phe Pro Gly Asn Glu
        35                  40                  45

Arg Glu Ser Ile Ala Thr Ile Ser Ser Gly Gly Phe Thr Asn Tyr Ala
    50                  55                  60

Asp Ser Val Lys Gly Arg Phe Thr Ile Ser Arg Asp Asn Ala Lys Asn
65                  70                  75                  80

Thr Val Tyr Leu Gln Met Asn Ser Leu Lys Pro Glu Asp Thr Ala Val
                85                  90                  95

Tyr Phe Cys Gly Ala Thr Phe Leu Arg Ser Asp Gly His His Thr Ile
            100                 105                 110

Asn Gly Gln Gly Thr Gln Val Thr Val Ser Ser Gly Gly Gly Gly Ser
        115                 120                 125

Gly Gly Gly Ser Glu Val Gln Leu Val Glu Ser Gly Gly Gly Leu Val
    130                 135                 140

Gln Pro Gly Gly Ser Leu Lys Leu Ser Cys Ala Ala Ser Gly Phe Thr
145                 150                 155                 160

Phe Asn Lys Tyr Ala Ile Asn Trp Val Arg Gln Ala Pro Gly Lys Gly
                165                 170                 175

Leu Glu Trp Val Ala Arg Ile Arg Ser Lys Tyr Asn Asn Tyr Ala Thr
            180                 185                 190

Tyr Tyr Ala Asp Gln Val Lys Asp Arg Phe Thr Ile Ser Arg Asp Asp
        195                 200                 205

Ser Lys Asn Thr Ala Tyr Leu Gln Met Asn Asn Leu Lys Thr Glu Asp
    210                 215                 220

Thr Ala Val Tyr Tyr Cys Val Arg His Ala Asn Phe Gly Asn Ser Tyr
225                 230                 235                 240

Ile Ser Tyr Trp Ala Tyr Trp Gly Gln Gly Thr Leu Val Thr Val Ser
                245                 250                 255

Ser Gly Gly Gly Gly Ser Gly Gly Gly Gly Ser Gly Gly Gly Gly Ser
            260                 265                 270

Gln Thr Val Val Thr Gln Glu Pro Ser Leu Thr Val Ser Pro Gly Gly
        275                 280                 285

Thr Val Thr Leu Thr Cys Ala Ser Ser Thr Gly Ala Val Thr Ser Gly
    290                 295                 300
```

```
Asn Tyr Pro Asn Trp Val Gln Gln Lys Pro Gly Gln Ala Pro Arg Gly
305                 310                 315                 320

Leu Ile Gly Gly Thr Lys Phe Leu Val Pro Gly Thr Pro Ala Arg Phe
                325                 330                 335

Ser Gly Ser Leu Leu Gly Gly Lys Ala Ala Leu Thr Leu Ser Gly Val
            340                 345                 350

Gln Pro Glu Asp Glu Ala Glu Tyr Tyr Cys Thr Leu Trp Tyr Ser Asn
        355                 360                 365

Arg Trp Val Phe Gly Gly Gly Thr Lys Leu Thr Val Leu His His His
    370                 375                 380

His His His
385
```

<210> SEQ ID NO 189
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 189

```
Gly Gly Gly Ser Gln Val Gln Leu Gln Glu Ser Gly Gly Gly Leu Val
1               5                   10                  15

Gln Ala Gly Gly Ser Leu Arg Leu Ser Cys Ala Ala Ser Gly Phe Ile
            20                  25                  30

Phe Arg Ala Ala Ser Met Gly Trp Phe Arg Gln Ser Pro Gly Asn Glu
        35                  40                  45

Arg Glu Leu Val Ala Thr Val Ser Ser Gly Gly Phe Thr Asn Tyr Ala
    50                  55                  60

Asp Ser Val Lys Gly Arg Phe Thr Ile Ser Arg Asp Asn Ala Lys Asn
65                  70                  75                  80

Thr Val Tyr Leu Gln Met Asn Ser Leu Lys Pro Glu Asp Thr Ala Val
                85                  90                  95

Tyr Phe Cys Gly Ala Thr Phe Val Arg Ser Asp Gly His His Thr Ile
            100                 105                 110

Tyr Gly Gln Gly Thr Gln Val Thr Val Ser Ser Gly Gly Gly Gly Ser
        115                 120                 125

Gly Gly Gly Ser Glu Val Gln Leu Val Glu Ser Gly Gly Gly Leu Val
    130                 135                 140

Gln Pro Gly Gly Ser Leu Lys Leu Ser Cys Ala Ala Ser Gly Phe Thr
145                 150                 155                 160

Phe Asn Lys Tyr Ala Ile Asn Trp Val Arg Gln Ala Pro Gly Lys Gly
                165                 170                 175

Leu Glu Trp Val Ala Arg Ile Arg Ser Lys Tyr Asn Asn Tyr Ala Thr
            180                 185                 190

Tyr Tyr Ala Asp Gln Val Lys Asp Arg Phe Thr Ile Ser Arg Asp Asp
        195                 200                 205

Ser Lys Asn Thr Ala Tyr Leu Gln Met Asn Asn Leu Lys Thr Glu Asp
    210                 215                 220

Thr Ala Val Tyr Tyr Cys Val Arg His Ala Asn Phe Gly Asn Ser Tyr
225                 230                 235                 240

Ile Ser Tyr Trp Ala Tyr Trp Gly Gln Gly Thr Leu Val Thr Val Ser
                245                 250                 255

Ser Gly Gly Gly Gly Ser Gly Gly Gly Gly Ser Gly Gly Gly Gly Ser
            260                 265                 270
```

```
Gln Thr Val Val Thr Gln Glu Pro Ser Leu Thr Val Ser Pro Gly Gly
        275                 280                 285

Thr Val Thr Leu Thr Cys Ala Ser Ser Thr Gly Ala Val Thr Ser Gly
    290                 295                 300

Asn Tyr Pro Asn Trp Val Gln Gln Lys Pro Gly Gln Ala Pro Arg Gly
305                 310                 315                 320

Leu Ile Gly Gly Thr Lys Phe Leu Val Pro Gly Thr Pro Ala Arg Phe
                325                 330                 335

Ser Gly Ser Leu Leu Gly Gly Lys Ala Ala Leu Thr Leu Ser Gly Val
            340                 345                 350

Gln Pro Glu Asp Glu Ala Glu Tyr Tyr Cys Thr Leu Trp Tyr Ser Asn
        355                 360                 365

Arg Trp Val Phe Gly Gly Gly Thr Lys Leu Thr Val Leu His His His
    370                 375                 380

His His His
385
```

<210> SEQ ID NO 190
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

```
Gly Gly Gly Ser Gln Val Gln Leu Gln Glu Ser Gly Gly Gly Leu Val
1               5                   10                  15

Gln Ala Gly Gly Ser Leu Arg Leu Ser Cys Val His Ser Gly Ser Ile
            20                  25                  30

Phe Arg Ala Ser Thr Met Ala Trp Tyr Arg Gln Ala Pro Gly Lys Gln
        35                  40                  45

Arg Glu Leu Val Ala Gln Ile Met Ser Gly Gly Gly Thr Asn Tyr Ala
    50                  55                  60

Gly Ser Val Lys Gly Arg Phe Thr Ile Ser Arg Asp Asn Ala Asn Asn
65                  70                  75                  80

Thr Val Tyr Leu Gln Met Asn Ser Leu Lys Pro Glu Asp Thr Ala Val
                85                  90                  95

Tyr Tyr Cys Asn Ala Ala Gln Ile Thr Ser Trp Gly Pro Lys Val Tyr
            100                 105                 110

Trp Gly Gln Gly Thr Gln Val Thr Val Ser Ser Gly Gly Gly Gly Ser
        115                 120                 125

Gly Gly Gly Ser Glu Val Gln Leu Val Glu Ser Gly Gly Gly Leu Val
    130                 135                 140

Gln Pro Gly Gly Ser Leu Lys Leu Ser Cys Ala Ala Ser Gly Phe Thr
145                 150                 155                 160

Phe Asn Lys Tyr Ala Ile Asn Trp Val Arg Gln Ala Pro Gly Lys Gly
                165                 170                 175

Leu Glu Trp Val Ala Arg Ile Arg Ser Lys Tyr Asn Asn Tyr Ala Thr
            180                 185                 190

Tyr Tyr Ala Asp Gln Val Lys Asp Arg Phe Thr Ile Ser Arg Asp Asp
        195                 200                 205

Ser Lys Asn Thr Ala Tyr Leu Gln Met Asn Asn Leu Lys Thr Glu Asp
    210                 215                 220

Thr Ala Val Tyr Tyr Cys Val Arg His Ala Asn Phe Gly Asn Ser Tyr
225                 230                 235                 240
```

Ile Ser Tyr Trp Ala Tyr Trp Gly Gln Gly Thr Leu Val Thr Val Ser
245 250 255

Ser Gly Gly Gly Gly Ser Gly Gly Gly Gly Ser Gly Gly Gly Gly Ser
260 265 270

Gln Thr Val Val Thr Gln Glu Pro Ser Leu Thr Val Ser Pro Gly Gly
275 280 285

Thr Val Thr Leu Thr Cys Ala Ser Ser Thr Gly Ala Val Thr Ser Gly
290 295 300

Asn Tyr Pro Asn Trp Val Gln Gln Lys Pro Gly Gln Ala Pro Arg Gly
305 310 315 320

Leu Ile Gly Gly Thr Lys Phe Leu Val Pro Gly Thr Pro Ala Arg Phe
325 330 335

Ser Gly Ser Leu Leu Gly Gly Lys Ala Ala Leu Thr Leu Ser Gly Val
340 345 350

Gln Pro Glu Asp Glu Ala Glu Tyr Tyr Cys Thr Leu Trp Tyr Ser Asn
355 360 365

Arg Trp Val Phe Gly Gly Gly Thr Lys Leu Thr Val Leu His His His
370 375 380

His His His
385

<210> SEQ ID NO 191
<211> LENGTH: 380
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 191

Gly Gly Gly Ser Gln Val Gln Leu Gln Glu Ser Gly Gly Gly Leu Val
1 5 10 15

Gln Pro Gly Gly Ser Leu Arg Leu Ser Cys Ala Ala Ser Gly Phe Thr
20 25 30

Phe Ser Asp Trp Ala Met Ser Trp Val Arg Gln Ala Pro Gly Lys Gly
35 40 45

Leu Glu Trp Val Ser Ser Ile His Tyr Gly Asp His Thr Thr His Tyr
50 55 60

Ala Asp Phe Val Lys Gly Arg Phe Thr Ile Ser Arg Asp Asp Ala Lys
65 70 75 80

Asn Thr Leu Tyr Leu Gln Met Asn Ser Leu Lys Pro Glu Asp Thr Ala
85 90 95

Val Tyr Tyr Cys Glu Lys Gly Thr Thr Arg Gly Gln Gly Thr Gln Val
100 105 110

Thr Val Ser Ser Gly Gly Gly Gly Ser Gly Gly Gly Ser Glu Val Gln
115 120 125

Leu Val Glu Ser Gly Gly Gly Leu Val Gln Pro Gly Gly Ser Leu Lys
130 135 140

Leu Ser Cys Ala Ala Ser Gly Phe Thr Phe Asn Lys Tyr Ala Ile Asn
145 150 155 160

Trp Val Arg Gln Ala Pro Gly Lys Gly Leu Glu Trp Val Ala Arg Ile
165 170 175

Arg Ser Lys Tyr Asn Asn Tyr Ala Thr Tyr Tyr Ala Asp Gln Val Lys
180 185 190

Asp Arg Phe Thr Ile Ser Arg Asp Asp Ser Lys Asn Thr Ala Tyr Leu
195 200 205

Gln Met Asn Asn Leu Lys Thr Glu Asp Thr Ala Val Tyr Tyr Cys Val
210 215 220

Arg His Ala Asn Phe Gly Asn Ser Tyr Ile Ser Tyr Trp Ala Tyr Trp
225 230 235 240

Gly Gln Gly Thr Leu Val Thr Val Ser Ser Gly Gly Gly Gly Ser Gly
245 250 255

Gly Gly Gly Ser Gly Gly Gly Gly Ser Gln Thr Val Val Thr Gln Glu
260 265 270

Pro Ser Leu Thr Val Ser Pro Gly Gly Thr Val Thr Leu Thr Cys Ala
275 280 285

Ser Ser Thr Gly Ala Val Thr Ser Gly Asn Tyr Pro Asn Trp Val Gln
290 295 300

Gln Lys Pro Gly Gln Ala Pro Arg Gly Leu Ile Gly Gly Thr Lys Phe
305 310 315 320

Leu Val Pro Gly Thr Pro Ala Arg Phe Ser Gly Ser Leu Leu Gly Gly
325 330 335

Lys Ala Ala Leu Thr Leu Ser Gly Val Gln Pro Glu Asp Glu Ala Glu
340 345 350

Tyr Tyr Cys Thr Leu Trp Tyr Ser Asn Arg Trp Val Phe Gly Gly Gly
355 360 365

Thr Lys Leu Thr Val Leu His His His His His His
370 375 380

<210> SEQ ID NO 192
<211> LENGTH: 390
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 192

Gly Gly Gly Ser Gln Val Gln Leu Gln Glu Ser Gly Gly Gly Leu Val
1 5 10 15

Gln Pro Gly Ala Ser Leu Arg Val Ser Cys Ala Ala Ser Glu Tyr Ile
20 25 30

Leu Ser Met Tyr Arg Met Ala Trp Tyr Arg Gln Ala Pro Gly Lys Val
35 40 45

Arg Glu Leu Val Ala Asp Met Ser Ser Gly Gly Thr Thr Asn Tyr Ala
50 55 60

Asp Phe Val Lys Gly Arg Phe Thr Ile Ser Arg Asp Asn Asp Arg Asn
65 70 75 80

Thr Val Tyr Leu Gln Met Asn Arg Leu Gln Pro Glu Asp Thr Ala Ala
85 90 95

Tyr Tyr Cys Asn Val Ala Gly Arg Thr Gly Pro Pro Ser Tyr Asp Ala
100 105 110

Phe Asn Asn Trp Gly Gln Gly Thr Gln Val Thr Val Ser Ser Gly Gly
115 120 125

Gly Gly Ser Gly Gly Gly Ser Glu Val Gln Leu Val Glu Ser Gly Gly
130 135 140

Gly Leu Val Gln Pro Gly Gly Ser Leu Lys Leu Ser Cys Ala Ala Ser
145 150 155 160

Gly Phe Thr Phe Asn Lys Tyr Ala Ile Asn Trp Val Arg Gln Ala Pro
165 170 175

```
Gly Lys Gly Leu Glu Trp Val Ala Arg Ile Arg Ser Lys Tyr Asn Asn
            180                 185                 190

Tyr Ala Thr Tyr Tyr Ala Asp Gln Val Lys Asp Arg Phe Thr Ile Ser
        195                 200                 205

Arg Asp Asp Ser Lys Asn Thr Ala Tyr Leu Gln Met Asn Asn Leu Lys
    210                 215                 220

Thr Glu Asp Thr Ala Val Tyr Tyr Cys Val Arg His Ala Asn Phe Gly
225                 230                 235                 240

Asn Ser Tyr Ile Ser Tyr Trp Ala Tyr Trp Gly Gln Gly Thr Leu Val
                245                 250                 255

Thr Val Ser Ser Gly Gly Gly Gly Ser Gly Gly Gly Gly Ser Gly Gly
            260                 265                 270

Gly Gly Ser Gln Thr Val Val Thr Gln Glu Pro Ser Leu Thr Val Ser
        275                 280                 285

Pro Gly Gly Thr Val Thr Leu Thr Cys Ala Ser Ser Thr Gly Ala Val
    290                 295                 300

Thr Ser Gly Asn Tyr Pro Asn Trp Val Gln Gln Lys Pro Gly Gln Ala
305                 310                 315                 320

Pro Arg Gly Leu Ile Gly Gly Thr Lys Phe Leu Val Pro Gly Thr Pro
                325                 330                 335

Ala Arg Phe Ser Gly Ser Leu Leu Gly Gly Lys Ala Ala Leu Thr Leu
            340                 345                 350

Ser Gly Val Gln Pro Glu Asp Glu Ala Glu Tyr Tyr Cys Thr Leu Trp
        355                 360                 365

Tyr Ser Asn Arg Trp Val Phe Gly Gly Gly Thr Lys Leu Thr Val Leu
    370                 375                 380

His His His His His His
385                 390


<210> SEQ ID NO 193
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gly Gly Gly Ser Gln Val Gln Leu Gln Glu Ser Gly Gly Gly Leu Val
1               5                   10                  15

Gln Ala Gly Gly Ser Leu Arg Leu Ser Cys Ala Ala Ser Gly Phe Ile
            20                  25                  30

Phe Arg Ala Ala Ser Met Asp Trp Tyr Arg Gln Ser Pro Gly Thr Gln
        35                  40                  45

Pro Glu Leu Val Ala Thr Ile Ser Ser Thr Gly Phe Thr Asn Tyr Ala
    50                  55                  60

Asn Ser Val Lys Gly Arg Phe Thr Ile Ser Arg Asp Asn Ala Lys Asn
65                  70                  75                  80

Thr Val Tyr Leu Gln Met Asn Ser Leu Lys Pro Glu Asp Thr Ala Val
                85                  90                  95

Tyr Phe Cys Gly Ala Thr Phe Leu Arg Ser Asp Gly Gln His Ser Ile
            100                 105                 110

Tyr Gly Gln Gly Thr Gln Val Thr Val Ser Ser Gly Gly Gly Gly Ser
        115                 120                 125

Gly Gly Gly Ser Glu Val Gln Leu Val Glu Ser Gly Gly Gly Leu Val
    130                 135                 140
```

Gln Pro Gly Gly Ser Leu Lys Leu Ser Cys Ala Ala Ser Gly Phe Thr
145 150 155 160

Phe Asn Lys Tyr Ala Ile Asn Trp Val Arg Gln Ala Pro Gly Lys Gly
165 170 175

Leu Glu Trp Val Ala Arg Ile Arg Ser Lys Tyr Asn Asn Tyr Ala Thr
180 185 190

Tyr Tyr Ala Asp Gln Val Lys Asp Arg Phe Thr Ile Ser Arg Asp Asp
195 200 205

Ser Lys Asn Thr Ala Tyr Leu Gln Met Asn Asn Leu Lys Thr Glu Asp
210 215 220

Thr Ala Val Tyr Tyr Cys Val Arg His Ala Asn Phe Gly Asn Ser Tyr
225 230 235 240

Ile Ser Tyr Trp Ala Tyr Trp Gly Gln Gly Thr Leu Val Thr Val Ser
245 250 255

Ser Gly Gly Gly Gly Ser Gly Gly Gly Gly Ser Gly Gly Gly Gly Ser
260 265 270

Gln Thr Val Val Thr Gln Glu Pro Ser Leu Thr Val Ser Pro Gly Gly
275 280 285

Thr Val Thr Leu Thr Cys Ala Ser Ser Thr Gly Ala Val Thr Ser Gly
290 295 300

Asn Tyr Pro Asn Trp Val Gln Gln Lys Pro Gly Gln Ala Pro Arg Gly
305 310 315 320

Leu Ile Gly Gly Thr Lys Phe Leu Val Pro Gly Thr Pro Ala Arg Phe
325 330 335

Ser Gly Ser Leu Leu Gly Gly Lys Ala Ala Leu Thr Leu Ser Gly Val
340 345 350

Gln Pro Glu Asp Glu Ala Glu Tyr Tyr Cys Thr Leu Trp Tyr Ser Asn
355 360 365

Arg Trp Val Phe Gly Gly Gly Thr Lys Leu Thr Val Leu His His His
370 375 380

His His His
385

<210> SEQ ID NO 194
<211> LENGTH: 390
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 194

Gly Gly Gly Ser Gln Val Gln Leu Gln Glu Ser Gly Gly Gly Leu Val
1 5 10 15

Gln Pro Gly Gly Ser Leu Arg Leu Ser Cys Ala Ala Ser Gly Arg Ile
20 25 30

Asn Ser Ile Asn Thr Met Gly Trp Tyr Arg Gln Ala Pro Gly Asn Gln
35 40 45

Arg Glu Leu Val Ala Glu Ile Thr Arg Gly Gly Thr Thr Asn Tyr Ala
50 55 60

Asp Ser Val Gln Gly Arg Tyr Ala Ile Ser Arg Asp Asn Ala Lys Asn
65 70 75 80

Leu Val Tyr Leu Gln Met Asn Ser Leu Lys Pro Glu Asp Thr Asp Val
85 90 95

```
Tyr Tyr Cys Asn Ala Gln Thr Phe Pro Thr Phe Ser Arg Pro Thr Gly
            100                 105                 110

Leu Asp Tyr Trp Gly Gln Gly Thr Gln Val Thr Val Ser Ser Gly Gly
        115                 120                 125

Gly Gly Ser Gly Gly Gly Ser Glu Val Gln Leu Val Glu Ser Gly Gly
    130                 135                 140

Gly Leu Val Gln Pro Gly Gly Ser Leu Lys Leu Ser Cys Ala Ala Ser
145                 150                 155                 160

Gly Phe Thr Phe Asn Lys Tyr Ala Ile Asn Trp Val Arg Gln Ala Pro
                165                 170                 175

Gly Lys Gly Leu Glu Trp Val Ala Arg Ile Arg Ser Lys Tyr Asn Asn
            180                 185                 190

Tyr Ala Thr Tyr Tyr Ala Asp Gln Val Lys Asp Arg Phe Thr Ile Ser
        195                 200                 205

Arg Asp Asp Ser Lys Asn Thr Ala Tyr Leu Gln Met Asn Asn Leu Lys
    210                 215                 220

Thr Glu Asp Thr Ala Val Tyr Tyr Cys Val Arg His Ala Asn Phe Gly
225                 230                 235                 240

Asn Ser Tyr Ile Ser Tyr Trp Ala Tyr Trp Gly Gln Gly Thr Leu Val
                245                 250                 255

Thr Val Ser Ser Gly Gly Gly Gly Ser Gly Gly Gly Gly Ser Gly Gly
            260                 265                 270

Gly Gly Ser Gln Thr Val Val Thr Gln Glu Pro Ser Leu Thr Val Ser
        275                 280                 285

Pro Gly Gly Thr Val Thr Leu Thr Cys Ala Ser Ser Thr Gly Ala Val
    290                 295                 300

Thr Ser Gly Asn Tyr Pro Asn Trp Val Gln Gln Lys Pro Gly Gln Ala
305                 310                 315                 320

Pro Arg Gly Leu Ile Gly Gly Thr Lys Phe Leu Val Pro Gly Thr Pro
                325                 330                 335

Ala Arg Phe Ser Gly Ser Leu Leu Gly Gly Lys Ala Ala Leu Thr Leu
            340                 345                 350

Ser Gly Val Gln Pro Glu Asp Glu Ala Glu Tyr Tyr Cys Thr Leu Trp
        355                 360                 365

Tyr Ser Asn Arg Trp Val Phe Gly Gly Gly Thr Lys Leu Thr Val Leu
    370                 375                 380

His His His His His His
385                 390
```

<210> SEQ ID NO 195
<211> LENGTH: 390
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 195

```
Gly Gly Gly Ser Gln Val Gln Leu Gln Glu Ser Gly Gly Gly Leu Val
1               5                   10                  15

Gln Pro Gly Gly Ser Leu Arg Leu Ser Cys Ala Ala Ser Glu Ser Ile
            20                  25                  30

Ser Ser Phe Ile Ala Val Gly Trp Tyr Arg Gln Ala Pro Gly Lys Glu
        35                  40                  45

Arg Glu Leu Val Ala Gly Ile Asn Arg Ser Gly Phe Thr Tyr Tyr Thr
    50                  55                  60
```

```
Asp Ser Val Lys Gly Arg Phe Ser Ile Ser Arg Asp Asn Ala Lys Asn
65                  70                  75                  80

Thr Val Leu Leu Gln Met Thr Ser Leu Lys Pro Glu Asp Thr Ala Val
                85                  90                  95

Tyr Tyr Cys Asn Ala Gly Gly Leu Tyr Phe Ser Asn Ala Tyr Thr Gln
            100                 105                 110

Gly Asp Tyr Trp Gly Gln Gly Thr Gln Val Thr Val Ser Ser Gly Gly
        115                 120                 125

Gly Gly Ser Gly Gly Gly Ser Glu Val Gln Leu Val Glu Ser Gly Gly
    130                 135                 140

Gly Leu Val Gln Pro Gly Gly Ser Leu Lys Leu Ser Cys Ala Ala Ser
145                 150                 155                 160

Gly Phe Thr Phe Asn Lys Tyr Ala Ile Asn Trp Val Arg Gln Ala Pro
                165                 170                 175

Gly Lys Gly Leu Glu Trp Val Ala Arg Ile Arg Ser Lys Tyr Asn Asn
            180                 185                 190

Tyr Ala Thr Tyr Tyr Ala Asp Gln Val Lys Asp Arg Phe Thr Ile Ser
        195                 200                 205

Arg Asp Asp Ser Lys Asn Thr Ala Tyr Leu Gln Met Asn Asn Leu Lys
    210                 215                 220

Thr Glu Asp Thr Ala Val Tyr Tyr Cys Val Arg His Ala Asn Phe Gly
225                 230                 235                 240

Asn Ser Tyr Ile Ser Tyr Trp Ala Tyr Trp Gly Gln Gly Thr Leu Val
                245                 250                 255

Thr Val Ser Ser Gly Gly Gly Gly Ser Gly Gly Gly Gly Ser Gly Gly
            260                 265                 270

Gly Gly Ser Gln Thr Val Val Thr Gln Glu Pro Ser Leu Thr Val Ser
        275                 280                 285

Pro Gly Gly Thr Val Thr Leu Thr Cys Ala Ser Ser Thr Gly Ala Val
    290                 295                 300

Thr Ser Gly Asn Tyr Pro Asn Trp Val Gln Gln Lys Pro Gly Gln Ala
305                 310                 315                 320

Pro Arg Gly Leu Ile Gly Gly Thr Lys Phe Leu Val Pro Gly Thr Pro
                325                 330                 335

Ala Arg Phe Ser Gly Ser Leu Leu Gly Gly Lys Ala Ala Leu Thr Leu
            340                 345                 350

Ser Gly Val Gln Pro Glu Asp Glu Ala Glu Tyr Tyr Cys Thr Leu Trp
        355                 360                 365

Tyr Ser Asn Arg Trp Val Phe Gly Gly Gly Thr Lys Leu Thr Val Leu
    370                 375                 380

His His His His His His
385                 390
```

<210> SEQ ID NO 196
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

```
Gly Gly Gly Ser Gln Val Gln Leu Gln Glu Ser Gly Gly Gly Leu Val
1               5                   10                  15

Gln Ala Gly Gly Ser Leu Lys Leu Ser Cys Ala Ala Ser Gly Asn Val
            20                  25                  30
```

```
Phe Arg Ala Ala Thr Met Ala Trp Tyr Arg Gln Ala Pro Glu Lys Gln
        35                  40                  45

Arg Glu Met Val Ala Thr Ile Ala Ser Gly Gly Thr Thr Asn Tyr Ala
    50                  55                  60

Asp Phe Val Lys Gly Arg Phe Thr Ile Ser Arg Asp Asn Ala Lys Asn
65                  70                  75                  80

Thr Val Tyr Leu Gln Met Asn Thr Leu Lys Pro Glu Asp Thr Ala Val
                85                  90                  95

Tyr Tyr Cys Asn Ala Gly Tyr Leu Thr Ser Leu Gly Pro Lys Asn Tyr
            100                 105                 110

Trp Gly Gln Gly Thr Gln Val Thr Val Ser Ser Gly Gly Gly Gly Ser
        115                 120                 125

Gly Gly Gly Ser Glu Val Gln Leu Val Glu Ser Gly Gly Gly Leu Val
    130                 135                 140

Gln Pro Gly Gly Ser Leu Lys Leu Ser Cys Ala Ala Ser Gly Phe Thr
145                 150                 155                 160

Phe Asn Lys Tyr Ala Ile Asn Trp Val Arg Gln Ala Pro Gly Lys Gly
                165                 170                 175

Leu Glu Trp Val Ala Arg Ile Arg Ser Lys Tyr Asn Asn Tyr Ala Thr
            180                 185                 190

Tyr Tyr Ala Asp Gln Val Lys Asp Arg Phe Thr Ile Ser Arg Asp Asp
        195                 200                 205

Ser Lys Asn Thr Ala Tyr Leu Gln Met Asn Asn Leu Lys Thr Glu Asp
    210                 215                 220

Thr Ala Val Tyr Tyr Cys Val Arg His Ala Asn Phe Gly Asn Ser Tyr
225                 230                 235                 240

Ile Ser Tyr Trp Ala Tyr Trp Gly Gln Gly Thr Leu Val Thr Val Ser
                245                 250                 255

Ser Gly Gly Gly Gly Ser Gly Gly Gly Gly Ser Gly Gly Gly Gly Ser
            260                 265                 270

Gln Thr Val Val Thr Gln Glu Pro Ser Leu Thr Val Ser Pro Gly Gly
        275                 280                 285

Thr Val Thr Leu Thr Cys Ala Ser Ser Thr Gly Ala Val Thr Ser Gly
    290                 295                 300

Asn Tyr Pro Asn Trp Val Gln Gln Lys Pro Gly Gln Ala Pro Arg Gly
305                 310                 315                 320

Leu Ile Gly Gly Thr Lys Phe Leu Val Pro Gly Thr Pro Ala Arg Phe
                325                 330                 335

Ser Gly Ser Leu Leu Gly Gly Lys Ala Ala Leu Thr Leu Ser Gly Val
            340                 345                 350

Gln Pro Glu Asp Glu Ala Glu Tyr Tyr Cys Thr Leu Trp Tyr Ser Asn
        355                 360                 365

Arg Trp Val Phe Gly Gly Gly Thr Lys Leu Thr Val Leu His His His
    370                 375                 380

His His His
385
```

<210> SEQ ID NO 197
<211> LENGTH: 380
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 197

Gly Gly Gly Ser Gln Val Gln Leu Gln Glu Ser Gly Gly Gly Ser Val
1               5                   10                  15

Gln Ala Gly Gly Ser Leu Arg Leu Ser Cys Ala Ala Ser Gly Phe Thr
            20                  25                  30

Phe Ser Ser Tyr Tyr Met Ser Trp Val Arg Gln Ala Pro Gly Lys Gly
        35                  40                  45

Leu Glu Trp Val Ser Gly Ile His Tyr Thr Gly Asp Trp Thr Asn Tyr
    50                  55                  60

Ala Asp Ser Val Lys Gly Arg Phe Thr Ile Ser Arg Asp Asn Ala Lys
65                  70                  75                  80

Asn Glu Leu Tyr Leu Glu Met Asn Asn Leu Lys Pro Glu Asp Thr Ala
                85                  90                  95

Val Tyr Tyr Cys Ala Arg Gly Ser Asp Lys Gly Gln Gly Thr Gln Val
            100                 105                 110

Thr Val Ser Ser Gly Gly Gly Gly Ser Gly Gly Gly Ser Glu Val Gln
        115                 120                 125

Leu Val Glu Ser Gly Gly Gly Leu Val Gln Pro Gly Gly Ser Leu Lys
    130                 135                 140

Leu Ser Cys Ala Ala Ser Gly Phe Thr Phe Asn Lys Tyr Ala Ile Asn
145                 150                 155                 160

Trp Val Arg Gln Ala Pro Gly Lys Gly Leu Glu Trp Val Ala Arg Ile
                165                 170                 175

Arg Ser Lys Tyr Asn Asn Tyr Ala Thr Tyr Tyr Ala Asp Gln Val Lys
            180                 185                 190

Asp Arg Phe Thr Ile Ser Arg Asp Asp Ser Lys Asn Thr Ala Tyr Leu
        195                 200                 205

Gln Met Asn Asn Leu Lys Thr Glu Asp Thr Ala Val Tyr Tyr Cys Val
    210                 215                 220

Arg His Ala Asn Phe Gly Asn Ser Tyr Ile Ser Tyr Trp Ala Tyr Trp
225                 230                 235                 240

Gly Gln Gly Thr Leu Val Thr Val Ser Ser Gly Gly Gly Gly Ser Gly
                245                 250                 255

Gly Gly Gly Ser Gly Gly Gly Gly Ser Gln Thr Val Val Thr Gln Glu
            260                 265                 270

Pro Ser Leu Thr Val Ser Pro Gly Gly Thr Val Thr Leu Thr Cys Ala
        275                 280                 285

Ser Ser Thr Gly Ala Val Thr Ser Gly Asn Tyr Pro Asn Trp Val Gln
    290                 295                 300

Gln Lys Pro Gly Gln Ala Pro Arg Gly Leu Ile Gly Gly Thr Lys Phe
305                 310                 315                 320

Leu Val Pro Gly Thr Pro Ala Arg Phe Ser Gly Ser Leu Leu Gly Gly
                325                 330                 335

Lys Ala Ala Leu Thr Leu Ser Gly Val Gln Pro Glu Asp Glu Ala Glu
            340                 345                 350

Tyr Tyr Cys Thr Leu Trp Tyr Ser Asn Arg Trp Val Phe Gly Gly Gly
        355                 360                 365

Thr Lys Leu Thr Val Leu His His His His His His
    370                 375                 380

<210> SEQ ID NO 198
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

```
Gly Gly Gly Ser Gln Val Gln Leu Gln Glu Ser Gly Gly Gly Leu Val
1               5                   10                  15

Gln Ala Gly Gly Ser Leu Arg Leu Ser Cys Ala Pro Ser Gly Arg Thr
            20                  25                  30

Ser Ser Ile Phe Gly Met Gly Trp Phe Arg Gln Ala Pro Gly Lys Glu
        35                  40                  45

Arg Glu Phe Val Ala Ser Ile Asn Trp Ser Gly Gly Ser Thr Ser Tyr
    50                  55                  60

Ala Asp Ser Val Lys Gly Arg Phe Thr Ile Ser Arg Asp Asn Ala Lys
65                  70                  75                  80

Asn Glu Met Tyr Leu Gln Met Asn Ser Leu Lys Phe Glu Asp Thr Ala
                85                  90                  95

Val Tyr Val Cys Ala Ala Ala Val Leu Thr Asn Lys Pro Ser Trp Asn
            100                 105                 110

Phe Trp Gly Gln Gly Thr Gln Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Gly Ser Leu Lys Leu Ser Cys Ala Ala Ser Gly Phe
145                 150                 155                 160

Thr Phe Asn Lys Tyr Ala Ile Asn Trp Val Arg Gln Ala Pro Gly Lys
                165                 170                 175

Gly Leu Glu Trp Val Ala Arg Ile Arg Ser Lys Tyr Asn Asn Tyr Ala
            180                 185                 190

Thr Tyr Tyr Ala Asp Gln Val Lys Asp Arg Phe Thr Ile Ser Arg Asp
        195                 200                 205

Asp Ser Lys Asn Thr Ala Tyr Leu Gln Met Asn Asn Leu Lys Thr Glu
    210                 215                 220

Asp Thr Ala Val Tyr Tyr Cys Val Arg His Ala Asn Phe Gly Asn Ser
225                 230                 235                 240

Tyr Ile Ser Tyr Trp Ala Tyr Trp Gly Gln Gly Thr Leu Val Thr Val
                245                 250                 255

Ser Ser Gly Gly Gly Ser Gly Gly Gly Gly Ser Gly Gly Gly Gly
            260                 265                 270

Ser Gln Thr Val Val Thr Gln Glu Pro Ser Leu Thr Val Ser Pro Gly
        275                 280                 285

Gly Thr Val Thr Leu Thr Cys Ala Ser Ser Thr Gly Ala Val Thr Ser
    290                 295                 300

Gly Asn Tyr Pro Asn Trp Val Gln Gln Lys Pro Gly Gln Ala Pro Arg
305                 310                 315                 320

Gly Leu Ile Gly Gly Thr Lys Phe Leu Val Pro Gly Thr Pro Ala Arg
                325                 330                 335

Phe Ser Gly Ser Leu Leu Gly Gly Lys Ala Ala Leu Thr Leu Ser Gly
            340                 345                 350

Val Gln Pro Glu Asp Glu Ala Glu Tyr Tyr Cys Thr Leu Trp Tyr Ser
        355                 360                 365

Asn Arg Trp Val Phe Gly Gly Gly Thr Lys Leu Thr Val Leu His His
    370                 375                 380
```

His His His His
385

<210> SEQ ID NO 199
<211> LENGTH: 389
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 199

Gly Gly Gly Ser Gln Val Gln Leu Gln Glu Ser Gly Gly Gly Leu Val
1 5 10 15

Gln Ala Gly Gly Ser Leu Arg Leu Ser Cys Ala Ala Ser Gly Pro Ile
20 25 30

Phe Ser Asp Thr Ile Arg Thr Met Gly Trp Tyr Arg Gln Ala Ala Gly
35 40 45

Lys Gln Arg Glu Leu Val Ala Thr Ile Ala Ser Phe Pro Ser Arg Thr
50 55 60

Asn Tyr Val Asp Ser Val Lys Gly Arg Phe Thr Ile Ser Arg Asp Ile
65 70 75 80

Ala Lys Asn Thr Val Tyr Leu Gln Met Asp Ser Leu Lys Pro Glu Asp
85 90 95

Thr Ala Val Tyr Tyr Cys Asn Val Asp Leu Ala Ser Ile Pro Thr Lys
100 105 110

Thr Tyr Trp Gly Gln Gly Thr Gln Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Gly Ser Leu Lys Leu Ser Cys Ala Ala Ser Gly
145 150 155 160

Phe Thr Phe Asn Lys Tyr Ala Ile Asn Trp Val Arg Gln Ala Pro Gly
165 170 175

Lys Gly Leu Glu Trp Val Ala Arg Ile Arg Ser Lys Tyr Asn Asn Tyr
180 185 190

Ala Thr Tyr Tyr Ala Asp Gln Val Lys Asp Arg Phe Thr Ile Ser Arg
195 200 205

Asp Asp Ser Lys Asn Thr Ala Tyr Leu Gln Met Asn Asn Leu Lys Thr
210 215 220

Glu Asp Thr Ala Val Tyr Tyr Cys Val Arg His Ala Asn Phe Gly Asn
225 230 235 240

Ser Tyr Ile Ser Tyr Trp Ala Tyr Trp Gly Gln Gly Thr Leu Val Thr
245 250 255

Val Ser Ser Gly Gly Gly Gly Ser Gly Gly Gly Gly Ser Gly Gly Gly
260 265 270

Gly Ser Gln Thr Val Val Thr Gln Glu Pro Ser Leu Thr Val Ser Pro
275 280 285

Gly Gly Thr Val Thr Leu Thr Cys Ala Ser Ser Thr Gly Ala Val Thr
290 295 300

Ser Gly Asn Tyr Pro Asn Trp Val Gln Gln Lys Pro Gly Gln Ala Pro
305 310 315 320

Arg Gly Leu Ile Gly Gly Thr Lys Phe Leu Val Pro Gly Thr Pro Ala
325 330 335

Arg Phe Ser Gly Ser Leu Leu Gly Gly Lys Ala Ala Leu Thr Leu Ser
340 345 350

```
Gly Val Gln Pro Glu Asp Glu Ala Glu Tyr Tyr Cys Thr Leu Trp Tyr
        355                 360                 365

Ser Asn Arg Trp Val Phe Gly Gly Gly Thr Lys Leu Thr Val Leu His
    370                 375                 380

His His His His His
385


<210> SEQ ID NO 200
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Gly Gly Gly Ser Gln Val Gln Leu Gln Glu Ser Gly Gly Gly Leu Val
1               5                   10                  15

Gln Ala Gly Gly Ser Leu Arg Leu Ser Cys Ala Ala Ser Gly Ser Ile
            20                  25                  30

Phe Gly Ile Asn Ala Met Gly Trp Tyr Arg Gln Ala Pro Gly Lys Gln
        35                  40                  45

Arg Glu Ser Val Ala Phe Ile Thr Ile Gly Gly Asn Thr Asn Tyr Leu
    50                  55                  60

Asp Ser Val Lys Gly Arg Phe Thr Ile Ser Arg Asp Asn Ala Lys Asn
65                  70                  75                  80

Thr Val Tyr Leu Gln Met Asn Gly Leu Lys Pro Glu Asp Thr Ala Val
                85                  90                  95

Tyr Tyr Cys Asn Thr Asn Pro Pro Leu Ile Leu Thr Ala Gly Gly Leu
            100                 105                 110

Tyr Trp Gly Gln Gly Thr Gln Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Gly Ser Leu Lys Leu Ser Cys Ala Ala Ser Gly Phe
145                 150                 155                 160

Thr Phe Asn Lys Tyr Ala Ile Asn Trp Val Arg Gln Ala Pro Gly Lys
                165                 170                 175

Gly Leu Glu Trp Val Ala Arg Ile Arg Ser Lys Tyr Asn Asn Tyr Ala
            180                 185                 190

Thr Tyr Tyr Ala Asp Gln Val Lys Asp Arg Phe Thr Ile Ser Arg Asp
        195                 200                 205

Asp Ser Lys Asn Thr Ala Tyr Leu Gln Met Asn Asn Leu Lys Thr Glu
    210                 215                 220

Asp Thr Ala Val Tyr Tyr Cys Val Arg His Ala Asn Phe Gly Asn Ser
225                 230                 235                 240

Tyr Ile Ser Tyr Trp Ala Tyr Trp Gly Gln Gly Thr Leu Val Thr Val
                245                 250                 255

Ser Ser Gly Gly Gly Gly Ser Gly Gly Gly Gly Ser Gly Gly Gly Gly
            260                 265                 270

Ser Gln Thr Val Val Thr Gln Glu Pro Ser Leu Thr Val Ser Pro Gly
        275                 280                 285

Gly Thr Val Thr Leu Thr Cys Ala Ser Ser Thr Gly Ala Val Thr Ser
    290                 295                 300

Gly Asn Tyr Pro Asn Trp Val Gln Gln Lys Pro Gly Gln Ala Pro Arg
305                 310                 315                 320
```

Gly Leu Ile Gly Gly Thr Lys Phe Leu Val Pro Gly Thr Pro Ala Arg
325 330 335

Phe Ser Gly Ser Leu Leu Gly Gly Lys Ala Ala Leu Thr Leu Ser Gly
340 345 350

Val Gln Pro Glu Asp Glu Ala Glu Tyr Tyr Cys Thr Leu Trp Tyr Ser
355 360 365

Asn Arg Trp Val Phe Gly Gly Gly Thr Lys Leu Thr Val Leu His His
370 375 380

His His His His
385

<210> SEQ ID NO 201
<211> LENGTH: 389
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 201

Gly Gly Gly Ser Gln Val Gln Leu Gln Glu Ser Gly Gly Gly Leu Val
1 5 10 15

Gln Pro Gly Gly Ser Leu Arg Leu Ser Cys Ala Thr Ser Ala Asn Arg
20 25 30

Phe Asn Ile Asn Val Met Gly Trp Tyr Arg Gln Ala Pro Gly Gln Gln
35 40 45

Arg Glu Leu Val Ala Thr Ile Asn Ile Gly Gly Ser Thr Asp Tyr Ala
50 55 60

Asp Ser Val Lys Gly Arg Phe Thr Ile Ser Arg Asp Asn Ala Lys Asn
65 70 75 80

Thr Val Tyr Leu Gln Leu Ser Asp Leu Lys Pro Glu Asp Thr Ala Val
85 90 95

Tyr Tyr Cys Asn Val Lys Leu Arg Val Ser Gly Pro Thr Gly Pro Asn
100 105 110

Val Tyr Trp Gly Gln Gly Thr Gln Val Thr Val Ser Ser Gly Gly Gly
115 120 125

Gly Ser Gly Gly Gly Ser Glu Val Gln Leu Val Glu Ser Gly Gly Gly
130 135 140

Leu Val Gln Pro Gly Gly Ser Leu Lys Leu Ser Cys Ala Ala Ser Gly
145 150 155 160

Phe Thr Phe Asn Lys Tyr Ala Ile Asn Trp Val Arg Gln Ala Pro Gly
165 170 175

Lys Gly Leu Glu Trp Val Ala Arg Ile Arg Ser Lys Tyr Asn Asn Tyr
180 185 190

Ala Thr Tyr Tyr Ala Asp Gln Val Lys Asp Arg Phe Thr Ile Ser Arg
195 200 205

Asp Asp Ser Lys Asn Thr Ala Tyr Leu Gln Met Asn Asn Leu Lys Thr
210 215 220

Glu Asp Thr Ala Val Tyr Tyr Cys Val Arg His Ala Asn Phe Gly Asn
225 230 235 240

Ser Tyr Ile Ser Tyr Trp Ala Tyr Trp Gly Gln Gly Thr Leu Val Thr
245 250 255

Val Ser Ser Gly Gly Gly Gly Ser Gly Gly Gly Gly Ser Gly Gly Gly
260 265 270

Gly Ser Gln Thr Val Val Thr Gln Glu Pro Ser Leu Thr Val Ser Pro
275 280 285

Gly Gly Thr Val Thr Leu Thr Cys Ala Ser Ser Thr Gly Ala Val Thr
290 295 300

Ser Gly Asn Tyr Pro Asn Trp Val Gln Gln Lys Pro Gly Gln Ala Pro
305 310 315 320

Arg Gly Leu Ile Gly Gly Thr Lys Phe Leu Val Pro Gly Thr Pro Ala
325 330 335

Arg Phe Ser Gly Ser Leu Leu Gly Gly Lys Ala Ala Leu Thr Leu Ser
340 345 350

Gly Val Gln Pro Glu Asp Glu Ala Glu Tyr Tyr Cys Thr Leu Trp Tyr
355 360 365

Ser Asn Arg Trp Val Phe Gly Gly Gly Thr Lys Leu Thr Val Leu His
370 375 380

His His His His His
385

<210> SEQ ID NO 202
<211> LENGTH: 384
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 202

Gly Gly Gly Ser Gln Val Gln Leu Gln Glu Ser Gly Gly Gly Leu Val
1 5 10 15

Gln Ala Gly Gly Ser Leu Lys Leu Ser Cys Thr Ala Ser Gly Thr Ile
20 25 30

Leu Ser Thr Met Ala Trp Tyr Arg Gln Ala Pro Gly Lys Gln Arg Glu
35 40 45

Leu Val Ala Thr Ile Ser Arg Gly Gly Thr Thr Asn Tyr Ser Asp Ser
50 55 60

Val Lys Gly Arg Phe Ala Ile Ser Arg Asp Ser Thr Lys Asn Thr Val
65 70 75 80

Tyr Leu Gln Met Asn Ser Leu Lys Pro Glu Asp Thr Ala Val Tyr Tyr
85 90 95

Cys Asn Thr Pro Leu Thr Asp Tyr Gly Met Gly Tyr Asn Trp Gly Gln
100 105 110

Gly Thr Gln Val Thr Val Ser Ser Gly Gly Gly Gly Ser Gly Gly Gly
115 120 125

Ser Glu Val Gln Leu Val Glu Ser Gly Gly Gly Leu Val Gln Pro Gly
130 135 140

Gly Ser Leu Lys Leu Ser Cys Ala Ala Ser Gly Phe Thr Phe Asn Lys
145 150 155 160

Tyr Ala Ile Asn Trp Val Arg Gln Ala Pro Gly Lys Gly Leu Glu Trp
165 170 175

Val Ala Arg Ile Arg Ser Lys Tyr Asn Asn Tyr Ala Thr Tyr Tyr Ala
180 185 190

Asp Gln Val Lys Asp Arg Phe Thr Ile Ser Arg Asp Asp Ser Lys Asn
195 200 205

Thr Ala Tyr Leu Gln Met Asn Asn Leu Lys Thr Glu Asp Thr Ala Val
210 215 220

Tyr Tyr Cys Val Arg His Ala Asn Phe Gly Asn Ser Tyr Ile Ser Tyr
225 230 235 240

Trp Ala Tyr Trp Gly Gln Gly Thr Leu Val Thr Val Ser Ser Gly Gly
245 250 255

Gly Gly Ser Gly Gly Gly Gly Ser Gly Gly Gly Gly Ser Gln Thr Val
260 265 270

Val Thr Gln Glu Pro Ser Leu Thr Val Ser Pro Gly Gly Thr Val Thr
275 280 285

Leu Thr Cys Ala Ser Ser Thr Gly Ala Val Thr Ser Gly Asn Tyr Pro
290 295 300

Asn Trp Val Gln Gln Lys Pro Gly Gln Ala Pro Arg Gly Leu Ile Gly
305 310 315 320

Gly Thr Lys Phe Leu Val Pro Gly Thr Pro Ala Arg Phe Ser Gly Ser
325 330 335

Leu Leu Gly Gly Lys Ala Ala Leu Thr Leu Ser Gly Val Gln Pro Glu
340 345 350

Asp Glu Ala Glu Tyr Tyr Cys Thr Leu Trp Tyr Ser Asn Arg Trp Val
355 360 365

Phe Gly Gly Gly Thr Lys Leu Thr Val Leu His His His His His His
370 375 380

<210> SEQ ID NO 203
<211> LENGTH: 388
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 203

Gly Gly Gly Ser Gln Val Gln Leu Gln Glu Ser Gly Gly Gly Leu Val
1 5 10 15

Gln Ala Gly Gly Ser Leu Arg Leu Ser Cys Ala Val Ser Gly Ser Ile
20 25 30

Phe Ser Leu Asn Thr Leu Ala Trp Tyr Arg Gln Ala Pro Gly Arg Gln
35 40 45

Arg Asp Leu Ile Ala Arg Ile Thr Gly Gly Gly Thr Thr Val Tyr Ala
50 55 60

Asp Ser Val Lys Gly Arg Phe Thr Ile Ser Arg Asp Asn Ala Lys Asn
65 70 75 80

Thr Val Tyr Leu Gln Met Asn Ser Leu Lys Pro Glu Asp Thr Ala Val
85 90 95

Tyr Tyr Cys Asn Leu Met Val Arg His Pro Ser Gly Ser Thr Tyr Glu
100 105 110

Tyr Trp Gly Gln Gly Thr Gln Val Thr Val Ser Ser Gly Gly Gly Gly
115 120 125

Ser Gly Gly Gly Ser Glu Val Gln Leu Val Glu Ser Gly Gly Gly Leu
130 135 140

Val Gln Pro Gly Gly Ser Leu Lys Leu Ser Cys Ala Ala Ser Gly Phe
145 150 155 160

Thr Phe Asn Lys Tyr Ala Ile Asn Trp Val Arg Gln Ala Pro Gly Lys
165 170 175

Gly Leu Glu Trp Val Ala Arg Ile Arg Ser Lys Tyr Asn Asn Tyr Ala
180 185 190

Thr Tyr Tyr Ala Asp Gln Val Lys Asp Arg Phe Thr Ile Ser Arg Asp
195 200 205

Asp Ser Lys Asn Thr Ala Tyr Leu Gln Met Asn Asn Leu Lys Thr Glu
210 215 220

Asp Thr Ala Val Tyr Tyr Cys Val Arg His Ala Asn Phe Gly Asn Ser
225 230 235 240

Tyr Ile Ser Tyr Trp Ala Tyr Trp Gly Gln Gly Thr Leu Val Thr Val
245 250 255

Ser Ser Gly Gly Gly Gly Ser Gly Gly Gly Gly Ser Gly Gly Gly Gly
260 265 270

Ser Gln Thr Val Val Thr Gln Glu Pro Ser Leu Thr Val Ser Pro Gly
275 280 285

Gly Thr Val Thr Leu Thr Cys Ala Ser Ser Thr Gly Ala Val Thr Ser
290 295 300

Gly Asn Tyr Pro Asn Trp Val Gln Gln Lys Pro Gly Gln Ala Pro Arg
305 310 315 320

Gly Leu Ile Gly Gly Thr Lys Phe Leu Val Pro Gly Thr Pro Ala Arg
325 330 335

Phe Ser Gly Ser Leu Leu Gly Gly Lys Ala Ala Leu Thr Leu Ser Gly
340 345 350

Val Gln Pro Glu Asp Glu Ala Glu Tyr Tyr Cys Thr Leu Trp Tyr Ser
355 360 365

Asn Arg Trp Val Phe Gly Gly Gly Thr Lys Leu Thr Val Leu His His
370 375 380

His His His His
385

<210> SEQ ID NO 204
<211> LENGTH: 380
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 204

Gly Gly Gly Ser Gln Val Gln Leu Gln Glu Ser Gly Gly Gly Leu Val
1 5 10 15

Gln Pro Gly Gly Ser Leu Arg Leu Ser Cys Ala Ala Ser Gly Phe Thr
20 25 30

Phe Ser Asp Trp Ala Met Ser Trp Val Arg Gln Ala Pro Gly Lys Gly
35 40 45

Leu Glu Trp Val Ser Gly Ile His Tyr Gly Asp His Thr Thr His Tyr
50 55 60

Ala Asp Phe Val Lys Gly Arg Phe Thr Ile Ser Arg Asp Asp Ala Lys
65 70 75 80

Asn Thr Leu Tyr Leu Gln Met Asn Ser Leu Lys Pro Glu Asp Thr Ala
85 90 95

Val Tyr Tyr Cys Ala Arg Gly Ser Thr Lys Gly Gln Gly Thr Gln Val
100 105 110

Thr Val Ser Ser Gly Gly Gly Gly Ser Gly Gly Gly Ser Glu Val Gln
115 120 125

Leu Val Glu Ser Gly Gly Gly Leu Val Gln Pro Gly Gly Ser Leu Lys
130 135 140

Leu Ser Cys Ala Ala Ser Gly Phe Thr Phe Asn Lys Tyr Ala Ile Asn
145 150 155 160

Trp Val Arg Gln Ala Pro Gly Lys Gly Leu Glu Trp Val Ala Arg Ile
165 170 175

```
Arg Ser Lys Tyr Asn Asn Tyr Ala Thr Tyr Tyr Ala Asp Gln Val Lys
            180                 185                 190

Asp Arg Phe Thr Ile Ser Arg Asp Asp Ser Lys Asn Thr Ala Tyr Leu
        195                 200                 205

Gln Met Asn Asn Leu Lys Thr Glu Asp Thr Ala Val Tyr Tyr Cys Val
    210                 215                 220

Arg His Ala Asn Phe Gly Asn Ser Tyr Ile Ser Tyr Trp Ala Tyr Trp
225                 230                 235                 240

Gly Gln Gly Thr Leu Val Thr Val Ser Ser Gly Gly Gly Gly Ser Gly
                245                 250                 255

Gly Gly Gly Ser Gly Gly Gly Gly Ser Gln Thr Val Val Thr Gln Glu
            260                 265                 270

Pro Ser Leu Thr Val Ser Pro Gly Gly Thr Val Thr Leu Thr Cys Ala
        275                 280                 285

Ser Ser Thr Gly Ala Val Thr Ser Gly Asn Tyr Pro Asn Trp Val Gln
    290                 295                 300

Gln Lys Pro Gly Gln Ala Pro Arg Gly Leu Ile Gly Gly Thr Lys Phe
305                 310                 315                 320

Leu Val Pro Gly Thr Pro Ala Arg Phe Ser Gly Ser Leu Leu Gly Gly
                325                 330                 335

Lys Ala Ala Leu Thr Leu Ser Gly Val Gln Pro Glu Asp Glu Ala Glu
            340                 345                 350

Tyr Tyr Cys Thr Leu Trp Tyr Ser Asn Arg Trp Val Phe Gly Gly Gly
        355                 360                 365

Thr Lys Leu Thr Val Leu His His His His His His
    370                 375                 380
```

<210> SEQ ID NO 205
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

```
Gly Gly Gly Ser Gln Val Gln Leu Gln Glu Ser Gly Gly Gly Leu Val
1               5                   10                  15

Gln Ala Gly Gly Ser Leu Arg Leu Ser Cys Ala Ala Ser Gly Phe Ile
            20                  25                  30

Phe Arg Ala Ala Ser Met Ala Trp Tyr Arg Gln Ser Pro Gly Asn Glu
        35                  40                  45

Arg Glu Leu Val Ala Ser Ile Ser Ser Gly Ala Phe Thr Asn Tyr Ala
    50                  55                  60

Asp Ser Val Lys Ala Arg Phe Thr Ile Ser Arg Asp Asn Ala Lys Asn
65                  70                  75                  80

Thr Val Tyr Leu Gln Met Asn Ser Leu Lys Pro Glu Asp Thr Ala Val
                85                  90                  95

Tyr Phe Cys Gly Ala Thr Phe Leu Arg Ser Asp Gly His His Thr Ile
            100                 105                 110

Asn Gly Gln Gly Thr Gln Val Thr Val Ser Ser Gly Gly Gly Ser
        115                 120                 125

Gly Gly Gly Ser Glu Val Gln Leu Val Glu Ser Gly Gly Gly Leu Val
    130                 135                 140

Gln Pro Gly Gly Ser Leu Lys Leu Ser Cys Ala Ala Ser Gly Phe Thr
145                 150                 155                 160
```

Phe Asn Lys Tyr Ala Ile Asn Trp Val Arg Gln Ala Pro Gly Lys Gly
165 170 175

Leu Glu Trp Val Ala Arg Ile Arg Ser Lys Tyr Asn Asn Tyr Ala Thr
180 185 190

Tyr Tyr Ala Asp Gln Val Lys Asp Arg Phe Thr Ile Ser Arg Asp Asp
195 200 205

Ser Lys Asn Thr Ala Tyr Leu Gln Met Asn Asn Leu Lys Thr Glu Asp
210 215 220

Thr Ala Val Tyr Tyr Cys Val Arg His Ala Asn Phe Gly Asn Ser Tyr
225 230 235 240

Ile Ser Tyr Trp Ala Tyr Trp Gly Gln Gly Thr Leu Val Thr Val Ser
245 250 255

Ser Gly Gly Gly Gly Ser Gly Gly Gly Gly Ser Gly Gly Gly Gly Ser
260 265 270

Gln Thr Val Val Thr Gln Glu Pro Ser Leu Thr Val Ser Pro Gly Gly
275 280 285

Thr Val Thr Leu Thr Cys Ala Ser Ser Thr Gly Ala Val Thr Ser Gly
290 295 300

Asn Tyr Pro Asn Trp Val Gln Gln Lys Pro Gly Gln Ala Pro Arg Gly
305 310 315 320

Leu Ile Gly Gly Thr Lys Phe Leu Val Pro Gly Thr Pro Ala Arg Phe
325 330 335

Ser Gly Ser Leu Leu Gly Gly Lys Ala Ala Leu Thr Leu Ser Gly Val
340 345 350

Gln Pro Glu Asp Glu Ala Glu Tyr Tyr Cys Thr Leu Trp Tyr Ser Asn
355 360 365

Arg Trp Val Phe Gly Gly Gly Thr Lys Leu Thr Val Leu His His His
370 375 380

His His His
385

<210> SEQ ID NO 206
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 206

Gly Gly Gly Ser Gln Val Gln Leu Gln Glu Ser Gly Gly Gly Leu Val
1 5 10 15

Gln Ala Gly Gly Ser Leu Arg Leu Ser Cys Ala Ala Ser Gly Ile Ile
20 25 30

Phe Arg Gly Thr Thr Met Gly Trp Phe Arg Gln Ala Pro Gly Lys Gln
35 40 45

Arg Glu Ser Val Ala Ser Ile Ser Pro Leu Gly Thr Thr Ser Tyr Ser
50 55 60

Gly Ser Val Glu Gly Arg Phe Thr Val Ser Arg Asp Asn Ala Lys Asn
65 70 75 80

Thr Leu Phe Leu Gln Met Asn Ser Leu Lys Ser Glu Asp Thr Ala Val
85 90 95

Tyr Tyr Cys Asn Ala Ile Gln Val Thr Asn Val Gly Pro Arg Val Tyr
100 105 110

Trp Gly Gln Gly Thr Gln Val Thr Val Ser Ser Gly Gly Gly Gly Ser
115 120 125

```
Gly Gly Gly Ser Glu Val Gln Leu Val Glu Ser Gly Gly Gly Leu Val
    130                 135                 140

Gln Pro Gly Gly Ser Leu Lys Leu Ser Cys Ala Ala Ser Gly Phe Thr
145                 150                 155                 160

Phe Asn Lys Tyr Ala Ile Asn Trp Val Arg Gln Ala Pro Gly Lys Gly
                165                 170                 175

Leu Glu Trp Val Ala Arg Ile Arg Ser Lys Tyr Asn Asn Tyr Ala Thr
            180                 185                 190

Tyr Tyr Ala Asp Gln Val Lys Asp Arg Phe Thr Ile Ser Arg Asp Asp
        195                 200                 205

Ser Lys Asn Thr Ala Tyr Leu Gln Met Asn Asn Leu Lys Thr Glu Asp
    210                 215                 220

Thr Ala Val Tyr Tyr Cys Val Arg His Ala Asn Phe Gly Asn Ser Tyr
225                 230                 235                 240

Ile Ser Tyr Trp Ala Tyr Trp Gly Gln Gly Thr Leu Val Thr Val Ser
                245                 250                 255

Ser Gly Gly Gly Gly Ser Gly Gly Gly Gly Ser Gly Gly Gly Gly Ser
            260                 265                 270

Gln Thr Val Val Thr Gln Glu Pro Ser Leu Thr Val Ser Pro Gly Gly
        275                 280                 285

Thr Val Thr Leu Thr Cys Ala Ser Ser Thr Gly Ala Val Thr Ser Gly
    290                 295                 300

Asn Tyr Pro Asn Trp Val Gln Gln Lys Pro Gly Gln Ala Pro Arg Gly
305                 310                 315                 320

Leu Ile Gly Gly Thr Lys Phe Leu Val Pro Gly Thr Pro Ala Arg Phe
                325                 330                 335

Ser Gly Ser Leu Leu Gly Gly Lys Ala Ala Leu Thr Leu Ser Gly Val
            340                 345                 350

Gln Pro Glu Asp Glu Ala Glu Tyr Tyr Cys Thr Leu Trp Tyr Ser Asn
        355                 360                 365

Arg Trp Val Phe Gly Gly Gly Thr Lys Leu Thr Val Leu His His His
    370                 375                 380

His His His
385
```

<210> SEQ ID NO 207
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

```
Glu Val Gln Leu Val Glu Ser Gly Gly Gly Leu Val Gln Pro Gly Gly
1               5                   10                  15

Ser Leu Thr Leu Ser Cys Ala Ala Ser Gly Phe Ala Phe Gly Asn His
            20                  25                  30

Trp Met Tyr Trp Tyr Arg Gln Ala Pro Gly Arg Gly Arg Glu Leu Val
        35                  40                  45

Ala Ser Ile Ser Ser Gly Gly Ser Thr Asn Tyr Val Asp Ser Val Lys
    50                  55                  60

Gly Arg Phe Thr Ile Ser Arg Asp Asn Ala Lys Asn Thr Leu Tyr Leu
65                  70                  75                  80
```

Gln Met Asn Ser Leu Arg Ala Glu Asp Thr Ala Val Tyr Tyr Cys Gly
85 90 95

Thr Ser Asp Asn Trp Gly Gln Gly Thr Leu Val Thr Val Ser Ser
100 105 110

<210> SEQ ID NO 208
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 208

Glu Val Gln Leu Leu Glu Ser Gly Gly Gly Leu Val Gln Pro Gly Gly
1 5 10 15

Ser Leu Thr Leu Ser Cys Ala Ala Ser Gly Phe Ile Phe Arg Ala Ala
20 25 30

Ser Met Asp Trp Tyr Arg Gln Phe Pro Gly Asn Glu Arg Glu Ser Ile
35 40 45

Ala Thr Ile Ser Ser Gly Gly Phe Thr Asn Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Gly
85 90 95

Ala Thr Phe Leu Arg Ser Asp Gly His His Thr Ile Asn Gly Gln Gly
100 105 110

Thr Leu Val Thr Val Ser Ser
115

<210> SEQ ID NO 209
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 209

Glu Val Gln Leu Leu Glu Ser Gly Gly Gly Leu Val Gln Pro Gly Gly
1 5 10 15

Ser Leu Thr Leu Ser Cys Ala Ala Ser Gly Phe Ile Phe Arg Ala Ala
20 25 30

Ser Met Ala Trp Tyr Arg Gln Ser Pro Gly Asn Glu Arg Glu Leu Val
35 40 45

Ala Ser Ile Ser Ser Gly Ala Phe Thr Asn Tyr Ala Asp Ser Val Lys
50 55 60

Ala Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Gly
85 90 95

Ala Thr Phe Leu Arg Ser Asp Gly His His Thr Ile Asn Gly Gln Gly
100 105 110

Thr Leu Val Thr Val Ser Ser
115

<210> SEQ ID NO 210

<211> LENGTH: 382
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 210

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Glu Val Gln Leu Val Glu Ser
260 265 270

Gly Gly Gly Leu Val Gln Pro Gly Gly Ser Leu Thr Leu Ser Cys Ala
275 280 285

Ala Ser Gly Phe Ala Phe Gly Asn His Trp Met Tyr Trp Tyr Arg Gln
290 295 300

Ala Pro Gly Arg Gly Arg Glu Leu Val Ala Ser Ile Ser Ser Gly Gly
305 310 315 320

Ser Thr Asn Tyr Val Asp Ser Val Lys Gly Arg Phe Thr Ile Ser Arg
325 330 335

Asp Asn Ala Lys Asn Thr Leu Tyr Leu Gln Met Asn Ser Leu Arg Ala
340 345 350

Glu Asp Thr Ala Val Tyr Tyr Cys Gly Thr Ser Asp Asn Trp Gly Gln
355 360 365

Gly Thr Leu Val Thr Val Ser Ser His His His His His His
370 375 380

<210> SEQ ID NO 211
<211> LENGTH: 390
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 211

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Glu Val Gln Leu Leu Glu Ser
260 265 270

Gly Gly Gly Leu Val Gln Pro Gly Gly Ser Leu Thr Leu Ser Cys Ala
275 280 285

Ala Ser Gly Phe Ile Phe Arg Ala Ala Ser Met Asp Trp Tyr Arg Gln
290 295 300

Phe Pro Gly Asn Glu Arg Glu Ser Ile Ala Thr Ile Ser Ser Gly Gly
305 310 315 320

Phe Thr Asn Tyr Ala Asp Ser Val Lys Gly Arg Phe Thr Ile Ser Arg
325 330 335

Asp Asn Ser Lys Asn Thr Leu Tyr Leu Gln Met Asn Ser Leu Arg Ala
340 345 350

Glu Asp Thr Ala Val Tyr Tyr Cys Gly Ala Thr Phe Leu Arg Ser Asp
355 360 365

Gly His His Thr Ile Asn Gly Gln Gly Thr Leu Val Thr Val Ser Ser
370 375 380

His His His His His His
385 390

<210> SEQ ID NO 212
<211> LENGTH: 390
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 212

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Glu Val Gln Leu Leu Glu Ser
260 265 270

Gly Gly Gly Leu Val Gln Pro Gly Gly Ser Leu Thr Leu Ser Cys Ala
275 280 285

Ala Ser Gly Phe Ile Phe Arg Ala Ala Ser Met Ala Trp Tyr Arg Gln
290 295 300

Ser Pro Gly Asn Glu Arg Glu Leu Val Ala Ser Ile Ser Ser Gly Ala
305 310 315 320

```
Phe Thr Asn Tyr Ala Asp Ser Val Lys Ala Arg Phe Thr Ile Ser Arg
                325                 330                 335

Asp Asn Ser Lys Asn Thr Leu Tyr Leu Gln Met Asn Ser Leu Arg Ala
            340                 345                 350

Glu Asp Thr Ala Val Tyr Tyr Cys Gly Ala Thr Phe Leu Arg Ser Asp
        355                 360                 365

Gly His His Thr Ile Asn Gly Gln Gly Thr Leu Val Thr Val Ser Ser
    370                 375                 380

His His His His His His
385                 390


<210> SEQ ID NO 213
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25


<210> SEQ ID NO 214
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25


<210> SEQ ID NO 215
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25


<210> SEQ ID NO 216
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 216

Gln Val Gln Leu Gln Glu Ser Gly Gly Gly Leu Val Gln Ala Gly Gly
1 5 10 15

Ser Leu Arg Leu Ser Cys Ala Ala Ser
20 25

<210> SEQ ID NO 217
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 217

Gln Val Gln Leu Gln Glu Ser Gly Gly Gly Leu Val Gln Ala Gly Gly
1 5 10 15

Ser Leu Arg Leu Ser Cys Ala Ala Ser
20 25

<210> SEQ ID NO 218
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 218

Gln Val Gln Leu Gln Glu Ser Gly Gly Gly Leu Val His Thr Gly Gly
1 5 10 15

Ser Leu Arg Leu Ser Cys Ala Ala Ser
20 25

<210> SEQ ID NO 219
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

Gln Val Gln Leu Gln Glu Ser Gly Gly Gly Leu Val Gln Ala Gly Gly
1 5 10 15

Ser Leu Arg Leu Ser Cys Ala Ala Ser
20 25

<210> SEQ ID NO 220
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 220

Gln Val Gln Leu Gln Glu Ser Gly Gly Gly Leu Val His Thr Gly Gly
1 5 10 15

Ser Leu Arg Leu Ser Cys Ala Phe Ser
20 25

<210> SEQ ID NO 221

<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Gln Val Gln Leu Gln Glu Ser Gly Gly Gly Leu Val Gln Pro Gly Gly
1 5 10 15

Ser Leu Arg Leu Ser Cys Ala Ala Ser
20 25

<210> SEQ ID NO 222
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 222

Gln Val Gln Leu Gln Glu Ser Gly Gly Gly Ser Val Leu Ala Gly Gly
1 5 10 15

Ser Leu Arg Leu Ser Cys Ala Ala Ser
20 25

<210> SEQ ID NO 223
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 223

Gln Val Gln Leu Gln Glu Ser Gly Gly Gly Ser Val Gln Ala Gly Gly
1 5 10 15

Ser Leu Arg Leu Ser Cys Ala Ala Ser
20 25

<210> SEQ ID NO 224
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 224

Gln Val Gln Leu Gln Glu Ser Gly Gly Gly Leu Val Gln Pro Gly Gly
1 5 10 15

Ser Leu Arg Leu Ser Cys Ala Ala Ser
20 25

<210> SEQ ID NO 225
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 225

Gln Val Gln Leu Gln Glu Ser Gly Gly Gly Leu Val Gln Pro Gly Gly
1 5 10 15

```
Ser Leu Arg Leu Ser Cys Ala Ala Ser
            20                  25


<210> SEQ ID NO 226
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gln Val Gln Leu Gln Glu Ser Gly Gly Gly Leu Val Gln Ala Gly Gly
1               5                   10                  15

Ser Leu Lys Leu Ser Cys Ala Ala Ser
            20                  25


<210> SEQ ID NO 227
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25


<210> SEQ ID NO 228
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25


<210> SEQ ID NO 229
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25


<210> SEQ ID NO 230
<211> LENGTH: 25
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 230

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 231
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 232
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 233
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 234
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 235
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 235

```
Gln Val Gln Leu Gln Glu Ser Gly Gly Gly Leu Val Gln Pro Gly Ala
1               5                   10                  15

Ser Leu Arg Val Ser Cys Ala Ala Ser
            20                  25
```

<210> SEQ ID NO 236
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 236

```
Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 237
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 237

```
Gln Val Gln Leu Gln Glu Ser Gly Gly Gly Leu Val Gln Thr Gly Gly
1               5                   10                  15

Ser Leu Arg Leu Ser Cys Ala Ala Ser
            20                  25
```

<210> SEQ ID NO 238
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 238

```
Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25
```

<210> SEQ ID NO 239
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 239

Gln Val Gln Leu Gln Glu Ser Gly Gly Gly Leu Val Gln Ala Gly Gly
1 5 10 15

Ser Leu Arg Leu Ser Cys Ala Pro Ser
20 25

<210> SEQ ID NO 240
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 240

Gln Val Gln Leu Gln Glu Ser Gly Gly Gly Leu Val Gln Ala Gly Gly
1 5 10 15

Ser Leu Arg Leu Ser Cys Ala Ala Ser
20 25

<210> SEQ ID NO 241
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 241

Gln Val Gln Leu Gln Glu Ser Gly Gly Gly Leu Val Gln Ala Gly Gly
1 5 10 15

Ser Leu Arg Leu Ser Cys Ala Ala Ser
20 25

<210> SEQ ID NO 242
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 242

Gln Val Gln Leu Gln Glu Ser Gly Gly Gly Leu Val Gln Pro Gly Gly
1 5 10 15

Ser Leu Arg Leu Ser Cys Ala Thr Ser
20 25

<210> SEQ ID NO 243
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Gln Val Gln Leu Gln Glu Ser Gly Gly Gly Leu Val Gln Ala Gly Gly
1 5 10 15

Ser Leu Lys Leu Ser Cys Thr Ala Ser
20 25

<210> SEQ ID NO 244

<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 244

Gln Val Gln Leu Gln Glu Ser Gly Gly Gly Leu Val Gln Ala Gly Gly
1 5 10 15

Ser Leu Arg Leu Ser Cys Ala Val Ser
20 25

<210> SEQ ID NO 245
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 245

Gln Val Gln Leu Gln Glu Ser Gly Gly Gly Leu Val Gln Ala Gly Gly
1 5 10 15

Ser Leu Arg Leu Ser Cys Ala Ala Ser
20 25

<210> SEQ ID NO 246
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 246

Gln Val Gln Leu Gln Glu Ser Gly Gly Gly Leu Val Gln Pro Gly Gly
1 5 10 15

Ser Leu Arg Leu Ser Cys Ala Ser Ser
20 25

<210> SEQ ID NO 247
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 247

Gln Val Gln Leu Gln Glu Ser Gly Gly Gly Leu Val Gln Ala Gly Gly
1 5 10 15

Ser Leu Arg Leu Ser Cys Ala Ala Ser
20 25

<210> SEQ ID NO 248
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 248

Gln Val Gln Leu Gln Glu Ser Gly Gly Gly Leu Val Gln Ala Gly Gly
1 5 10 15

```
Ser Leu Arg Leu Ser Cys Ala Ala Pro
            20                  25


<210> SEQ ID NO 249
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gln Val Gln Leu Gln Glu Ser Gly Gly Gly Leu Val Gln Ala Gly Gly
1               5                   10                  15

Ser Leu Arg Leu Ser Cys Val His Ser
            20                  25


<210> SEQ ID NO 250
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25


<210> SEQ ID NO 251
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Trp Tyr Arg Gln Ser Pro Gly Asn Glu Arg Glu Leu Val Ala
1               5                   10


<210> SEQ ID NO 252
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Trp Phe Arg Gln Ser Pro Gly Asn Glu Arg Glu Leu Val Ala
1               5                   10


<210> SEQ ID NO 253
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Trp Tyr Arg Gln Phe Pro Gly Asn Glu Arg Glu Ser Ile Ala
1               5                   10
```

<210> SEQ ID NO 254
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 254

Trp Phe Arg Gln Ser Pro Gly Asn Glu Arg Glu Leu Val Ala
1 5 10

<210> SEQ ID NO 255
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 255

Trp Tyr Arg Gln Ser Pro Gly Thr Gln Pro Glu Leu Val Ala
1 5 10

<210> SEQ ID NO 256
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 256

Trp Phe Arg Gln Ala Pro Gly Lys Glu Arg Glu Phe Val Ala
1 5 10

<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 257

Trp Phe Arg Gln Ala Pro Gly Lys Glu Arg Glu Phe Val Ala
1 5 10

<210> SEQ ID NO 258
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 258

Trp Phe Arg Gln Ala Pro Gly Lys Glu Arg Glu Phe Val Ala
1 5 10

<210> SEQ ID NO 259
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 259

Trp Phe Arg Gln Ala Pro Gly Lys Glu Arg Glu Phe Val Ala
1               5                   10

<210> SEQ ID NO 260
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Trp Val Arg Gln Ala Pro Gly Lys Gly Leu Glu Trp Val Ser
1               5                   10

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Trp Val Arg Gln Ala Pro Gly Lys Gly Leu Glu Trp Val Ser
1               5                   10

<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Trp Val Arg Gln Ala Pro Gly Lys Gly Leu Glu Trp Val Ser
1               5                   10

<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Trp Val Arg Gln Ala Pro Gly Lys Gly Leu Glu Trp Val Ser
1               5                   10

<210> SEQ ID NO 264
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Trp Tyr Arg Gln Ala Pro Glu Lys Gln Arg Glu Met Val Ala
1               5                   10

<210> SEQ ID NO 265
<211> LENGTH: 14

<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (9)..(9)
<223> OTHER INFORMATION: Any amino acid

<400> SEQUENCE: 265

Trp Tyr Arg Gln Ala Pro Glu Lys Xaa Arg Glu Met Val Ala
1 5 10

<210> SEQ ID NO 266
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 266

Trp Tyr Arg Gln Val Pro Glu Lys Gln Arg Glu Met Val Ala
1 5 10

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 267

Trp Tyr Arg Gln Ala Pro Gly Arg Gly Arg Glu Leu Val Ala
1 5 10

<210> SEQ ID NO 268
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 268

Trp Tyr Arg Gln Ala Pro Gly Arg Gly Arg Glu Leu Val Ala
1 5 10

<210> SEQ ID NO 269
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 269

Trp Tyr Arg Gln Ala Pro Gly Arg Gly Arg Glu Leu Val Ala
1 5 10

<210> SEQ ID NO 270
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 270

Trp Tyr Arg Gln Ser Pro Gly Asn Glu Arg Glu Leu Val Ala
1 5 10

<210> SEQ ID NO 271
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 271

Trp Tyr Arg Gln Ser Pro Gly Asn Glu Arg Glu Leu Val Ala
1 5 10

<210> SEQ ID NO 272
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 272

Trp Tyr Arg Gln Ala Pro Gly Lys Val Arg Glu Leu Val Ala
1 5 10

<210> SEQ ID NO 273
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 273

Trp Tyr Arg Gln Ala Pro Gly Lys Val Arg Glu Leu Val Ala
1 5 10

<210> SEQ ID NO 274
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

Trp Tyr Arg Gln Ala Pro Gly Lys Glu Arg Glu Leu Val Ala
1 5 10

<210> SEQ ID NO 275
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Trp Tyr Arg Gln Ala Pro Gly Lys Glu Arg Glu Leu Val Ala
1 5 10

<210> SEQ ID NO 276
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Trp Tyr Arg Gln Ala Pro Gly Lys Gln His Glu Leu Val Ala
1 5 10

<210> SEQ ID NO 277
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

Trp Phe Arg Gln Ala Pro Gly Lys Glu Arg Glu Phe Val Ala
1 5 10

<210> SEQ ID NO 278
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

Trp Tyr Arg Gln Ala Ala Gly Lys Gln Arg Glu Leu Val Ala
1 5 10

<210> SEQ ID NO 279
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 279

Trp Tyr Arg Gln Ala Pro Gly Lys Gln Arg Glu Ser Val Ala
1 5 10

<210> SEQ ID NO 280
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 280

Trp Tyr Arg Gln Ala Pro Gly Gln Gln Arg Glu Leu Val Ala
1 5 10

<210> SEQ ID NO 281
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 281

Trp Tyr Arg Gln Ala Pro Gly Lys Gln Arg Glu Leu Val Ala
1               5                   10

<210> SEQ ID NO 282
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Trp Tyr Arg Gln Ala Pro Gly Arg Gln Arg Asp Leu Ile Ala
1               5                   10

<210> SEQ ID NO 283
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Trp Phe Arg Gln Ala Pro Gly Lys Gln Arg Glu Ser Val Ala
1               5                   10

<210> SEQ ID NO 284
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Trp Phe Arg Gln Ala Pro Gly Lys Glu Arg Glu Gly Val Ser
1               5                   10

<210> SEQ ID NO 285
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Trp Tyr Arg Gln Ala Pro Gly Lys Gln Arg Glu Phe Val Ala
1               5                   10

<210> SEQ ID NO 286
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Trp Phe Arg Gln Ala Pro Gly Lys Glu Arg Glu Gly Val Ser
1               5                   10

<210> SEQ ID NO 287
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 287

Trp Tyr Arg Gln Ala Pro Gly Lys Gln Arg Glu Leu Val Ala
1 5 10

<210> SEQ ID NO 288
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 288

Trp Tyr Arg Gln Ala Pro Gly Asn Gln Arg Glu Leu Val Ala
1 5 10

<210> SEQ ID NO 289
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 289

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Phe Cys Gly Ala
20 25 30

<210> SEQ ID NO 290
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 290

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Phe Cys Gly Ala
20 25 30

<210> SEQ ID NO 291
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 291

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Phe Cys Gly Ala
20 25 30

<210> SEQ ID NO 292
<211> LENGTH: 32

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 292

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Phe Cys Gly Ala
20 25 30

<210> SEQ ID NO 293
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 293

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Phe Cys Gly Ala
20 25 30

<210> SEQ ID NO 294
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 294

Arg Phe Thr Ile Ser Arg Asp Asn Thr Lys Asn Thr Val Tyr Leu Gln
1 5 10 15

Met Asn Ser Leu Lys Pro Glu Asp Thr Ala Val Tyr Tyr Cys Ala Ala
20 25 30

<210> SEQ ID NO 295
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 295

Arg Phe Thr Ile Ser Arg Asp Asn Thr Lys Asn Thr Val Tyr Leu Gln
1 5 10 15

Met Asn Ser Leu Lys Pro Glu Asp Thr Ala Val Tyr Tyr Cys Ala Ala
20 25 30

<210> SEQ ID NO 296
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 296

Arg Phe Thr Ile Ser Arg Asp Asn Thr Lys Asn Thr Val Tyr Leu Gln
1 5 10 15

Met Asn Ser Leu Arg Pro Glu Asp Thr Ala Val Tyr Tyr Cys Ala Ala
20 25 30

<210> SEQ ID NO 297
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 297

Arg Phe Thr Ile Ser Arg Asp Asn Thr Lys Asn Thr Val Tyr Leu Gln
1 5 10 15

Met Asn Ser Leu Lys Pro Glu Asp Thr Ala Val Tyr Tyr Cys Ala Ala
20 25 30

<210> SEQ ID NO 298
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 298

Arg Phe Thr Ile Ser Arg Asp Asn Ala Lys Asn Glu Leu Tyr Leu Glu
1 5 10 15

Met Asn Asn Leu Lys Pro Glu Asp Thr Ala Val Tyr Tyr Cys Ala Arg
20 25 30

<210> SEQ ID NO 299
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 299

Arg Phe Thr Ile Ser Arg Asp Asn Ala Lys Asn Glu Leu Tyr Leu Glu
1 5 10 15

Met Asn Asn Leu Lys Pro Glu Asp Thr Ala Val Tyr Tyr Cys Ala Arg
20 25 30

<210> SEQ ID NO 300
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 300

Arg Phe Thr Ile Ser Arg Asp Asp Ala Lys Asn Thr Leu Tyr Leu Gln
1 5 10 15

Met Asn Ser Leu Lys Pro Glu Asp Thr Ala Val Tyr Tyr Cys Ala Arg
20 25 30

<210> SEQ ID NO 301
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 301

Arg Phe Thr Ile Ser Arg Asp Asp Ala Lys Asn Thr Leu Tyr Leu Gln
1 5 10 15

Met Asn Ser Leu Lys Pro Glu Asp Thr Ala Val Tyr Tyr Cys Glu Lys
20 25 30

<210> SEQ ID NO 302
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 302

Arg Phe Thr Ile Ser Arg Asp Asn Ala Lys Asn Thr Val Tyr Leu Gln
1 5 10 15

Met Asn Thr Leu Lys Pro Glu Asp Thr Ala Val Tyr Tyr Cys Asn Ala
20 25 30

<210> SEQ ID NO 303
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 303

Arg Phe Thr Ile Ser Arg Asp Asn Ala Lys Asn Thr Val Tyr Leu Gln
1 5 10 15

Met Asn Thr Leu Lys Pro Glu Asp Thr Ala Val Tyr Tyr Cys Asn Ala
20 25 30

<210> SEQ ID NO 304
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 304

Arg Phe Thr Ile Ser Arg Asp Asn Ala Lys Asn Thr Val Tyr Leu Gln
1 5 10 15

Met Asn Thr Leu Lys Pro Glu Asp Thr Ala Val Tyr Tyr Cys Asn Ala
20 25 30

<210> SEQ ID NO 305
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 305

Arg Phe Thr Ile Ser Arg Asp Asn Ala Arg Asn Thr Val Tyr Leu Gln
1 5 10 15

Met Tyr Ser Leu Lys Pro Glu Asp Thr Ala Val Tyr Tyr Cys Gly Thr
20 25 30

<210> SEQ ID NO 306

<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Arg Phe Thr Ile Ser Arg Asp Asn Ala Arg Asn Thr Val Tyr Leu Gln
1               5                   10                  15

Met Tyr Ser Leu Arg Pro Glu Asp Thr Ala Val Tyr Tyr Cys Gly Thr
            20                  25                  30

<210> SEQ ID NO 307
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Arg Phe Thr Ile Ser Arg Asp Asn Ala Arg Asn Thr Val Tyr Leu Gln
1               5                   10                  15

Met Tyr Ser Leu Lys Pro Glu Asp Thr Ala Val Tyr Tyr Cys Gly Thr
            20                  25                  30

<210> SEQ ID NO 308
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Arg Phe Thr Ile Ser Arg Asp Asn Ala Lys Asn Thr Gly Tyr Leu Gln
1               5                   10                  15

Met Asn Ser Leu Lys Pro Glu Asp Thr Ala Val Tyr Phe Cys Ala Ala
            20                  25                  30

<210> SEQ ID NO 309
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Arg Phe Thr Ile Ser Arg Asp Asn Ala Lys Asn Thr Gly Tyr Leu Gln
1               5                   10                  15

Met Asn Ser Leu Lys Pro Glu Asp Thr Ala Val Tyr Phe Cys Ala Ala
            20                  25                  30

<210> SEQ ID NO 310
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Arg Phe Thr Ile Ser Arg Asp Asn Asp Arg Asn Thr Val Tyr Leu Gln
1               5                   10                  15

Met Asn Arg Leu Gln Pro Glu Asp Thr Ala Ala Tyr Tyr Cys Asn Val
20 25 30

<210> SEQ ID NO 311
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 311

Arg Phe Thr Ile Ser Arg Asp Asn Asp Arg Asn Thr Val Tyr Leu Gln
1 5 10 15

Met Asn Arg Leu Gln Pro Glu Asp Thr Ala Ala Tyr Tyr Cys Asn Val
20 25 30

<210> SEQ ID NO 312
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 312

Arg Phe Ser Ile Ser Arg Asp Asn Ala Lys Asn Thr Val Leu Leu Gln
1 5 10 15

Met Thr Ser Leu Lys Pro Glu Asp Thr Ala Val Tyr Tyr Cys Asn Ala
20 25 30

<210> SEQ ID NO 313
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 313

Arg Phe Ser Ile Ser Arg Asp Asn Ala Lys Asn Thr Val Leu Leu Gln
1 5 10 15

Met Thr Ser Leu Lys Pro Glu Asp Thr Ala Val Tyr Tyr Cys Asn Ala
20 25 30

<210> SEQ ID NO 314
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 314

Arg Phe Thr Ile Ser Arg Asp Asn Ala Lys Lys Thr Val Tyr Leu Gln
1 5 10 15

Met Asn Ser Leu Lys Pro Asp Asp Thr Ala Val Tyr Tyr Cys Asn Ala
20 25 30

<210> SEQ ID NO 315
<211> LENGTH: 32
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 315

Arg Phe Thr Ile Ser Arg Asp Asn Ala Lys Asn Glu Met Tyr Leu Gln
1               5                   10                  15

Met Asn Ser Leu Lys Phe Glu Asp Thr Ala Val Tyr Val Cys Ala Ala
            20                  25                  30

<210> SEQ ID NO 316
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Arg Phe Thr Ile Ser Arg Asp Ile Ala Lys Asn Thr Val Tyr Leu Gln
1               5                   10                  15

Met Asp Ser Leu Lys Pro Glu Asp Thr Ala Val Tyr Tyr Cys Asn Val
            20                  25                  30

<210> SEQ ID NO 317
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Arg Phe Thr Ile Ser Arg Asp Asn Ala Lys Asn Thr Val Tyr Leu Gln
1               5                   10                  15

Met Asn Gly Leu Lys Pro Glu Asp Thr Ala Val Tyr Tyr Cys Asn Thr
            20                  25                  30

<210> SEQ ID NO 318
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Arg Phe Thr Ile Ser Arg Asp Asn Ala Lys Asn Thr Val Tyr Leu Gln
1               5                   10                  15

Leu Ser Asp Leu Lys Pro Glu Asp Thr Ala Val Tyr Tyr Cys Asn Val
            20                  25                  30

<210> SEQ ID NO 319
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Arg Phe Ala Ile Ser Arg Asp Ser Thr Lys Asn Thr Val Tyr Leu Gln
1               5                   10                  15

Met Asn Ser Leu Lys Pro Glu Asp Thr Ala Val Tyr Tyr Cys Asn Thr
            20                  25                  30

<210> SEQ ID NO 320
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 320

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Leu
            20                  25                  30
```

<210> SEQ ID NO 321
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 321

```
Arg Phe Thr Val Ser Arg Asp Asn Ala Lys Asn Thr Leu Phe Leu Gln
1               5                   10                  15

Met Asn Ser Leu Lys Ser Glu Asp Thr Ala Val Tyr Tyr Cys Asn Ala
            20                  25                  30
```

<210> SEQ ID NO 322
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 322

```
Arg Phe Thr Ile Ser Arg Asp Asn Ala Lys Asn Thr Val Asp Leu Gln
1               5                   10                  15

Met Ile Ser Leu Arg Pro Glu Asp Thr Ala Val Tyr Tyr Cys Ala Ala
            20                  25                  30
```

<210> SEQ ID NO 323
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 323

```
Arg Phe Thr Ile Ser Arg Asp Asn Thr Lys Asn Thr Val Tyr Leu Gln
1               5                   10                  15

Met Asn Tyr Leu Lys Pro Glu Asp Thr Ala Val Tyr Tyr Cys Ala Thr
            20                  25                  30
```

<210> SEQ ID NO 324
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 324

Arg Phe Thr Ile Ser Ser Asp Asn Ala Lys Asn Thr Val Tyr Leu Gln
1               5                   10                  15

Met Asn Ser Val Lys Thr Asp Asp Thr Ala Val Tyr Tyr Cys Ala Val
            20                  25                  30

<210> SEQ ID NO 325
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Arg Phe Thr Ile Ser Arg Asp Asn Ala Asn Asn Thr Val Tyr Leu Gln
1               5                   10                  15

Met Asn Ser Leu Lys Pro Glu Asp Thr Ala Val Tyr Tyr Cys Asn Ala
            20                  25                  30

<210> SEQ ID NO 326
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Arg Tyr Ala Ile Ser Arg Asp Asn Ala Lys Asn Leu Val Tyr Leu Gln
1               5                   10                  15

Met Asn Ser Leu Lys Pro Glu Asp Thr Asp Val Tyr Tyr Cys Asn Ala
            20                  25                  30

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Asn Gly Gln Gly Thr Gln Val Thr Val Ser Ser
1               5                   10

<210> SEQ ID NO 328
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Tyr Gly Gln Gly Thr Gln Val Thr Val Ser Ser
1               5                   10

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Asn Gly Gln Gly Thr Gln Val Thr Val Ser Ser
1 5 10

<210> SEQ ID NO 330
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 330

Tyr Gly Gln Gly Thr Gln Val Thr Val Ser Ser
1 5 10

<210> SEQ ID NO 331
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 331

Tyr Gly Gln Gly Thr Gln Val Thr Val Ser Ser
1 5 10

<210> SEQ ID NO 332
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 332

Trp Gly Gln Gly Thr Gln Val Thr Val Ser Ser
1 5 10

<210> SEQ ID NO 333
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 333

Trp Gly Gln Gly Thr Gln Val Thr Val Ser Ser
1 5 10

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 334

Trp Gly Gln Gly Thr Gln Val Thr Val Ser Ser
1 5 10

<210> SEQ ID NO 335
<211> LENGTH: 11

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 335

Trp Gly Gln Gly Thr Gln Val Thr Val Ser Ser
1 5 10

<210> SEQ ID NO 336
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 336

Lys Gly Gln Gly Thr Gln Val Thr Val Ser Ser
1 5 10

<210> SEQ ID NO 337
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 337

Lys Gly Gln Gly Thr Gln Val Thr Val Ser Ser
1 5 10

<210> SEQ ID NO 338
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 338

Lys Gly Gln Gly Thr Gln Val Thr Val Ser Ser
1 5 10

<210> SEQ ID NO 339
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 339

Arg Gly Gln Gly Thr Gln Val Thr Val Ser Ser
1 5 10

<210> SEQ ID NO 340
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 340

Trp Gly Gln Gly Thr Gln Val Thr Val Ser Ser
1 5 10

<210> SEQ ID NO 341
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 341

Trp Gly Gln Gly Thr Gln Val Thr Val Ser Ser
1 5 10

<210> SEQ ID NO 342
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 342

Trp Gly Gln Gly Thr Gln Val Thr Val Ser Ser
1 5 10

<210> SEQ ID NO 343
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 343

Trp Gly Gln Gly Thr Gln Val Thr Val Ser Ser
1 5 10

<210> SEQ ID NO 344
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 344

Trp Gly Gln Gly Thr Gln Val Thr Val Ser Ser
1 5 10

<210> SEQ ID NO 345
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 345

Trp Gly Gln Gly Thr Gln Val Thr Val Ser Ser
1 5 10

<210> SEQ ID NO 346
<211> LENGTH: 11

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 346

Trp Gly Gln Gly Thr Gln Val Thr Val Ser Ser
1 5 10

<210> SEQ ID NO 347
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 347

Trp Gly Gln Gly Thr Gln Val Thr Val Ser Ser
1 5 10

<210> SEQ ID NO 348
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 348

Trp Gly Gln Gly Thr Gln Val Thr Val Ser Ser
1 5 10

<210> SEQ ID NO 349
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 349

Trp Gly Gln Gly Thr Gln Val Thr Val Ser Ser
1 5 10

<210> SEQ ID NO 350
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 350

Trp Gly Gln Gly Thr Gln Val Thr Val Ser Ser
1 5 10

<210> SEQ ID NO 351
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 351

Trp Gly Gln Gly Thr Gln Val Thr Val Ser Ser
1 5 10

<210> SEQ ID NO 352
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 352

Trp Gly Gln Gly Thr Gln Val Thr Val Ser Ser
1 5 10

<210> SEQ ID NO 353
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

Trp Gly Gln Gly Thr Gln Val Thr Val Ser Ser
1 5 10

<210> SEQ ID NO 354
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 354

Trp Gly Gln Gly Thr Gln Val Thr Val Ser Ser
1 5 10

<210> SEQ ID NO 355
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 355

Trp Gly Gln Gly Thr Gln Val Thr Val Ser Ser
1 5 10

<210> SEQ ID NO 356
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 356

Trp Gly Gln Gly Thr Gln Val Thr Val Ser Ser
1 5 10

<210> SEQ ID NO 357
<211> LENGTH: 11

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 357

Trp Gly Gln Gly Thr Gln Val Thr Val Ser Ser
1               5                   10

<210> SEQ ID NO 358
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 358

Trp Gly Gln Gly Thr Gln Val Thr Val Ser Ser
1               5                   10

<210> SEQ ID NO 359
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 359

Trp Gly Gln Gly Thr Gln Val Thr Val Ser Ser
1               5                   10

<210> SEQ ID NO 360
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 360

Gln Gly Gln Gly Thr Gln Val Thr Val Ser Ser
1               5                   10

<210> SEQ ID NO 361
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 361

Trp Gly His Gly Thr Gln Val Thr Val Ser Ser
1               5                   10

<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 362

Trp Gly Gln Gly Thr Gln Val Thr Val Ser Ser
1 5 10

<210> SEQ ID NO 363
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 363

Trp Gly Gln Gly Thr Gln Val Thr Val Ser Ser
1 5 10

<210> SEQ ID NO 364
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 364

Trp Gly Gln Gly Thr Gln Val Thr Val Ser Ser
1 5 10

<210> SEQ ID NO 365
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(20)
<223> OTHER INFORMATION: This sequence may encompass 1-10 "Gly Ser" repeating units

<400> SEQUENCE: 365

Gly Ser Gly Ser Gly Ser Gly Ser Gly Ser Gly Ser Gly Ser Gly Ser
1 5 10 15

Gly Ser Gly Ser
20

<210> SEQ ID NO 366
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(30)
<223> OTHER INFORMATION: This sequence may encompass 1-10 "Gly Gly Ser" repeating units

<400> SEQUENCE: 366

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser Gly Gly Ser
20 25 30

```
<210> SEQ ID NO 367
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units

<400> SEQUENCE: 367

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40


<210> SEQ ID NO 368
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Ser
      Gly" repeating units

<400> SEQUENCE: 368

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40


<210> SEQ ID NO 369
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Ser
      Gly Gly" repeating units

<400> SEQUENCE: 369

Gly Gly Ser Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Gly Gly Gly Gly Ser Gly Gly Gly Gly Ser
        35                  40                  45

Gly Gly
    50


<210> SEQ ID NO 370
```

<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units

<400> SEQUENCE: 370

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50
```

<210> SEQ ID NO 371
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Gly" repeating units

<400> SEQUENCE: 371

```
Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly
    50
```

<210> SEQ ID NO 372
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-10 "Gly Gly Gly"
      repeating units

<400> SEQUENCE: 372

```
Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
            20                  25                  30
```

<210> SEQ ID NO 373
<211> LENGTH: 20

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 373

Gly Gly Gly Gly Ser Gly Gly Gly Gly Ser Gly Gly Gly Gly Ser Gly
1 5 10 15

Gly Gly Gly Ser
20

<210> SEQ ID NO 374
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 374

Gly Gly Gly Gly Ser Gly Gly Gly Gly Ser Gly Gly Gly Gly Ser
1 5 10 15

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 375

Gly Gly Gly Gly Ser Gly Gly Gly Ser
1 5

<210> SEQ ID NO 376
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 376

Leu Pro Glu Thr Gly
1 5

<210> SEQ ID NO 377
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 377

His His His His His His
1 5

<210> SEQ ID NO 378
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 378

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser
        115

<210> SEQ ID NO 379
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Ile Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Gln Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Ala Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Ala Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Val Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Thr Leu Trp Tyr Ser Asn Arg Trp Val Phe
225 230 235 240

Gly Gly Gly Thr Lys Leu Thr Val Leu
245

<210> SEQ ID NO 380
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 380

Gly Gly Gly Gly Gly Leu Asp Gly Asn Glu Glu Pro Gly Gly
1 5 10

<210> SEQ ID NO 381
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 381

Ala Pro Gly Lys Gly
1 5

<210> SEQ ID NO 382
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 382

Gly Gly Gln Asp Gly Asn Glu Glu Met Gly Gly Gly
1 5 10

<210> SEQ ID NO 383
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 383

Gly Gly Gln Asp Gly Asn Glu Glu Gly Gly
1 5 10

<210> SEQ ID NO 384
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 384

Gly Gly Gly Gly Gln Asp Gly Asn Glu Glu Met Gly Gly Gly Gly Gly
1 5 10 15

<210> SEQ ID NO 385
<211> LENGTH: 7

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 385

Ala Pro Phe Gly Ser Glu Met
1 5

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 386

Ala Trp Asn Gly Pro Tyr Glu
1 5

<210> SEQ ID NO 387
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 387

Ala Gln Asp Asn Gly Asp Thr Lys Thr Gly
1 5 10

<210> SEQ ID NO 388
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 388

Ala Glu Ala Lys Glu Thr Gln Gly
1 5

<210> SEQ ID NO 389
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 389

Ala Thr Arg Arg Glu Gln Val Glu Gly
1 5

<210> SEQ ID NO 390
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 390

Ala Gln Ala Pro Ser Gln Pro
1 5

<210> SEQ ID NO 391
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 391

Ala Thr Arg Ser Arg Thr Arg Asn Asp Gly
1 5 10

<210> SEQ ID NO 392
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 392

Ala Asp Val Asp Ala Pro Asp Gly Leu Gly
1 5 10

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 393

Ala Ala Asp Ile Ser Asp Pro Gly Gly
1 5

<210> SEQ ID NO 394
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 394

Ala Leu Ser Val Asp Pro Ser Gly
1 5

<210> SEQ ID NO 395
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 395

Ala Arg Leu Ser Val Asp Pro Gly
1 5

<210> SEQ ID NO 396
<211> LENGTH: 8

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 396

Ala Val Glu Ala Ala Asp Arg Gly
1 5

<210> SEQ ID NO 397
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 397

Gly Gly Pro Asp Gly Asn Glu Glu Met Gly Gly Gly
1 5 10

<210> SEQ ID NO 398
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 398

Gly Gly Phe Asp Gly Asn Glu Glu Met Gly Gly Gly
1 5 10

<210> SEQ ID NO 399
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 399

Gly Gly Gly Asp Gly Asn Glu Glu Met Gly Gly Gly
1 5 10

<210> SEQ ID NO 400
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 400

Gly Gly Glu Met Asp Gly Glu Gly Gln Asn Gly Gly
1 5 10

<210> SEQ ID NO 401
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 401

Gly Gly Gly Gly Gly Pro Asp Gly Asn Glu Glu Pro Gly Gly
1 5 10

<210> SEQ ID NO 402
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 402

Gly Gly Gly Gly Ser Leu Asp Gly Asn Glu Glu Pro Gly Gly
1 5 10

<210> SEQ ID NO 403
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 403

Gly Gly Gly Gly Ala Leu Asp Gly Asn Glu Glu Pro Gly Gly
1 5 10

<210> SEQ ID NO 404
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 404

Gly Gly Gly Gly Gly Leu Asp Gly Asn Glu Glu Pro Gly Gly
1 5 10

<210> SEQ ID NO 405
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 405

Gly Gly Gly Ala Leu Asp Gly Asn Glu Glu Pro Gly Gly
1 5 10

<210> SEQ ID NO 406
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 406

Gly Gly Gly Gly Gly Pro Asp Gly Asn Glu Glu Pro Gly Gly Gly
1 5 10 15

<210> SEQ ID NO 407
<211> LENGTH: 14

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Gly Gly Ser Gly Ala Leu Asp Gly Asn Glu Glu Pro Gly Gly
1               5                   10

<210> SEQ ID NO 408
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Gly Gly Ser Gly Ser Leu Asp Gly Asn Glu Glu Pro Gly Gly
1               5                   10

<210> SEQ ID NO 409
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Gly Gly Ser Gly Gly Pro Asp Gly Asn Glu Glu Pro Gly Gly
1               5                   10

<210> SEQ ID NO 410
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Gly Gly Val Arg Asp Gly Pro Asp Gly Asn Glu Glu Pro Gly Gly
1               5                   10                  15

<210> SEQ ID NO 411
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gly Gly Ser Gly Gly Pro Asp Gly Asn Glu Glu Pro Gly Gly Gly Gly
1               5                   10                  15

<210> SEQ ID NO 412
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Gly Gly Gly Arg Gly Pro Asp Gly Asn Glu Glu Pro Gly Gly
1 5 10

<210> SEQ ID NO 413
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 413

Gly Gly Ser Gly Gly Leu Asp Gly Asn Glu Glu Pro Gly Gly
1 5 10

<210> SEQ ID NO 414
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 414

Gly Gly Gly Val Gly Pro Asp Gly Asn Glu Glu Pro Gly Gly
1 5 10

<210> SEQ ID NO 415
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 415

Gly Gly Gly Glu Gly Pro Asp Gly Asn Glu Glu Pro Gly Gly
1 5 10

<210> SEQ ID NO 416
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 416

Gly Gly Gly Val Ala Leu Asp Gly Asn Glu Glu Pro Gly Gly
1 5 10

<210> SEQ ID NO 417
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 417

Gly Gly Gly Arg Ala Leu Asp Gly Asn Glu Glu Pro Gly Gly
1 5 10

<210> SEQ ID NO 418
<211> LENGTH: 14

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Gly Gly Tyr Ala Gly Leu Asp Gly Asn Glu Glu Pro Gly Gly
1               5                   10

<210> SEQ ID NO 419
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Gly Gly Ala Gly Gly Pro Asp Gly Asn Glu Glu Pro Gly Gly
1               5                   10

<210> SEQ ID NO 420
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Gly Gly Arg Gly Gly Pro Asp Gly Asn Glu Glu Pro Gly Gly
1               5                   10

<210> SEQ ID NO 421
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Gly Gly Gly Gly Pro Asp Gly Asn Glu Glu Pro Gly Gly Gly Gly
1               5                   10                  15

<210> SEQ ID NO 422
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Gly Gly Gly Glu Ala Leu Asp Gly Asn Glu Glu Pro Gly Gly
1               5                   10

<210> SEQ ID NO 423
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Gly Gly Asp Ala Ser Leu Asp Gly Asn Glu Glu Pro Gly Gly
1 5 10

<210> SEQ ID NO 424
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 424

Gly Gly Arg Asp Ala Pro Asp Gly Asn Glu Glu Gly Gly
1 5 10

<210> SEQ ID NO 425
<211> LENGTH: 8
<212> TYPE: PRT
<213> ORGANISM: Unknown
<220> FEATURE:
<223> OTHER INFORMATION: Description of Unknown: Cleavage sequence

<400> SEQUENCE: 425

Lys Arg Ala Leu Gly Leu Pro Gly
1 5

<210> SEQ ID NO 426
<211> LENGTH: 40
<212> TYPE: PRT
<213> ORGANISM: Unknown
<220> FEATURE:
<223> OTHER INFORMATION: Description of Unknown: Cleavage sequence

<400> SEQUENCE: 426

Asp Glu Asp Glu Asp Glu Asp Glu Asp Glu Asp Glu Asp Glu Asp Glu
1 5 10 15

Arg Pro Leu Ala Leu Trp Arg Ser Asp Arg Asp Arg Asp Arg Asp Arg
20 25 30

Asp Arg Asp Arg Asp Arg Asp Arg
35 40

<210> SEQ ID NO 427
<211> LENGTH: 5
<212> TYPE: PRT
<213> ORGANISM: Unknown
<220> FEATURE:
<223> OTHER INFORMATION: Description of Unknown: Cleavage sequence
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Leu or Ile
<220> FEATURE:
<221> NAME/KEY: MOD_RES
<222> LOCATION: (5)..(5)
<223> OTHER INFORMATION: Ser or Thr

<400> SEQUENCE: 427

Pro Arg Xaa Xaa Xaa
1 5

<210> SEQ ID NO 428
<211> LENGTH: 5
<212> TYPE: PRT
<213> ORGANISM: Unknown
<220> FEATURE:
<223> OTHER INFORMATION: Description of Unknown:
      Cleavage sequence

<400> SEQUENCE: 428

Leu Glu Ala Thr Ala
1               5

<210> SEQ ID NO 429
<211> LENGTH: 10
<212> TYPE: PRT
<213> ORGANISM: Unknown
<220> FEATURE:
<223> OTHER INFORMATION: Description of Unknown:
      Cleavage sequence

<400> SEQUENCE: 429

Gly Gly Ala Ala Asn Leu Val Arg Gly Gly
1               5                   10

<210> SEQ ID NO 430
<211> LENGTH: 10
<212> TYPE: PRT
<213> ORGANISM: Unknown
<220> FEATURE:
<223> OTHER INFORMATION: Description of Unknown:
      Cleavage sequence

<400> SEQUENCE: 430

Ser Gly Arg Ile Gly Phe Leu Arg Thr Ala
1               5                   10

<210> SEQ ID NO 431
<211> LENGTH: 6
<212> TYPE: PRT
<213> ORGANISM: Unknown
<220> FEATURE:
<223> OTHER INFORMATION: Description of Unknown:
      Cleavage sequence

<400> SEQUENCE: 431

Pro Leu Gly Leu Ala Gly
1               5

<210> SEQ ID NO 432
<211> LENGTH: 6
<212> TYPE: PRT
<213> ORGANISM: Unknown
<220> FEATURE:
<223> OTHER INFORMATION: Description of Unknown:
      Cleavage sequence
<220> FEATURE:
<221> NAME/KEY: MOD_RES
<222> LOCATION: (6)..(6)
<223> OTHER INFORMATION: Any amino acid

<400> SEQUENCE: 432

Pro Leu Gly Leu Ala Xaa
1               5

<210> SEQ ID NO 433
<211> LENGTH: 6
<212> TYPE: PRT

```
<213> ORGANISM: Unknown
<220> FEATURE:
<223> OTHER INFORMATION: Description of Unknown:
      Cleavage sequence
<220> FEATURE:
<221> NAME/KEY: MOD_RES
<222> LOCATION: (4)..(4)
<223> OTHER INFORMATION: Cys(me)

<400> SEQUENCE: 433

Pro Leu Gly Cys Ala Gly
1               5


<210> SEQ ID NO 434
<211> LENGTH: 8
<212> TYPE: PRT
<213> ORGANISM: Unknown
<220> FEATURE:
<223> OTHER INFORMATION: Description of Unknown:
      Cleavage sequence

<400> SEQUENCE: 434

Glu Ser Pro Ala Tyr Tyr Thr Ala
1               5


<210> SEQ ID NO 435
<211> LENGTH: 6
<212> TYPE: PRT
<213> ORGANISM: Unknown
<220> FEATURE:
<223> OTHER INFORMATION: Description of Unknown:
      Cleavage sequence

<400> SEQUENCE: 435

Arg Leu Gln Leu Lys Leu
1               5


<210> SEQ ID NO 436
<211> LENGTH: 7
<212> TYPE: PRT
<213> ORGANISM: Unknown
<220> FEATURE:
<223> OTHER INFORMATION: Description of Unknown:
      Cleavage sequence

<400> SEQUENCE: 436

Arg Leu Gln Leu Lys Ala Cys
1               5


<210> SEQ ID NO 437
<211> LENGTH: 7
<212> TYPE: PRT
<213> ORGANISM: Unknown
<220> FEATURE:
<223> OTHER INFORMATION: Description of Unknown:
      Cleavage sequence
<220> FEATURE:
<221> NAME/KEY: MOD_RES
<222> LOCATION: (3)..(3)
<223> OTHER INFORMATION: Cit
<220> FEATURE:
<221> NAME/KEY: MOD_RES
<222> LOCATION: (5)..(5)
<223> OTHER INFORMATION: Hof

<400> SEQUENCE: 437

Glu Pro Xaa Gly Xaa Tyr Leu
1               5
```

<210> SEQ ID NO 438
<211> LENGTH: 5
<212> TYPE: PRT
<213> ORGANISM: Unknown
<220> FEATURE:
<223> OTHER INFORMATION: Description of Unknown:
Cleavage sequence

<400> SEQUENCE: 438

Ser Gly Arg Ser Ala
1 5

<210> SEQ ID NO 439
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 439

Asp Ala Phe Lys
1

<210> SEQ ID NO 440
<211> LENGTH: 5
<212> TYPE: PRT
<213> ORGANISM: Unknown
<220> FEATURE:
<223> OTHER INFORMATION: Description of Unknown:
Cleavage sequence

<400> SEQUENCE: 440

Gly Gly Gly Arg Arg
1 5

<210> SEQ ID NO 441
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 441

Gly Phe Leu Gly
1

<210> SEQ ID NO 442
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 442

Ala Leu Ala Leu
1

<210> SEQ ID NO 443
<211> LENGTH: 2
<212> TYPE: PRT
<213> ORGANISM: Unknown
<220> FEATURE:
<223> OTHER INFORMATION: Description of Unknown:
Cleavage sequence

<400> SEQUENCE: 443

Phe Lys
1

<210> SEQ ID NO 444
<211> LENGTH: 3
<212> TYPE: PRT
<213> ORGANISM: Unknown
<220> FEATURE:
<223> OTHER INFORMATION: Description of Unknown:
Cleavage sequence

<400> SEQUENCE: 444

Asn Leu Leu
1

<210> SEQ ID NO 445
<211> LENGTH: 5
<212> TYPE: PRT
<213> ORGANISM: Unknown
<220> FEATURE:
<223> OTHER INFORMATION: Description of Unknown:
Cleavage sequence
<220> FEATURE:
<221> NAME/KEY: MOD_RES
<222> LOCATION: (3)..(3)
<223> OTHER INFORMATION: Cys(Et)

<400> SEQUENCE: 445

Pro Ile Cys Phe Phe
1 5

<210> SEQ ID NO 446
<211> LENGTH: 8
<212> TYPE: PRT
<213> ORGANISM: Unknown
<220> FEATURE:
<223> OTHER INFORMATION: Description of Unknown:
Cleavage sequence

<400> SEQUENCE: 446

Gly Gly Pro Arg Gly Leu Pro Gly
1 5

<210> SEQ ID NO 447
<211> LENGTH: 6
<212> TYPE: PRT
<213> ORGANISM: Unknown
<220> FEATURE:
<223> OTHER INFORMATION: Description of Unknown:
Cleavage sequence

<400> SEQUENCE: 447

His Ser Ser Lys Leu Gln
1 5

<210> SEQ ID NO 448
<211> LENGTH: 7
<212> TYPE: PRT
<213> ORGANISM: Unknown
<220> FEATURE:
<223> OTHER INFORMATION: Description of Unknown:
Cleavage sequence

<400> SEQUENCE: 448

His Ser Ser Lys Leu Gln Leu
1 5

<210> SEQ ID NO 449
<211> LENGTH: 9
<212> TYPE: PRT
<213> ORGANISM: Unknown
<220> FEATURE:
<223> OTHER INFORMATION: Description of Unknown:
Cleavage sequence

<400> SEQUENCE: 449

His Ser Ser Lys Leu Gln Glu Asp Ala
1 5

<210> SEQ ID NO 450
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 450

Leu Val Leu Ala Ser Ser Ser Phe Gly Tyr
1 5 10

<210> SEQ ID NO 451
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 451

Gly Val Ser Gln Asn Tyr Pro Ile Val Gly
1 5 10

<210> SEQ ID NO 452
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 452

Gly Val Val Gln Ala Ser Cys Arg Leu Ala
1 5 10

<210> SEQ ID NO 453
<211> LENGTH: 4
<212> TYPE: PRT
<213> ORGANISM: Unknown
<220> FEATURE:
<223> OTHER INFORMATION: Description of Unknown:
Cleavage sequence
<220> FEATURE:
<221> NAME/KEY: MOD_RES
<222> LOCATION: (2)..(2)
<223> OTHER INFORMATION: Pip

<400> SEQUENCE: 453

Phe Xaa Arg Ser
1

<210> SEQ ID NO 454
<211> LENGTH: 6
<212> TYPE: PRT

<213> ORGANISM: Unknown
<220> FEATURE:
<223> OTHER INFORMATION: Description of Unknown:
      Cleavage sequence

<400> SEQUENCE: 454

Asp Pro Arg Ser Phe Leu
1               5

<210> SEQ ID NO 455
<211> LENGTH: 6
<212> TYPE: PRT
<213> ORGANISM: Unknown
<220> FEATURE:
<223> OTHER INFORMATION: Description of Unknown:
      Cleavage sequence

<400> SEQUENCE: 455

Pro Pro Arg Ser Phe Leu
1               5

<210> SEQ ID NO 456
<211> LENGTH: 4
<212> TYPE: PRT
<213> ORGANISM: Unknown
<220> FEATURE:
<223> OTHER INFORMATION: Description of Unknown:
      Cleavage sequence

<400> SEQUENCE: 456

Asp Glu Val Asp
1

<210> SEQ ID NO 457
<211> LENGTH: 5
<212> TYPE: PRT
<213> ORGANISM: Unknown
<220> FEATURE:
<223> OTHER INFORMATION: Description of Unknown:
      Cleavage sequence

<400> SEQUENCE: 457

Asp Glu Val Asp Pro
1               5

<210> SEQ ID NO 458
<211> LENGTH: 8
<212> TYPE: PRT
<213> ORGANISM: Unknown
<220> FEATURE:
<223> OTHER INFORMATION: Description of Unknown:
      Cleavage sequence

<400> SEQUENCE: 458

Lys Gly Ser Gly Asp Val Glu Gly
1               5

<210> SEQ ID NO 459
<211> LENGTH: 6
<212> TYPE: PRT
<213> ORGANISM: Unknown
<220> FEATURE:
<223> OTHER INFORMATION: Description of Unknown:
      Cleavage sequence

<400> SEQUENCE: 459

Gly Trp Glu His Asp Gly
1               5

<210> SEQ ID NO 460
<211> LENGTH: 7
<212> TYPE: PRT
<213> ORGANISM: Unknown
<220> FEATURE:
<223> OTHER INFORMATION: Description of Unknown:
Cleavage sequence

<400> SEQUENCE: 460

Glu Asp Asp Asp Asp Lys Ala
1 5

<210> SEQ ID NO 461
<211> LENGTH: 9
<212> TYPE: PRT
<213> ORGANISM: Unknown
<220> FEATURE:
<223> OTHER INFORMATION: Description of Unknown:
Cleavage sequence

<400> SEQUENCE: 461

Lys Gln Glu Gln Asn Pro Gly Ser Thr
1 5

<210> SEQ ID NO 462
<211> LENGTH: 6
<212> TYPE: PRT
<213> ORGANISM: Unknown
<220> FEATURE:
<223> OTHER INFORMATION: Description of Unknown:
Cleavage sequence

<400> SEQUENCE: 462

Gly Lys Ala Phe Arg Arg
1 5

<210> SEQ ID NO 463
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 463

Asp Ala Phe Lys
1

<210> SEQ ID NO 464
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 464

Asp Val Leu Lys
1

<210> SEQ ID NO 465
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 465

Asp Ala Phe Lys
1

<210> SEQ ID NO 466
<211> LENGTH: 7
<212> TYPE: PRT
<213> ORGANISM: Unknown
<220> FEATURE:
<223> OTHER INFORMATION: Description of Unknown:
Cleavage sequence

<400> SEQUENCE: 466

Ala Leu Leu Leu Ala Leu Leu
1 5

<210> SEQ ID NO 467
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 467

Lys Pro Leu Gly Leu Gln Ala Arg Val Val
1 5 10

<210> SEQ ID NO 468
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 468

Pro Gln Ala Ser Thr Gly Arg Ser Gly Gly
1 5 10

<210> SEQ ID NO 469
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 469

Pro Gln Gly Ser Thr Gly Arg Ala Ala Gly
1 5 10

<210> SEQ ID NO 470
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 470

Pro Pro Ala Ser Ser Gly Arg Ala Gly Gly
1 5 10

<210> SEQ ID NO 471
<211> LENGTH: 9

<212> TYPE: PRT
<213> ORGANISM: Unknown
<220> FEATURE:
<223> OTHER INFORMATION: Description of Unknown:
Cleavage sequence

<400> SEQUENCE: 471

Pro Ile Pro Val Gln Gly Arg Ala His
1 5

<210> SEQ ID NO 472
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 472

Glu Val Gln Leu Val Glu Ser Gly Gly Gly Leu Val Gln Pro Gly Asn
1 5 10 15

Ser Leu Arg Leu Ser Cys Ala Ala Ser Gly Phe Thr Phe Ser Lys Phe
20 25 30

Gly Met Ser Trp Val Arg Gln Gly Gly Gly Gly Gly Leu Asp Gly Asn
35 40 45

Glu Glu Pro Gly Gly Leu Glu Trp Val Ser Ser Ile Ser Gly Ser Gly
50 55 60

Arg Asp Thr Leu Tyr Ala Asp Ser Val Lys Gly Arg Phe Thr Ile Ser
65 70 75 80

Arg Asp Asn Ala Lys Thr Thr Leu Tyr Leu Gln Met Asn Ser Leu Arg
85 90 95

Pro Glu Asp Thr Ala Val Tyr Tyr Cys Thr Ile Gly Gly Ser Leu Ser
100 105 110

Val Ser Ser Gln Gly Thr Leu Val Thr Val Ser Ser
115 120

<210> SEQ ID NO 473
<211> LENGTH: 143
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 473

Glu Val Gln Leu Val Glu Ser Gly Gly Gly Leu Val Gln Pro Gly Asn
1 5 10 15

Ser Leu Arg Leu Ser Cys Ala Ala Ser Gly Phe Thr Phe Ser Lys Phe
20 25 30

Gly Met Ser Trp Val Arg Gln Gly Gly Gly Gly Gly Leu Asp Gly Asn
35 40 45

Glu Glu Pro Gly Gly Leu Glu Trp Val Ser Ser Ile Ser Gly Ser Gly
50 55 60

Arg Asp Thr Leu Tyr Ala Asp Ser Val Lys Gly Arg Phe Thr Ile Ser
65 70 75 80

Arg Asp Asn Ala Lys Thr Thr Leu Tyr Leu Gln Met Asn Ser Leu Arg
85 90 95

Pro Glu Asp Thr Ala Val Tyr Tyr Cys Thr Ile Gly Gly Ser Leu Ser
100 105 110

```
Val Ser Ser Gln Gly Thr Leu Val Thr Val Ser Ser Gly Gly Gly Gly
        115                 120                 125

Lys Pro Leu Gly Leu Gln Ala Arg Val Val Gly Gly Gly Gly Thr
    130                 135                 140


<210> SEQ ID NO 474
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Val Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Thr Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Asn Lys Tyr Ala Ile Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Gln Val Lys Asp
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Ala Asn Phe Gly Asn Ser Tyr Ile Ser Tyr Trp Ala Tyr Trp Gly
225                 230                 235                 240

Gln Gly Thr Leu Val Thr Val Ser Ser
                245


<210> SEQ ID NO 475
<211> LENGTH: 342
<212> TYPE: PRT
<213> ORGANISM: Homo sapiens

<400> SEQUENCE: 475

Met Glu Thr Lys His Leu Gly Arg Gly Gly Ala Gly Arg Ala Gly Pro
1               5                   10                  15

His Leu Trp Arg Gly Pro Arg Pro Asn Cys Ser Ala Gly Ala Gly Gly
            20                  25                  30
```

```
Gly Glu Pro Thr His Ser Pro Asn Ser Arg Ala Val Thr His Gln Arg
        35                  40                  45

Ala Pro Ala Ala Arg Glu Cys Val Cys Glu Asn Tyr Lys Leu Ala Val
    50                  55                  60

Asn Cys Phe Val Asn Asn Asn Arg Gln Cys Gln Cys Thr Ser Val Gly
65                  70                  75                  80

Ala Gln Asn Thr Val Ile Cys Ser Lys Leu Ala Ala Lys Cys Leu Val
                85                  90                  95

Met Lys Ala Glu Met Asn Gly Ser Lys Leu Gly Arg Arg Ala Lys Pro
            100                 105                 110

Glu Gly Ala Leu Gln Asn Asn Asp Gly Leu Tyr Asp Pro Asp Cys Asp
        115                 120                 125

Glu Ser Gly Leu Phe Lys Ala Lys Gln Cys Asn Gly Thr Ser Met Cys
    130                 135                 140

Trp Cys Val Asn Thr Ala Gly Val Arg Arg Thr Asp Lys Asp Thr Glu
145                 150                 155                 160

Ile Thr Cys Ser Glu Arg Val Arg Thr Tyr Trp Ile Ile Ile Glu Leu
                165                 170                 175

Lys His Lys Ala Arg Glu Lys Pro Tyr Asp Ser Lys Ser Leu Arg Thr
            180                 185                 190

Ala Leu Gln Lys Glu Ile Thr Thr Arg Tyr Gln Leu Asp Pro Lys Phe
        195                 200                 205

Ile Thr Ser Ile Leu Tyr Glu Asn Asn Val Ile Thr Ile Asp Leu Val
    210                 215                 220

Gln Asn Ser Ser Gln Lys Thr Gln Asn Asp Val Asp Ile Ala Asp Val
225                 230                 235                 240

Ala Tyr Tyr Phe Glu Lys Asp Val Lys Gly Glu Ser Leu Phe His Ser
                245                 250                 255

Lys Lys Met Asp Leu Thr Val Asn Gly Glu Gln Leu Asp Leu Asp Pro
            260                 265                 270

Gly Gln Thr Leu Ile Tyr Tyr Val Asp Glu Lys Ala Pro Glu Phe Ser
        275                 280                 285

Met Gln Gly Leu Lys Ala Gly Val Ile Ala Val Ile Val Val Val Val
    290                 295                 300

Ile Ala Val Val Ala Gly Ile Val Val Leu Val Ile Ser Arg Lys Lys
305                 310                 315                 320

Arg Met Ala Lys Tyr Glu Lys Ala Glu Ile Lys Glu Met Gly Glu Met
                325                 330                 335

His Arg Glu Leu Asn Ala
            340
```

<210> SEQ ID NO 476
<211> LENGTH: 288
<212> TYPE: PRT
<213> ORGANISM: Macaca fascicularis

<400> SEQUENCE: 476

```
Cys Val Cys Glu Asn Tyr Lys Leu Ala Val Asn Cys Phe Leu Asn Asp
1               5                   10                  15

Asn Gly Gln Cys Gln Cys Thr Ser Ile Gly Ala Gln Asn Thr Val Leu
            20                  25                  30

Cys Ser Lys Leu Ala Ala Lys Cys Leu Val Met Lys Ala Glu Met Asn
        35                  40                  45
```

```
Gly Ser Lys Leu Gly Arg Arg Ala Lys Pro Glu Gly Ala Leu Gln Asn
    50                  55                  60

Asn Asp Gly Leu Tyr Asp Pro Asp Cys Asp Glu Ser Gly Leu Phe Lys
65                  70                  75                  80

Ala Lys Gln Cys Asn Gly Thr Ser Thr Cys Trp Cys Val Asn Thr Ala
                85                  90                  95

Gly Val Arg Arg Thr Asp Lys Asp Thr Glu Ile Thr Cys Ser Glu Arg
            100                 105                 110

Val Arg Thr Tyr Trp Ile Ile Ile Glu Leu Lys His Lys Ala Arg Glu
        115                 120                 125

Lys Pro Tyr Asp Val Gln Ser Leu Arg Thr Ala Leu Glu Glu Ala Ile
    130                 135                 140

Lys Thr Arg Tyr Gln Leu Asp Pro Lys Phe Ile Thr Asn Ile Leu Tyr
145                 150                 155                 160

Glu Asp Asn Val Ile Thr Ile Asp Leu Val Gln Asn Ser Ser Gln Lys
                165                 170                 175

Thr Gln Asn Asp Val Asp Ile Ala Asp Val Ala Tyr Tyr Phe Glu Lys
            180                 185                 190

Asp Val Lys Gly Glu Ser Leu Phe His Ser Lys Lys Met Asp Leu Arg
        195                 200                 205

Val Asn Gly Glu Gln Leu Asp Leu Asp Pro Gly Gln Thr Leu Ile Tyr
    210                 215                 220

Tyr Val Asp Glu Lys Ala Pro Glu Phe Ser Met Gln Gly Leu Lys Ala
225                 230                 235                 240

Gly Val Ile Ala Val Ile Val Val Val Val Ile Ala Ile Val Ala Gly
                245                 250                 255

Ile Val Val Leu Val Ile Ser Arg Lys Lys Arg Met Ala Lys Tyr Glu
            260                 265                 270

Lys Ala Glu Ile Lys Glu Met Gly Glu Ile His Arg Glu Leu Asn Ala
        275                 280                 285


<210> SEQ ID NO 477
<211> LENGTH: 315
<212> TYPE: PRT
<213> ORGANISM: Mus musculus

<400> SEQUENCE: 477

Met Ala Gly Pro Gln Ala Leu Ala Phe Gly Leu Leu Leu Ala Val Val
1               5                   10                  15

Thr Ala Thr Leu Ala Ala Ala Gln Arg Asp Cys Val Cys Asp Asn Tyr
            20                  25                  30

Lys Leu Ala Thr Ser Cys Ser Leu Asn Glu Tyr Gly Glu Cys Gln Cys
        35                  40                  45

Thr Ser Tyr Gly Thr Gln Asn Thr Val Ile Cys Ser Lys Leu Ala Ser
    50                  55                  60

Lys Cys Leu Ala Met Lys Ala Glu Met Thr His Ser Lys Ser Gly Arg
65                  70                  75                  80

Arg Ile Lys Pro Glu Gly Ala Ile Gln Asn Asn Asp Gly Leu Tyr Asp
                85                  90                  95

Pro Asp Cys Asp Glu Gln Gly Leu Phe Lys Ala Lys Gln Cys Asn Gly
            100                 105                 110

Thr Ala Thr Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140
```

```
Ile Ile Glu Leu Lys His Lys Glu Arg Glu Ser Pro Tyr Asp His Gln
145                 150                 155                 160

Ser Leu Gln Thr Ala Leu Gln Glu Ala Phe Thr Ser Arg Tyr Lys Leu
                165                 170                 175

Asn Gln Lys Phe Ile Lys Asn Ile Met Tyr Glu Asn Asn Val Ile Thr
            180                 185                 190

Ile Asp Leu Met Gln Asn Ser Ser Gln Lys Thr Gln Asp Asp Val Asp
        195                 200                 205

Ile Ala Asp Val Ala Tyr Tyr Phe Glu Lys Asp Val Lys Gly Glu Ser
    210                 215                 220

Leu Phe His Ser Ser Lys Ser Met Asp Leu Arg Val Asn Gly Glu Pro
225                 230                 235                 240

Leu Asp Leu Asp Pro Gly Gln Thr Leu Ile Tyr Tyr Val Asp Glu Lys
                245                 250                 255

Ala Pro Glu Phe Ser Met Gln Gly Leu Thr Ala Gly Ile Ile Ala Val
            260                 265                 270

Ile Val Val Val Ser Leu Ala Val Ile Ala Gly Ile Val Val Leu Val
        275                 280                 285

Ile Ser Thr Arg Lys Lys Ser Ala Lys Tyr Glu Lys Ala Glu Ile Lys
    290                 295                 300

Glu Met Gly Glu Ile His Arg Glu Leu Asn Ala
305                 310                 315


<210> SEQ ID NO 478
<211> LENGTH: 314
<212> TYPE: PRT
<213> ORGANISM: Homo sapiens

<400> SEQUENCE: 478

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
        35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205
```

Ile Ala Asp Val Ala Tyr Tyr Phe Glu Lys Asp Val Lys Gly Glu Ser
    210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
        275                 280                 285

Ser Arg Lys Lys Arg Met Ala Lys Tyr Glu Lys Ala Glu Ile Lys Glu
    290                 295                 300

Met Gly Glu Met His Arg Glu Leu Asn Ala
305                 310

<210> SEQ ID NO 479
<211> LENGTH: 242
<212> TYPE: PRT
<213> ORGANISM: Homo sapiens

<400> SEQUENCE: 479

Gln Glu Glu Cys Val Cys Glu Asn Tyr Lys Leu Ala Val Asn Cys Phe
1               5                   10                  15

Val Asn Asn Asn Arg Gln Cys Gln Cys Thr Ser Val Gly Ala Gln Asn
            20                  25                  30

Thr Val Ile Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
    50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Met Cys Trp Cys Val
                85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Ile Glu Leu Lys His Lys
        115                 120                 125

Ala Arg Glu Lys Pro Tyr Asp Ser Lys Ser Leu Arg Thr Ala Leu Gln
    130                 135                 140

Lys Glu Ile Thr Thr Arg Tyr Gln Leu Asp Pro Lys Phe Ile Thr Ser
145                 150                 155                 160

Ile Leu Tyr Glu Asn Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
        195                 200                 205

Asp Leu Thr Val Asn Gly Glu Gln Leu Asp Leu Asp Pro Gly Gln Thr
    210                 215                 220

Leu Ile Tyr Tyr Val Asp Glu Lys Ala Pro Glu Phe Ser Met Gln Gly
225                 230                 235                 240

Leu Lys

<210> SEQ ID NO 480

<211> LENGTH: 242
<212> TYPE: PRT
<213> ORGANISM: Macaca fascicularis

<400> SEQUENCE: 480

```
Gln Lys Glu Cys Val Cys Glu Asn Tyr Lys Leu Ala Val Asn Cys Phe
1               5                   10                  15

Leu Asn Asp Asn Gly Gln Cys Gln Cys Thr Ser Ile Gly Ala Gln Asn
            20                  25                  30

Thr Val Leu Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
    50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Thr Cys Trp Cys Val
                85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Ile Glu Leu Lys His Lys
        115                 120                 125

Ala Arg Glu Lys Pro Tyr Asp Val Gln Ser Leu Arg Thr Ala Leu Glu
    130                 135                 140

Glu Ala Ile Lys Thr Arg Tyr Gln Leu Asp Pro Lys Phe Ile Thr Asn
145                 150                 155                 160

Ile Leu Tyr Glu Asp Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
        195                 200                 205

Asp Leu Arg Val Asn Gly Glu Gln Leu Asp Leu Asp Pro Gly Gln Thr
    210                 215                 220

Leu Ile Tyr Tyr Val Asp Glu Lys Ala Pro Glu Phe Ser Met Gln Gly
225                 230                 235                 240

Leu Lys
```

<210> SEQ ID NO 481
<211> LENGTH: 243
<212> TYPE: PRT
<213> ORGANISM: Mus musculus

<400> SEQUENCE: 481

```
Gln Arg Asp Cys Val Cys Asp Asn Tyr Lys Leu Ala Thr Ser Cys Ser
1               5                   10                  15

Leu Asn Glu Tyr Gly Glu Cys Gln Cys Thr Ser Tyr Gly Thr Gln Asn
            20                  25                  30

Thr Val Ile Cys Ser Lys Leu Ala Ser Lys Cys Leu Ala Met Lys Ala
        35                  40                  45

Glu Met Thr His Ser Lys Ser Gly Arg Arg Ile Lys Pro Glu Gly Ala
    50                  55                  60

Ile Gln Asn Asn Asp Gly Leu Tyr Asp Pro Asp Cys Asp Glu Gln Gly
65                  70                  75                  80

Leu Phe Lys Ala Lys Gln Cys Asn Gly Thr Ala Thr Cys Trp Cys Val
                85                  90                  95
```

```
Asn Thr Ala Gly Val Arg Arg Thr Asp Lys Asp Thr Glu Ile Thr Cys
            100                 105                 110

Ser Glu Arg Val Arg Thr Tyr Trp Ile Ile Ile Glu Leu Lys His Lys
        115                 120                 125

Glu Arg Glu Ser Pro Tyr Asp His Gln Ser Leu Gln Thr Ala Leu Gln
    130                 135                 140

Glu Ala Phe Thr Ser Arg Tyr Lys Leu Asn Gln Lys Phe Ile Lys Asn
145                 150                 155                 160

Ile Met Tyr Glu Asn Asn Val Ile Thr Ile Asp Leu Met Gln Asn Ser
                165                 170                 175

Ser Gln Lys Thr Gln Asp Asp Val Asp Ile Ala Asp Val Ala Tyr Tyr
            180                 185                 190

Phe Glu Lys Asp Val Lys Gly Glu Ser Leu Phe His Ser Ser Lys Ser
        195                 200                 205

Met Asp Leu Arg Val Asn Gly Glu Pro Leu Asp Leu Asp Pro Gly Gln
    210                 215                 220

Thr Leu Ile Tyr Tyr Val Asp Glu Lys Ala Pro Glu Phe Ser Met Gln
225                 230                 235                 240

Gly Leu Thr


<210> SEQ ID NO 482
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 482

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Arg Gln Ser Thr Phe Met Ala Met Asp
        35                  40                  45

Met Pro Ile Leu Glu Trp Val Ser Ser Ile Ser Gly Ser Gly Arg Asp
    50                  55                  60

Thr Leu Tyr Ala Asp Ser Val Lys Gly Arg Phe Thr Ile Ser Arg Asp
65                  70                  75                  80

Asn Ala Lys Thr Thr Leu Tyr Leu Gln Met Asn Ser Leu Arg Pro Glu
                85                  90                  95

Asp Thr Ala Val Tyr Tyr Cys Thr Ile Gly Gly Ser Leu Ser Val Ser
            100                 105                 110

Ser Gln Gly Thr Leu Val Thr Val Ser Ser
        115                 120


<210> SEQ ID NO 483
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Glu Val Gln Leu Val Glu Ser Gly Gly Gly Leu Val Gln Pro Gly Asn
1               5                   10                  15
```

Ser Leu Arg Leu Ser Cys Ala Ala Ser Gly Phe Thr Phe Ser Lys Phe
20 25 30

Gly Met Ser Trp Val Arg Gln Gln Ala Tyr Trp Trp Gly Asn Ser Arg
35 40 45

Asp Leu Glu Trp Val Ser Ser Ile Ser Gly Ser Gly Arg Asp Thr Leu
50 55 60

Tyr Ala Asp Ser Val Lys Gly Arg Phe Thr Ile Ser Arg Asp Asn Ala
65 70 75 80

Lys Thr Thr Leu Tyr Leu Gln Met Asn Ser Leu Arg Pro Glu Asp Thr
85 90 95

Ala Val Tyr Tyr Cys Thr Ile Gly Gly Ser Leu Ser Val Ser Ser Gln
100 105 110

Gly Thr Leu Val Thr Val Ser Ser
115 120

<210> SEQ ID NO 484
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 484

Glu Val Gln Leu Leu Glu Ser Gly Gly Gly Leu Val Gln Pro Gly Gly
1 5 10 15

Ser Leu Thr Leu Ser Cys Ala Ala Ser Gly Phe Ile Phe Arg Ala Ala
20 25 30

Ser Met Ala Trp Tyr Arg Gln Ser Pro Gly Asn Glu Arg Glu Leu Val
35 40 45

Ala Ser Ile Ser Ser Gly Ala Phe Thr Asn Tyr Ala Asp Ser Val Lys
50 55 60

Ala Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Gly
85 90 95

Ala Thr Phe Leu Arg Ser Asp Gly His His Thr Ile Asn Gly Gln Gly
100 105 110

Thr Leu Val Thr Val Ser Ser
115

<210> SEQ ID NO 485
<211> LENGTH: 372
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 485

Met Ala Leu Pro Val Thr Ala Leu Leu Leu Pro Leu Ala Leu Leu Leu
1 5 10 15

His Ala Ala Arg Pro Glu Val Gln Leu Leu Glu Ser Gly Gly Gly Leu
20 25 30

Val Gln Pro Gly Gly Ser Leu Thr Leu Ser Cys Ala Ala Ser Gly Phe
35 40 45

```
Ile Phe Arg Ala Ala Ser Met Ala Trp Tyr Arg Gln Ser Pro Gly Asn
    50                  55                  60

Glu Arg Glu Leu Val Ala Ser Ile Ser Ser Gly Ala Phe Thr Asn Tyr
65                  70                  75                  80

Ala Asp Ser Val Lys Ala Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Gly Ala Thr Phe Leu Arg Ser Asp Gly His His Thr
        115                 120                 125

Ile Asn Gly Gln Gly Thr Leu Val Thr Val Ser Ser Thr Ser Asp Tyr
    130                 135                 140

Lys Asp Asp Asp Asp Lys Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Lys Arg Gly Arg Lys Lys
    210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu Arg Val Lys Phe Ser Arg Ser Ala Asp Ala Pro Ala
            260                 265                 270

Tyr Gln Gln Gly Gln Asn Gln Leu Tyr Asn Glu Leu Asn Leu Gly Arg
        275                 280                 285

Arg Glu Glu Tyr Asp Val Leu Asp Lys Arg Arg Gly Arg Asp Pro Glu
    290                 295                 300

Met Gly Gly Lys Pro Arg Arg Lys Asn Pro Gln Glu Gly Leu Tyr Asn
305                 310                 315                 320

Glu Leu Gln Lys Asp Lys Met Ala Glu Ala Tyr Ser Glu Ile Gly Met
                325                 330                 335

Lys Gly Glu Arg Arg Arg Gly Lys Gly His Asp Gly Leu Tyr Gln Gly
            340                 345                 350

Leu Ser Thr Ala Thr Lys Asp Thr Tyr Asp Ala Leu His Met Gln Ala
        355                 360                 365

Leu Pro Pro Arg
    370
```

<210> SEQ ID NO 486
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 486

```
Met Ala Leu Pro Val Thr Ala Leu Leu Leu Pro Leu Ala Leu Leu Leu
1               5                   10                  15
```

```
His Ala Ala Arg Pro Glu Val Gln Leu Val Glu Ser Gly Gly Gly Leu
            20                  25                  30

Val Gln Pro Gly Asn Ser Leu Arg Leu Ser Cys Ala Ala Ser Gly Phe
        35                  40                  45

Thr Phe Ser Lys Phe Gly Met Ser Trp Val Arg Gln Ala Pro Gly Lys
    50                  55                  60

Gly Leu Glu Trp Val Ser Ser Ile Ser Gly Ser Gly Arg Asp Thr Leu
65                  70                  75                  80

Tyr Ala Asp Ser Val Lys Gly Arg Phe Thr Ile Ser Arg Asp Asn Ala
                85                  90                  95

Lys Thr Thr Leu Tyr Leu Gln Met Asn Ser Leu Arg Pro Glu Asp Thr
            100                 105                 110

Ala Val Tyr Tyr Cys Thr Ile Gly Gly Ser Leu Ser Val Ser Ser Gln
        115                 120                 125

Gly Thr Leu Val Thr Val Ser Ser Gly Ser Gly Gly Ser Gly Gly Gly
    130                 135                 140

Gly Ser Gly Gly Gly Gly Gly Ser Gly Glu Val Gln Leu Leu Glu Ser
145                 150                 155                 160

Gly Gly Gly Leu Val Gln Pro Gly Gly Ser Leu Thr Leu Ser Cys Ala
                165                 170                 175

Ala Ser Gly Phe Ile Phe Arg Ala Ala Ser Met Ala Trp Tyr Arg Gln
            180                 185                 190

Ser Pro Gly Asn Glu Arg Glu Leu Val Ala Ser Ile Ser Ser Gly Ala
        195                 200                 205

Phe Thr Asn Tyr Ala Asp Ser Val Lys Ala Arg Phe Thr Ile Ser Arg
    210                 215                 220

Asp Asn Ser Lys Asn Thr Leu Tyr Leu Gln Met Asn Ser Leu Arg Ala
225                 230                 235                 240

Glu Asp Thr Ala Val Tyr Tyr Cys Gly Ala Thr Phe Leu Arg Ser Asp
                245                 250                 255

Gly His His Thr Ile Asn Gly Gln Gly Thr Leu Val Thr Val Ser Ser
            260                 265                 270

Thr Ser Asp Tyr Lys Asp Asp Asp Asp Lys Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Lys Arg
            340                 345                 350

Gly Arg Lys Lys Leu Leu Tyr Ile Phe Lys Gln Pro Phe Met Arg Pro
        355                 360                 365

Val Gln Thr Thr Gln Glu Glu Asp Gly Cys Ser Cys Arg Phe Pro Glu
    370                 375                 380

Glu Glu Glu Gly Gly Cys Glu Leu Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430
```

Arg Asp Pro Glu Met Gly Gly Lys Pro Arg Arg Lys Asn Pro Gln Glu
435 440 445

Gly Leu Tyr Asn Glu Leu Gln Lys Asp Lys Met Ala Glu Ala Tyr Ser
450 455 460

Glu Ile Gly Met Lys Gly Glu Arg Arg Arg Gly Lys Gly His Asp Gly
465 470 475 480

Leu Tyr Gln Gly Leu Ser Thr Ala Thr Lys Asp Thr Tyr Asp Ala Leu
485 490 495

His Met Gln Ala Leu Pro Pro Arg
500

<210> SEQ ID NO 487
<211> LENGTH: 511
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 487

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

Val Gln Pro Gly Asn Ser Leu Arg Leu Ser Cys Ala Ala Ser Gly Phe
35 40 45

Thr Phe Ser Lys Phe Gly Met Ser Trp Val Arg Gln Arg Gln Ser Thr
50 55 60

Phe Met Ala Met Asp Met Pro Ile Leu Glu Trp Val Ser Ser Ile Ser
65 70 75 80

Gly Ser Gly Arg Asp Thr Leu Tyr Ala Asp Ser Val Lys Gly Arg Phe
85 90 95

Thr Ile Ser Arg Asp Asn Ala Lys Thr Thr Leu Tyr Leu Gln Met Asn
100 105 110

Ser Leu Arg Pro Glu Asp Thr Ala Val Tyr Tyr Cys Thr Ile Gly Gly
115 120 125

Ser Leu Ser Val Ser Ser Gln Gly Thr Leu Val Thr Val Ser Ser Gly
130 135 140

Ser Gly Gly Ser Gly Gly Gly Ser Gly Gly Gly Gly Gly Ser Gly
145 150 155 160

Glu Val Gln Leu Leu Glu Ser Gly Gly Gly Leu Val Gln Pro Gly Gly
165 170 175

Ser Leu Thr Leu Ser Cys Ala Ala Ser Gly Phe Ile Phe Arg Ala Ala
180 185 190

Ser Met Ala Trp Tyr Arg Gln Ser Pro Gly Asn Glu Arg Glu Leu Val
195 200 205

Ala Ser Ile Ser Ser Gly Ala Phe Thr Asn Tyr Ala Asp Ser Val Lys
210 215 220

Ala Arg Phe Thr Ile Ser Arg Asp Asn Ser Lys Asn Thr Leu Tyr Leu
225 230 235 240

Gln Met Asn Ser Leu Arg Ala Glu Asp Thr Ala Val Tyr Tyr Cys Gly
245 250 255

Ala Thr Phe Leu Arg Ser Asp Gly His His Thr Ile Asn Gly Gln Gly
260 265 270

Thr Leu Val Thr Val Ser Ser Thr Ser Asp Tyr Lys Asp Asp Asp Asp
275 280 285

```
Lys Thr Thr Thr Pro Ala Pro Arg Pro Pro Thr Pro Ala Pro Thr Ile
    290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Phe Ala Cys Asp Ile Tyr
                325                 330                 335

Ile Trp Ala Pro Leu Ala Gly Thr Cys Gly Val Leu Leu Leu Ser Leu
            340                 345                 350

Val Ile Thr Leu Tyr Lys Arg Gly Arg Lys Lys Leu Leu Tyr Ile Phe
        355                 360                 365

Lys Gln Pro Phe Met Arg Pro Val Gln Thr Thr Gln Glu Glu Asp Gly
    370                 375                 380

Cys Ser Cys Arg Phe Pro Glu Glu Glu Glu Gly Gly Cys Glu Leu Arg
385                 390                 395                 400

Val Lys Phe Ser Arg Ser Ala Asp Ala Pro Ala Tyr Gln Gln Gly Gln
                405                 410                 415

Asn Gln Leu Tyr Asn Glu Leu Asn Leu Gly Arg Arg Glu Glu Tyr Asp
            420                 425                 430

Val Leu Asp Lys Arg Arg Gly Arg Asp Pro Glu Met Gly Gly Lys Pro
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg
            500                 505                 510
```

<210> SEQ ID NO 488
<211> LENGTH: 509
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 488

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Asn Ser Leu Arg Leu Ser Cys Ala Ala Ser Gly Phe
        35                  40                  45

Thr Phe Ser Lys Phe Gly Met Ser Trp Val Arg Gln Gln Ala Tyr Trp
    50                  55                  60

Trp Gly Asn Ser Arg Asp Leu Glu Trp Val Ser Ser Ile Ser Gly Ser
65                  70                  75                  80

Gly Arg Asp Thr Leu Tyr Ala Asp Ser Val Lys Gly Arg Phe Thr Ile
                85                  90                  95

Ser Arg Asp Asn Ala Lys Thr Thr Leu Tyr Leu Gln Met Asn Ser Leu
            100                 105                 110

Arg Pro Glu Asp Thr Ala Val Tyr Tyr Cys Thr Ile Gly Gly Ser Leu
        115                 120                 125
```

```
Ser Val Ser Ser Gln Gly Thr Leu Val Thr Val Ser Ser Gly Ser Gly
    130                 135                 140

Gly Ser Gly Gly Gly Gly Ser Gly Gly Gly Gly Gly Ser Gly Glu Val
145                 150                 155                 160

Gln Leu Leu Glu Ser Gly Gly Gly Leu Val Gln Pro Gly Gly Ser Leu
                165                 170                 175

Thr Leu Ser Cys Ala Ala Ser Gly Phe Ile Phe Arg Ala Ala Ser Met
            180                 185                 190

Ala Trp Tyr Arg Gln Ser Pro Gly Asn Glu Arg Glu Leu Val Ala Ser
        195                 200                 205

Ile Ser Ser Gly Ala Phe Thr Asn Tyr Ala Asp Ser Val Lys Ala Arg
    210                 215                 220

Phe Thr Ile Ser Arg Asp Asn Ser Lys Asn Thr Leu Tyr Leu Gln Met
225                 230                 235                 240

Asn Ser Leu Arg Ala Glu Asp Thr Ala Val Tyr Tyr Cys Gly Ala Thr
                245                 250                 255

Phe Leu Arg Ser Asp Gly His His Thr Ile Asn Gly Gln Gly Thr Leu
            260                 265                 270

Val Thr Val Ser Ser Thr Ser Asp Tyr Lys Asp Asp Asp Asp Lys Thr
        275                 280                 285

Thr Thr Pro Ala Pro Arg Pro Pro Thr Pro Ala Pro Thr Ile Ala Ser
    290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
                325                 330                 335

Ala Pro Leu Ala Gly Thr Cys Gly Val Leu Leu Leu Ser Leu Val Ile
            340                 345                 350

Thr Leu Tyr Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505
```

<210> SEQ ID NO 489
<211> LENGTH: 513
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 489

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

Val Gln Pro Gly Asn Ser Leu Arg Leu Ser Cys Ala Ala Ser Gly Phe
35 40 45

Thr Phe Ser Lys Phe Gly Met Ser Trp Val Arg Gln Arg Gln Ser Thr
50 55 60

Phe Met Ala Met Asp Met Pro Ile Leu Glu Trp Val Ser Ser Ile Ser
65 70 75 80

Gly Ser Gly Arg Asp Thr Leu Tyr Ala Asp Ser Val Lys Gly Arg Phe
85 90 95

Thr Ile Ser Arg Asp Asn Ala Lys Thr Thr Leu Tyr Leu Gln Met Asn
100 105 110

Ser Leu Arg Pro Glu Asp Thr Ala Val Tyr Tyr Cys Thr Ile Gly Gly
115 120 125

Ser Leu Ser Val Ser Ser Gln Gly Thr Leu Val Thr Val Ser Ser Gly
130 135 140

Gly Gly Gly Pro Gln Gly Ser Thr Gly Arg Ala Ala Gly Gly Gly Gly
145 150 155 160

Gly Thr Glu Val Gln Leu Leu Glu Ser Gly Gly Gly Leu Val Gln Pro
165 170 175

Gly Gly Ser Leu Thr Leu Ser Cys Ala Ala Ser Gly Phe Ile Phe Arg
180 185 190

Ala Ala Ser Met Ala Trp Tyr Arg Gln Ser Pro Gly Asn Glu Arg Glu
195 200 205

Leu Val Ala Ser Ile Ser Ser Gly Ala Phe Thr Asn Tyr Ala Asp Ser
210 215 220

Val Lys Ala Arg Phe Thr Ile Ser Arg Asp Asn Ser Lys Asn Thr Leu
225 230 235 240

Tyr Leu Gln Met Asn Ser Leu Arg Ala Glu Asp Thr Ala Val Tyr Tyr
245 250 255

Cys Gly Ala Thr Phe Leu Arg Ser Asp Gly His His Thr Ile Asn Gly
260 265 270

Gln Gly Thr Leu Val Thr Val Ser Ser Thr Ser Asp Tyr Lys Asp Asp
275 280 285

Asp Asp Lys Thr Thr Thr Pro Ala Pro Arg Pro Pro Thr Pro Ala Pro
290 295 300

Thr Ile Ala Ser Gln Pro Leu Ser Leu Arg Pro Glu Ala Cys Arg Pro
305 310 315 320

Ala Ala Gly Gly Ala Val His Thr Arg Gly Leu Asp Phe Ala Cys Asp
325 330 335

Ile Tyr Ile Trp Ala Pro Leu Ala Gly Thr Cys Gly Val Leu Leu Leu
340 345 350

Ser Leu Val Ile Thr Leu Tyr Lys Arg Gly Arg Lys Lys Leu Leu Tyr
355 360 365

Ile Phe Lys Gln Pro Phe Met Arg Pro Val Gln Thr Thr Gln Glu Glu
370 375 380

Asp Gly Cys Ser Cys Arg Phe Pro Glu Glu Glu Glu Gly Gly Cys Glu
385 390 395 400

```
Leu Arg Val Lys Phe Ser Arg Ser Ala Asp Ala Pro Ala Tyr Gln Gln
                405                 410                 415

Gly Gln Asn Gln Leu Tyr Asn Glu Leu Asn Leu Gly Arg Arg Glu Glu
            420                 425                 430

Tyr Asp Val Leu Asp Lys Arg Arg Gly Arg Asp Pro Glu Met Gly Gly
        435                 440                 445

Lys Pro Arg Arg Lys Asn Pro Gln Glu Gly Leu Tyr Asn Glu Leu Gln
    450                 455                 460

Lys Asp Lys Met Ala Glu Ala Tyr Ser Glu Ile Gly Met Lys Gly Glu
465                 470                 475                 480

Arg Arg Arg Gly Lys Gly His Asp Gly Leu Tyr Gln Gly Leu Ser Thr
                485                 490                 495

Ala Thr Lys Asp Thr Tyr Asp Ala Leu His Met Gln Ala Leu Pro Pro
            500                 505                 510

Arg


<210> SEQ ID NO 490
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Asn Ser Leu Arg Leu Ser Cys Ala Ala Ser Gly Phe
        35                  40                  45

Thr Phe Ser Lys Phe Gly Met Ser Trp Val Arg Gln Gln Ala Tyr Trp
    50                  55                  60

Trp Gly Asn Ser Arg Asp Leu Glu Trp Val Ser Ser Ile Ser Gly Ser
65                  70                  75                  80

Gly Arg Asp Thr Leu Tyr Ala Asp Ser Val Lys Gly Arg Phe Thr Ile
                85                  90                  95

Ser Arg Asp Asn Ala Lys Thr Thr Leu Tyr Leu Gln Met Asn Ser Leu
            100                 105                 110

Arg Pro Glu Asp Thr Ala Val Tyr Tyr Cys Thr Ile Gly Gly Ser Leu
        115                 120                 125

Ser Val Ser Ser Gln Gly Thr Leu Val Thr Val Ser Ser Gly Gly Gly
    130                 135                 140

Gly Pro Gln Gly Ser Thr Gly Arg Ala Ala Gly Gly Gly Gly Gly Thr
145                 150                 155                 160

Glu Val Gln Leu Leu Glu Ser Gly Gly Gly Leu Val Gln Pro Gly Gly
                165                 170                 175

Ser Leu Thr Leu Ser Cys Ala Ala Ser Gly Phe Ile Phe Arg Ala Ala
            180                 185                 190

Ser Met Ala Trp Tyr Arg Gln Ser Pro Gly Asn Glu Arg Glu Leu Val
        195                 200                 205

Ala Ser Ile Ser Ser Gly Ala Phe Thr Asn Tyr Ala Asp Ser Val Lys
    210                 215                 220

Ala Arg Phe Thr Ile Ser Arg Asp Asn Ser Lys Asn Thr Leu Tyr Leu
225                 230                 235                 240
```

Gln Met Asn Ser Leu Arg Ala Glu Asp Thr Ala Val Tyr Tyr Cys Gly
245 250 255

Ala Thr Phe Leu Arg Ser Asp Gly His His Thr Ile Asn Gly Gln Gly
260 265 270

Thr Leu Val Thr Val Ser Ser Thr Ser Asp Tyr Lys Asp Asp Asp Asp
275 280 285

Lys Thr Thr Thr Pro Ala Pro Arg Pro Pro Thr Pro Ala Pro Thr Ile
290 295 300

Ala Ser Gln Pro Leu Ser Leu Arg Pro Glu Ala Cys Arg Pro Ala Ala
305 310 315 320

Gly Gly Ala Val His Thr Arg Gly Leu Asp Phe Ala Cys Asp Ile Tyr
325 330 335

Ile Trp Ala Pro Leu Ala Gly Thr Cys Gly Val Leu Leu Leu Ser Leu
340 345 350

Val Ile Thr Leu Tyr Lys Arg Gly Arg Lys Lys Leu Leu Tyr Ile Phe
355 360 365

Lys Gln Pro Phe Met Arg Pro Val Gln Thr Thr Gln Glu Glu Asp Gly
370 375 380

Cys Ser Cys Arg Phe Pro Glu Glu Glu Glu Gly Gly Cys Glu Leu Arg
385 390 395 400

Val Lys Phe Ser Arg Ser Ala Asp Ala Pro Ala Tyr Gln Gln Gly Gln
405 410 415

Asn Gln Leu Tyr Asn Glu Leu Asn Leu Gly Arg Arg Glu Glu Tyr Asp
420 425 430

Val Leu Asp Lys Arg Arg Gly Arg Asp Pro Glu Met Gly Gly Lys Pro
435 440 445

Arg Arg Lys Asn Pro Gln Glu Gly Leu Tyr Asn Glu Leu Gln Lys Asp
450 455 460

Lys Met Ala Glu Ala Tyr Ser Glu Ile Gly Met Lys Gly Glu Arg Arg
465 470 475 480

Arg Gly Lys Gly His Asp Gly Leu Tyr Gln Gly Leu Ser Thr Ala Thr
485 490 495

Lys Asp Thr Tyr Asp Ala Leu His Met Gln Ala Leu Pro Pro Arg
500 505 510

<210> SEQ ID NO 491
<211> LENGTH: 368
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 491

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Ala Leu
20 25 30

Val Gln Pro Gly Gly Ser Leu Arg Leu Ser Cys Ala Ala Ser Gly Phe
35 40 45

Pro Val Asn Arg Tyr Ser Met Arg Trp Tyr Arg Gln Ala Pro Gly Lys
50 55 60

Glu Arg Glu Trp Val Ala Gly Met Ser Ser Ala Gly Asp Arg Ser Ser
65 70 75 80

Tyr Glu Asp Ser Val Lys Gly Arg Phe Thr Ile Ser Arg Asp Asp Ala
85 90 95

Arg Asn Thr Val Tyr Leu Gln Met Asn Ser Leu Lys Pro Glu Asp Thr
100 105 110

Ala Val Tyr Tyr Cys Asn Val Asn Val Gly Phe Glu Tyr Trp Gly Gln
115 120 125

Gly Thr Gln Val Thr Val Ser Ser Thr Ser Asp Tyr Lys Asp Asp Asp
130 135 140

Asp Lys Thr Thr Thr Pro Ala Pro Arg Pro Pro Thr Pro Ala Pro Thr
145 150 155 160

Ile Ala Ser Gln Pro Leu Ser Leu Arg Pro Glu Ala Cys Arg Pro Ala
165 170 175

Ala Gly Gly Ala Val His Thr Arg Gly Leu Asp Phe Ala Cys Asp Ile
180 185 190

Tyr Ile Trp Ala Pro Leu Ala Gly Thr Cys Gly Val Leu Leu Leu Ser
195 200 205

Leu Val Ile Thr Leu Tyr Lys Arg Gly Arg Lys Lys Leu Leu Tyr Ile
210 215 220

Phe Lys Gln Pro Phe Met Arg Pro Val Gln Thr Thr Gln Glu Glu Asp
225 230 235 240

Gly Cys Ser Cys Arg Phe Pro Glu Glu Glu Glu Gly Gly Cys Glu Leu
245 250 255

Arg Val Lys Phe Ser Arg Ser Ala Asp Ala Pro Ala Tyr Gln Gln Gly
260 265 270

Gln Asn Gln Leu Tyr Asn Glu Leu Asn Leu Gly Arg Arg Glu Glu Tyr
275 280 285

Asp Val Leu Asp Lys Arg Arg Gly Arg Asp Pro Glu Met Gly Gly Lys
290 295 300

Pro Arg Arg Lys Asn Pro Gln Glu Gly Leu Tyr Asn Glu Leu Gln Lys
305 310 315 320

Asp Lys Met Ala Glu Ala Tyr Ser Glu Ile Gly Met Lys Gly Glu Arg
325 330 335

Arg Arg Gly Lys Gly His Asp Gly Leu Tyr Gln Gly Leu Ser Thr Ala
340 345 350

Thr Lys Asp Thr Tyr Asp Ala Leu His Met Gln Ala Leu Pro Pro Arg
355 360 365

<210> SEQ ID NO 492
<211> LENGTH: 507
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 492

Glu Val Gln Leu Val Glu Ser Gly Gly Gly Leu Val Gln Pro Gly Asn
1 5 10 15

Ser Leu Arg Leu Ser Cys Ala Ala Ser Gly Phe Thr Phe Ser Lys Phe
20 25 30

Gly Met Ser Trp Val Arg Gln Ala Pro Gly Lys Gly Leu Glu Trp Val
35 40 45

Ser Ser Ile Ser Gly Ser Gly Arg Asp Thr Leu Tyr Ala Asp Ser Val
50 55 60

Lys Gly Arg Phe Thr Ile Ser Arg Asp Asn Ala Lys Thr Thr Leu Tyr
65 70 75 80

```
Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser Gly Gly Gly Gly Ser Gly Gly Gly Ser Gln Thr Val Val
        115                 120                 125

Thr Gln Glu Pro Ser Leu Thr Val Ser Pro Gly Gly Thr Val Thr Leu
    130                 135                 140

Thr Cys Ala Ser Ser Thr Gly Ala Val Thr Ser Gly Asn Tyr Pro Asn
145                 150                 155                 160

Trp Val Gln Gln Lys Pro Gly Gln Ala Pro Arg Gly Leu Ile Gly Gly
                165                 170                 175

Thr Lys Phe Leu Val Pro Gly Thr Pro Ala Arg Phe Ser Gly Ser Leu
            180                 185                 190

Leu Gly Gly Lys Ala Ala Leu Thr Leu Ser Gly Val Gln Pro Glu Asp
        195                 200                 205

Glu Ala Glu Tyr Tyr Cys Thr Leu Trp Tyr Ser Asn Arg Trp Val Phe
    210                 215                 220

Gly Gly Gly Thr Lys Leu Thr Val Leu Gly Gly Gly Gly Ser Gly Gly
225                 230                 235                 240

Gly Gly Ser Gly Gly Gly Gly Ser Glu Val Gln Leu Val Glu Ser Gly
                245                 250                 255

Gly Gly Leu Val Gln Pro Gly Gly Ser Leu Lys Leu Ser Cys Ala Ala
            260                 265                 270

Ser Gly Phe Thr Phe Asn Lys Tyr Ala Ile Asn Trp Val Arg Gln Ala
        275                 280                 285

Pro Gly Lys Gly Leu Glu Trp Val Ala Arg Ile Arg Ser Lys Tyr Asn
    290                 295                 300

Asn Tyr Ala Thr Tyr Tyr Ala Asp Gln Val Lys Asp Arg Phe Thr Ile
305                 310                 315                 320

Ser Arg Asp Asp Ser Lys Asn Thr Ala Tyr Leu Gln Met Asn Asn Leu
                325                 330                 335

Lys Thr Glu Asp Thr Ala Val Tyr Tyr Cys Val Arg His Ala Asn Phe
            340                 345                 350

Gly Asn Ser Tyr Ile Ser Tyr Trp Ala Tyr Trp Gly Gln Gly Thr Leu
        355                 360                 365

Val Thr Val Ser Ser Gly Gly Gly Ser Gly Gly Gly Ser Glu Val
    370                 375                 380

Gln Leu Leu Glu Ser Gly Gly Gly Leu Val Gln Pro Gly Gly Ser Leu
385                 390                 395                 400

Thr Leu Ser Cys Ala Ala Ser Gly Phe Ile Phe Arg Ala Ala Ser Met
                405                 410                 415

Ala Trp Tyr Arg Gln Ser Pro Gly Asn Glu Arg Glu Leu Val Ala Ser
            420                 425                 430

Ile Ser Ser Gly Ala Phe Thr Asn Tyr Ala Asp Ser Val Lys Ala Arg
        435                 440                 445

Phe Thr Ile Ser Arg Asp Asn Ser Lys Asn Thr Leu Tyr Leu Gln Met
    450                 455                 460

Asn Ser Leu Arg Ala Glu Asp Thr Ala Val Tyr Tyr Cys Gly Ala Thr
465                 470                 475                 480

Phe Leu Arg Ser Asp Gly His His Thr Ile Asn Gly Gln Gly Thr Leu
                485                 490                 495
```

Val Thr Val Ser Ser His His His His His His
500 505

<210> SEQ ID NO 493
<211> LENGTH: 503
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 493

Gln Val Gln Leu Val Glu Ser Gly Gly Ala Leu Val Gln Pro Gly Gly
1 5 10 15

Ser Leu Arg Leu Ser Cys Ala Ala Ser Gly Phe Pro Val Asn Arg Tyr
20 25 30

Ser Met Arg Trp Tyr Arg Gln Ala Pro Gly Lys Glu Arg Glu Trp Val
35 40 45

Ala Gly Met Ser Ser Ala Gly Asp Arg Ser Ser Tyr Glu Asp Ser Val
50 55 60

Lys Gly Arg Phe Thr Ile Ser Arg Asp Asp Ala Arg Asn Thr Val Tyr
65 70 75 80

Leu Gln Met Asn Ser Leu Lys Pro Glu Asp Thr Ala Val Tyr Tyr Cys
85 90 95

Asn Val Asn Val Gly Phe Glu Tyr Trp Gly Gln Gly Thr Gln Val Thr
100 105 110

Val Ser Ser Gly Gly Gly Gly Ser Gly Gly Gly Ser Glu Val Gln Leu
115 120 125

Val Glu Ser Gly Gly Gly Leu Val Gln Pro Gly Asn Ser Leu Arg Leu
130 135 140

Ser Cys Ala Ala Ser Gly Phe Thr Phe Ser Lys Phe Gly Met Ser Trp
145 150 155 160

Val Arg Gln Ala Pro Gly Lys Gly Leu Glu Trp Val Ser Ser Ile Ser
165 170 175

Gly Ser Gly Arg Asp Thr Leu Tyr Ala Asp Ser Val Lys Gly Arg Phe
180 185 190

Thr Ile Ser Arg Asp Asn Ala Lys Thr Thr Leu Tyr Leu Gln Met Asn
195 200 205

Ser Leu Arg Pro Glu Asp Thr Ala Val Tyr Tyr Cys Thr Ile Gly Gly
210 215 220

Ser Leu Ser Val Ser Ser Gln Gly Thr Leu Val Thr Val Ser Ser Gly
225 230 235 240

Gly Gly Gly Ser Gly Gly Gly Ser Glu Val Gln Leu Val Glu Ser Gly
245 250 255

Gly Gly Leu Val Gln Pro Gly Gly Ser Leu Lys Leu Ser Cys Ala Ala
260 265 270

Ser Gly Phe Thr Phe Asn Lys Tyr Ala Ile Asn Trp Val Arg Gln Ala
275 280 285

Pro Gly Lys Gly Leu Glu Trp Val Ala Arg Ile Arg Ser Lys Tyr Asn
290 295 300

Asn Tyr Ala Thr Tyr Tyr Ala Asp Gln Val Lys Asp Arg Phe Thr Ile
305 310 315 320

Ser Arg Asp Asp Ser Lys Asn Thr Ala Tyr Leu Gln Met Asn Asn Leu
325 330 335

Lys Thr Glu Asp Thr Ala Val Tyr Tyr Cys Val Arg His Ala Asn Phe
340 345 350

```
Gly Asn Ser Tyr Ile Ser Tyr Trp Ala Tyr Trp Gly Gln Gly Thr Leu
        355                 360                 365

Val Thr Val Ser Ser Gly Gly Gly Gly Ser Gly Gly Gly Gly Ser Gly
    370                 375                 380

Gly Gly Gly Ser Gln Thr Val Val Thr Gln Glu Pro Ser Leu Thr Val
385                 390                 395                 400

Ser Pro Gly Gly Thr Val Thr Leu Thr Cys Ala Ser Ser Thr Gly Ala
                405                 410                 415

Val Thr Ser Gly Asn Tyr Pro Asn Trp Val Gln Gln Lys Pro Gly Gln
            420                 425                 430

Ala Pro Arg Gly Leu Ile Gly Gly Thr Lys Phe Leu Val Pro Gly Thr
        435                 440                 445

Pro Ala Arg Phe Ser Gly Ser Leu Leu Gly Gly Lys Ala Ala Leu Thr
    450                 455                 460

Leu Ser Gly Val Gln Pro Glu Asp Glu Ala Glu Tyr Tyr Cys Thr Leu
465                 470                 475                 480

Trp Tyr Ser Asn Arg Trp Val Phe Gly Gly Gly Thr Lys Leu Thr Val
                485                 490                 495

Leu His His His His His His
            500
```

<210> SEQ ID NO 494
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

```
Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Val Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Thr Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Asn Lys Tyr Ala Ile Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Gln Val Lys Asp
            180                 185                 190

Arg Phe Thr Ile Ser Arg Asp Asp Ser Lys Asn Thr Ala Tyr Leu Gln
        195                 200                 205
```

Met Asn Asn Leu Lys Thr Glu Asp Thr Ala Val Tyr Tyr Cys Val Arg
210 215 220

His Ala Asn Phe Gly Asn Ser Tyr Ile Ser Tyr Trp Ala Tyr Trp Gly
225 230 235 240

Gln Gly Thr Leu Val Thr Val Ser Ser Gly Gly Gly Gly Ser Gly Gly
245 250 255

Gly Ser Glu Val Gln Leu Leu Glu Ser Gly Gly Gly Leu Val Gln Pro
260 265 270

Gly Gly Ser Leu Thr Leu Ser Cys Ala Ala Ser Gly Phe Ile Phe Arg
275 280 285

Ala Ala Ser Met Ala Trp Tyr Arg Gln Ser Pro Gly Asn Glu Arg Glu
290 295 300

Leu Val Ala Ser Ile Ser Ser Gly Ala Phe Thr Asn Tyr Ala Asp Ser
305 310 315 320

Val Lys Ala Arg Phe Thr Ile Ser Arg Asp Asn Ser Lys Asn Thr Leu
325 330 335

Tyr Leu Gln Met Asn Ser Leu Arg Ala Glu Asp Thr Ala Val Tyr Tyr
340 345 350

Cys Gly Ala Thr Phe Leu Arg Ser Asp Gly His His Thr Ile Asn Gly
355 360 365

Gln Gly Thr Leu Val Thr Val Ser Ser His His His His His His
370 375 380

<210> SEQ ID NO 495
<211> LENGTH: 526
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 495

Glu Val Gln Leu Val Glu Ser Gly Gly Gly Leu Val Gln Pro Gly Asn
1 5 10 15

Ser Leu Arg Leu Ser Cys Ala Ala Ser Gly Phe Thr Phe Ser Lys Phe
20 25 30

Gly Met Ser Trp Val Arg Gln Gly Gly Gly Gly Gly Leu Asp Gly Asn
35 40 45

Glu Glu Pro Gly Gly Leu Glu Trp Val Ser Ser Ile Ser Gly Ser Gly
50 55 60

Arg Asp Thr Leu Tyr Ala Asp Ser Val Lys Gly Arg Phe Thr Ile Ser
65 70 75 80

Arg Asp Asn Ala Lys Thr Thr Leu Tyr Leu Gln Met Asn Ser Leu Arg
85 90 95

Pro Glu Asp Thr Ala Val Tyr Tyr Cys Thr Ile Gly Gly Ser Leu Ser
100 105 110

Val Ser Ser Gln Gly Thr Leu Val Thr Val Ser Ser Gly Gly Gly Gly
115 120 125

Ser Gly Gly Gly Gly Ser Gly Gly Val Val Gly Gly Gly Gly Thr Gln
130 135 140

Thr Val Val Thr Gln Glu Pro Ser Leu Thr Val Ser Pro Gly Gly Thr
145 150 155 160

Val Thr Leu Thr Cys Ala Ser Ser Thr Gly Ala Val Thr Ser Gly Asn
165 170 175

Tyr Pro Asn Trp Val Gln Gln Lys Pro Gly Gln Ala Pro Arg Gly Leu
180 185 190

Ile Gly Gly Thr Lys Phe Leu Val Pro Gly Thr Pro Ala Arg Phe Ser
195 200 205

Gly Ser Leu Leu Gly Gly Lys Ala Ala Leu Thr Leu Ser Gly Val Gln
210 215 220

Pro Glu Asp Glu Ala Glu Tyr Tyr Cys Thr Leu Trp Tyr Ser Asn Arg
225 230 235 240

Trp Val Phe Gly Gly Gly Thr Lys Leu Thr Val Leu Gly Gly Gly Gly
245 250 255

Ser Gly Gly Gly Gly Ser Gly Gly Gly Gly Ser Glu Val Gln Leu Val
260 265 270

Glu Ser Gly Gly Gly Leu Val Gln Pro Gly Gly Ser Leu Lys Leu Ser
275 280 285

Cys Ala Ala Ser Gly Phe Thr Phe Asn Lys Tyr Ala Ile Asn Trp Val
290 295 300

Arg Gln Ala Pro Gly Lys Gly Leu Glu Trp Val Ala Arg Ile Arg Ser
305 310 315 320

Lys Tyr Asn Asn Tyr Ala Thr Tyr Tyr Ala Asp Gln Val Lys Asp Arg
325 330 335

Phe Thr Ile Ser Arg Asp Asp Ser Lys Asn Thr Ala Tyr Leu Gln Met
340 345 350

Asn Asn Leu Lys Thr Glu Asp Thr Ala Val Tyr Tyr Cys Val Arg His
355 360 365

Ala Asn Phe Gly Asn Ser Tyr Ile Ser Tyr Trp Ala Tyr Trp Gly Gln
370 375 380

Gly Thr Leu Val Thr Val Ser Ser Gly Gly Gly Gly Ser Gly Gly Gly
385 390 395 400

Ser Glu Val Gln Leu Leu Glu Ser Gly Gly Gly Leu Val Gln Pro Gly
405 410 415

Gly Ser Leu Thr Leu Ser Cys Ala Ala Ser Gly Phe Ile Phe Arg Ala
420 425 430

Ala Ser Met Ala Trp Tyr Arg Gln Ser Pro Gly Asn Glu Arg Glu Leu
435 440 445

Val Ala Ser Ile Ser Ser Gly Ala Phe Thr Asn Tyr Ala Asp Ser Val
450 455 460

Lys Ala Arg Phe Thr Ile Ser Arg Asp Asn Ser Lys Asn Thr Leu Tyr
465 470 475 480

Leu Gln Met Asn Ser Leu Arg Ala Glu Asp Thr Ala Val Tyr Tyr Cys
485 490 495

Gly Ala Thr Phe Leu Arg Ser Asp Gly His His Thr Ile Asn Gly Gln
500 505 510

Gly Thr Leu Val Thr Val Ser Ser His His His His His His
515 520 525

<210> SEQ ID NO 496
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 496

Glu Val Gln Leu Leu Glu Ser Gly Gly Gly Leu Val Gln Pro Gly Gly
1 5 10 15

```
Ser Leu Thr Leu Ser Cys Ala Ala Ser Gly Phe Ile Phe Arg Ala Ala
            20                  25                  30

Ser Met Asp Trp Tyr Arg Gln Phe Pro Gly Asn Glu Arg Glu Ser Ile
        35                  40                  45

Ala Thr Ile Ser Ser Gly Gly Phe Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Ala Thr Phe Leu Arg Ser Asp Gly His His Thr Ile Trp Gly Gln Gly
            100                 105                 110

Thr Leu Val Thr Val Ser Ser
        115


<210> SEQ ID NO 497
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 497

Glu Val Gln Leu Leu Glu Ser Gly Gly Gly Leu Val Gln Pro Gly Gly
1               5                   10                  15

Ser Leu Thr Leu Ser Cys Ala Ala Ser Gly Phe Ile Phe Arg Ala Ala
            20                  25                  30

Ser Met Ala Trp Tyr Arg Gln Ser Pro Gly Asn Glu Arg Glu Leu Val
        35                  40                  45

Ala Ser Ile Ser Ser Gly Ala Phe Thr Asn Tyr Ala Asp Ser Val Lys
    50                  55                  60

Ala Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Ala Thr Phe Leu Arg Ser Asp Gly His His Thr Ile Trp Gly Gln Gly
            100                 105                 110

Thr Leu Val Thr Val Ser Ser
        115


<210> SEQ ID NO 498
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 498

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60
```

```
Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Pro Gln Ala Ser Thr Gly Arg Ser Gly Gly Gly Gly Gly Gly Thr Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Leu Glu Ser Gly Gly Gly Leu Val Gln Pro Gly
                405                 410                 415

Gly Ser Leu Thr Leu Ser Cys Ala Ala Ser Gly Phe Ile Phe Arg Ala
            420                 425                 430

Ala Ser Met Ala Trp Tyr Arg Gln Ser Pro Gly Asn Glu Arg Glu Leu
        435                 440                 445

Val Ala Ser Ile Ser Ser Gly Ala Phe Thr Asn Tyr Ala Asp Ser Val
    450                 455                 460

Lys Ala Arg Phe Thr Ile Ser Arg Asp Asn Ser Lys Asn Thr Leu Tyr
465                 470                 475                 480
```

```
Leu Gln Met Asn Ser Leu Arg Ala Glu Asp Thr Ala Val Tyr Tyr Cys
                485                 490                 495

Gly Ala Thr Phe Leu Arg Ser Asp Gly His His Thr Ile Trp Gly Gln
            500                 505                 510

Gly Thr Leu Val Thr Val Ser Ser His His His His His His
        515                 520                 525


<210> SEQ ID NO 499
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 499

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Pro Gln Gly Ser Thr Gly Arg Ala Ala Gly Gly Gly Gly Gly Thr Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320
```

```
Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Leu Glu Ser Gly Gly Gly Leu Val Gln Pro Gly
                405                 410                 415

Gly Ser Leu Thr Leu Ser Cys Ala Ala Ser Gly Phe Ile Phe Arg Ala
            420                 425                 430

Ala Ser Met Ala Trp Tyr Arg Gln Ser Pro Gly Asn Glu Arg Glu Leu
        435                 440                 445

Val Ala Ser Ile Ser Ser Gly Ala Phe Thr Asn Tyr Ala Asp Ser Val
    450                 455                 460

Lys Ala Arg Phe Thr Ile Ser Arg Asp Asn Ser Lys Asn Thr Leu Tyr
465                 470                 475                 480

Leu Gln Met Asn Ser Leu Arg Ala Glu Asp Thr Ala Val Tyr Tyr Cys
                485                 490                 495

Gly Ala Thr Phe Leu Arg Ser Asp Gly His His Thr Ile Trp Gly Gln
            500                 505                 510

Gly Thr Leu Val Thr Val Ser Ser His His His His His His
        515                 520                 525
```

<210> SEQ ID NO 500
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Pro Gln Gly Ser Thr Ala Arg Ser Ala Gly Gly Gly Gly Gly Thr Gln
    130                 135                 140

Thr Val Val Thr Gln Glu Pro Ser Leu Thr Val Ser Pro Gly Gly Thr
145                 150                 155                 160
```

Val Thr Leu Thr Cys Ala Ser Ser Thr Gly Ala Val Thr Ser Gly Asn
165 170 175

Tyr Pro Asn Trp Val Gln Gln Lys Pro Gly Gln Ala Pro Arg Gly Leu
180 185 190

Ile Gly Gly Thr Lys Phe Leu Val Pro Gly Thr Pro Ala Arg Phe Ser
195 200 205

Gly Ser Leu Leu Gly Gly Lys Ala Ala Leu Thr Leu Ser Gly Val Gln
210 215 220

Pro Glu Asp Glu Ala Glu Tyr Tyr Cys Thr Leu Trp Tyr Ser Asn Arg
225 230 235 240

Trp Val Phe Gly Gly Gly Thr Lys Leu Thr Val Leu Gly Gly Gly Gly
245 250 255

Ser Gly Gly Gly Gly Ser Gly Gly Gly Gly Ser Glu Val Gln Leu Val
260 265 270

Glu Ser Gly Gly Gly Leu Val Gln Pro Gly Gly Ser Leu Lys Leu Ser
275 280 285

Cys Ala Ala Ser Gly Phe Thr Phe Asn Lys Tyr Ala Ile Asn Trp Val
290 295 300

Arg Gln Ala Pro Gly Lys Gly Leu Glu Trp Val Ala Arg Ile Arg Ser
305 310 315 320

Lys Tyr Asn Asn Tyr Ala Thr Tyr Tyr Ala Asp Gln Val Lys Asp Arg
325 330 335

Phe Thr Ile Ser Arg Asp Asp Ser Lys Asn Thr Ala Tyr Leu Gln Met
340 345 350

Asn Asn Leu Lys Thr Glu Asp Thr Ala Val Tyr Tyr Cys Val Arg His
355 360 365

Ala Asn Phe Gly Asn Ser Tyr Ile Ser Tyr Trp Ala Tyr Trp Gly Gln
370 375 380

Gly Thr Leu Val Thr Val Ser Ser Gly Gly Gly Gly Ser Gly Gly Gly
385 390 395 400

Ser Glu Val Gln Leu Leu Glu Ser Gly Gly Gly Leu Val Gln Pro Gly
405 410 415

Gly Ser Leu Thr Leu Ser Cys Ala Ala Ser Gly Phe Ile Phe Arg Ala
420 425 430

Ala Ser Met Ala Trp Tyr Arg Gln Ser Pro Gly Asn Glu Arg Glu Leu
435 440 445

Val Ala Ser Ile Ser Ser Gly Ala Phe Thr Asn Tyr Ala Asp Ser Val
450 455 460

Lys Ala Arg Phe Thr Ile Ser Arg Asp Asn Ser Lys Asn Thr Leu Tyr
465 470 475 480

Leu Gln Met Asn Ser Leu Arg Ala Glu Asp Thr Ala Val Tyr Tyr Cys
485 490 495

Gly Ala Thr Phe Leu Arg Ser Asp Gly His His Thr Ile Trp Gly Gln
500 505 510

Gly Thr Leu Val Thr Val Ser Ser His His His His His His
515 520 525

<210> SEQ ID NO 501
<211> LENGTH: 526
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 501

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Lys Pro Leu Gly Leu Gln Ala Arg Val Val Gly Gly Gly Gly Thr Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Leu Glu Ser Gly Gly Gly Leu Val Gln Pro Gly
                405                 410                 415
```

```
Gly Ser Leu Thr Leu Ser Cys Ala Ala Ser Gly Phe Ile Phe Arg Ala
            420                 425                 430

Ala Ser Met Ala Trp Tyr Arg Gln Ser Pro Gly Asn Glu Arg Glu Leu
        435                 440                 445

Val Ala Ser Ile Ser Ser Gly Ala Phe Thr Asn Tyr Ala Asp Ser Val
    450                 455                 460

Lys Ala Arg Phe Thr Ile Ser Arg Asp Asn Ser Lys Asn Thr Leu Tyr
465                 470                 475                 480

Leu Gln Met Asn Ser Leu Arg Ala Glu Asp Thr Ala Val Tyr Tyr Cys
                485                 490                 495

Gly Ala Thr Phe Leu Arg Ser Asp Gly His His Thr Ile Asn Gly Gln
            500                 505                 510

Gly Thr Leu Val Thr Val Ser Ser His His His His His His
        515                 520                 525


<210> SEQ ID NO 502
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 502

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Ser Gly Gly Gly Gly Ser Gly Gly Val Val Gly Gly Gly Gly Thr Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240
```

```
Trp Val Phe Gly Gly Gly Thr Lys Leu Thr Val Leu Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Leu Glu Ser Gly Gly Gly Leu Val Gln Pro Gly
                405                 410                 415

Gly Ser Leu Thr Leu Ser Cys Ala Ala Ser Gly Phe Ile Phe Arg Ala
            420                 425                 430

Ala Ser Met Ala Trp Tyr Arg Gln Ser Pro Gly Asn Glu Arg Glu Leu
        435                 440                 445

Val Ala Ser Ile Ser Ser Gly Ala Phe Thr Asn Tyr Ala Asp Ser Val
    450                 455                 460

Lys Ala Arg Phe Thr Ile Ser Arg Asp Asn Ser Lys Asn Thr Leu Tyr
465                 470                 475                 480

Leu Gln Met Asn Ser Leu Arg Ala Glu Asp Thr Ala Val Tyr Tyr Cys
                485                 490                 495

Gly Ala Thr Phe Leu Arg Ser Asp Gly His His Thr Ile Trp Gly Gln
            500                 505                 510

Gly Thr Leu Val Thr Val Ser Ser His His His His His His
        515                 520                 525
```

<210> SEQ ID NO 503
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 503

```
Gly Gly Gly Gly Pro Gln Ala Ser Thr Gly Arg Ser Gly Gly Gly Gly
1               5                   10                  15

Gly Gly
```

<210> SEQ ID NO 504
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 504

Gly Gly Gly Gly Pro Gln Gly Ser Thr Gly Arg Ala Ala Gly Gly Gly
1 5 10 15

Gly Gly

<210> SEQ ID NO 505
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 505

Gly Gly Gly Gly Pro Gln Gly Ser Thr Ala Arg Ser Ala Gly Gly Gly
1 5 10 15

Gly Gly

<210> SEQ ID NO 506
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 506

Gly Gly Gly Gly Lys Pro Leu Gly Leu Gln Ala Arg Val Val Gly Gly
1 5 10 15

Gly Gly

<210> SEQ ID NO 507
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 507

Gly Gly Gly Gly Ser Gly Gly Gly Gly Ser Gly Gly Val Val Gly Gly
1 5 10 15

Gly Gly

<210> SEQ ID NO 508
<211> LENGTH: 8
<212> TYPE: PRT
<213> ORGANISM: Unknown
<220> FEATURE:
<223> OTHER INFORMATION: Description of Unknown: Cleavage sequence

<400> SEQUENCE: 508

Lys Arg Ala Leu Gly Leu Pro Gly
1 5

<210> SEQ ID NO 509
<211> LENGTH: 40
<212> TYPE: PRT
<213> ORGANISM: Unknown
<220> FEATURE:
<223> OTHER INFORMATION: Description of Unknown: Cleavage sequence

<400> SEQUENCE: 509

Asp Glu Asp Glu Asp Glu Asp Glu Asp Glu Asp Glu Asp Glu Asp Glu
1 5 10 15

Arg Pro Leu Ala Leu Trp Arg Ser Asp Arg Asp Arg Asp Arg Asp Arg
20 25 30

Asp Arg Asp Arg Asp Arg Asp Arg
35 40

<210> SEQ ID NO 510
<211> LENGTH: 5
<212> TYPE: PRT
<213> ORGANISM: Unknown
<220> FEATURE:
<223> OTHER INFORMATION: Description of Unknown:
Cleavage sequence
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Leu or Ile
<220> FEATURE:
<221> NAME/KEY: MOD_RES
<222> LOCATION: (5)..(5)
<223> OTHER INFORMATION: Ser or Thr

<400> SEQUENCE: 510

Pro Arg Xaa Xaa Xaa
1 5

<210> SEQ ID NO 511
<211> LENGTH: 5
<212> TYPE: PRT
<213> ORGANISM: Unknown
<220> FEATURE:
<223> OTHER INFORMATION: Description of Unknown:
Cleavage sequence

<400> SEQUENCE: 511

Leu Glu Ala Thr Ala
1 5

<210> SEQ ID NO 512
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 512

Gly Gly Ala Ala Asn Leu Val Arg Gly Gly
1 5 10

<210> SEQ ID NO 513
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 513

Ser Gly Arg Ile Gly Phe Leu Arg Thr Ala
1 5 10

<210> SEQ ID NO 514
<211> LENGTH: 6
<212> TYPE: PRT
<213> ORGANISM: Unknown
<220> FEATURE:
<223> OTHER INFORMATION: Description of Unknown:
      Cleavage sequence

<400> SEQUENCE: 514

Pro Leu Gly Leu Ala Gly
1               5

<210> SEQ ID NO 515
<211> LENGTH: 6
<212> TYPE: PRT
<213> ORGANISM: Unknown
<220> FEATURE:
<223> OTHER INFORMATION: Description of Unknown:
      Cleavage sequence
<220> FEATURE:
<221> NAME/KEY: MOD_RES
<222> LOCATION: (6)..(6)
<223> OTHER INFORMATION: Any amino acid

<400> SEQUENCE: 515

Pro Leu Gly Leu Ala Xaa
1               5

<210> SEQ ID NO 516
<211> LENGTH: 6
<212> TYPE: PRT
<213> ORGANISM: Unknown
<220> FEATURE:
<223> OTHER INFORMATION: Description of Unknown:
      Cleavage sequence
<220> FEATURE:
<221> NAME/KEY: MOD_RES
<222> LOCATION: (4)..(4)
<223> OTHER INFORMATION: Cys(me)

<400> SEQUENCE: 516

Pro Leu Gly Cys Ala Gly
1               5

<210> SEQ ID NO 517
<211> LENGTH: 8
<212> TYPE: PRT
<213> ORGANISM: Unknown
<220> FEATURE:
<223> OTHER INFORMATION: Description of Unknown:
      Cleavage sequence

<400> SEQUENCE: 517

Glu Ser Pro Ala Tyr Tyr Thr Ala
1               5

<210> SEQ ID NO 518
<211> LENGTH: 6
<212> TYPE: PRT
<213> ORGANISM: Unknown
<220> FEATURE:
<223> OTHER INFORMATION: Description of Unknown:
      Cleavage sequence

<400> SEQUENCE: 518

Arg Leu Gln Leu Lys Leu
1               5

<210> SEQ ID NO 519
<211> LENGTH: 7
<212> TYPE: PRT
<213> ORGANISM: Unknown
<220> FEATURE:
<223> OTHER INFORMATION: Description of Unknown:
Cleavage sequence

<400> SEQUENCE: 519

Arg Leu Gln Leu Lys Ala Cys
1 5

<210> SEQ ID NO 520
<211> LENGTH: 7
<212> TYPE: PRT
<213> ORGANISM: Unknown
<220> FEATURE:
<223> OTHER INFORMATION: Description of Unknown:
Cleavage sequence
<220> FEATURE:
<221> NAME/KEY: MOD_RES
<222> LOCATION: (3)..(3)
<223> OTHER INFORMATION: Cit
<220> FEATURE:
<221> NAME/KEY: MOD_RES
<222> LOCATION: (5)..(5)
<223> OTHER INFORMATION: Hof

<400> SEQUENCE: 520

Glu Pro Xaa Gly Xaa Tyr Leu
1 5

<210> SEQ ID NO 521
<211> LENGTH: 5
<212> TYPE: PRT
<213> ORGANISM: Unknown
<220> FEATURE:
<223> OTHER INFORMATION: Description of Unknown:
Cleavage sequence

<400> SEQUENCE: 521

Ser Gly Arg Ser Ala
1 5

<210> SEQ ID NO 522

<400> SEQUENCE: 522

000

<210> SEQ ID NO 523
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 523

Asp Ala Phe Lys
1

<210> SEQ ID NO 524
<211> LENGTH: 5
<212> TYPE: PRT
<213> ORGANISM: Unknown
<220> FEATURE:
<223> OTHER INFORMATION: Description of Unknown:
Cleavage sequence

<400> SEQUENCE: 524

Gly Gly Gly Arg Arg
1 5

<210> SEQ ID NO 525
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 525

Gly Phe Leu Gly
1

<210> SEQ ID NO 526
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 526

Ala Leu Ala Leu
1

<210> SEQ ID NO 527
<211> LENGTH: 2
<212> TYPE: PRT
<213> ORGANISM: Unknown
<220> FEATURE:
<223> OTHER INFORMATION: Description of Unknown:
Cleavage sequence

<400> SEQUENCE: 527

Phe Lys
1

<210> SEQ ID NO 528
<211> LENGTH: 3
<212> TYPE: PRT
<213> ORGANISM: Unknown
<220> FEATURE:
<223> OTHER INFORMATION: Description of Unknown:
Cleavage sequence

<400> SEQUENCE: 528

Asn Leu Leu
1

<210> SEQ ID NO 529
<211> LENGTH: 5
<212> TYPE: PRT
<213> ORGANISM: Unknown
<220> FEATURE:
<223> OTHER INFORMATION: Description of Unknown:
Cleavage sequence
<220> FEATURE:
<221> NAME/KEY: MOD_RES
<222> LOCATION: (3)..(3)
<223> OTHER INFORMATION: Cys(Et)

<400> SEQUENCE: 529

Pro Ile Cys Phe Phe
1 5

<210> SEQ ID NO 530
<211> LENGTH: 8
<212> TYPE: PRT
<213> ORGANISM: Unknown
<220> FEATURE:
<223> OTHER INFORMATION: Description of Unknown:
Cleavage sequence

<400> SEQUENCE: 530

Gly Gly Pro Arg Gly Leu Pro Gly
1 5

<210> SEQ ID NO 531
<211> LENGTH: 6
<212> TYPE: PRT
<213> ORGANISM: Unknown
<220> FEATURE:
<223> OTHER INFORMATION: Description of Unknown:
Cleavage sequence

<400> SEQUENCE: 531

His Ser Ser Lys Leu Gln
1 5

<210> SEQ ID NO 532
<211> LENGTH: 7
<212> TYPE: PRT
<213> ORGANISM: Unknown
<220> FEATURE:
<223> OTHER INFORMATION: Description of Unknown:
Cleavage sequence

<400> SEQUENCE: 532

His Ser Ser Lys Leu Gln Leu
1 5

<210> SEQ ID NO 533
<211> LENGTH: 9
<212> TYPE: PRT
<213> ORGANISM: Unknown
<220> FEATURE:
<223> OTHER INFORMATION: Description of Unknown:
Cleavage sequence

<400> SEQUENCE: 533

His Ser Ser Lys Leu Gln Glu Asp Ala
1 5

<210> SEQ ID NO 534
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 534

Leu Val Leu Ala Ser Ser Ser Phe Gly Tyr
1 5 10

<210> SEQ ID NO 535
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 535

Gly Val Ser Gln Asn Tyr Pro Ile Val Gly
1 5 10

<210> SEQ ID NO 536
<211> LENGTH: 10
<212> TYPE: PRT
<213> ORGANISM: Unknown
<220> FEATURE:
<223> OTHER INFORMATION: Description of Unknown:
Cleavage sequence

<400> SEQUENCE: 536

Gly Val Val Gln Ala Ser Cys Arg Leu Ala
1 5 10

<210> SEQ ID NO 537
<211> LENGTH: 4
<212> TYPE: PRT
<213> ORGANISM: Unknown
<220> FEATURE:
<223> OTHER INFORMATION: Description of Unknown:
Cleavage sequence
<220> FEATURE:
<221> NAME/KEY: MOD_RES
<222> LOCATION: (2)..(2)
<223> OTHER INFORMATION: Pip

<400> SEQUENCE: 537

Phe Xaa Arg Ser
1

<210> SEQ ID NO 538
<211> LENGTH: 6
<212> TYPE: PRT
<213> ORGANISM: Unknown
<220> FEATURE:
<223> OTHER INFORMATION: Description of Unknown:
Cleavage sequence

<400> SEQUENCE: 538

Asp Pro Arg Ser Phe Leu
1 5

<210> SEQ ID NO 539
<211> LENGTH: 6
<212> TYPE: PRT
<213> ORGANISM: Unknown
<220> FEATURE:
<223> OTHER INFORMATION: Description of Unknown:
Cleavage sequence

<400> SEQUENCE: 539

Pro Pro Arg Ser Phe Leu
1 5

<210> SEQ ID NO 540
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 540

Asp Glu Val Asp
1

<210> SEQ ID NO 541
<211> LENGTH: 5
<212> TYPE: PRT
<213> ORGANISM: Unknown
<220> FEATURE:
<223> OTHER INFORMATION: Description of Unknown:
Cleavage sequence

<400> SEQUENCE: 541

Asp Glu Val Asp Pro
1 5

<210> SEQ ID NO 542
<211> LENGTH: 8
<212> TYPE: PRT
<213> ORGANISM: Unknown
<220> FEATURE:
<223> OTHER INFORMATION: Description of Unknown:
Cleavage sequence

<400> SEQUENCE: 542

Lys Gly Ser Gly Asp Val Glu Gly
1 5

<210> SEQ ID NO 543
<211> LENGTH: 6
<212> TYPE: PRT
<213> ORGANISM: Unknown
<220> FEATURE:
<223> OTHER INFORMATION: Description of Unknown:
Cleavage sequence

<400> SEQUENCE: 543

Gly Trp Glu His Asp Gly
1 5

<210> SEQ ID NO 544
<211> LENGTH: 7
<212> TYPE: PRT
<213> ORGANISM: Unknown
<220> FEATURE:
<223> OTHER INFORMATION: Description of Unknown:
Cleavage sequence

<400> SEQUENCE: 544

Glu Asp Asp Asp Asp Lys Ala
1 5

<210> SEQ ID NO 545
<211> LENGTH: 9
<212> TYPE: PRT
<213> ORGANISM: Unknown
<220> FEATURE:
<223> OTHER INFORMATION: Description of Unknown:
Cleavage sequence

<400> SEQUENCE: 545

Lys Gln Glu Gln Asn Pro Gly Ser Thr
1 5

<210> SEQ ID NO 546
<211> LENGTH: 6
<212> TYPE: PRT
<213> ORGANISM: Unknown
<220> FEATURE:
<223> OTHER INFORMATION: Description of Unknown:
Cleavage sequence

<400> SEQUENCE: 546

Gly Lys Ala Phe Arg Arg
1 5

<210> SEQ ID NO 547
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 547

Asp Ala Phe Lys
1

<210> SEQ ID NO 548
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 548

Asp Val Leu Lys
1

<210> SEQ ID NO 549
<211> LENGTH: 4
<212> TYPE: PRT
<213> ORGANISM: Unknown
<220> FEATURE:
<223> OTHER INFORMATION: Description of Unknown:
Cleavage sequence

<400> SEQUENCE: 549

Asp Ala Phe Lys
1

<210> SEQ ID NO 550
<211> LENGTH: 7
<212> TYPE: PRT
<213> ORGANISM: Unknown
<220> FEATURE:
<223> OTHER INFORMATION: Description of Unknown:
Cleavage sequence

<400> SEQUENCE: 550

Ala Leu Leu Leu Ala Leu Leu
1 5

<210> SEQ ID NO 551
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 551

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 552
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 552

Gly Leu Leu Val Ala Gly Val Leu Val Leu Leu Val Ser Leu Gly Val
1 5 10 15

Ala Ile His Leu Cys Cys
20

<210> SEQ ID NO 553
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 553

Ala Leu Ile Val Leu Gly Gly Val Ala Gly Leu Leu Leu Phe Ile Gly
1 5 10 15

Leu Gly Ile Phe Phe Cys Val Arg Cys
20 25

<210> SEQ ID NO 554
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 554

Leu Cys Tyr Leu Leu Asp Gly Ile Leu Phe Ile Tyr Gly Val Ile Leu
1 5 10 15

Thr Ala Leu Phe Leu Arg Val
20

<210> SEQ ID NO 555
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 555

Trp Val Leu Val Val Val Gly Gly Val Leu Ala Cys Tyr Ser Leu Leu
1 5 10 15

Val Thr Val Ala Phe Ile Ile Phe Trp Val
20 25

<210> SEQ ID NO 556
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 556

Ala Ala Ile Leu Gly Leu Gly Leu Val Leu Gly Leu Leu Gly Pro Leu
1 5 10 15

Ala Ile Leu Leu Ala Leu Tyr Leu Leu
20 25

<210> SEQ ID NO 557
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 557

Ala Leu Pro Ala Ala Leu Ala Val Ile Ser Phe Leu Leu Gly Leu Gly
1 5 10 15

Leu Gly Val Ala Cys Val Leu Ala
20

<210> SEQ ID NO 558
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 558

Cys Pro Glu Pro Lys Ser Cys Asp Thr Pro Pro Pro Cys Pro Arg
1 5 10 15

<210> SEQ ID NO 559
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 559

Glu Leu Lys Thr Pro Leu Gly Asp Thr Thr His Thr
1 5 10

<210> SEQ ID NO 560
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 560

Lys Ser Cys Asp Lys Thr His Thr Cys Pro
1 5 10

<210> SEQ ID NO 561
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 561

Lys Cys Cys Val Asp Cys Pro
1 5

<210> SEQ ID NO 562
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 562

Lys Tyr Gly Pro Pro Cys Pro
1 5

<210> SEQ ID NO 563
<211> LENGTH: 15
<212> TYPE: PRT
<213> ORGANISM: Homo sapiens

<400> SEQUENCE: 563

Glu Pro Lys Ser Cys Asp Lys Thr His Thr Cys Pro Pro Cys Pro
1 5 10 15

<210> SEQ ID NO 564
<211> LENGTH: 12
<212> TYPE: PRT
<213> ORGANISM: Homo sapiens

<400> SEQUENCE: 564

Glu Arg Lys Cys Cys Val Glu Cys Pro Pro Cys Pro
1 5 10

<210> SEQ ID NO 565
<211> LENGTH: 17
<212> TYPE: PRT
<213> ORGANISM: Homo sapiens

<400> SEQUENCE: 565

Glu Leu Lys Thr Pro Leu Gly Asp Thr Thr His Thr Cys Pro Arg Cys
1 5 10 15

Pro

<210> SEQ ID NO 566
<211> LENGTH: 12
<212> TYPE: PRT
<213> ORGANISM: Homo sapiens

<400> SEQUENCE: 566

Ser Pro Asn Met Val Pro His Ala His His Ala Gln
1 5 10

<210> SEQ ID NO 567
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 567

Glu Pro Lys Ser Cys Asp Lys Thr Tyr Thr Cys Pro Pro Cys Pro
1 5 10 15

<210> SEQ ID NO 568
<211> LENGTH: 45
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 568

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 569
<211> LENGTH: 518
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 569

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Ser Gly Gly Gly Gly Ser Gly Gly Val Val Gly Gly Gly Gly Thr Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255
```

```
Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Val Glu Ser Gly Gly Gly Leu Val Gln Pro Gly
                405                 410                 415

Gly Ser Leu Thr Leu Ser Cys Ala Ala Ser Gly Phe Ala Phe Gly Asn
            420                 425                 430

His Trp Met Tyr Trp Tyr Arg Gln Ala Pro Gly Arg Gly Arg Glu Leu
        435                 440                 445

Val Ala Ser Ile Ser Ser Gly Gly Ser Thr Asn Tyr Val Asp Ser Val
    450                 455                 460

Lys Gly Arg Phe Thr Ile Ser Arg Asp Asn Ala Lys Asn Thr Leu Tyr
465                 470                 475                 480

Leu Gln Met Asn Ser Leu Arg Ala Glu Asp Thr Ala Val Tyr Tyr Cys
                485                 490                 495

Gly Thr Ser Asp Asn Trp Gly Gln Gly Thr Leu Val Thr Val Ser Ser
            500                 505                 510

His His His His His His
        515
```

<210> SEQ ID NO 570
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 570

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80
```

```
Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser Gly Gly Gly Gly Ser Gly Gly Gly Ser Gln Thr Val Val
        115                 120                 125

Thr Gln Glu Pro Ser Leu Thr Val Ser Pro Gly Gly Thr Val Thr Leu
    130                 135                 140

Thr Cys Ala Ser Ser Thr Gly Ala Val Thr Ser Gly Asn Tyr Pro Asn
145                 150                 155                 160

Trp Val Gln Gln Lys Pro Gly Gln Ala Pro Arg Gly Leu Ile Gly Gly
                165                 170                 175

Thr Lys Phe Leu Val Pro Gly Thr Pro Ala Arg Phe Ser Gly Ser Leu
            180                 185                 190

Leu Gly Gly Lys Ala Ala Leu Thr Leu Ser Gly Val Gln Pro Glu Asp
        195                 200                 205

Glu Ala Glu Tyr Tyr Cys Thr Leu Trp Tyr Ser Asn Arg Trp Val Phe
    210                 215                 220

Gly Gly Gly Thr Lys Leu Thr Val Leu Gly Gly Gly Gly Ser Gly Gly
225                 230                 235                 240

Gly Gly Ser Gly Gly Gly Gly Ser Glu Val Gln Leu Val Glu Ser Gly
                245                 250                 255

Gly Gly Leu Val Gln Pro Gly Gly Ser Leu Lys Leu Ser Cys Ala Ala
            260                 265                 270

Ser Gly Phe Thr Phe Asn Lys Tyr Ala Ile Asn Trp Val Arg Gln Ala
        275                 280                 285

Pro Gly Lys Gly Leu Glu Trp Val Ala Arg Ile Arg Ser Lys Tyr Asn
    290                 295                 300

Asn Tyr Ala Thr Tyr Tyr Ala Asp Gln Val Lys Asp Arg Phe Thr Ile
305                 310                 315                 320

Ser Arg Asp Asp Ser Lys Asn Thr Ala Tyr Leu Gln Met Asn Asn Leu
                325                 330                 335

Lys Thr Glu Asp Thr Ala Val Tyr Tyr Cys Val Arg His Ala Asn Phe
            340                 345                 350

Gly Asn Ser Tyr Ile Ser Tyr Trp Ala Tyr Trp Gly Gln Gly Thr Leu
        355                 360                 365

Val Thr Val Ser Ser Gly Gly Gly Gly Ser Gly Gly Gly Ser Glu Val
    370                 375                 380

Gln Leu Val Glu Ser Gly Gly Gly Leu Val Gln Pro Gly Gly Ser Leu
385                 390                 395                 400

Thr Leu Ser Cys Ala Ala Ser Gly Phe Ala Phe Gly Asn His Trp Met
                405                 410                 415

Tyr Trp Tyr Arg Gln Ala Pro Gly Arg Gly Arg Glu Leu Val Ala Ser
            420                 425                 430

Ile Ser Ser Gly Gly Ser Thr Asn Tyr Val Asp Ser Val Lys Gly Arg
        435                 440                 445

Phe Thr Ile Ser Arg Asp Asn Ala Lys Asn Thr Leu Tyr Leu Gln Met
    450                 455                 460

Asn Ser Leu Arg Ala Glu Asp Thr Ala Val Tyr Tyr Cys Gly Thr Ser
465                 470                 475                 480

Asp Asn Trp Gly Gln Gly Thr Leu Val Thr Val Ser Ser His His His
                485                 490                 495

His His His
```

<210> SEQ ID NO 571
<211> LENGTH: 390
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 571

Val Val Gly Gly Gly Gly Thr Gln Thr Val Val Thr Gln Glu Pro Ser
1 5 10 15

Leu Thr Val Ser Pro Gly Gly Thr Val Thr Leu Thr Cys Ala Ser Ser
20 25 30

Thr Gly Ala Val Thr Ser Gly Asn Tyr Pro Asn Trp Val Gln Gln Lys
35 40 45

Pro Gly Gln Ala Pro Arg Gly Leu Ile Gly Gly Thr Lys Phe Leu Val
50 55 60

Pro Gly Thr Pro Ala Arg Phe Ser Gly Ser Leu Leu Gly Gly Lys Ala
65 70 75 80

Ala Leu Thr Leu Ser Gly Val Gln Pro Glu Asp Glu Ala Glu Tyr Tyr
85 90 95

Cys Thr Leu Trp Tyr Ser Asn Arg Trp Val Phe Gly Gly Gly Thr Lys
100 105 110

Leu Thr Val Leu Gly Gly Gly Gly Ser Gly Gly Gly Gly Ser Gly Gly
115 120 125

Gly Gly Ser Glu Val Gln Leu Val Glu Ser Gly Gly Gly Leu Val Gln
130 135 140

Pro Gly Gly Ser Leu Lys Leu Ser Cys Ala Ala Ser Gly Phe Thr Phe
145 150 155 160

Asn Lys Tyr Ala Ile Asn Trp Val Arg Gln Ala Pro Gly Lys Gly Leu
165 170 175

Glu Trp Val Ala Arg Ile Arg Ser Lys Tyr Asn Asn Tyr Ala Thr Tyr
180 185 190

Tyr Ala Asp Gln Val Lys Asp Arg Phe Thr Ile Ser Arg Asp Asp Ser
195 200 205

Lys Asn Thr Ala Tyr Leu Gln Met Asn Asn Leu Lys Thr Glu Asp Thr
210 215 220

Ala Val Tyr Tyr Cys Val Arg His Ala Asn Phe Gly Asn Ser Tyr Ile
225 230 235 240

Ser Tyr Trp Ala Tyr Trp Gly Gln Gly Thr Leu Val Thr Val Ser Ser
245 250 255

Gly Gly Gly Gly Ser Gly Gly Gly Ser Glu Val Gln Leu Leu Glu Ser
260 265 270

Gly Gly Gly Leu Val Gln Pro Gly Gly Ser Leu Thr Leu Ser Cys Ala
275 280 285

Ala Ser Gly Phe Ile Phe Arg Ala Ala Ser Met Ala Trp Tyr Arg Gln
290 295 300

Ser Pro Gly Asn Glu Arg Glu Leu Val Ala Ser Ile Ser Ser Gly Ala
305 310 315 320

Phe Thr Asn Tyr Ala Asp Ser Val Lys Ala Arg Phe Thr Ile Ser Arg
325 330 335

Asp Asn Ser Lys Asn Thr Leu Tyr Leu Gln Met Asn Ser Leu Arg Ala
340 345 350

Glu Asp Thr Ala Val Tyr Tyr Cys Gly Ala Thr Phe Leu Arg Ser Asp
355 360 365

Gly His His Thr Ile Trp Gly Gln Gly Thr Leu Val Thr Val Ser Ser
370 375 380

His His His His His His
385 390

<210> SEQ ID NO 572
<211> LENGTH: 507
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 572

Glu Val Gln Leu Val Glu Ser Gly Gly Gly Leu Val Gln Pro Gly Asn
1 5 10 15

Ser Leu Arg Leu Ser Cys Ala Ala Ser Gly Phe Thr Phe Ser Lys Phe
20 25 30

Gly Met Ser Trp Val Arg Gln Ala Pro Gly Lys Gly Leu Glu Trp Val
35 40 45

Ser Ser Ile Ser Gly Ser Gly Arg Asp Thr Leu Tyr Ala Asp Ser Val
50 55 60

Lys Gly Arg Phe Thr Ile Ser Arg Asp Asn Ala Lys Thr Thr Leu Tyr
65 70 75 80

Leu Gln Met Asn Ser Leu Arg Pro Glu Asp Thr Ala Val Tyr Tyr Cys
85 90 95

Thr Ile Gly Gly Ser Leu Ser Val Ser Ser Gln Gly Thr Leu Val Thr
100 105 110

Val Ser Ser Gly Gly Gly Gly Ser Gly Gly Gly Ser Gln Thr Val Val
115 120 125

Thr Gln Glu Pro Ser Leu Thr Val Ser Pro Gly Gly Thr Val Thr Leu
130 135 140

Thr Cys Ala Ser Ser Thr Gly Ala Val Thr Ser Gly Asn Tyr Pro Asn
145 150 155 160

Trp Val Gln Gln Lys Pro Gly Gln Ala Pro Arg Gly Leu Ile Gly Gly
165 170 175

Thr Lys Phe Leu Val Pro Gly Thr Pro Ala Arg Phe Ser Gly Ser Leu
180 185 190

Leu Gly Gly Lys Ala Ala Leu Thr Leu Ser Gly Val Gln Pro Glu Asp
195 200 205

Glu Ala Glu Tyr Tyr Cys Thr Leu Trp Tyr Ser Asn Arg Trp Val Phe
210 215 220

Gly Gly Gly Thr Lys Leu Thr Val Leu Gly Gly Gly Gly Ser Gly Gly
225 230 235 240

Gly Gly Ser Gly Gly Gly Gly Ser Glu Val Gln Leu Val Glu Ser Gly
245 250 255

Gly Gly Leu Val Gln Pro Gly Gly Ser Leu Lys Leu Ser Cys Ala Ala
260 265 270

Ser Gly Phe Thr Phe Asn Lys Tyr Ala Ile Asn Trp Val Arg Gln Ala
275 280 285

Pro Gly Lys Gly Leu Glu Trp Val Ala Arg Ile Arg Ser Lys Tyr Asn
290 295 300

Asn Tyr Ala Thr Tyr Tyr Ala Asp Gln Val Lys Asp Arg Phe Thr Ile
305 310 315 320

Ser Arg Asp Asp Ser Lys Asn Thr Ala Tyr Leu Gln Met Asn Asn Leu
325 330 335

Lys Thr Glu Asp Thr Ala Val Tyr Tyr Cys Val Arg His Ala Asn Phe
340 345 350

Gly Asn Ser Tyr Ile Ser Tyr Trp Ala Tyr Trp Gly Gln Gly Thr Leu
355 360 365

Val Thr Val Ser Ser Gly Gly Gly Gly Ser Gly Gly Gly Ser Glu Val
370 375 380

Gln Leu Leu Glu Ser Gly Gly Gly Leu Val Gln Pro Gly Gly Ser Leu
385 390 395 400

Thr Leu Ser Cys Ala Ala Ser Gly Phe Ile Phe Arg Ala Ala Ser Met
405 410 415

Ala Trp Tyr Arg Gln Ser Pro Gly Asn Glu Arg Glu Leu Val Ala Ser
420 425 430

Ile Ser Ser Gly Ala Phe Thr Asn Tyr Ala Asp Ser Val Lys Ala Arg
435 440 445

Phe Thr Ile Ser Arg Asp Asn Ser Lys Asn Thr Leu Tyr Leu Gln Met
450 455 460

Asn Ser Leu Arg Ala Glu Asp Thr Ala Val Tyr Tyr Cys Gly Ala Thr
465 470 475 480

Phe Leu Arg Ser Asp Gly His His Thr Ile Trp Gly Gln Gly Thr Leu
485 490 495

Val Thr Val Ser Ser His His His His His His
500 505

<210> SEQ ID NO 573
<211> LENGTH: 526
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 573

Glu Val Gln Leu Val Glu Ser Gly Gly Gly Leu Val Gln Pro Gly Asn
1 5 10 15

Ser Leu Arg Leu Ser Cys Ala Ala Ser Gly Phe Thr Phe Ser Lys Phe
20 25 30

Gly Met Ser Trp Val Arg Gln Gly Gly Gly Gly Gly Leu Asp Gly Asn
35 40 45

Glu Glu Pro Gly Gly Leu Glu Trp Val Ser Ser Ile Ser Gly Ser Gly
50 55 60

Arg Asp Thr Leu Tyr Ala Asp Ser Val Lys Gly Arg Phe Thr Ile Ser
65 70 75 80

Arg Asp Asn Ala Lys Thr Thr Leu Tyr Leu Gln Met Asn Ser Leu Arg
85 90 95

Pro Glu Asp Thr Ala Val Tyr Tyr Cys Thr Ile Gly Gly Ser Leu Ser
100 105 110

Val Ser Ser Gln Gly Thr Leu Val Thr Val Ser Ser Gly Gly Gly Gly
115 120 125

Ser Gly Gly Gly Ser Gly Gly Val Val Gly Gly Gly Gly Thr Gln
130 135 140

Thr Val Val Thr Gln Glu Pro Ser Leu Thr Val Ser Pro Gly Gly Thr
145 150 155 160

Val Thr Leu Thr Cys Ala Ser Ser Thr Gly Ala Val Thr Ser Gly Asn
165 170 175

```
Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Leu Glu Ser Gly Gly Gly Leu Val Gln Pro Gly
                405                 410                 415

Gly Ser Leu Thr Leu Ser Cys Ala Ala Ser Gly Phe Ile Phe Arg Ala
            420                 425                 430

Ala Ser Met Asp Trp Tyr Arg Gln Phe Pro Gly Asn Glu Arg Glu Ser
        435                 440                 445

Ile Ala Thr Ile Ser Ser Gly Gly Phe Thr Asn Tyr Ala Asp Ser Val
    450                 455                 460

Lys Gly Arg Phe Thr Ile Ser Arg Asp Asn Ser Lys Asn Thr Leu Tyr
465                 470                 475                 480

Leu Gln Met Asn Ser Leu Arg Ala Glu Asp Thr Ala Val Tyr Tyr Cys
                485                 490                 495

Gly Ala Thr Phe Leu Arg Ser Asp Gly His His Thr Ile Trp Gly Gln
            500                 505                 510

Gly Thr Leu Val Thr Val Ser Ser His His His His His His
        515                 520                 525
```

<210> SEQ ID NO 574
<211> LENGTH: 390
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 574

```
Val Val Gly Gly Gly Gly Thr Gln Thr Val Val Thr Gln Glu Pro Ser
1               5                   10                  15
```

```
Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
    210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Glu Val Gln Leu Leu Glu Ser
            260                 265                 270

Gly Gly Gly Leu Val Gln Pro Gly Gly Ser Leu Thr Leu Ser Cys Ala
        275                 280                 285

Ala Ser Gly Phe Ile Phe Arg Ala Ala Ser Met Asp Trp Tyr Arg Gln
    290                 295                 300

Phe Pro Gly Asn Glu Arg Glu Ser Ile Ala Thr Ile Ser Ser Gly Gly
305                 310                 315                 320

Phe Thr Asn Tyr Ala Asp Ser Val Lys Gly Arg Phe Thr Ile Ser Arg
                325                 330                 335

Asp Asn Ser Lys Asn Thr Leu Tyr Leu Gln Met Asn Ser Leu Arg Ala
            340                 345                 350

Glu Asp Thr Ala Val Tyr Tyr Cys Gly Ala Thr Phe Leu Arg Ser Asp
        355                 360                 365

Gly His His Thr Ile Trp Gly Gln Gly Thr Leu Val Thr Val Ser Ser
    370                 375                 380

His His His His His His
385                 390
```

<210> SEQ ID NO 575
<211> LENGTH: 507
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 575

Glu Val Gln Leu Val Glu Ser Gly Gly Gly Leu Val Gln Pro Gly Asn
1 5 10 15

Ser Leu Arg Leu Ser Cys Ala Ala Ser Gly Phe Thr Phe Ser Lys Phe
20 25 30

Gly Met Ser Trp Val Arg Gln Ala Pro Gly Lys Gly Leu Glu Trp Val
35 40 45

Ser Ser Ile Ser Gly Ser Gly Arg Asp Thr Leu Tyr Ala Asp Ser Val
50 55 60

Lys Gly Arg Phe Thr Ile Ser Arg Asp Asn Ala Lys Thr Thr Leu Tyr
65 70 75 80

Leu Gln Met Asn Ser Leu Arg Pro Glu Asp Thr Ala Val Tyr Tyr Cys
85 90 95

Thr Ile Gly Gly Ser Leu Ser Val Ser Ser Gln Gly Thr Leu Val Thr
100 105 110

Val Ser Ser Gly Gly Gly Gly Ser Gly Gly Gly Ser Gln Thr Val Val
115 120 125

Thr Gln Glu Pro Ser Leu Thr Val Ser Pro Gly Gly Thr Val Thr Leu
130 135 140

Thr Cys Ala Ser Ser Thr Gly Ala Val Thr Ser Gly Asn Tyr Pro Asn
145 150 155 160

Trp Val Gln Gln Lys Pro Gly Gln Ala Pro Arg Gly Leu Ile Gly Gly
165 170 175

Thr Lys Phe Leu Val Pro Gly Thr Pro Ala Arg Phe Ser Gly Ser Leu
180 185 190

Leu Gly Gly Lys Ala Ala Leu Thr Leu Ser Gly Val Gln Pro Glu Asp
195 200 205

Glu Ala Glu Tyr Tyr Cys Thr Leu Trp Tyr Ser Asn Arg Trp Val Phe
210 215 220

Gly Gly Gly Thr Lys Leu Thr Val Leu Gly Gly Gly Gly Ser Gly Gly
225 230 235 240

Gly Gly Ser Gly Gly Gly Gly Ser Glu Val Gln Leu Val Glu Ser Gly
245 250 255

Gly Gly Leu Val Gln Pro Gly Gly Ser Leu Lys Leu Ser Cys Ala Ala
260 265 270

Ser Gly Phe Thr Phe Asn Lys Tyr Ala Ile Asn Trp Val Arg Gln Ala
275 280 285

Pro Gly Lys Gly Leu Glu Trp Val Ala Arg Ile Arg Ser Lys Tyr Asn
290 295 300

Asn Tyr Ala Thr Tyr Tyr Ala Asp Gln Val Lys Asp Arg Phe Thr Ile
305 310 315 320

Ser Arg Asp Asp Ser Lys Asn Thr Ala Tyr Leu Gln Met Asn Asn Leu
325 330 335

Lys Thr Glu Asp Thr Ala Val Tyr Tyr Cys Val Arg His Ala Asn Phe
340 345 350

Gly Asn Ser Tyr Ile Ser Tyr Trp Ala Tyr Trp Gly Gln Gly Thr Leu
355 360 365

Val Thr Val Ser Ser Gly Gly Gly Gly Ser Gly Gly Gly Ser Glu Val
370 375 380

Gln Leu Leu Glu Ser Gly Gly Gly Leu Val Gln Pro Gly Gly Ser Leu
385 390 395 400

```
Thr Leu Ser Cys Ala Ala Ser Gly Phe Ile Phe Arg Ala Ala Ser Met
                405                 410                 415

Asp Trp Tyr Arg Gln Phe Pro Gly Asn Glu Arg Glu Ser Ile Ala Thr
            420                 425                 430

Ile Ser Ser Gly Gly Phe Thr Asn Tyr Ala Asp Ser Val Lys Gly Arg
        435                 440                 445

Phe Thr Ile Ser Arg Asp Asn Ser Lys Asn Thr Leu Tyr Leu Gln Met
    450                 455                 460

Asn Ser Leu Arg Ala Glu Asp Thr Ala Val Tyr Tyr Cys Gly Ala Thr
465                 470                 475                 480

Phe Leu Arg Ser Asp Gly His His Thr Ile Trp Gly Gln Gly Thr Leu
                485                 490                 495

Val Thr Val Ser Ser His His His His His His
            500                 505


<210> SEQ ID NO 576
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 576

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Pro Gln Ala Ser Thr Gly Arg Ser Gly Gly Gly Gly Gly Gly Ser Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240
```

```
Trp Val Phe Gly Gly Gly Thr Lys Leu Thr Val Leu Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Val Glu Ser Gly Gly Gly Leu Val Gln Pro Gly
                405                 410                 415

Gly Ser Leu Thr Leu Ser Cys Ala Ala Ser Gly Phe Ala Phe Gly Asn
            420                 425                 430

His Trp Met Tyr Trp Tyr Arg Gln Ala Pro Gly Arg Gly Arg Glu Leu
        435                 440                 445

Val Ala Ser Ile Ser Ser Gly Gly Ser Thr Asn Tyr Val Asp Ser Val
    450                 455                 460

Lys Gly Arg Phe Thr Ile Ser Arg Asp Asn Ala Lys Asn Thr Leu Tyr
465                 470                 475                 480

Leu Gln Met Asn Ser Leu Arg Ala Glu Asp Thr Ala Val Tyr Tyr Cys
                485                 490                 495

Gly Thr Ser Asp Asn Trp Gly Gln Gly Thr Leu Val Thr Val Ser Ser
            500                 505                 510

His His His His His His
        515


<210> SEQ ID NO 577
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 577

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80
```

```
Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Pro Gln Ala Ser Thr Gly Arg Ser Gly Gly Gly Gly Gly Gly Thr Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Leu Glu Ser Gly Gly Gly Leu Val Gln Pro Gly
                405                 410                 415

Gly Ser Leu Thr Leu Ser Cys Ala Ala Ser Gly Phe Ile Phe Arg Ala
            420                 425                 430

Ala Ser Met Ala Trp Tyr Arg Gln Ser Pro Gly Asn Glu Arg Glu Leu
        435                 440                 445

Val Ala Ser Ile Ser Ser Gly Ala Phe Thr Asn Tyr Ala Asp Ser Val
    450                 455                 460

Lys Ala Arg Phe Thr Ile Ser Arg Asp Asn Ser Lys Asn Thr Leu Tyr
465                 470                 475                 480

Leu Gln Met Asn Ser Leu Arg Ala Glu Asp Thr Ala Val Tyr Tyr Cys
                485                 490                 495
```

```
Gly Ala Thr Phe Leu Arg Ser Asp Gly His His Thr Ile Asn Gly Gln
            500                 505                 510

Gly Thr Leu Val Thr Val Ser Ser His His His His His His
        515                 520                 525


<210> SEQ ID NO 578
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 578

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Pro Gln Ala Ser Thr Gly Arg Ser Gly Gly Gly Gly Gly Gly Ser Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335
```

```
Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Leu Glu Ser Gly Gly Gly Leu Val Gln Pro Gly
                405                 410                 415

Gly Ser Leu Thr Leu Ser Cys Ala Ala Ser Gly Phe Ile Phe Arg Ala
            420                 425                 430

Ala Ser Met Ala Trp Tyr Arg Gln Ser Pro Gly Asn Glu Arg Glu Leu
        435                 440                 445

Val Ala Ser Ile Ser Ser Gly Ala Phe Thr Asn Tyr Ala Asp Ser Val
    450                 455                 460

Lys Ala Arg Phe Thr Ile Ser Arg Asp Asn Ser Lys Asn Thr Leu Tyr
465                 470                 475                 480

Leu Gln Met Asn Ser Leu Arg Ala Glu Asp Thr Ala Val Tyr Tyr Cys
                485                 490                 495

Gly Ala Thr Phe Leu Arg Ser Asp Gly His His Thr Ile Trp Gly Gln
            500                 505                 510

Gly Thr Leu Val Thr Val Ser Ser His His His His His His
        515                 520                 525
```

<210> SEQ ID NO 579
<211> LENGTH: 482
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 579

```
Gln Glu Glu Cys Val Cys Glu Asn Tyr Lys Leu Ala Val Asn Cys Phe
1               5                   10                  15

Val Asn Asn Asn Arg Gln Cys Gln Cys Thr Ser Val Gly Ala Gln Asn
            20                  25                  30

Thr Val Ile Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
    50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Met Cys Trp Cys Val
                85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Ile Glu Leu Lys His Lys
        115                 120                 125

Ala Arg Glu Lys Pro Tyr Asp Ser Lys Ser Leu Arg Thr Ala Leu Gln
    130                 135                 140

Lys Glu Ile Thr Thr Arg Tyr Gln Leu Asp Pro Lys Phe Ile Thr Ser
145                 150                 155                 160

Ile Leu Tyr Glu Asn Asn Val Ile Thr Ile Asp Leu Val Gln Asn Ser
                165                 170                 175
```

```
Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
        195                 200                 205

Asp Leu Thr Val Asn Gly Glu Gln Leu Asp Leu Asp Pro Gly Gln Thr
    210                 215                 220

Leu Ile Tyr Tyr Val Asp Glu Lys Ala Pro Glu Phe Ser Met Gln Gly
225                 230                 235                 240

Leu Lys Asp Tyr Lys Asp Asp Asp Asp Lys Gly Gly Gly Gly Ser Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys


<210> SEQ ID NO 580
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 580

Gln Lys Glu Cys Val Cys Glu Asn Tyr Lys Leu Ala Val Asn Cys Phe
1               5                   10                  15

Leu Asn Asp Asn Gly Gln Cys Gln Cys Thr Ser Ile Gly Ala Gln Asn
            20                  25                  30

Thr Val Leu Cys Ser Lys Leu Ala Ala Lys Cys Leu Val Met Lys Ala
        35                  40                  45
```

```
Glu Met Asn Gly Ser Lys Leu Gly Arg Arg Ala Lys Pro Glu Gly Ala
    50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Thr Cys Trp Cys Val
                85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Ile Glu Leu Lys His Lys
        115                 120                 125

Ala Arg Glu Lys Pro Tyr Asp Val Gln Ser Leu Arg Thr Ala Leu Glu
    130                 135                 140

Glu Ala Ile Lys Thr Arg Tyr Gln Leu Asp Pro Lys Phe Ile Thr Asn
145                 150                 155                 160

Ile Leu Tyr Glu Asp Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
        195                 200                 205

Asp Leu Arg Val Asn Gly Glu Gln Leu Asp Leu Asp Pro Gly Gln Thr
    210                 215                 220

Leu Ile Tyr Tyr Val Asp Glu Lys Ala Pro Glu Phe Ser Met Gln Gly
225                 230                 235                 240

Leu Lys Asp Tyr Lys Asp Asp Asp Asp Lys Gly Gly Gly Gly Ser Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460
```

```
Glu Ala Leu His Asn His Tyr Thr Gln Lys Ser Leu Ser Leu Ser Pro
465                 470                 475                 480

Gly Lys


<210> SEQ ID NO 581
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Gly Gly Gly Gly Thr
1               5


<210> SEQ ID NO 582
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Trp Gly Gln Gly Thr Leu Val Thr Val Ser Ser
1               5                   10


<210> SEQ ID NO 583
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Gly Ser Gly Gly Ser
1               5


<210> SEQ ID NO 584
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Gly Gly Gly Ser
1


<210> SEQ ID NO 585
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Gly Gly Ser Gly
1


<210> SEQ ID NO 586
<211> LENGTH: 5
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 586

Gly Gly Ser Gly Gly
1 5

<210> SEQ ID NO 587
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 587

Gly Ser Gly Ser Gly
1 5

<210> SEQ ID NO 588
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 588

Gly Ser Gly Gly Gly
1 5

<210> SEQ ID NO 589
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 589

Gly Gly Gly Ser Gly
1 5

<210> SEQ ID NO 590
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 590

Gly Ser Ser Ser Gly
1 5

<210> SEQ ID NO 591
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 591

Asp Lys Thr His Thr
1 5

<210> SEQ ID NO 592
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 592

Cys Pro Pro Cys
1

<210> SEQ ID NO 593
<211> LENGTH: 20
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
Gly Ser" repeating units

<400> SEQUENCE: 593

Gly Gly Gly Gly Ser Gly Gly Gly Gly Ser Gly Gly Gly Gly Ser Gly
1 5 10 15

Gly Gly Gly Ser
20

<210> SEQ ID NO 594
<211> LENGTH: 20
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (1)..(20)
<223> OTHER INFORMATION: This sequence may encompass 2-4 "Gly Gly Gly
Gly Ser" repeating units

<400> SEQUENCE: 594

Gly Gly Gly Gly Ser Gly Gly Gly Gly Ser Gly Gly Gly Gly Ser Gly
1 5 10 15

Gly Gly Gly Ser
20

<210> SEQ ID NO 595
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (1)..(15)
<223> OTHER INFORMATION: This sequence may encompass 1-3 "Gly Gly Gly
Gly Ser" repeating units

<400> SEQUENCE: 595

Gly Gly Gly Gly Ser Gly Gly Gly Gly Ser Gly Gly Gly Gly Ser
1 5 10 15